United States Patent
Degnan et al.

(10) Patent No.: US 8,691,821 B2
(45) Date of Patent: Apr. 8, 2014

(54) OXAZOLIDINONES AS MODULATORS OF MGLUR5

(75) Inventors: Andrew P. Degnan, Rocky Hill, CT (US); Hong Huang, Durham, CT (US); Lawrence B. Snyder, Killingworth, CT (US); Fukang Yang, Madison, CT (US); Kevin W. Gillman, Madison, CT (US); Michael F. Parker, Higganum, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 14 days.

(21) Appl. No.: 13/287,487

(22) Filed: Nov. 2, 2011

(65) Prior Publication Data

US 2012/0283264 A1 Nov. 8, 2012

Related U.S. Application Data

(60) Provisional application No. 61/412,541, filed on Nov. 11, 2010.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *A01N 43/40* | (2006.01) |
| *A61K 31/44* | (2006.01) |
| *A01N 43/76* | (2006.01) |
| *A61K 31/42* | (2006.01) |
| *C07D 401/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 421/00* | (2006.01) |

(52) U.S. Cl.
USPC ........... 514/249; 514/333; 514/340; 514/376; 546/256

(58) Field of Classification Search
None
See application file for complete search history.

(56) References Cited

FOREIGN PATENT DOCUMENTS

| WO | WO 2005/094822 | 10/2005 |
| WO | WO 2011/051201 | 5/2011 |

OTHER PUBLICATIONS

Lee et al. (Acta Neurobiol Exp 2004, 64: 89-98).*

* cited by examiner

*Primary Examiner* — James D Anderson
*Assistant Examiner* — William Lee
(74) *Attorney, Agent, or Firm* — James Epperson

(57) ABSTRACT

The disclosure generally relates to compounds of formula I, including their salts, as well as compositions and methods of using the compounds. The compounds are ligands, agonists and partial agonists for the mGluR5 receptor and may be useful for the treatment of various disorders of the central nervous system.

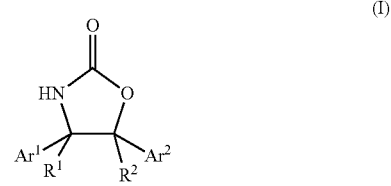

(I)

14 Claims, No Drawings

OXAZOLIDINONES AS MODULATORS OF MGLUR5

CROSS REFERENCE TO RELATED APPLICATIONS

This patent application claims the benefit of U.S. provisional patent application No. 61/412,541 filed Nov. 11, 2010.

BACKGROUND OF THE INVENTION

The disclosure generally relates to compounds of formula I, including their salts, as well as compositions and methods of using the compounds. The compounds are ligands, agonists and partial agonists for the mGluR5 receptor and may be useful for the treatment of various disorders of the central nervous system.

Glutamate is the major excitatory neurotransmitter in the mammalian brain, playing an important physiological role in a wide variety of processes. Glutamatergic neurotransmission is predominantly mediated through activation of cell surface receptors including ligand-gated ion channels (ionotropic receptors) and metabotropic glutamate G protein coupled receptors (mGluRs). The metabotropic glutamate receptor family is comprised of 8 family members that are part of the family 3 GPCR superfamily. These receptors are further subdivided into Group I (mGluR 1, 5), Group II (mGluR 2, 3) and Group III (mGluR 4, 6, 7, 8) based upon sequence homology, receptor signaling, and pharmacology.

The Group I receptor mGluR5 has emerged as a target of potential therapeutic utility in a number of disease states (see: Rodriguez, A. L., et al. Current Opinion in Drug Discovery & Development (2007), 10(6), 715-722. and Chen, Y., et al. Drugs of the Future (2008), 33(4), 355-360. and Lindsley, C. W., et al. Current Opinion in Drug Discovery & Development (2009), 12(4), 446-457). The receptor is expressed broadly throughout the CNS with predominant post-synaptic localization, although pre-synaptic expression is also present. mGluR5 is a Gαq-coupled receptor activating phospholipase C and elevating intracellular calcium levels, leading to activation of downstream signaling molecules. Many studies have demonstrated a role for the receptor in regulating NMDA receptor activity as well as synaptic plasticity, suggesting this receptor plays a key role in glutamatergic signal transduction.

Based on the expression pattern and functional role of mGluR5, this receptor has emerged as an important target for drug discovery in a number of therapeutic indications. Evaluation of genetically modified mice lacking mGluR5 as well as compounds that modulate receptor function suggest ligands that modulate mGluR5 receptor function have therapeutic utility in CNS and peripheral disease states including, but not limited to, schizophrenia (see: Conn, P. J., et al. Trends in Pharmacological Sciences (2009), 30(1), 25-31; and Kanuma, K., et al. Recent Patents on CNS Drug Discovery (2010), 5(1), 23-34), cognitive impairment (see: Simonyi, A., et al. European Journal of Pharmacology (2010), 639(1-3), 17-25), Alzheimer's disease, Parkinson's disease (see: Johnson, K. A., et al. CNS & Neurological Disorders Drug Targets (2009), 8(6), 475-491), Parkinson's disease levodopa-induced dyskinesia (see: Rylander, D., et al. Neurobiology of Disease (2010), 39(3), 352-361), addiction (see: Olive, M. F. Current Drug Abuse Reviews (2009), 2(1), 83-98), anxiety (see: Jacob, W., et al. Neuropharmacology (2009), 57(2), 97-108), depression (see: Witkin, J. M., et al. CNS & Neurological Disorders: Drug Targets (2007), 6(2), 87-100), psychosis, epilepsy, Fragile X (see: Dolen, G., et al. Journal of Physiology (Oxford, United Kingdom) (2008), 586(6), 1503-1508), gastroesophageal reflux disease (see: Boeckxstaens, G. E. Expert Opinion on Emerging Drugs (2009), 14(3), 481-491), migraine (see: Marin, J., et al. Expert Opinion on Investigational Drugs (2010), 19(4), 555-561), pain, and others.

The invention provides technical advantages, for example, the compounds are novel and are ligands for the mGluR receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders related to levels of tachykinins or serotonin or both.

One aspect of the invention is a compound of formula I

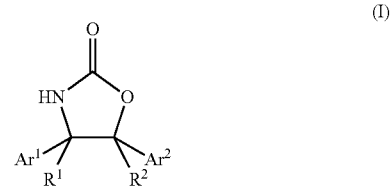

where:
$R^1$ is hydrogen or alkyl;
$R^2$ is hydrogen or alkyl;
$R^3$ is

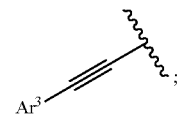

$Ar^1$ is phenyl or a 6 membered heteroaryl containing 1-3 heteroatoms in which $Ar^1$ is substituted with 1 $R^3$ substituent and with 0-3 substituents selected from halo, alkyl, haloalkyl, alkoxy, and haloalkoxy;
$Ar^2$ is aryl or heteroaryl, and is substituted with 0-3 substituents selected from halo, cyano, alkyl, haloalkyl, hydroxy, alkoxy, haloalkoxy, and phenyl; and
$Ar^3$ is aryl or heteroaryl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino;
or a pharmaceutically acceptable salt thereof.

Another aspect of the invention is a compound of formula I where:
$Ar^1$ is phenyl, pyridinyl, pyrazinyl, pyrimidinyl, or pyridazinyl, and is substituted with 1 $R^3$ substituent and with 0-3 substituents selected from halo, alkyl, haloalkyl, alkoxy, and haloalkoxy;
$Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from halo, cyano, alkyl, haloalkyl, hydroxy, alkoxy, haloalkoxy, and phenyl; and $Ar^3$ is phenyl, pyridinyl, pyrazinyl, pyrimidinyl, pyridazinyl, imidazolyl, oxazolyl, thiazolyl, quinolinyl, isoquinolinyl, quinoxalinyl, or pyrrolopyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino;
or a pharmaceutically acceptable salt thereof.

Another aspect of the invention is a compound of formula I where $Ar^1$ is phenyl, pyridinyl, or pyrimidinyl and is substituted with 1 $R^3$ substituent and with 0-1 halo or alkoxy substituents; $Ar^2$ is phenyl, pyridinyl, pyrazinyl, pyrimidinyl, pyridazinyl, thienyl, pyrazolyl, oxazolyl, oxadiazolyl, or tetrazolyl, and is substituted with 0-3 substituents selected from halo, cyano, alkyl, haloalkyl, hydroxy, alkoxy, and phenyl; and $Ar^3$ is phenyl, pyridinyl, pyrazinyl, pyrimidinyl, pyridazinyl, imidazolyl, thiazolyl, isoquinolinyl, quinolinyl, quinoxalinyl, or pyrrolopyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

Another aspect of the invention is a compound of formula I where $Ar^1$ is phenyl, pyridinyl, halopyridinyl, alkoxypyridinyl, or pyrimidinyl; $Ar^2$ is phenyl, cyanophenyl, halophenyl, dihalophenyl, (haloalkyl)phenyl, alkylphenyl, dialkylphenyl, hydroxyphenyl, alkoxyphenyl, pyridinyl, pyrazinyl, pyrimidinyl, pyridazinyl, thienyl, (alkyl)pyrazolyl, oxazolyl, (alkyl)oxadiazolyl, (phenyl)oxadiazolyl, (pyridinyl)oxadiazolyl, or tetrazolyl; and $Ar^3$ is phenyl, cyanophenyl, halophenyl, dihalophenyl, alkylphenyl, (haloalkyl)phenyl, alkoxyphenyl, (haloalkoxy)phenyl, (alkylthio)phenyl, (amino)phenyl, alkylaminophenyl, dialkylaminophenyl, alkoxycarbonylphenyl, alkylcarbonylphenyl, pyridinyl, cyanopyridinyl, halopyridinyl, alkylpyridinyl, cycloalkylpyridinyl, alkoxypyridinyl, pyrazinyl, pyrimidinyl, alkoxypyrimidinyl, aminopyrimidinyl, alkylaminopyrimidinyl, dialkylaminopyrimidinyl, pyridazinyl, pyrrolopyridinyl, isoquinolinyl, quinoxalinyl, imidazolyl, thiazolyl, or alkylthiazolyl; or a pharmaceutically acceptable salt thereof.

Another aspect of the invention is a compound of formula I 4 where $R^1$ is hydrogen or methyl; $R^2$ is hydrogen or methyl; $Ar^1$ is phenyl, pyridinyl, fluoropyridinyl, methoxypyridinyl, or pyrimidinyl and is substituted with 1 $R^3$ substituent; $Ar^2$ is phenyl, cyanophenyl, chlorophenyl, dichlorophenyl, fluorophenyl, difluorophenyl, trifluoromethylphenyl, methylphenyl, dimethylphenyl, trifluoromethylphenyl, hydroxyphenyl, methoxyphenyl, pyridinyl, pyrazinyl, pyrimidinyl, pyridazinyl, thienyl, (methyl)pyrazolyl, oxazolyl, (methyl)oxadiazolyl, (phenyl)oxadiazolyl, (pyridinyl)oxadiazolyl, or tetrazolyl; and $Ar^3$ is phenyl, cyanophenyl, chlorophenyl, dichlorophenyl, fluorophenyl, difluorophenyl, methylphenyl, t-butylphenyl, trifluoromethylphenyl, methoxyphenyl, trifluoromethoxyphenyl, methylthiophenyl, (amino)phenyl, dimethylaminophenyl, methoxycarbonylphenyl, methylcarbonylphenyl, pyridinyl, cyanopyridinyl, chloropyridinyl, fluoropyridinyl, methylpyridinyl, cyclopropylpyridinyl, methoxypyridinyl, pyrazinyl, pyrimidinyl, ethoxypyrimidinyl, methylaminopyrimidinyl, pyridazinyl, pyrrolopyridinyl, isoquinolinyl, quinoxalinyl, imidazolyl, thiazolyl, or methylthiazolyl; or a pharmaceutically acceptable salt thereof.

Another aspect of the invention is a compound of formula I where $R^1$ is hydrogen; $R^2$ is hydrogen; $Ar^1$ is phenyl or pyridinyl substituted in the meta position with $R^3$; $Ar^2$ is aryl or heteroaryl, and is substituted with 0-3 substituents selected from halo, cyano, alkyl, haloalkyl, hydroxy, alkoxy, haloalkoxy, and phenyl; $Ar^3$ is phenyl or pyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

Another aspect of the invention is a compound of formula I where $R^1$ is hydrogen; $R^2$ is hydrogen; $Ar^1$ is phenyl or pyridinyl substituted in the meta position with $R^3$; $Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from halo, cyano, alkyl, haloalkyl, hydroxy, alkoxy, haloalkoxy, and phenyl; $Ar^3$ is phenyl or pyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

Another aspect of the invention is a compound of formula I where $R^1$ is hydrogen; $R^2$ is hydrogen; $Ar^1$ is phenyl or pyridinyl substituted in the meta position with $R^3$; $Ar^2$ is phenyl, pyridinyl, pyrazinyl, pyrimidinyl, pyridazinyl, thienyl, pyrazolyl, oxazolyl, oxadiazolyl, or tetrazolyl, and is substituted with 0-3 substituents selected from halo, cyano, alkyl, haloalkyl, hydroxy, alkoxy, and phenyl; $Ar^3$ is phenyl or pyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

Another aspect of the invention is a compound of formula I where $R^1$ is hydrogen; $R^2$ is hydrogen; $Ar^1$ is phenyl or pyridinyl substituted in the meta position with $R^3$; $Ar^2$ is phenyl, cyanophenyl, halophenyl, dihalophenyl, (haloalkyl)phenyl, alkylphenyl, dialkylphenyl, hydroxyphenyl, alkoxyphenyl, pyridinyl, pyrazinyl, pyrimidinyl, pyridazinyl, thienyl, (alkyl)pyrazolyl, oxazolyl, (alkyl)oxadiazolyl, (phenyl)oxadiazolyl, (pyridinyl)oxadiazolyl, or tetrazolyl; $Ar^3$ is phenyl, cyanophenyl, halophenyl, dihalophenyl, dihalophenyl, alkylphenyl, (haloalkyl)phenyl, alkoxyphenyl, (haloalkoxy)phenyl, (alkylthio)phenyl, (amino)phenyl, alkylaminophenyl, dialkylaminophenyl, alkoxycarbonylphenyl, alkylcarbonylphenyl, pyridinyl, cyanopyridinyl, halopyridinyl, alkylpyridinyl, cycloalkylpyridinyl, alkoxypyridinyl, pyrazinyl, pyrimidinyl, alkoxypyrimidinyl, aminopyrimidinyl, alkylaminopyrimidinyl, dialkylaminopyrimidinyl, pyridazinyl, pyrrolopyridinyl, isoquinolinyl, quinoxalinyl, imidazolyl, thiazolyl, or alkylthiazolyl; or a pharmaceutically acceptable salt thereof.

Another aspect of the invention is a compound of formula I where $R^1$ is hydrogen; $R^2$ is hydrogen; $Ar^1$ is phenyl or pyridinyl substituted in the meta position with $R^3$; $Ar^2$ is phenyl, cyanophenyl, chlorophenyl, dichlorophenyl, fluorophenyl, difluorophenyl, trifluoromethylphenyl, methylphenyl, dimethylphenyl, trifluoromethylphenyl, hydroxyphenyl, methoxyphenyl, pyridinyl, pyrazinyl, pyrimidinyl, pyridazinyl, thienyl, (methyl)pyrazolyl, oxazolyl, (methyl)oxadiazolyl, (phenyl)oxadiazolyl, (pyridinyl)oxadiazolyl, or tetrazolyl; $Ar^3$ is phenyl, cyanophenyl, chlorophenyl, dichlorophenyl, fluorophenyl, difluorophenyl, methylphenyl, t-butylphenyl, trifluoromethylphenyl, methoxyphenyl, trifluoromethoxyphenyl, methylthiophenyl, (amino)phenyl, dimethylaminophenyl, methoxycarbonylphenyl, methylcarbonylphenyl, pyridinyl, cyanopyridinyl, chloropyridinyl, fluoropyridinyl, methylpyridinyl, cyclopropylpyridinyl, methoxypyridinyl, pyrazinyl, pyrimidinyl, ethoxypyrimidinyl, methylaminopyrimidinyl, pyridazinyl, pyrrolopyridinyl, isoquinolinyl, quinoxalinyl, imidazolyl, thiazolyl, or methylthiazolyl; or a pharmaceutically acceptable salt thereof.

Another aspect of the invention is a compound of formula I with the indicated stereochemisty

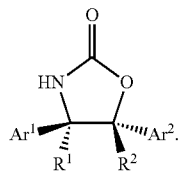

Another aspect of the invention is a compound of formula I where:
$R^1$ is hydrogen or alkyl;
$R^2$ is hydrogen or alkyl;
$R^3$ is

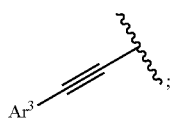

$Ar^1$ phenyl or pyridinyl and is substituted with 1 $R^3$ substituent and with 0-3 substituents selected from halo, alkyl, haloalkyl, alkoxy, and haloalkoxy;
$Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, oxathiadiazolyl, tetrazolyl, or benzimidazolyl, and is substituted with 0-3 substituents selected from halo, cyano, alkyl, haloalkyl, alkoxy, and haloalkoxy; and
$Ar^3$ is phenyl, pyridinyl, pyrazinyl, pyrimidinyl, pyridazinyl, imidazolyl, oxazolyl, thiazolyl, quinolinyl, isoquinolinyl, quinoxalinyl, or pyrrolopyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino;
or a pharmaceutically acceptable salt thereof.

Another aspect of the invention is a compound of formula I where $R^1$ is hydrogen or alkyl; $R^2$ is hydrogen or alkyl; $R^3$ is

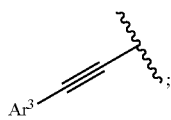

$Ar^1$ phenyl or pyridinyl and is substituted with 1 $R^3$ substituent and with 0-1 halo substituents; $Ar^2$ is phenyl, pyridinyl, pyrazinyl, pyrimidinyl, pyridazinyl, thienyl, oxadiazolyl, or tetrazolyl, and is substituted with 0-3 substituents selected from halo, cyano, alkyl, haloalkyl, and alkoxy; and $Ar^3$ is phenyl, pyridinyl, pyrazinyl, pyrimidinyl, pyridazinyl, imidazolyl, thiazolyl, quinolinyl, quinoxalinyl, or pyrrolopyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

Another aspect of the invention is a compound of formula I where $R^1$ is hydrogen or methyl; $R^2$ is hydrogen or methyl; $R^3$ is

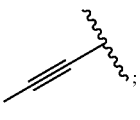

$Ar^1$ phenyl or pyridinyl and is substituted with 1 $R^3$ substituent and with 0-1 fluoro substituents; $Ar^2$ is phenyl, pyridinyl, pyrazinyl, pyrimidinyl, pyridazinyl, thienyl, oxadiazolyl, or tetrazolyl, and is substituted with 0-2 substituents selected from fluoro, chloro, cyano, methyl, trifluoromethyl, and methoxy; and $Ar^3$ is phenyl, pyridinyl, pyrazinyl, pyrimidinyl, pyridazinyl, imidazolyl, thiazolyl, quinolinyl, quinoxalinyl, or pyrrolopyridinyl, and is substituted with 0-2 substituents selected from fluoro, chloro, cyano, methyl, trifluoromethyl, cyclopropyl, hydroxy, methoxy, ethoxy, trifluoromethoxy, acetyl, methoxycarbonyl, methylthio, amino, methylamino, and dimethylamino; or a pharmaceutically acceptable salt thereof.

Another aspect of the invention is a compound of formula I where $R^1$ is hydrogen; $R^2$ is hydrogen; $Ar^1$ is phenyl, pyridinyl, halopyridinyl, alkoxypyridinyl, or pyrimidinyl substituted in the meta position with $R^3$.

Another aspect of the invention is a compound of formula I where $Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from halo, cyano, alkyl, haloalkyl, hydroxy, alkoxy, haloalkoxy, and phenyl; $Ar^3$ is phenyl or pyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

Another aspect of the invention is a compound of formula I where $Ar^2$ is phenyl, pyridinyl, pyrazinyl, pyrimidinyl, pyridazinyl, thienyl, pyrazolyl, oxazolyl, oxadiazolyl, or tetrazolyl, and is substituted with 0-3 substituents selected from halo, cyano, alkyl, haloalkyl, hydroxy, alkoxy, and phenyl; $Ar^3$ is phenyl or pyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

Another aspect of the invention is a compound of formula I where $Ar^2$ is phenyl, cyanophenyl, halophenyl, dihalophenyl, (haloalkyl)phenyl, alkylphenyl, dialkylphenyl, hydroxyphenyl, alkoxyphenyl, pyridinyl, pyrazinyl, pyrimidinyl, pyridazinyl, thienyl, (alkyl)pyrazolyl, oxazolyl, (alkyl)oxadiazolyl, (phenyl)oxadiazolyl, (pyridinyl)oxadiazolyl, or tetrazolyl; $Ar^3$ is phenyl, cyanophenyl, halophenyl, dihalophenyl, dihalophenyl, alkylphenyl, (haloalkyl)phenyl, alkoxyphenyl, (haloalkoxy)phenyl, (alkylthio)phenyl, (amino)phenyl, alkylaminophenyl, dialkylaminophenyl, alkoxycarbonylphenyl, alkylcarbonylphenyl, pyridinyl, cyanopyridinyl, halopyridinyl, alkylpyridinyl, cycloalkylpyridinyl, alkoxypyridinyl, pyrazinyl, pyrimidinyl, alkoxypyrimidinyl, aminopyrimidinyl, alkylaminopyrimidinyl, dialkylaminopyrimidinyl, pyridazinyl, pyrrolopyridinyl, isoquinolinyl, quinoxalinyl, imidazolyl, thiazolyl, or alkylthiazolyl; or a pharmaceutically acceptable salt thereof.

Another aspect of the invention is a compound of formula I where Ar² is phenyl, cyanophenyl, chlorophenyl, dichlorophenyl, fluorophenyl, difluorophenyl, trifluoromethylphenyl, methylphenyl, dimethylphenyl, trifluoromethylphenyl, hydroxyphenyl, methoxyphenyl, pyridinyl, pyrazinyl, pyrimidinyl, pyridazinyl, thienyl, (methyl)pyrazolyl, oxazolyl, (methyl)oxadiazolyl, (phenyl)oxadiazolyl, (pyridinyl)oxadiazolyl, or tetrazolyl; Ar³ is phenyl, cyanophenyl, chlorophenyl, dichlorophenyl, fluorophenyl, difluorophenyl, methylphenyl, t-butylphenyl, trifluoromethylphenyl, methoxyphenyl, trifluoromethoxyphenyl, methylthiophenyl, (amino)phenyl, dimethylaminophenyl, methoxycarbonylphenyl, methylcarbonylphenyl, pyridinyl, cyanopyridinyl, chloropyridinyl, fluoropyridinyl, methylpyridinyl, cyclopropylpyridinyl, methoxypyridinyl, pyrazinyl, pyrimidinyl, ethoxypyrimidinyl, methylaminopyrimidinyl, pyridazinyl, pyrrolopyridinyl, isoquinolinyl, quinoxalinyl, imidazolyl, thiazolyl, or methylthiazolyl; or a pharmaceutically acceptable salt thereof.

Another aspect of the invention is a compound of formula I where R¹ is hydrogen or methyl.

Another aspect of the invention is a compound of formula I where R² is hydrogen or methyl.

Another aspect of the invention is a compound of formula I where R¹ and R² is hydrogen.

Another aspect of the invention is a compound of formula I where Ar¹ has 3,5-pyridindiyl (meta) regiochemistry.

Another aspect of the invention is a compound of formula I where Ar¹ has 2,6-pyridinyl (meta) regiochemistry.

Another aspect of the invention is a compound of formula I where Ar² is dihalophenyl.

Another aspect of the invention is a compound of formula I where Ar² is 2,5-difluorophenyl.

Another aspect of the invention is a compound of formula I where Ar³ is phenyl.

For a compound of formula I, the scope of any instance of a variable substituent, including R¹, R², R³, Ar¹, Ar², and Ar³ can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art. The relative and absolute stereochemistry of formula I compounds depicted in the specific embodiments section (and the intermediates used to prepare them) represent the most likely stereoisomer based on the data collected for each compound.

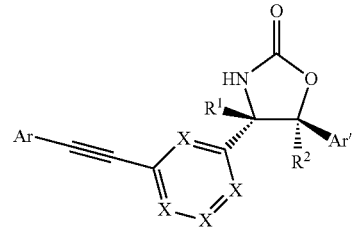

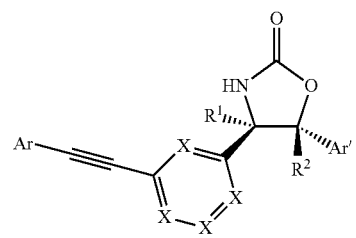

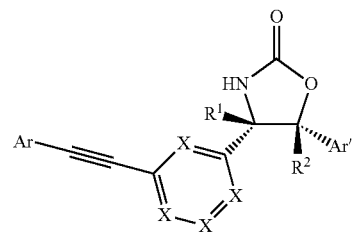

-continued

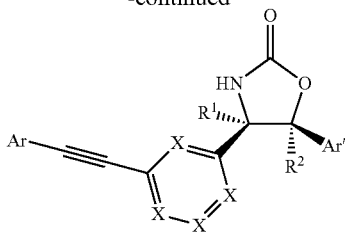

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

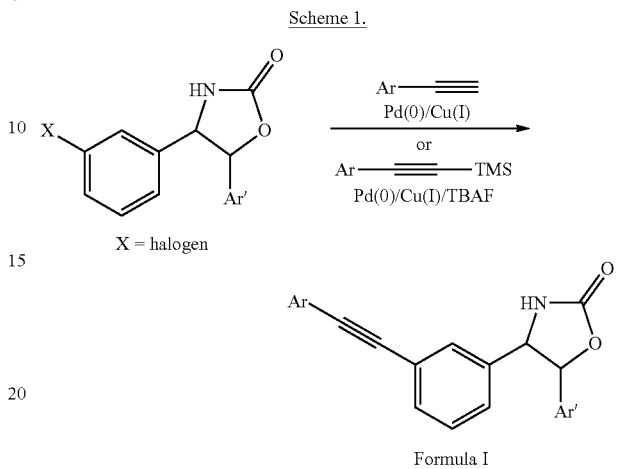

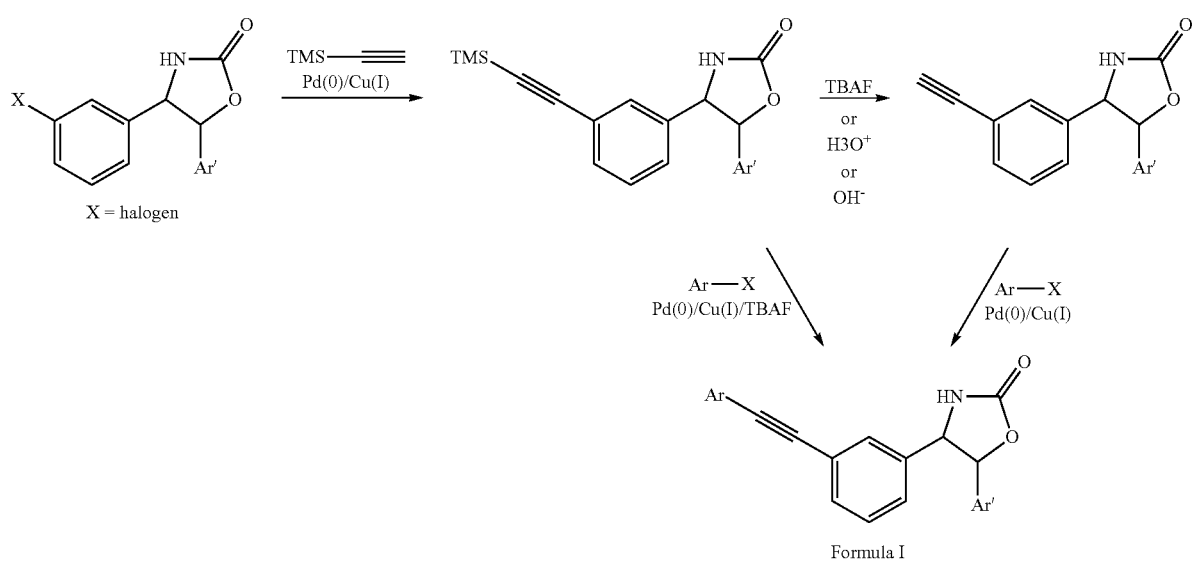

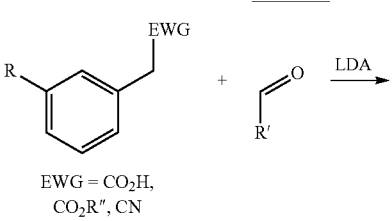

-continued
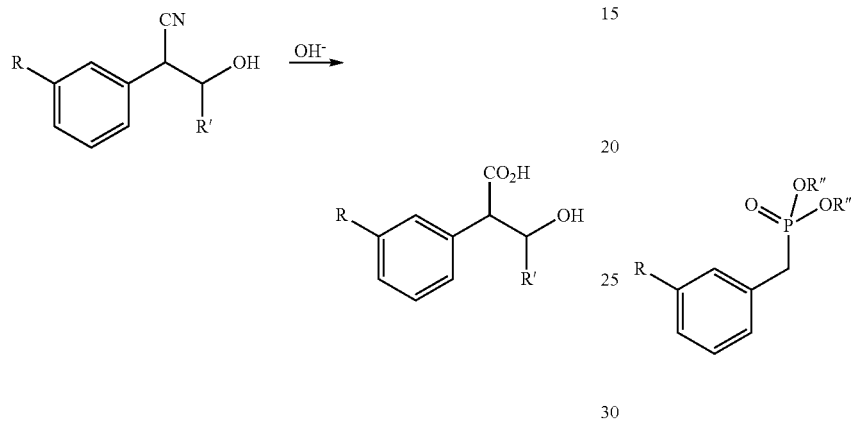
Scheme 4.
Scheme 5.
Scheme 6.
Scheme 7.
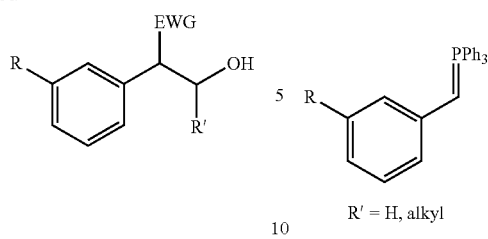
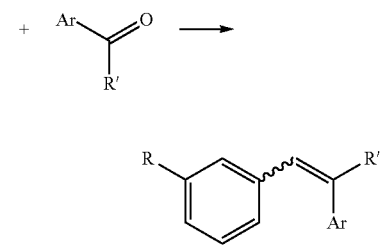
Scheme 8.
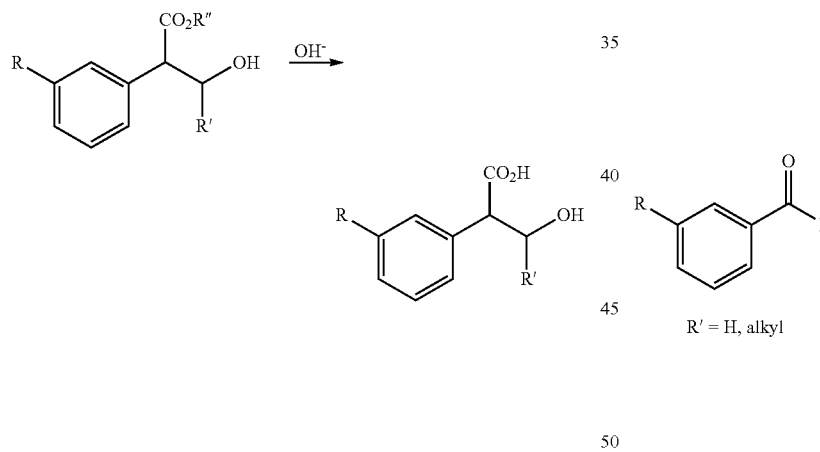
Scheme 9.
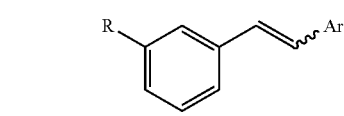
R' = H, alkyl
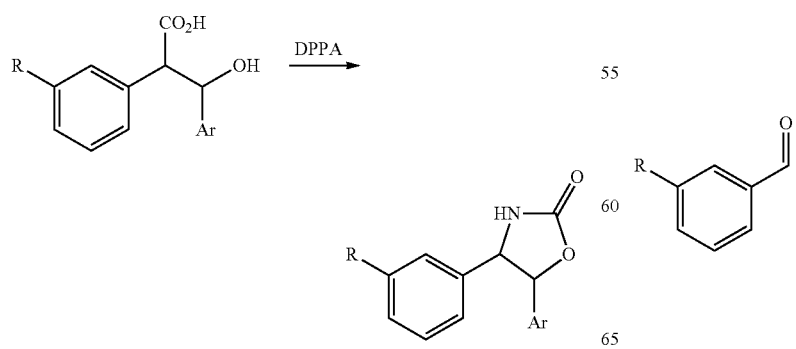
Scheme 10.
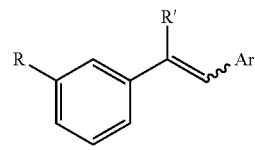
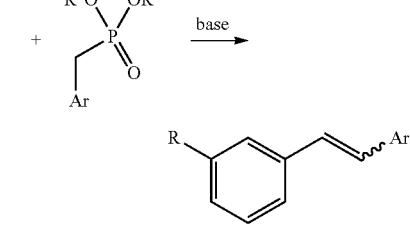

Scheme 11.
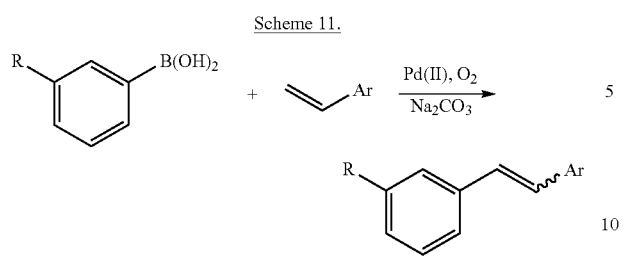
Scheme 12.
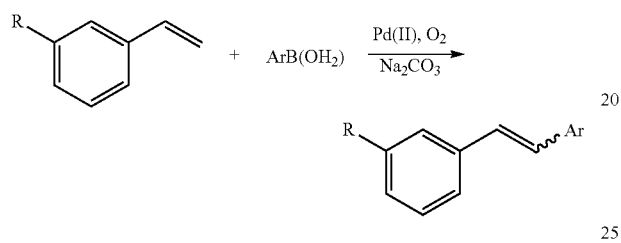
Scheme 13.
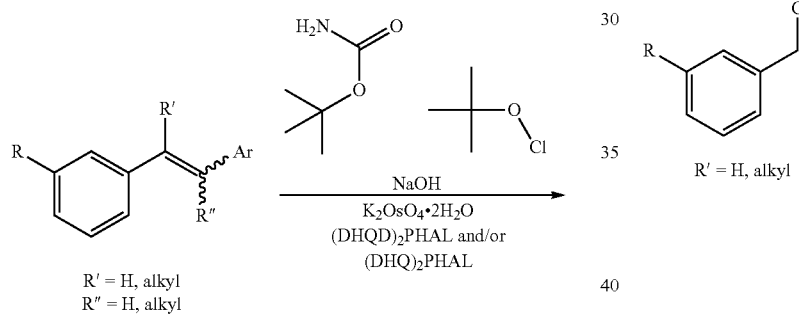
Scheme 14.
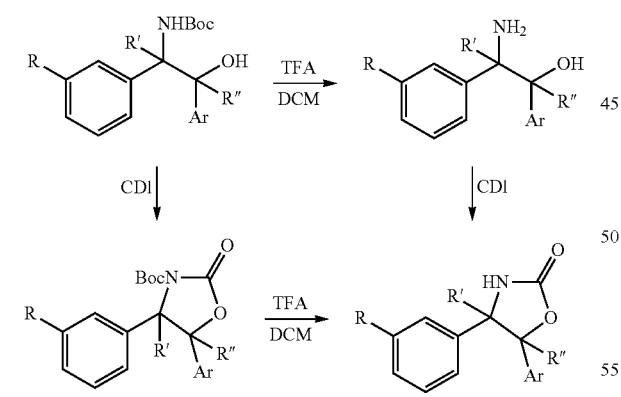
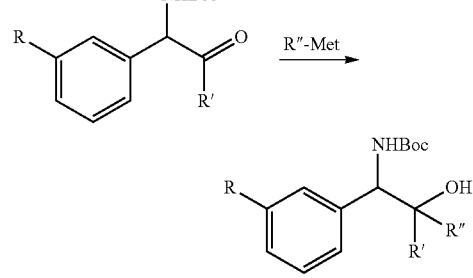
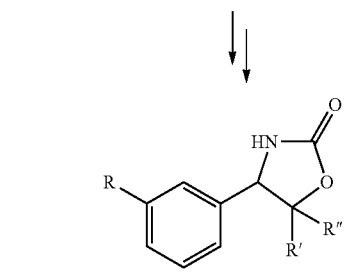
Scheme 15.
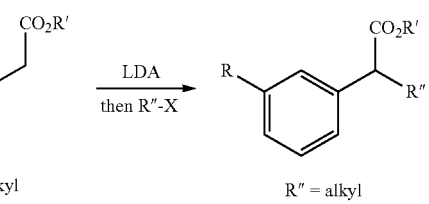
Scheme 16.
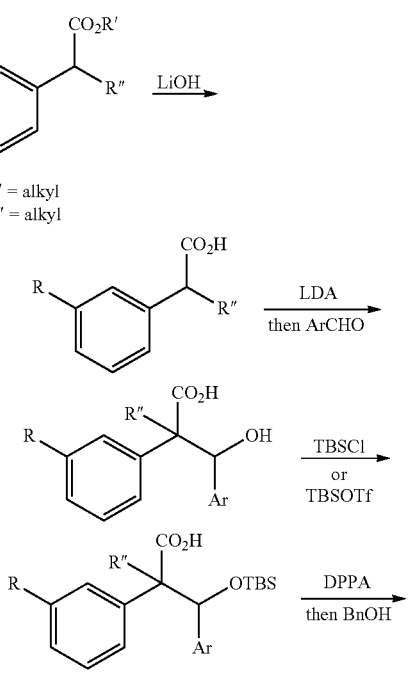

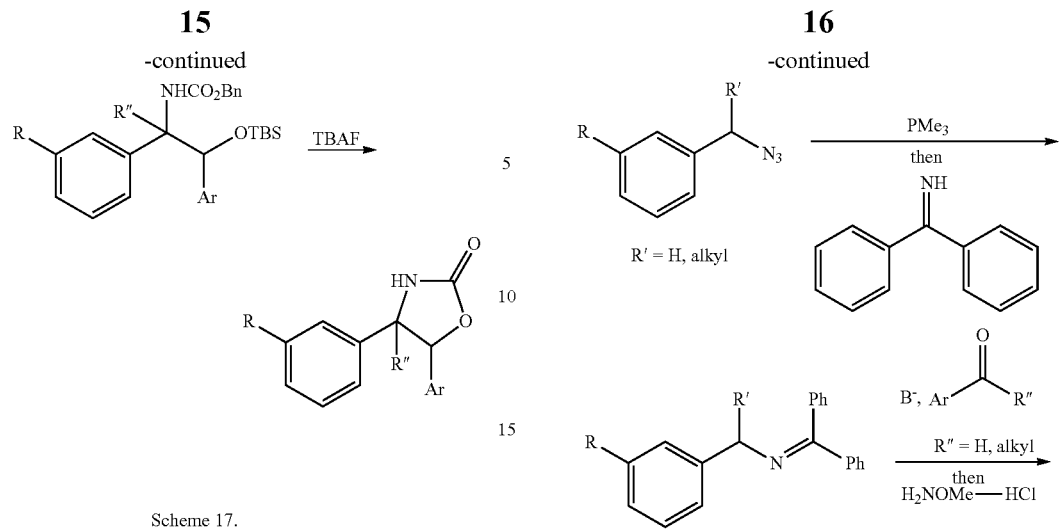
Scheme 17.
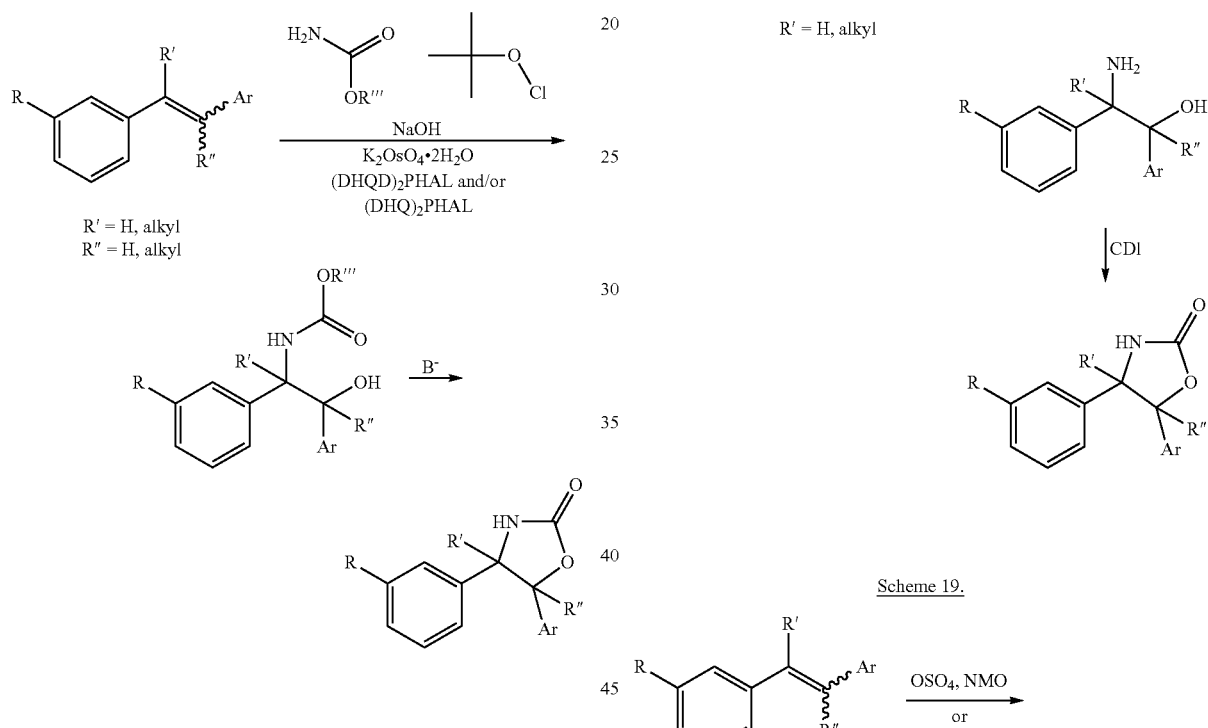
Scheme 18.
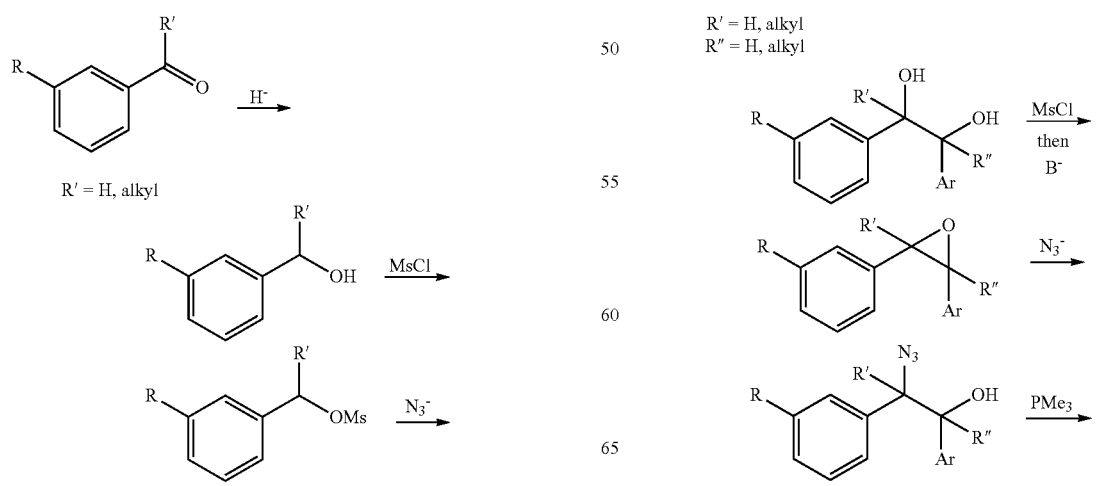
Scheme 19.

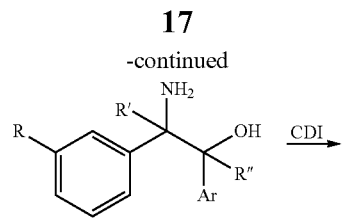
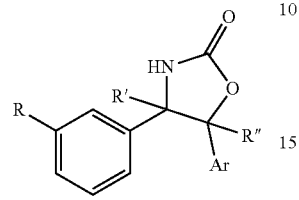
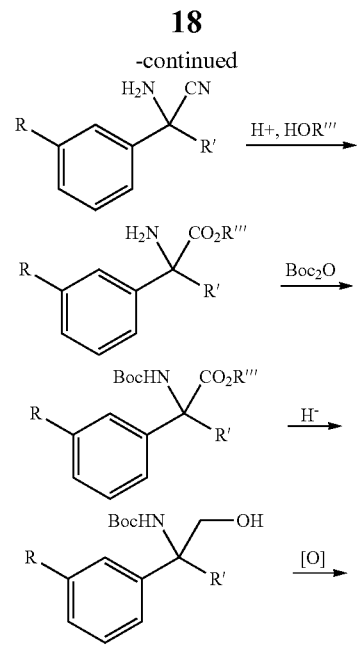
Scheme 20.
Scheme 21.
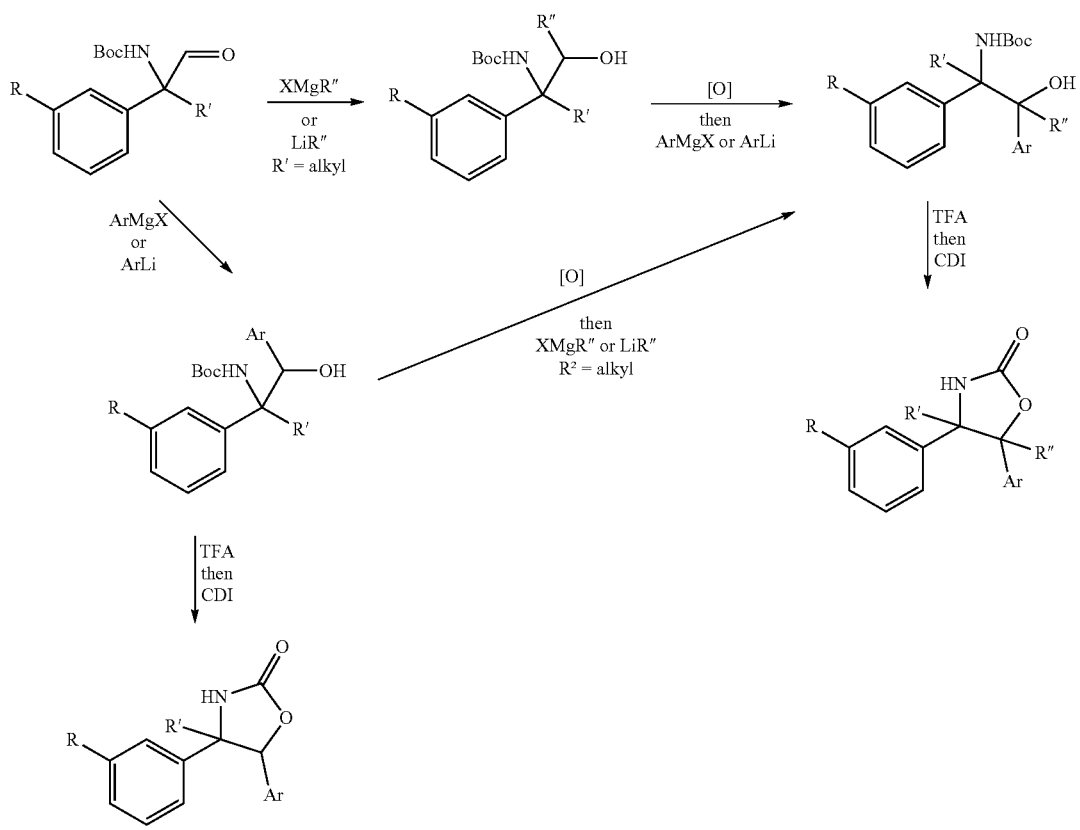

Biological Methods mGluR5 FLIPR Assay.

HEK293 (ZF) cells stably transfected with human mGluR5A (pIRES neo) and the rat glutamate-aspartate transporter (GLAST; pIRES puro) are grown in a monolayer culture at 37° C. in 5% $CO_2$ and fed with Minimum Essential Medium (MEM) supplemented with 10% dialysed fetal bovine serum. 24 hours prior to assay, cells are enzymatically dissociated from the culture flask (Trypsin, 0.25%), spun down (1000 rpm, 3 min), resuspended, and plated on Greiner black clear bottomed PDL-coated 384-well plates at a density of 30 thousand cells/well. On the day of the experiment, media is removed from the cell plates and replaced with Molecular Devices Calcium 4 microfluorometric $Ca^{++}$ sensitive dye in assay buffer (HBSS; Gibco #14025+20 mM HEPES and 250 uM probenacid). Plates are incubated in dye at 37° C. in 5% $CO_2$ for 60 minutes prior to delivery of test compounds in assay buffer. Test compounds are incubated with cells in the presence of dye for 10 minutes prior to being read on the FLIPR platform (Molecular Devices). A $Ca^{++}$ signal is induced in the assay plates via the delivery of an ~$EC_{10}$ concentration of the endogenous agonist 1-glutamate; images are acquired at 1 Hz for 100 seconds post-delivery of agonist stimulus. Positive modulator activity (i.e. the ability of test compounds to increase the $Ca^{++}$ response to a submaximal concentration of agonist) is normalized to a saturating concentration of a known mGluR5 PAM run in each assay plate. An $EC_{50}$ concentration of test compounds is derived from 4-parameter logistic curve fits of transformed fluorescence data via proprietary software suite.

| Example | mGluR5 $EC_{50}$ |
|---|---|
| 1 | A |
| 2 | C |
| 3 | B |
| 4 | C |
| 5 | A |
| 6 | C |
| 7 | C |
| 8 | C |
| 9 | C |
| 10 | A |
| 11 | C |
| 12 | C |
| 13 | C |
| 14 | C |
| 15 | C |
| 16 | A |
| 17 | C |
| 18 | C |
| 19 | C |
| 20 | A |
| 21 | A |
| 22 | C |
| 23 | A |
| 24 | C |
| 25 | C |
| 26 | B |
| 27 | C |
| 28 | C |
| 29 | C |
| 30 | C |
| 31 | C |
| 32 | C |
| 33 | A |
| 34 | C |
| 35 | A |
| 36 | C |
| 37 | A |
| 38 | C |
| 39 | A |
| 40 | C |
| 41 | A |
| 42 | C |
| 43 | A |
| 44 | C |
| 45 | A |
| 46 | A |
| 47 | A |
| 48 | C |
| 49 | C |
| 50 | B |
| 51 | A |
| 52 | C |
| 53 | C |
| 54 | C |
| 55 | A |
| 56 | C |
| 57 | C |
| 58 | C |
| 59 | A |
| 60 | C |
| 61 | A |
| 62 | C |
| 63 | A |
| 64 | C |
| 65 | B |
| 66 | B |
| 67 | C |
| 68 | A |
| 69 | A |
| 70 | C |
| 71 | B |
| 72 | A |
| 73 | A |
| 74 | C |
| 75 | C |
| 76 | C |
| 77 | C |
| 78 | C |
| 79 | A |
| 80 | A |
| 81 | A |
| 82 | B |
| 83 | B |
| 84 | C |
| 85 | C |
| 86 | A |
| 87 | C |
| 88 | C |
| 89 | C |
| 90 | C |
| 91 | B |
| 92 | C |
| 93 | C |
| 94 | C |
| 95 | A |
| 96 | B |
| 97 | C |
| 98 | C |
| 99 | A |
| 100 | B |
| 101 | A |
| 102 | C |
| 103 | A |
| 104 | A |
| 105 | C |
| 106 | A |
| 107 | A |
| 108 | C |
| 109 | A |
| 110 | C |
| 111 | A |
| 112 | A |
| 113 | B |
| 114 | A |
| 115 | C |
| 116 | A |

-continued

| Example | mGluR5 EC$_{50}$ |
|---|---|
| 117 | A |
| 118 | C |
| 119 | C |
| 120 | C |
| 121 | A |
| 122 | C |
| 123 | B |
| 124 | C |
| 125 | C |
| 126 | C |
| 127 | B |
| 128 | C |
| 129 | C |
| 130 | C |
| 131 | A |
| 132 | C |
| 133 | A |
| 134 | C |
| 135 | A |
| 136 | C |
| 137 | B |
| 138 | A |
| 139 | A |
| 140 | A |
| 141 | A |
| 142 | A |
| 143 | A |
| 144 | A |
| 145 | A |
| 146 | A |
| 147 | C |
| 148 | C |
| 149 | B |
| 150 | C |
| 151 | C |
| 152 | C |
| 153 | B |
| 154 | C |
| 155 | C |
| 156 | A |
| 157 | A |
| 158 | C |
| 159 | C |
| 160 | C |
| 161 | C |
| 162 | C |
| 163 | C |
| 164 | C |
| 165 | C |
| 166 | C |
| 167 | C |
| 168 | C |
| 169 | C |
| 170 | A |
| 171 | A |
| 172 | A |
| 173 | A |
| 174 | C |
| 175 | A |
| 176 | A |
| 177 | C |
| 178 | B |
| 179 | A |
| 180 | B |
| 181 | B |
| 182 | A |
| 183 | A |
| 184 | A |
| 185 | A |
| 186 | A |
| 187 | A |
| 188 | C |
| 189 | C |
| 190 | C |
| 191 | C |
| 192 | C |
| 193 | A |
| 194 | B |

-continued

| Example | mGluR5 EC$_{50}$ |
|---|---|
| 195 | C |
| 196 | A |
| 197 | C |
| 198 | A |
| 199 | C |
| 200 | C |
| 201 | B |
| 202 | C |
| 203 | A |
| 204 | A |
| 205 | A |
| 206 | B |
| 207 | C |
| 208 | A |
| 209 | A |
| 210 | A |
| 211 | A |
| 212 | A |
| 213 | A |
| 214 | A |
| 215 | A |
| 216 | A |
| 217 | A |
| 218 | C |
| 219 | A |
| 220 | B |
| 221 | C |
| 222 | A |
| 223 | B |
| 224 | C |
| 225 | C |
| 226 | A |
| 227 | A |
| 228 | C |
| 229 | A |
| 230 | C |
| 231 | A |
| 232 | C |
| 233 | A |
| 234 | A |
| 235 | B |
| 236 | C |
| 237 | B |
| 238 | C |
| 239 | A |
| 240 | C |
| 241 | C |
| 242 | C |
| 243 | B |
| 244 | C |
| 245 | C |
| 246 | C |
| 247 | C |
| 248 | C |
| 249 | C |
| 250 | C |
| 251 | C |
| 252 | C |
| 253 | C |
| 254 | C |
| 255 | C |
| 256 | A |
| 257 | B |
| 258 | A |
| 259 | A |
| 260 | C |
| 261 | C |
| 262 | B |
| 263 | C |
| 264 | B |
| 265 | B |
| 266 | B |
| 267 | B |
| 268 | C |
| 269 | C |
| 270 | C |
| 271 | C |
| 272 | C |

| Example | mGluR5 EC$_{50}$ |
|---|---|
| 273 | C |
| 274 | C |
| 275 | A |
| 276 | B |
| 277 | A |
| 278 | C |
| 279 | A |
| 280 | C |
| 281 | C |
| 282 | A |
| 283 | A |
| 284 | A |
| 285 | B |
| 286 | A |
| 287 | B |
| 288 | B |
| 289 | A |
| 290 | C |
| 291 | B |
| 292 | A |
| 293 | C |
| 294 | A |
| 295 | C |
| 296 | A |
| 297 | A |
| 298 | B |
| 299 | A |
| 300 | A |
| 301 | A |
| 302 | A |
| 303 | C |
| 304 | A |
| 305 | C |
| 306 | C |
| 307 | C |
| 308 | C |
| 309 | A |
| 310 | C |
| 311 | A |
| 312 | C |
| 313 | B |
| 314 | C |
| 315 | C |
| 316 | C |
| 317 | C |
| 318 | A |
| 319 | C |
| 320 | A |
| 321 | C |
| 322 | A |
| 323 | C |
| 324 | A |
| 325 | C |
| 326 | C |
| 327 | C |
| 328 | C |
| 329 | C |
| 330 | A |
| 331 | C |
| 332 | C |
| 333 | C |
| 334 | C |
| 335 | C |
| 336 | C |
| 337 | B |
| 338 | C |
| 339 | C |
| 340 | C |
| 341 | C |
| 342 | A |
| 343 | C |
| 344 | A |
| 345 | C |
| 346 | A |
| 347 | C |
| 348 | C |
| 349 | B |
| 350 | C |
| 351 | B |
| 352 | C |
| 353 | A |
| 354 | B |
| 355 | A |
| 356 | B |
| 357 | A |
| 358 | C |
| 359 | B |
| 360 | A |
| 361 | C |
| 362 | A |
| 363 | A |
| 364 | C |
| 365 | A |
| 366 | C |
| 367 | C |
| 368 | B |
| 369 | C |
| 370 | A |
| 371 | C |
| 372 | A |
| 373 | C |
| 374 | C |
| 375 | A |
| 376 | B |
| 377 | C |
| 378 | A |
| 379 | C |
| 380 | A |
| 381 | B |
| 382 | B |
| 383 | C |
| 384 | C |
| 385 | C |
| 386 | C |
| 387 | C |
| 388 | B |
| 389 | C |
| 390 | B |
| 391 | C |
| 392 | A |
| 393 | C |
| 394 | C |
| 395 | B |
| 396 | A |
| 397 | A |
| 398 | B |
| 399 | A |
| 400 | A |
| 401 | A |
| 402 | C |
| 403 | A |
| 404 | A |
| 405 | A |
| 406 | B |
| 407 | A |
| 408 | B |
| 409 | B |
| 410 | C |

A = less than 100 nM; B = between 100 nM and 1 uM; C = greater than 1 uM

| Example | mGluR5 EC$_{50}$ (nM) |
|---|---|
| 1 | 39 |
| 2 | >30000 |
| 3 | 283 |
| 4 | >30000 |
| 18 | >30000 |
| 21 | 1.0 |
| 26 | 367 |
| 35 | 6.3 |
| 45 | 3.8 |

-continued

| Example | mGluR5 EC$_{50}$ (nM) |
|---|---|
| 47 | 7.4 |
| 50 | 353 |
| 52 | >30000 |
| 57 | >30000 |
| 58 | >30000 |
| 64 | >30000 |
| 65 | 139 |
| 71 | 325 |
| 74 | >30000 |
| 75 | >30000 |
| 76 | >30000 |
| 105 | >30000 |
| 117 | 4.7 |
| 125 | >30000 |
| 126 | >30000 |
| 135 | 8.5 |
| 138 | 0.43 |
| 142 | 3.7 |
| 149 | 106 |
| 153 | 188 |
| 158 | >30000 |
| 176 | 5.2 |
| 178 | 117 |
| 180 | 259 |
| 181 | 279 |
| 185 | 17.4 |
| 194 | 281 |
| 203 | 2.5 |
| 205 | 2.2 |
| 234 | 2.7 |
| 235 | 211 |
| 243 | 272 |
| 257 | 164 |
| 259 | 1.9 |
| 273 | >3000 |
| 276 | 468 |
| 277 | 21.5 |
| 294 | 2.7 |
| 297 | 4.7 |
| 298 | 232 |
| 306 | >3000 |
| 312 | >3000 |
| 325 | >1500 |
| 326 | >3000 |
| 334 | >3000 |
| 337 | 688 |
| 346 | 13.3 |
| 349 | 305 |
| 354 | 392 |
| 360 | 2.0 |
| 370 | 31.8 |
| 382 | 537 |
| 398 | 141 |
| 402 | >3000 |

Pharmaceutical Compositions and Methods of Treatment

Compounds of formula I bind to mGluR 5 and can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of schizophrenia, cognitive impairment, Alzheimer's disease, Parkinson's disease, Parkinson's disease levodopa-induced dyskinesia, addiction, anxiety, depression, psychosis, epilepsy, Fragile X, gastroesophageal reflux disease, migraine, pain, borderline personality disorder, bipolar disorder, or other neurological and/or psychiatric disorder associated with glutamate dysfunction, which comprises administering to a patient a therapeutically affective amount of a compound of formula I.

Another aspect of the invention is a method for the treatment of schizophrenia which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of schizophrenia, cognitive impairment, Alzheimer's disease, Parkinson's disease, Parkinson's disease levodopa-induced dyskinesia, addiction, anxiety, depression, psychosis, epilepsy, Fragile X, gastroesophageal reflux disease, migraine, pain, borderline personality disorder, bipolar disorder, or other neurological and/or psychiatric disorder associated with glutamate dysfunction.

Another aspect of the invention is the use of a compound of formula I in the manufacture of a medicament for the treatment of Alzheimer's disease.

Another aspect of the invention is the use of a compound of formula I in the manufacture of a medicament for the treatment of schizophrenia.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred.

Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. The following HPLC conditions may be used where indicated.

Preparative HPLC Method 1: Sunfire C18 19×100 mm, A=90% $H_2O$/10% MeOH, B=90% MeOH/10% $H_2O$, Modifier 0.1% TFA, 0.00 min=0% B, 10.0 min=100% B, 15.0 min=100% B, Flow rate=25 mL/min.

Preparative HPLC Method 2: Chiralpak AD 21×250 20 μM, A=Heptane, B=Ethanol, 0.00 min=30% B, 15.0 min=100% B, 250 min=100% B, Flow Rate=20 ml/min.

Preparative HPLC Method 3: Chiralpak AD 21×250 20 μM, A=Heptane, B=Ethanol, 0.00 min=20% B, 25.0 min=100% B, 300 min=100% B, Flow Rate=20 ml/min.

Preparative HPLC Method 4: Sunfire C18 19×100 mm, A=90% $H_2O$/10% MeOH, B=90% MeOH/10% $H_2O$, Modifier 0.1% TFA, 0.00 min=20% B, 15.0 min=100% B, 22.0 min=100% B, Flow rate=25 mL/min.

Preparative HPLC Method 5: Xbridge C18 19×100 mm 5 μOBD, A=95% $H_2O$/5% Acetonitrile, B=95% Acetonitrile/5% $H_2O$, Modifier 10 mM Ammonium Acetate, 0.00 min=20% B, 10.0 min=100% B, 15.0 min=100% B, Flow rate=20 mL/min.

Preparative HPLC Method 6: Sunfire C18 30×100 mm 5μ, A=90% $H_2O$/10% MeOH, B=90% MeOH/10% $H_2O$, Modifier 0.1% TFA, 0.00 min=30% B, 10.0 min=100% B, 15.0 min=100% B, Flow rate=35 mL/min.

Preparative HPLC Method 7: Sunfire C18 30×100 mm, A=90% $H_2O$/10% ACN, B=90% ACN/10% $H_2O$, Modifier 0.1% TFA, 0.00 min=30% B, 12.0 min=100% B, 26.0 min=100% B, Flow rate=35 mL/min.

Preparative HPLC Method 8: Sunfire C18 30×100 mm, A=90% $H_2O$/10% MeOH, B=90% MeOH/10% $H_2O$, Modifier 0.1% TFA, 0.00 min=30% B, 12.0 min=100% B, 18.0 min=100% B, Flow rate=35 mL/min.

Preparative HPLC Method 9: Waters Atlantis 30×100 mm, A=90% $H_2O$/10% MeOH, B=90% MeOH/10% $H_2O$, Modifier 0.1% TFA, 0.00 min=30% B, 12.0 min=100% B, 18.0 min=100% B, Flow rate=35 mL/min.

Preparative HPLC Method 10: Waters Atlantis 30×100 mm, A=90% $H_2O$/10% MeOH, B=90% MeOH/10% $H_2O$, Modifier 0.1% TFA, 0.00 min=30% B, 15.0 min=100% B, 20.0 min=100% B, Flow rate=35 mL/min.

Preparative HPLC Method 11: Waters Atlantis 30×100 mm, A=90% $H_2O$/10% MeOH, B=90% MeOH/10% $H_2O$, Modifier 0.1% TFA, 0.00 min=40% B, 15.0 min=100% B, 23.0 min=100% B, Flow rate=35 mL/min.

Preparative HPLC Method 12: Chiralpak AS 21×250 mm 10 μM, A=0.1% diethylamine/Heptane, B=Ethanol, 0.00 min=40% B, 400 min=40% B, Flow Rate=15 ml/min.

Preparative HPLC method 13: SunFire 30×150 mm OBD, A=95% $H_2O$/5% ACN, B=95% ACN/5% $H_2O$, Modifier 10 mM $NH_4OAc$, 0.00 min=10% B, 20 min=100% B 25 min=100% B, Flow rate=40 mL/min.

Preparative HPLC Method 14: Chiralpak AS 21×250 mm 10 μM, A=0.1% diethylamine/Heptane, B=Ethanol, 0.00 min=10% B, 400 min=10% B, Flow Rate=15 ml/min.

Preparative HPLC Method 15: Sunfire C18 30×100 mm 5μ, A=90% $H_2O$/10% MeOH, B=90% MeOH/10% $H_2O$, Modifier 0.1% TFA, 0.00 min=30% B, 10.0 min=100% B, 15.0 min=100% B, Flow rate=35 mL/min.

Preparative HPLC Method 16: Sunfire C18 30×100 mm 5μ, A=90% $H_2O$/10% MeOH, B=90% MeOH/10% $H_2O$, Modifier 0.1% TFA, 0.00 min=25% B, 18.0 min=90% B, 25.0 min=100% B, Flow rate=35 mL/min.

Analytical HPLC method 1: Phenomenex Luna 3.0×50 mm S10, A=95% $H_2O$/5% MeOH, B=95% MeOH/5% $H_2O$, Modifier 10 mM Ammonium Acetate, 0.00 min=0% B, 2.0 min=100% B, 3.0 min=100% B, Flow rate=4 mL/min.

Analytical HPLC method 2: Phenomenex Luna 3.0×50 mm S10, A=90% $H_2O$/10% MeOH, B=90% MeOH/10% $H_2O$, Modifier 0.1% TFA, 0.00 min=0% B, 2.0 min=100% B, 3.0 min=100% B, Flow rate=4 mL/min.

Analytical HPLC method 3: YMC ODS-A 4.6×50 mm S5, A=90% $H_2O$/10% MeOH, B=90% MeOH/10% $H_2O$, Modifier 0.1% TFA, 0.00 min=0% B, 12.0 min=100% B, 15.0 min=100% B, Flow rate=5 mL/min.

Analytical HPLC method 4: Chiralpak AD-H analytical column, 4.6×250 mm, 5 μm, Mobile Phase: 15% MeOH in $CO_2$ @ 150 Bar, Temp: 35° C., Flow rate: 2.0 mL/min. for 30 min, UV monitored @ 258 nm.

Analytical HPLC method 5: XTERRA 4.6×30 mm S5, A=90% $H_2O$/10% MeOH, B=90% MeOH/10% $H_2O$, Modifier 0.1% TFA, 0.00 min=0% B, 12.0 min=100% B, 15.0 min=100% B, Flow rate=5 mL/min.

Analytical HPLC method 6: Waters Sunfire 4.6×30 mm 5μ, A=90% $H_2O$/10% MeOH, B=90% MeOH/10% $H_2O$, Modifier 0.1% TFA, 0.00 min=0% B, 3.0 min=100% B, 4.0 min=100% B, Flow rate=4 mL/min.

Analytical HPLC method 7: Xbridge C18 4.6×50 mm 5μ, A=95% $H_2O$/5% Methanol, B=95% Methanol/5% $H_2O$, Modifier 10 mM Ammonium Acetate, 0.00 min=0% B, 4.0 min=100% B, 5.0 min=100% B, Flow rate=4 mL/min.

Analytical HPLC method 8: Xbridge C18 4.6×50 mm 5μ, A=95% $H_2O$/5% MeOH, B=95% MeOH/5% $H_2O$, Modifier 10 mM Ammonium Acetate, 0.00 min=0% B, 2.0 min=100% B, 3.0 min=100% B, Flow rate=4 mL/min.

Analytical HPLC method 9: Xbridge C18 4.6×100 mm 5μ, A=Water; B=ACN; Modifier=10 mM Ammonium Acetate, 0.00 min=30% B, 8.0 min=95% B, Flow rate=1 mL/min.

Analytical HPLC method 10: Phenomenex Luna 30×2.0 mm 3μ, A=95% $H_2O$/5% MeOH, B=95% MeOH/5% $H_2O$, Modifier 10 mM Ammonium Acetate, 0.00 min=0% B, 2.0 min=100% B, 3.0 min=100% B, Flow rate=1 mL/min.

Analytical HPLC method 11: Phenomenex Luna 2.0×50 mm 3μ, A=95% $H_2O$/5% MeOH, B=95% MeOH/5% $H_2O$, Modifier 10 mM Ammonium Acetate, 0.00 min=0% B, 4.0 min=100% B, 5.0 min=100% B, Flow rate=0.8 mL/min.

Analytical HPLC method 12: Xbridge C18 2.1×50 mm 3μ, A=95% $H_2O$/5% MeOH, B=95% MeOH/5% $H_2O$, Modifier 10 mM Ammonium Acetate, 0.00 min=0% B, 4.0 min=100% B, 5.0 min=100% B, Flow rate=0.8 mL/min.

Analytical HPLC method 13: Phenomenex Luna 3.0×50 mm S10, A=95% $H_2O$/5% MeOH, B=95% MeOH/5% $H_2O$, Modifier 10 mM Ammonium Acetate, 0.00 min=0% B, 3.0 min=100% B, 4.0 min=100% B, Flow rate=4 mL/min.

Analytical HPLC method 14: Phenomenex Luna 3.0×30 mm 3 um, A=90% $H_2O$/10% MeOH, B=90% MeOH/10% $H_2O$, Modifier 0.1% TFA, 0.00 min=0% B, 2.0 min=100% B, 3.0 min=100% B, Flow rate=1 mL/min.

Analytical HPLC method 15: Phenomenex LUNA C18, 50×2 3μ, A=90% H$_2$O/10% CH$_3$CN, B=90% CH$_3$CN/10% H$_2$O, Modifier 0.1% TFA, 0.00 min=0% B, 4.0 min=100% B, 4.0 min=100% B, Flow rate=0.8 mL/min.

Preparative SFC Method 1: Chiralcel OJ-H analytical column, 4.6×250 mm, 5 μm, Mobile Phase: 45% MeOH (0.1% DEA) in CO$_2$; Temp: 35° C.; Flow rate: 70.0 mL/min. for 32 min; UV monitored @ 258 nm.

Preparative SFC Method 2: Chiralpak AD-H preparative column, 21×250 mm, 5 μm, Mobile Phase: 15% MeOH in CO$_2$ @ 150 Bar, Temp: 35° C., Flow rate: 45.0 mL/min. for 35 min, UV monitored @ 258 nm.

Preparative SFC Method 3: ChiralPak AS-H (30×250 mm) 5 μm, Mobile Phase: 25% MeOH (w/0.1% DEA)/75% CO$_2$, Pressure: 150 bar, Temperature: 35° C., Flow Rate: 70 mL/min, UV: 280 nm, Collection: Manual.

Preparative SFC Method 4: ChiralPak AD-H (30×250 mm) 5 μm, Mobile Phase: 17% MeOH (w/0.1% DEA)/83% CO2, Pressure: 150 bar, Temperature: 35° C., Flow Rate: 70 mL/min, UV: 280 nM, Collection: Manual.

Preparative SFC Method 5: ChiralPak AD-H (21×250 mm) 5 μm, Mobile Phase: 50% MeOH (w/0.1% DEA), Pressure: 150 bar, Temperature: 35° C., Flow Rate: 45 mL/min, UV: 283 nM, Collection: Manual.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "cc" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

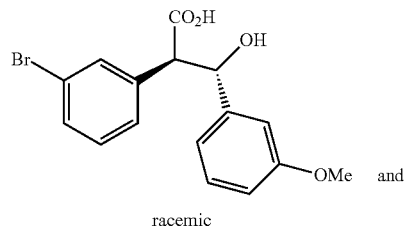

Intermediate 1 racemic

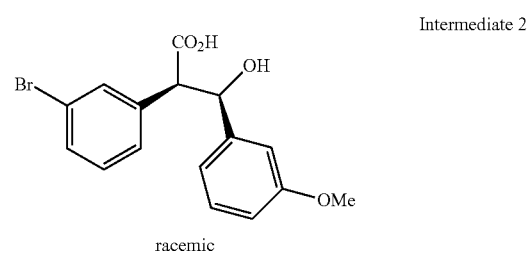

Intermediate 2 racemic (±)-(2R,3S)-2-(3-Bromophenyl)-3-hydroxy-3-(3-methoxyphenyl)propanoic acid and (±)-(2R,3R)-2-(3-bromophenyl)-3-hydroxy-3-(3-methoxyphenyl) propanoic acid To a solution of diisopropylamine (19.7 mL, 138 mmol) in tetrahydrofuran (50 mL) at −78° C. was added nBuLi (2.5 M in hexane, 55.8 mL, 140 mmol) dropwise. The reaction was allowed to gradually warm in the bath to −30° C., held there for 5 min, and re-cooled to −78° C. The reaction was treated with 2-(3-bromophenyl)acetic acid (15 g, 70 mmol) in tetrahydrofuran (200 mL) over 10 minutes. The ice bath was removed and stirring continued for 1.5 h. The reaction was cooled to 0° C., and treated with a solution of 3-methoxybenzaldehyde (8.49 mL, 69.8 mmol) in tetrahydrofuran (50 mL). The reaction was allowed to gradually warm to room temperature overnight. The reaction was poured onto ice water and extracted with diethyl ether. The ethereal was discarded. The aqueous layer was acidified by addition of concentrated hydrochloric acid at 0° C. until it was very acidic. The product was extracted with diethyl ether (3×). The ethereal was washed with brine, dried over magnesium sulfate, and concentrated to give 24.8 g (83%) as a colorless viscous gum as a racemic mixture of diastereomers which was used without purification. Mass spec.: 374.03 (MNa)$^+$.

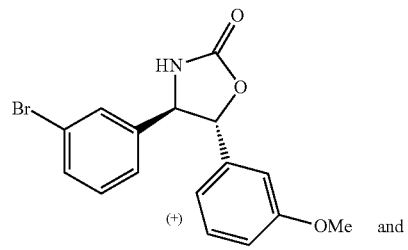

Intermediate 3

Intermediate 4

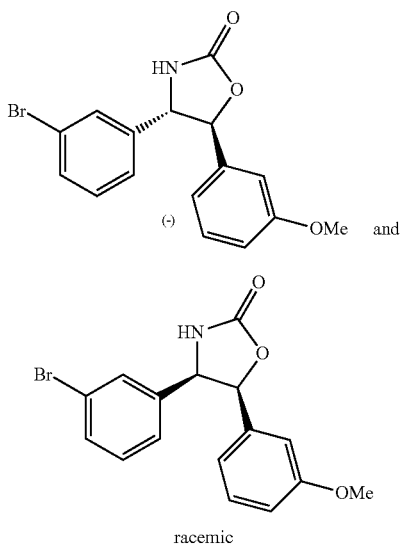

(+)-(4R,5R)-4-(3-Bromophenyl)-5-(3-methoxyphenyl)oxazolidin-2-one and (−)-(4S,5S)-4-(3-bromophenyl)-5-(3-methoxyphenyl)oxazolidin-2-one and (±)-(4R,5S)-4-(3-bromophenyl)-5-(3-methoxyphenyl)oxazolidin-2-one A mixture of (±)-(2R,3S)-2-(3-bromophenyl)-3-hydroxy-3-(3-methoxyphenyl)propanoic acid and (±)-(2R,3R)-2-(3-bromophenyl)-3-hydroxy-3-(3-methoxyphenyl)propanoic acid (23.9 g, 68 mmol) was dissolved in toluene (500 mL) and treated with triethylamine (9.5 mL, 68.1 mmol), stirred briefly, and treated with diphenyl phosphorazidate (14.7 mL, 68.1 mmol) slowly over 15 min. The reaction was fitted with an internal thermometer and gradually warmed to 60° C. After reaching 60° C., the reaction was heated for 3 h at that temperature and then allowed to cool to room temperature and stirred overnight. The reaction was quenched by addition of sat'd ammonia in water. After stirring 10 min, the reaction was diluted with 500 mL diethyl ether and the layers separated. The organics were washed with brine, dried over magnesium sulfate, concentrated, and purified by column chromatography (silica gel, 25%-->75% EtOAc/Hex). The first product to elute was the trans product ((±)-(4R,5R)-4-(3-bromophenyl)-5-(3-methoxyphenyl)oxazolidin-2-one, 7.73 g). $^1$H-NMR (CDCl$_3$, 500 MHz) δ 7.50-7.60 (m, 2H), 7.20-7.40 (m, 3H), 6.96 (m, 1H), 6.82-6.90 (m, 2H), 5.74 (bs, 1H), 5.27 (d, J=7.3, 1H), 4.74 (d, J=7.3, 1H), 3.84 (s, 3H). $^{13}$C-NMR (CDCl$_3$, 126 MHz) δ 160.0, 158.9, 140.8, 138.5, 132.0, 130.7, 130.1, 129.4, 125.1, 123.2, 118.0, 114.8, 111.1, 85.7, 64.2, 55.3. The enantiomers were separated by chiral SFC (chiralcel OJ-H, 20% MeOH/CO2). Enantiomer 1: (−)-(4S,5S)-4-(3-bromophenyl)-5-(3-methoxyphenyl)oxazolidin-2-one. Enantiomer 2: (+)-(4R,5R)-4-(3-bromophenyl)-5-(3-methoxyphenyl)oxazolidin-2-one. The second product to elute from the silica gel column was the cis product ((±)-(4R,5S)-4-(3-bromophenyl)-5-(3-methoxyphenyl)oxazolidin-2-one, 264 mg). $^1$H-NMR (CDCl$_3$, 500 MHz) δ 7.27 (m, 1H), 7.16 (s, 1H), 7.08 (dd, J=8.2, 7.6, 1H), 6.99 (dd, J=7.9, 7.6, 1H), 6.89 (d, J=7.6, 1H), 6.69 (dd, J=8.2, 2.4, 1H), 6.61 (m, 2H), 6.47 (bs, 1H), 5.92 (d, J=8.2, 1H), 5.15 (d, J=8.2, 1H), 3.65 (s, 3H). $^{13}$C-NMR (CDCl$_3$, 126 MHz) δ 159.4, 159.3, 138.5, 135.4, 131.3, 130.0, 129.8, 129.1, 125.5, 122.4, 118.4, 114.7, 111.1, 82.0, 60.7, 55.3.

Intermediate 6

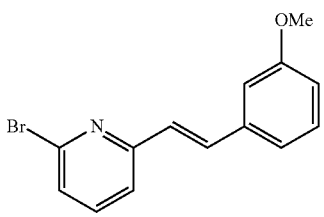

(E)-2-Bromo-6-(3-methoxystyryl)pyridine

To a solution of diethyl 3-methoxybenzylphosphonate (0.5 g, 1.94 mmol) in dimethylformamide (5 mL) at room temperature was added sodium methoxide (0.209 g, 3.87 mmol) and 18-Crown-6 (0.205 g, 0.77 mmol). After stirring at room temperature for 5 min, the reaction was cooled to 0° C. and treated with a solution of 6-bromopicolinaldehyde (0.432 g, 2.32 mmol) in dimethylformamide (2 mL) dropwise. When addition was complete, the ice bath was removed and the reaction stirred at room temperature for 1 h. The reaction was heated to 120° C. and held there for 2 h. The reaction was cooled to room temperature and stirred overnight. The resulting suspension was poured into water (70 mL) with vigorous stirring. The resulting suspension was extracted with diethyl ether (2×), washed with brine, dried over magnesium sulfate, and concentrated. The resulting residue was suspended in ethanol (ca. 10 ml). The resulting solution was placed in the freezer and held there for 3 h. The resulting precipitate was collected by filtration to give 150 mg (27%) as a white powder. $^1$H-NMR (CDCl$_3$, 500 MHz) δ 7.61 (d, J=15.9, 1H), 7.49 (dd, J=7.6, 7.6, 1H), 7.22-7.36 (m, 3H), 7.16 (d, J=7.6, 1H), 7.10 (m, 1H), 7.07 (d, J=15.9, 1H), 6.87 (dd, J=8.2, 2.1, 1H), 3.84 (s, 3H). $^{13}$C-NMR (CDCl$_3$, 126 MHz) δ 160.0, 157.1, 142.3, 138.9, 137.7, 134.4, 129.8, 126.7, 126.3, 120.7, 120.1, 114.8, 112.3, 55.4. Mass spec.: 290.01 (MH)$^+$.

Intermediate 7

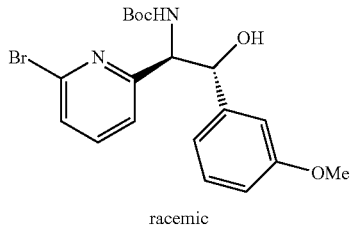

(±)-tert-Butyl (1R,2R)-1-(6-bromopyridin-2-yl)-2-hydroxy-2-(3-methoxyphenyl)ethylcarbamate To a solution of tert-butyl carbamate (109 mg, 0.931 mmol) in acetonitrile (5 mL) at 0° C. was added tert-butyl hypochlorite (0.105 mL, 0.93 mmol). After stirring for 5 min, the reaction was treated with silver oxide (108 mg, 0.465 mmol). After stirring for 10 min, the resulting suspension was treated with (E)-2-bromo-6-(3-methoxystyryl)pyridine (180 mg, 0.620 mmol), osmium tetroxide (0.1 mL, 0.32 mmol), and water (0.025 mL, 1.37 mmol). The ice bath was removed and stirring continued for 8 h. The reaction was filtered and treated with a solution of sodium sulfite (5% in water, 1.5 mL). The resulting solution was heated to 50° C. and held there for 8 h. The reaction was cooled to room temperature and diluted with ethyl acetate. The organics were washed with water, then brine, dried over magnesium sulfate, concentrated, and purified by column chromatography (25% EtOAc/Hex). HNMR of the purified material suggested that it was ca. 1:1 mixture of regioisomers. The product (114 mg, 43%) was used as a mixture of regioisomers. Mass spec.: 423.09 (MH)+.

Intermediate 8

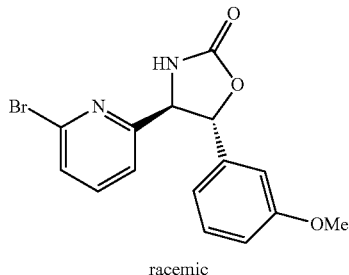

racemic (±)-(4R,5R)-4-(6-Bromopyridin-2-yl)-5-(3-methoxyphenyl)oxazolidin-2-one (±)-tert-Butyl (1R,2R)-1-(6-bromopyridin-2-yl)-2-hydroxy-2-(3-methoxyphenyl)ethylcarbamate (114 mg, 0.135 mmol) was dissolved in trifluoroacetic acid (10% in dichloromethane, 5 mL) and stirred at room temperature for 2 h. The reaction was concentrated under a stream of nitrogen, dissolved in methanol, and loaded onto a strong cation exchange cartridge. The cartridge was flushed with several volumes of methanol which were discarded. The product was eluted with 2M ammonia in methanol and concentrated. The resulting residue was suspended in tetrahydrofuran (2 mL), cooled to 0° C., and treated with carbonyldiimidazole (43.7 mg, 0.27 mmol) in a single portion. The resulting suspension was stirred at 0° C. for 5 min. The ice bath was removed and stirring continued for 1 h. The reaction was quenched by addition of 2M ammonia in methanol and concentrated. The resulting residue was dissolved in a minimum of ethyl acetate and poured into water. The organics were diluted with several volumes of diethyl ether. The ethereal was washed with water (2×), then brine, dried over magnesium sulfate, and concentrated. Column chromatography (25%-->50% EtOAc/Hex) gave 25 mg (53%). $^1$H-NMR (CDCl$_3$, 500 MHz) δ 7.64 (dd, J=7.9, 7.6, 1H), 7.51 (d, J=7.9, 1H), 7.40 (d, J=7.6, 1H), 7.35 (dd, J=8.2, 8.2, 1H), 7.03 (m, 2H), 6.93 (m, 1H), 6.84 (bs, 1H), 5.60 (d, J=5.5, 1H), 4.91 (d, J=5.8, 1H), 3.85 (s, 3H). $^{13}$C-NMR (CDCl$_3$, 126 MHz) δ 160.2, 159.9, 159.1, 142.6, 139.8, 139.7, 130.2, 128.2, 119.7, 117.8, 114.8, 111.0, 83.4, 64.4, 55.5. Mass spec.: 349.04 (MH)+.

Intermediate 9

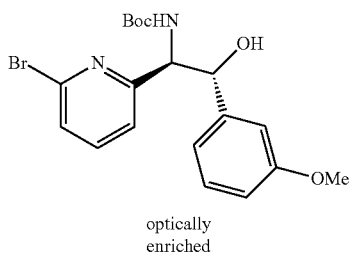

optically enriched

Optically-enriched tert-butyl (1R,2R)-1-(6-bromopyridin-2-yl)-2-hydroxy-2-(3-methoxyphenyl)ethylcarbamate To tert-butyl carbamate (688 mg, 5.88 mmol) in propanol (10 mL) was added sodium hydroxide (231 mg, 5.78 mmol) in water (20 mL) followed by tert-butyl hypochlorite (0.652 mL, 5.78 mmol). The solution was cooled to 0° C. and (DHQD)$_2$PHAL (89 mg, 0.114 mmol) was added in propanol (3 mL) followed by (E)-2-bromo-6-(3-methoxystyryl)pyridine (550 mg, 1.90 mmol) in propanol (10 mL). To this was added potassium osmate dihydrate (27.9 mg, 0.076 mmol) as a solid in one portion. The reaction was allowed to gradually warm to room temperature overnight. The reaction was placed in a cool bath (ca. 15° C.) and quenched by addition of sodiumthiosulfate (1.1 g) in water (8 mL). The reaction was stirred at room temperature for 30 min. The reaction was diluted with 1:1 diethylether/ethyl acetate, washed with water (2×), then brine, dried over magnesium sulfate, and concentrated. Column chromatography (20%-->50% EtOAc/Hex) gave 860 mg (107% yield) as a mixture of regioisomers. Mass spec.: 444.98 (MNa)+.

Intermediate 10

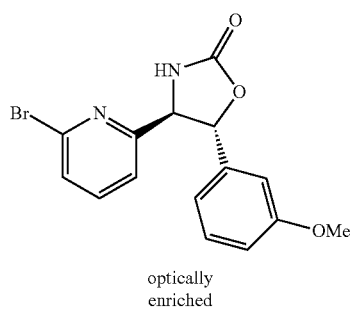

optically enriched

Optically-enriched (4R,5R)-4-(6-bromopyridin-2-yl)-5-(3-methoxyphenyl)oxazolidin-2-one Optically-enriched tert-butyl (1R,2R)-1-(6-bromopyridin-2-yl)-2-hydroxy-2-(3-methoxyphenyl)ethylcarbamate (860 mg, 1.02 mmol) was dissolved in trifluoroacetic acid (15% in dichloromethane, 25 mL) and stirred at room temperature for 1 h. The reaction was concentrated, dissolved in methanol, and loaded onto a strong cation exchange cartridge. The cartridge was flushed with several volumes of methanol which were discarded. The product was eluted with 2M ammonia in methanol and concentrated. The resulting residue was suspended in tetrahydrofuran (20 mL), cooled to 0° C., and treated with carbonyldiimidazole (201 mg, 1.24 mmol) in a single portion. The resulting suspension was stirred at 0° C. for 5 min. The ice bath was removed and stirring continued for 1 h. Upon warming to room temperature, everything went into solution. The reaction was quenched by addition of 2M ammonia in methanol and concentrated. The resulting residue was dissolved in a minimum of ethyl acetate and poured into water. The organics were diluted with several volumes of diethyl ether. The ethereal was washed with water (2×), then brine, dried over magnesium sulfate, and concentrated. Column chromatography (25%-->50% EtOAc/Hex) gave 92 mg (26%). $^1$H-NMR (CDCl$_3$, 500 MHz) δ 7.64 (dd, J=7.9, 7.6, 1H), 7.51 (d, J=7.9, 1H), 7.40 (d, J=7.6, 1H), 7.35 (dd, J=8.2, 8.2, 1H), 7.03 (m, 2H), 6.93 (m, 1H), 6.84 (bs, 1H), 5.60 (d, J=5.5, 1H), 4.91 (d, J=5.8, 1H), 3.85 (s, 3H). $^{13}$C-NMR (CDCl$_3$, 126 MHz) δ 160.2, 159.9, 159.1, 142.6, 139.8, 139.7, 130.2, 128.2, 119.7, 117.8, 114.8, 111.0, 83.4, 64.4, 55.5. Mass spec.: 349.04 (MH)$^+$.

Intermediate 11

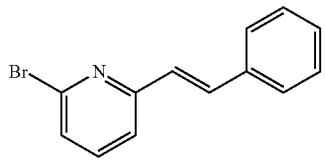

(E)-2-Bromo-6-styrylpyridine

To a solution of diethyl benzylphosphonate (4.57 mL, 21.91 mmol) in dimethylformamide (50 mL) at room temperature was added sodium methoxide (2.367 g, 43.8 mmol) and 18-Crown-6 (2.316 g, 8.76 mmol). After stirring at room temperature for 5 min, the reaction was cooled to 0° C. and treated with 6-bromopicolinaldehyde (4.89 g, 26.3 mmol) as a solid in one portion. The ice bath was removed and the reaction stirred at room temperature for 1 h. The reaction was gradually warmed to 120° C. and held there for 2 h. The reaction was cooled to room temperature and poured into water (500 mL) with vigorous stirring. The resulting suspension was extracted with diethyl ether, washed with water (3×), then brine, dried over magnesium sulfate, and concentrated to an oil. The oil was dissolved in hexanes and reconcentrated to give something that appeared to be crashing out as a solid. The resulting residue (solid in oil) was suspended in ethanol, concentrated, and pumped under high vacuum to give a dark-colored, moist solid. The resulting residue was suspended in ethanol (total volume (solid+solution)=20 ml). The resulting suspension was placed in the freezer and held there overnight. The resulting precipitate was collected by filtration to give 2.46 g (43%) as a faint tan powder. $^1$H-NMR (CDCl$_3$, 500 MHz) δ 7.69 (d, J=16.2, 1H), 7.60 (d, J=8.9, 2H), 7.53 (dd, J=7.9, 7.6, 1H), 7.41 (dd, J=7.6, 7.3, 2H), 7.31-7.38 (m, 3H), 7.11 (d, J=16.2, 1H). $^{13}$C-NMR (CDCl$_3$, 126 MHz) δ 157.2, 142.3, 138.8, 136.3, 134.5, 128.9, 128.8, 127.4, 126.4, 126.2, 120.7.

Intermediate 12

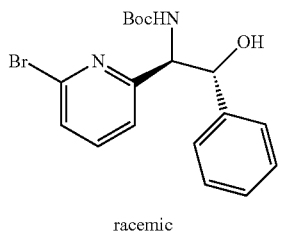

racemic (±)-tert-Butyl (1R,2R)-1-(6-bromopyridin-2-yl)-2-hydroxy-2-phenylethylcarbamate To tert-butyl carbamate (2.094 g, 17.88 mmol) in propanol (24 mL) was added sodium hydroxide (0.703 g, 17.59 mmol) in water (45 mL) followed by tert-butyl hypochlorite (1.99 mL, 17.59 mmol). The solution was cooled to 0° C. and treated with a solution of (DHQD)$_2$PHAL (0.112 g, 0.144 mmol) and (DHQ)$_2$PHAL (0.112 g, 0.144 mmol) in propanol (21 mL). The reaction was diluted with propanol (30 ml), and treated with (E)-2-bromo-6-styrylpyridine (1.5 g, 5.77 mmol) as a solid in one portion. To this was added potassium osmate dihydrate (0.085 g, 0.231 mmol) as a solid in one portion. The ice bath was removed and stirring continued for 1.5 h at room temperature. The reaction was placed in a cool bath (ca. 15° C.) and quenched by addition of sodiumthiosulfate (2.1 g) in water (12 mL). The reaction was stirred at room temperature for 30 min. The reaction was diluted with 1:1 diethylether/ethyl acetate, washed with water (2×), then brine, dried over magnesium sulfate, and concentrated. Column chromatography (20%-->50% EtOAc/Hex) gave 1.1 g (49%) as a mixture of regioisomers. The reaction was azeotroped with toluene and pumped under high vacuum (2 cycles) to aid in the removal of an unknown impurity. The material was used without additional purification. Mass spec.: 393.1 (MH)$^+$.

Intermediate 13

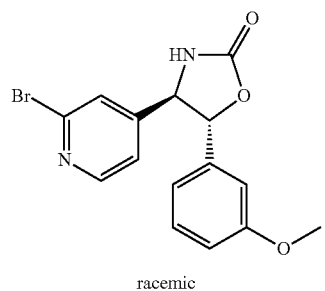

racemic (±)-(4R,5R)-4-(2-Bromopyridin-4-yl)-5-(3-methoxyphenyl)oxazolidin-2-one

Prepared according to the same procedure as (±)-tert-Butyl (1R,2R)-1-(6-bromopyridin-2-yl)-2-hydroxy-2-phenylethylcarbamate, starting with 2-bromoisonicotinaldehyde and diethyl-3-methoxybenzylphosphonate. $^1$H-NMR (CDCl$_3$, 500 MHz) δ 8.42 (d, J=5.2 Hz, 1H), 7.48 (s, 1H), 7.37 (t, J=8.2 Hz, 1H), 7.20 (d, J=5.2 Hz, 1H), 6.98 (m, 1H), 6.86 (s, 1H), 6.71 (s, 1H), 5.18 (d, J=7.3 Hz, 1H), 4.79 (d, J=7.3 Hz, 1H), 3.84 (s, 3H); $^{13}$C NMR (126 MHz, CDCl$_3$) δ ppm 160.4, 158.6, 151.1, 150.6, 143.3, 138.0, 130.5, 125.6, 120.3, 118.2, 115.3, 111.6, 85.1, 63.3, 55.5. Mass spec.: 349.0 (MH)$^+$.

Intermediate 14

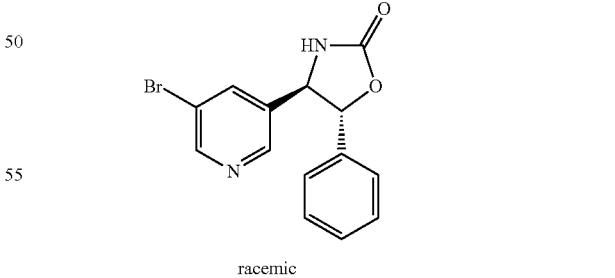

racemic (±)-(4R,5R)-4-(5-Bromopyridin-3-yl)-5-phenyloxazolidin-2-one

Prepared according to the same procedure as (±)-tert-Butyl (1R,2R)-1-(6-bromopyridin-2-yl)-2-hydroxy-2-phenylethylcarbamate, starting with 5-bromonicotinaldehyde and diethylbenzylphosphonate. $^1$H-NMR (CDCl$_3$, 500 MHz) δ 8.67 (d, J=2.1 Hz, 1H), 8.37 (d, J=1.5 Hz, 1H), 7.91 (t, J=2.1 Hz, 1H), 7.43 (m, 3H), 7.30 (m, 2H), 7.12 (bs, 1H), 5.25 (d, J=7.6 Hz, 1H), 4.84 (d, J=7.6 Hz, 1H); $^{13}$C NMR (126 MHz, CDCl$_3$) δ ppm 159.0, 151.6, 146.4, 136.7, 136.4, 136.1, 129.7, 129.3, 126.1, 125.5, 121.6, 85.7, 62.3, 60.5. Mass spec.: 320.95 (MH)$^+$.

Intermediate 15

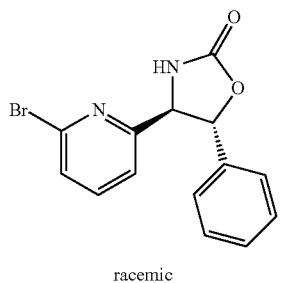

racemic (±)-(4R,5R)-4-(6-Bromopyridin-2-yl)-5-phenyloxazolidin-2-one (±)-tert-Butyl (1R,2R)-1-(6-bromopyridin-2-yl)-2-hydroxy-2-phenylethylcarbamate (1.1 g, 1.40 mmol) was dissolved in trifluoroacetic acid (25% in dichloromethane, 25 mL) and stirred at room temperature for 1 h. The reaction was concentrated, dissolved in methanol, and loaded onto a strong cation exchange cartridge. The cartridge was flushed with several volumes of methanol which were discarded. The product was eluted with 2M ammonia in methanol and concentrated. The resulting residue was suspended in tetrahydrofuran (25 mL), cooled to 0° C., and treated with carbonyldiimidazole (580 mg, 3.58 mmol) in a single portion. The resulting suspension was stirred at 0° C. for 5 min. The ice bath was removed and stirring continued for 1 h. The reaction was treated with an additional portion of carbonyldiimidazole (90 mg) and stirred at room temperature for 2 h. The reaction was quenched by addition of 2M ammonia in methanol and concentrated. The resulting residue was purified by column chromatography (25%-->50% EtOAc/Hex) to give nearly pure product. The material was further purified by trituration of the solid with diethyl ether. $^1$H-NMR (CDCl$_3$, 500 MHz) δ 7.65 (dd, J=7.6, 7.6, 1H), 7.52 (d, J=7.6, 1H), 7.37-7.50 (m, 6H), 6.83 (bs, 1H), 5.63 (d, J=5.5, 1H), 4.92 (d, J=5.5, 1H). $^{13}$C-NMR (CDCl$_3$, 126 MHz) δ 159.9, 159.2, 142.6, 139.7, 138.2, 129.13, 129.08, 128.2, 125.8, 119.6, 83.6, 64.4. Mass spec.: 319.1 (MH)$^+$.

Intermediate 16

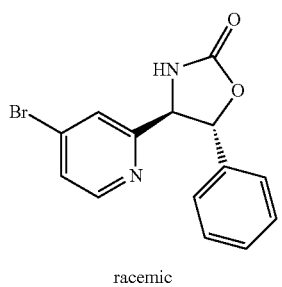

racemic (±)-(4R,5R)-4-(4-Bromopyridin-2-yl)-5-phenyloxazolidin-2-one

Prepared according to the same procedure as (±)-(4R,5R)-4-(6-bromopyridin-2-yl)-5-phenyloxazolidin-2-one, starting with 4-bromopicolinaldehyde. $^1$H-NMR (CDCl$_3$, 500 MHz) δ 8.49 (d, J=5.5, 1H), 7.63 (d, J=1.8, 1H), 7.50 (dd, J=5.2, 1.8, 1H), 7.36-7.48 (m, 5H), 6.77 (bs, 1H), 5.60 (d, J=5.5, 1H), 4.93 (d, J=5.5, 1H). $^{13}$C-NMR (CDCl$_3$, 126 MHz) δ 160.2, 159.1, 151.0, 138.3, 134.3, 129.12, 129.09, 127.0, 125.7, 124.3, 83.7, 64.6. Mass spec.: 319.1 (MH)$^+$.

Intermediate 17

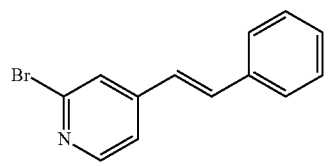

(E)-2-Bromo-4-styrylpyridine

To a solution of diethyl benzylphosphonate (4.57 mL, 21.91 mmol) in dimethylformamide (50 mL) at room temperature was added sodium methoxide (2.367 g, 43.8 mmol) and 18-Crown-6 (2.316 g, 8.76 mmol). After stirring at room temperature for 5 min, the reaction was cooled to 0° C. and treated with 2-bromoisonicotinaldehyde (4.89 g, 26.3 mmol) as a solid in one portion. The ice bath was removed and the reaction stirred at room temperature for 1 h. The reaction was gradually warmed to 120° C. and held there for 2 h. The reaction was cooled to room temperature and poured into water (500 mL) with vigorous stirring. The resulting suspension was extracted with diethyl ether (3×), washed with water, then brine, dried over magnesium sulfate, and concentrated to an oil. The resulting residue was purified by column chromatography (6% EtOAc/Hex-->12% EtOAc/Hex) to give 2.12 g (37%) as an oil. $^1$H-NMR (CDCl$_3$, 500 MHz) δ 8.35 (d, J=5.2, 1H), 7.52-7.62 (m, 3H), 7.43 (m, 2H), 7.30-7.40 (m, 3H), 6.98 (d, J=16.2, 1H). $^{13}$C-NMR (CDCl$_3$, 126 MHz) δ 150.4, 147.7, 143.1, 135.8, 134.8, 129.3, 129.0, 127.3, 125.0, 124.6, 120.1.

Intermediate 18

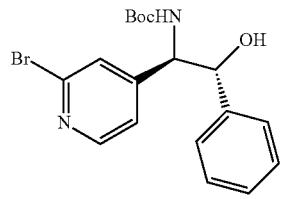

optically enriched

Optically-enriched tert-butyl (1R,2R)-1-(2-bromopyridin-4-yl)-2-hydroxy-2-phenylethylcarbamate To a solution of tert-butyl carbamate (2.96 g, 25.3 mmol) in propanol (30 mL) was added sodium hydroxide (0.994 g, 24.86 mmol) in water (54 mL) followed by tert-butyl hypochlorite (2.81 mL, 24.86 mmol). After 5 min, the solution was cooled to 0° C. and treated with a solution of (DHQD)$_2$PHAL (0.317 g, 0.407 mmol) in propanol (30 mL).

To this was added a solution of (E)-2-bromo-4-styrylpyridine (2.12 g, 8.15 mmol) in propanol (51 mL). To this was added potassium osmate dihydrate (0.120 g, 0.326 mmol) as a solid in one portion. The reaction was allowed to gradually warm in the glass dewar overnight. In the morning, the bath was still cool (5° C.). The reaction was quenched by addition of sodiumthiosulfate (2.7 g) in water (30 mL). The cooling bath was removed and the reaction stirred for 30 min. The reaction was poured into water (ca. 400 mL) and extracted with diethyl ether (2×). The combined organics were washed with water (2×), then brine, dried over magnesium sulfate, and concentrated. The resulting residue was concentrated from toluene (3×) to help remove an unknown impurity. The resulting residue was purified by column chromatography (25%-->40% EtOAc/Hex) to give 1.85 g (58%) as a mixture of regioisomers which was used without further purification. Mass spec.: 393.15 (MH)+.

Intermediate 19

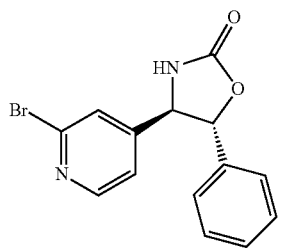

(4R,5R)-4-(2-Bromopyridin-4-yl)-5-phenyloxazolidin-2-one

Optically-enriched tert-butyl (1R,2R)-1-(2-bromopyridin-4-yl)-2-hydroxy-2-phenylethylcarbamate (1.85 g, 2.35 mmol) was dissolved in trifluoroacetic acid (25% in dichloromethane, 40 mL) and stirred at room temperature for 1 h. LC/MS shows clean conversion to product. The reaction was concentrated, dissolved in methanol, and loaded onto a strong cation exchange cartridge. The cartridge was flushed with several volumes of methanol which were discarded. The product was eluted with 2M ammonia in methanol and concentrated. The resulting residue was suspended in tetrahydrofuran (50 mL), cooled to 0° C., and treated with carbonyldiimidazole (0.763 g, 4.70 mmol) in a single portion. The resulting suspension was stirred at 0° C. for 5 min. The ice bath was removed and stirring continued for 1 h. The reaction was re-cooled to 0° C., and treated with an additional portion of carbonyldiimidazole (160 mg) and stirred at room temperature for 2 h. The reaction was quenched by addition of 2M ammonia in methanol and concentrated. The resulting residue was purified by column chromatography (25%-->50% EtOAc/Hex) to give the optically-enriched product. The minor enantiomer was removed by SFC Prep HPLC (Chiralpak AS-H, 25% MeOH in CO2) to give 452 mg (30%). $^1$H-NMR (CDCl$_3$, 500 MHz) δ 8.42 (d, J=5.2, 1H), 7.40-7.56 (m, 4H), 7.33 (m, 2H), 7.19 (dd, J=5.2, 1.2, 1H), 6.95 (bs, 1H), 5.21 (d, J=7.3, 1H), 4.81 (d, J=7.3, 1H). $^{13}$C-NMR (CDCl$_3$, 126 MHz) δ 158.9, 151.1, 150.6, 143.3, 136.4, 129.9, 129.4, 126.2, 125.6, 120.3, 85.3, 63.4. Mass spec.: 319.04 (MH)+.

Intermediate 20

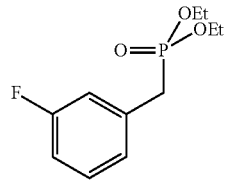

Diethyl 3-fluorobenzylphosphonate

A flask was charged with 1-(bromomethyl)-3-fluorobenzene (7.5 mL, 61.1 mmol) and treated with triethylphosphite (21.39 mL, 122 mmol) dropwise with stirring. Upon completion of the addition, the reaction was fitted with a reflux condenser (no cooling) and a slow stream of nitrogen was passed over the reaction mixture. The reaction was slowly warmed to 150° C. and held there for 2 h. The reaction was cooled to room temperature and concentrated under high vacuum to remove most of the excess triethylphosphite. The resulting residue was purified by column chromatography (50%-->100% EtOAc/Hex) to give 15.13 g (quant.) as a colorless oil. $^1$H-NMR (CDCl$_3$, 500 MHz) δ 7.29 (m, 1H), 7.10 (m, 1H), 7.05 (m, 1H), 6.97 (m, 1H), 4.06 (m, 4H), 3.16 (d, J=21.7, 2H), 1.28 (t, J=7.0, 6H). $^{13}$C-NMR (CDCl$_3$, 126 MHz) δ 162.85 (dd, J=246, 3.8), 134.2 (t, J=8.6), 130.0 (dd, J=7.7, 2.9), 125.6 (dd, J=6.7, 2.9), 116.9 (dd, J=22, 6.7, 114.0 (dd, J=21, 2.9), 62.3 (d, J=6.7), 33.7 (dd, J=138, 1.9, 16.5 (d, J=5.8).

Intermediate 21

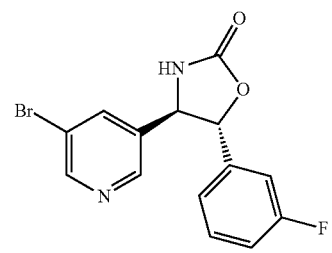

(4R,5R)-4-(5-Bromopyridin-3-yl)-5-(3-fluorophenyl)oxazolidin-2-one

Prepared according to the same procedure as (4R,5R)-4-(2-bromopyridin-4-yl)-5-phenyloxazolidin-2-one, starting with diethyl 3-fluorobenzylphosphonate and 5-bromonicotinaldehyde. $^1$H-NMR (CDCl$_3$, 500 MHz) δ 8.72 (d, J=2.1, 1H), 8.41 (d, J=1.8, 1H), 7.94 (dd, J=2.1, 1.8, 1H), 7.42 (ddd, J=7.9, 7.9, 5.8, 1H), 7.14 (ddd, J=8.6, 8.6, 2.4, 1H), 7.01-7.10 (m, 2H), 6.78 (bs, 1H), 5.27 (d, J=7.3, 1H), 4.81 (d, J=7.3, 1H). $^{13}$C-NMR (CDCl$_3$, 126 MHz) δ 163.2 (d, J=249), 158.5, 152.0, 146.4, 138.5 (d, J=6.7), 136.7, 135.7, 131.1 (d, J=8.6), 121.6 (d, J=17), 116.8 (d, J=21), 113.0 (d, J=22), 84.8, 62.2. Mass spec.: 337.06 (MH)+.

Intermediate 22

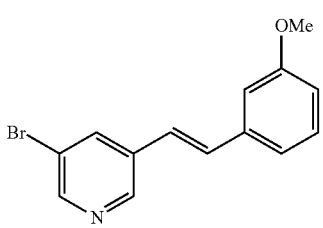

(E)-3-Bromo-5-(3-methoxystyryl)pyridine

To a solution of diethyl 3-methoxybenzylphosphonate (5 g, 19.36 mmol) in dimethylformamide (50 mL) at room temperature was added sodium methoxide (2.092 g, 38.7 mmol) and 18-Crown-6 (2.047 g, 7.74 mmol). After stirring at room temperature for 5 min, the reaction was cooled to 0° C. and treated with 5-bromonicotinaldehyde (4.32 g, 23.23 mmol) as a solid in one portion. The ice bath was removed and the reaction stirred at room temperature for 2 h. The reaction was poured into water (500 mL) with vigorous stirring. The resulting suspension was extracted with diethyl ether, washed with water (3×), then brine, dried over magnesium sulfate, and concentrated to an oil which crystallized upon standing. The solid was triturated with a minimum of ethanol (ca. 12 mL) and placed in the freezer for 72 h. The resulting solid was broken up with a spatula, collected by filtration, and rinsed with a minimum of cold ethanol to give 3.79 g (68%) as a white crystalline solid. $^1$H-NMR (CDCl$_3$, 500 MHz) δ 8.64 (d, J=1.8, 1H), 8.57 (d, J=2.1, 1H), 8.00 (dd, J=2.1, 1.8, 1H), 7.33 (dd, J=7.9, 7.9, 1H), 7.10-7.20 (m, 2H), 7.07 (m, 1H), 7.01 (d, J=16.5, 1H), 6.91 (dd, J=7.6, 2.1, 1H), 3.88 (s, 3H). $^{13}$C-NMR (CDCl$_3$, 126 MHz) δ 160.1, 149.5, 146.7, 137.7, 135.1, 134.8, 132.4, 130.0, 123.7, 121.1, 119.6, 114.4, 112.2, 55.4. Mass spec.: 290.14 (MH)$^+$.

Intermediate 23

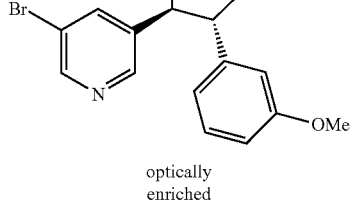

Optically-enriched tert-butyl (1R,2R)-1-(5-bromopyridin-3-yl)-2-hydroxy-2-(3-methoxyphenyl)ethylcarbamate To a solution of tert-butyl carbamate (4.63 g, 39.5 mmol) in propanol (45 mL) was added sodium hydroxide (1.556 g, 38.9 mmol) in water (81 mL) followed by tert-butyl hypochlorite (4.39 mL, 38.9 mmol). After 5 min, the solution was cooled to 0° C. and treated with a solution of (DHQD)$_2$PHAL (0.497 g, 0.638 mmol) in propanol (45 mL). To this was added a solution of (E)-3-bromo-5-(3-methoxystyryl)pyridine (3.7 g, 12.75 mmol) in propanol (76 mL). To this was added potassium osmate dihydrate (0.188 g, 0.510 mmol) as a solid in one portion. The reaction was allowed to gradually warm in the glass dewar over 36 h. The reaction was quenched by addition of sodiumthiosulfate (4.2 g) in water (45 mL). After stirring for 30 min, the reaction was poured into water (ca. 600 mL) and extracted with diethyl ether (2×). The combined organics were washed with water (2×), then brine, dried over magnesium sulfate, and concentrated. The resulting residue was concentrated from toluene (3×) to help remove an unknown impurity. The resulting residue was purified by column chromatography (25%-->40% EtOAc/Hex) to give 3.76 g (70%) as a mixture of regioisomers which was used without further purification. Mass spec.: 423.15 (MH)$^+$.

Intermediate 24

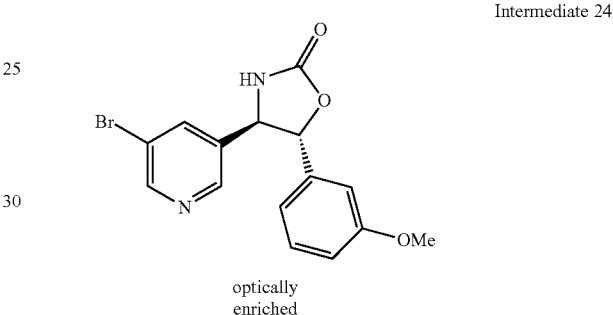

Optically-enriched (4R,5R)-4-(5-bromopyridin-3-yl)-5-(3-methoxyphenyl)oxazolidin-2-one Optically-enriched tert-butyl (1R,2R)-1-(5-bromopyridin-3-yl)-2-hydroxy-2-(3-methoxyphenyl)ethylcarbamate (3.76 g, 4.44 mmol) was dissolved in trifluoroacetic acid (25% in dichloromethane, 40 mL) and stirred at room temperature for 1 h. The reaction was concentrated, dissolved in methanol, and loaded onto a strong cation exchange cartridge. The cartridge was flushed with several volumes of methanol which were discarded. The product was eluted with 2M ammonia in methanol and concentrated. The resulting residue was suspended in tetrahydrofuran (40 mL), cooled to 0° C., and treated with carbonyldiimidazole (1.46 g, 9.00 mmol) in a single portion. The resulting suspension was stirred at 0° C. for 5 min. The ice bath was removed and stirring continued for 1 h. The reaction was re-cooled to 0° C., and treated with an additional portion of carbonyldiimidazole (500 mg) and stirred at room temperature for 1 h. The reaction was quenched by addition of 2M ammonia in methanol and concentrated. The resulting residue was purified by column chromatography (25%-->50% EtOAc/Hex) to give 660 mg (21%). $^1$H-NMR (CDCl$_3$, 500 MHz) δ 8.69 (d, J=2.1, 1H), 8.39 (d, J=2.1, 1H), 7.92 (dd, J=2.1, 1.8, 1H), 7.34 (dd, J=7.9, 7.9, 1H), 6.95 (dd, J=8.6, 1.8, 1H), 6.77-6.91 (m, 3H), 5.22 (d, J=7.6, 1H), 4.82 (d, J=7.6, 1H), 3.82 (s, 3H). $^{13}$C-NMR (CDCl$_3$, 126 MHz) δ 160.3, 158.9, 151.7, 146.4, 137.8, 136.7, 136.0, 130.5, 121.6, 118.1, 115.2, 111.4, 85.6, 62.2, 55.5. Mass spec.: 349.12 (MH)$^+$.

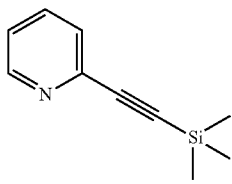

Intermediate 25

2-((Trimethylsilyl)ethynyl)pyridine

A flask was charged with 2-bromopyridine (1.21 mL, 12.66 mmol) and triethylamine (40 mL) and sparged with nitrogen for 15 min. To this was added ethynyltrimethylsilane (1.97 mL, 13.92 mmol) and the reaction was purged 15 min longer. To this was added copper(I) iodide (0.121 g, 0.633 mmol), and Pd(PPh$_3$)$_2$Cl$_2$ (0.444 g, 0.633 mmol). Reaction stirred at room temperature for 72 h. The reaction was diluted with ethyl acetate (60 mL) and poured into water. The black heterogeneous emulsion was filtered through a plug of celite and the layers separated. The organics were washed with brine, dried over magnesium sulfate, and concentrated. Column chromatography (5%-->15% EtOAc/Hex) gave 1.73 g (78%) as a dark oil. $^1$H-NMR (CDCl$_3$, 500 MHz) δ 8.58 (m, 1H), 7.66 (ddd, J=7.9, 7.9, 1.8, 1H), 7.47 (m, 1H), 7.24 (ddd, J=7.6, 4.9, 1.2, 1H), 0.29 (s, 9H). $^{13}$C-NMR (CDCl$_3$, 126 MHz) δ 150.1, 143.2, 136.1, 127.4, 123.1, 103.8, 94.9, −0.2. Mass spec.: 176.14 (MH)$^+$.

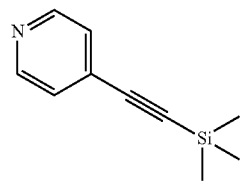

Intermediate 27

4-((Trimethylsilyl)ethynyl)pyridine

A flask was charged with 4-bromopyridine.HCl (2.46 g, 12.65 mmol) and triethylamine (40 mL) and sparged with nitrogen for 15 min. To this was added ethynyltrimethylsilane (1.967 mL, 13.92 mmol) and purged 15 min longer. To this was added copper(I) iodide (0.120 g, 0.633 mmol), and Pd(PPh$_3$)$_2$Cl$_2$ (0.444 g, 0.633 mmol). The reaction was stirred at room temperature for 72 h. The reaction was warmed to 50° C. and held at that temperature for 24 h. The reaction was diluted with ethyl acetate (60 mL) and poured into water. The black heterogeneous emulsion was filtered through a plug of celite and the layers separated. The organics were washed with brine, dried over magnesium sulfate, and concentrated. Column chromatography (5%-->25% EtOAc/Hex) gave 667 mg (30%) as a dark oil. $^1$H-NMR (CDCl$_3$, 500 MHz) δ 8.58 (d, J=6.1, 2H), 7.33 (d, J=6.1, 2H), 0.29 (s, 9H). $^{13}$C-NMR (CDCl$_3$, 126 MHz) δ 149.8, 131.3, 125.9, 102.1, 100.1, −0.2. Mass spec.: 176.14 (MH)$^+$.

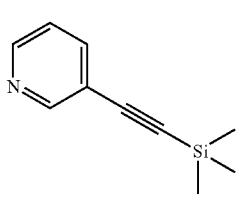

Intermediate 26

3-((Trimethylsilyl)ethynyl)pyridine

A flask was charged with 3-bromopyridine (1.22 mL, 12.66 mmol) and triethylamine (40 mL) and sparged with nitrogen for 15 min. To this was added ethynyltrimethylsilane (1.97 mL, 13.92 mmol) and the reaction purged 15 min longer. To this was added copper(I) iodide (0.121 g, 0.633 mmol), and Pd(PPh$_3$)$_2$Cl$_2$ (0.444 g, 0.633 mmol). The reaction was stirred at room temperature for 72 h. The reaction was diluted with ethyl acetate (60 mL) and poured into water. The black heterogeneous emulsion was filtered through a plug of celite and the layers separated. The organics were washed with brine, dried over magnesium sulfate, and concentrated. Column chromatography (5%-->15% EtOAc/Hex) gave 1.70 g (77%) as a dark oil. $^1$H-NMR (CDCl$_3$, 500 MHz) δ 8.71 (m, 1H), 8.55 (dd, J=4.9, 1.5, 1H), 7.76 (ddd, J=7.9, 1.8, 1.8, 1H), 7.26 (ddd, J=7.9, 4.9, 0.6, 1H), 0.29 (s, 9H). $^{13}$C-NMR (CDCl$_3$, 126 MHz) δ 152.8, 148.8, 138.9, 123.0, 120.4, 101.6, 98.3, −0.1. Mass spec.: 176.14 (MH)$^+$.

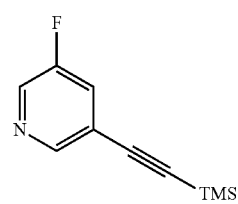

Intermediate 28

3-Fluoro-5-(trimethylsilyl)ethynyl)phenyl)pyridine

3-Bromo-5-fluoropyridine (2 g, 11.36 mmol) in triethylamine (35 mL) was purged with nitrogen for 15 minutes. Ethynyltrimethylsilane (1.77 mL, 12.50 mmol) was added and the reaction mixture purged with nitrogen for another 15 minutes. To this was added copper(I) iodide (0.108 g, 0.568 mmol) and Pd(PPh$_3$)$_2$Cl$_2$ (0.399 g, 0.568 mmol). The reaction was stirred at room temperature over the weekend. The reaction was diluted with ethyl acetate and poured into water. The black heterogeneous emulsion was filtered through a plug of celite and the layers separated. The organics were washed with brine, dried over anhydrous magnesium sulfate, filtered, and concentrated. Biotage purification eluting with 5% ethyl acetate/hexane gave 1.5 g (68%) as a yellow oil. $^1$H-NMR (CDCl$_3$, 500 MHz) δ 8.59 (bs, 2H), 7.47 (d, J=8.6 Hz, 1H), 0.28 (s, 9H); $^{13}$C NMR (126 MHz, CDCl$_3$) δ ppm 148.5, 137.5, 137.3, 125.4, 125.3, 100.1, 99.9, 0.20. Mass spec.: 194.0 (MH)$^+$.

Intermediate 29

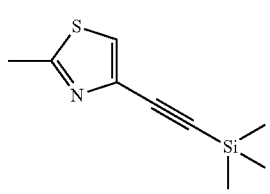

2-Methyl-4-((trimethylsilyl)ethynyl)thiazole

A flask was charged with 4-bromo-2-methylthiazole (400 mg, 2.247 mmol) and triethylamine (8 mL) and sparged with nitrogen for 15 min. To this was added ethynyltrimethylsilane (0.381 mL, 2.70 mmol) and purged 15 min longer. To this was added copper(I) iodide (21.39 mg, 0.112 mmol), and Pd(PPh$_3$)$_2$Cl$_2$ (79 mg, 0.112 mmol). The reaction stirred at room temperature for 72 h. The reaction was diluted with ethyl acetate (16 mL) and poured into water. The black heterogeneous emulsion was filtered through a plug of celite and the layers separated. The organics were washed with brine, dried over magnesium sulfate, and concentrated. Column chromatography (5%-->6% EtOAc/Hex) gave 307 mg (70%) as a light amber oil. $^1$H-NMR (CDCl$_3$, 500 MHz) δ 7.34 (s, 1H), 2.72 (s, 3H), 0.27 (s, 9H). $^{13}$C-NMR (CDCl$_3$, 126 MHz) δ 165.6, 137.0, 123.0, 98.4, 94.6, 19.3, −0.1.

Intermediate 30

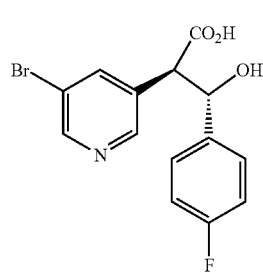

racemic (±)-(2R,3S)-2-(5-Bromopyridin-3-yl)-3-(4-fluorophenyl)-3-hydroxypropanoic acid To a solution of diisopropylamine (8.98 mL, 63 mmol) in tetrahedrofuran (22.5 mL) in 1 L flask at −78° C. was added n-butyllithium (25.2 mL, 2.5M in hexane, 63.0 mmol) dropwise. The reaction was allowed to gradually warm in the bath to −30° C., and held there for 5 minutes. It was re-cooled to −78° C. and treated with solid 2-(5-bromopyridin-3-yl)acetic acid (6.80 g, 31.5 mmol) and tetrahydrofuran (78 mL). The ice bath was removed and stirring continued for 1.5 h. The reaction was again cooled to 0° C., and treated with a solution of 4-fluorobenzaldehyde (3.38 mL, 31.5 mmol) in tetrahydrofuran (22.5 mL). The reaction was allowed to gradually warm to room temperature overnight. The reaction solution, after removal of the solid by filtration, was acidified with citric acid to pH ca. 4. It was extracted with diethyl ether and concentrated. The resulting residue was dried three times with toluene and the crude product (ca. 10.1 g) was used in the next reaction without further purification. Mass spec.: 340.9 (MH)$^+$.

Intermediate 31

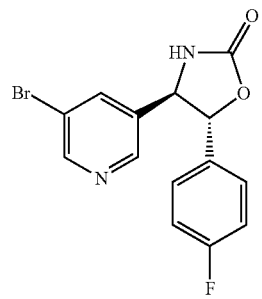

racemic (±)-(4R,5R)-4-(5-Bromopyridin-3-yl)-5-(4-fluorophenyl)oxazolidin-2-one (±)-(2R,3S)-2-(5-Bromopyridin-3-yl)-3-(4-fluorophenyl)-3-hydroxypropanoic acid (10.10 g, 29.7 mmol) in toluene (120 mL) was treated with TEA (4.14 mL, 29.7 mmol), stirred briefly, and then treated with diphenyl phosphorazidate (8.17 g, 29.7 mmol) slowly. The reaction was heated under nitrogen at 60° C. overnight. The reaction was quenched by addition of saturated ammonia in water. After stirring 10 minutes, the reaction was diluted with diethyl ether. The organics were washed with brine, dried over anhydrous magnesium sulfate, filtered, and concentrated. Biotage purification eluting with 50% ethyl acetate/hexane gave 320 mg (3%) as light yellow foam solid. $^1$H-NMR (CDCl$_3$, 400 MHz) δ 8.75 (d, J=2.0 Hz, 1H), 8.40 (d, J=1.8 Hz, 1H), 7.93 (t, J=2.0 Hz, 1H), 7.32 (m, 2H), 7.16 (t, J=8.5 Hz, 2H), 5.91 (bs, 1H), 5.27 (d, J=7.8 Hz, 1H), 4.80 (d, J=8.3 Hz, 1H); $^{13}$C NMR (100.6 MHz, CDCl$_3$) δ ppm 164.2, 161.7, 158.1, 151.4, 145.9, 136.2, 135.2, 131.6, 131.5, 127.7, 127.6, 121.2, 116.1, 115.9, 84.7, 61.9. Mass spec.: 338.8 (MH)$^+$.

Intermediate 32

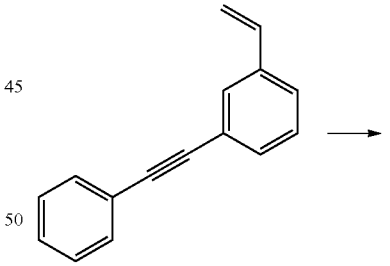

(S)-tert-Butyl 2-hydroxy-1-(3-(phenylethynyl)phenyl)ethylcarbamate

To tert-butyl carbamate (1396 mg, 11.91 mmol) in propanol (25 mL) was added sodium hydroxide (469 mg, 11.72 mmol) in water (40 mL) followed by tert-butyl hypochlorite (1.323 mL, 11.72 mmol). The solution was cooled to 0° C., (DHQ)₂PHAL (180 mg, 0.231 mmol) was added in propanol (25 mL) followed by 1-(phenylethynyl)-3-vinylbenzene (785 mg, 3.84 mmol; Tsuda, Katsuyuki; Tsutsumi, Kenichi; Yaegashi, Manabu; Miyajima, Masahiro; Ishizone, Takashi; Hirao, Akira; Ishii, Fumiaki; Kakuchi, Toyoji. Polymer Bulletin (Berlin) (1998), 40(6), 651) in propanol (20 mL) and potassium osmate dihydrate (56.6 mg, 0.154 mmol). After 1 h, TLC (25% EtOAc/Hex; UV) of the yellow solution showed consumption of starting material with two new spots evident at $R_f$ 0.15 (major) and $R_f$ 0.30 (minor). Quenched with 50 mL saturated sodium sulfite. Extracted with 2×100 mL ethyl acetate, washed combined organics with 30 mL brine, dried over MgSO₄, filtered and concentrated. The orange residue was dissolved in dichloromethane, applied to a 40 g silica gel cartridge prepacked with 5% ethyl acetate/hexanes and eluted with 5 to 30% ethyl acetate/hexanes over 800 mL resulting in partial separation of regioisomers. Repooled mixed fractions, concentrated and rechromatographed to give the title compound (664 mg, 51%). ¹H NMR (500 MHz, CHLOROFORM-d) δ ppm 7.53-7.60 (2H, m), 7.51 (1H, s), 7.48 (1H, d, J=7.63 Hz), 7.33-7.42 (4H, m), 7.30 (1H, d, J=8.85 Hz), 5.39 (1H, br. s.), 4.80 (1H, br. s.), 3.86 (2H, br. s.), 2.63 (1H, br. s.), 1.47 (9H, br. s.).

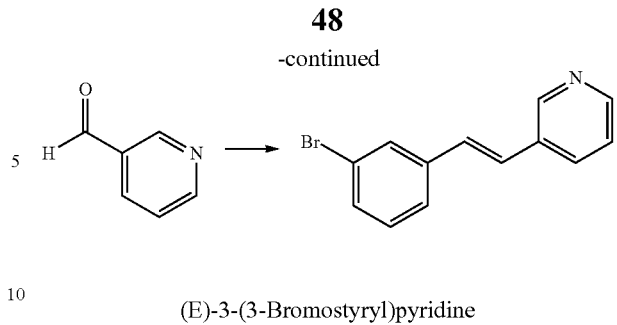

(E)-3-(3-Bromostyryl)pyridine

To diethyl 3-bromobenzylphosphonate (Kennedy, G. Perboni, A. D. Tetrahedron Lett. 1996, 37, 7611-7614; 1.91 g, 6.22 mmol) in dimethylformamide (20 mL) was added sodium methanolate (0.672 g, 12.44 mmol) followed by 18-crown-6 (0.658 g, 2.488 mmol) and nicotinaldehyde (0.666 g, 6.22 mmol). The reaction mixture was heated to 120° C. for 2 h at which time the heating bath was turned off and the reaction mixture was allowed to reach ambient temperature over 18 h. The mixture was poured into water and extracted with 3×75 mL ethyl acetate. The combined organics were washed with brine, dried over MgSO₄, filtered and concentrated in vacuo to 1.7 g amber liquid which was loaded onto a 90 g silica gel cartridge and eluted with 5 to 60% ethyl acetate/hexanes over 1300 mL. The major spot ($R_f$=0.45; 50% ethyl acetate/hexanes; UV) was collected and concentrated to 939 mg as a colorless oil. ¹H NMR (500 MHz, CHLOROFORM-d) δ ppm 8.72 (1H, d, J=1.83 Hz), 8.50 (1H, dd, J=4.73, 1.68 Hz), 7.81 (1H, dt, J=8.01, 1.95 Hz), 7.67 (1H, t, J=1.68 Hz), 7.37-7.46 (2H, m), 7.29 (1H, dd, J=7.93, 4.88 Hz), 7.20-7.25 (1H, m), 7.07 (2H, s).

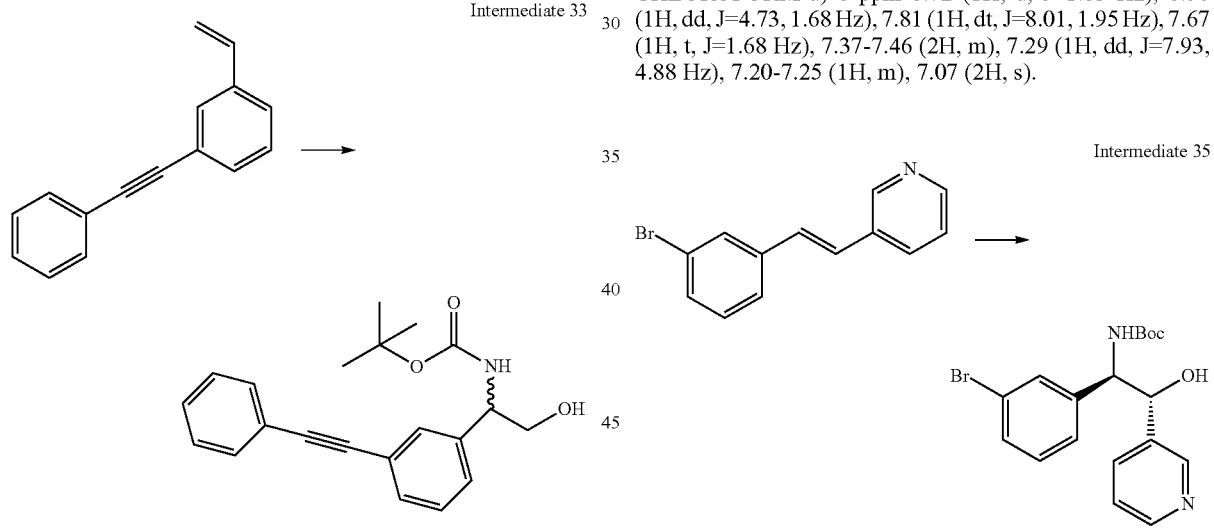

Intermediate 33

(±)-tert-Butyl 2-hydroxy-1-(3-(phenylethynyl)phenyl)ethylcarbamate was prepared identically to the procedure describing the preparation of (S)-tert-butyl 2-hydroxy-1-(3-(phenylethynyl)phenyl)ethylcarbamate except that an equimolar mixture of (DHQ)₂PHAL and (DHQD)₂PHAL was used.

Intermediate 34

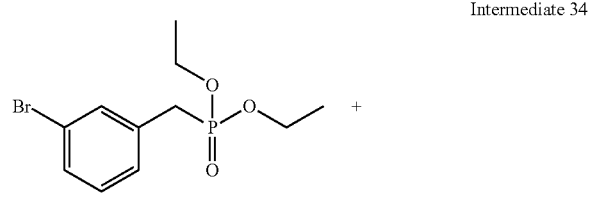

Intermediate 35

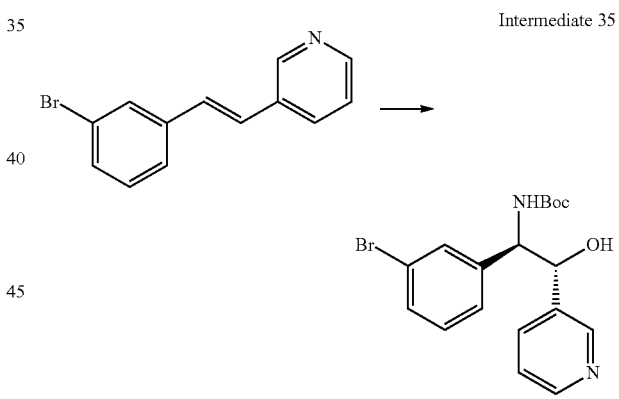

(±)-tert-Butyl (1R,2R)-1-(3-bromophenyl)-2-hydroxy-2-(pyridin-3-yl)ethylcarbamate To tert-butyl carbamate (1256 mg, 10.73 mmol) in propanol (25 mL) was added sodium hydroxide (422 mg, 10.55 mmol) in water (30 mL) followed by tert-butyl hypochlorite (1.191 mL, 10.55 mmol). The solution was cooled to 0° C. and (DHQD)₂PHAL (67.4 mg, 0.086 mmol) and (DHQ)₂PHAL (67.4 mg, 0.086 mmol) were added in propanol (20 mL) followed by (E)-3-(3-bromostyryl)pyridine (900 mg, 3.46 mmol) in propanol (25 mL) and finally potassium osmate dihydrate (51.0 mg, 0.138 mmol) in one portion. The mixture was allowed to stir overnight and come to ambient temperature in the process. The mixture was quenched with sodium sulfite (50 mL) and the mixture was extracted with 3×50 mL ethyl acetate and the combined organics were washed with sodium sulfite (25 mL) and brine (25 mL), dried over MgSO₄, filtered and concentrated to an amber oil which was loaded with dichloromethane onto a 90 g silica gel cartridge pre-equilibrated with 5% ethyl acetate/hexanes. Elution with 5 to 100% ethyl acetate over 2.5 L provided 965 mg (71%) as a mixture of regioisomers. LC/MS (analytical HPLC method 1; 1.63 min): Anal. Calcd. for [M+H]⁺ C₁₈H₂₁BrN₂O₃: 393.07. found 392.97.

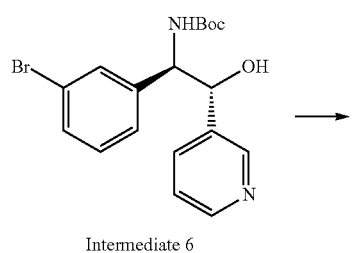

Intermediate 6

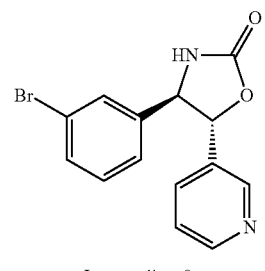

Intermediate 8

Trans-4-(3-bromophenyl)-5-(pyridin-3-yl)oxazolidin-2-one

To a mixture of (±)-tert-butyl (1R,2R)-1-(3-bromophenyl)-2-hydroxy-2-(pyridin-3-yl)ethylcarbamate (1.1 g, 2.80 mmol), was added 50 mL 4N HCl/Dioxane. The reaction mixture was allowed to stir at ambient temperature overnight and which time the white slurry was concentrated in vacuo and placed on high vac for 18 h. The resulting colorless solid was dissolved in tetrahydrofuran (25 mL) and Hunig's Base (0.586 mL, 3.36 mmol). To this solution was added carbonyldiimidazole (0.544 g, 3.36 mmol) and after 1 h, the reaction mixture was concentrated in vacuo and loaded with dichloromethane onto a 90 g silica gel cartridge prepacked with 25% ethyl acetate/hexanes. Elution was performed with 25 to 100% ethyl acetate/hexanes over 1200 mL then 100% ethyl acetate for 500 mL. Fractions containing the top spot (R_f=0.45 in 75% ethyl acetate/hexanes; UV) were pooled and concentrated to give 266 mg of trans-4-(3-bromophenyl)-5-(pyridin-3-yl)oxazolidin-2-one as a colorless solid. Anal. Calcd. for [M+H]⁺ C₁₄H₁₁BrN₂O₂: 319.00. found 318.85. ¹H NMR (500 MHz, CHLOROFORM-d) δ ppm 8.66 (1H, dd, J=4.88, 1.53 Hz), 8.49 (1H, d, J=2.14 Hz), 7.72 (1H, dt, J=7.93, 1.98 Hz), 7.48-7.57 (2H, m), 7.40 (1H, dd, J=7.78, 4.73 Hz), 7.27-7.33 (1H, m), 7.22 (1H, d, J=7.63 Hz), 6.87 (1H, s), 5.30 (1H, d, J=7.63 Hz), 4.77 (1H, d, J=7.32 Hz). ¹³C NMR (126 MHz, CHLOROFORM-d) δ ppm 158.53, 150.80, 147.61, 140.18, 133.76, 132.84, 132.57, 131.09, 129.48, 125.23, 124.07, 123.64, 83.74, 64.20.

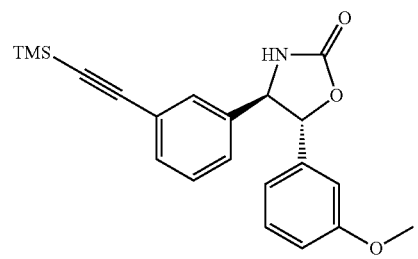

Intermediate 37

(4R,5R)-5-(3-Methoxyphenyl-4-(3-(trimethylsilyl)ethynyl)phenyl)oxazolidin-2-one

A solution of (4R,5R)-4-(3-bromophenyl)-5-(3-methoxyphenyl)oxazolidin-2-one (4.3 g, 12.35 mmol) in triethylamine (12 mL) was purged with nitrogen for one h. The reaction was treated with triphenylphosphine (91 mg, 0.346 mmol), ethynyltrimethylsilane (1.83 mL, 12.97 mmol), and purged 10 minutes longer. To this was added dichlorobis(triphenylphosphine)palladium(II) (20 mg, 0.028 mmol) and copper(I) iodide (4.48 mg, 0.0235 mmol). After purging 10 min longer, the reaction was heated at 95° C. overnight. The reaction was cooled to room temperature, diluted with diethyl ether, filtered to remove the solid, and concentrated. The resulting residue was dissolved in diethyl ether, washed with water, then brine, dried over anhydrous magnesium sulfate, and concentrated. Biotage purification eluting with 35% ethyl acetate/hexane gave 2.25 g (50%) as a white foam solid. ¹H-NMR (CDCl₃, 500 MHz) δ 7.49 (m, 2H), 7.38-7.31 (m, 2H), 7.25 (d, J=7.9 Hz, 1H), 6.93 (dd, J=8.4, 2.1 Hz, 1H), 6.85 (m, 2H), 6.19 (s, 1H), 5.25 (d, J=7.3 Hz, 1H), 4.73 (d, J=7.3 Hz, 1H), 3.82 (s, 3H), 0.28 (s, 9H); ¹³C NMR (126 MHz, CDCl₃) δ ppm 160.2, 158.8, 138.8, 132.6, 130.2, 129.2, 126.7, 124.4, 118.1, 115.0, 111.1, 104.2, 95.5, 85.9, 64.6, 55.5, 00.1. Mass spec.: 366.13 (MH)⁺.

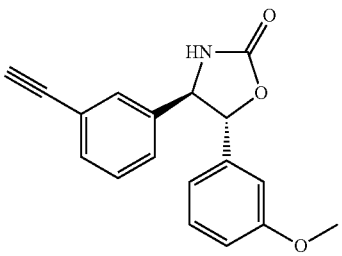

Intermediate 38

(4R,5R)-4-(3-Ethnylphenyl-5-(3-methoxyphenyl)oxazolidin-2-one

To a solution of potassium hydroxide (0.691 g, 12.31 mmol) in 14.5 mL of methanol was added solution of (4R,5R)-5-(3-methoxyphenyl-4-(3-(trimethylsilyl)ethynyl)phenyl)oxazolidin-2-one (2.25 g, 6.16 mmol) in 1.5 mL of methanol, the resulting solution was stirred at room temperature for 1.5 h. The reaction was diluted with water. The reaction was extracted with diethyl ether (3×), washed with brine, dried over anhydrous magnesium sulfate, and concentrated. Biotage purification, eluting with 40% ethyl acetate/hexane, gave 1.68 g (87%) as a white solid. ¹H-NMR (CDCl₃, 400 MHz) δ 7.54 (m, 1H), 7.50 (s, 1H), 7.40 (t, J=7.5 Hz, 1H), 7.33 (m, 2H), 6.95 (m, 1H), 6.86 (m, 2H), 5.55 (s, 1H), 5.27 (d, J=7.3 Hz, 1H), 4.74 (d, J=7.3 Hz, 1H), 3.83 (s, 3H), 3.14 (s, 1H); $^{13}$C NMR (126 MHz, CDCl$_3$) δ ppm 160.2, 158.7, 139.0, 138.8, 132.8, 130.22, 130.18, 129.4, 127.0, 123.4, 118.1, 115.0, 111.2, 85.9, 82.9, 78.4, 64.6, 55.5. Mass spec.: 366.13 (MH)$^+$.

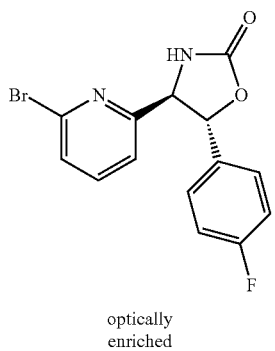

Intermediate 39 optically enriched

Optically-enriched (4R,5R)-4-(6-bromopyridin-2-yl)-5-(4-fluorophenyl)oxazolidin-2-one Prepared according to the same procedure as optically-enriched (4R,5R)-4-(5-bromopyridin-3-yl)-5-(3-methoxyphenyl)oxazolidin-2-one, starting with 6-bromopicolinaldehyde and diethyl 4-fluorobenzylphosphonate. $^1$H-NMR (CDCl$_3$, 500 MHz) δ 7.65 (dd, J=7.9, 7.6, 1H), 7.51 (d, J=7.6, 1H), 7.46 (dd, J=8.9, 5.2, 2H), 7.41 (d, J=7.6, 1H), 7.13 (m, 3H), 5.61 (d, J=7.5, 1H), 4.90 (d, J=5.8, 1H). $^{13}$C-NMR (CDCl$_3$, 126 MHz) δ 163.1 (d, J=249), 159.4 (d, J=55), 142.6, 139.8, 134.0, 128.3, 127.8, 127.7, 119.6, 116.2, 116.0, 83.1, 64.4.

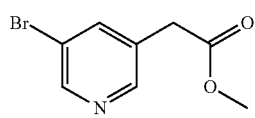

Intermediate 40

Methyl 2-(5-bromopyridin-3-yl)acetate 2-(5-bromopyridin-3-yl)acetic acid (5.00 g, 23.14 mmol) in methanol (55 mL) at 0° C. was added thionyl chloride (2.196 mL, 30.1 mmol) slowly, pyridine (2.434 mL, 30.1 mmol) was added slowly after and the reaction was stirred at room temperature overnight. Solvent was removed in vacuo and the residue was diluted with water and extracted with ethyl acetate, the organics was washed with brine, dried over magnesium sulfate, filtered and concentrated. Biotage purification (35% EtOAc/Hex) gave title compound (4.73 g, 20.6 mmol, 89% yield). $^1$H-NMR (CDCl$_3$, 500 MHz) δ 8.63 (d, J=2.14 Hz, 1H), 8.47 (d, J=1.83 Hz, 1H), 7.84 (dd, J=2.14, 1.83 Hz, 1H), 3.76 (s, 3H), 3.65 (s, 2H). Mass spec.: 230.9 (MH)$^+$.

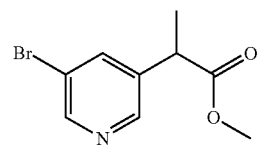

Intermediate 41

Methyl 2-(5-bromopyridin-3-yl)propanote

To a solution of diidopropylamine (3.52 mL, 24.72 mmol) in tetrahydrofuran (3.5 mL) at −78° C. was added n-butyl lithium (2.5 M in hexane, 8.24 mL, 20.60 mmol) drop wise, it was allowed to gradually warm in the bath to −30° C., held at this temperature for 5 min, and re-cooled to −78° C. The reaction was then treated with methyl 2-(5-bromopyridin-3-yl)acetate (4.74 g, 20.60 mmol) in tetrahydrofuran (60 mL) slowly. The ice bath was removed and stirring continued for 1.5 hours. The reaction was cooled to 0° C., and treated with iodomethane (2.057 mL, 33.0 mmol), and it was allowed to gradually warm to room temperature overnight. The reaction was poured onto ice water and extracted with ethyl acetate. The organics were washed with brine, dried over magnesium sulfate, and concentrated. Biotage purification (30% EtOAc/Hex) gave title compound (3.4 g, 13.9 mmol, 67.6% yield). Mass spec.: 244.9 (MH)$^+$.

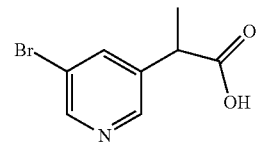

Intermediate 42

2-(5-Bromopyridin-3-yl)propanoic acid

Methyl 2-(5-bromopyridin-3-yl)propanote (3.33 g, 13.62 mmol) in Methanol (60 mL) at 0° C. was added lithium hydroxide (22.70 mL, 68.1 mmol), it was stirred at room temperature for an hour. Methanol was removed and water was added, the aqueous was acidified to pH~6/7 with 1N hydrochloric acid, the solid was filtered out and dried to give 2.1 g of product. The aqueous was further extracted with ethyl acetate, the organics was washed with brine, dried over magnesium sulfate, filtered and concentrated to give another 1.03 g of product (total 3.13 g, 12.83 mmol, 94% yield). Mass spec.: 230.9 (MH)$^+$.

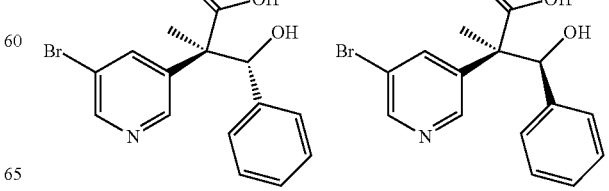

Intermediate 43

(±)-(2R,3R)-2-(5-Bromopyridin-3-yl)-3-hydroxy-2-methyl-3-phenylpropanoic acid, and (±)-(2R,3S)-2-(5-bromopyridin-3-yl)-3-hydroxy-2-methyl-3-phenylpropanoic acid To a solution of diisopropylamine (1.028 mL, 7.22 mmol) in tetrahydrofuran (2.6 mL) at −78° C. was added n-butyl lithium (2.5 M in hexane, 2.89 mL, 7.22 mmol) drop wise. The reaction was allowed to gradually warm in the bath to −30° C., it was held at this temperature for 5 minutes, and re-cooled to −78° C. It was treated with 2-(5-bromopyridin-3-yl)propanoic acid (0.830 g, 3.61 mmol) in tetrahydrofuran (10 mL) over 10 minutes. The ice bath was removed and stirring continued for 1.5 hours. It was then cooled to 0° C., and treated with a solution of benzaldehyde (0.367 mL, 3.61 mmol) in tetrahydrofuran (2.6 mL), and allowed to gradually warm to room temperature overnight. The reaction was poured onto ice water, acidified by addition of 1N hydrochloric acid till PH~5/6, extracted with ether. The ethereal was washed with brine, dried over magnesium sulfate, and concentrated to give mixture of title compounds (0.82 g, 2.44 mmol, 67.6% yield) as yellow viscous foam. Mass spec.: 336.9 (MH)$^+$.

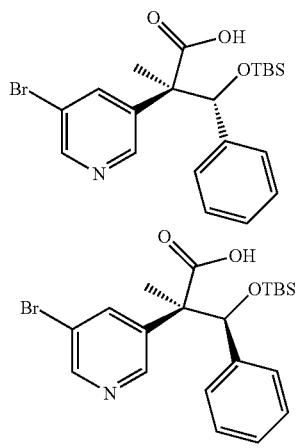

Intermediate 44

(±)-(2R,3R)-2-(5-Bromopyridin-3-yl)-3-(tert-butyldimethylsdyloxy)-2-methyl-3-phenylpropanoate, and (±)-(2R,3S)-2-(5-bromopyridin-3-yl)-3-(tert-butyldimethylsdyloxy)-2-methyl-3-phenylpropanoate (±)-(2R,3R)-2-(5-bromopyridin-3-yl)-3-hydroxy-2-methyl-3-phenylpropanoic acid, and (±)-(2R,3S)-2-(5-bromopyridin-3-yl)-3-hydroxy-2-methyl-3-phenylpropanoic acid (0.820 g, 2.439 mmol) in dichloromethane (3.5 mL) was added 2,6-lutidine (0.597 mL, 5.12 mmol), it was cooled to 0° C., tert-butyldimethylsilyl trifluoromethanesulfonate (1.120 mL, 4.88 mmol) was added slowly, and stirred at room temperature for 2 hours. The reaction was diluted with ether and washed with water, the organics were washed with brine, dried over magnesium sulfate, filtered and concentrated. It was again dissolved in methanol (17.5 mL), potassium carbonate (6.10 mL, 12.20 mmol) was added and stirred at room temperature for an hour, methanol was removed, acidified with 1N hydrochloric acid and extracted with ethyl acetate. The organics was washed with brine, dried over magnesium sulfate, filtered and concentrated to give mixture of title compounds (0.945 g, 2.1 mmol, 86% yield). Mass spec.: 451.2 (MH)$^+$.

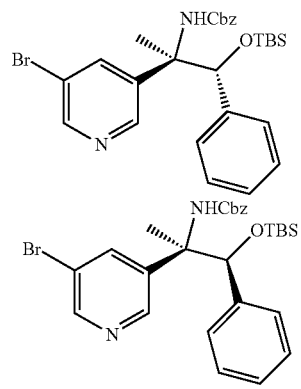

Intermediate 45

(±)-Benzyl (2R,3R)-2-(5-bromopyridin-3-yl)-1-(tert-butyldimethylsdyloxy)-1-phenylpropan-2-ylcarbamate and (±)-benzyl (2R,3S)-2-(5-bromopyridin-3-yl)-1-(tert-butyldimethylsdyloxy)-1-phenylpropan-2-ylcarbamate (±)-(2R,3R)-2-(5-bromopyridin-3-yl)-3-(tert-butyldimethylsilyloxy)-2-methyl-3-phenylpropanoate, and (±)-(2R,3S)-2-(5-bromopyridin-3-yl)-3-(tert-butyldimethylsilyloxy)-2-methyl-3-phenylpropanoate (945 mg, 2.098 mmol) in toluene (10.5 mL, 99 mmol) was treated with phenylmethanol (0.217 mL, 2.098 mmol), triethylamine (0.585 mL, 4.20 mmol), stirred briefly, and treated with diphenyl phosphorazidate (0.454 mL, 2.098 mmol) slowly. The reaction was heated under nitrogen at 60° C. overnight. Reaction was quenched by water and concentrated. Biotage purification (20% EtOAc/Hex) gave mixture of title compounds (0.44 g, 0.79 mmol, 37.7% yield) as clear oil. Mass spec.: 556.9 (MH)$^+$.

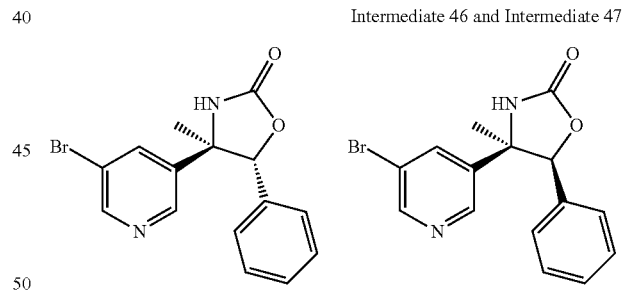

Intermediate 46 and Intermediate 47

(±)-(4R,5R)-4-(5-Bromopyridin-3-yl)-4-methyl-5-phenyloxazolidin-2-one and (±)-(4R,5S)-4-(5-Bromopyridin-3-yl)-4-methyl-5-phenyloxazolidin-2-one (±)-benzyl (2R,3R)-2-(5-bromopyridin-3-yl)-1-(tert-butyldimethylsilyloxy)-1-phenylpropan-2-ylcarbamate and (±)-benzyl (2R,3S)-2-(5-bromopyridin-3-yl)-1-(tert-butyldimethylsilyloxy)-1-phenylpropan-2-ylcarbamate (440 mg, 0.792 mmol) in tetrahydrofuran (12 mL) was added tetra-butyl ammonium fluoride (1.584 mL, 1.584 mmol), it was stirred at 60° C. overnight. Water was added to the reaction and it was extracted with ethyl acetate, the organics was washed with brine, dried over magnesium sulfate, filtered and concentrated. Biotage purification (50% EtOAc/Hex) gave (±)-(4R,5R)-4-(5-bromopyridin-3-yl)-4-methyl-5-phenyloxazolidin-2-one (150 mg, 0.450 mmol, 56.8% yield), and (±)-(4R,5S)-4-(5-bromopyridin-3-yl)-4-methyl-5-phenyloxazolidin-2-one (22 mg, 0.066 mmol, 8.34% yield). (±)-(4R,5R)-4-(5-bromopyridin-3-yl)-4-methyl-5-phenyloxazolidin-2-one: ¹H-NMR (CDCl₃, 500 MHz) δ 8.69 (d, J=2.14 Hz, 1H), 8.57 (d, J=1.83 Hz, 1H), 8.02 (m, 1H), 7.42 (m, 3H), 7.19-7.21 (m, 3H), 5.42 (s, 1H), 1.32 (s, 3H). ¹³C-NMR (CDCl₃, 126 MHz) δ 158.8, 150.7, 145.7, 140.7, 136.4, 133.0, 129.5, 128.9, 126.3, 121.3, 88.0, 63.3, 23.0. (±)-(4R,5S)-4-(5-bromopyridin-3-yl)-4-methyl-5-phenyloxazolidin-2-one: ¹H-NMR (CDCl₃, 500 MHz) δ 8.41 (d, J=2.14 Hz, 1H), 8.11 (d, J=2.14 Hz, 1H), 7.43 (m, 1H), 7.21 (m, 3H), 6.96 (m, 3H), 5.56 (s, 1H), 1.96 (s, 3H). ¹³C-NMR (CDCl₃, 126 MHz) δ 158.7, 150.7, 149.8, 145.7, 137.8, 136.5, 133.7, 129.3, 128.6, 126.2, 120.4, 88.8, 63.7, 27.0. Mass spec.: 333.0 (MH)⁺.

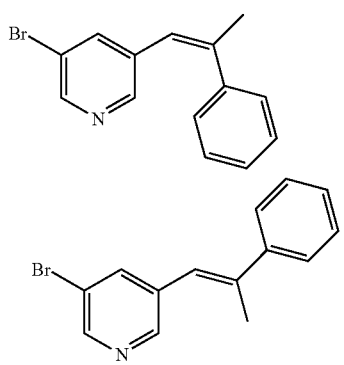

Intermediate 48

(Z)-3-Bromo-5-(2-phenylprop-1-enyl)pyridine and (E)-3-bromo-5-(2-phenylprop-1-enyl)pyridine To a solution of diethyl 1-phenylethylphosphonate (4.62 mL, 20.64 mmol) in N,N-dimethylformamide (47 mL, 607 mmol) at room temperature was added sodium methoxide (2.347 g, 41.3 mmol) and 18-Crown-6 (2.182 g, 8.26 mmol). After stirring at room temperature for 5 minutes, the reaction was cooled to 0° C. and treated with a solution of 5-bromonicotinaldehyde (4.61 g, 24.77 mmol) in N,N-dimethylformamide (18.6 mL) drop wise. When addition was complete, the ice bath was removed and the reaction stirred at room temperature for 1 hour, it was then heated at 120° C. for 2 hours, and slowly cooled down to room temperature overnight. The resulting suspension was poured into water with vigorous stirring, it was then extracted with ether, washed with brine, dried over magnesium sulfate, and concentrated. Biotage purification (7% EtOAc/Hex) gave mixture of title compounds (4 g, 5.25 mmol, 25.5% yield, 3:1 mixture of Z/E product). ¹H-NMR (CDCl₃, 40 MHz) δ 8.59 (d, J=2.26 Hz, 1H), 8.55 (d, J=1.76 Hz, 1H), 8.39 (d, J=2.26 Hz, 0.2H), 8.13 (d, J=1.76 Hz, 0.2H), 7.84 (m, 1H), 7.40-7.30 (m, 3H), 7.24-7.20 (m, 1H), 7.07 (m, 0.22H), 7.05 (m, 0.48H), 7.03 (m, 0.22H), 6.94-6.92 (m, 0.22H), 6.90-6.88 (m, 0.22), 6.74 (s, 1H), 6.41 (s, 1H), 2.29 (d, J=1.25 Hz, 3H), 2.26 (d, J=1.51 Hz, 0.67H). Mass spec.: 274.3 (MH)⁺.

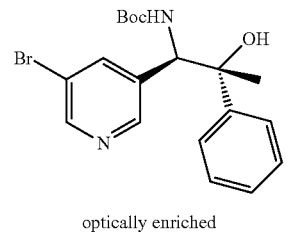

Intermediate 49 optically enriched tert-Butyl (1R,2R)-1-(5-bromopyridin-3-yl)-2-phenylpropylcarbamate To a solution of tert-butyl carbamate (1.907 g, 16.28 mmol) in propanol (4.6 mL) was added sodium hydroxide (0.641 g, 16.02 mmol) in water (8 mL) followed by tert-butyl hypochlorite (1.808 ml, 16.02 mmol). After 5 minutes, the solution was cooled to 0° C. and treated with a solution of (DHQD)₂PHAL (0.245 g, 0.315 mmol) in propanol (4.6 mL). To this was added a solution of (Z)-3-bromo-5-(2-phenylprop-1-enyl)pyridine and (E)-3-bromo-5-(2-phenylprop-1-enyl)pyridine (1.440 g, 5.25 mmol) in propanol (7.8 mL), and potassium osmate dihydrate (0.077 g, 0.210 mmol) as a solid in one portion. The ice bath was removed and stirring continued overnight. The reaction was quenched by addition of a solution of sodium thiosulfate (1.84 g) in water (23 mL). After 30 minutes, the reaction was diluted with ether, washed with water, then brine, dried over MgSO4, and concentrated. Biotage purification (20%-50% EtOAc/Hex) gave title compound (1.18 g, 2.90 mmol, 55% yield) as colored semi-solid. Mass spec.: 407.0 (MH)⁺.

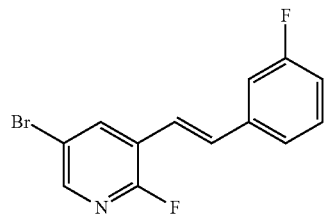

Intermediate 50

(E)-5-Bromo-2-fluoro-3-(3-fluorostyryl)pyridine

To a 100 mL round bottom flask was added 1-fluoro-3-vinylbenzene (1.2 g, 9.82 mmol), 5-bromo-2-fluoropyridin-3-ylboronic acid (3.24 g, 14.74 mmol), and Sodium carbonate (2.60 g, 24.56 mmol) in dimethylformamide (32.7 ml). The reaction vessel was sealed and purged with oxygen via a balloon for 5 min. After purging with oxygen, palladium (II) acetate (0.221 g, 0.982 mmol) added and immediately purged with oxygen for (15 min.). The reaction was kept under a blanket of oxygen and left to stir overnight at room temperature. The reaction was then quenched with water and extracted with ethylacetate (3×). The organic layer was separated, washed with brine, dried over sodium sulfate, and concentrated in vacuo. The crude oil was loaded onto 90 g silica gel cartridge and the product was eluted with 5% DCM/Hex. The product fractions were collected and concentrated to afford 0.712 g (22%) as an off white crystalline solid. ¹H-NMR (CDCl₃, 400 MHz) δ 8.16 (s, 1H), 8.09 (dd, J=8.5, 2.3, 1H), 7.42-7.29 (m, 2H), 7.27-7.17 (m, 2H), 7.11-7.01 (m, 2H), LC/Mass spec. (Analytical HPLC method 2): RT=2.88 min. Mass=296.01 (MH)⁺.

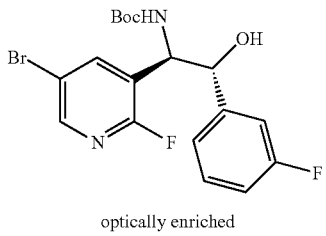

Intermediate 51

Optically-enriched tert-butyl (1R,2R)-1-(5-bromo-2-fluoropyridin-3-yl)-2-(3-fluorophenyl)-2-hydroxyethylcarbamate To a solution of tert-butyl carbamate (363 mg, 3.10 mmol) in propanol (10 mL) was added sodium hydroxide (122 mg, 3.05 mmol) in water (4 mL) followed by tert-butyl hypochlorite (331 mg, 3.05 mmol). After 5 min the solution was cooled to 0° C. and treated with a solution of (DHQD)2PHAL (38.9 mg, 0.050 mmol) in propanol (4 mL). To this solution was added a solution of (E)-5-bromo-2-fluoro-3-(3-fluorostyryl) pyridine (296 mg, 1.0 mmol) in propanol (10 mL). To this solution was added potassium osmate dihydrate (14.73 mg, 0.040 mmol) in one portion. The reaction turned light orange and was allowed to stir at 0° C. for 1 hr. The ice bath was then removed and the reaction was allowed to warm to room temperature and stirred overnight. The reaction was quenched with a 10% solution of sodium thiosulfate and stirred for 30 min. The reaction was then extracted with diethylether (3×). The combined organic extracts were combined washed with water, then brine. The organic layer was separated, dried over sodium sulfate and evaporated in vacuo. The crude residue was purified by silica gel chromatography 25% EtOAc/75% Hexanes to 50%/50% EtOAc/Hexanes to afford tert-butyl (1R,2R)-1-(5-bromo-2-fluoropyridin-3-yl)-2-(3-fluorophenyl)-2-hydroxyethylcarbamate (223 mg, 0.520 mmol, 52.0% yield) along with its regioisomer as an inseparable mixture. LC/Mass spec. (Analytical HPLC method 2): RT=2.11 min. Mass=453.14 (MNa)⁺.

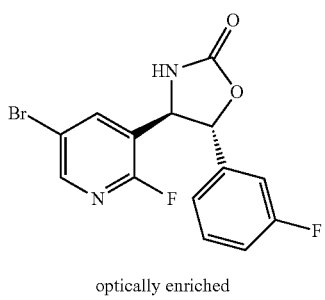

Intermediate 52

Optically-enriched (4R,5R)-4-(5-bromo-2-fluoropyridin-3-yl)-5-(3-fluorophenyl)oxazolidin-2-one To a 25 mL round bottom flask was added tert-butyl (1R,2R)-1-(5-bromo-2-fluoropyridin-3-yl)-2-(3-fluorophenyl)-2-hydroxyethylcarbamate (223 mg, 0.520 mmol) in dichloromethane (4 mL). To this solution was added trifluoroacetic acid (1.014 mL, 13.16 mmol) and the reaction was allowed to stir over night at room temperature. The reaction solvent was then evaporated in vacuo. The crude reaction mixture was then dissolved in 5 mL of 2N ammonia in methanol and stirred for 5 min. The solvent was then evaporated in vacuo and the crude residue was diluted with dry tetrahydrofuran (4 mL) and carbonyldiimidazole (168 mg, 1.039 mmol) was added and the reaction was stirred at room temperature for 1 hr. The reaction solvent was then evaporated in vacuo and the crude solid was purified by silica gel chromatography 10% EtOAc/90% Hexanes to 30% EtOAc/70% Hexanes affording (4R,5R)-4-(5-bromo-2-fluoropyridin-3-yl)-5-(3-fluorophenyl)oxazolidin-2-one (25 mg, 0.070 mmol, 13.55% yield) and (4R,5R)-5-(5-bromo-2-fluoropyridin-3-yl)-4-(3-fluorophenyl)oxazolidin-2-one (17 mg, 0.048 mmol, 9.2% yield) as an inseparable mixture. ¹H-NMR (CDCl₃, 400 MHz) δ 8.33 (d, J=2.3, 1H), 7.47-7.41 (m, 1H), 7.19-7.11 (m, 3H), 5.64 (s, 1H), 5.36 (d, J=5.0, 1H), 5.00 (d, J=5.0, 1H), LC/Mass spec. (Analytical HPLC method 2): RT=2.09 min. Mass=355.09 (MH)⁺.

Intermediate 53

Optically-enriched (4R,5R)-4-(2-fluoro-5-((trimethylsilyl)-ethynyl)pyridin-3-yl)-5-(3-fluorophenyl) oxazolidin-2-one To a sealable microwave vial was added (4R,5R)-4-(5-bromo-2-fluoropyridin-3-yl)-5-(3-fluorophenyl)oxazolidin-2-one (105 mg, 0.296 mmol), copper(I) iodide (1.689 mg, 8.87 μmol), triphenylphosphine (23.26 mg, 0.089 mmol) and triethylamine (4 mL). The solution was stirred and ethynyltrimethylsilane (43.6 mg, 0.443 mmol) was added and the reaction mixture was degassed with nitrogen for 10 min. To this mixture was added bis(triphenylphosphine)palladium(II) chloride (4.15 mg, 5.91 μmol) in one portion and the reaction vessel was sealed and heated to 90° C. overnight. The reaction was cooled to room temperature, the solvent was evaporated in vacuo and the crude solid was added to a silica gel column and eluted with 20% EtOAc/80% Hexanes affording (4R,5R)-4-(2-fluoro-5-((trimethylsilyl)ethynyl)pyridin-3-yl)-5-(3-fluorophenyl)oxazolidin-2-one (77 mg, 0.207 mmol, 69.9% yield) as an off white solid. ¹H-NMR (CDCl₃, 400 MHz) δ 8.35 (s, 1H), 8.04 (dd, J=8.0, 4.0, 1H), 7.47-7.41 (m, 1H), 7.18-7.12 (m, 3H), 5.44 (brs, 1H), 5.36 (d, J=4.0, 1H) 5.00 (d, J=5.0, 1H), 0.30 (s, 9H), LC/Mass spec. (Analytical HPLC method 2): RT=2.23 min. Mass=373.19 (MH)⁺.

Intermediate 54

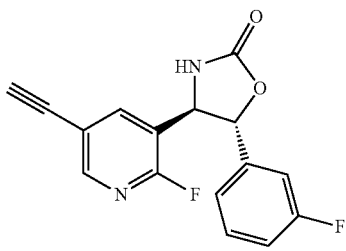

(4R,5R)-4-(5-Ethynyl-2-fluoropyridin-3-yl)-5-(3-fluorophenyl)oxazolidin-2-one

To a 25 mL round bottom flask was added (4R,5R)-4-(2-fluoro-5-((trimethylsilyl)ethynyl)pyridin-3-yl)-5-(3-fluorophenyl)oxazolidin-2-one (77 mg, 0.207 mmol) in MeOH (4 mL). The solution was stirred and potassium carbonate (28.6 mg, 0.207 mmol) was added in one portion and the reaction was allowed to stir for 30 min. The reaction was complete by TLC and LC/MS. The reaction solvent was then evaporated in vacuo and the crude solid was dissolved in dichloromethane and washed with saturated ammonium chloride. The organic layer was separated, dried over sodium sulfate, and evaporated in vacuo to afford (4R,5R)-4-(5-ethynyl-2-fluoropyridin-3-yl)-5-(3-fluorophenyl)oxazolidin-2-one (60 mg, 0.180 mmol, 87% yield) as an off white solid. This material was used as is without purification. $^1$H-NMR (CDCl$_3$, 400 MHz) δ 8.39 (s, 1H), 8.07 (dd, J=8.0, 2.0, 1H), 7.47-7.42 (m, 1H), 7.19-7.12 (m, 3H), 5.86 (brs, 1H), 5.37 (d, J=4.0, 1H), 5.02 (s, J=4.0, 1H), 3.31 (s, 1H). LC/Mass spec. (Analytical HPLC method 2): RT=1.82 min. Mass=301.19 (MH)$^+$.

Intermediate 55

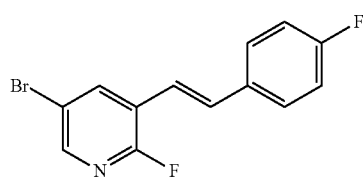

(E)-5-Bromo-2-fluoro-3-(4-fluorostyryl)pyridine

To a 15 mL round bottom flask was added 5-bromo-2-fluoropyridin-3-ylboronic acid (895 mg, 4.07 mmol), sodium carbonate (863 mg, 8.14 mmol) and 1-fluoro-4-vinylbenzene (647 mg, 5.29 mmol) in dimethylformamide (8 mL). The solution was stirred at room temperature and the flask was purged with oxygen for 3 min. To the purged flask was quickly added palladium(II) acetate (91 mg, 0.407 mmol) and the reaction flask was again sealed and purged with oxygen for 15 min. The reaction mixture was then stirred at room temperature overnight. The next day the reaction was quenched with water and diluted with ethylacetate. The organic layer was separated, washed with brine, dried over sodium sulfate and evaporated in vacuo. The crude oil was purified by silica gel chromatography eluting with 0% EtOAc/100% hexanes to 15% EtOAc/85% hexanes affording (E)-5-bromo-2-fluoro-3-(4-fluorostyryl)pyridine (380 mg, 1.283 mmol, 31.5% yield) as a white solid. $^1$H-NMR (CDCl$_3$, 400 MHz) δ 8.15 (s, 1H), 8.09 (dd, J=8.0, 2.0, 1H), 7.55-7.52 (m, 2H), 7.22 (d, J=16.0, 1H), 7.13-7.09 (m, 2H), 7.00 (d, J=16.0, 1H), LC/Mass spec. (Analytical HPLC method 2): RT=2.31 min. Mass=296.08 (MH)$^+$.

Intermediate 56

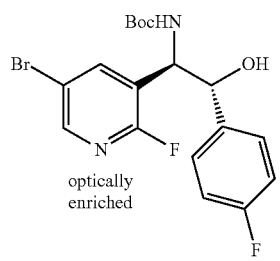

Optically-enriched tert-butyl (1R,2R)-1-(5-bromo-2-fluoropyridin-3-yl)-2-(4-fluorophenyl)-2-hydroxyethylcarbamate To a solution of tert-butyl carbamate (1431 mg, 12.22 mmol) in propanol (10 mL) was added sodium hydroxide (481 mg, 12.02 mmol) in water (4 mL) followed by tert-butyl hypochlorite (1305 mg, 12.02 mmol). After 5 min the solution was cooled to 0° C. and treated with a solution of (DHQD)2PHAL (154 mg, 0.197 mmol) in propanol (4 mL). To this solution was added a solution of (E)-5-bromo-2-fluoro-3-(4-fluorostyryl)pyridine (1167 mg, 3.94 mmol) in propanol (10 mL). To this solution was added potassium osmate dihydrate (58.1 mg, 0.158 mmol) in one portion. The reaction turned light orange and was allowed to stir at 0° C. for 1 hr. The ice bath was then removed and the reaction was allowed to warm to room temperature and stirred over night. The reaction was quenched with a 10% solution of sodium thiosulfate and stirred for 30 min. The reaction was then extracted with diethylether (3×). The combined organic extracts were combined washed with water, then brine. The organic layer was separated, dried over sodium sulfate and evaporated in vacuo. The crude residue was purified by silica gel chromatography 5% acetone/95% Hexanes to 50%/50% Acetone/Hexanes to afford tert-butyl (1R,2R)-1-(5-bromo-2-fluoropyridin-3-yl)-2-(4-fluorophenyl)-2-hydroxyethylcarbamate (1450 mg, 3.38 mmol, 86% yield) along with its regioisomer as an inseparable mixture. LC/Mass spec. (Analytical HPLC method 2): RT=2.07 min. Mass=429.30 (MH)$^+$.

Intermediate 57

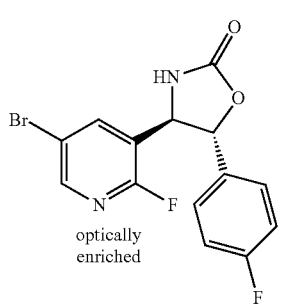

Optically-enriched (4R,5R)-4-(5-bromo-2-fluoropyridin-3-yl)-5-(4-fluorophenyl)oxazolidin-2-one To a 25 mL round bottom flask was added tert-butyl (1R, 2R)-1-(5-bromo-2-fluoropyridin-3-yl)-2-(4-fluorophenyl)-

2-hydroxyethylcarbamate (1450 mg, 3.38 mmol) in dichloromethane (12 mL). To this solution was added trifluoroacetic acid (2.60 mL, 33.8 mmol) and the reaction was allowed to stir over night at room temperature. The reaction solvent was evaporated in vacuo and the crude oil was diluted with diethylether and washed with saturated sodium bicarbonate. The organic layer was separated, dried over sodium sulfate and the solvent was then evaporated in vacuo and the crude residue was diluted with dry tetrahydrofuran. The solution was cooled to 0° C. and carbonyldiimidazole (282 mg, 1.74 mmol) was added and the reaction was allowed to stir overnight. The reaction solvent was then evaporated in vacuo and the crude residue was diluted with 2N ammonia in methanol and stirred for 15 min. The solvent was then evaporated in vacuo and the crude solid was purified by silica gel chromatography 15% EtOAc/85% Hexanes to 50% EtOAc/50% Hexanes affording the desired product and its regioisomer as an inseparable mixture. The inseparable mixture was further purified by reverse phase chromatography using a sunfire col 30×100 45%-55% MeOH/H2O 0.1% TFA over a 20 minute run time affording (4R,5R)-4-(5-bromo-2-fluoropyridin-3-yl)-5-(4-fluorophenyl)oxazolidin-2-one (180 mg, 0.507 mmol, 10.99% yield). $^1$H-NMR (CDCl$_3$, 400 MHz) δ 8.33 (s, 1H), 8.10 (d, J=8.0), 7.42-7.38 (m, 2H), 7.19-7.15 (m, 2H), 5.81 (brs, 1H), 5.36 (d, J=4.0, 1H), 5.01 (d, J=4.0, 1H), LC/Mass spec. (Analytical HPLC method 2): RT=2.17 min. Mass=356.96 (MH)$^+$.

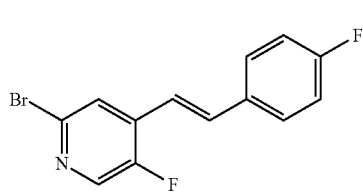

Intermediate 58

(E)-2-Bromo-5-fluoro-4-(4-fluorostyryl)pyridine

To a 25 mL round bottom flask was added 2-bromo-5-fluoropyridin-4-ylboronic acid (1440 mg, 6.55 mmol), sodium carbonate (1085 mg, 10.23 mmol), and 1-fluoro-4-vinylbenzene (500 mg, 4.09 mmol) in dimethylformamide (8 mL). The solution was stirred at room temperature and the flask was purged with oxygen for 3 min. To the purged flask was quickly added diacetoxypalladium (92 mg, 0.409 mmol) and the reaction flask was again sealed and purged with oxygen for 15 min. The reaction mixture was then stirred at room temperature overnight. The next day the reaction was quenched with water and diluted with ethylacetate (3×). The organic layer was separated, washed with brine, dried over sodium sulfate and evaporated in vacuo. The crude oil was purified by silica gel chromatography eluting with 0% EtOAc/100% hexanes to 25% EtOAc/85% hexanes affording (E)-2-bromo-5-fluoro-4-(4-fluorostyryl)pyridine (100 mg, 0.338 mmol, 8.25% yield) as a white solid. $^1$H-NMR (CDCl$_3$, 400 MHz) δ 8.45 (s, 1H), 8.25 (m, 1H), 7.58-7.57 (m, 2H), 7.36 (d, J=16.0, 1H), 7.15-7.11 (m, 2H), 7.04 (d, J=16.0, 1H), LC/Mass spec. (Analytical HPLC method 2): RT=2.76 min. Mass=295.98 (MH)$^+$.

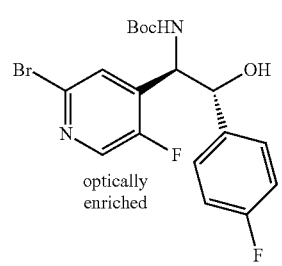

Intermediate 59

Optically-enriched tert-butyl (1R,2R)-1-(2-bromo-5-fluoropyridin-4-yl)-2-(4-fluorophenyl)-2-hydroxyethylcarbamate To a solution of tert-butyl carbamate (189 mg, 1.612 mmol) in propanol (4 mL) was added sodium hydroxide (54.1 mg, 1.352 mmol) in water (2 mL) followed by tert-butyl hypochlorite (172 mg, 1.586 mmol). After 5 min the solution was cooled to 0° C. and treated with a solution of (DHQD)2PHAL (20.26 mg, 0.026 mmol) in propanol (1 mL). To this solution was added a solution of (E)-2-bromo-5-fluoro-4-(4-fluorostyryl)pyridine (154 mg, 0.520 mmol) in propanol (7 mL). To this solution was added potassium osmate dihydrate (7.66 mg, 0.021 mmol) dissolved in water (3 mL) in one portion. The reaction turned light orange and was allowed to stir at 0° C. overnight. The reaction was complete the next morning after warming to room temperature. The reaction was then quenched with a 10% solution of sodium thiosulfate and stirred for 30 min. The reaction was then extracted with diethylether (3×). The combined organic extracts were combined washed with water, then brine. The organic layer was separated, dried over sodium sulfate and evaporated in vacuo. The crude residue was purified by silica gel chromatography 25% EtOAc/75% Hexanes to 50%/50% EtOAc/Hexanes to afford tert-butyl (1R,2R)-1-(2-bromo-5-fluoropyridin-4-yl)-2-(4-fluorophenyl)-2-hydroxyethylcarbamate (56 mg, 0.130 mmol, 62.7% yield) along with its regioisomer as an inseparable mixture. LC/Mass spec. (Analytical HPLC method 2): RT=2.09 min. Mass=431.05 (MH)$^+$.

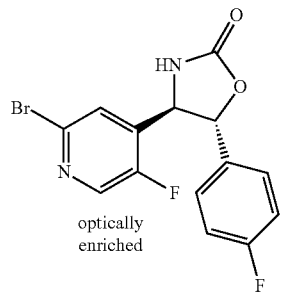

Intermediate 60

Optically-enriched (4R,5R)-4-(2-bromo-5-fluoropyridin-4-yl)-5-(4-fluorophenyl)oxazolidin-2-one To a 25 mL round bottom flask was added tert-butyl (1R,2R)-1-(2-bromo-5-fluoropyridin-4-yl)-2-(4-fluorophenyl)-2-hydroxyethylcarbamate (141 mg, 0.328 mmol) in dichloromethane (4 mL). To this solution was added trifluoroacetic acid (0.253 mL, 3.28 mmol) and the reaction was allowed to stir over night at room temperature. The next day the reaction was checked by LC/MS and was complete. The reaction solvent was evaporated in vacuo and the crude oil was diluted with diethylether and washed with saturated sodium bicarbonate. The organic layer was separated, dried over sodium sulfate and the solvent was then evaporated in vacuo and the crude residue was diluted with dry tetrahydrofuran. The solution was cooled to 0° C. and carbonyldiimidazole (53.3 mg, 0.328 mmol) was added and the reaction was allowed to stir overnight. The reaction was complete by LC/MS. The reaction solvent was then evaporated in vacuo and the crude solid was purified by silica gel chromatography 15% EtOAc/85% Hexanes to 50% EtOAc/50% Hexanes affording (4R,5R)-4-(2-bromo-5-fluoropyridin-4-yl)-5-(4-fluorophenyl)oxazolidin-2-one (20 mg, 0.056 mmol, 42.9% yield) and its regioisomer as an inseparable mixture. LC/Mass spec. (Analytical HPLC method 2): RT=1.79 min. Mass=354.89 (MH)$^+$.

Intermediate 61

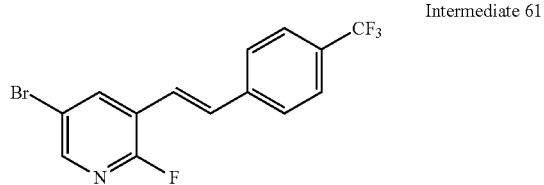 [SMILES: Fc1ncc(Br)cc1/C=C/c1ccc(C(F)(F)F)cc1]

(E)-5-Bromo-2-fluoro-3-(4-(trifluoromethyl)styryl)pyridine

To a 15 mL round bottom flask was added 5-bromo-2-fluoropyridin-3-ylboronic acid (400 mg, 1.820 mmol), SODIUM CARBONATE (386 mg, 3.64 mmol) and 1-(trifluoromethyl)-4-vinylbenzene (407 mg, 2.366 mmol) in dimethylformamide (6 mL). The solution was stirred at room temperature and the flask was purged with oxygen for 3 min. To the purged flask was quickly added palladium(II) acetate (40.9 mg, 0.182 mmol) and the reaction flask was again sealed and purged with oxygen for 15 min. The reaction mixture was then stirred at room temperature overnight and monitored by TLC to determine when the reaction was complete. The next day the reaction was complete by LC/MS. There was no boronic acid left so the reaction was quenched with water and diluted with ethylacetate. The organic layer was separated, washed with brine, dried over sodium sulfate and evaporated in vacuo. The crude oil was puried by silica gel chromatography eluting with 0% EtOAc/100% hexanes to 15% EtOAc/85% hexanes affording (E)-5-bromo-2-fluoro-3-(4-(trifluoromethyl)styryl)pyridine (177 mg, 0.511 mmol, 28.1% yield) as a white solid. $^1$H-NMR (CDCl$_3$, 400 MHz) δ 8.19 (s, 1H), 8.12 (dd, J=8.0, 4.0, 1H), 7.66 (m, 4H), 7.29 (d, J=16.0, 1H), 7.17 (d, J=16.0, 1H).

Intermediate 62

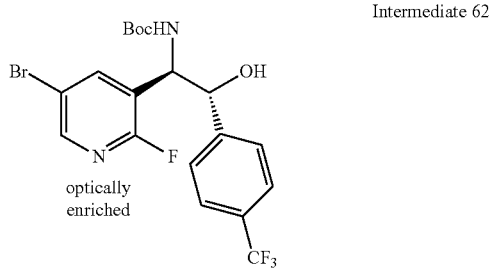 [SMILES: CC(C)(C)OC(=O)N[C@H](c1cc(Br)cnc1F)[C@H](O)c1ccc(C(F)(F)F)cc1]

Optically-enriched tert-butyl (1R,2R)-1-(5-bromo-2-fluoropyridin-3-yl)-2-hydroxy-2-(4-(trifluoromethyl)phenyl)ethylcarbamate To a solution of tert-butyl carbamate (189 mg, 1.612 mmol) in propanol (7 mL) was added sodium hydroxide (54.1 mg, 1.352 mmol) in water (4 mL) followed by tert-butyl hypochlorite (172 mg, 1.586 mmol) (freshly prepared following an org synthesis prep). After 5 min the solution was cooled to 0° C. and treated with a solution of (DHQD)2PHAL (20.26 mg, 0.026 mmol) in propanol (4 mL). To this solution was added a solution of (E)-5-bromo-2-fluoro-3-(4-(trifluoromethyl)styryl)pyridine (180 mg, 0.520 mmol) in propanol (10 mL). To this solution was added potassium osmate dihydrate (7.66 mg, 0.021 mmol) in one portion. The reaction turned light orange and was allowed to stir at 0° C. overnight allowing the reaction to warm up to room temperature. The reaction was quenched with a 10% solution of sodium thiosulfate and stirred for 30 min. The reaction was then extracted with diethylether (3×). The combined organic extracts were combined washed with water, then brine. The organic layer was separated, dried over sodium sulfate and evaporated in vacuo. The crude residue was purified by silica gel chromatography 25% EtOAc/75% Hexanes to 50%/50% EtOAc/Hexanes to afford tert-butyl (1R,2R)-1-(5-bromo-2-fluoropyridin-3-yl)-2-hydroxy-2-(4-(trifluoromethyl)phenyl)ethylcarbamate (250 mg, 0.530 mmol, 99% yield) as an inseparable mixture with its regioisomer. LC/Mass spec. (Analytical HPLC method 2): RT=2.78 min. Mass=503.07 (MNa)$^+$.

Intermediate 63

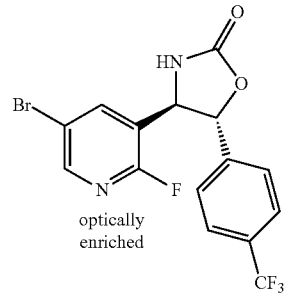

Optically-enriched (4R,5R)-4-(5-bromo-2-fluoropyridin-3-yl)-5-(4-(trifluoromethyl)phenyl)oxazolidin-2-one To a 25 mL round bottom flask was added tert-butyl (1R,2R)-1-(5-bromo-2-fluoropyridin-3-yl)-2-hydroxy-2-(4-(trifluoromethyl)phenyl)ethylcarbamate (250 mg, 0.53 mmol) in dichloromethane (8 mL). To this solution was added trifluoroacetic acid (1.021 mL, 13.25 mmol) and the reaction was allowed to stir over night at room temperature. The reaction solvent was evaporated in vacuo and the crude oil was diluted with ethylacetate and washed with saturated sodium bicarbonate. The organic layer was separated, dried over sodium sulfate and the solvent was then evaporated in vacuo and the crude residue was diluted with dry tetrahydrofuran. The solution was cooled to 0° C. and carbonyldiimidazole (86 mg, 0.530 mmol) was added and the reaction was allowed to stir overnight. The reaction solvent was then evaporated in vacuo and the crude solid was purified by silica gel chromatography 15% EtOAc/85% Hexanes to 50% EtOAc/50% Hexanes affording (4R,5R)-4-(5-bromo-2-fluoropyridin-3-yl)-5-(4-(trifluoromethyl)phenyl)oxazolidin-2-one (84 mg, 0.207 mmol, 39.1% yield) and its regioisomer as an inseparable mixture. LC/Mass spec. (Analytical HPLC method 2): RT=2.44 min. Mass=406.91 (MH)$^+$.

Intermediate 64

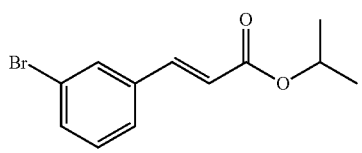

(E)-Isopropyl 3-(3-bromophenyl)acrylate

To a solution of (E)-3-(3-bromophenyl)acrylic acid (7.5 g, 32.4 mmol) in propan-2-ol (50 mL, 832 mmol) was added dropwise H$_2$SO$_4$ (0.431 mL, 8.09 mmol). The reaction was heated to reflux for 18 h then it was concentrated in vacuo providing a brown liquid which was redissolved in 50 mL ethylacetate. 1N NaOH was added dropwise until the aqueous mixture reached pH10. The organic layer was collected and washed with aqueous sodium bicarbonate (sat), brine, dried over magnesium sulfate, filtered and concentrated providing (E)-isopropyl 3-(3-bromophenyl)acrylate (8.4202 g, 29.7 mmol, 92% yield) as a yellow liquid. $^1$H NMR (500 MHz, DMSO) δ 7.98 (s, 1H), 7.74 (d, J=7.8 Hz, 1H), 7.67-7.55 (m, 2H), 7.37 (t, J=7.9 Hz, 1H), 6.70 (d, J=16.0 Hz, 1H), 5.02 (dt, J=12.5, 6.2 Hz, 1H), 1.26 (d, J=6.3 Hz, 6H). Mass spec.: 270.88 (MH)$^+$.

Intermediate 65

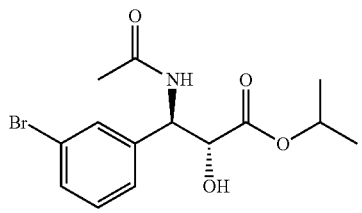

(2R,3R)-Isopropyl 3-acetamido-3-(3-bromophenyl)-2-hydroxypropanoate

To a solution of lithium hydroxide monohydrate (0.091 mL, 3.27 mmol) and potassium osmium oxide (VI) (0.049 g, 0.149 mmol) in water (9 mL) was added t-BuOH (18.00 mL), (DHQD)$_2$ PHAL (0.139 g, 0.178 mmol) and the mixture was stirred for 10 min. Water (18.00 mL) was added, and the mixture was immersed in a cooling bath set at 4° C. (E)-isopropyl 3-(3-bromophenyl)acrylate (0.8 g, 2.97 mmol) was added to the reaction mixture. 30 minutes later N-bromoacetamide (0.451 g, 3.27 mmol) was added in one portion and the mixture was vigorously stirred at the same temperature. After 20 h, the reaction mixture was treated with sodium sulfite (1.5 g, 11.90 mmol). After stirring at ambient temperature for 30 min, ethyl acetate (20 mL) was added. The organic layer was separated, and the water layer was extracted with ethyl acetate (3×25 mL). The combined organics were washed with brine (20 mL), and dried over magnesium sulfate. After evaporation of the solvent, the crude was purified by Preparative HPLC Method 10 providing (2S,3R)-isopropyl 3-acetamido-3-(3-bromophenyl)-2-hydroxypropanoate (136.2 mg, 0.396 mmol, 13.31% yield) as a white solid. $^1$H NMR (500 MHz, DMSO-d$_6$) δ ppm 1.07 (d, J=6.41 Hz, 3H) 1.18 (d, J=6.10 Hz, 3H) 1.86 (s, 3H) 4.29 (dd, J=6.10, 3.97 Hz, 1H) 4.85 (t, J=6.26 Hz, 1H) 5.24 (dd, J=9.31, 4.12 Hz, 1H) 5.69 (d, J=6.10 Hz, 1H) 7.28 (t, J=7.78 Hz, 1H) 7.34 (d, J=7.93 Hz, 1H) 7.44 (dt, J=7.71, 1.49 Hz, 1H) 7.50-7.57 (m, 1H) 8.38 (d, J=9.16 Hz, 1H). Mass spec.: 345.91 (MH)$^+$.

Intermediate 66

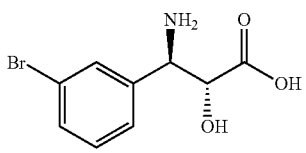

(2R,3R)-3-Amino-3-(3-bromophenyl)-2-hydroxypropanoic acid (2S,3R)-isopropyl 3-acetamido-3-(3-bromophenyl)-2-hydroxypropanoate (123 mg, 0.357 mmol) in 10% HCl (12.7 ml) was heated to reflux for four hours at which time the reaction mixture was concentrated providing (2S,3R)-3-amino-3-(3-bromophenyl)-2-hydroxypropanoic acid, HCl (90 mg, 0.273 mmol, 76% yield) as a grey solid. $^1$H NMR (500 MHz, DMSO-d$_6$) δ ppm 4.34 (d, J=5.49 Hz, 1H) 4.43 (br. s., 1H) 6.67 (br. s., 1H) 7.35-7.42 (m, 1H) 7.54 (d, J=7.63 Hz, 1H) 7.58-7.63 (m, 1H) 7.79 (s, 1H) 8.61 (br. s., 2H) 13.04 (br. s., 1H). Mass spec.: 261.91 (MH)$^+$.

Intermediate 67

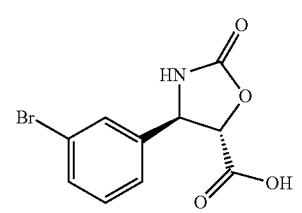

(4R,5S)-4-(3-Bromophenyl)-2-oxooxazolidine-5-carboxylic acid

To triphosgene (36.5 mg, 0.123 mmol) and Na$_2$CO$_3$ (65.2 mg, 0.615 mmol) in Water (2.000 mL) at 0° C. was added dropwise a solution of (2S,3R)-3-amino-3-(3-bromophenyl)-2-hydroxypropanoic acid (20 mg, 0.077 mmol) in Water (0.5 mL)/1,4-Dioxane (0.5 mL). After 15 min, the ice bath was removed and stirring was continued for one hour. ethylacetate (1 ml) was added to the reaction mixture and after five minutes the ethylacetate layer was discarded and the aqueous layer was acidified to pH 2 and extracted with ethylacetate (5 mL×3). The combined organics were dried over magnesium sulfate, filtered and concentrated providing (4R,5S)-4-(3-bromophenyl)-2-oxooxazolidine-5-carboxylic acid (14.2 mg, 0.047 mmol, 61.3% yield) as a white solid. Mass spec.: 287.79 (MH)$^+$.

Intermediate 68

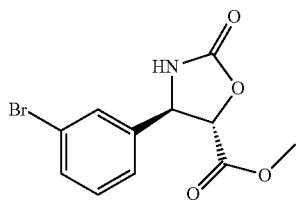

(4R,5S)-Methyl 4-(3-bromophenyl)-2-oxooxazolidine-5-carboxylate

To a solution of (4R,5S)-4-(3-bromophenyl)-2-oxooxazolidine-5-carboxylic acid (20 mg, 0.070 mmol) in tetrahydrofuran (2 mL)/methanol (0.500 mL) was added trimethylsilyldiazomethane (0.063 mL, 0.126 mmol) dropwise at 0° C. After 3 h, the reaction was allowed to warm to ambient temperature and stirred for an additional 15 h, at which time it was concentrated in vacuo to provide (4R,5S)-methyl 4-(3-bromophenyl)-2-oxooxazolidine-5-carboxylate (18.2 mg, 0.058 mmol, 82% yield). $^1$H NMR (500 MHz, DMSO-d$_6$) δ ppm 3.78 (s, 3H) 4.98 (d, J=4.88 Hz, 1H) 5.01-5.04 (m, 1H) 7.37-7.45 (m, 2H) 7.56 (s, 1H) 7.57-7.61 (m, 1H) 8.60 (s, 1H). Mass spec.: 301.77 (MH)$^+$.

Intermediate 69

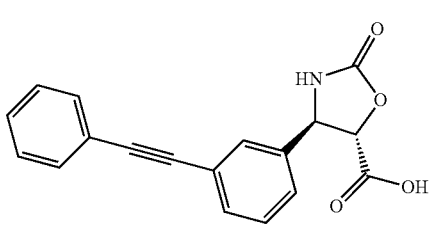

(4R,5S)-2-Oxo-4-(3-(phenylethynyl)phenyl)oxazolidine-5-carboxylic acid

This intermediate was prepared using the same procedure as described for the preparation of (+)-(4R,5R)-5-(3-Methoxyphenyl)-4-(3-(phenylethynyl)phenyl)-oxazolidin-2-one.
$^1$H NMR (500 MHz, DMSO-d$_6$) δ ppm 4.85 (br. s., 1H) 4.94-5.02 (m, 1H) 7.37-7.69 (m, 9H) 8.52 (s, 1H) 13.58-13.78 (m, 1H). Mass spec.: 307.91 (MH)$^+$.

Intermediate 70

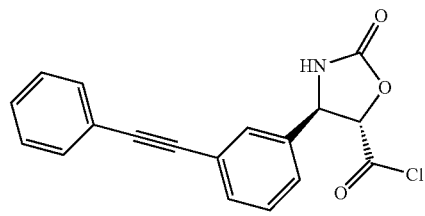

(4R,5S)-2-Oxo-4-(3-(phenylethynyl)phenyl)oxazolidine-5-carbonyl chloride

To a solution of (4R,5S)-2-oxo-4-(3-(phenylethynyl)phenyl)oxazolidine-5-carboxylic acid (120 mg, 0.390 mmol) in dichloromethane (5 mL) was added thionyl chloride (0.285 mL, 3.90 mmol) and the solution was heated to reflux for 3 h. The reaction mixture was concentrated in vacuo providing (4R,5S)-2-oxo-4-(3-(phenylethynyl)phenyl)oxazolidine-5-carbonyl chloride (127 mg, 0.370 mmol, 95% yield) as a light brown wax.

Intermediate 71

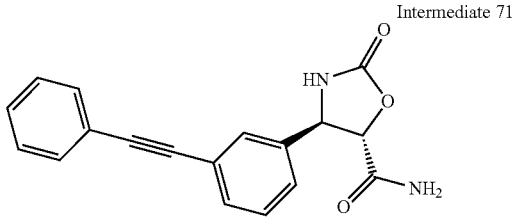 [SMILES: NC(=O)[C@H]1OC(=O)N[C@@H]1c1cccc(C#Cc2ccccc2)c1]

(4R,5S)-2-Oxo-4-(3-(phenylethynyl)phenyl)oxazolidine-5-carboxamide

To (4R,5S)-2-oxo-4-(3-(phenylethynyl)phenyl)oxazolidine-5-carbonyl chloride (120 mg, 0.368 mmol) in tetrahydrofuran (1 mL) was added ammonium hydroxide (3 mL, 23.11 mmol) dropwise. One hour later, the reaction mixture was extracted with ethylacetate (10 mL×3) and the combined organic layer was dried over magnesium sulfate, filtered, and concentrated to obtain (4R,5S)-2-oxo-4-(3-(phenylethynyl)phenyl)oxazolidine-5-carboxamide (114 mg, 0.354 mmol, 96% yield) as a white solid. $^1$H NMR (500 MHz, DMSO-d$_6$) δ ppm 4.66 (d, J=5.49 Hz, 1H) 4.88 (d, J=5.49 Hz, 1H) 7.37-7.68 (m, 11H) 7.79 (s, 1H). Mass spec.: 307.1 (MH)$^+$.

Intermediate 72

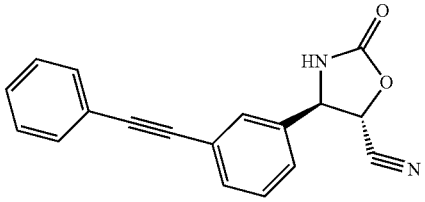

(4R,5S)-2-Oxo-4-(3-(phenylethynyl)phenyl)oxazolidine-5-carbonitrile

To a solution of (4R,5S)-2-oxo-4-(3-(phenylethynyl)phenyl)oxazolidine-5-carboxamide (80 mg, 0.261 mmol) in dichloromethane (2 mL) was added phosphorus oxychloride (0.243 mL, 2.61 mmol). The reaction was heated to reflux for 4 h and sodium bicarbonate (sat) was added until pH 7. The reaction mixture was back extracted with dichloromethane (3×5 mL) and the combined organic layers were dried over magnesium sulfate, filtered and concentrated to yield a yellow wax that was purified by Preparative HPLC Method 6 providing (4R,5S)-2-oxo-4-(3-(phenylethynyl)phenyl)oxazolidine-5-carbonitrile (53 mg, 0.178 mmol, 68.3% yield) $^1$H NMR (500 MHz, DMSO-d$_6$) δ ppm 5.36 (d, J=4.27 Hz, 1H) 5.63 (d, J=4.27 Hz, 1H) 7.39-7.49 (m, 4H) 7.52 (t, J=7.93 Hz, 1H) 7.56-7.64 (m, 4H) 8.76 (br. s., 1H).

Intermediate 73

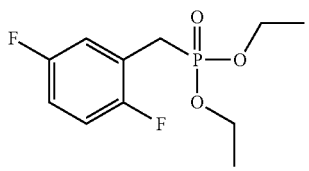

Diethyl 2,5-difluorobenzylphosphonate

A mixture of 2-(bromomethyl)-1,4-difluorobenzene (3 g, 14.49 mmol) and triethyl phosphite (7.72 ml, 43.5 mmol) was heated to 160° C. with stirring for 4 hours, cooled to ambient temperature and concentrated under high vacuum to remove most triethyl phosphite. The resulting residue was purified by column chromatography (20% to 30% EtOAc/Toluene) providing diethyl 2,5-difluorobenzylphosphonate (3.76 g, 13.52 mmol, 93% yield) as colorless oil. $^1$H NMR (500 MHz, DMSO-$d_6$) δ 7.30-7.10 (m, 3H), 4.05-3.91 (m, 4H), 3.31-3.20 (m, 2H), 1.18 (t, J=7.0 Hz, 6H). MS Anal. Calcd. for [M+H]$^+$ $C_{11}H_{16}F_2O_3P$: 265.2. found 265.3.

Intermediate 74

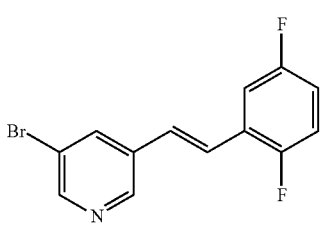

(E)-3-Bromo-5-(2,5-difluorostyryl)pyridine

To a stirred solution of diethyl 2,5-difluorobenzylphosphonate (63.5 g, 240 mmol) and 5-bromonicotinaldehyde (50.7 g, 264 mmol) in tetrahydrofuran (1923 ml) was added potassium tert-butoxide in tetrahydrofuran (312 ml, 312 mmol) at −10° C. After three hours, the reaction mixture was allowed to warm to ambient temperature and stirring was continued for another 16 hours at which time the reaction mixture was diluted with ether (800 mL) and washed with H$_2$O. The organic layer was dried over anhydrous magnesium sulfate, filtered and concentrated to provide a yellow wax to which was added 300 mL of hexane and after sonication filtered to provide (E)-3-bromo-5-(2,5-difluorostyryl)pyridine (54 g, 173 mmol, 72.1%) as a white solid. $^1$H NMR (500 MHz, DMSO-$d_6$) δ 8.78 (d, J=1.8 Hz, 1H), 8.63 (d, J=2.1 Hz, 1H), 8.44 (t, J=2.0 Hz, 1H), 7.67 (ddd, J=9.4, 6.0, 3.2 Hz, 1H), 7.56-7.48 (m, 1H), 7.46-7.40 (m, 1H), 7.34 (td, J=9.6, 4.6 Hz, 1H), 7.24 (tt, J=8.3, 3.6 Hz, 1H). MS Anal. Calcd. for [M+H]$^+$ $C_{13}H_9BrF_2N$: 296.0. found 298.1.

Intermediate 75

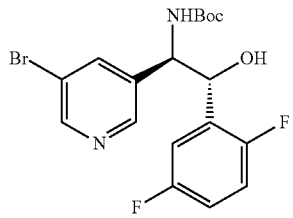

Tert-butyl (1R,2R)-1-(5-bromopyridin-3-yl)-2-(2,5-difluorophenyl)-2-hydroxyethylcarbamate A solution of tert-butyl carbamate (4.18 g, 35.0 mmol) in propanol (39 ml) was sequentially treated with sodium hydroxide (1.376 g, 34.4 mmol) in water (72 ml) and tert-butyl hypochlorite (3.88 ml, 34.4 mmol). After 5 min of stirring, the reaction mixture was cooled to 0° C. A solution of (DHQD)$_2$PHAL (0.555 g, 0.677 mmol) in propanol (39 ml), a solution of (E)-3-bromo-5-(2,5-difluorostyryl)pyridine (3.34 g, 11.28 mmol) in propanol (68 ml), and potassium osmate dihydrate (0.166 g, 0.451 mmol) were sequentially added. The reaction mixture was stirred for three additional hours at 0° C., warmed to ambient temperature and after an additional 16 hours the light yellow homogenous solution was quenched with saturated aqueous sodium sulfite (100 mL). The aqueous phase was extracted with ethyl acetate (2×50 mL), the combined organic phases were washed with brine (100 mL), dried over anhydrous magnesium sulfate and concentrated to afford a residue which was purified via column chromatography (25% to 40% EtOAc/Hex) to provide tert-butyl (1R,2R)-1-(5-bromopyridin-3-yl)-2-(2,5-difluorophenyl)-2-hydroxyethylcarbamate (2.2991 g, 5.09 mmol, 45.1% yield) as an optically enriched mixture of enantiomers. $^1$H NMR (500 MHz, DMSO-$d_6$) δ 8.56 (d, J=1.8 Hz, 1H), 8.40 (s, 1H), 8.03 (s, 1H), 7.52 (d, J=9.5 Hz, 1H), 7.25 (br. s., 1H), 7.10 (t, J=5.6 Hz, 2H), 5.89 (d, J=4.9 Hz, 1H), 5.03 (t, J=5.0 Hz, 1H), 4.83 (dd, J=8.9, 5.2 Hz, 1H), 1.40-1.34 (m, 9H), MS Anal. Calcd. for [M+H]$^+$ $C_{18}H_{20}BrF_2N_2O_3$: 429.1. found 431.3.

Intermediate 76

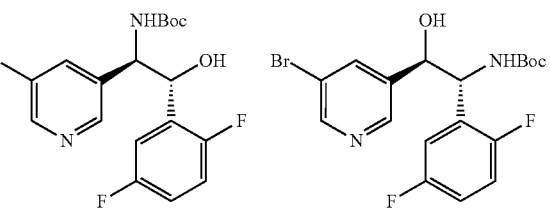

mixture, optically enriched

Mixture of tert-butyl((1R,2R)-1-(5-bromopyridin-3-yl)-2-(2,5-difluorophenyl)-2-hydroxyethyl)carbamate and tert-butyl((1R,2R)-2-(5-bromopyridin-3-yl)-1-(2,5-difluorophenyl)-2-hydroxyethyl)carbamate To a solution of tert-butyl carbamate (83 g, 709 mmol) in 1-propanol (780 mL) was added 0.5 M of aqueous sodium hydroxide (1418 mL, 709 mmol), followed by tert-butyl hypochlorite (77 g, 709 mmol) (internal temperature 28.2°

C.). The reaction mixture was stirred at ambient temperature for 10 min. To this reaction mixture was added (DHQD)$_2$PHAL (5.52 g, 7.09 mmol) and 1-propanol (780 mL), followed by (E)-3-bromo-5-(2,5-difluorostyryl)pyridine (70.0 g, 236 mmol) and 1-propanol (780 mL). This white mixture was cooled to 0° C. with a methanol/ice bath. Then potassium osmate dihydrate (2.61 g, 7.09 mmol) was added to this mixture. After 30 min of stirring, the ice bath was removed. The reaction was stirred at room temperature overnight. After 16 h, the reaction mixture was partitioned with water (1 L) and EtOAc (2.4 L). The organic layer was washed with 5% sodium sulfite three times (Note: Each wash was mechanically stirred for 10 min to ensure reduction of osmium. The first two washes were dark; the third wash was clear. The organic layer was washed with brine (3×500 mL), dried (sodium sulfate), filtered, and concentrated to give 136 g of crude tert-butyl((1R,2R)-1-(5-bromopyridin-3-yl)-2-(2,5-difluorophenyl)-2-hydroxyethyl)carbamate and tert-butyl((1R,2R)-2-(5-bromopyridin-3-yl)-1-(2,5-difluorophenyl)-2-hydroxyethyl)carbamate (ca. 6:1 ratio). LC/MS (ES$^+$) 430.9 (M+H, 100).

Intermediate 77

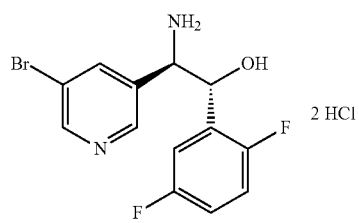

(1R,2R)-2-Amino-2-(5-bromopyridin-3-yl)-1-(2,5-difluorophenyl)ethanol

To a stirred solution of tert-butyl tert-butyl (1R,2R)-1-(5-bromopyridin-3-yl)-2-(2,5-difluorophenyl)-2-hydroxyethylcarbamate (2.30 g, 5.09 mmol) in methylene chloride (30 mL) was added HCl in dioxane (30 ml, 120 mmol). The reaction mixture was placed in an oil bath set to 50° C. After three hours, the reaction mixture was concentrated providing (1R,2R)-2-amino-2-(5-bromopyridin-3-yl)-1-(2,5-difluorophenyl)ethanol 2HCl salt (2.10 g, 4.97 mmol, 98% yield) as an optically enriched yellow wax. $^1$H NMR (500 MHz, DMSO-d$_6$) δ 8.95 (d, J=3.7 Hz, 2H), 8.64 (d, J=2.4 Hz, 1H), 8.45 (d, J=1.5 Hz, 1H), 8.31 (t, J=2.0 Hz, 1H), 7.47-7.09 (m, 3H), 7.04 (td, J=9.2, 4.4 Hz, 1H), 5.29 (d, J=9.2 Hz, 1H), 4.57 (dd, J=9.0, 5.3 Hz, 1H). Anal. Calcd. for [M+H]$^+$ C$_{13}$H$_{12}$BrF$_2$N$_2$O: 329.0. found 331.2.

Intermediate 78

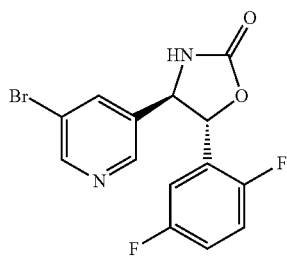

(4R,5R)-4-(5-Bromopyridin-3-yl)-5-(2,5-difluorophenyl)oxazolidin-2-one

To optically enriched (1R,2R)-2-amino-2-(5-bromopyridin-3-yl)-1-(2,5-difluorophenyl)ethanol, 2 HCl (2.019 g, 4.82 mmol) in tetrahydrofuran (98 ml) was added diisopropylethylamine (2.95 ml, 16.87 mmol) and the resultant solution was stirred for ten minutes at ambient temperature, cooled to 0° C. and carbonyldiimidazole (1.094 g, 6.75 mmol) was added. After an additional three hours at 0° C. the reaction mixture was warmed to ambient temperature and allowed to stir for another 16 hours. 2M NH$_3$ in methanol (5 ml) was added and after ten minutes the suspension was filtered and concentrated to a pink oil which was purified by column chromatography (25% to 40% EtOAc/Hex) providing (4R,5R)-4-(5-bromopyridin-3-yl)-5-(2,5-difluorophenyl)oxazolidin-2-one (1.353 g, 3.62 mmol, 75% yield) as an optically enriched white solid. $^1$H NMR (500 MHz, DMSO-d$_6$) δ 8.80-8.68 (m, 1H), 8.55 (d, J=2.1 Hz, 2H), 8.16 (t, J=2.1 Hz, 1H), 7.46-7.28 (m, 3H), 5.71-5.58 (m, 1H), 5.02 (d, J=6.7 Hz, 1H). MS Anal. Calcd. for [M+H]$^+$ C$_{14}$H$_{10}$BrF$_2$N$_2$O$_2$: 355.0. found 357.2.

Intermediate 79

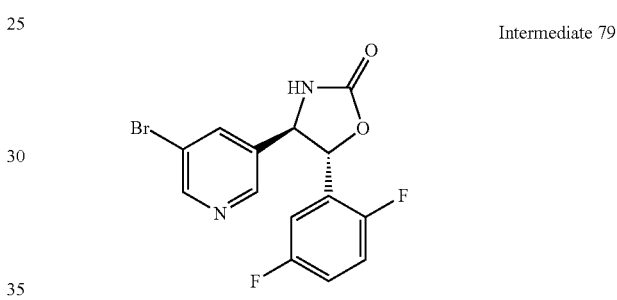

(4R,5R)-4-(5-Bromopyridin-3-yl)-5-(2,5-difluorophenyl)oxazolidin-2-one

Method-2

A mixture of tert-butyl((1R,2R)-1-(5-bromopyridin-3-yl)-2-(2,5-difluorophenyl)-2-hydroxyethyl)carbamate and tert-butyl((1R,2R)-2-(5-bromopyridin-3-yl)-1-(2,5-difluorophenyl)-2-hydroxyethyl)carbamate (about 6:1 ratio) (101 g, 236 mmol) in tetrahydrofuran (590 mL) was cooled to −7° C. with a methanol/ice bath. To this mixture was added a solution of 1 M potassium tert-butoxide in tetrahydrofuran (590 mL, 590 mmol) via an addition funnel while maintaining the internal temperature <3° C. The reaction mixture was stirred with a cooling bath for 30 min and then allowed to warm up to room temperature. After 20 h, the reaction was deemed complete by LC/MS. The reaction mixture was concentrated to dryness to give crude product. Another identical scale reaction was performed. The crude products of the two batches were combined to work up together. They were treated with ethyl acetate (1.75 L) and water (1.75 L). The layers were separated. The organic layer was washed with brine (1.75 L), dried (sodium sulfate), and evaporated to give 161.5 g of crude product as a brown solid. This was purified by ISCO to give 67.1 g (42% yield). LC/MS (ES+) 355/357 (M+H, 100; Br isotope pattern); $^1$H NMR (400 MHz, CDCl$_3$) δ 8.75 (d, J=2.2 Hz, 1H), 8.53 (d, J=1.8 Hz, 1H), 7.97 (t, J=2.0 Hz, 1H), 7.29-7.23 (m, 2H), 7.18-7.09 (m, 2H), 6.40 (s, 1H), 5.56 (d, J=5.7 Hz, 1H), 4.84 (d, J=5.5 Hz, 1H); Calcd for C$_{14}$H$_9$N$_2$BrF$_2$O$_2$: C, 47.34; H, 2.55; N, 7.86; Br, 22.50; F, 10.69. Found: C, 47.29; H, 2.61; N, 7.87; Br, 22.40; F, 10.37.

Note: Chiral HPLC of the above sample showed 4.7% of the enantiomer. The (4S,5S) enantiomer can be purged by recrystallization from methanol to give >99.9 ee with 67% recovery.

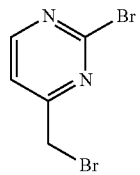

Intermediate 80

2-Bromo-4-(bromomethyl)pyrimidine

To a stirred solution of 2-bromo-4-methylpyrimidine (1.5 g, 8.67 mmol) in $CCl_4$ (15 mL) was added NBS (3.39 g, 19.07 mmol) and benzoyl peroxide (0.476 g, 1.907 mmol) then it was heated to 80° C. After 48 hours, the reaction mixture was cooled to ambient temperature and filtered. The black solid was discarded and liquid was concentrated to brown solid which was purified by column chromatography (10% EtOAc/Hex) to obtained a yellow solid of 2-bromo-4-(bromomethyl)pyrimidine (437.6 mg, 1.737 mmol, 20.04% yield). $^1$H NMR (500 MHz, DMSO-$d_6$) δ 8.74 (d, J=4.9 Hz, 1H), 7.75 (d, J=4.9 Hz, 1H), 4.66 (s, 2H)), Mass spec.: 252.9 (MH)$^+$.

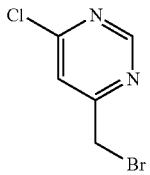

Intermediate 81

4-(Bromomethyl)-6-chloropyrimidine

Prepared according to the same procedure as 2-bromo-4-(bromomethyl)pyrimidine, starting with 4-chloro-6-methylpyrimidine. $^1$H NMR (500 MHz, DMSO-$d_6$) δ 9.07 (s, 1H), 7.91 (d, J=0.9 Hz, 1H), 4.66 (s, 2H), Mass spec.: 208.9 (MH)$^+$.

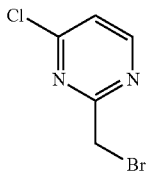

Intermediate 82

2-(Bromomethyl)-4-chloropyrimidine

Prepared according to the same procedure as 2-bromo-4-(bromomethyl)pyrimidine, starting with 4-chloro-2-methylpyrimidine. $^1$H NMR (500 MHz, DMSO-$d_6$) δ 8.83 (d, J=5.5 Hz, 1H), 7.69 (d, J=5.5 Hz, 1H), 4.68 (s, 2H), Mass spec.: 208.9 (MH)$^+$.

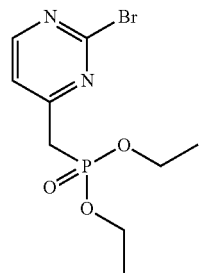

Intermediate 83

Diethyl(2-bromopyrimidin-4-yl)methylphosphonate

Prepared according to the same procedure as diethyl 2,5-difluorobenzylphosphonate, starting with 2-bromo-4-(bromomethyl)pyrimidine. $^1$H NMR (500 MHz, DMSO-$d_6$) δ 8.69-8.58 (m, 1H), 7.67-7.44 (m, 1H), 4.14-3.91 (m, 4H), 3.62-3.43 (m, 2H), 1.42-1.09 (m, 6H), Mass spec.: 310.1 (MH)$^+$.

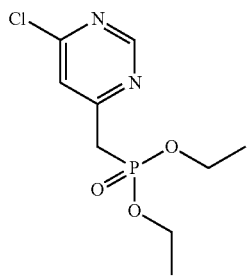

Intermediate 84

Diethyl(6-chloropyrimidin-4-yl)methylphosphonate

Prepared according to the same procedure as diethyl 2,5-difluorobenzylphosphonate, starting with 4-(bromomethyl)-6-chloropyrimidine. $^1$H NMR (500 MHz, DMSO-$d_6$) δ 9.00 (s, 1H), 7.68 (dd, J=2.3, 1.1 Hz, 1H), 4.21-3.88 (m, 4H), 3.74-3.45 (m, 2H), 1.20 (t, J=7.0 Hz, 6H), Mass spec.: 265.1 (MH)$^+$.

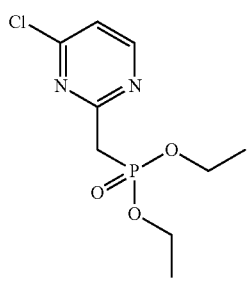

Intermediate 85

Diethyl(4-chloropyrimidin-2-yl)methylphosphonate

Prepared according to the same procedure as diethyl 2,5-difluorobenzylphosphonate, starting with 2-(bromomethyl)-4-chloropyrimidine. Analytical HPLC method: Phenomenex LUNA C18, 50×2 3μ, A=90% $H_2O$/10% $CH_3CN$, B=90%

CH₃CN/10% H₂O, Modifier 0.1% TFA, 0.00 min=0% B, 4.0 min=100% B, 5.0 min=100% B, Flow rate=0.8 mL/min. Mass spec.: 265.1 (MH)⁺.

Intermediate 86

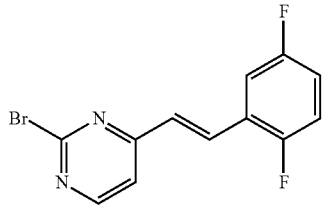

(E)-2-Bromo-4-(2,5-difluorostyryl)pyrimidine

Prepared according to the same procedure as (E)-3-bromo-5-(2,5-difluorostyryl)pyridine, starting with diethyl (2-bromopyrimidin-4-yl)methylphosphonate. ¹H NMR (500 MHz, DMSO-d₆) δ 8.70 (d, J=5.2 Hz, 1H), 7.93 (d, J=16.2 Hz, 1H), 7.83 (ddd, J=9.3, 5.8, 3.2 Hz, 1H), 7.72 (d, J=5.2 Hz, 1H), 7.46 (d, J=16.2 Hz, 1H), 7.43-7.30 (m, 2H), Mass spec.: 299.1 (MH)⁺.

Intermediate 87

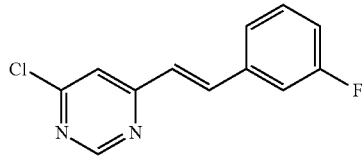

(E)-4-Chloro-6-(3-fluorostyryl)pyrimidine

Prepared according to the same procedure as (E)-3-bromo-5-(2,5-difluorostyryl)pyridine, starting with diethyl diethyl (6-chloropyrimidin-4-yl)methylphosphonate. ¹H NMR (500 MHz, DMSO-d₆) δ 9.01 (s, 1H), 8.01 (d, J=15.9 Hz, 1H), 7.82 (d, J=0.9 Hz, 1H), 7.62 (dd, J=10.4, 1.8 Hz, 1H), 7.59-7.55 (m, 1H), 7.54-7.47 (m, 1H), 7.39 (d, J=16.2 Hz, 1H), 7.26 (td, J=8.5, 2.6 Hz, 1H), Mass spec.: 235.1 (MH)⁺.

Intermediate 88

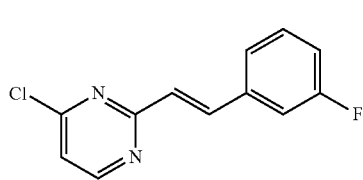

(E)-4-Chloro-2-(3-fluorostyryl)pyrimidine

Prepared according to the same procedure as (E)-3-bromo-5-(2,5-difluorostyryl)pyridine, starting with diethyl diethyl (4-chloropyrimidin-2-yl)methylphosphonate. ¹H NMR (500 MHz, DMSO-d₆) δ 8.80 (d, J=5.2 Hz, 1H), 7.95 (d, J=16.2 Hz, 1H), 7.71 (d, J=10.4 Hz, 1H), 7.62 (d, J=7.6 Hz, 1H), 7.57 (d, J=5.2 Hz, 1H), 7.52-7.44 (m, 1H), 7.36 (d, J=16.2 Hz, 1H), 7.23 (td, J=8.5, 2.7 Hz, 1H), Mass spec.: 235.1 (MH)⁺.

Intermediate 89

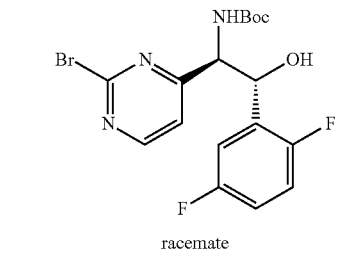

racemate

Tert-butyl(1R,2R)-1-(2-bromopyrimidin-4-yl)-2-(2,5-difluorophenyl)-2-hydroxyethylcarbamate Prepared according to the same procedure as tert-butyl (1R,2R)-1-(5-bromopyridin-3-yl)-2-(2,5-difluorophenyl)-2-hydroxyethylcarbamate, starting with (E)-2-bromo-4-(2,5-difluorostyryl)pyrimidine. ¹H NMR (500 MHz, DMSO-d₆) δ 8.70 (d, J=5.2 Hz, 1H), 7.65 (d, J=5.2 Hz, 1H), 7.45 (d, J=9.8 Hz, 1H), 7.29 (ddd, J=9.0, 5.3, 3.4 Hz, 1H), 7.22-7.10 (m, 2H), 5.82 (d, J=5.2 Hz, 1H), 5.46-5.30 (m, 1H), 4.85 (dd, J=9.8, 3.1 Hz, 1H), 1.29-1.03 (m, 9H), Mass spec.: 432.1 (MH)⁺.

Intermediate 90

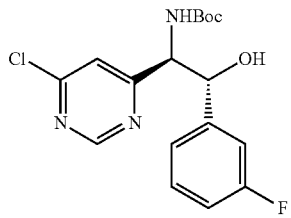

racemate

Tert-butyl(1R,2R)-1-(6-chloropyrimidin-4-yl)-2-(3-fluorophenyl)-2-hydroxyethylcarbamate Prepared according to the same procedure as tert-butyl (1R,2R)-1-(5-bromopyridin-3-yl)-2-(2,5-difluorophenyl)-2-hydroxyethylcarbamate, starting with (E)-4-chloro-6-(3-fluorostyryl)pyrimidine. ¹H NMR (500 MHz, DMSO-d₆) δ 9.03 (s, 1H), 7.78 (s, 1H), 7.41-7.31 (m, 1H), 7.27-7.14 (m, 3H), 7.06 (t, J=8.5 Hz, 1H), 5.69 (d, J=5.5 Hz, 1H), 5.15-5.05 (m, 1H), 4.87 (dd, J=9.5, 3.1 Hz, 1H), 1.25 (s, 9H), Mass spec.: 368.2 (MH)⁺.

Intermediate 91

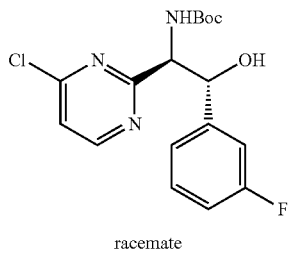

racemate

Tert-butyl(1R,2R)-1-(4-chloropyrimidin-2-yl)-2-(3-fluorophenyl)-2-hydroxyethylcarbamate and tert-butyl(1S,2S)-1-(4-chloropyrimidin-2-yl)-2-(3-fluorophenyl)-2-hydroxyethylcarbamate Prepared according to the same procedure as tert-butyl (1R,2R)-1-(5-bromopyridin-3-yl)-2-(2,5-difluorophenyl)-2-hydroxyethylcarbamate, starting with (E)-4-chloro-2-(3-fluorostyryl)pyrimidine. $^1$H NMR (500 MHz, DMSO-d$_6$) δ 8.78 (d, J=5.5 Hz, 1H), 7.62 (d, J=5.2 Hz, 1H), 7.41-7.27 (m, 1H), 7.24-7.13 (m, 1H), 7.11-6.98 (m, 1H), 6.67 (d, J=9.5 Hz, 1H), 5.65 (d, J=6.4 Hz, 2H), 5.23-5.15 (m, 1H), 4.89 (dd, J=9.5, 3.7 Hz, 1H), 1.29 (s, 9H), Mass pec.: 368.2 (MH)$^+$.

Intermediate 92

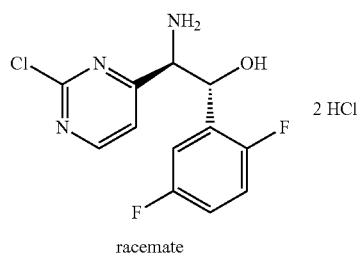

racemate (1R,2R)-2-Amino-2-(2-chloropyrimidin-4-yl)-1-(2,5-difluorophenyl)ethanol 2HCl Prepared according to the same procedure as (1R,2R)-2-amino-2-(5-bromopyridin-3-yl)-1-(2,5-difluorophenyl)ethanol, starting with tert-butyl(1R,2R)-1-(2-bromopyrimidin-4-yl)-2-(2,5-difluorophenyl)-2-hydroxyethylcarbamate. Analytical HPLC method: Phenomenex LUNA C18, 50×2 3μ, A=90% H$_2$O/10% CH$_3$CN, B=90% CH$_3$CN/10% H$_2$O, Modifier 0.1% TFA, 0.00 min=0% B, 4.0 min=100% B, 5.0 min=100% B, Flow rate=0.8 mL/min. T$_R$=1.937 min Mass spec.: 286.1 (MH)$^+$.

Intermediate 93

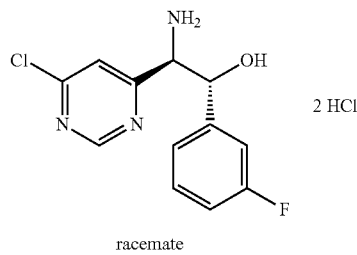

racemate (1R,2R)-2-Amino-2-(6-chloropyrimidin-4-yl)-1-(3-fluorophenyl)ethanol 2HCl Prepared according to the same procedure as (1R,2R)-2-amino-2-(5-bromopyridin-3-yl)-1-(2,5-difluorophenyl)ethanol, starting with tert-butyl(1R,2R)-1-(6-chloropyrimidin-4-yl)-2-(3-fluorophenyl)-2-hydroxyethylcarbamate. Analytical HPLC method: Phenomenex LUNA C18, 50×2 3μ, A=90% H$_2$O/10% CH$_3$CN, B=90% CH$_3$CN/10% H$_2$O, Modifier 0.1% TFA, 0.00 min=0% B, 4.0 min=100% B, 5.0 min=100% B, Flow rate=0.8 mL/min., T$_R$=1.460 min, Mass spec.: 268.1 (MH)$^+$.

Intermediate 94

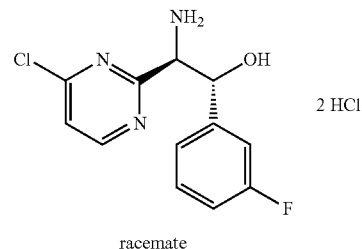

racemate (1R,2R)-2-Amino-2-(4-chloropyrimidin-2-yl)-1-(3-fluorophenyl)ethanol 2HCl Prepared according to the same procedure as (1R,2R)-2-amino-2-(5-bromopyridin-3-yl)-1-(2,5-difluorophenyl)ethanol, starting with tert-butyl (1R,2R)-1-(6-chloropyrimidin-4-yl)-2-(3-fluorophenyl)-2-hydroxyethylcarbamate. Analytical HPLC method: Phenomenex LUNA C18, 50×2 3μ, A=90% H$_2$O/10% CH$_3$CN, B=90% CH$_3$CN/10% H$_2$O, Modifier 0.1% TFA, 0.00 min=0% B, 4.0 min=100% B, 5.0 min=100% B, Flow rate=0.8 mL/min., T$_R$=1.823 min, Mass spec.: 268.1

Intermediate 95

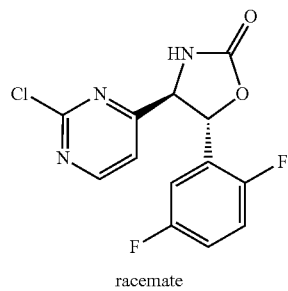

racemate (4R,5R)-4-(2-Chloropyrimidin-4-yl)-5-(2,5-difluorophenyl)oxazolidin-2-one Prepared according to the same procedure as (4R,5R)-4-(5-bromopyridin-3-yl)-5-(2,5-difluorophenyl)oxazolidin-2-one, starting with (1R,2R)-2-amino-2-(2-chloropyrimidin-4-yl)-1-(2,5-difluorophenyl)ethanol 2HCl. $^1$H NMR (500 MHz, DMSO-d$_6$) δ 8.88 (d, J=4.9 Hz, 1H), 8.69 (s, 1H), 7.68 (d, J=5.2 Hz, 1H), 7.50-7.28 (m, 3H), 5.71 (d, J=5.5 Hz, 1H), 5.04 (d, J=5.5 Hz, 1H), Mass spec.: 312.1 (MH)$^+$.

Intermediate 96

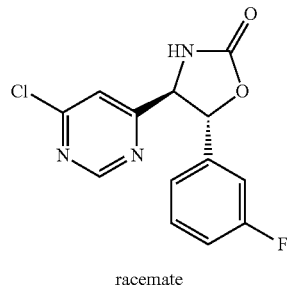

racemate

(4R,5R)-4-(6-Chloropyrimidin-4-yl)-5-(3-fluorophenyl)oxazolidin-2-one

Prepared according to the same procedure as (4R,5R)-4-(5-bromopyridin-3-yl)-5-(2,5-difluorophenyl)oxazolidin-2-one, starting with (1R,2R)-2-amino-2-(6-chloropyrimidin-4-yl)-1-(3-fluorophenyl)ethanol 2HCl. $^1$H NMR (500 MHz, DMSO-d$_6$) δ 9.13 (s, 1H), 8.55 (s, 1H), 7.86 (s, 1H), 7.52 (td, J=7.9, 6.1 Hz, 1H), 7.42-7.17 (m, 3H), 5.62 (d, J=4.9 Hz, 1H), 4.93 (d, J=5.2 Hz, 1H), Mass spec.: 294.1 (MH)$^+$.

Intermediate 97

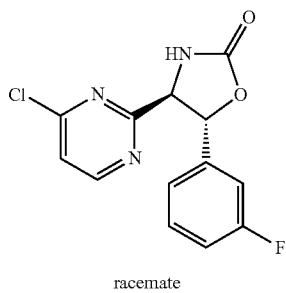

racemate

(4R,5R)-4-(4-Chloropyrimidin-2-yl)-5-(3-fluorophenyl)oxazolidin-2-one

Prepared according to the same procedure as (4R,5R)-4-(5-bromopyridin-3-yl)-5-(2,5-difluorophenyl)oxazolidin-2-one, starting with (1R,2R)-2-amino-2-(4-chloropyrimidin-2-yl)-1-(3-fluorophenyl)ethanol 2HCl, Analytical HPLC method: Phenomenex LUNA C18, 50×2 3μ, A=90% H$_2$O/10% CH$_3$CN, B=90% CH$_3$CN/10% H$_2$O, Modifier 0.1% TFA, 0.00 min=0% B, 4.0 min=100% B, 5.0 min=100% B, Flow rate=0.8 mL/min., T$_R$=2.483 min, Mass spec.: 294.1 (MH)$^+$.

Intermediate 98

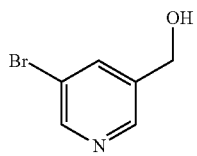

(5-Bromopyridin-3-yl)methanol

To a stirred solution of 5-bromonicotinaldehyde (5 g, 26.9 mmol) in ethanol (Volume: 100 mL) was added sodium borohydride (0.610 g, 16.13 mmol) slowly over five min at ambient temperature. A half hour later, the reaction mixture was placed in an ice bath then slowly added 50 mL saturated ammonium chloride and stirred for 5 min. After that the reaction mixture was concentrated in vacuo to provide a white solid to which was partitioned between water and ether. The ethereal layer was dried over magnesium sulfate, and concentrated to give a clear liquid of (5-bromopyridin-3-yl)methanol (4.8 g, 24.25 mmol, 90% yield). $^1$H NMR (500 MHz, DMSO-d$_6$) δ 8.59 (d, J=2.1 Hz, 1H), 8.51 (d, J=1.5 Hz, 1H), 8.01-7.93 (m, 1H), 5.46 (t, J=5.6 Hz, 1H), 4.55 (d, J=5.5 Hz, 2H), Mass spec.: 188.0 (MH)$^+$.

Intermediate 99

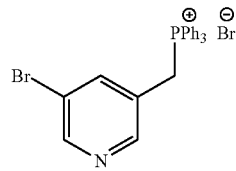

3-Bromo-5-((tri-phenylphosphino)methyl)pyridine bromide salt

To a solution of (5-bromopyridin-3-yl)methanol (1 g, 5.32 mmol) in acetic acid (Volume: 2 mL) was added hydrogen bromide (1.324 mL, 11.70 mmol) and triphenylphosphine (1.726 g, 6.38 mmol) then heat to 90° C. for four days, cooled to ambient temperature. The reaction mixture was wash with ether (20 mL×2) and EtOAc (20 mL×2) then was filtered and concentrated under high vacuum to remove solvent and provide a white solid of 3-bromo-5-((tri-phenylphosphino)methyl)pyridine bromide salt (3.05 g, 4.89 mmol, 92% yield). $^1$H NMR (500 MHz, DMSO-d$_6$) δ 8.64 (s, 1H), 8.24 (s, 1H), 7.94 (t, J=7.0 Hz, 3H), 7.83-7.70 (m, 12H), 7.46 (d, J=1.5 Hz, 1H), 5.32 (d, J=15.6 Hz, 2H), Mass spec.: 434.2 (MH)$^+$.

Intermediate 100 and Intermediate 101

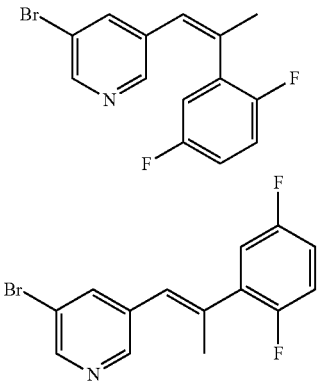

(Z)-3-Bromo-5-(2-(2,5-difluorophenyl)prop-1-enyl)pyridine/(E)-3-bromo-5-(2-(2,5-difluorophenyl)prop-1-enyl)pyridine To a stirred solution of 3-bromo-5-((tri-phenylphosphino)methyl)pyridine bromide salt (200 mg, 0.337 mmol) in tetrahydrofuran (Volume: 4 mL) was added sodium hydride (90 mg, 0.843 mmol) at 0° C. A half hour later, 2',5'-difluoroacetophenone (47.0 mL, 0.371 mmol) in tetrahydrofuran (Volume: 1 mL) was added to above solution. Ice bath was removed and heat it to reflux for overnight. Next morning, 10 mL water was added slowly then was extracted by ether (10 mL×3), combined all organic layers, dried over magnesium sulfate, concentrated and obtained a yellow oil which was purified by Preparative HPLC (Preparative HPLC Method 21) and obtained (Z)-3-bromo-5-(2-(2,5-difluorophenyl)prop-1-enyl)pyridine (22 mg, 0.071 mmol, 21.04%). $^1$H NMR (500 MHz, DMSO-d$_6$) δ 8.45 (d, J=2.1 Hz, 1H), 8.11 (d, J=1.5 Hz, 1H), 7.49 (t, J=2.0 Hz, 1H), 7.36-7.17 (m, 3H), 6.71 (s, 1H), 2.20 (d, J=1.2 Hz, 3H), Mass spec.: 312.1 (MH)$^+$. and (E)-3-bromo-5-(2-(2,5-difluorophenyl)prop-1- enyl)pyridine (18 mg, 0.058 mmol, 17.21%). $^1$H NMR (500 MHz, DMSO-$d_6$) δ 8.64 (dd, J=6.7, 1.8 Hz, 2H), 8.11 (t, J=1.8 Hz, 1H), 7.38 (ddd, J=9.3, 6.1, 3.2 Hz, 1H), 7.32 (td, J=9.7, 4.7 Hz, 1H), 7.28-7.21 (m, 1H), 6.72 (s, 1H), 2.23 (t, J=1.5 Hz, 3H), Mass spec.: 312.1 (MH)$^+$.

Intermediate 102 and Intermediate 103

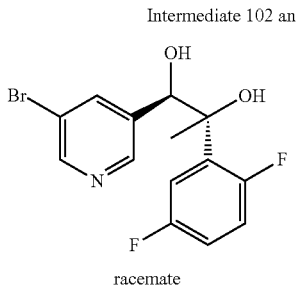

racemate

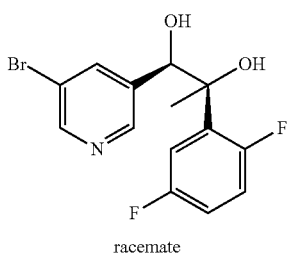

racemate (1R,2S)-1-(5-Bromopyridin-3-yl)-2-(2,5-difluorophenyl)propane-1,2-diol/(1R,2R)-1-(5-bromopyridin-3-yl)-2-(2,5-difluorophenyl)propane-1,2-diol To a stirred solution of (E)-3-bromo-5-(2-(2,5-difluorophenyl)prop-1-enyl)pyridine/(Z)-3-bromo-5-(2-(2,5-difluorophenyl)prop-1-enyl)pyridine (0.7 g, 2.257 mmol), NMO (1.058 g, 9.03 mmol) in acetone (Volume: 30 mL), Water (Volume: 3.33 mL) was added osmium tetroxide (0.354 mL, 0.045 mmol) at ambient temperature. After 18 hours, the reaction mixture was cooled to 0° C., and treated with a solution of sodium thiosulfate (1.3 g) in water (12 mL) and stirred 30 min at ambient temperature, the reaction mixture was poured into water (30 mL) and diluted with ether (30 mL). The ethereal layer was washed with water (20 mL×3), then brine, dried over magnesium sulfate, and concentrated to provide a white solid which was purified via column chromatography (30% to 45% EtOAc/Hex) to provide (1R,2S)-1-(5-bromopyridin-3-yl)-2-(2,5-difluorophenyl)propane-1,2-diol (138.1 mg, 0.401 mmol, 31.1% yield). $^1$H NMR (500 MHz, DMSO-$d_6$) δ 8.60 (d, J=2.1 Hz, 1H), 8.48 (d, J=1.5 Hz, 1H), 7.95 (t, J=2.0 Hz, 1H), 7.24 (ddd, J=10.1, 6.3, 3.4 Hz, 1H), 7.21-7.09 (m, 2H), 5.71 (d, J=5.2 Hz, 1H), 5.56 (s, 1H), 4.89 (d, J=5.5 Hz, 1H), 1.31 (d, J=1.2 Hz, 3H), Mass spec.: 346.0 (MH)$^+$. and (1R,2R)-1-(5-bromopyridin-3-yl)-2-(2,5-difluorophenyl)propane-1,2-diol (250 mg, 0.726 mmol, 56.3% yield). $^1$H NMR (500 MHz, DMSO-$d_6$) δ 8.44 (d, J=2.4 Hz, 1H), 8.02 (d, J=1.5 Hz, 1H), 7.75 (t, J=2.0 Hz, 1H), 7.20 (ddd, J=11.1, 9.0, 4.6 Hz, 1H), 7.07 (ddt, J=8.9, 7.4, 3.6 Hz, 1H), 6.93 (ddd, J=10.0, 6.2, 3.4 Hz, 1H), 5.96 (d, J=5.8 Hz, 1H), 5.66 (s, 1H), 4.84 (d, J=5.2 Hz, 1H), 1.63 (d, J=1.5 Hz, 3H), Mass spec.: 346.0 (MH)$^+$.

Intermediate 104 and Intermediate 105

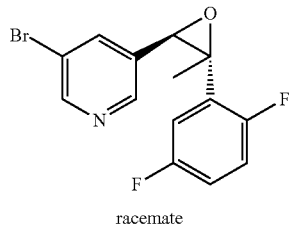

racemate

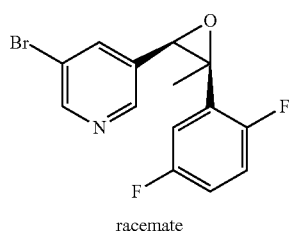

racemate

3-Bromo-5-((2R,3R)-3-(2,5-difluorophenyl)-3-methyloxiran-2-yl)pyridine/3-bromo-5-((2R,3S)-3-(2,5-difluorophenyl)-3-methyloxiran-2-yl)pyridine To a stirred solution of (1R,2S)-1-(5-bromopyridin-3-yl)-2-(2,5-difluorophenyl)propane-1,2-diol/(1R,2R)-1-(5-bromopyridin-3-yl)-2-(2,5-difluorophenyl)propane-1,2-diol (640 mg, 0.930 mmol) in methylene chloride (12 mL) was added Et$_3$N (0.168 mL, 1.209 mmol) and methanesulfonylchloride (0.152 mL, 1.953 mmol) at −10° C. After 1 hour, the reaction mixture was warmed to ambient temperature and continue stirred for 18 hours. 80 mL ether was added to reaction mixture then washed by water, brine, dried by magnesium sulfate, concentrated to provide 0.81 g off white solid which was dissolved in methanol (70 mL) then added potassium carbonate (643 mg, 4.65 mmol) at once at ambient temperature. After one hour, the reaction mixture was concentrated to provide a yellow solid that was dissolved in 40 mL ether then washed with water, brine, dried by magnesium sulfate to give a yellow liquid that was purified via column chromatography (2% to 5% EtOAc/Hex) to provide 3-bromo-5-((2R,3R)-3-(2,5-difluorophenyl)-3-methyloxiran-2-yl)pyridine (304.6 mg, 0.887 mmol, 95% yield). $^1$H NMR (500 MHz, DMSO-$d_6$) δ 8.74 (d, J=2.4 Hz, 1H), 8.62 (d, J=1.5 Hz, 1H), 8.10 (t, J=1.8 Hz, 1H), 7.41 (ddd, J=8.9, 5.6, 3.2 Hz, 1H), 7.38-7.33 (m, 1H), 7.32-7.25 (m, 1H), 4.36 (s, 1H), 1.36 (d, J=0.6 Hz, 3H), Mass spec.: 328.0 (MH)$^+$. and 3-bromo-5-((2R,3S)-3-(2,5-difluorophenyl)-3-methyloxiran-2-yl)pyridine (108.4 mg, 0.316 mmol, 34.0% yield). $^1$H NMR (500 MHz, DMSO-$d_6$) δ 8.50 (d, J=2.1 Hz, 1H), 8.28 (d, J=1.5 Hz, 1H), 7.63 (t, J=2.0 Hz, 1H), 7.30 (ddd, J=8.5, 5.4, 3.2 Hz, 1H), 7.19-7.03 (m, 2H), 4.51 (s, 1H), 1.73 (s, 3H), Mass spec.: 326.0 (MH)$^+$.

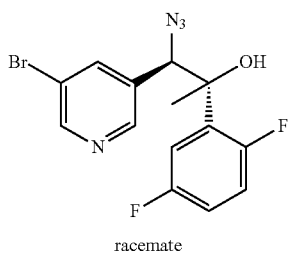

Intermediate 106 racemate

(1R,2R)-1-Azido-1-(5-bromopyridin-3-yl)-2-(2,5-difluorophenyl)propan-2-ol

Placed 3-bromo-5-((2R,3S)-3-(2,5-difluorophenyl)-3-methyloxiran-2-yl)pyridine (100 mg, 0.307 mmol), methanol (12 mL), water (1.500 mL), ammonium chloride (32.8 mg, 0.613 mmol), and sodium azide (120 mg, 1.840 mmol) in a microware tube and stirred for five minutes then sealed the tube and lowed it to a 110° C. oil bath for 18 hour. The reaction mixture was concentrate to provide a white solid to which was added 25 mL water then extracted it by ether (25 mL×3). Combined all ether layer, dried over magnesium sulfate, concentrated to afford clear wax which was purified via column chromatography (5% to 35% EtOAc/Hex) to provide (1R,2R)-1-azido-1-(5-bromopyridin-3-yl)-2-(2,5-difluorophenyl)propan-2-ol (96.2 mg, 0.248 mmol, 81% yield). $^1$H NMR (500 MHz, DMSO-$d_6$) δ 8.73 (d, J=2.1 Hz, 1H), 8.60 (d, J=1.8 Hz, 1H), 8.06 (t, J=1.8 Hz, 1H), 7.40 (ddd, J=9.8, 6.2, 3.2 Hz, 1H), 7.33-7.15 (m, 2H), 6.14 (s, 1H), 5.13 (s, 1H), 1.33 (d, J=0.9 Hz, 3H), Mass spec.: 371.1 (MH)$^+$.

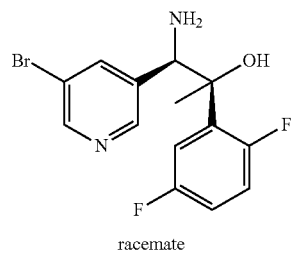

Intermediate 108 racemate

(1R,2S)-1-Amino-1-(5-bromopyridin-3-yl)-2-(2,5-difluorophenyl)propan-2-ol

To a solution of (1R,2S)-1-azido-1-(5-bromopyridin-3-yl)-2-(2,5-difluorophenyl)propan-2-ol (44 mg, 0.119 mmol) in tetrahydrofuran (2 mL) at 0° C. was added trimethylphosphine (0.179 mL, 0.179 mmol) drop wise. Ice bath was removed once no more nitrogen gas come out. One hour later, water (0.1000 mL) was added and continuously stirred for 18 hours. The reaction mixture was concentrated to afford a yellow oil that was redissolved in 5 mL ether then washed with 10 mL water. The ether layer was dried by magnesium sulfate, filtered, and concentrated to provide a light yellow of (1R,2S)-1-amino-1-(5-bromopyridin-3-yl)-2-(2,5-difluorophenyl)propan-2-ol (42.2 mg, 0.111 mmol, 93% yield). $^1$H NMR (500 MHz, DMSO-$d_6$) δ 8.36 (d, J=2.1 Hz, 1H), 8.01 (d, J=1.8 Hz, 1H), 7.73 (t, J=2.0 Hz, 1H), 7.15 (ddd, J=11.1, 8.9, 4.7 Hz, 1H), 7.06-6.98 (m, 1H), 6.90 (ddd, J=9.9, 6.3, 3.4 Hz, 1H), 5.70 (s, 1H), 4.13 (s, 1H), 3.33 (s, 2H), 1.65 (d, J=1.5 Hz, 3H), Mass spec.: 345.1 (MH)$^+$.

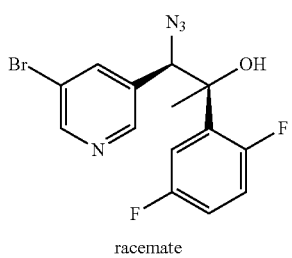

Intermediate 107 racemate

(1R,2S)-1-Azido-1-(5-bromopyridin-3-yl)-2-(2,5-difluorophenyl)propan-2-ol

Prepared according to the same procedure as (1R,2R)-1-azido-1-(5-bromopyridin-3-yl)-2-(2,5-difluorophenyl)propan-2-ol, starting with 3-bromo-5-((2R,3R)-3-(2,5-difluorophenyl)-3-methyloxiran-2-yl)pyridine $^1$H NMR (400 MHz, DMSO-$d_6$) δ 8.57 (d, J=2.3 Hz, 1H), 8.32 (d, J=1.8 Hz, 1H), 7.86 (t, J=2.0 Hz, 1H), 7.20 (ddd, J=11.0, 9.0, 4.6 Hz, 1H), 7.15-7.02 (m, 2H), 6.38 (s, 1H), 5.08 (s, 1H), 1.72 (d, J=1.3 Hz, 3H). Mass spec.: 371.1 (MH)$^+$.

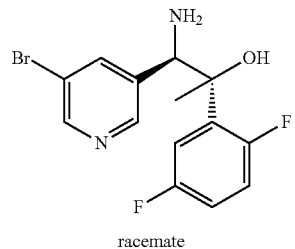

Intermediate 109 racemate

(1R,2R)-1-Amino-1-(5-bromopyridin-3-yl)-2-(2,5-difluorophenyl)propan-2-ol

Prepared according to the same procedure as (1R,2S)-1-amino-1-(5-bromopyridin-3-yl)-2-(2,5-difluorophenyl)propan-2-ol, starting with (1R,2R)-1-azido-1-(5-bromopyridin-3-yl)-2-(2,5-difluorophenyl)propan-2-ol $^1$H NMR (500 MHz, DMSO-$d_6$) δ 8.57 (d, J=2.1 Hz, 1H), 8.45 (d, J=1.5 Hz, 1H), 8.03 (t, J=1.8 Hz, 1H), 7.38-7.31 (m, 1H), 7.23-7.10 (m, 2H), 5.60 (s, 1H), 4.18 (s, 1H), 1.91 (br. s., 2H), 1.24 (d, J=1.2 Hz, 3H), Mass spec.: 343.1 (MH)$^+$.

85

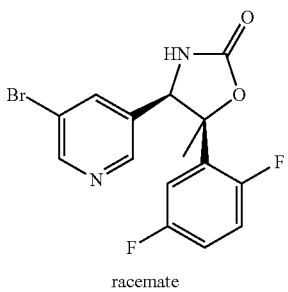

Intermediate 110 racemate (4R,5S)-4-(5-Bromopyridin-3-yl)-5-(2,5-difluorophenyl)-5-methyloxazolidin-2-one Prepared according to the same procedure as ((4R,5R)-4-(5-bromopyridin-3-yl)-5-(2,5-difluorophenyl)oxazolidin-2-one, starting with (1R,2S)-1-amino-1-(5-bromopyridin-3-yl)-2-(2,5-difluorophenyl)propan-2-ol. $^1$H NMR (500 MHz, DMSO-d$_6$) δ 8.64 (s, 1H), 8.52-8.46 (m, 1H), 8.29 (s, 1H), 7.66 (s, 1H), 7.19 (ddd, J=9.2, 5.9, 3.2 Hz, 1H), 7.13-7.06 (m, 1H), 7.00 (ddd, J=10.6, 9.2, 4.6 Hz, 1H), 5.15 (d, J=1.8 Hz, 1H), 1.89 (s, 3H), Mass spec.: 371.1 (MH)$^+$.

Intermediate 111 racemate (4R,5R)-4-(5-Bromopyridin-3-yl)-5-(2,5-difluorophenyl)-5-methyloxazolidin-2-one Prepared according to the same procedure as (4R,5R)-4-(5-bromopyridin-3-yl)-5-(2,5-difluorophenyl)oxazolidin-2-one, starting with (1R,2R)-1-amino-1-(5-bromopyridin-3-yl)-2-(2,5-difluorophenyl)propan-2-ol. $^1$H NMR (500 MHz, DMSO-d$_6$) δ 8.77 (d, J=2.4 Hz, 1H), 8.51 (d, J=1.5 Hz, 1H), 7.95 (t, J=2.0 Hz, 1H), 7.46 (ddd, J=10.9, 9.1, 4.4 Hz, 1H), 7.40-7.33 (m, 1H), 7.25 (ddd, J=9.3, 6.1, 3.2 Hz, 1H), 5.15 (d, J=1.5 Hz, 1H), 1.85 (s, 1H) 1.25 (s, 3H), Mass spec.: 371.1 (MH)$^+$.

Intermediate 112

86

(E)-4-Bromo-2-(4-fluorostyryl)pyridine

A solution of (E)-4-fluorostyrylboronic acid (5 g, 30.1 mmol) and 2,4-dibromopyridine (6.49 g, 27.4 mmol) in tetrahydrofuran (150 mL) was purged with nitrogen for 20 min. To this was added Pd(Ph$_3$P)$_4$ (2.37 g, 2.05 mmol) and a 10% w/w solution of thallium(I) hydroxide (137 g, 62 mmol) in water. The reaction was stirred under nitrogen at room temperature. After 3 h, the gray suspension was diluted with dichloromethane and filtered through celite. The organics were washed with water, dried over magnesium sulfate, and concentrated. The resulting residue was purified by column chromatography (5%→13% EtOAc/Hex) to give 2.65 g (33%). $^1$H NMR (CDCl$_3$) Shift: 8.43 (d, J=5.2 Hz, 1H), 7.64 (d, J=15.9 Hz, 1H), 7.50-7.59 (m, 3H), 7.34 (dd, J=5.3, 1.7 Hz, 1H), 7.10 (t, J=8.7 Hz, 2H), 7.02 (d, J=16.2 Hz, 1H). $^{13}$C NMR (CDCl$_3$) Shift: 163.1, 157.0, 150.4, 133.3, 133.2, 132.5, 129.0, 126.4, 125.3, 116.0. $^{19}$F NMR (CDCl$_3$) Shift: −112.69 (bs, 1F). Mass spec.: 278.2 (MH)$^+$.

Intermediate 113

1,4-Difluoro-2-vinylbenzene

To a suspension of methyltriphenylphosphonium bromide (26.4 g, 73.9 mmol) in tetrahydrofuran (350 mL) at 0° C. was added nBuLi (2.5M in hexane, 29.6 mL, 73.9 mmol). After addition was complete, the reaction was stirred at 0° C. for 10 min. To this was added 2,5-difluorobenzaldehyde (5.35 mL, 49.3 mmol). The ice bath was removed, and stirring continued for 1 h. The reaction was quenched by addition of saturated ammonium chloride. The reaction was poured into ether, washed with water (3×), then brine, dried over magnesium sulfate, and concentrated. Column chromatography (2.5% EtOAc/Hex) gave 2.1 g (30%) as a colorless oil. $^1$H NMR (CDCl$_3$) Shift: 7.20 (ddd, J=9.2, 5.9, 3.2 Hz, 1H), 7.02 (td, J=9.3, 4.6 Hz, 1H), 6.90-6.97 (m, 1H), 6.86 (dd, J=17.7, 11.3 Hz, 1H), 5.84 (d, J=17.7 Hz, 1H), 5.45 (d, J=11.0 Hz, 1H). $^{13}$C NMR (CDCl$_3$) Shift: 158.6, 156.3, 128.6, 126.8, 117.6, 116.8, 115.6, 113.0. 19F NMR (CDCl$_3$) Shift: −120.17- 119.46 (m, 1F), −125.20 (d, J=17.3 Hz, 1F).

Intermediate 114

(E)-2-Bromo-4-(2,5-difluorostyryl)-5-fluoropyridine

A suspension of 2-bromo-5-fluoropyridin-4-ylboronic acid (1.569 g, 7.14 mmol) and 1,4-difluoro-2-vinylbenzene (1

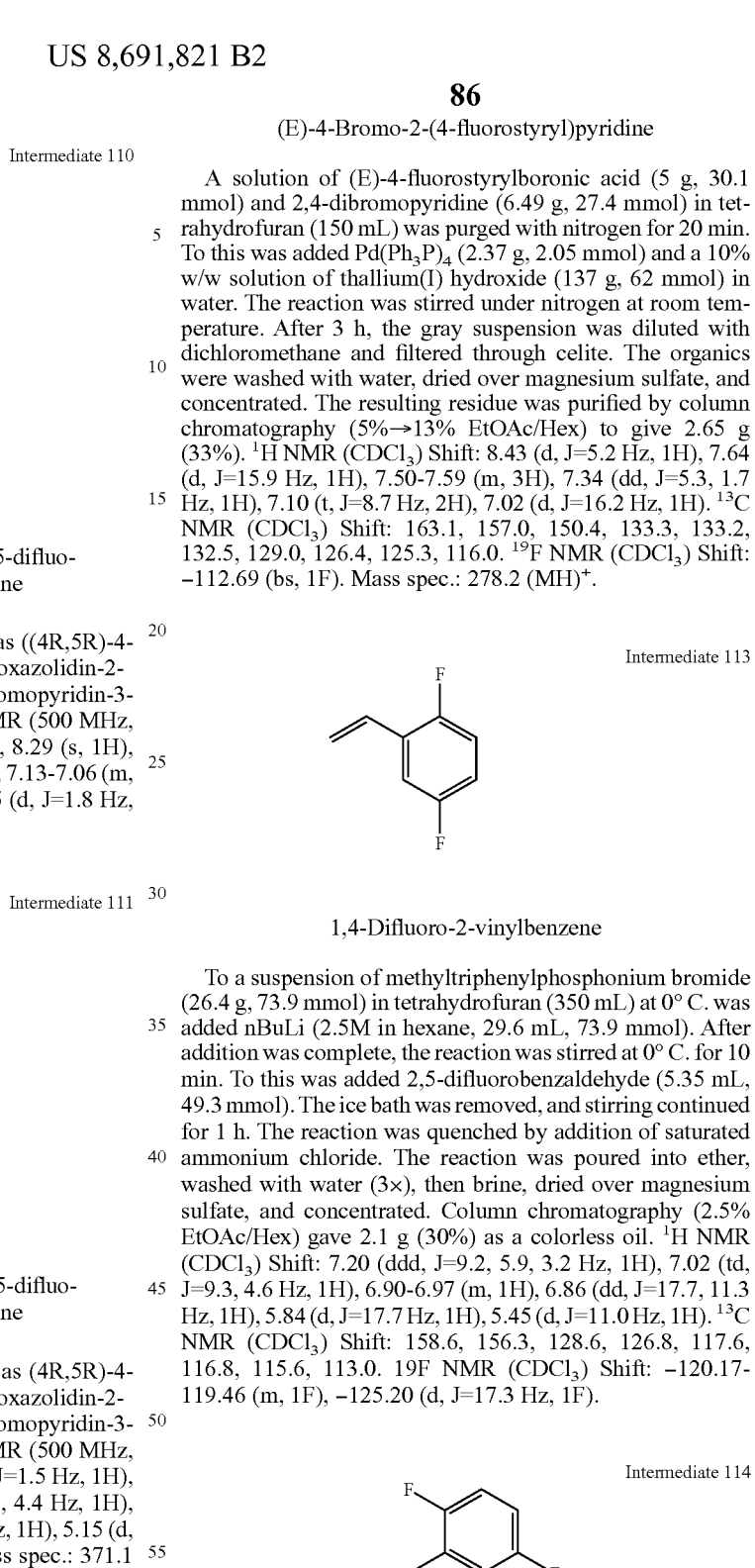

g, 7.14 mmol) in dimethylformamide (20 mL) was flushed with a balloon of oxygen. To this was added sodium carbonate (1.51 g, 14.3 mmol) and palladium(II) acetate (0.16 g, 0.71 mmol) as solids in one portion. The flask was flushed with another balloon of oxygen and fitted with a balloon of oxygen. The reaction was warmed to 50° C. After 1 h, the reaction was treated with a second portion of sodium carbonate (0.75 g) and boronic acid (1.6 g). This process was repeated twice more (total boronic acid addition=6.3 g). The reaction was cooled to room temperature, diluted with ether, washed with water (3×), then brine, dried over magnesium sulfate, and concentrated. Column chromatography (2.5%→5% EtOAc/Hex) gave 89 mg (4.0%) as a white solid. $^1$H NMR (CDCl$_3$) Shift: 8.28 (d, J=1.8 Hz, 1H), 7.68 (d, J=5.5 Hz, 1H), 7.49 (d, J=16.5 Hz, 1H), 7.33 (ddd, J=8.9, 5.8, 3.1 Hz, 1H), 7.17 (d, J=16.8 Hz, 1H), 6.98-7.14 (m, 2H). $^{19}$F NMR (CDCl$_3$) Shift: −118.54 (d, J=13.0 Hz, 1F), −122.71 (br. s., 1F), −135.71 (br. s., 1F). Mass spec.: 314.0 (MH)$^+$.

Intermediate 115

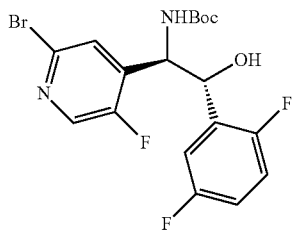

Optically-enriched tert-butyl (1R,2R)-1-(2-bromo-5-fluoropyridin-4-yl)-2-(2,5-difluorophenyl)-2-hydroxyethylcarbamate To tert-butyl carbamate (206 mg, 1.76 mmol) in propanol (1 mL) was added sodium hydroxide (69.1 mg, 1.73 mmol) in water (1.9 mL) followed by tert-butyl hypochlorite (0.195 mL, 1.73 mmol). After 5 min, the solution was cooled to 0° C. and treated with a solution of (DHQD)$_2$PHAL (22.1 mg, 0.028 mmol) in propanol (0.9 mL). The reaction was diluted with propanol (1.25 mL) and treated with (E)-2-bromo-4-(2,5-difluorostyryl)-5-fluoropyridine (89 mg, 0.28 mmol) as a solid in one portion. To this was added potassium osmate dihydrate (8.4 mg, 0.023 mmol) as a solid in one portion. The reaction was allowed to gradually warm to room temperature in the dewar over 8 h. The reaction was cooled to 0° C. and quenched by addition of sodiumthiosulfate (210 mg) in water (1 mL). The reaction was stirred at room temperature for 30 min. The reaction was extracted with ether (2×). The ethereal was washed with water (2×), then brine, dried over magnesium sulfate, and concentrated to give a solid (quant.). The material was used without purification. Mass spec.: 447.1 (MH)$^+$.

Intermediate 116

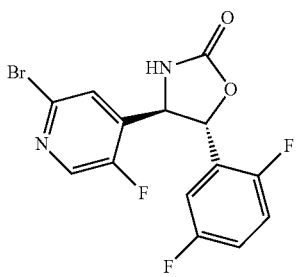

Optically-enriched (4R,5R)-4-(2-bromo-5-fluoropyridin-4-yl)-5-(2,5-difluorophenyl)oxazolidin-2-one Optically-enriched tert-butyl (1R,2R)-1-(2-bromo-5-fluoropyridin-4-yl)-2-(2,5-difluorophenyl)-2-hydroxyethylcarbamate (253 mg, 0.283 mmol) was dissolved in trifluoroacetic acid (10% in dichloromethane, 10 mL) and stirred at room temperature overnight. In the morning, the reaction was concentrated and loaded onto a strong cation exchange cartridge. The cartridge was flushed with several volumes of methanol which were discarded. The crude aminoalcohol was eluted with 2M ammonia in methanol and concentrated to give 53 mg as a solid. The crude solid was dissolved in tetrahydrofuran (5 mL), cooled to 0° C., and treated with carbonyldiimidazole (45.9 mg, 0.283 mmol). After 5 min, the ice bath was removed, and stirring continued for 1 h. The reaction was quenched by addition of 2M ammonia in methanol. The reaction was concentrated and purified by column chromatography (25%→50% EtOAc/Hex) to give 20 mg (9.5%). Mass spec.: 373.1 (MH)$^+$.

Intermediate 117

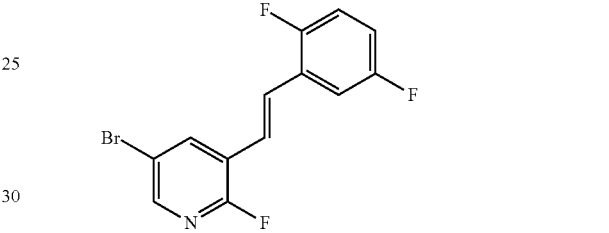

(E)-5-Bromo-3-(2,5-difluorostyryl)-2-fluoropyridine

A round bottom flask was charged with 1,4-difluoro-2-vinylbenzene (1 g, 7.14 mmol), 5-bromo-2-fluoro-3-(4,4,5,5-tetramethyl-1,3,2-dioxaborolan-2-yl)pyridine (2.69 g, 8.92 mmol), and DMF (27 mL). The resulting mixture was purged with a stream of oxygen for 10 min. To this was added sodium carbonate (1.89 g, 17.8 mmol) and palladium (II) acetate (0.128 g, 0.571 mmol) as a solid in a single portion. The reaction was purged with oxygen for 5 min. The reaction was fitted with a balloon of oxygen and stirred at room temperature overnight. In the morning, the reaction was diluted with ethyl acetate and poured into water. The mixture was treated with excess celite and filtered to remove solids. The organic layer was washed with water (2×), then brine, dried over magnesium sulfate, and concentrated. Column chromatography (10% EtOAc/Hex) gave 409 mg (17%). $^1$H NMR (CDCl$_3$) δ: 8.16-8.22 (m, 1H), 8.13 (dd, J=8.2, 2.4 Hz, 1H), 7.29-7.39 (m, 2H), 7.06-7.20 (m, 2H), 6.97-7.06 (m, 1H). $^{19}$F NMR (CDCl$_3$) δ: −74.07 (d, J=8.7 Hz, 1F), −118.78 (d, J=8.7 Hz, 1F), −123.39 (br. s., 1F). Mass spec.: 314.1 (MH)$^+$.

Intermediate 118

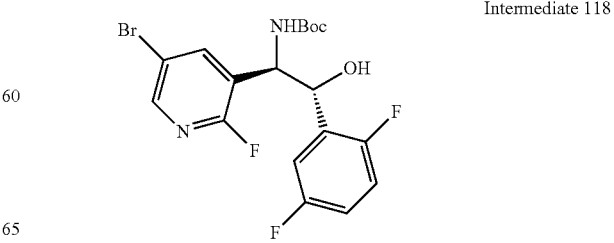

Optically-enriched tert-butyl (1R,2R)-1-(5-bromo-2-fluoropyridin-3-yl)-2-(2,5-difluorophenyl)-2-hydroxyethylcarbamate To tert-butyl carbamate (0.462 g, 3.95 mmol) in propanol (6 mL) was added sodium hydroxide (0.155 g, 3.88 mmol) in water (12 mL) followed by tert-butyl hypochlorite (0.438 mL, 3.88 mmol). The solution was cooled to 0° C., and (DHQD)$_2$PHAL (0.060 g, 0.076 mmol) was added in propanol (6 mL), followed by (E)-5-bromo-3-(2,5-difluorostyryl)-2-fluoropyridine (0.4 g, 1.273 mmol) as a solid. The remaining residue was dissolved in propanol (12 mL) and added to the reaction mixture to give a suspension. To this was added potassium osmate dihydrate (0.019 g, 0.051 mmol) as a solid in one portion. The reaction was allowed to gradually warm in the dewar overnight. The reaction was recooled to 0° C., and the reaction quenched by addition of sodium thiosulfate (0.5 g) in water (3 mL). The ice bath was removed, and the reaction stirred at room temperature for 30 min. The reaction was diluted with diethyl ether, washed with water (2×), then brine, dried over magnesium sulfate, and concentrated. Column chromatography (25% EtOAc/Hex) gave 0.445 g (78%) as a white foam solid. Mass spec.: 447.1 (MH)$^+$.

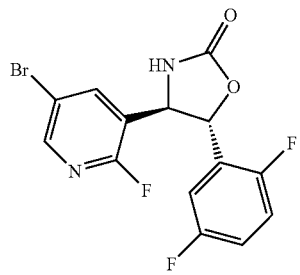

Intermediate 119

(4R,5R)-4-(5-Bromo-2-fluoropyridin-3-yl)-5-(2,5-difluorophenyl)oxazolidin-2-one

To a solution of optically-enriched tert-butyl (1R,2R)-1-(5-bromo-2-fluoropyridin-3-yl)-2-(2,5-difluorophenyl)-2-hydroxyethylcarbamate (380 mg, 0.850 mmol) in dichloromethane (6 mL) at room temperature was added hydrochloric acid (4M in dioxane, 10 mL, 40.0 mmol). The resulting solution was placed in a 45° C. bath. After 20 min, the reaction was concentrated. The resulting viscous oil was dissolved in and reconcentrated from tetrahydrofuran (3×) to give a white solid. The resulting residue was suspended in tetrahydrofuran (15 mL), and treated with diethylisopropylamine (0.297 mL, 1.70 mmol). After stirring briefly, the mixture was cooled to 0° C. and treated with carbonyldiimidazole (207 mg, 1.27 mmol) as a solid in one portion. The ice bath was removed and stirring continued for 1.5 h. The reaction was quenched by addition of 2M ammonia in methanol and concentrated. The material was purified by column chromatography (EtOAc/Hex) to give the product as a mixture of regioisomers. The material was re-purified by chiral prep HPLC (Chiralcel OJ, 30% EtOH/heptane/0.1% DEA) to afford 88 mg (25%). $^1$H NMR (CDCl$_3$) δ: 8.33 (dd, J=2.3, 1.4 Hz, 1H), 8.11 (dd, J=8.2, 2.1 Hz, 1H), 7.21-7.27 (m, 1H), 7.09-7.17 (m, 2H), 6.48 (br. s., 1H), 5.58 (d, J=5.8 Hz, 1H), 5.04 (d, J=5.5 Hz, 1H). $^{19}$F NMR (CDCl$_3$) δ: −74.27 (br. s., 1F), −116.97 (d, J=17.3 Hz, 1F), −123.78-123.41 (m, 1F). Mass spec.: 373.0 (MH)$^+$.

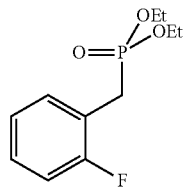

Intermediate 120

Diethyl 2-fluorobenzylphosphonate

Prepared according to the method used to prepare diethyl 3-fluorobenzylphosphonate starting with 1-(bromomethyl)-2-fluorobenzene. $^1$H NMR (CDCl$_3$) δ: 7.36 (t, J=7.5 Hz, 1H), 7.19-7.25 (m, 1H), 7.07-7.13 (m, 1H), 7.04 (t, J=9.2 Hz, 1H), 3.99-4.08 (m, 4H), 3.15-3.24 (m, 2H), 1.25 (td, J=7.0, 0.9 Hz, 6H).

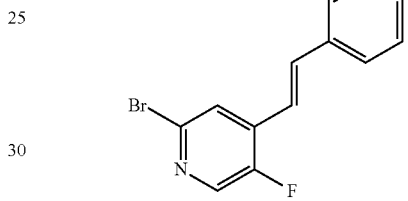

Intermediate 121

(E)-2-Bromo-5-fluoro-4-(2-fluorostyryl)pyridine

To a solution of 2-bromo-5-fluoroisonicotinaldehyde (2 g, 9.80 mmol) and diethyl 2-fluorobenzylphosphonate (2.66 g, 10.78 mmol) in tetrahydrofuran (80 mL) at 0° C., was added potassium tert-butoxide(1M in tetrahydrofuran, 12.75 mL, 12.75 mmol) dropwise over a couple of minutes. When addition was complete, the reaction was allowed to stir at 0° C. for 45 min and quenched by addition of saturated ammonium chloride. The reaction was diluted with ether, washed with water (4×), then brine, dried over magnesium sulfate, and concentrated. Column chromatography (8%→15% EtOAc/Hex) gave 450 mg as an oil with solid crystallizing from the mixture. The material was triturated with hexanes (2×) to give a fine white powder. $^1$H NMR (CDCl$_3$) δ: 8.26 (d, J=1.5 Hz, 1H), 7.69 (d, J=5.5 Hz, 1H), 7.64 (td, J=7.6, 1.5 Hz, 1H), 7.54 (d, J=16.8 Hz, 1H), 7.30-7.41 (m, 1H), 7.17-7.26 (m, 2H), 7.11-7.17 (m, 1H). $^{13}$C NMR (CDCl$_3$) δ: 161.0, 156.7, 138.8, 136.6, 135.5, 131.0, 129.3, 127.9, 124.6, 123.7, 119.4, 116.3. $^{19}$F NMR (CDCl$_3$) δ: −116.72 (br. s., 1F), −136.08 (br. s., 1F).

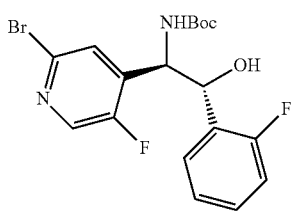

Intermediate 122

Optically-enriched tert-butyl (1R,2R)-1-(2-bromo-5-fluoropyridin-4-yl)-2-(2-fluorophenyl)-2-hydroxy-ethylcarbamate To tert-butyl carbamate (150 mg, 1.28 mmol) in n-propanol (1.75 mL) was added sodium hydroxide (49.8 mg, 1.25 mmol) in water (3.5 mL) followed by tert-butyl hypochlorite (0.141 mL, 1.246 mmol). After 5 min, the solution was cooled to 0° C. and treated with a solution of DHQD2(PHAL) (16.57 mg, 0.021 mmol) in n-propanol (1.75 mL). The reaction was diluted with n-propanol (3.5 mL) and treated with (E)-2-bromo-5-fluoro-4-(2-fluorostyryl)pyridine (90 mg, 0.304 mmol) as a solid in one portion. To this was added potassium osmate dihydrate (5.60 mg, 0.015 mmol) as a solid in one portion. The reaction was allowed to gradually warm to room temperature in the dewar overnight. The reaction was cooled to 0° C. and quenched by addition of sodium thiosulfate (150 mg) in water (3 mL). The ice bath was removed and stirring continued for 30 min. The reaction was diluted with ether, washed with water (3×), then brine, dried over magnesium sulfate, and concentrated. Column chromatography (25% EtOAc/Hex) gave 93 mg (36%) as a foam solid. Mass spec.: 429.1 (MH)+.

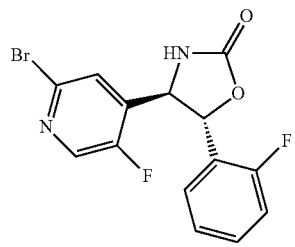

Intermediate 123

Optically-enriched (4R,5R)-4-(2-bromo-5-fluoropyridin-4-yl)-5-(2-fluorophenyl)oxazolidin-2-one To a solution of optically-enriched tert-butyl (1R,2R)-1-(2-bromo-5-fluoropyridin-4-yl)-2-(2-fluorophenyl)-2-hydroxyethylcarbamate (93 mg, 0.108 mmol) in dichloromethane (2 mL) at room temperature was added hydrogen chloride (4M in dioxane, 2 mL, 8 mmol). The reaction was warmed to 45° C. and held at that temperature for 1 h. The reaction was concentrated. The reaction was concentrated twice more from tetrahydrofuran. The resulting residue was suspended in tetrahydrofuran (2 mL), cooled to 0° C., and treated with diethylisopropylamine (0.038 mL, 0.217 mmol) and carbonyldiimidazole (26.3 mg, 0.162 mmol). After 5 min, the ice bath was removed and stirring continued for 3 h. The reaction was quenched by addition of 2M ammonia in methanol and concentrated. The resulting residue was suspended in dichloromethane, diluted with ethyl acetate, washed with brine, dried over magnesium sulfate, and concentrated. Column chromatography (25%→50% EtOAc/Hex) gave 37.8 mg (49%) as a colorless film. HNMR showed that it was a 1:1 mixture of regioisomers. The mixture was used without separation. Mass spec.: 355.0 (MH)+.

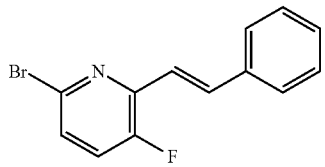

Intermediate 124

(E)-6-Bromo-3-fluoro-2-styrylpyridine

To a solution of 6-bromo-3-fluoropicolinaldehyde (2.147 g, 10.5 mmol) and diethyl benzylphosphonate (2.413 mL, 11.6 mmol) in tetrahydrofuran (80 mL) at 0° C., was added potassium tert-butoxide(1M in tetrahydrofuran, 11.6 mL, 11.6 mmol) dropwise over a couple of minutes. When addition was complete, the reaction was allowed to stir at 0° C. for 45 min and quenched by addition of saturated ammonium chloride. The reaction was diluted with ether, washed with water (4×), then brine, dried over magnesium sulfate, and concentrated. Column chromatography (8%→15% EtOAc/Hex) gave 121 mg (4.1%). $^1$H NMR (CDCl$_3$) δ: 7.86 (d, J=16.2 Hz, 1H), 7.64 (d, J=7.3 Hz, 2H), 7.39-7.47 (m, 2H), 7.22-7.39 (m, 4H). $^{19}$F NMR (CDCl$_3$) δ: −130.05 (br. s., 1F). Mass spec.: 278.0 (MH)+.

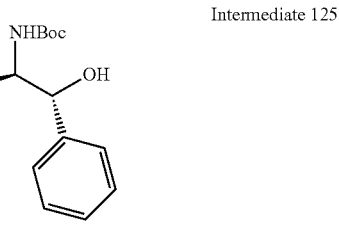

Intermediate 125

Optically-enriched tert-butyl (1R,2R)-1-(6-bromo-3-fluoropyridin-2-yl)-2-hydroxy-2-phenylethylcarbamate To tert-butyl carbamate (214 mg, 1.827 mmol) in n-propanol (1.75 mL) was added sodium hydroxide (71.3 mg, 1.784 mmol) in water (3.5 mL) followed by tert-butyl hypochlorite (0.201 mL, 1.78 mmol). After 5 min, the solution was cooled to 0° C. and treated with a solution of DHQD$_2$(PHAL) (23.7 mg, 0.030 mmol) in n-propanol (1.75 mL). The reaction was diluted with n-propanol (3.5 mL), and treated with (E)-6-bromo-3-fluoro-2-styrylpyridine (121 mg, 0.435 mmol) as a solid in one portion. To this was added potassium osmate dihydrate (8.01 mg, 0.022 mmol) as a solid in one portion. The reaction was allowed to gradually warm to room temperature in the dewar overnight. The reaction was cooled to 0° C. and quenched by addition of sodium thiosulfate (150 mg) in water (3 mL). The ice bath was removed and stirring continued for 30 min. The reaction was diluted with ether, washed with water (3×), then brine, dried over magnesium sulfate, and concentrated. Column chromatography (25% EtOAc/Hex) gave 208 mg (quant.). Mass spec.: 411.1 (MH)+.

Intermediate 126

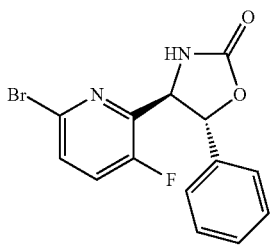

Optically-enriched (4R,5R)-4-(6-bromo-3-fluoropyridin-2-yl)-5-phenyloxazolidin-2-one Optically-enriched tert-butyl (1R,2R)-1-(6-bromo-3-fluoropyridin-2-yl)-2-hydroxy-2-phenylethylcarbamate (208 mg, 0.506 mmol) was dissolved in trifluoroacetic acid (25% in dichloromethane, 10 mL). After 2 h at room temperature, the reaction was concentrated. The resulting residue was loaded onto a strong cation exchange cartridge which was flushed with several volumes of methanol and discarded. The product was eluted with 2M ammonia in methanol and concentrated. The resulting residue was suspended in tetrahydrofuran (2 mL), cooled to 0° C., and treated with carbonyldiimidazole (123 mg, 0.759 mmol). After 5 min, the ice bath was removed and stirring continued overnight. The reaction was quenched by addition of 2M ammonia in methanol and concentrated. The resulting residue was purified by column chromatography (25%→50% EtOAc/Hex) to give 96 mg (28%) as a white foam solid. Mass spec.: 337.0 (MH)+.

Intermediate 127

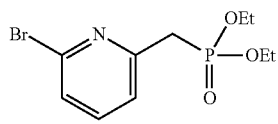

Diethyl(6-bromopyridin-2-yl)methylphosphonate

To a solution of (6-bromopyridin-2-yl)methanol (12.5 g, 66.5 mmol) and triethylamine (12.1 mL, 86 mmol) in dichloromethane (150 mL) at 0° C. was added methanesulfonylchloride (5.44 mL, 69.8 mmol) dropwise. After 1 h at 0° C., the reaction was diluted with ether, quenched by addition of saturated sodium bicarbonate, and stirred for 30 min at 0° C. The layers were separated and the organics washed with water, then brine, dried over magnesium sulfate, and concentrated (quant.). Mass spec.: 266.0 (MH)+.

To a suspension of sodium hydride (5.32 g, 133 mmol) in tetrahydrofuran (250 mL) in a room temperature bath was added diethylphosphite (17.2 mL, 133 mmol) dropwise. After addition was complete, the room temperature bath was removed. After 2 h, the resulting mixture was cooled to 0° C. and treated with a solution of the crude mesylate in tetrahydrofuran (125 mL). After 1 h at 0° C., the ice bath was removed and stirring continued for 2 h. The reaction was poured into ether (1 L), washed with water (3×), then brine, dried over MgSO3, and concentrated. Column chromatography (50% EtOAc/Hex→100% EtOAc) gave 12.58 g (61%) as a faint yellow oil. 1H NMR (CDCl3) δ: 7.49-7.56 (m, 1H), 7.39 (td, J=8.2, 2.3 Hz, 2H), 4.07-4.17 (m, 4H), 3.35-3.46 (m, 2H), 1.31 (t, J=7.0 Hz, 6H). 13C NMR (CDCl3) δ: 154.2, 141.5, 138.9, 126.4, 123.3, 62.5, 36.3, 16.4. Mass spec.: 308.1 (MH)+.

Intermediate 128

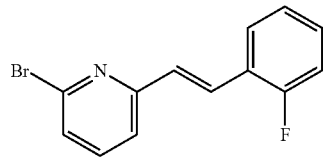

(E)-2-Bromo-6-(2-fluorostyryl)pyridine

To a solution of diethyl (6-bromopyridin-2-yl)methylphosphonate (320 mg, 1.039 mmol) in tetrahydrofuran (9.4 mL) was added 2-fluorobenzaldehyde (129 mg, 1.04 mmol). The resulting solution was cooled to 0° C., and treated with potassium tert-butoxide (1M in tetrahydrofuran, 1.1 mL, 1.1 mmol). After 15 min at 0° C., the reaction was quenched by addition of saturated ammonium chloride and concentrated. The resulting residue was dissolved in ether, washed with water, then brine, dried over magnesium sulfate, and concentrated to give an oil which solidified upon standing. The solid was triturated with hexane to afford 215 mg (78%). 1H NMR (CDCl3) δ: 7.78 (d, J=16.2 Hz, 1H), 7.64 (td, J=7.6, 1.5 Hz, 1H), 7.50-7.58 (m, 1H), 7.37 (t, J=7.8 Hz, 2H), 7.29-7.34 (m, 1H), 7.15-7.26 (m, 2H), 7.12 (dd, J=10.5, 8.7 Hz, 1H). 13C NMR (CDCl3) δ: 161.1, 157.0, 142.3, 138.9, 130.1, 129.0, 128.4, 127.2, 126.5, 124.4, 124.2, 120.8, 116.1 19F NMR (CDCl3) δ: −116.28 (br. s., 1F). Mass spec.: 278.0 (MH)+.

Intermediate 129

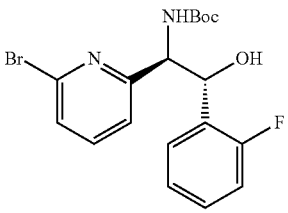

Optically-enriched tert-butyl (1R,2R)-1-(6-bromopyridin-2-yl)-2-(2-fluorophenyl)-2-hydroxyethylcarbamate To tert-butyl carbamate (270 mg, 2.31 mmol) in propanol (3 mL) was added sodium hydroxide (91 mg, 2.27 mmol) in water (6 mL) followed by tert-butyl hypochlorite (0.256 mL, 2.27 mmol). The solution was cooled to 0° C. and (DHQD)2PHAL (34.8 mg, 0.045 mmol) was added in propanol (3 mL) followed by (E)-2-bromo-6-(2-fluorostyryl)pyridine (207 mg, 0.744 mmol) in propanol (6 mL). To this was added potassium osmate dihydrate (10.97 mg, 0.030 mmol) as a solid in one portion. The reaction was allowed to gradually warm to room temperature in the dewar overnight. The reaction was cooled to 0° C. and quenched by addition of sodiumthiosulfate (300 mg) in water (3 mL). The reaction was stirred at room temperature for 30 min. The reaction was diluted with ether, washed with water (2×), then brine, dried over magnesium sulfate, and concentrated. Column chromatography (15%→30% EtOAc/Hex) gave 375 mg (quant.). Mass spec.: 411.2 (MH)+.

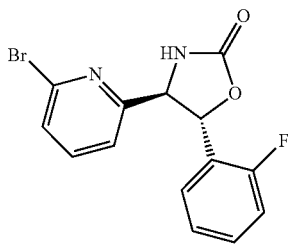

Intermediate 130

Optically-enriched (4R,5R)-4-(6-bromopyridin-2-yl)-5-(2-fluorophenyl)oxazolidin-2-one To a solution of optically-enriched tert-butyl (1R,2R)-1-(6-bromopyridin-2-yl)-2-(2-fluorophenyl)-2-hydroxyethylcarbamate (375 mg, 0.912 mmol) in dichloromethane (4 mL) at room temperature was added hydrogen chloride (4M in dioxane, 3 mL, 12 mmol). After 15 min at room temperature, the reaction was warmed to 45° C. and held at that temperature for 15 min. The reaction was cooled and concentrated. The reaction was concentrated twice more from tetrahydrofuran. The resulting residue was suspended in tetrahydrofuran (10 mL), cooled to 0° C., and treated with diisopropylethylamine (0.319 mL, 1.82 mmol) and carbonyldiimidazole (222 mg, 1.368 mmol). After 5 min, the ice bath was removed and stirring continued for 3 h. The reaction was quenched by addition of 2M ammonia in methanol and concentrated. The resulting residue was suspended in dichloromethane, diluted with ethyl acetate, washed with brine, dried over magnesium sulfate, and concentrated. Column chromatography (25%→50% EtOAc/Hex) gave 75 mg. $^1$H NMR (CDCl$_3$) δ: 7.60-7.68 (m, 1H), 7.46-7.56 (m, 2H), 7.35-7.45 (m, 2H), 7.24 (td, J=7.7, 1.0 Hz, 1H), 7.12 (ddd, J=10.3, 8.3, 1.0 Hz, 1H), 7.03 (s, 1H), 5.80 (d, J=5.3 Hz, 1H), 4.93 (d, J=5.3 Hz, 1H). $^{13}$C NMR (CDCl$_3$) δ: 160.9, 158.9, 158.4, 142.0, 139.2, 130.5, 127.8, 127.2, 125.0, 124.3, 119.6, 115.6, 78.5, 63.1. $^{19}$F NMR (CDCl$_3$) δ: −121.48-113.54 (m, 1F). Mass spec.: 337.1 (MH)$^+$.

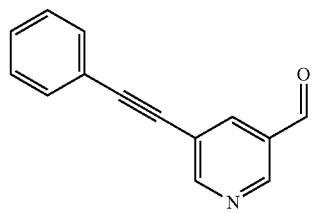

Intermediate 131

5-(Phenylethynyl)nicotinaldehyde

A solution of 5-bromonicotinaldehyde (15 g, 81 mmol) and ethynylbenzene (9.74 mL, 89 mmol) in triethylamine (150 mL) was purged with nitrogen for 30 min. The reaction was treated with triphenylphosphine (0.656 g, 2.50 mmol), and purged 10 minutes longer. To this was added bis(triphenylphosphine)palladium dichloride (0.147 g, 0.210 mmol) and copper(I) iodide (0.032 g, 0.169 mmol). After purging 10 min longer, the reaction was warmed to a gentle reflux. The reaction was heated at reflux for 24 h. The reaction was cooled to room temperature, diluted with ethyl acetate, poured into water, and the layers were separated. The organics were washed again with water, then brine, dried over magnesium sulfate, and concentrated. Column chromatography (20% EtOAc/Hex) gave 16.05 g (96%) as faint yellow crystalline solid. $^1$H NMR (CDCl$_3$) δ: 10.16 (s, 1H), 9.01 (dd, J=17.1, 1.8 Hz, 2H), 8.30 (t, J=2.0 Hz, 1H), 7.54-7.66 (m, 2H), 7.38-7.47 (m, 3H). $^{13}$C NMR (CDCl$_3$) δ: 190.2, 156.8, 150.3, 138.2, 131.9, 130.9, 129.4, 128.7, 122.0, 121.5, 94.5, 84.7. Mass spec.: 208.0 (MH)$^+$.

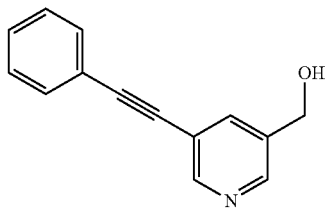

Intermediate 132

(5-(Phenylethynyl)pyridin-3-yl)methanol

To a suspension of 5-(Phenylethynyl)nicotinaldehyde (7.0 g, 33.8 mmol) in ethanol (150 mL), immersed in a room temperature bath to moderate any potential exotherm, was added sodium borohydride (0.639 g, 16.9 mmol) in one portion. After 30 min at room temperature, the reaction was cooled to 0° C. and quenched by the cautious addition of saturated ammonium chloride. The reaction was concentrated and partitioned between water and ether. The aqueous was extracted with ether (2×). The organics were washed with brine, dried over magnesium sulfate, and concentrated to give a faint yellow solid. Material was used without purification. $^1$H NMR (CDCl$_3$) δ: 8.39-8.81 (m, 2H), 7.88 (s, 1H), 7.51-7.61 (m, 2H), 7.34-7.44 (m, 3H), 4.77 (s, 2H), 3.21 (br. s., 1H). $^{13}$C NMR (CDCl$_3$) δ: 151.1, 147.1, 137.3, 131.8, 129.0, 128.6, 122.5, 93.0, 85.9, 62.3. Mass spec.: 210.1 (MH)$^+$.

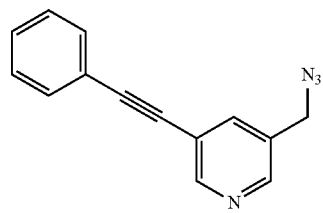

Intermediate 133

3-(Azidomethyl)-5-(phenylethynyl)pyridine

To a solution of (5-(phenylethynyl)pyridin-3-yl)methanol (7.0 g, 33.5 mmol) and triethylamine (6.06 mL, 43.5 mmol) in dichloromethane (150 mL) at 0° C. was added methanesulfonylchloride (2.74 mL, 35.1 mmol) dropwise. After 30 min at 0° C., the reaction was diluted with ether, quenched by addition of saturated sodium bicarbonate, and stirred for 30 min at 0° C. The layers were separated. The organics were washed with water, then brine, dried over magnesium sulfate, and concentrated to afford the crude mesylate which was used without purification. Mass spec.: 288.1 (MH)$^+$.

To a solution of the crude mesylate (9.6 g, 33.4 mmol) in dimethylformamide (134 mL) at 0° C. was added sodium azide (4.34 g, 66.8 mmol). The reaction was stirred at 0° C. for 1 h. The reaction was diluted with ether, washed with water, then brine, dried over magnesium sulfate, and concentrated to give 7.83 g (90%) as a light yellow oil which was used without purification. $^1$H NMR (CDCl$_3$) δ: 8.76 (d, J=1.8 Hz, 1H), 8.53 (d, J=2.1 Hz, 1H), 7.83 (t, J=2.1 Hz, 1H), 7.54-7.63 (m, 2H), 7.37-7.45 (m, 3H), 4.44 (s, 2H). $^{13}$C NMR (CDCl$_3$) δ: 152.1, 148.0, 138.0, 131.9, 130.9, 129.1, 128.6, 122.4, 120.8, 93.4, 85.5, 51.9. Mass spec.: 235.1 (MH)$^+$.

Intermediate 134

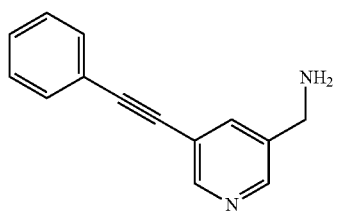

(5-(Phenylethynyl)pyridin-3-yl)methanamine

To a solution of 3-(azidomethyl)-5-(phenylethynyl)pyridine (7.8 g, 33.3 mmol) in tetrahydrofuran (101 mL) at 0° C. was added trimethylphosphine (1M in tetrahydrofuran, 49.9 mL, 49.9 mmol). After evolution of nitrogen had slowed, the ice bath was removed and stirring continued for 1 h. To this was added water (6.0 mL, 333 mmol) and the mixture stirred at room temperature for 2 h. The reaction was concentrated, dissolved in ether, washed with water (5×), then brine, dried over potassium carbonate, filtered, and concentrated to give 5.96 g (77%) as a faint yellow solid which was used without purification. $^1$H NMR (CDCl$_3$) δ: 8.67 (d, J=1.8 Hz, 1H), 8.52 (d, J=2.1 Hz, 1H), 7.85 (t, J=2.0 Hz, 1H), 7.53-7.61 (m, 2H), 7.35-7.44 (m, 3H), 3.95 (s, 2H), 1.45 (d, J=5.2 Hz, 2H)$^1$H NMR (CDCl$_3$) δ: 8.67 (d, J=1.8 Hz, 1H), 8.52 (d, J=2.1 Hz, 1H), 7.85 (t, J=2.0 Hz, 1H), 7.53-7.61 (m, 2H), 7.35-7.44 (m, 3H), 3.95 (s, 2H), 1.45 (d, J=5.2 Hz, 2H). $^{13}$C NMR (CDCl$_3$) δ: 150.8, 147.9, 137.8, 137.4, 131.8, 128.9, 128.6, 122.7, 120.3, 92.7, 86.1, 43.7. Mass spec.: 209.1 (MH)$^+$.

Intermediate 135

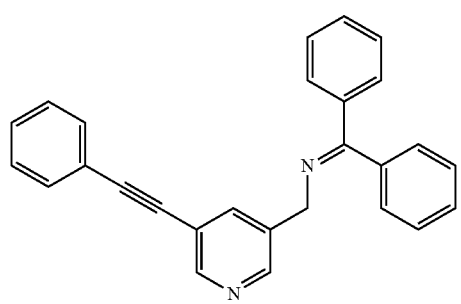

N-(Diphenylmethylene)-1-(5-(phenylethynyl)pyridin-3-yl)methanamine

A flask was charged with (5-(phenylethynyl)pyridin-3-yl)methanamine (5.95 g, 28.6 mmol). The oil was concentrated from toluene (2×) to remove any possible moisture. The oil was dissolved in dichloromethane (30 mL) and treated with benzophenone imine (5.03 mL, 30.0 mmol). The reaction was stirred at room temperature for 1 h. The reaction was heated to reflux, applying a gentle stream of nitrogen at the top of the reflux condensor to allow removal of expelled ammonia. After 8 h, the reaction was cooled to room temperature and allowed to stir at room temperature over the weekend. The reaction was concentrated to give the crude product as a viscous oil. The oil was dissolved in toluene to give a total volume of 50 mL (assumed concentration=0.21 g/mL). This intermediate was stored as a solution in toluene and was dispensed as such for subsequent chemistries. Data for the neat, crude title compound is as follows: $^1$H NMR (CDCl$_3$) δ: 8.68 (d, J=1.8 Hz, 1H), 8.51 (d, J=1.8 Hz, 1H), 7.88 (s, 1H), 7.69-7.77 (m, 2H), 7.36-7.61 (m, 11H), 7.24 (dd, J=7.8, 1.7 Hz, 2H), 4.63 (s, 2H). $^{13}$C NMR (CDCl$_3$) δ: 170.2, 150.6, 148.3, 139.4, 137.8, 136.5, 135.8, 131.8, 130.5, 128.9, 128.9, 128.8, 128.7, 128.5, 128.4, 128.3, 127.7, 122.8, 120.2, 92.5, 86.4, 54.7.

Intermediate 136

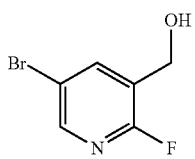

(5-Bromo-2-fluoropyridin-3-yl)methanol

To a suspension of 5-bromo-2-fluoronicotinaldehyde (5.00 g, 24.51 mmol) in ethanol (125 mL) immersed in a room temperature bath to moderate any potential exotherm was added sodium borohydride (0.464 g, 12.26 mmol) in one portion. After 30 minutes at room temperature, LC/MS indicated clean, complete conversion to the product. The reaction was cooled to 0 C and quenched by the cautious addition of saturated ammonium chloride solution (effervescence). The reaction was concentrated and partitioned between water and ether. The etheral was washed with water (2×), then brine, dried over anhydrous magnesium sulfate and concentrated to give a yellow oil which solidified upon standing to give 4.66 g (92% yield) of title compound as yellow crystalline solid. $^1$H-NMR (CDCl$_3$, 500 MHz) δ: 8.21 (s, 1H), 8.08 (ddd, J=8.3, 1.6, 0.8 Hz, 1H), 4.70-4.88 (m, 2H). Mass spec.: 206.0 (MH)$^+$.

Intermediate 137

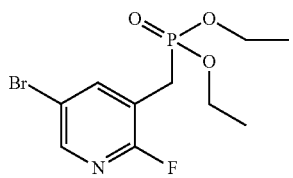

Diethyl(5-Bromo-2-fluoropyridin-3-yl)methylphosphonate

Prepared according to the same procedure as diethyl (6-bromopyridin-2-yl)methylphosphonate, starting with (5-Bromo-2-fluoropyridin-3-yl)methanol. $^1$H-NMR (CDCl$_3$, 500 MHz) δ: 8.18 (d, J=1.2 Hz, 1H), 7.94 (dt, J=8.4, 2.5 Hz, 1H), 4.10-4.16 (m, 4H), 3.10-3.20 (m, 2H), 1.31 (t, J=7.2 Hz, 6H). $^{13}$C-NMR (CDCl$_3$, 126 MHz) δ: 147.1, 144.5, 117.0, 116.5, 62.7, 26.9, 25.7, 16.5. Mass spec.: 328.0 (MH)$^+$.

Intermediate 138

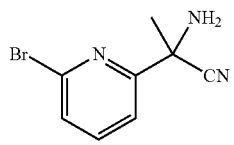

2-Amino-2-(6-bromopyridin-2-yl)propanenitrile

A 250 mL round-bottomed flask equipped with a magnetic stirring bar was charged with 1-(6-bromopyridin-2-yl)ethanone (5.00 g, 25.00 mmol), ammonium chloride (1.538 g, 28.7 mmol), ammonia (3.3 mL, 25.00 mmol), ethanol (7.5 mL), and water (6.3 mL). The resulting suspension was treated with sodium cyanide (1.409 g, 28.7 mmol), and the flask was quickly sealed with a rubber stopper. The mixture was stirred overnight. The reaction was extracted with dichloromethane (3×), the combined organic layer was washed with water to remove the remaining sodium cyanide, dried with anhydrous magnesium sulfate, and concentrated under reduced pressure to afford title compound (quant.) as yellowish sticky oil residue which was used without purification. Mass spec.: 225.9 (MH)$^+$.

Intermediate 139

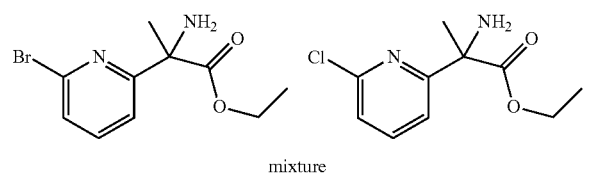

mixture

Mixture of ethyl 2-amino-2-(6-bromopyridin-2-yl)propanoate and ethyl 2-amino-2-(6-chloropyridin-2-yl)propanoate A dry 3-neck round-bottom flask (250 mL) was attached via an adaptor and rubber tubing to a funnel submerged in saturated sodium bicarbonate. The flasked was cooled to 0° C. and anhydrous ethanol (127.5 mL) was added. The ethanol was saturated with hydrochloric acid (g) for 10 min. 2-Amino-2-(6-bromopyridin-2-yl)propanenitrile (5.65 g, 25 mmol) in ethanol (13 mL) was added to the reaction mixture and stirred at 65° C. under nitrogen balloon for 24 h. Reaction was cooled to room temperature, concentrated under reduced pressure, and partitioned between water (250 mL) and ethyl acetate (250 mL). The aqueous layer was isolated, saturated sodium bicarbonate was added to adjust solution PH to 8, and the product extracted into ethyl acetate (3×250 mL). The combined organics were dried with anhydrous magnesium sulfate, filtered, and concentrated under reduced pressure to afford 4.45 g as dark yellow oil which was used without purification. Mass spec.: 229.0, 273.0 (MH)$^+$.

Intermediate 140

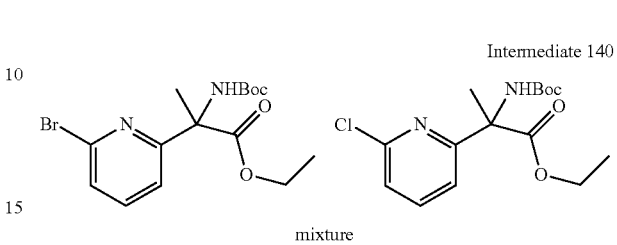

mixture

Mixture of ethyl 2-(6-bromopyridin-2-yl)-2-(tert-butoxycarbonylamino)propanate and ethyl 2-(6-chloropyridin-2-yl)-2-(tert-butoxycarbonylamino)propanate To a solution of ethyl 2-amino-2-(6-bromopyridin-2-yl)propanoate and ethyl 2-amino-2-(6-chloropyridin-2-yl)propanoate (4.45 g, 16.29 mmol) in tetrahydrofuran (150 mL) at 0° C. was added di-tert-butyl dicarbonate (7.11 g, 32.6 mmol). After stirring at room temperature for an hour, the reaction was heated at reflux overnight. The reaction was cooled to room temperature and concentrated under reduced pressure. Biotage purification (10% EtOAc/Hex) gave 6.2 g as a clear sticky oil. Mass spec.: 351.1, 395.0 (MNa)$^+$.

Intermediate 141

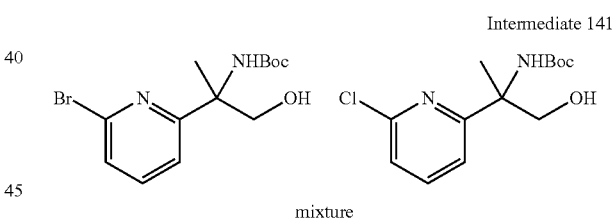

mixture

Tert-butyl 2-(6-bromopyridin-2-yl)-1-hydroxypropan-2-ylcarbamate and tert-butyl 2-(6-chloropyridin-2-yl)-1-hydroxypropan-2-ylcarbamate A solution of ethyl 2-(6-bromopyridin-2-yl)-2-(tert-butoxycarbonylamino)propanate and ethyl 2-(6-chloropyridin-2-yl)-2-(tert-butoxycarbonylamino)propanate (6.00 g, 16.08 mmol) in tetrahydrofuran (150 mL) was cooled to 0° C. To this was added lithium borohydride (2.0M solution in tetrahydrofuran, 16.08 mL, 32.2 mmol). The reaction was allowed to warm to room temperature over 3 h, recooled to 0° C., quenched by addition of methanol, diluted with water (300 mL), and extracted with ethyl acetate (2×300 mL). The organics were combined, washed with brine, dried over anhydrous magnesium sulfate, filtered, and concentrated in vacuo to give 5.3 g as clear sticky oil. Mass spec.: 309.1, 353.0 (MNa)$^+$.

Intermediate 142

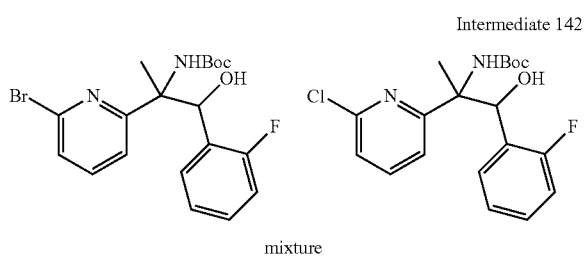 [SMILES: CC(C)(C)OC(=O)NC(C)(c1cccc(Br)n1)C(O)c1ccccc1F ; CC(C)(C)OC(=O)NC(C)(c1cccc(Cl)n1)C(O)c1ccccc1F]

mixture

Tert-butyl 2-(6-bromopyridin-2-yl)-1-(2-fluorophenyl)-1-hydroxypropan-2-ylcarbamate and tert-butyl 2-(6-chloropyridin-2-yl)-1-(2-fluorophenyl)-1-hydroxypropan-2-ylcarbamate To a solution of tert-butyl 2-(6-bromopyridin-2-yl)-1-hydroxypropan-2-ylcarbamate and tert-butyl 2-(6-chloropyridin-2-yl)-1-hydroxypropan-2-ylcarbamate (400 mg, 1.208 mmol) in tetrahydrofuran (10 mL) was added Dess-Martin-Periodinane (307 mg, 0.725 mmol). After 2 h, the reaction was quenched with 1:1 saturated sodium bicarbonate and sodium hydrogen sulfite and extracted into dichloromethane. The organic layer was washed with water, brine, and dried with anhydrous magnesium sulfate, filtered and concentrated. Biotage purification to afford 325 mg as a mixture of the two aldehydes as clear sticky oil.

In a separate flask, isopropylmagnesium chloride (0.664 mL, 1.328 mmol) was added to a solution of 1-bromo-2-fluorobenzene (0.132 mL, 1.208 mmol) in tetrahydrofuran (1.5 mL) at 0° C. The solution was stirred at 0° C. for 1.25 h, then cooled to −78 C. To this was added the above prepared aldehyde in tetrahydrofuran (1.5 mL) dropwise. The reaction was warmed slowly to 0° C. (over 2 h) and quenched by addition of a cold aqueous solution of ammonium chloride. The reaction mixture was extracted with ethyl acetate, and the organics washed with water, then brine, dried over anhydrous magnesium sulfate, filtered, and concentrated in vacuo. Biotage purification (15% EtOAc/Hex) gave 200 mg (39% yield) as a white foam solid. Mass spec.: 403.1 (MNa)$^+$, 447.1 (MH)$^+$.

Intermediate 143

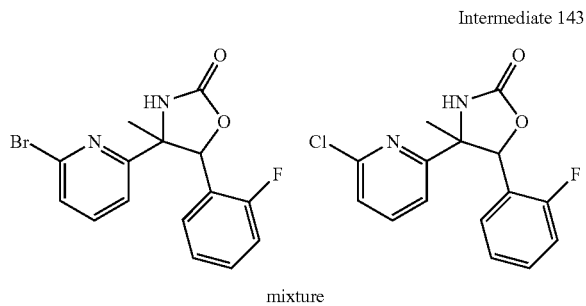 [SMILES: CC1(c2cccc(Br)n2)NC(=O)OC1c1ccccc1F ; CC1(c2cccc(Cl)n2)NC(=O)OC1c1ccccc1F]

mixture

4-(6-Bromopyridin-2-yl)-5-(2-fluorophenyl)-4-methyloxazolidin-2-one and 4-(6-chloropyridin-2-yl)-5-(2-fluorophenyl)-4-methyloxazolidin-2-one To a cold (0° C.) solution of tert-butyl 2-(6-bromopyridin-2-yl)-1-(2-fluorophenyl)-1-hydroxypropan-2-ylcarbamate and tert-butyl 2-(6-chloropyridin-2-yl)-1-(2-fluorophenyl)-1-hydroxypropan-2-ylcarbamate (200 mg, 0.470 mmol) in tetrahydrofuran (4.5 mL) was added a solution of potassium tert-butoxide (1M solution in tetrahydrofuran, 0.564 mL, 0.564 mmol) dropwise. After 5 minutes, the ice bath was removed and stirring continued for 1 h. The reaction was cooled to 0° C., quenched by addition of saturated ammonium chloride, and concentrated. The residue was dissolved in dichloromethane, washed with water, dried over anhydrous magnesium sulfate, and concentrated. Biotage purification (40% EtOAc/Hex) gave 114 mg of title compounds as white foam solid. Mass spec.: 307.1, 351.1 (MH)$^+$.

Intermediate 144

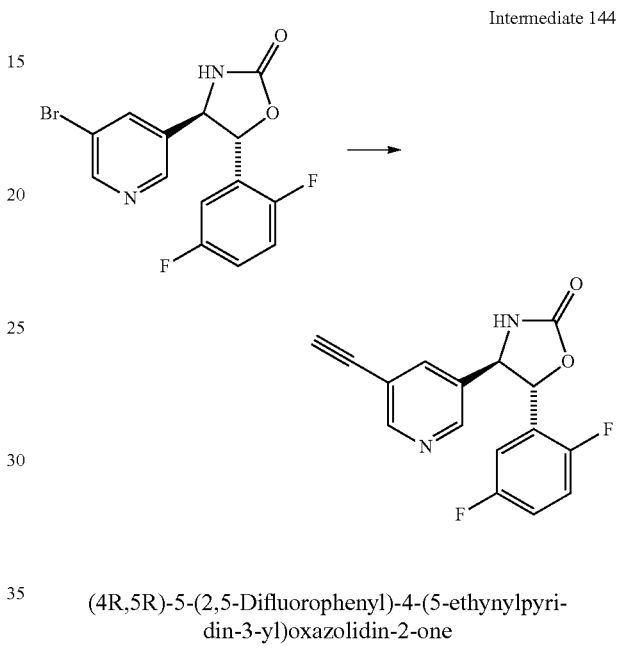

(4R,5R)-5-(2,5-Difluorophenyl)-4-(5-ethynylpyridin-3-yl)oxazolidin-2-one

To a slurry of (4R,5R)-4-(5-bromopyridin-3-yl)-5-(2,5-difluorophenyl)oxazolidin-2-one (1.00 g, 2.82 mmol) in triethylamine (30 mL) was bubbled nitrogen for 20 min at which time ethynyltrimethylsilane (0.557 mL, 3.94 mmol) was added with continued nitrogen bubbling for 5 min before adding bis(triphenylphosphine) palladium (II) chloride (0.148 g, 0.211 mmol), triphenylphosphine (0.133 g, 0.507 mmol), and copper (I) iodide (0.161 g, 0.845 mmol) together in 1 portion. After 5 min additional bubbling of nitrogen, the vessel was capped and placed in a 70° C. bath. After 18 h, the vessel was cooled to ambient temperature, concentrated in vacuo dissolved in ethyl acetate, washed with water and brine, dried over MgSO$_4$, filtered and concentrated in vacuo to a black tar which was dissolved in methanol (30 mL). Potassium carbonate (0.428 g, 3.10 mmol) was added and after 30 min, the reaction was concentrated and dissolved in ethyl acetate, washed with water, brine, dried over MgSO$_4$, filtered and concentrated in vacuo to a black tar which was loaded with dichloormethane onto a 40 g silica gel cartridge. Elution with 5 to 75% EtOAc/Hex over 6 column volumes then 75% EtOAc over 2 column volumes. Fractions containing the main peak were concentrated to (4R,5R)-5-(2,5-difluorophenyl)-4-(5-ethynylpyridin-3-yl)oxazolidin-2-one (766 mg; 91%) as a yellow oil which crystallized upon standing. $^1$H NMR (500 MHz, CDCl$_3$) δ ppm 8.75 (1H, d, J=1.83 Hz), 8.52 (1H, d, J=2.14 Hz), 7.87 (1H, t, J=1.98 Hz), 7.17-7.24 (1H, m), 6.98-7.15 (2H, m), 5.52 (2H, d, J=5.49 Hz), 4.80 (1H, d, J=5.80 Hz), 3.30 (1H, s). Mass Spectral Anal. Calcd. for [M+H]$^+$ C$_{16}$H$_{10}$F$_2$N$_2$O$_2$: 301.07. found 301.01.

Intermediate 145 and Intermediate 146

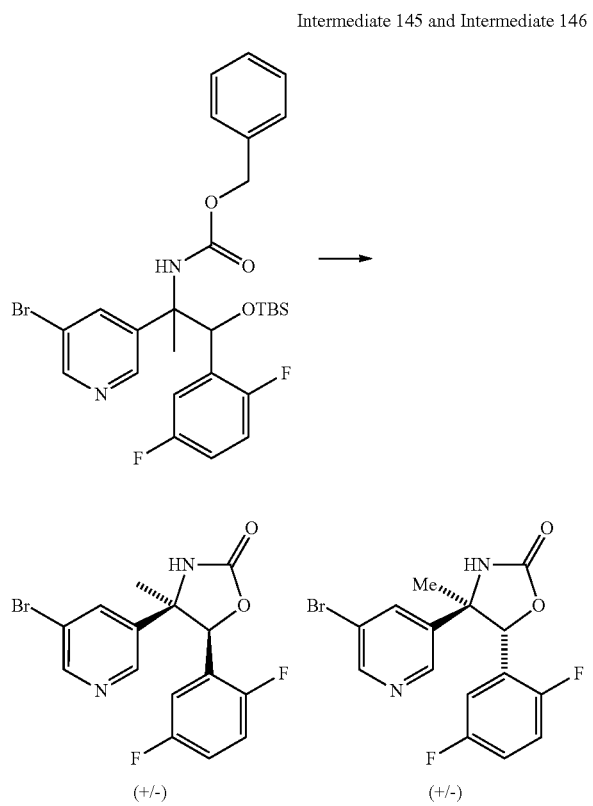

Cis-4-(5-bromopyridin-3-yl)-5-(2,5-difluorophenyl)-4-methyloxazolidin-2-one and trans-4-(5-bromopyridin-3-yl)-5-(2,5-difluorophenyl)-4-methyloxazolidin-2-one To benzyl 2-(5-bromopyridin-3-yl)-1-(tert-butyldimethylsilyloxy)-1-(2,5-difluorophenyl)propan-2-ylcarbamate (80 mg, 0.135 mmol) in tetrahydrofuran (2 mL) was added TBAF (0.176 mL, 0.176 mmol) dropwise over 5 min. After 2 h, the reaction vessel was placed in a heat bath set to 60° C. for an additional 18 h at which time it was diluted with ethyl acetate, washed with water, dried over magnesium sulfate, filtered and concentrated to 79 mg oil which was purified via preparative liquid chromatography (Sunfire C18 OBD 30×100 mm 5 µm, A=95% H$_2$O/5% Acetonitrile, B=95% Acetonitrile/5% H$_2$O, Modifier 10 mM Ammonium Acetate, 0.00 min=10% B, 8.0 min=100% B, 13.0 min=100% B, Flow rate=40 mL/min) providing 11 mg (22%) Cis-4-(5-bromopyridin-3-yl)-5-(2,5-difluorophenyl)-4-methyloxazolidin-2-one and 27 mg (54%) trans-4-(5-bromopyridin-3-yl)-5-(2,5-difluorophenyl)-4-methyloxazolidin-2-one. Data for cis isomer: $^1$H NMR (500 MHz, CDCl$_3$) δ ppm 8.44 (1H, d, J=2.14 Hz), 8.29 (1H, d, J=1.83 Hz), 7.59 (1H, t, J=1.98 Hz), 6.85 (2H, td, J=6.33, 1.37 Hz), 6.73-6.81 (1H, m), 6.68 (1H, br. s.), 5.81 (1H, s), 2.03 (3H, s). Mass Spectral Anal. Calcd. for [M+H]$^+$ C$_{15}$H$_{11}$BrF$_2$N$_2$O$_2$: 369.0. found 369.0. Data for trans isomer: $^1$H NMR (500 MHz, CDCl$_3$) δ ppm 8.69 (1H, d, J=2.14 Hz), 8.66 (1H, d, J=1.83 Hz), 8.01 (1H, t, J=1.98 Hz), 7.17-7.30 (1H, m), 7.02-7.15 (2H, m), 6.83 (1H, br. s.), 5.74 (1H, s), 1.40 (3H, s). Mass Spectral Anal. Calcd. for [M+H]$^+$ C$_{15}$H$_{11}$BrF$_2$N$_2$O$_2$: 369.0. found 369.0.

Intermediate 147

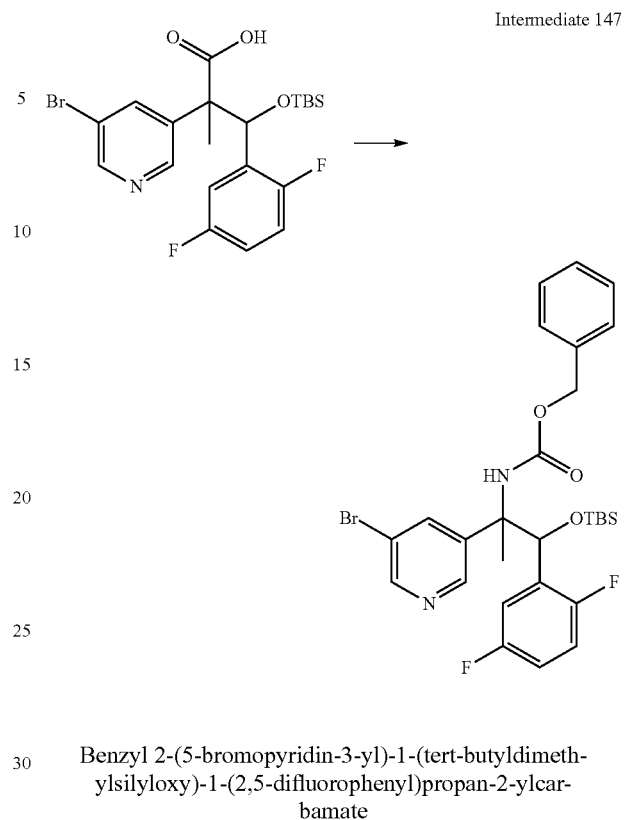

Benzyl 2-(5-bromopyridin-3-yl)-1-(tert-butyldimethylsilyloxy)-1-(2,5-difluorophenyl)propan-2-ylcarbamate To crude 2-(5-bromopyridin-3-yl)-3-(tert-butyldimethylsilyloxy)-3-(2,5-difluorophenyl)-2-methylpropanoic acid (450 mg, 0.925 mmol) in toluene (12 mL) was added benzyl alcohol (0.096 mL, 0.925 mmol), triethylamine (0.258 mL, 1.850 mmol) and diphenyl phosphorazidate (0.200 mL, 0.925 mmol). The mixture was placed in a heat bath set to 60° C. for 18 h, concentrated and purified via preparative liquid chromatography (Sunfire C18 OBD 30×100 mm 5 µm, A=95% H$_2$O/5% Acetonitrile, B=95% Acetonitrile/5% H$_2$O, Modifier 10 mM Ammonium Acetate, 0.00 min=0% B, 8.0 min=100% B, 13.0 min=100% B, Flow rate=40 mL/min) providing 80 mg (15%) benzyl 2-(5-bromopyridin-3-yl)-1-(tert-butyldimethylsilyloxy)-1-(2,5-difluorophenyl)propan-2-ylcarbamate. Mass Spectral Anal. Calcd. for [M+H]$^+$ C$_{28}$H$_{33}$BrF$_2$N$_2$O$_2$Si: 591.1. found 590.0.

Intermediate 148

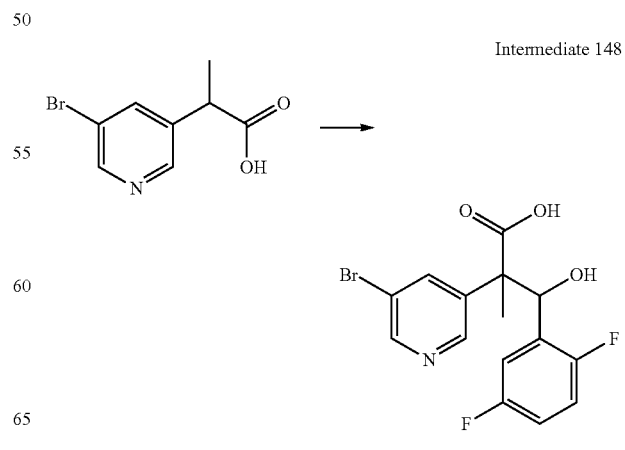

2-(5-Bromopyridin-3-yl)-3-(2,5-difluorophenyl)-3-hydroxy-2-methylpropanoic acid In a flame dried flask under nitrogen was added diisopropylamine (0.976 mL, 6.85 mmol), tetrahydrofuran (4 mL) and the vessel was cooled to −78° C. n-BuLi (2.74 mL, 6.85 mmol) was added dropwise and after 10 min, the reaction was warmed to −15° C. and held there for 10 min before recooling to −78° C. 2-(5-bromopyridin-3-yl)propanoic acid (750 mg, 3.26 mmol) held in a flame dried flask was dissolved in tetrahydrofuran (4 mL) and added dropwise to the preformed LDA resulting in a kool-aid orange solution. The ice bath was again removed and the reaction was allowed to stir at ambient temperature for 1.5 h, recooled to −78° C. and 2,5-difluorobenzaldehyde (0.779 mL, 7.17 mmol) in 2 mL tetrahydrofuran was added over 10 min. After 1 h, the reaction was quenched with 10% citric acid and the volatiles were removed under vacuum. The residue was extracted with 3 portions ether, washed with brine, dried over MgSO4, filtered and concentrated to 1.31 g red gum which was used immediately in the next step.

Intermediate 149

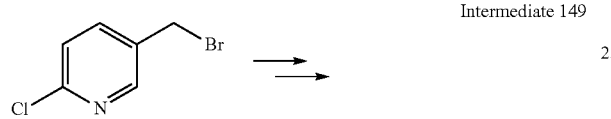

(4R,5R)-4-(6-Chloropyridin-3-yl)-5-(3-fluorophenyl)oxazolidin-2-one

Prepared from 5-(bromomethyl)-2-chloropyridine in similar fashion to the preparation of (4R,5R)-4-(5-bromopyridin-3-yl)-5-(2,5-difluorophenyl)oxazolidin-2-one from 3-bromo-5-(bromomethyl)pyridine. $^1$H NMR (500 MHz, CDCl$_3$) δ ppm 8.19-8.36 (1H, m), 7.72 (1H, dd, J=8.39, 2.59 Hz), 7.42-7.49 (1H, m), 7.32-7.42 (1H, m), 6.94-7.08 (2H, m), 5.56 (1H, s), 5.23 (1H, d, J=7.63 Hz), 4.77 (1H, d, J=7.63 Hz). Mass Spectral Anal. Calcd. for [M+H]$^+$ C$_{14}$H$_{10}$ClFN$_2$O$_2$: 293.0. found 293.1.

Example 1

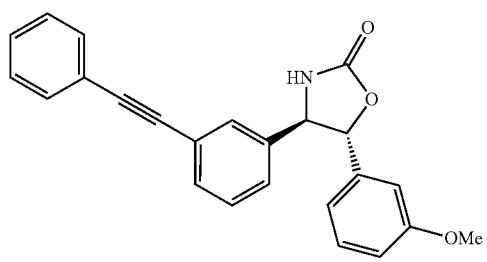 [SMILES: COc1cccc([C@H]2OC(=O)N[C@@H]2c2cccc(C#Cc3ccccc3)c2)c1]

(+)-(4R,5R)-5-(3-Methoxyphenyl)-4-(3-(phenylethynyl)phenyl)oxazolidin-2-one

A suspension of (+)-(4R,5R)-4-(3-bromophenyl)-5-(3-methoxyphenyl)oxazolidin-2-one (2.4 g, 6.89 mmol) in triethylamine (24 mL, 172 mmol) was purged with nitrogen for 1 h (volume dropped by ca. 5 mL). The reaction was treated with triphenylphosphine (0.152 g, 0.579 mmol) and ethynylbenzene (0.776 mL, 7.07 mmol), and purged 10 minutes longer. To this was added PdCl2(PPh3)$_2$ (0.034 g, 0.048 mmol) and copper(I) iodide (7.88 mg, 0.041 mmol). After purging 10 min longer, the reaction was warmed to a vigorous reflux. The reaction was heated at reflux overnight. In the morning, the reaction was cooled to room temperature, diluted with diethyl ether, washed with water (3×), then brine, dried over magnesium sulfate, and concentrated. Column chromatography (25%-->40% EtOAc/Hex) gave 2.2 g (80%) as a colorless foam solid. $^1$H-NMR (CDCl$_3$, 500 MHz) δ 7.56 (m, 4H), 7.36-7.45 (m, 4H), 7.34 (m, 1H), 7.30 (m, 1H), 6.92-6.98 (m, 1H), 6.85-6.90 (m, 2H), 5.93 (bs, 1H), 5.31 (d, J=7.3, 1H), 4.78 (d, J=7.3, 1H), 3.84 (s, 3H). $^{13}$C-NMR (CDCl$_3$, 126 MHz) δ 160.2, 158.6, 138.92, 138.85, 132.3, 131.8, 130.2, 129.6, 129.4, 128.7, 128.5, 126.4, 124.6, 122.9, 118.1, 115.0, 111.2, 90.6, 88.6, 85.9, 64.6, 55.5. Mass spec.: 370.18 (MH)$^+$.

Example 2

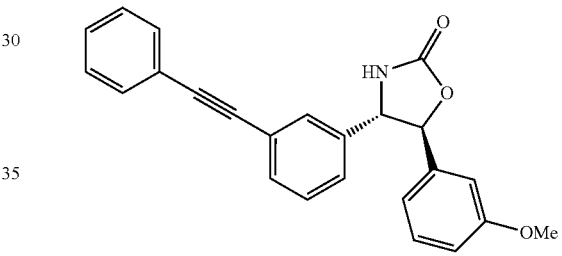

(4S,5S)-5-(3-Methoxyphenyl)-4-(3-(phenylethynyl)phenyl)oxazolidin-2-one

Prepared according to the same procedure as (+)-(4R,5R)-5-(3-methoxyphenyl)-4-(3-(phenylethynyl)phenyl)oxazolidin-2-one, starting with (−)-(4S,5S)-4-(3-bromophenyl)-5-(3-methoxyphenyl)oxazolidin-2-one and phenylacetylene. $^1$H-NMR (CDCl$_3$, 500 MHz) δ 7.56 (m, 4H), 7.36-7.45 (m, 4H), 7.34 (m, 1H), 7.30 (m, 1H), 6.92-6.98 (m, 1H), 6.85-6.90 (m, 2H), 5.93 (bs, 1H), 5.31 (d, J=7.3, 1H), 4.78 (d, J=7.3, 1H), 3.84 (s, 3H). $^{13}$C-NMR (CDCl$_3$, 126 MHz) δ 160.2, 158.6, 138.92, 138.85, 132.3, 131.8, 130.2, 129.6, 129.4, 128.7, 128.5, 126.4, 124.6, 122.9, 118.1, 115.0, 111.2, 90.6, 88.6, 85.9, 64.6, 55.5. Mass spec.: 370.14 (MH)$^+$.

Example 3 and Example 4

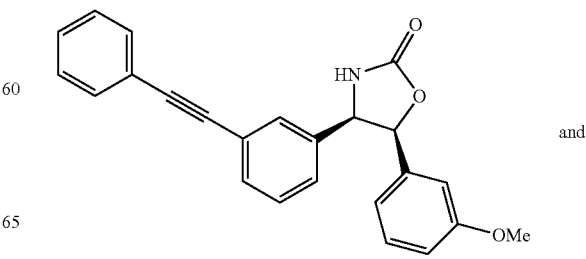

and

-continued

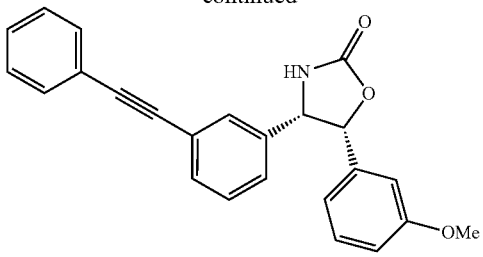

(4R,5S)-5-(3-Methoxyphenyl)-4-(3-(phenylethynyl)phenyl)oxazolidin-2-one and (4S,5R)-5-(3-Methoxyphenyl)-4-(3-(phenylethynyl)phenyl)oxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5S)-4-(3-bromophenyl)-5-(3-methoxyphenyl)oxazolidin-2-one and phenylacetylene. $^1$H-NMR (CDCl$_3$, 500 MHz) δ 7.53 (m, 2H), 7.37 (m, 3H), 7.31 (m, 1H), 7.24 (m, 1H), 7.09 (dd, J=7.6, 7.6, 1H), 7.06 (dd, J=7.9, 7.9, 1H), 6.88 (bd, J=7.9, 1H), 6.67 (dd, J=8.2, 2.1, 1H), 6.62 (d, J=7.6, 1H), 6.51 (m, 1H), 6.41 (m, 1H), 5.93 (d, J=8.2, 1H), 5.17 (d, J=8.2, 1H), 3.64 (s, 3H). $^{13}$C-NMR (CDCl$_3$, 126 MHz) δ 159.8, 159.5, 136.7, 135.7, 131.7, 131.5, 130.1, 129.2, 128.6, 128.5, 128.4, 127.0, 123.5, 123.0, 118.7, 114.8, 111.3, 90.0, 88.8, 82.2, 61.2, 55.4. Enantiomers were resolved by SFC Prep HPLC (Chiralpak AD-H, 35% MeOH in CO2). Enantiomer 1=first enantiomer to elute from Prep (Example 3): Mass spec.: 370.15 (MH)$^+$. Enantiomer 2=second enantiomer to elute from Prep (Example 4): Mass spec.: 370.11 (MH)$^+$.

Example 5 and Example 6

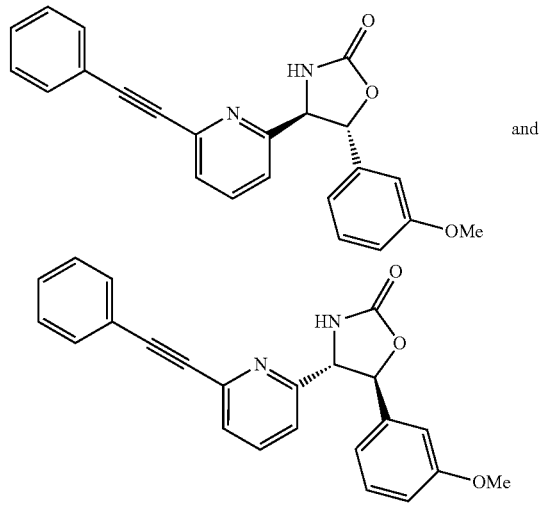

(4R,5R)-5-(3-Methoxyphenyl)-4-(6-(phenylethynyl)pyridin-2-yl)oxazolidin-2-one and (4S,5S)-5-(3-Methoxyphenyl)-4-(6-(phenylethynyl)pyridin-2-yl)oxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(6-bromopyridin-2-yl)-5-(3-methoxyphenyl)oxazolidin-2-one and phenylacetylene. $^1$H-NMR (CDCl$_3$, 500 MHz) δ 7.80 (dd, J=7.9, 7.6, 1H), 7.64 (m, 2H), 7.56 (d, J=7.6, 1H), 7.31-7.47 (m, 5H), 7.04 (m, 2H), 6.94 (m, 1H), 5.85 (bs, 1H), 5.61 (d, J=5.8, 1H), 4.98 (d, J=5.8, 1H), 3.85 (s, 3H). $^{13}$C-NMR (CDCl$_3$, 126 MHz) δ 160.2, 158.8, 158.5, 143.9, 139.7, 137.7, 132.2, 130.2, 129.4, 128.6, 127.3, 122.0, 119.8, 117.9, 114.9, 111.1, 90.3, 88.3, 83.7, 64.9, 55.5. Enantiomers were resolved by SFC Prep HPLC (Chiralpak AD-H, 45% MeOH in CO2). Enantiomer 1=first enantiomer to elute from Prep (Example 5). Enantiomer 2=second enantiomer to elute from Prep (Example 6):

Example 7

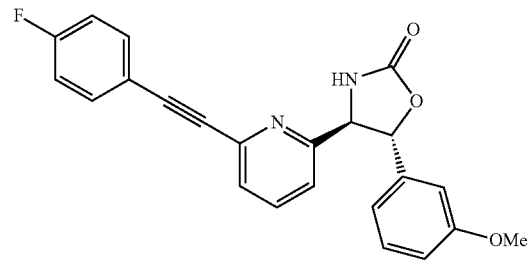 [SMILES: COc1cccc([C@H]2OC(=O)N[C@@H]2c2cccc(C#Cc3ccc(F)cc3)n2)c1]

(4R,5R)-4-(6-((4-Fluorophenyl)ethynyl)pyridin-2-yl)-5-(3-methoxyphenyl)oxazolidin-2-one Prepared according to the same procedure as (+)-(4R,5R)-5-(3-methoxyphenyl)-4-(3-(phenylethynyl)phenyl)oxazolidin-2-one, starting with optically-enriched (4R,5R)-4-(6-bromopyridin-2-yl)-5-(3-methoxyphenyl)oxazolidin-2-one and 1-ethynyl-4-fluorobenzene. $^1$H-NMR (CDCl$_3$, 500 MHz) δ 7.79 (dd, J=7.9, 7.6, 1H), 7.61 (m, 2H), 7.54 (d, J=7.6, 1H), 7.36 (m, 2H), 7.10 (m, 2H), 7.04 (m, 2H), 6.94 (m, 1H), 6.40 (bs, 1H), 5.62 (d, J=5.8, 1H), 4.98 (d, J=5.8, 1H), 3.85 (s, 3H). $^{13}$C-NMR (CDCl$_3$, 126 MHz) δ 163.2 (d, J=251), 160.1, 158.9, 143.7, 139.8, 137.7, 134.2 (d, J=7.7), 130.2, 127.2, 120.0, 117.9, 116.0 (d, J=23), 114.8, 111.2, 89.1, 88.1, 83.7, 64.9, 55.5. Mass spec.: 389.17 (MH)$^+$.

Example 8

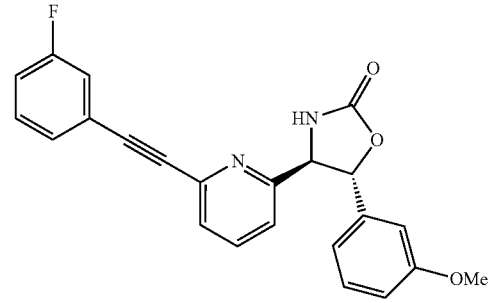 [SMILES: COc1cccc([C@H]2OC(=O)N[C@@H]2c2cccc(C#Cc3cccc(F)c3)n2)c1]

(4R,5R)-4-(6-((3-Fluorophenyl)ethynyl)pyridin-2-yl)-5-(3-methoxyphenyl)oxazolidin-2-one Prepared according to the same procedure as (+)-(4R,5R)-5-(3-methoxyphenyl)-4-(3-(phenylethynyl)phenyl)oxazolidin-2-one, starting with optically-enriched (4R,5R)-4-(6-bromopyridin-2-yl)-5-(3-methoxyphenyl)oxazolidin-2-one and 1-ethynyl-3-fluorobenzene. $^1$H-NMR (CDCl$_3$, 500 MHz) δ 7.81 (d, J=7.9, 7.6, 1H), 7.57 (dd, J=7.9, 0.6, 1H), 7.30-7.45 (M, 5H), 7.13 (m, 1H), 7.04 (m, 2H), 6.95 (m, 1H), 6.00 (bs, 1H), 5.62 (d, J=6.1, 1H), 4.97 (dd, J=5.8, 0.6, 1H), 3.86 (s, 3H). $^{13}$C-NMR (CDCl$_3$, 126 MHz) δ 162.5 (d, J=248), 160.2, 159.0, 158.6, 143.5, 139.7, 137.8, 130.20 (d, J=8.6), 130.19, 128.1 (d, J=2.9), 127.4, 123.9 (d, J=10), 120.1, 119.0 (d, J=23), 117.9, 116.8 (d, J=21), 114.8, 111.2, 89.0, 88.7 (d, J=3.8), 83.7, 64.9, 55.5.

Example 9

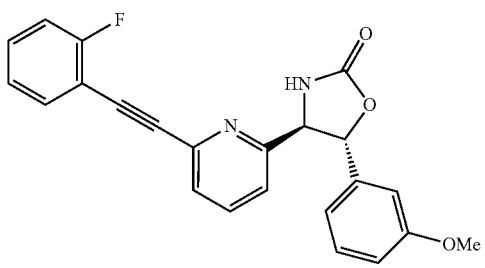 [SMILES: COc1cccc([C@H]2OC(=O)N[C@@H]2c2cccc(C#Cc3ccccc3F)n2)c1]

(4R,5R)-4-(6-((2-Fluorophenyl)ethynyl)pyridin-2-yl)-5-(3-methoxyphenyl)oxazolidin-2-one Prepared according to the same procedure as (+)-(4R,5R)-5-(3-methoxyphenyl)-4-(3-(phenylethynyl)phenyl)oxazolidin-2-one, starting with optically-enriched (4R,5R)-4-(6-bromopyridin-2-yl)-5-(3-methoxyphenyl)oxazolidin-2-one and 1-ethynyl-2-fluorobenzene. $^1$H-NMR (CDCl$_3$, 500 MHz) δ 7.81 (dd, J=7.9, 7.6, 1H), 7.63 (ddd, J=7.6, 7.0, 1.2, 1H), 7.60 (d, J=7.6, 1H), 7.41 (m, 2H), 7.36 (dd, J=7.9, 7.9, 1H), 7.18 (m, 2H), 7.05 (m, 2H), 6.94 (m, 1H), 5.89 (bs, 1H), 5.62 (d, J=5.8, 1H), 4.98 (d, J=6.1, 1H), 3.86 (s, 3H). $^{13}$C-NMR (CDCl$_3$, 126 MHz) δ 163.1 (d, J=253), 162.1, 160.2, 158.9, 158.6, 143.6, 139.8, 137.7, 134.0, 131.2 (d, J=7.7), 130.2, 127.4, 124.2 (d, J=3.8), 120.1, 117.9, 115.8 (d, J=21), 114.9, 111.0, 93.1, 83.7, 83.5, 64.9, 55.5.

Example 10 and Example 11

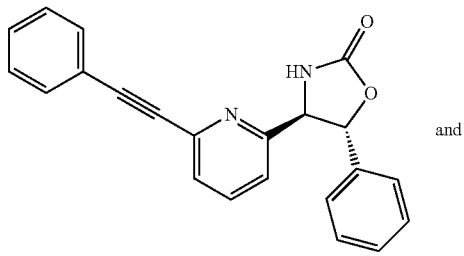

and

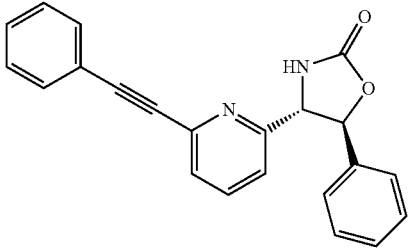

(4R,5R)-5-Phenyl-4-(6-(phenylethynyl)pyridin-2-yl)oxazolidin-2-one and (4S,5S)-5-phenyl-4-(6-(phenylethynyl)pyridin-2-yl)oxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(6-bromopyridin-2-yl)-5-phenyloxazolidin-2-one and phenylacetylene. $^1$H-NMR (CDCl$_3$, 500 MHz) δ 7.78 (dd, J=7.9, 7.6, 1H), 7.63 (m, 2H), 7.35-7.50 (m, 9H), 6.88 (bs, 1H), 5.66 (d, J=5.8, 1H), 5.01 (d, J=5.8, 1H). $^{13}$C-NMR (CDCl$_3$, 126 MHz) δ 159.4, 158.9, 143.8, 138.2, 137.8, 132.2, 129.4, 129.1, 129.0, 128.6, 127.3, 125.9, 122.0, 120.0, 90.4, 88.3, 83.9, 64.9. Enantiomers were resolved by SFC Prep HPLC (Chiralpak AD-H, 45% MeOH in CO2). Enantiomer 1=first enantiomer to elute from Prep (Example 10): Mass spec.: 341.2 (MH)$^+$. Enantiomer 2=second enantiomer to elute from Prep (Example 11): Mass spec.: 341.2 (MH)$^+$.

Example 12 and Example 13

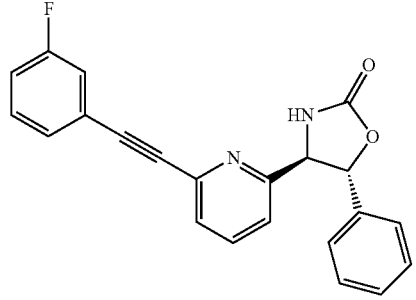

and

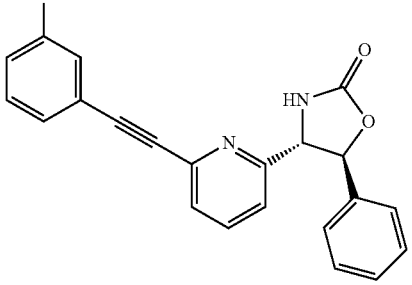

(4R,5R)-4-(6-O-Fluorophenyl)ethynyl)pyridin-2-yl)-5-phenyloxazolidin-2-one and (4S,5S)-4-(6-((3-fluorophenyl)ethynyl)pyridin-2-yl)-5-phenyloxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(6-bromopyridin-2-yl)-5-phenyloxazolidin-2-one and 1-ethynyl-3-fluorobenzene. ¹H-NMR (CDCl₃, 500 MHz) δ 7.79 (dd, J=7.9, 7.6, 1H), 7.55 (d, J=7.6, 1H), 7.35-7.51 (m, 8H), 7.32 (ddd, J=9.2, 2.4, 1.2, 1H), 7.12 (m, 1H), 6.90 (bs, 1H), 5.66 (d, J=5.5, 1H), 4.99 (d, J=5.5, 1H). ¹³C-NMR (CDCl₃, 126 MHz) δ 162.4 (d, J=248), 159.3, 159.1, 143.4, 138.3, 137.8, 130.2 (d, J=8.6), 129.08, 129.05, 128.1 (d, J=2.9), 127.3, 125.9, 123.9 (d, J=9.6), 120.3, 119.0 (d, J=23), 116.7 (d, J=21), 89.0, 88.7 (d, J=2.9), 83.9, 64.9. Enantiomers were resolved by SFC Prep HPLC (Chiralpak AD-H, 45% MeOH in CO2). Enantiomer 1=first enantiomer to elute from Prep (Example 12): Mass spec.: 359.2 (MH)⁺. Enantiomer 2=second enantiomer to elute from Prep (Example 13): Mass spec.: 359.2 (MH)⁺.

Example 14 and Example 15

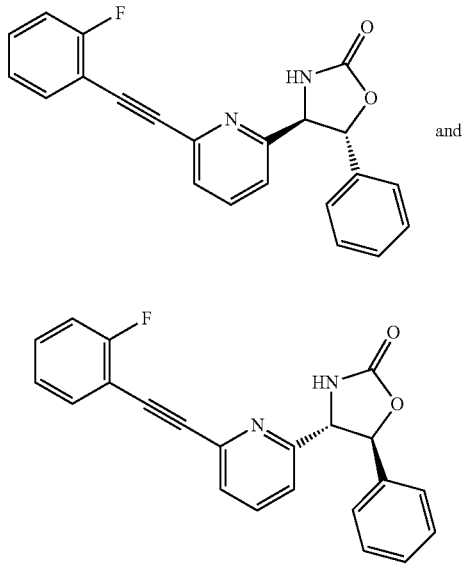

(4R,5R)-4-(6-((2-Fluorophenyl)ethynyl)pyridin-2-yl)-5-phenyloxazolidin-2-one and (4S,5S)-4-(6-((2-fluorophenyl)ethynyl)pyridin-2-yl)-5-phenyloxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(6-bromopyridin-2-yl)-5-phenyloxazolidin-2-one and 1-ethynyl-2-fluorobenzene. ¹H-NMR (CDCl₃, 500 MHz) δ 7.79 (dd, J=7.9, 7.6, 1H), 7.61 (ddd, J=7.6, 7.3, 1.6, 1H), 7.57 (dd, J=7.6, 0.6, 1H), 7.35-7.50 (m, 7H), 7.17 (m, 2H), 6.88 (bs, 1H), 5.66 (d, J=5.8, 1H), 5.01 (d, J=5.8, 1H). ¹³C-NMR (CDCl₃, 126 MHz) δ 163.1 (d, J=252), 159.4, 159.0, 143.4, 138.2, 137.9, 134.0, 131.2 (d, J=8.6), 129.1, 129.0, 127.4, 125.9, 124.2 (d, J=3.8), 120.3, 115.8 (d, J=21), 110.8 (d, J=15), 93.0 (d, J=2.9), 83.9, 83.7, 64.9. Enantiomers were resolved by SFC Prep HPLC (Chiralpak AD-H, 45% MeOH in CO2). Enantiomer 1=first enantiomer to elute from Prep (Example 14): Mass spec.: 359.2 (MH)⁺. Enantiomer 2=second enantiomer to elute from Prep (Example 15): Mass spec.: 359.2 (MH)⁺.

Example 16 and Example 17

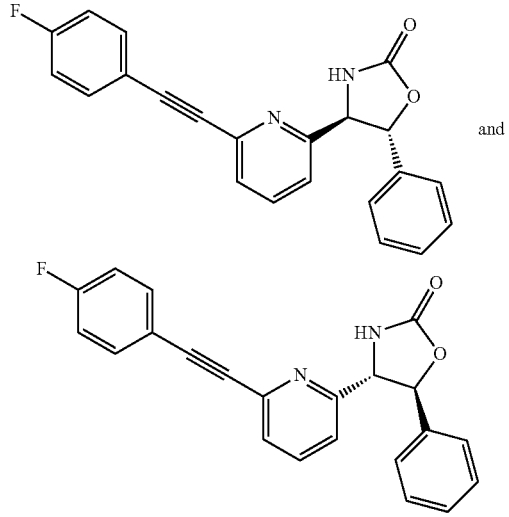

(4R,5R)-4-(6-((4-Fluorophenyl)ethynyl)pyridin-2-yl)-5-phenyloxazolidin-2-one and (4S,5S)-4-(6-((4-fluorophenyl)ethynyl)pyridin-2-yl)-5-phenyloxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(6-bromopyridin-2-yl)-5-phenyloxazolidin-2-one and 1-ethynyl-4-fluorobenzene. ¹H-NMR (CDCl₃, 500 MHz) δ 7.78 (dd, J=7.9, 7.6, 1H), 7.61 (m, 2H), 7.53 (d, J=7.6, 1H), 7.36-7.50 (m, 6H), 7.10 (m, 2H), 6.80 (bs, 1H), 5.65 (d, J=5.5, 1H), 4.99 (d, J=5.5, 1H). ¹³C-NMR (CDCl₃, 126 MHz) δ 163.2 (d, J=251), 159.3, 159.0, 143.7, 138.2, 137.8, 134.2 (d, J=8.6), 129.09, 129.05, 127.2, 125.9, 120.0, 118.1 (d, J=3.8), 116.0 (d, J=23), 89.2, 88.1, 83.9, 64.9. Enantiomers were resolved by SFC Prep HPLC (Chiralpak AD-H, 45% MeOH in CO2). Enantiomer 1=first enantiomer to elute from Prep (Example 16): Mass spec.: 360.2 (MH)⁺. Enantiomer 2=second enantiomer to elute from Prep (Example 17): Mass spec.: 360.2 (MH)⁺.

Example 18 and Example 19

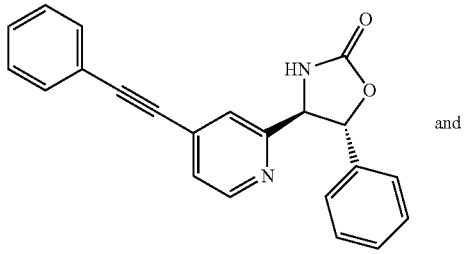

-continued

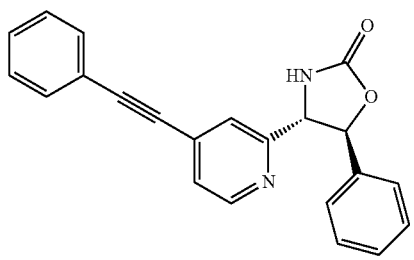

(4R,5R)-5-Phenyl-4-(4-(phenylethynyl)pyridin-2-yl)oxazolidin-2-one and (4S,5S)-5-phenyl-4-(4-(phenylethynyl)pyridin-2-yl)oxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(4-bromopyridin-2-yl)-5-phenyloxazolidin-2-one and phenylacetylene. $^1$H-NMR (CDCl$_3$, 500 MHz) δ 8.65 (d, J=5.2, 1H), 7.59 (m, 2H), 7.53 (s, 1H), 7.35-7.50 (m, 9H), 6.89 (bs, 1H), 5.63 (d, J=5.5, 1H), 4.95 (d, J=5.8, 1H). $^{13}$C-NMR (CDCl$_3$, 126 MHz) δ 159.1, 157.4, 149.7, 139.8, 133.1, 132.0, 129.4, 129.2, 128.7, 128.5, 126.2, 125.5, 122.8, 121.9, 95.0, 86.3, 85.0, 61.8. Enantiomers were resolved by Prep HPLC (Chiralpak AD, A=heptane, B=ethanol, 10%-->50% over 25 min) Enantiomer 1=first enantiomer to elute from Prep (Example 18): Mass spec.: 341.2 (MH)$^+$. Enantiomer 2=second enantiomer to elute from Prep (Example 19): Mass spec.: 341.2 (MH)$^+$.

Example 20

(4R,5R)-5-Phenyl-4-(2-(phenylethynyl)pyridin-4-yl)oxazolidin-2-one

Prepared according to the same procedure as (+)-(4R,5R)-5-(3-methoxyphenyl)-4-(3-(phenylethynyl)phenyl)oxazolidin-2-one, starting with (4R,5R)-4-(2-bromopyridin-4-yl)-5-phenyloxazolidin-2-one and phenylacetylene. $^1$H-NMR (CDCl$_3$, 500 MHz) δ 8.64 (d, J=4.9, 1H), 7.60 (m, 2H), 7.50 (m, 1H), 7.45 (m, 3H), 7.40 (m, 3H), 7.34 (m, 2H), 7.17 (dd, J=5.2, 1.5, 1H), 6.73 (bs, 1H), 5.25 (d, J=7.3, 1H), 4.82 (d, J=7.3, 1H). $^{13}$C-NMR (CDCl$_3$, 126 MHz) δ 158.8, 151.0, 148.1, 144.6, 136.7, 132.2, 129.7, 129.4, 129.3, 128.6, 126.2, 124.4, 121.9, 120.2, 90.5, 88.2, 85.4, 63.7. Mass spec.: 341.2 (MH)$^+$.

Example 21

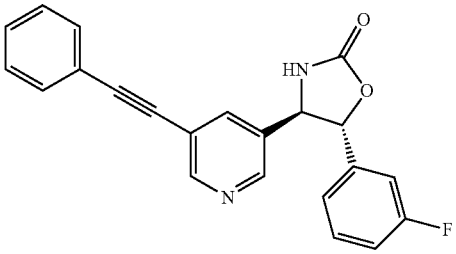 [SMILES: O=C1N[C@H](c2cncc(C#Cc3ccccc3)c2)[C@@H](c2cccc(F)c2)O1]

(4R,5R)-5-(3-Fluorophenyl)-4-(5-(phenylethynyl)pyridin-3-yl)oxazolidin-2-one

Prepared according to the same procedure as (+)-(4R,5R)-5-(3-methoxyphenyl)-4-(3-(phenylethynyl)phenyl)oxazolidin-2-one, starting with (4R,5R)-4-(5-bromopyridin-3-yl)-5-(3-fluorophenyl)oxazolidin-2-one and phenylacetylene. $^1$H-NMR (CDCl$_3$, 500 MHz) δ 8.78 (bs, 1H), 8.42 (bs, 1H), 7.90 (m, 1H), 7.57 (m, 2H), 7.35-7.45 (m, 4H), 7.02-7.17 (m, 3H), 6.83 (bs, 1H), 5.30 (d, J=7.3, 1H), 4.83 (d, J=7.3, 1H). $^{13}$C-NMR (CDCl$_3$, 126 MHz) δ 164.2, 162.2, 158.6, 152.9, 146.9, 139.1 (d, J=7.7), 136.4, 133.7 (br), 131.9, 131.1 (d, J=8.6), 129.3, 128.7, 122.1, 121.6 (d, J=2.9), 116.6 (d, J=21), 113.0 (d, J=23), 94.2, 85.2, 84.9, 62.5. Mass spec.: 359.3 (MH)$^+$.

Example 22

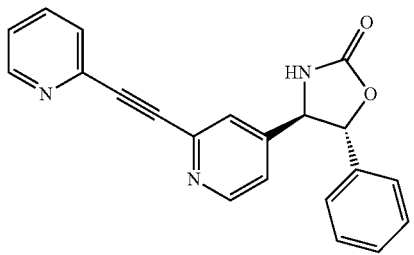 [SMILES: O=C1N[C@H](c2ccnc(C#Cc3ccccn3)c2)[C@@H](c2ccccc2)O1]

(4R,5R)-5-Phenyl-4-(2-(pyridin-2-ylethynyl)pyridin-4-yl)oxazolidin-2-one

A solution of (4R,5R)-4-(2-bromopyridin-4-yl)-5-phenyloxazolidin-2-one (20 mg, 0.063 mmol) and 2-((trimethylsilyl)ethynyl)pyridine (10.99 mg, 0.063 mmol) in dimethylformamide (300 mL) was purged with nitrogen for 30 min. The reaction was treated with triphenylphosphine (4.93 mg, 0.019 mmol), and purged 10 minutes longer. To this was added PdCl$_2$(PPh$_3$)$_2$ (2.199 mg, 3.13 mmol) and copper(I) iodide (1.193 mg, 6.27 mmol). After purging 10 min longer, the reaction was treated with triethylamine (13.1 mL, 0.094 mmol) and placed in an 85° C. oil bath. To this was added tetrabutylammonium fluoride (1M in tetrahydrofuran, 68.9 mL, 0.069 mmol) dropwise. The reaction was stirred at this temperature for 1 h. The reaction was cooled to room temperature, diluted with ethyl acetate, washed with water, then brine, dried over magnesium sulfate, and concentrated. Column chromatography (50%-->100% EtOAc/Hex) gave 19 mg (89%) as a foam solid. $^1$H-NMR (CDCl$_3$, 500 MHz) δ 8.68 (d, J=4.6, 1H), 8.60 (d, J=5.2, 1H), 7.73 (ddd, J=7.9, 7.6, 1.6, 1H), 7.59 (d, J=7.6, 1H), 7.38-7.50 (m, 5H), 7.33 (m, 3H), 7.25 (m, 1H), 5.19 (d, J=7.3, 1H), 4.88 (d, J=7.3, 1H). $^{13}$C-NMR (CDCl$_3$, 126 MHz) δ 158.8, 151.0, 150.3, 148.6, 143.3, 142.1, 136.7, 136.6, 129.6, 129.3, 127.9, 126.2, 125.1, 123.9, 120.9, 88.5, 87.4, 85.2, 63.6. Mass spec.: 342.0 (MH)$^+$.

Example 23

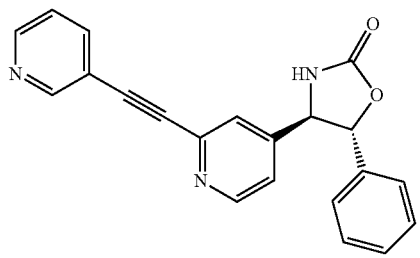 [SMILES: O=C1N[C@H](c2ccnc(C#Cc3cccnc3)c2)[C@@H](c2ccccc2)O1]

(4R,5R)-5-Phenyl-4-(2-(pyridin-3-ylethynyl)pyridin-4-yl)oxazolidin-2-one

Prepared according to the same procedure as (4R,5R)-5-phenyl-4-(2-(pyridin-2-ylethynyl)pyridin-4-yl)oxazolidin-2-one, starting with (4R,5R)-4-(2-bromopyridin-4-yl)-5-phenyloxazolidin-2-one and 3-((trimethylsilyl)ethynyl)pyridine. $^1$H-NMR (CDCl$_3$, 500 MHz) δ 8.82 (bs, 1H), 8.67 (bs, 1H), 7.90 (d, J=7.6, 1H), 7.55 (bs, 1H), 7.30-7.51 (m, 6H), 7.21 (d, J=4.0, 1H), 6.94 (bs, 1H), 5.24 (d, J=7.0, 1H), 4.84 (d, J=7.0, 1H). $^{13}$C-NMR (CDCl$_3$, 126 MHz) δ 158.9, 151.1, 148.3, 143.9, 139.0, 136.6, 129.8, 129.4, 126.1, 124.6, 120.8, 91.3, 86.9, 85.3, 63.7. Mass spec.: 342.0 (MH)$^+$.

Example 24 and Example 25

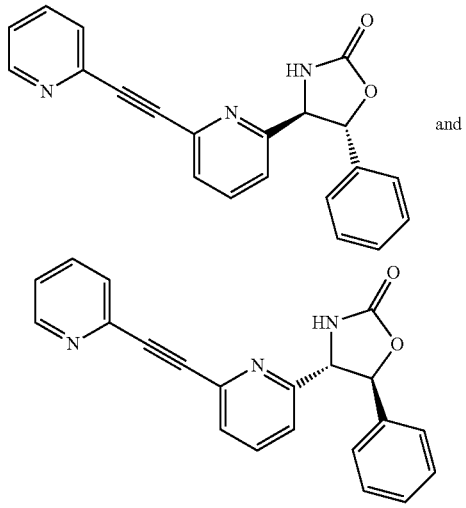

and (4R,5R)-5-Phenyl-4-(6-(pyridin-2-ylethynyl)pyridin-2-yl)oxazolidin-2-one and (4S,5S)-5-phenyl-4-(6-(pyridin-2-ylethynyl)pyridin-2-yl)oxazolidin-2-one Prepared according to the same procedure as (4R,5R)-5-phenyl-4-(2-(pyridin-2-ylethynyl)pyridin-4-yl)oxazolidin-2-one, starting with (±)-(4R,5R)-4-(6-bromopyridin-2-yl)-5-phenyloxazolidin-2-one and 2-((trimethylsilyl)ethynyl)pyridine. $^1$H-NMR (CDCl$_3$, 500 MHz) δ 8.69 (d, J=4.3, 1H), 7.70-7.81 (m, 2H), 7.63 (d, J=7.9, 1H), 7.56 (d, J=7.3, 1H), 7.47 (m, 2H), 7.35-7.45 (m, 4H), 7.33 (dd, J=7.6, 4.9, 1.2, 1H), 7.15 (bs, 1H), 5.63 (d, J=5.5, 1H), 4.99 (d, J=5.5, 1H). $^{13}$C-NMR (CDCl$_3$, 126 MHz) δ 159.4, 159.2, 150.3, 142.8, 142.4, 138.5, 137.7, 136.5, 129.01, 128.97, 127.9, 127.6, 125.8, 123.8, 120.5, 88.4, 87.7, 83.7, 64.9. Enantiomers were resolved by Prep HPLC (Chiralpak AD, A=heptane, B=ethanol, 30%-->100% over 25 min). Enantiomer 1=first enantiomer to elute from Prep (Example 24): Mass spec.: 342.0 (MH)$^+$. Enantiomer 2=second enantiomer to elute from Prep (Example 25): Mass spec.: 342.0 (MH)$^+$.

Example 26 and Example 27

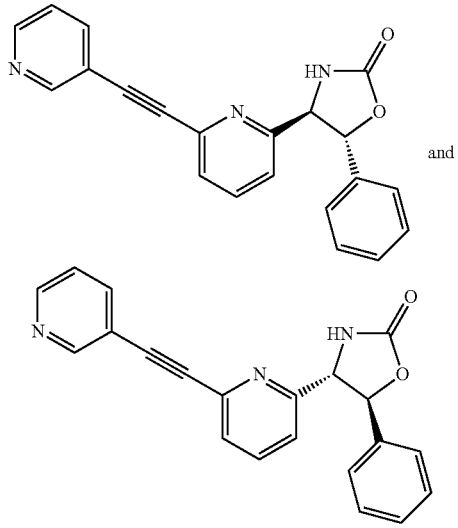

(4R,5R)-5-Phenyl-4-(6-(pyridin-3-ylethynyl)pyridin-2-yl)oxazolidin-2-one and (4S,5S)-5-phenyl-4-(6-(pyridin-3-ylethynyl)pyridin-2-yl)oxazolidin-2-one Prepared according to the same procedure as (4R,5R)-5-phenyl-4-(2-(pyridin-2-ylethynyl)pyridin-4-yl)oxazolidin-2-one, starting with (±)-(4R,5R)-4-(6-bromopyridin-2-yl)-5-phenyloxazolidin-2-one and 3-((trimethylsilyl)ethynyl)pyridine. $^1$H-NMR (CDCl$_3$, 500 MHz) δ 8.89 (bs, 1H), 8.68 (bs, 1H), 7.91 (d, J=7.9, 1H), 7.79 (dd, J=7.9, 7.6, 1H), 7.56 (d, J=7.6, 1H), 7.30-7.50 (m, 7H), 7.03 (bs, 1H), 5.65 (d, J=5.5, 1H), 4.98 (d, J=5.8, 1H). $^{13}$C-NMR (CDCl$_3$, 126 MHz) δ 159.3, 159.2, 152.7, 149.5, 143.1, 139.1, 138.3, 137.8, 129.0, 127.4, 125.9, 120.5, 91.5, 86.4, 83.7, 65.0. Enantiomers were resolved by Prep HPLC (Chiralpak AD, A=heptane, B=ethanol, 35%-->100% over 25 min) Enantiomer 1=first enantiomer to elute from Prep (Example 26):

Mass spec.: 342.0 (MH)⁺. Enantiomer 2=second enantiomer to elute from Prep (Example 27): Mass spec.: 342.0 (MH)⁺.

Example 28 and Example 29

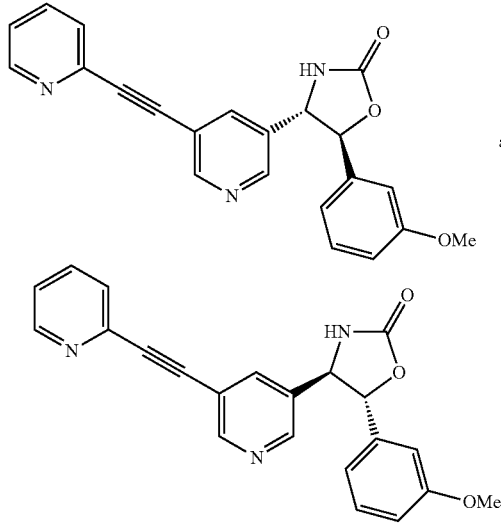

(4S,5S)-5-(3-Methoxyphenyl)-4-(5-(pyridin-2-yl-ethynyl)pyridin-3-yl)oxazolidin-2-one and (4R,5R)-5-(3-methoxyphenyl)-4-(5-(pyridin-2-ylethynyl)pyridin-3-yl)oxazolidin-2-one Prepared according to the same procedure as (4R,5R)-5-phenyl-4-(2-(pyridin-2-ylethynyl)pyridin-4-yl)oxazolidin-2-one, starting with optically-enriched (4R,5R)-4-(5-bromopyridin-3-yl)-5-(3-methoxyphenyl)oxazolidin-2-one and 2-((trimethylsilyl)ethynyl)pyridine. ¹H-NMR (CDCl₃, 500 MHz) δ 8.87 (d, J=1.8, 1H), 8.69 (m, 1H), 8.51 (d, J=2.1, 1H), 7.96 (dd, J=2.1, 1.8, 1H), 7.77 (ddd, J=7.9, 7.6, 1.8, 1H), 7.60 (m, 1H), 7.35 (m, 2H), 6.98 (dd, J=7.6, 2.0, 1H), 6.89 (m, 1H), 6.86 (d, J=7.6, 1H), 5.50 (bs, 1H), 5.30 (d, J=7.6, 1H), 4.84 (d, J=7.3, 1H), 3.85 (s, 3H). Enantiomers were resolved by SFC Prep HPLC (Chiralpak AD-H, 50% MeOH in CO2). Enantiomer 1=first enantiomer to elute from Prep (Example 28): Mass spec.: 372.0 (MH)⁺. Enantiomer 2=second enantiomer to elute from Prep (Example 29): Mass spec.: 372.0 (MH)⁺.

Example 30 and Example 31

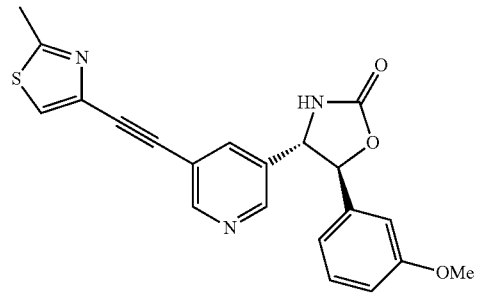

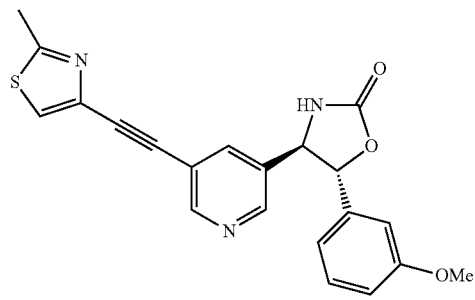

(4S,5S)-5-(3-Methoxyphenyl)-4-(5-((2-methylthi-azol-4-yl)ethynyl)pyridin-3-yl)oxazolidin-2-one and (4R,5R)-5-(3-methoxyphenyl)-4-(5-((2-methylthi-azol-4-yl)ethynyl)pyridin-3-yl)oxazolidin-2-one Prepared according to the same procedure as (4R,5R)-5-phenyl-4-(2-(pyridin-2-ylethynyl)pyridin-4-yl)oxazolidin-2-one, starting with optically-enriched (4R,5R)-4-(5-bromopyridin-3-yl)-5-(3-methoxyphenyl)oxazolidin-2-one and 2-methyl-4-((trimethylsilyl)ethynyl)thiazole. ¹H-NMR (CDCl₃, 500 MHz) δ 8.83 (d, J=1.8, 1H), 8.48 (d, J=2.1, 1H), 7.91 (m, 1H), 7.50 (s, 1H), 7.36 (dd, J=7.9, 7.9, 1H), 6.97 (dd, J=8.2, 2.1, 1H), 6.88 (bs, 1H), 6.85 (d, J=7.6, 1H), 5.48 (bs, 1H), 5.29 (d, J=7.6, 1H), 4.83 (d, J=7.6, 1H), 3.85 (s, 3H). ¹³C-NMR (CDCl₃, 126 MHz) δ 166.4, 160.3, 158.7, 152.7, 147.3, 138.0, 136.6, 135.9, 130.4, 123.9, 118.1, 115.2, 111.3, 87.9, 85.6, 84.8, 62.5, 55.5, 19.3. Enantiomers were resolved by SFC Prep HPLC (Chiralpak AD-H, 50% MeOH in CO2). Enantiomer 1=first enantiomer to elute from Prep (Example 30): Mass spec.: 392.0 (MH)⁺. Enantiomer 2=second enantiomer to elute from Prep (Example 31): Mass spec.: 392.0 (MH)⁺.

Example 32 and Example 33

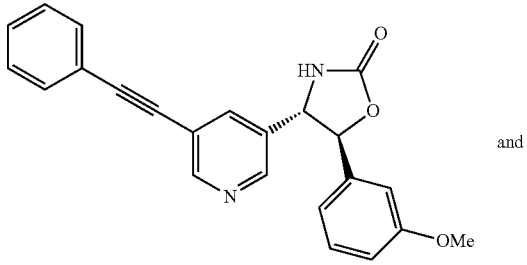

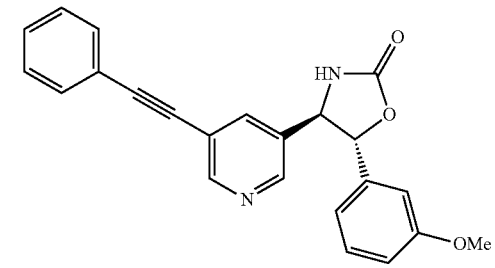

(4S,5S)-5-(3-Methoxyphenyl)-4-(5-(phenylethynyl)pyridin-3-yl)oxazolidin-2-one and (4R,5R)-5-(3-methoxyphenyl)-4-(5-(phenylethynyl)pyridin-3-yl)oxazolidin-2-one Prepared according to the same procedure as (4R,5R)-5-phenyl-4-(2-(pyridin-2-ylethynyl)pyridin-4-yl)oxazolidin-2-one, starting with optically-enriched (4R,5R)-4-(5-bromopyridin-3-yl)-5-(3-methoxyphenyl)oxazolidin-2-one and trimethyl(phenylethynyl)silane. $^1$H-NMR (CDCl$_3$, 500 MHz) δ 8.79 (bs, 1H), 8.43 (bs, 1H), 7.90 (s, 1H), 7.57 (m, 2H), 7.40 (m, 3H), 7.34 (dd, J=7.9, 7.9, 1H), 6.96 (dd, J=7.6, 1.8, 1H), 6.86 (m, 2H), 6.60 (bs, 1H), 5.28 (d, J=7.3, 1H), 4.85 (d, J=7.6, 1H), 3.83 (s, 3H). $^{13}$C-NMR (CDCl$_3$, 126 MHz) δ 160.3, 158.8, 152.8, 147.0, 138.1, 136.4, 133.9, 131.9, 130.4, 129.3, 128.6, 122.2, 121.3, 118.1, 115.2, 111.3, 94.1, 85.7, 85.3, 62.5, 55.5. Enantiomers were resolved by SFC Prep HPLC (Chiralpak AD-H, 50% MeOH in CO2). Enantiomer 1=first enantiomer to elute from Prep (Example 32): Mass spec.: 371.1 (MH)$^+$. Enantiomer 2=second enantiomer to elute from Prep (Example 33): Mass spec.: 371.2 (MH)$^+$.

Example 34

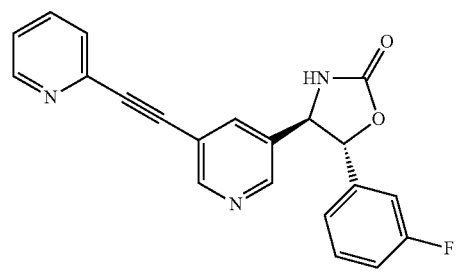 [SMILES: O=C1N[C@H](c2cncc(C#Cc3ccccn3)c2)[C@@H](c2cccc(F)c2)O1]

(4R,5R)-5-(3-Fluorophenyl)-4-(5-(pyridin-2-ylethynyl)pyridin-3-yl)oxazolidin-2-one Prepared according to the same procedure as (4R,5R)-5-phenyl-4-(2-(pyridin-2-ylethynyl)pyridin-4-yl)oxazolidin-2-one, starting with (4R,5R)-4-(5-bromopyridin-3-yl)-5-(3-fluorophenyl)oxazolidin-2-one and 2-((trimethylsilyl)ethynyl)pyridine. $^1$H-NMR (CDCl$_3$, 500 MHz) δ 8.80 (bs, 1H), 8.66 (d, J=3.7, 1H), 8.49 (bs, 1H), 7.94 (s, 1H), 7.75 (ddd, J=7.9, 7.6, 1.5, 1H), 7.58 (d, J=7.6, 1H), 7.41 (ddd, J=7.9, 7.9, 5.8, 1H), 7.33 (dd, J=7.3, 5.2, 1H), 7.09 (m, 3H), 6.97 (bs, 1H), 5.29 (d, J=7.6, 1H), 4.84 (d, J=7.3, 1H). $^{13}$C-NMR (CDCl$_3$, 126 MHz) δ 164.2, 162.2, 158.4, 153.1, 150.3, 147.6, 142.3, 139.1 (d, J=6.7), 136.9, 136.6, 131.1, 131.0, 127.6, 123.8, 121.6 (d, J=2.9), 116.6 (d, J=21), 113.0 (d, J=23), 104.3, 92.8, 84.8, 62.5. Mass spec.: 360.0 (MH)$^+$.

Example 35

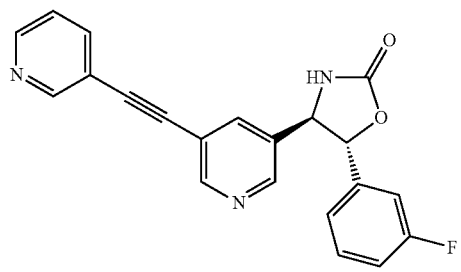 [SMILES: O=C1N[C@H](c2cncc(C#Cc3cccnc3)c2)[C@@H](c2cccc(F)c2)O1]

(4R,5R)-5-(3-Fluorophenyl)-4-(5-(pyridin-3-ylethynyl)pyridin-3-yl)oxazolidin-2-one Prepared according to the same procedure as (4R,5R)-5-phenyl-4-(2-(pyridin-2-ylethynyl)pyridin-4-yl)oxazolidin-2-one, starting with (4R,5R)-4-(5-bromopyridin-3-yl)-5-(3-fluorophenyl)oxazolidin-2-one and 3-((trimethylsilyl)ethynyl)pyridine. $^1$H-NMR (CDCl$_3$, 500 MHz) δ 8.10-9.50 (bm, 3H), 7.94 (s, 1H), 7.88 (d, J=7.9, 1H), 7.42 (m, 2H), 7.10 (m, 3H), 6.81 (bs, 1H), 5.31 (d, J=7.3, 1H), 4.85 (d, J=7.3, 1H). $^{13}$C-NMR (CDCl$_3$, 126 MHz) δ 164.2, 162.2, 158.4, 152.9, 147.4, 139.1 (d, J=6.7), 138.7, 136.5, 132.1 (d, J=11), 131.13, 131.06, 128.6 (d, J=12), 121.5 (d, J=3.8), 116.7 (d, J=21), 113.0 (d, J=23), 90.8, 88.5, 84.8, 62.5. Mass spec.: 360.0 (MH)$^+$.

Example 36 and Example 37

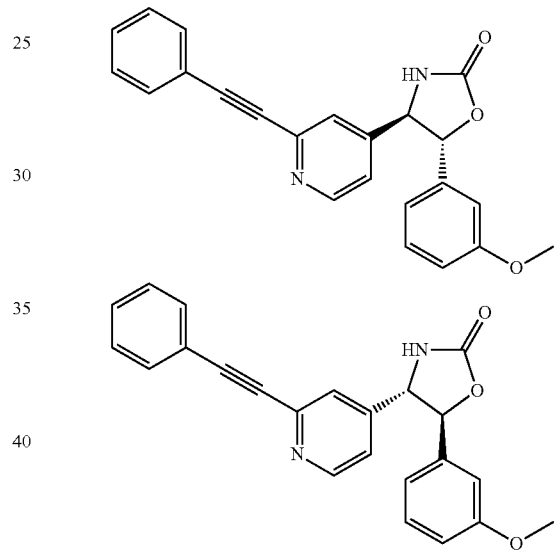

(4R,5R)-5-(3-Methoxyphenyl)-4-(2-(phenylethynyl)pyridin-4-yl)oxazolidin-2-one and (4S,5S)-5-(3-methoxyphenyl)-4-(2-(phenylethynyl)pyridin-4-yl)oxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(2-bromopyridin-4-yl)-5-(3-methoxyphenyl)oxazolidin-2-one and ethynylbenzene. $^1$H-NMR (CDCl$_3$, 500 MHz) δ 8.67 (d, J=4.9 Hz, 1H), 7.61 (m, 2H), 7.53 (s, 1H), 7.42-7.35 (m, 4H), 7.18 (dd, J=5.2, 1.5 Hz, 1H), 6.98 (m, 1H), 6.89 (m, 2H), 6.06 (s, 1H), 5.24 (d, J=7.0 Hz, 1H), 4.80 (d, J=7.0 Hz, 1H), 3.85 (s, 3H); $^{13}$C NMR (126 MHz, CDCl$_3$) δ ppm 160.3, 158.4, 151.0, 148.0, 144.7, 138.2, 132.2, 130.5, 129.4, 128.6, 124.4, 121.9, 120.2, 118.2, 115.2, 111.4, 90.6, 88.2, 85.2, 63.6, 55.5. Enantiomers were resolved by Prep HPLC (Chiralcel AD, A=heptane, B=ethanol, 35% isocratic over 40 min) Enantiomer 1=first enantiomer to elute from Prep (Example 36):

Mass spec.: 371.2 (MH)⁺. Enantiomer 2=second enantiomer to elute from Prep (Example 37): Mass spec.: 371.2 (MH)⁺.

Example 38 and Example 39

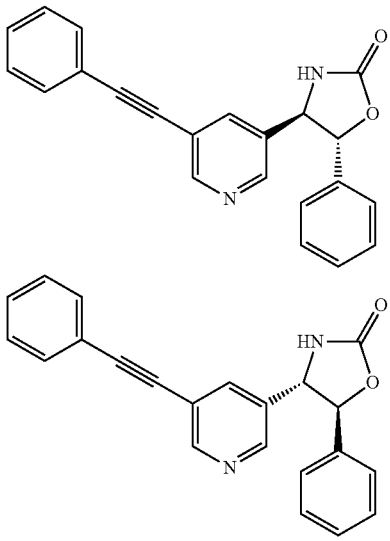

(4R,5R)-5-Phenyl-4-(5-(phenylethynyl)pyridin-3-yl)oxazolidin-2-one and (4S,5S)-5-phenyl-4-(5-(phenylethynyl)pyridin-3-yl)oxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(5-bromopyridin-3-yl)-5-phenyloxazolidin-2-one and ethynylbenzene. $^1$H-NMR (CDCl$_3$, 400 MHz) δ 8.79 (d, J=2.1 Hz, 1H), 8.42 (d, J=2.1 Hz, 1H), 7.91 (t, J=1.8 Hz, 1H), 7.58 (m, 2H), 7.45 (m, 3H), 7.41 (m, 3H), 7.34 (m, 2H), 6.24 (s, 1H), 5.33 (d, J=7.3 Hz, 1H), 4.86 (d, J=7.3 Hz, 1H); $^{13}$C NMR (126 MHz, CDCl$_3$) δ ppm 160.4, 158.4, 152.9, 147.0, 136.6, 136.3, 133.8, 131.9, 129.5, 129.3, 128.5, 126.0, 122.2, 121.4, 94.1, 85.8, 85.2, 62.5, 42.5. Enantiomers were resolved by Prep HPLC (Chiralpak AD, A=heptane, B=ethanol, 37% isocratic over 40 min) Enantiomer 1=first enantiomer to elute from Prep (Example 38): Mass spec.: 341.1 (MH)⁺. Enantiomer 2=second enantiomer to elute from Prep (Example 39): Mass spec.: 341.1 (MH)⁺.

Example 40 and Example 41

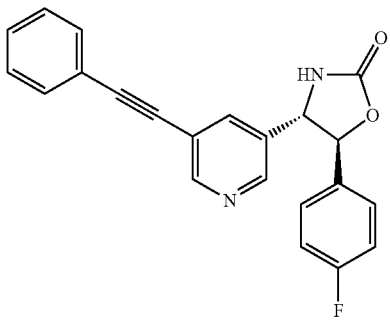

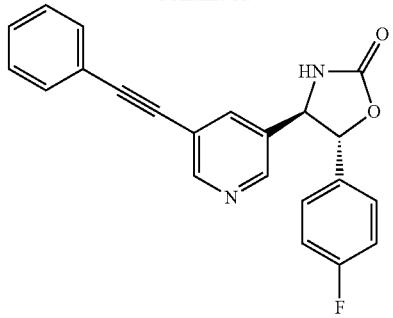

(4S,5S)-5-(4-fluorophenyl)-4-(5-(phenylethynyl)pyridin-3-yl)oxazolidin-2-one and (4R,5R)-5-(4-Fluorophenyl)-4-(5-(phenylethynyl)pyridin-3-yl)oxazolidin-2-one Prepared according to the same procedure as (+)-(4R,5R)-5-(3-methoxyphenyl)-4-(3-(phenylethynyl)phenyl)oxazolidin-2-one, starting with (±)-(4R,5R)-4-(5-bromopyridin-3-yl)-5-(4-fluorophenyl)oxazolidin-2-one and ethynylbenzene. $^1$H-NMR (CD$_3$OD, 500 MHz) δ 8.74 (s, 1H), 8.46 (s, 1H), 8.05 (m, 1H), 7.61-7.59 (m, 2H), 7.49-7.42 (m, 5H), 7.22 (t, J=8.6 Hz, 2H), 5.47 (d, J=7.6 Hz, 1H), 5.00 (d, J=7.6 Hz, 1H); $^{13}$C NMR (100.6 MHz, CD$_3$OD) δ ppm 165.9, 163.5, 160.7, 152.5, 147.6, 138.5, 136.5, 134.4, 134.3, 132.8, 130.3, 129.8, 129.7, 123.4, 117.0, 116.8, 94.7, 86.0, 85.7, 63.4. Enantiomers were resolved by Prep HPLC (Chiralcel OJ, A=heptane, B=ethanol, 75% isocratic over 45 min) Enantiomer 1=first enantiomer to elute from Prep (Example 40): Mass spec.: 359.1 (MH)⁺. Enantiomer 2=second enantiomer to elute from Prep (Example 41): Mass spec.: 359.1 (MH)⁺.

Example 42 and Example 43

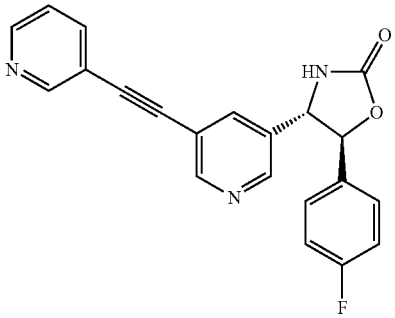

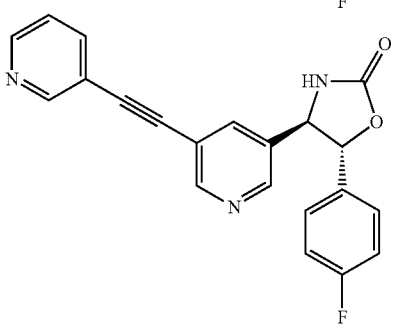

(4S,5S)-5-(4-fluorophenyl)-4-(5-(pyridin-3-ylethynyl)pyridin-3-yl)oxazolidin-2-one and (4R,5R)-5-(4-Fluorophenyl)-4-(5-(pyridin-3-ylethynyl)pyridin-3-yl)oxazolidin-2-one Prepared according to the same procedure as (4R,5R)-5-phenyl-4-(2-(pyridin-2-ylethynyl)pyridin-4-yl)oxazolidin-2-one, starting with (±)-(4R,5R)-4-(5-bromopyridin-3-yl)-5-(4-fluorophenyl)oxazolidin-2-one and 3-((trimethylsilyl)ethynyl)pyridine. ¹H-NMR (CD₃OD, 500 MHz) δ 9.08 (d, J=1.5 Hz, 1H), 8.90 (d, J=1.8 Hz, 1H), 8.84 (d, J=5.5 Hz, 1H), 8.62-8.59 (m, 2H), 8.24 (t, J=1.8 Hz, 1H), 7.99 (m, 1H), 7.47 (m, 2H), 7.20 (t, J=8.9 Hz, 2H), 5.46 (d, J=7.3 Hz, 1H), 5.06 (d, J=7.3 Hz, 1H); ¹³C NMR (126 MHz, CD₃OD) δ ppm 164.7, 162.8, 160.0, 159.7, 159.6, 159.3, 159.0, 151.0, 147.0, 146.7, 146.1, 143.9, 139.2, 136.4, 133.3, 128.8, 128.7, 126.7, 122.5, 120.4, 117.0, 116.1, 116.0, 114.7, 110.0, 90.7, 87.5, 84.9, 62.2. Enantiomers were resolved by Prep HPLC (Chiralcel OJ, A=heptane, B=ethanol, 50% isocratic over 35 min) Enantiomer 1=first enantiomer to elute from Prep (Example 42): Mass spec.: 360.4 (MH)⁺. Enantiomer 2=second enantiomer to elute from Prep (Example 43): Mass spec.: 360.4 (MH)⁺.

Example 44 and Example 45

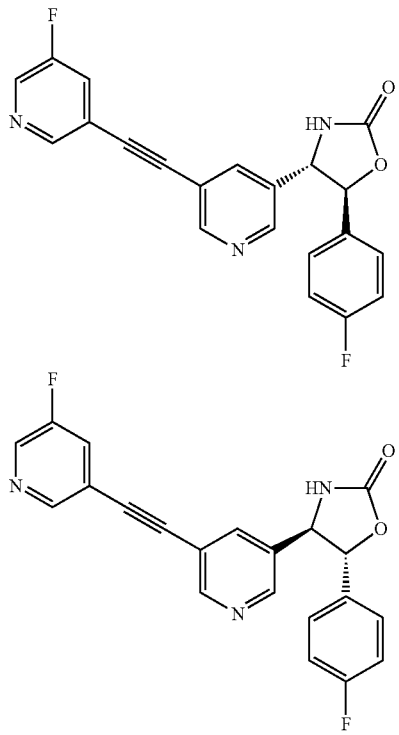

(4S,5S)-5-(4-fluorophenyl)-4-(5-((5-fluoropyridin-3-yl)ethynyl)pyridin-3-yl)oxazolidin-2-one and (4R,5R)-5-(4-Fluorophenyl)-4-(5-((5-fluoropyridin-3-yl)ethynyl)pyridin-3-yl)oxazolidin-2-one Prepared according to the same procedure as (4R,5R)-5-phenyl-4-(2-(pyridin-2-ylethynyl)pyridin-4-yl)oxazolidin-2-one, starting with (±)-(4R,5R)-4-(5-bromopyridin-3-yl)-5-(4-fluorophenyl)oxazolidin-2-one and 3-Fluoro-5-(trimethylsilyl)ethynyl)phenyl)pyridine. ¹H-NMR (CDCl₃, 500 MHz) δ 8.82 (s, 1H), 8.62 (s, 1H), 8.51 (m, 2H), 7.97 (s, 1H), 7.61 (m, 1H), 7.33 (m, 2H), 7.14 (t, J=8.6 Hz, 2H), 5.73 (s, 1H), 5.28 (d, J=7.6 Hz, 1H), 4.89 (d, J=7.3 Hz, 1H); ¹³C NMR (126 MHz, CDCl₃) δ ppm 164.5, 162.5, 159.9, 158.8, 157.9, 151.9, 148.0, 147.9, 146.7, 138.2, 138.0, 137.6, 134.6, 132.0, 128.2, 128.1, 125.9, 125.8, 120.6, 120.5, 116.6, 116.4, 89.3, 89.0, 85.1, 62.5, 62.4. Enantiomers were resolved by Prep HPLC (Chiralcel OJ, A=heptane, B=ethanol, 50% isocratic over 35 min). Enantiomer 1=first enantiomer to elute from Prep (Example 44): Mass spec.: 378.1 (MH)⁺. Enantiomer 2=second enantiomer to elute from Prep (Example 45): Mass spec.: 378.1 (MH)⁺.

Example 46

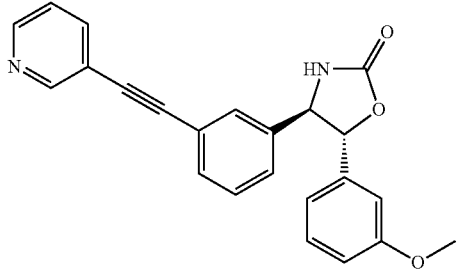 [SMILES: COc1cccc([C@H]2OC(=O)N[C@@H]2c2cccc(C#Cc3cccnc3)c2)c1]

(4R,5R)-5-(3-Methoxyphenyl)-4-(3-(pyridine-3-ylethynyl)oxazolidin-2-one

A solution of (4R,5R)-4-(3-ethnylphenyl-5-(3-methoxyphenyl)oxazolidin-2-one (20 mg, 0.068 mmol) and 3-bromopyridine (13.4 mL, 0.136 mmol) in triethylamine (0.5 mL, 3.07 mmol) was purged with nitrogen for 30 minutes. The reaction was treated with triphenylphosphine (4.83 mg, 0.018 mmol), and purged 10 min longer. To this was added dichlorobis(triphenylphosphine)palladium(II) (1.1 mg, 1.568 mmol) and copper(I) iodide (0.26 mg, 1.364 mmol). After purging 10 min longer, the reaction was heated at 90° C. for 16 h. The reaction was cooled to room temperature, diluted with diethyl ether, washed with water, then brine, dried over anhydrous magnesium sulfate, and concentrated. Biotage purification, eluting with 75% ethyl acetate/hexane, gave 15 mg (55%) as a white foam solid. ¹H-NMR (CDCl₃, 500 MHz) δ 8.79 (s, 1H), 8.59 (s, 1H), 7.84 (d, J=7.6 Hz, 1H), 7.58 (m, 2H), 7.45 (t, J=7.6 Hz, 1H), 7.34 (m, 3H), 6.95 (m, 1H), 6.88 (m, 2H), 6.01 (s, 1H), 5.30 (d, J=7.3 Hz, 1H), 4.78 (d, J=7.0 Hz, 1H), 3.84 (s, 3H); ¹³C NMR (126 MHz, CDCl₃) δ ppm 160.2, 158.6, 152.4, 148.9, 139.1, 138.8, 138.6, 132.4, 130.3, 129.7, 129.5, 127.0, 123.8, 118.1, 114.9, 111.22, 91.8, 87.1, 85.9, 64.6, 55.5. Mass spec.: 371.08 (MH)⁺.

Example 47

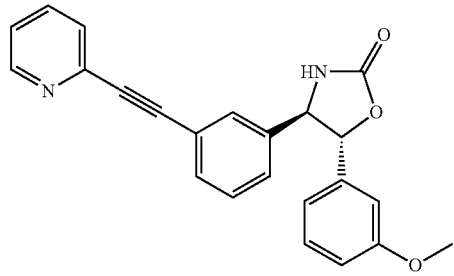

125

(4R,5R)-5-(3-Methoxyphenyl)-4-(3-(pyridin-2-yl-ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 2-bromopyridine. $^1$H-NMR (CDCl$_3$, 500 MHz) δ 8.79 (d, J=4.9 Hz, 1H), 8.03 (dd, J=7.6, 1.5 Hz, 1H), 7.74 (d, J=7.9 Hz, 1H), 7.67 (d, J=7.6 Hz, 1H), 7.64 (s, 1H), 7.56 (m, 1H), 7.47 (t, J=7.6 Hz, 1H), 7.39 (d, J=7.6 Hz, 1H), 7.34 (t, J=7.9 Hz, 1H), 6.95 (dd, J=8.2, 2.4 Hz, 1H), 6.87 (m, 2H), 6.09 (s, 1H), 5.29 (d, J=7.3 Hz, 1H), 4.81 (d, J=7.3 Hz, 1H), 3.83 (s, 3H); $^{13}$C NMR (126 MHz, CDCl$_3$) δ ppm 160.2, 158.8, 146.8, 140.2, 140.0, 139.2, 138.5, 33.1, 130.3, 129.7, 128.4, 128.2, 124.2, 122.2, 118.1, 115.0, 111.2, 86.0, 64.5, 55.5, 54.4. Mass spec.: 371.08 (MH)$^+$.

Example 48

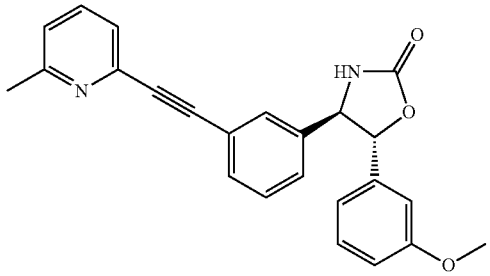

(4R,5R)-5-(3-Methoxyphenyl)-4-(3-((6-methylpyri-din-2-yl)ethnyl)phenyl)oxazolidin-2-one Prepared according to the same procedure as (4R,5R)-5-(3-methoxyphenyl)-4-(3-(pyridine-3-ylethynyl)oxazolidin-2-one, starting with 2-bromo-6-methylpyridine. $^1$H-NMR (CDCl$_3$, 500 MHz) δ 7.60 (m, 3H), 7.43 (t, J=7.6 Hz, 1H), 7.35 (m, 3H), 7.15 (d, J=7.6 Hz, 1H), 6.94 (dd, J=8.2, 2.4 Hz, 1H), 6.86 (m, 2H), 5.96 (s, 1H), 5.28 (d, J=7.3 Hz, 1H), 4.77 (d, J=7.3 Hz, 1H), 3.83 (s, 1H), 2.61 (s, 3H); $^{13}$C NMR (126 MHz, CDCl$_3$) δ ppm 160.2, 159.2, 158.5, 142.39, 139.0, 138.8, 136.6, 132.6, 130.3, 130.2, 129.5, 127.0, 124.6, 123.6, 123.0, 118.1, 115.0, 111.1, 109.7, 89.8, 87.8, 85.9, 64.6, 55.5, 24.7. Mass spec.: 385.12 (MH)$^+$.

Example 49

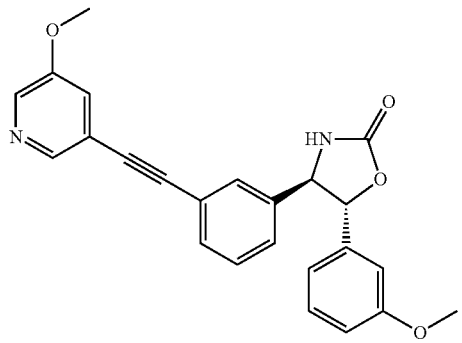 [SMILES: COc1cncc(C#Cc2cccc([C@H]3NC(=O)O[C@@H]3c3cccc(OC)c3)c2)c1]

126

(4R,5R)-5-(3-Methoxyphenyl)-4-(3-(5-methylpyri-din-3-yl)ethnyl)phenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-5-methylpyridine. $^1$H-NMR (CDCl$_3$, 400 MHz) δ 8.39 (d, J=1.5 Hz, 1H), 8.30 (d, J=2.8 Hz, 1H), 7.59 (m, 2H), 7.45 (t, J=7.9 Hz, 1H), 7.35 (m, 3H), 6.96 (m, 2H), 5.89 (s, 1H), 5.30 (d, J=7.3 Hz, 1H), 4.79 (d, J=7.3 Hz, 1H), 3.91 (s, 3H), 3.84 (s, 3H). Mass spec.: 401.2 (MH)$^+$.

Example 50

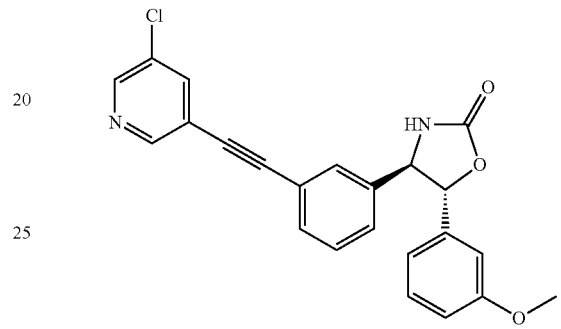

(4R,5R)-4-(3-((5-Chloropyridin-3-yl)ethnyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-5-chloropyridine. $^1$H-NMR (CDCl$_3$, 400 MHz) δ 8.90 (bs, 2H), 7.97 (s, 1H), 7.57 (m, 2H), 7.47 (t, J=7.8 Hz, 1H), 7.35 (m, 2H), 6.96 (m, 1H), 6.88 (m, 2H), 6.38 (bs, 1H), 5.30 (d, J=7.3 Hz, 1H), 4.82 (d, J=7.3 Hz, 1H), 3.84 (s, 3H); $^{13}$C NMR (100 Hz, CDCl$_3$) δ ppm 159.7, 138.6, 138.0, 132.1, 129.9, 129.4, 129.2, 127.1, 122.5, 117.6, 114.5, 110.9, 85.7, 64.1, 55.0. Mass spec.: 404.98 (MH)$^+$.

Example 51

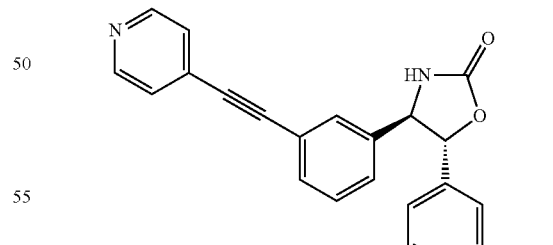

(4R,5R)-5-(3-Methoxyphenyl)-4-(3-(pyridine-4-yl)ethnyl)phenyl)oxazolidin-2-one Prepared according to the same procedure as (4R,5R)-5-(3-methoxyphenyl)-4-(3-(pyridine-3-ylethynyl)oxazolidin-2-one, starting with 4-bromopyridine hydrochloride. $^1$H-NMR (CDCl$_3$, 500 MHz) δ 8.89 (bs, 2H), 7.91 (s, 2H), 7.67 (m, 2H), 7.52 (t, J=7.9 Hz, 1H), 7.44 (d, J=7.9 Hz, 1H), 7.36 (t, J=7.6 Hz, 1H), 6.97 (dd, J=8.2, 2.4 Hz, 1H), 6.88 (m, 2H), 6.26 (s, 1H), 5.30 (d, J=7.0 Hz, 1H), 4.85 (d, J=7.0 Hz, 1H), 3.85 (s, 3H); $^{13}$C NMR (126 Hz, CDCl$_3$) δ ppm 160.3, 158.9, 139.6, 138.5, 133.0, 130.4, 130.3, 129.9, 128.9, 121.8, 118.1, 114.9, 111.5, 86.0, 64.4, 55.5. Mass spec.: 371.06 (MH)$^+$.

Example 52

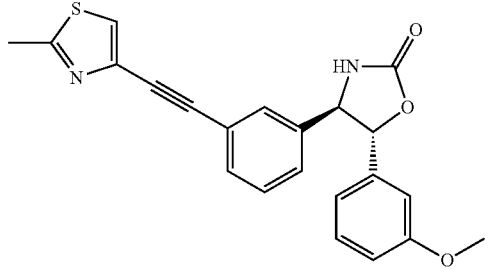

(4R,5R)-5-(3-Methoxyphenyl)-4-(3-((2-methylthiazol-4-yl)ethnyl)phenyl)oxazolidin-2-one Prepared according to the same procedure as (4R,5R)-5-(3-methoxyphenyl)-4-(3-(pyridine-3-ylethynyl)oxazolidin-2-one, starting with 4-bromo-2-methylthiazole. $^1$H-NMR (CDCl$_3$, 500 MHz) δ 7.59 (d, J=7.6 Hz, 1H), 7.55 (s, 1H), 7.44 (t, J=7.6 Hz, 1H), 7.34 (m, 2H), 6.95 (m, 1H), 6.87 (m, 2H), 6.22 (s, 1H), 5.32 (d, J=7.3 Hz, 1H), 4.81 (d, J=7.3 Hz, 1H), 3.84 (s, 3H), 2.81 (s, 3H); $^{13}$C NMR (126 Hz, CDCl$_3$) δ ppm 160.3, 138.7, 138.4, 132.5, 130.3, 129.8, 129.6, 127.0, 123.5, 118.0, 115.1, 111.2, 89.4, 86.3, 64.7, 55.5. Mass spec.: 391.0 (MH)$^+$.

Example 53

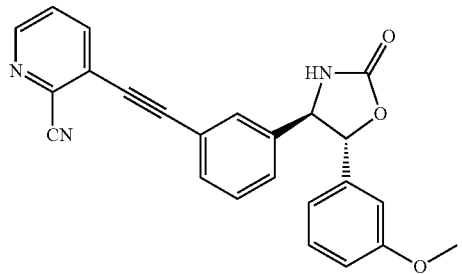 [SMILES: COc1cccc([C@H]2OC(=O)N[C@@H]2c2cccc(C#Cc3cccnc3C#N)c2)c1]

3-((3-((4R,5R)-5-(3-Methoxyphenyl)-2-oxooxazolidin-4-yl)phenyl)ethynyl)picolinonitrile Prepared according to the same procedure as (4R,5R)-5-(3-methoxyphenyl)-4-(3-(pyridine-3-ylethynyl)oxazolidin-2-one, starting with 3-bromopicolinonitrile. $^1$H-NMR (CDCl$_3$, 400 MHz) δ 8.68 (dd, J=4.8, 1.5 Hz, 1H), 7.98 (dd, J=8.0, 1.5 Hz, 1H), 7.68 (d, J=7.8 Hz, 1H), 7.61 (s, 1H), 7.56 (m, 1H), 7.48 (t, J=7.8 Hz, 1H), 7.36 (m, 2H), 6.95 (m, 1H), 6.87 (m, 2H), 6.95 (m, 1H), 6.87 (m, 2H), 6.32 (s, 1H), 5.31 (d, J=7.3 Hz, 1H), 4.84 (d, J=7.3 Hz, 1H), 3.84 (s, 3H); $^{13}$C NMR (100 Hz, CDCl$_3$) δ ppm 159.7, 158.9, 149.1, 139.0, 138.6, 137.9, 35.5, 132.5, 129.9, 129.4, 129.3, 127.5, 125.8, 124.6, 122.2, 117.6, 115.5, 114.6, 110.7, 97.6, 85.7, 83.3, 64.1, 55.0. Mass spec.: 394.04 (MH)$^-$.

Example 54

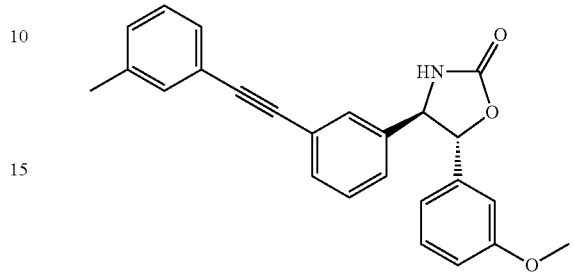

(4R,5R)-5-(3-Methoxyphenyl)-4-(3-(m-tolylethnyl)phenyl)oxazolidin-2-one

Prepared according to the same procedure as (4R,5R)-5-(3-methoxyphenyl)-4-(3-(pyridine-3-ylethynyl)oxazolidin-2-one, starting with 1-bromo-3-methylbenzene. $^1$H-NMR (CDCl$_3$, 500 MHz) δ 7.57 (d, J=7.6 Hz, 1H), 7.54 (s, 1H), 7.42 (t, J=7.6 Hz, 1H), 7.40 (s, 1H), 7.37-7.33 (m, 2H), 7.29-7.26 (m, 2H), 7.20 (d, J=7.6 Hz, 1H), 6.96 (m, 1H), 6.88 (m, 2H), 5.72 (s, 1H), 5.33 (d, J=7.3 Hz, 1H), 4.78 (d, J=7.3 Hz, 1H), 3.84 (s, 3H), 2.39 (s, 3H); $^{13}$C NMR (126 MHz, CDCl$_3$) δ ppm 160.2, 138.7, 138.2, 132.4, 132.3, 130.3, 129.6, 129.4, 128.8, 128.4, 126.3, 124.7, 122.7, 118.0, 115.0, 111.1, 90.8, 88.2, 86.1, 64.7, 55.5, 21.4. Mass spec.: 384.1 (MH)$^+$.

Example 55

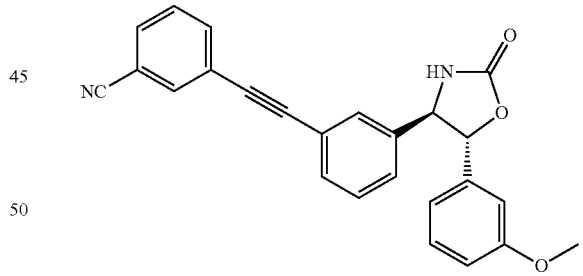

3-((3-(4R,5R)-5-(3-Methoxyphenyl)-2-oxazolidin-4-yl)phenyl)ethynyl)benzonitrile

Prepared according to the same procedure as (4R,5R)-5-(3-methoxyphenyl)-4-(3-(pyridine-3-ylethynyl)oxazolidin-2-one, starting with 3-bromobenzonitrile. $^1$H-NMR (CDCl$_3$, 500 MHz) δ 7.82 (s, 1H), 7.76 (d, J=7.9 Hz, 1H), 7.65 (d, J=7.6 Hz, 1H), 7.58 (s, 1H), 7.56 (d, J=4.9 Hz, 1H), 7.50 (t, J=7.9 Hz, 1H), 7.45 (t, J=7.9 Hz, 1H), 7.35 (m, 2H), 6.95 (m, 1H), 6.88 (m, 2H), 6.23 (bs, 1H), 5.30 (d, J=7.3 Hz, 1H), 4.81 (d, J=7.3 Hz, 1H), 3.84 (s, 3H); $^{13}$C NMR (126 MHz, CDCl$_3$) δ ppm 160.2, 139.1, 138.7, 135.8, 135.0, 132.4, 131.8, 130.3, 129.7, 129.6, 128.9, 127.1, 124.6, 123.6, 118.1, 114.9, 113.1, 111.3, 90.9, 88.0, 86.0, 64.6, 55.5. Mass spec.: 395.2 (MH)+.

Example 56

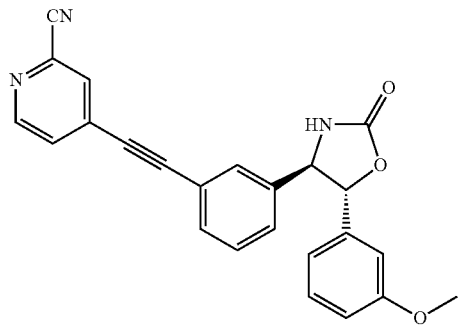

4-((3-((4R,5R)-5-(3-Methoxyphenyl)-2-oxooxazolidin-4-yl)phenyl)ethynyl)nicolinonitrile Prepared according to the same procedure as (4R,5R)-5-(3-methoxyphenyl)-4-(3-(pyridine-3-ylethynyl)oxazolidin-2-one, starting with 4-bromopicolinonitrile. ¹H-NMR (CDCl₃, 500 MHz) δ 8.74 (s, 1H), 7.80 (s, 1H), 7.60 (m, 3H), 7.49 (t, J=7.6 Hz, 1H), 7.39 (d, J=7.6 Hz, 1H), 7.35 (t, J=7.6 Hz, 1H), 6.97 (dd, J=8.2, 2.14 Hz, 1H), 6.88 (m, 2H), 6.27 (s, 1H), 5.29 (d, J=7.3 Hz, 1H), 4.83 (d, J=7.3 Hz, 1H), 3.84 (s, 3H); ¹³C NMR (126 Hz, CDCl₃) δ ppm 160.2, 151.2, 139.3, 138.5, 134.3, 132.9, 132.7, 130.34, 130.28, 130.0, 129.8, 128.7, 128.1, 122.5, 118.1, 116.8, 114.9, 111.4, 96.0, 86.0, 85.7, 64.5, 55.5, 50.9. Mass spec.: 396.27 (MH)+.

Example 57

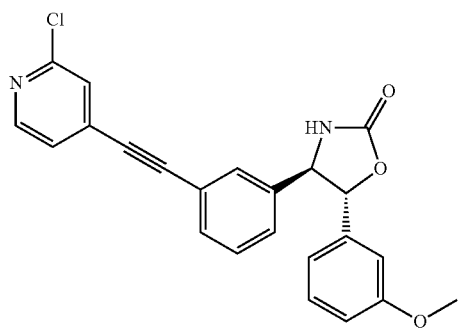 [SMILES: COc1cccc([C@H]2OC(=O)N[C@@H]2c2cccc(C#Cc3ccnc(C#N)c3)c2)c1]

(4R,5R)-4-(3-((2-Chloropyridin-4-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 4-bromo-2-chloropyridine. ¹H-NMR (CDCl₃, 500 MHz) δ 8.43 (d, J=5.2 Hz, 1H), 7.59 (m, 2H), 7.48 (m, 2H), 7.38-7.33 (m, 3H), 6.97 (dd, J=8.2, 2.4 Hz, 1H), 6.88 (m, 2H), 5.40 (s, 1H), 5.30 (d, J=7.0 Hz, 1H), 4.79 (d, J=7.3 Hz, 1H), 3.85 (s, 3H); ¹³C NMR (126 Hz, CDCl₃) δ ppm 160.2, 158.2, 151.9, 149.8, 139.2, 138.6, 133.9, 132.7, 130.3, 130.0, 129.7, 127.7, 126.2, 124.3, 123.0, 118.0, 114.9, 111.3, 94.3, 86.5, 85.9, 64.5, 55.5. Mass spec.: 405.1 (MH)+.

Example 58

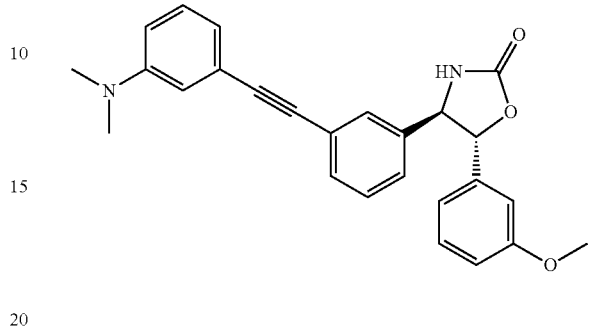

(4R,5R)-4-(3-((3-(Dimethylamino)phenyl)ethnyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-N,N-dimethylaniline. ¹H-NMR (CDCl₃, 500 MHz) δ 7.63-7.58 (m, 4H), 7.54 (m, 2H), 7.46 (t, J=7.9 Hz, 1H), 7.38-7.32 (m, 2H), 6.97 (m, 1H), 6.89 (m, 2H), 5.89 (s, 1H), 5.34 (d, J=7.0 Hz, 1H), 4.82 (d, J=7.3 Hz, 1H), 3.85 (s, 3H), 3.25 (s, 6H); ¹³C NMR (126 MHz, CDCl₃) δ ppm 160.3, 159.1, 144.4, 138.9, 138.5, 132.5, 131.6, 130.7, 130.4, 129.7, 129.6, 127.1, 125.5, 123.8, 122.3, 120.0, 118.0, 115.0, 111.3, 90.7, 88.6, 64.6, 55.5, 45.8. Mass spec.: 413.2 (MH)+.

Example 59

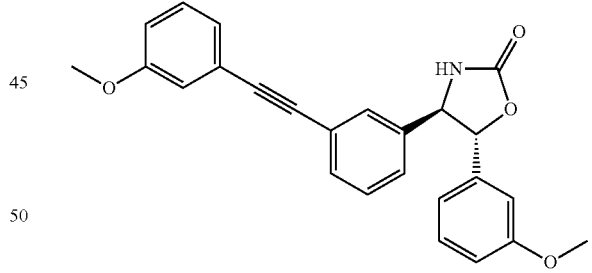

(4R,5R)-5-(3-Methoxyphenyl)-4-(3-((3-methoxyphenyl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 1-bromo-3-methoxybenzene. ¹H-NMR (CDCl₃, 500 MHz) δ 7.56 (m, 2H), 7.43 (t, J=7.6 Hz, 1H), 7.34 (t, J=7.9 Hz, 1H), 7.29 (m, 2H), 7.16 (d, J=7.3 Hz, 1H), 7.09 (m, 1H), 6.95 (m, 2H), 6.88 (m, 2H), 5.79 (bs, 1H), 5.32 (d, J=7.0 Hz, 1H), 4.78 (d, J=7.0 Hz, 1H), 3.86 (s, 3H), 3.84 (s, 3H); ¹³C NMR (126 Hz, CDCl₃) δ ppm 160.2, 159.5, 138.9, 138.8, 132.3, 131.8, 130.3, 129.7, 129.6, 129.4, 128.7, 128.5, 126.5, 126.4, 124.5, 124.3, 123.9, 118.1, 116.5, 115.4, 115.0, 111.2, 90.5, 88.4, 86.0, 64.6, 55.49, 55.45. Mass spec.: 400.25 (MH)+.

Example 60

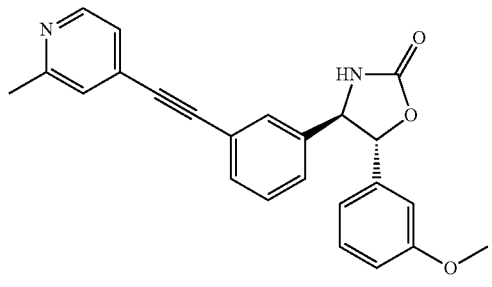

(4R,5R)-5-(3-Methoxyphenyl)-4-(3-((2-methylpyridin-4-yl)ethnyl)phenyl)oxazolidin-2-one Prepared according to the same procedure as (4R,5R)-5-(3-methoxyphenyl)-4-(3-(pyridine-3-ylethynyl)oxazolidin-2-one, starting with 4-bromo-2-methylpyridine. $^1$H-NMR (CDCl$_3$, 500 MHz) δ 8.82 (d, J=5.8 Hz, 1H), 7.71 (d, J=5.8 Hz, 1H), 7.68 (s, 1H), 7.64 (m, 2H), 7.51 (t, J=7.9 Hz, 1H), 7.43 (d, J=7.9 Hz, 1H), 7.36 (t, J=7.9 Hz, 1H), 6.97 (m, 1H), 6.88 (m, 2H), 6.38 (s, 1H), 5.28 (d, J=7.0 Hz, 1H), 4.84 (d, J=7.3 Hz, 1H), 3.84 (s, 3H), 2.85 (s, 3H); $^{13}$C NMR (126 Hz, CDCl$_3$) δ ppm 160.3, 158.9, 154.3, 142.1, 140.0, 139.7, 138.5, 133.0, 130.4, 130.3, 129.9, 129.0, 128.7, 125.7, 121.7, 118.1, 114.8, 111.5, 100.9, 86.0, 85.8, 64.4, 55.5, 19.9, 15.3. Mass spec.: 385.1 (MH)+.

Example 61

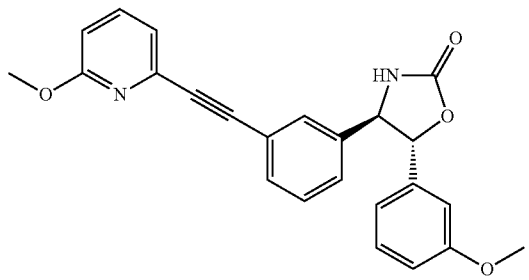

(4R,5R)-5-(3-Methoxyphenyl)-4-(3-O-methoxypyridin-2-yl)ethnyl)phenyl)oxazolidin-2-one Prepared according to the same procedure as (4R,5R)-5-(3-methoxyphenyl)-4-(3-(pyridine-3-ylethynyl)oxazolidin-2-one, starting with 2-bromo-6-methoxypyridine. $^1$H-NMR (CDCl$_3$, 500 MHz) δ 7.61 (m, 3H), 7.43 (t, J=7.6 Hz, 1H), 7.34 (m, 2H), 6.94 (dd, J=8.9, 2.4 Hz, 1H), 6.87 (m, 2H), 6.13 (s, 1H), 5.30 (d, J=7.3 Hz, 1H), 4.79 (d, J=7.3 Hz, 1H), 4.01 (s, 3H), 3.83 (s, 3H); $^{13}$C NMR (126 MHz, CDCl$_3$) δ ppm 160.2, 159.0, 138.9, 38.7, 132.7, 30.3, 130.1, 129.5, 127.0, 123.8, 118.1, 115.0, 111.2, 87.8, 86.0, 64.6, 55.5, 53.8. Mass spec.: 401.4 (MH)+.

Example 62

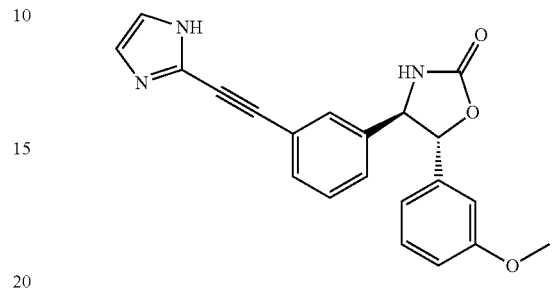

(4R,5R)-4-(3-((1H-imidazol-2-yl)ethnyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 2-bromo-1H-imidazole. $^1$H-NMR (CDCl$_3$, 500 MHz) δ 7.73 (bs, 1H), 7.61 (bs, 1H), 7.40 (d, J=7.3 Hz, 1H), 7.23 (m, 2H), 7.18 (s, 2H), 7.10 (m, 1H), 6.91 (m, 1H), 6.74 (m, 2H), 5.08 (d, J=7.3 Hz, 1H), 4.78 (d, J=7.6 Hz, 1H), 3.76 (s, 3H). Mass spec.: 360.1 (MH)+.

Example 63

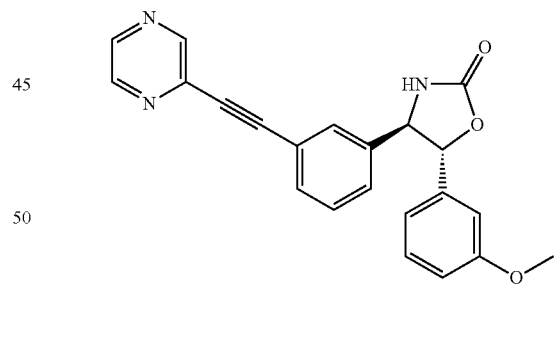

(4R,5R)-5-(3-Methoxyphenyl)-4-(3-(pyrazin-2-ylethynyl)phenyl)oxazolidin-2-one

Prepared according to the same procedure as (4R,5R)-5-(3-methoxyphenyl)-4-(3-(pyridine-3-ylethynyl)oxazolidin-2-one, starting with 2-bromopyrazine. $^1$H-NMR (CDCl$_3$, 500 MHz) δ 8.79 (bs, 2H), 7.64 (d, J=7.6 Hz, 1H), 7.61 (s, 1H), 7.47 (t, J=7.6 Hz, 1H), 7.39 (t, J=7.6 Hz, 1H), 7.34 (t, J=7.9 Hz, 1H), 6.95 (dd, J=8.2, 1.8 Hz, 1H), 6.87 (m, 2H), 6.35 (s, 1H), 5.29 (d, J=7.3 Hz, 1H), 4.82 (d, J=7.3 Hz, 1H), 3.83 (s, 3H); $^{13}$C NMR (126 MHz, CDCl$_3$) δ ppm 160.2, 159.0, 139.2, 138.6, 132.8, 130.3, 130.2, 129.7, 127.7, 122.6, 118.1, 115.0, 111.3, 92.7, 86.0, 64.6, 55.5. Mass spec.: 372.1 (MH)⁺.

Example 64

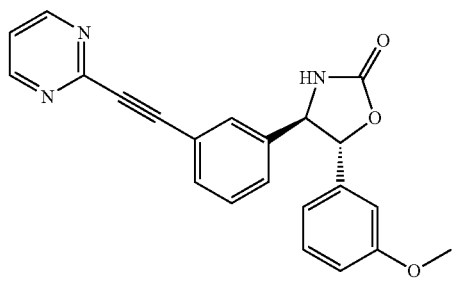 [SMILES: COc1cccc([C@H]2OC(=O)N[C@@H]2c2cccc(C#Cc3ncccn3)c2)c1]

(4R,5R)-5-(3-Methoxyphenyl)-4-(3-(pyrimidin-2-ylethynyl)phenyl)oxazolidin-2-one

Prepared according to the same procedure as (4R,5R)-5-(3-methoxyphenyl)-4-(3-(pyridine-3-ylethynyl)oxazolidin-2-one, starting with 2-bromopyrimidine. ¹H-NMR (CDCl₃, 500 MHz) δ 8.85 (d, J=4.9 Hz, 2H), 7.71 (d, J=7.6 Hz, 1H), 7.65 (s, 1H), 7.49 (t, J=7.6 Hz, 1H), 7.43 (d, J=7.9 Hz, 1H), 7.37-7.33 (m, 2H), 6.96 (dd, J=8.4, 2.4 Hz, 1H), 6.87 (m, 2H), 5.87 (s, 1H), 5.31 (d, J=7.3 Hz, 1H), 4.81 (d, J=7.6 Hz, 1H), 3.84 (s, 3H); ¹³C NMR (126 MHz, CDCl₃) δ ppm 160.2, 158.9, 157.5, 152.6, 138.9, 138.4, 133.3, 130.8, 130.3, 129.7, 127.9, 122.3, 120.2, 118.1, 115.1, 111.2, 88.1, 88.0, 86.1, 64.6, 55.5. Mass spec.: 370.3 (MH)⁻.

Example 65

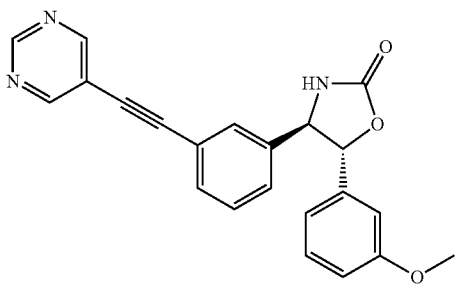 [SMILES: COc1cccc([C@H]2OC(=O)N[C@@H]2c2cccc(C#Cc3cncnc3)c2)c1]

(4R,5R)-5-(3-Methoxyphenyl)-4-(3-(pyrimidin-5-ylethynyl)phenyl)oxazolidin-2-one

Prepared according to the same procedure as (4R,5R)-5-(3-methoxyphenyl)-4-(3-(pyridine-3-ylethynyl)oxazolidin-2-one, starting with 5-bromopyrimidine. ¹H-NMR (CDCl₃, 500 MHz) δ 9.26 (bs, 1H), 9.01 (bs, 2H), 7.60 (m, 2H), 7.48 (t, J=7.6 Hz, 1H), 7.36 (m, 2H), 6.97 (m, 1H), 6.88 (m, 2H), 6.21 (s, 1H), 5.31 (d, J=7.3 Hz, 1H), 4.82 (d, J=7.3 Hz, 1H), 3.84 (s, 3H); ¹³C NMR (126 MHz, CDCl₃) δ ppm 160.2, 159.0, 158.7, 156.5, 139.2, 138.6, 132.5, 130.3, 129.8, 129.7, 127.6, 123.0, 118.1, 114.9, 111.4, 95.9, 86.0, 83.2, 64.6, 55.5. Mass spec.: 372.1 (MH)⁺.

Example 66

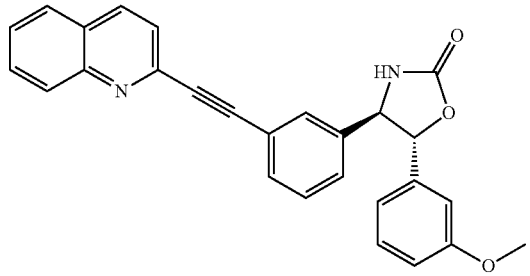 [SMILES: COc1cccc([C@H]2OC(=O)N[C@@H]2c2cccc(C#Cc3ccc4ccccc4n3)c2)c1]

(4R,5R)-5-(3-Methoxyphenyl)-4-(3-(quinolin-2-ylethynyl)phenyl)oxazolidin-2-one

Prepared according to the same procedure as (4R,5R)-5-(3-methoxyphenyl)-4-(3-(pyridine-3-ylethynyl)oxazolidin-2-one, starting with 2-bromoquinoline. ¹H-NMR (CDCl₃, 400 MHz) δ 8.49 (d, J=8.5 Hz, 1H), 8.40 (d, J=8.5 Hz, 1H), 7.96 (m, 2H), 7.75 (m, 4H), 7.51 (t, J=7.8 Hz, 1H), 7.42 (d, J=7.8 Hz, 1H), 7.35 (t, J=8.0 Hz, 1H), 6.96 (d, J=8.3 Hz, 1H), 6.90 (m, 2H), 5.75 (s, 1H), 5.32 (d, J=7.3 Hz, 1H), 4.83 (d, J=7.3 Hz, 1H), 3.84 (s, 3H); ¹³C NMR (126 MHz, CDCl₃) δ ppm 160.2, 158.6, 143.6, 140.7, 140.3, 139.3, 138.5, 133.4, 133.1, 130.7, 130.3, 129.8, 129.0, 128.6, 128.0, 127.6, 125.2, 124.4, 122.0, 118.1, 115.1, 111.2, 86.0, 64.5, 55.5. Mass spec.: 421.1 (MH)⁺.

Example 67

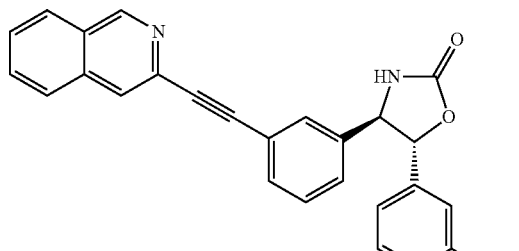

(4R,5R)-4-(3-(Isoquinolin-3-ylethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 3-bromoisoquinoline. ¹H-NMR (CDCl₃, 500 MHz) δ 9.57 (s, 1H), 8.22 (d, J=8.2 Hz, 1H), 8.15 (s, 1H), 7.98 (m, 2H), 7.83 (m, 1H), 7.67 (m, 2H), 7.45 (t, J=7.9 Hz, 1H), 7.34 (m, 2H), 6.94 (dd, J=8.2, 1.8 Hz, 1H), 6.88 (m, 2H), 6.29 (s, 1H), 5.29 (d, J=7.3 Hz, 1H), 4.82 (d, J=7.3 Hz, 1H), 3.83 (s, 3H); ¹³C NMR (126 MHz, CDCl₃) δ ppm 160.2, 158.9, 150.3, 139.2, 138.6, 137.2, 134.4, 132.8, 130.7, 130.3, 130.12, 130.08, 129.63, 129.57, 127.9, 127.0, 122.5, 118.1, 115.0, 111.2, 93.8, 86.0, 64.5, 55.5. Mass spec.: 421.1 (MH)+.

Example 68

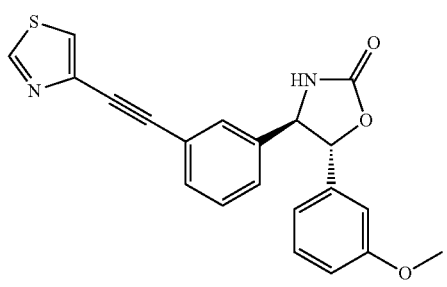 [SMILES: COc1cccc([C@H]2OC(=O)N[C@@H]2c2cccc(C#Cc3cscn3)c2)c1]

(4R,5R)-5-(3-Methoxyphenyl)-4-(3-(thiazol-4-yl)ethnyl)phenyl)oxazolidin-2-one

Prepared according to the same procedure as (4R,5R)-5-(3-methoxyphenyl)-4-(3-(pyridine-3-ylethynyl)oxazolidin-2-one, starting with 4-bromothiazole. $^1$H-NMR (CDCl$_3$, 500 MHz) δ 8.96 (bs, 1H), 7.67 (s, 1H), 7.61 (d, J=7.6 Hz, 1H), 7.56 (s, 1H), 7.44 (t, J=7.6 Hz, 1H), 7.34 (m, 2H), 6.95 (m, 1H), 6.87 (m, 2H), 6.03 (s, 1H), 5.30 (d, J=7.3 Hz, 1H), 4.80 (d, J=7.3 Hz, 1H), 3.84 (s, 3H); $^{13}$C NMR (126 Hz, CDCl$_3$) δ ppm 160.2, 158.9, 138.9, 138.6, 132.5, 130.3, 129.9, 129.6, 127.0, 123.5, 118.1, 115.0, 111.2, 89.0, 86.1, 64.6, 55.5. Mass spec.: 377.1 (MH)+.

Example 69

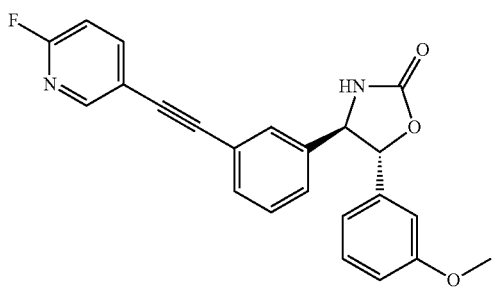 [SMILES: COc1cccc([C@H]2OC(=O)N[C@@H]2c2cccc(C#Cc3ccc(F)nc3)c2)c1]

(4R,5R)-4-(3-O-Fluoropyridin-3-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 5-bromo-2-fluoropyridine. $^1$H-NMR (CDCl$_3$, 400 MHz) δ 8.42 (d, J=2.0 Hz, 1H), 7.59 (m, 2H), 7.93 (dd, J=8.3, 2.3 Hz, 1H), 7.56 (m, 2H), 7.44 (t, J=7.8 Hz, 1H), 7.34 (m, 2H), 6.96 (m, 2H), 6.88 (m, 2H), 5.98 (s, 1H), 5.29 (d, J=7.0 Hz, 1H), 4.79 (d, J=7.0 Hz, 1H), 3.84 (s, 3H); $^{13}$C NMR (100.6 Hz, CDCl$_3$) δ ppm 163.6, 161.2, 159.8, 158.2, 150.3, 150.2, 143.3, 143.2, 138.7, 138.3, 131.8, 129.8, 129.14, 129.07, 126.6, 123.2, 117.6, 117.5, 114.4, 110.8, 109.4, 109.0, 91.1, 85.5, 85.3, 64.1, 55.0. Mass spec.: 389.02 (MH)+.

Example 70

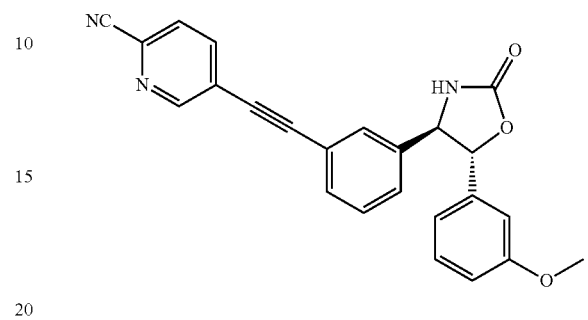

5-((3-((4R,5R)-5-(3-Methoxyphenyl)-2-oxazolidin-4-yl)phenyl)ethynyl)picolinonitrile Prepared according to the same procedure as (4R,5R)-5-(3-methoxyphenyl)-4-(3-(pyridine-3-ylethynyl)oxazolidin-2-one, starting with 5-bromopicolinonitrile. $^1$H-NMR (CDCl$_3$, 400 MHz) δ 8.85 (m, 1H), 7.96 (dd, J=8.0, 2.0 Hz, 1H), 7.72 (dd, J=8.0, 0.80 Hz, 1H), 7.62-7.59 (m, 2H), 7.48 (t, J=7.8 Hz, 1H), 7.38-7.33 (m, 2H), 6.97 (m, 1H), 6.89 (m, 2H), 5.93 (s, 1H), 5.31 (d, J=7.3 Hz, 1H)), 4.82 (d, J=7.0 Hz, 1H), 3.84 (s, 3H); $^{13}$C NMR (100.6 Hz, CDCl$_3$) δ ppm 159.8, 158.4, 152.8, 138.8, 138.0, 132.1, 131.8, 129.9, 129.4, 129.3, 127.4, 127.3, 123.4, 122.5, 117.6, 116.5, 114.4, 110.9, 95.5, 85.6, 85.2, 64.0, 55.0. Mass spec.: 394.1 (MH)+.

Example 71

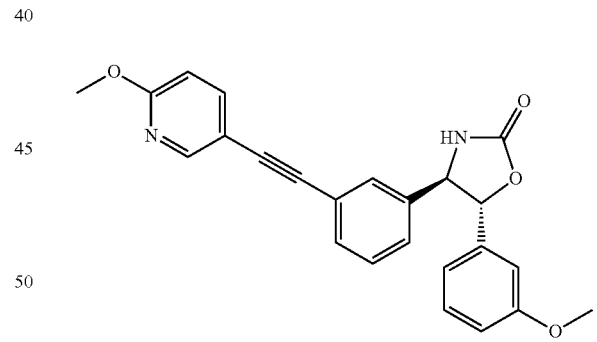

(4R,5R)-5-(3-Methoxyphenyl)-4-(3-((6-methoxypyridin-3-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 5-bromo-2-methoxypyridine. $^1$H-NMR (CDCl$_3$, 400 MHz) δ 8.44 (bs, 1H), 7.76 (d, J=8.8 Hz, 1H), 7.56 (m, 2H), 7.43 (t, J=7.5 Hz, 1H), 7.35 (t, J=8.3 Hz, 1H), 7.29 (m, 1H), 6.96 (m, 1H), 6.88 (m, 2H), 6.82 (bs, 1H), 6.02 (s, 1H), 5.33 (d, J=7.3 Hz, 1H), 4.80 (d, J=7.3 Hz, 1H), 4.01 (s, 3H), 3.84 (s, 3H); $^{13}$C NMR (100.6 Hz, CDCl$_3$) δ ppm 159.8, 158.7, 149.3, 141.3, 138.3, 138.1, 131.8, 129.8, 129.0, 129.03, 129.0, 126.1, 123.9, 117.6, 114.5, 110.8, 89.7, 86.7, 85.7, 64.2, 55.0, 53.8. Mass spec.: 401.1 (MH)+.

Example 72

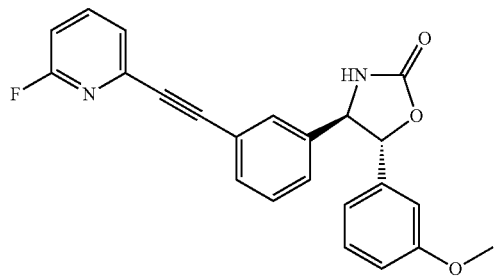 [SMILES: COc1cccc([C@H]2OC(=O)N[C@@H]2c2cccc(C#Cc3cccc(F)n3)c2)c1]

(4R,5R)-4-(3-((6-Fluoropyridin-2-yl)ethnyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 2-bromo-6-fluoropyridine. $^1$H-NMR (CDCl$_3$, 500 MHz) δ 7.83 (dd, J=15.6, 7.9 Hz, 1H), 7.63 (d, J=7.6 Hz, 1H), 7.58 (s, 1H), 7.45 (m, 2H), 7.35 (m, 2H), 6.96 (m, 2H), 6.87 (m, 2H), 6.24 (s, 1H), 5.31 (d, J=7.3 Hz, 1H), 4.82 (d, J=7.3 Hz, 1H), 3.84 (s, 3H); $^{13}$C NMR (126 MHz, CDCl$_3$) δ ppm 160.2, 159.3, 141.5, 141.0, 138.9, 138.4, 132.8, 130.3, 130.1, 129.6, 127.4, 124.9, 123.1, 118.1, 115.0, 111.3, 110.0, 109.7, 89.5, 88.2, 86.2, 64.7, 55.5. Mass spec.: 389.1 (MH)+.

Example 73

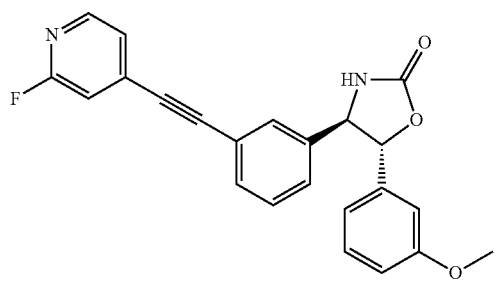 [SMILES: COc1cccc([C@H]2OC(=O)N[C@@H]2c2cccc(C#Cc3ccnc(F)c3)c2)c1]

(4R,5R)-4-(3-((2-Fluoropyridin-4-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 4-bromo-2-fluoropyridine. $^1$H-NMR (CDCl$_3$, 500 MHz) δ 8.33 (bs, 1H), 7.59 (m, 2H), 7.47 (t, J=7.6 Hz, 1H), 7.38-7.32 (m, 3H), 7.10 (bs, 1H), 6.96 (m, 1H), 6.88 (m, 2H), 6.20 (s, 1H), 5.30 (d, J=7.0 Hz, 1H), 4.82 (d, J=7.0 Hz, 1H), 3.84 (s, 3H); $^{13}$C NMR (126 Hz, CDCl$_3$) δ ppm 160.2, 139.2, 138.6, 132.7, 130.3, 129.9, 129.7, 127.7, 122.9, 118.1, 114.9, 111.4, 94.3, 86.6, 86.1, 64.6, 55.5. Mass spec.: 389.1 (MH)+.

Example 74

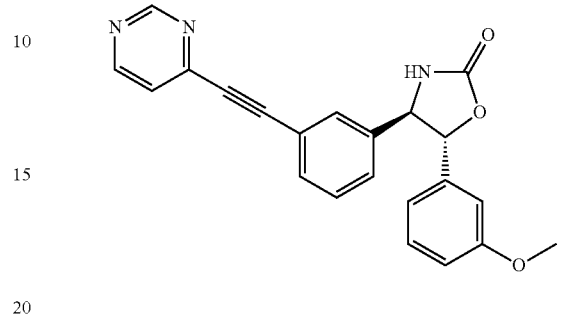

(4R,5R)-5-(3-Methoxyphenyl)-4-(3-(pyrimidin-4-ylethynyl)phenyl)oxazolidin-2-one

Prepared according to the same procedure as (4R,5R)-5-(3-methoxyphenyl)-4-(3-(pyridine-3-ylethynyl)oxazolidin-2-one, starting with 4-bromopyrimidine. $^1$H-NMR (CDCl$_3$, 500 MHz) δ 9.27 (d, J=1.2 Hz, 1H), 8.83 (d, J=5.2 Hz, 1H), 7.68 (d, J=7.6 Hz, 1H), 7.64 (s, 1H), 7.57 (dd, J=5.2, 1.2 Hz, 1H), 7.50 (t, J=7.9 Hz, 1H), 7.42 (d, J=7.9 Hz, 1H), 7.35 (t, J=7.9 Hz, 1H), 6.97 (dd, J=8.2, 2.4 Hz, 1H), 6.88 (m, 2H), 6.02 (s, 1H), 5.30 (d, J=7.3 Hz, 1H), 4.82 (d, J=7.3 Hz, 1H), 3.84 (s, 3H); $^{13}$C NMR (126 MHz, CDCl$_3$) δ ppm 160.3, 158.9, 158.3, 156.6, 151.0, 139.2, 138.4, 133.2, 130.5, 130.4, 129.8, 128.4, 123.8, 122.1, 118.1, 115.0, 111.3, 94.3, 87.1, 86.1, 64.6, 55.5. Mass spec.: 372.1 (MH)+.

Example 75

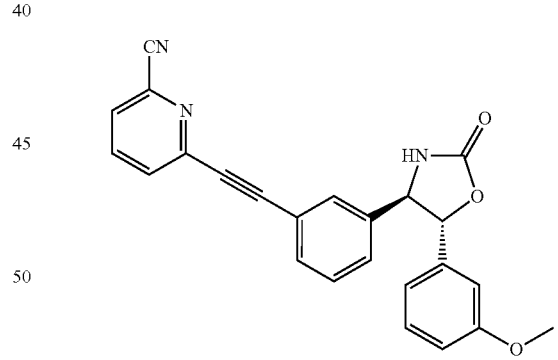

6-((3-((4R,5R)-5-(3-Methoxyphenyl)-2-oxooxazolidin-4-yl)phenyl)ethynyl)picolinonitrile Prepared according to the same procedure as (4R,5R)-5-(3-methoxyphenyl)-4-(3-(pyridine-3-ylethynyl)oxazolidin-2-one, starting with 6-bromopicolinonitrile. $^1$H-NMR (CDCl$_3$, 500 MHz) δ 7.89 (t, J=7.9 Hz, 1H), 7.75 (d, J=7.9 Hz, 1H), 7.67 (m, 2H), 7.62 (s, 1H), 7.48 (t, J=7.6 Hz, 1H), 7.39 (d, J=7.6 Hz, 1H), 7.35 (t, J=7.9 Hz, 1H), 6.96 (dd, J=8.6, 2.4 Hz, 1H), 6.87 (m, 2H), 6.16 (s, 1H), 5.30 (d, J=7.0 Hz, 1H), 4.82 (d, J=7.3 Hz, 1H), 3.84 (s, 3H); $^{13}$C NMR (126 MHz, CDCl$_3$) δ ppm 160.2, 159.0, 144.8, 139.1, 138.5, 137.6, 134.4, 132.9, 130.3, 129.7, 127.8, 127.5, 122.6, 118.1, 116.6, 115.0, 111.3, 90.7, 87.8, 86.1, 64.6, 55.5. Mass spec.: 394.2 (MH)⁺.

Example 76

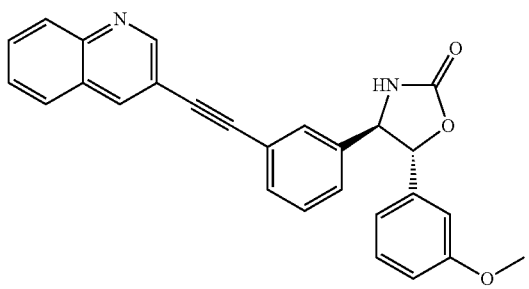 [SMILES: COc1cccc([C@H]2OC(=O)N[C@@H]2c2cccc(C#Cc3cnc4ccccc4c3)c2)c1]

(4R,5R)-5-(3-Methoxyphenyl)-4-(3-(quinolin-3-ylethynyl)phenyl)oxazolidin-2-one

Prepared according to the same procedure as (4R,5R)-5-(3-methoxyphenyl)-4-(3-(pyridine-3-ylethynyl)oxazolidin-2-one, starting with 3-bromoqinoline. ¹H-NMR (CDCl₃, 500 MHz) δ 9.32 (bs, 1H), 8.72 (s, 1H), 8.42 (d, J=7.0 Hz, 1H), 8.04 (d, J=7.9 Hz, 1H), 7.98 (t, J=7.3 Hz, 1H), 7.83 (t, J=7.9 Hz, 1H), 7.64 (m, 2H), 7.50 (t, J=7.9 Hz, 1H), 7.37 (m, 2H), 6.97 (dd, J=7.9, 2.1 Hz, 1H), 6.90 (m, 2H), 6.02 (s, 1H), 5.33 (d, J=7.0 Hz, 1H), 4.83 (d, J=7.3 Hz, 1H), 3.85 (s, 3H); ¹³C NMR (126 MHz, CDCl₃) δ ppm 160.2, 143.3, 139.2, 138.6, 133.3, 132.6, 130.3, 129.9, 129.8, 129.7, 128.2, 127.7, 122.9, 118.1, 115.0, 111.3, 94.3, 86.1, 64.6, 55.5. Mass spec.: 421.2 (MH)⁺.

Example 77

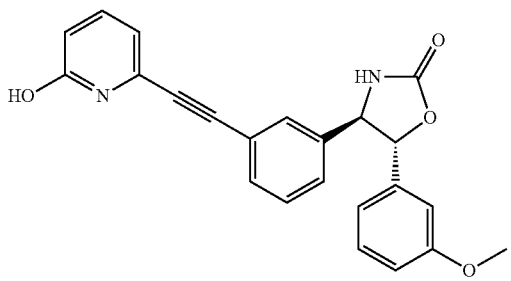 [SMILES: COc1cccc([C@H]2OC(=O)N[C@@H]2c2cccc(C#Cc3cccc(O)n3)c2)c1]

(4R,5R)-4-(3-((6-Hydroxypyridin-2-yl)ethnyl)phenyl)-5-(3-methoxyphenyl)-oxazolidin-2-one To a solution of (4R,5R)-5-(3-methoxyphenyl)-4-(3-((6-methoxypyridin-2-yl)ethnyl)phenyl)oxazolidin-2-one (11.50 mg, 0.029 mmol) in acetic acid (1 mL) was added sodium iodide (4.30 mg, 0.029 mmol), the reaction was heated at 100° C. for one h. The reaction was concentrated and the residue purified by Prep HPLC TFA-MeOH (Sunfire C18 19×100 mm 5 um, 30-100%, 15 min gradient, 25 mL/min flow rate) to give 7.1 mg (63%). ¹H-NMR (CDCl₃, 400 MHz) δ 7.65 (s, 1H), 7.58 (d, J=7.5 Hz, 1H), 7.52 (m, 1H), 7.42 (t, J=7.8 Hz, 1H), 7.32 (m, 2H), 6.94 (m, 1H), 6.87 (m, 2H), 6.72 (d, J=8.8 Hz, 1H), 6.65 (d, J=6.8 Hz, 1H), 6.54 (bs, 1H), 4.80 (d, J=7.0 Hz, 1H), 4.80 (d, J=7.0 Hz, 1H), 3.83 (s, 3H); ¹³C NMR (100.6 MHz, CDCl₃) δ ppm 163.9, 159.7, 158.4, 141.6, 139.0, 138.3, 132.0, 129.8, 129.7, 129.03, 128.98, 121.5, 119.9, 117.7, 114.5, 112.7, 110.8, 94.4, 85.3, 82.0, 64.0, 55.0. Mass spec.: 387.1 (MH)⁺.

Example 78

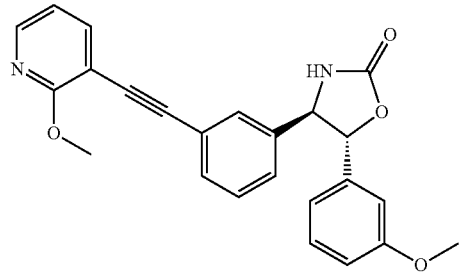 [SMILES: COc1cccc([C@H]2OC(=O)N[C@@H]2c2cccc(C#Cc3cccnc3OC)c2)c1]

(4R,5R)-5-(3-Methoxyphenyl)-4-(3-((2-methoxypyridin-3-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-2-methoxypyridine. ¹H-NMR (CDCl₃, 400 MHz) δ 8.20 (d, J=3.3 Hz, 1H), 7.80 (dd, J=7.5, 1.8 Hz, 1H), 7.59 (d, J=7.8 Hz, 1H), 7.56 (s, 1H), 7.42 (t, J=7.8 Hz, 1H), 7.34 (t, J=8.3 Hz, 1H), 7.29 (d, J=7.8 Hz, 1H), 6.94 (m, 2H), 6.87 (m, 2H), 6.15 (s, 1H), 5.32 (d, J=7.3 Hz, 1H), 4.80 (d, J=7.3 Hz, 1H), 4.08 (s, 3H), 3.83 (s, 3H); ¹³C NMR (100.6 Hz, CDCl₃) δ ppm 163.1, 159.7, 145.9, 141.6, 138.2, 138.1, 132.0, 129.8, 129.2, 129.0, 126.3, 123.9, 117.6, 116.2, 114.5, 110.8, 107.0, 93.4, 85.7, 84.7, 64.2, 55.0, 53.9. Mass spec.: 401.1 (MH)⁺.

Example 79

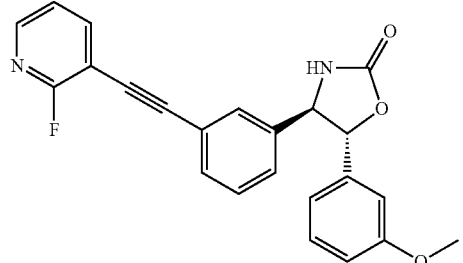

(4R,5R)-4-(3-((2-Fluoropyridin-3-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-2-fluoropyridine. ¹H-NMR (CDCl₃, 400 MHz) δ 8.24 (s, 1H), 7.96 (t, J=7.5 Hz, 1H), 7.61 (d, J=6.5 Hz, 1H), 7.57 (s, 1H), 7.46 (t, J=7.5 Hz, 1H), 7.35 (m, 2H), 7.25 (m, 1H), 6.96 (m, 1H), 6.88 (m, 2H), 6.00 (s, 1H), 5.32 (d, J=7.3 Hz, 1H), 4.81 (d, J=7.3 Hz, 1H), 3.84 (s, 3H); ¹³C NMR (100.6 Hz, CDCl₃) δ ppm 159.8, 146.5, 146.4, 143.1, 138.5, 138.1, 132.1, 129.8, 129.3, 129.1, 126.8, 123.0, 117.6, 114.6, 110.8, 94.6, 85.6, 81.6, 81.5, 64.1, 55.0. Mass spec.: 387.07 (MH)+.

Example 80

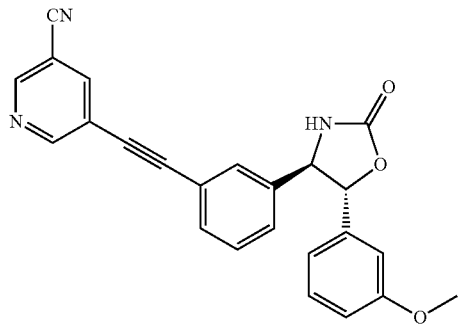 [SMILES: COc1cccc([C@H]2OC(=O)N[C@@H]2c2cccc(C#Cc3cncc(C#N)c3)c2)c1]

5-((3-((4R,5R)-5-(3-Methoxyphenyl)-2-oxooxazolidin-4-yl)-phenyl)ethynyl)nicotinonitrile Prepared according to the same procedure as (4R,5R)-5-(3-methoxyphenyl)-4-(3-(pyridine-3-ylethynyl)oxazolidin-2-one, starting with 5-bromonicotinonitrile. $^1$H-NMR (CDCl$_3$, 400 MHz) δ 8.12 (s, 1H), 7.59 (m, 2H), 7.48 (t, J=7.5 Hz, 1H), 7.36 (m, 2H), 6.97 (m, 1H), 6.89 (m, 2H), 6.19 (s, 1H), 5.30 (d, J=7.3 Hz, 1H), 4.82 (d, J=7.3 Hz, 1H), 3.84 (s, 3H); $^{13}$C NMR (100.6 Hz, CDCl$_3$) δ ppm 159.8, 158.6, 138.8, 138.1, 132.1, 129.9, 129.4, 129.2, 127.3, 122.3, 117.6, 114.4, 111.0, 94.2, 85.6, 64.1, 55.0. Mass spec.: 396.0 (MH)+.

Example 81

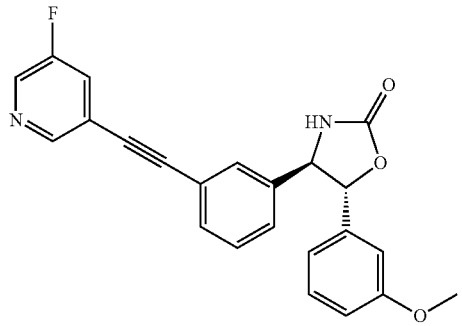

(4R,5R)-4-(3-((5-Fluoropyridin-3-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-5-fluoropyridine. $^1$H-NMR (CDCl$_3$, 500 MHz) δ 7.71 (s, 1H), 7.60 (d, J=7.6 Hz, 1H), 7.57 (s, 1H), 7.47 (t, J=7.6 Hz, 1H), 7.35 (m, 2H), 6.96 (m, 1H), 6.88 (m, 2H), 6.36 (s, 1H), 5.31 (d, J=7.0 Hz, 1H), 4.83 (d, J=7.3 Hz, 1H), 3.84 (s, 3H); $^{13}$C NMR (126 Hz, CDCl$_3$) δ ppm 160.2, 159.2, 139.2, 138.5, 132.6, 130.3, 129.9, 129.7, 127.6, 122.9, 118.1, 114.9, 111.4, 86.1, 64.6, 55.5. Mass spec.: 389.0 (MH)+.

Example 82

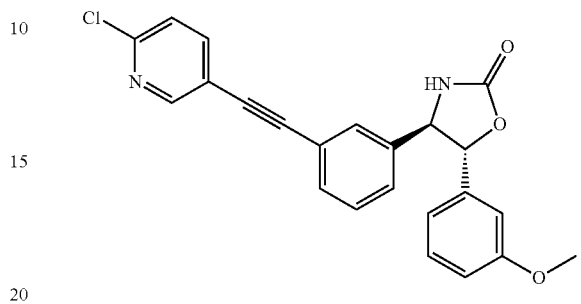

(4R,5R)-4-(3-((6-Chloropyridin-3-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 5-bromo-2-chloropyridine. $^1$H-NMR (CDCl$_3$, 500 MHz) δ 7.84 (d, J=7.6 Hz, 1H), 7.58 (d, J=7.9 Hz, 1H), 7.56 (s, 1H), 7.46 (t, J=7.6 Hz, 1H), 7.34 (m, 2H), 6.96 (m, 1H), 6.88 (m, 2H), 6.08 (s, 1H), 5.32 (d, J=7.0 Hz, 1H), 4.81 (d, J=7.3 Hz, 1H), 3.84 (s, 3H); $^{13}$C NMR (126 Hz, CDCl$_3$) δ ppm 160.2, 159.1, 139.0, 138.5, 132.4, 130.3, 129.7, 129.6, 127.2, 123.5, 118.1, 114.9, 111.3, 93.1, 86.1, 64.6, 55.5. Mass spec.: 404.95 (MH)+.

Example 83

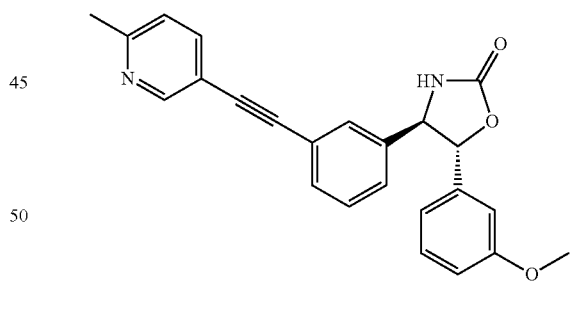

(4R,5R)-5-(3-Methoxyphenyl)-4-(3-((6-methylpyridin-3-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 5-bromo-2-methylpyridine. $^1$H-NMR (CDCl$_3$, 500 MHz) δ 8.96 (s, 1H), 8.24 (d, J=8.2 Hz, 1H), 7.60 (m, 3H), 7.47 (t, J=7.9 Hz, 1H), 7.36 (m, 2H), 6.96 (m, 1H), 6.87 (m, 2H), 6.39 (s, 1H), 5.28 (d, J=7.3 Hz, 1H), 4.82 (d, J=7.3 Hz, 1H), 3.84 (s, 3H), 2.86 (s, 3H); $^{13}$C NMR (126 Hz, CDCl$_3$) δ ppm 160.2, 159.2, 153.8, 145.3, 145.1, 139.3, 138.5, 132.6, 130.3, 129.9, 129.7, 128.0, 126.8, 122.4, 118.1, 114.9, 111.4, 95.5, 86.1, 83.3, 64.5, 55.5. Mass spec.: 385.1 (MH)+.

Example 84

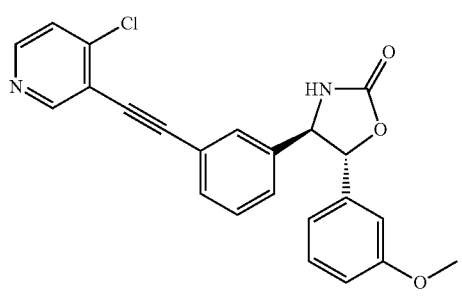

(4R,5R)-4-(3-((4-Chloropyridin-3-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-4-chloropyridine. $^1$H-NMR (CDCl$_3$, 500 MHz) δ 8.90 (bs, 1H), 8.60 (bs, 1H), 7.63 (m, 3H), 7.49 (t, J=7.6 Hz, 1H), 7.36 (m, 2H), 6.96 (d, J=8.2 Hz, 1H), 6.88 (m, 2H), 5.79 (s, 1H), 5.32 (d, J=7.3 Hz, 1H), 4.82 (d, J=7.3 Hz, 1H), 3.84 (s, 3H); $^{13}$C NMR (126 Hz, CDCl$_3$) δ ppm 160.2, 158.6, 151.5, 147.5, 147.0, 139.1, 138.5, 134.5, 132.7, 130.3, 129.9, 129.7, 128.7, 127.7, 123.0, 118.1, 115.0, 111.3, 97.9, 86.0, 83.1, 64.6, 55.5. Mass spec.: 404.9 (MH)+.

Example 85

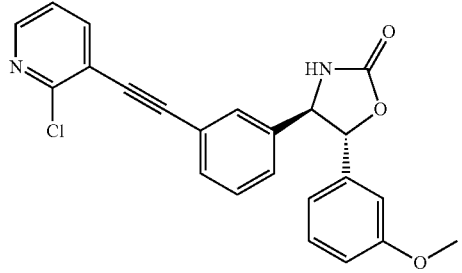 [SMILES: COc1cccc([C@H]2OC(=O)N[C@@H]2c2cccc(C#Cc3cccnc3Cl)c2)c1]

(4R,5R)-4-(3-((2-Chloropyridin-3-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-2-chloropyridine. $^1$H-NMR (CDCl$_3$, 500 MHz) δ 8.40 (d, J=4.0 Hz, 1H), 7.90 (d, J=7.6 Hz, 1H), 7.64 (d, J=7.6 Hz, 1H), 7.59 (s, 1H), 7.47 (t, J=7.6 Hz, 1H), 7.35 (m, 2H), 7.30 (m, 1H), 6.96 (d, J=8.6 Hz, 1H), 6.88 (m, 2H), 5.47 (s, 1H), 5.32 (d, J=7.3 Hz, 1H), 4.80 (d, J=7.3 Hz, 1H), 3.84 (s, 3H); $^{13}$C NMR (126 Hz, CDCl$_3$) δ ppm 160.2, 158.3, 148.6, 141.4, 139.0, 138.6, 132.5, 130.3, 129.7, 129.6, 127.3, 123.6, 122.1, 120.3, 118.0, 115.0, 111.2, 95.8, 85.9, 85.3, 64.5, 55.5. Mass spec.: 404.9 (MH)+.

Example 86

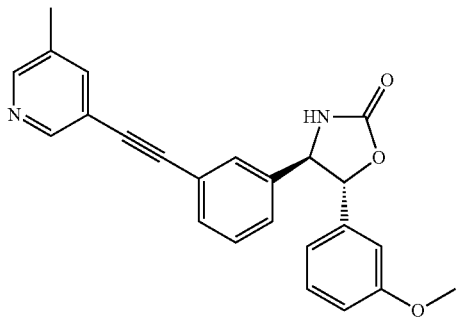 [SMILES: COc1cccc([C@H]2OC(=O)N[C@@H]2c2cccc(C#Cc3cncc(C)c3)c2)c1]

(4R,5R)-5-(3-Methoxyphenyl)-4-(3-((5-methylpyridin-3-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-5-methylpyridine. $^1$H-NMR (CDCl$_3$, 500 MHz) δ 8.82 (bs, 1H), 8.66 (bs, 1H), 8.20 (s, 1H), 7.60 (m, 2H), 7.49 (t, J=7.6 Hz, 1H), 7.37 (m, 2H), 6.97 (dd, J=8.2, 2.1 Hz, 1H), 6.88 (m, 2H), 6.24 (s, 1H), 5.31 (d, J=7.0 Hz, 1H), 4.83 (d, J=7.3 Hz, 1H), 3.84 (s, 3H), 2.59 (s, 3H); $^{13}$C NMR (126 Hz, CDCl$_3$) δ ppm 160.2, 159.2, 139.3, 138.4, 132.7, 130.4, 129.9, 129.8, 128.1, 122.4, 118.1, 114.9, 111.4, 86.1, 64.5, 55.5. Mass spec.: 385.1 (MH)+.

Example 87

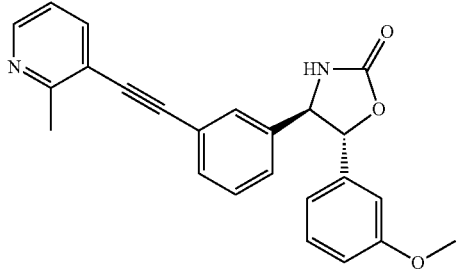 [SMILES: COc1cccc([C@H]2OC(=O)N[C@@H]2c2cccc(C#Cc3cccnc3C)c2)c1]

(4R,5R)-5-(3-Methoxyphenyl)-4-(3-((2-methylpyridin-3-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-2-methylpyridine. $^1$H-NMR (CDCl$_3$, 400 MHz) δ 8.82 (d, J=4.5 Hz, 1H), 8.32 (d, J=8.0 Hz, 1H), 7.70 (t, J=7.0 Hz, 1H), 7.61 (m, 2H), 7.50 (t, J=7.8 Hz, 1H), 7.36 (m, 2H), 6.97 (m, 1H), 6.88 (m, 2H), 6.34 (s, 1H), 5.29 (d, J=7.3 Hz, 1H), 4.84 (d, J=7.3 Hz, 1H), 3.84 (s, 3H), 3.00 (s, 3H); $^{13}$C NMR (100.6 Hz, CDCl$_3$) δ ppm 159.8, 158.5, 156.3, 145.1, 141.0, 139.0, 138.0, 132.1, 129.9, 129.3, 127.8, 123.2, 121.8, 117.6, 114.4, 111.0, 98.7, 85.5, 82.5, 64.0, 55.0. Mass spec.: 385.0 (MH)+.

Example 88

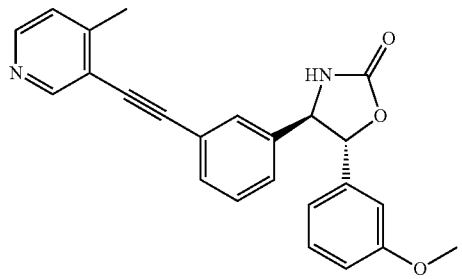 [SMILES: COc1cccc([C@H]2OC(=O)N[C@@H]2c2cccc(C#Cc3cnccc3C)c2)c1]

(4R,5R)-5-(3-Methoxyphenyl)-4-(3-((4-methylpyridin-3-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-4-methylpyridine. $^1$H-NMR (CDCl$_3$, 400 MHz) δ 8.93 (bs, 1H), 8.66 (bs, 1H), 7.70 (s, 1H), 7.61 (m, 2H), 7.49 (t, J=7.8 Hz, 1H), 7.36 (m, 2H), 6.96 (m, 1H), 6.88 (m, 2H), 6.30 (s, 1H), 5.30 (d, J=7.28 Hz, 1H), 4.83 (d, J=7.3 Hz, 1H), 3.84 (s, 3H), 2.77 (s, 3H); $^{13}$C NMR (100.6 Hz, CDCl$_3$) δ ppm 159.8, 157.6, 144.5, 140.4, 138.9, 138.0, 132.1, 129.9, 129.3, 127.7, 121.9, 117.6, 114.4, 111.0, 99.2, 85.6, 81.9, 64.1, 55.0. Mass spec.: 385.0 (MH)+.

Example 89

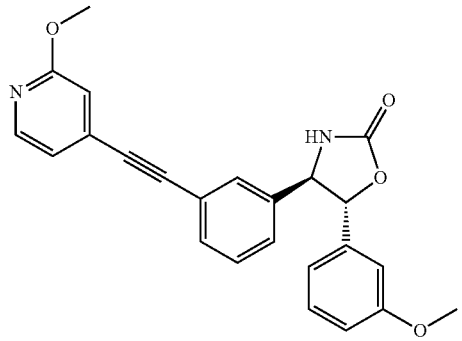 [SMILES: COc1cccc([C@H]2OC(=O)N[C@@H]2c2cccc(C#Cc3ccnc(OC)c3)c2)c1]

(4R,5R)-5-(3-Methoxyphenyl)-4-(3-((2-methoxypyridin-4-yl)ethnyl)phenyl)oxazolidin-2-one Prepared according to the same procedure as (4R,5R)-5-(3-methoxyphenyl)-4-(3-(pyridine-3-ylethynyl)oxazolidin-2-one, starting with 4-bromo-2-methylpyridine. $^1$H-NMR (CDCl$_3$, 500 MHz) δ 8.23 (d, J=5.5 Hz, 1H), 7.60 (d, J=7.6 Hz, 1H), 7.57 (s, 1H), 7.46 (t, J=7.6 Hz, 1H), 7.35 (m, 2H), 7.04 (m, 1H), 6.95 (m, 1H), 6.92 (s, 1H), 6.88 (m, 2H), 5.93 (s, 1H), 5.31 (d, J=7.3 Hz, 1H), 4.80 (d, J=7.3 Hz, 1H), 4.00 (s, 3H), 3.84 (s, 3H); $^{13}$C NMR (126 Hz, CDCl$_3$) δ ppm 164.2, 160.2, 158.8, 146.5, 139.1, 138.6, 134.2, 132.7, 130.3, 129.9, 129.6, 127.4, 123.4, 119.1, 118.0, 115.0, 113.0, 111.3, 92.9, 87.6, 86.0, 64.6, 55.5, 54.2. Mass spec.: 401.0 (MH)+.

Example 90

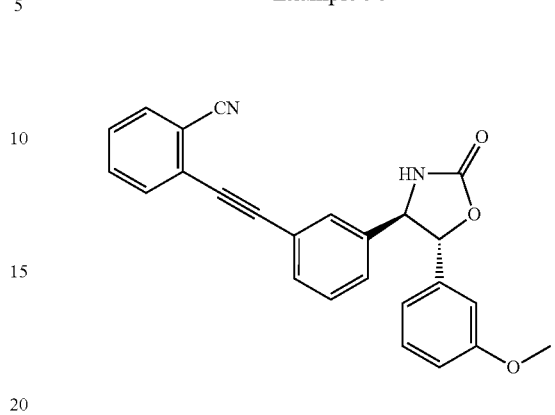

2-((3-((4R,5R)-5-(3-Methoxyphenyl)-2-oxooxazolidin-4-yl)phenyl)ethynyl)benzonitrile Prepared according to the same procedure as (4R,5R)-5-(3-methoxyphenyl)-4-(3-(pyridine-3-ylethynyl)oxazolidin-2-one, starting with 2-bromobenzonitrile. $^1$H-NMR (CDCl$_3$, 400 MHz) δ 7.71 (d, J=7.8 Hz, 1H), 7.66 (m, 2H), 7.61 (m, 2H), 7.46 (m, 2H), 7.34 (m, 2H), 6.96 (m, 1H), 6.89 (m, 2H), 5.85 (s, 1H), 5.32 (d, J=7.0 Hz, 1H), 4.80 (d, J=7.0 Hz, 1H), 3.84 (s, 3H); $^{13}$C NMR (100.6 Hz, CDCl$_3$) δ ppm 159.8, 138.6, 138.2, 132.4, 132.3, 132.1, 131.9, 129.8, 129.4, 129.1, 128.2, 126.9, 126.4, 122.9, 117.6, 115.1, 114.6, 110.6, 94.5, 86.1, 85.5, 64.1, 55.0. Mass spec.: 392.9 (MH)−.

Example 91

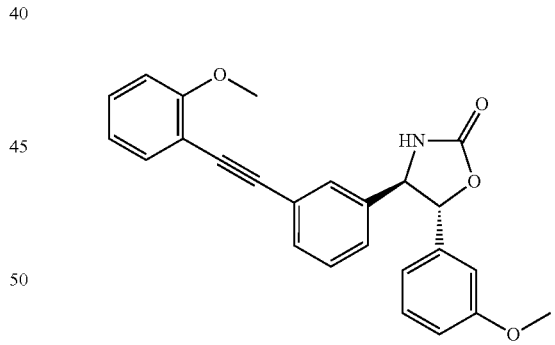

(4R,5R)-5-(3-Methoxyphenyl)-4-(3-((2-methoxyphenyl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 1-bromo-2-methoxybenzene. $^1$H-NMR (CDCl$_3$, 500 MHz) δ 7.59 (m, 2H), 7.53 (dd, J=7.3, 1.5 Hz, 1H), 7.41 (d, J=7.6 Hz, 1H), 7.35 (m, 2H), 7.27 (m, 1H), 6.96 (m, 3H), 6.88 (m, 2H), 5.60 (s, 1H), 5.33 (d, J=7.3 Hz, 1H), 4.77 (d, J=7.3 Hz, 1H), 3.95 (s, 3H), 3.84 (s, 3H); $^{13}$C NMR (126 Hz, CDCl$_3$) δ ppm 160.2, 160.1, 138.8, 138.6, 133.7, 132.4, 130.3, 130.2, 129.7, 129.3, 126.3, 124.9, 120.7, 118.1, 115.0, 112.1, 111.1, 110.8, 92.5, 87.0, 86.0, 64.7, 56.0, 55.5. Mass spec.: 399.97 (MH)+.

Example 92

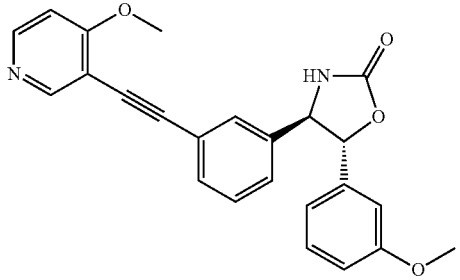 [SMILES: COc1cccc([C@H]2OC(=O)N[C@@H]2c2cccc(C#Cc3cnccc3OC)c2)c1]

(4R,5R)-5-(3-Methoxyphenyl)-4-(3-((4-methoxypyridin-3-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 3-bromo-4-fluoropyridine. $^1$H-NMR (CDCl$_3$, 400 MHz) δ 8.80 (bd, 2H), 7.61 (m, 2H), 7.47 (t, J=7.8 Hz, 1H), 7.35 (m, 3H), 6.96 (m, 1H), 6.88 (m, 2H), 6.12 (s, 1H), 5.29 (d, J=7.3 Hz, 1H), 4.82 (d, J=7.3 Hz, 1H), 4.22 (s, 3H), 3.84 (s, 3H); $^{13}$C NMR (100.6 Hz, CDCl$_3$) δ ppm 159.8, 138.8, 138.1, 132.2, 129.9, 129.3, 129.2, 127.7, 117.6, 114.4, 110.9, 85.5, 64.0, 57.5, 55.0. Mass spec.: 401.2 (MH)+.

Example 93

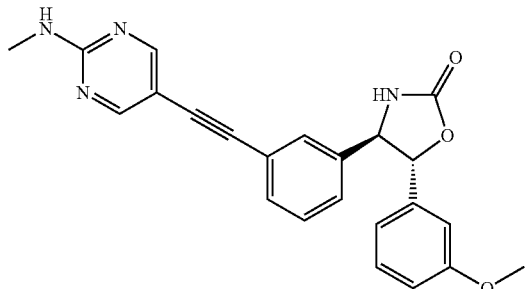

(4R,5R)-5-(3-Methoxyphenyl)-4-(3-((2-(methylamino)pyridin-5-yl)ethynyl)phenyl)oxazolidin-2-one Prepared according to the same procedure as (4R,5R)-5-(3-methoxyphenyl)-4-(3-(pyridine-3-ylethynyl)oxazolidin-2-one, starting with 5-bromo-N-methylpyrimidine-2-amine $^1$H-NMR (CDCl$_3$, 500 MHz) δ 9.27 (s, 1H), 8.76 (s, 1H), 8.26 (s, 1H), 7.55 (m, 2H), 7.46 (t, J=7.93 Hz, 1H), 7.35 (m, 2H), 6.97 (m, 1H), 6.88 (m, 2H), 5.47 (s, 1H), 5.31 (d, J=7.32 Hz, 1H), 4.79 (d, J=7.32 Hz, 1H), 3.85 (s, 3H), 3.16 (s, 3H). Mass spec.: 401.0 (MH)+.

Example 94

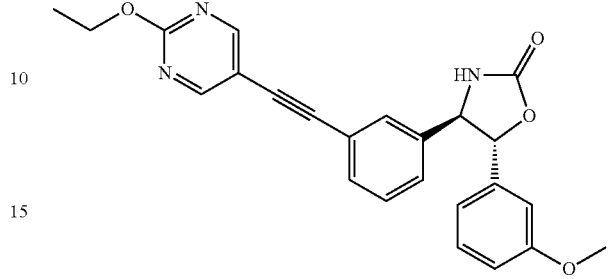

(4R,5R)-4-(3-((2-Ethoxypyrimidin-5-yl)ethynyl)phenyl)-5-(3-methoxyphenyl)oxazolidin-2-one Prepared according to the same procedure as (4R,5R)-5-(3-methoxyphenyl)-4-(3-(pyridine-3-ylethynyl)oxazolidin-2-one, starting with 5-bromo-2-ethoxypyrimidine. $^1$H-NMR (CDCl$_3$, 500 MHz) δ 8.90 (bs, 2H), 7.56 (m, 2H), 7.45 (t, J=7.9 Hz, 1H), 7.34 (m, 2H), 6.95 (m, 1H), 6.88 (m, 2H), 5.95 (s, 1H), 5.32 (d, J=7.3 Hz, 1H), 4.80 (d, J=7.3 Hz, 1H), 4.51 (q, J=6.4 Hz, 2H), 3.84 (s, 3H), 1.49 (t, J=6.7 Hz, 3H); $^{13}$C NMR (126 Hz, CDCl$_3$) δ ppm 160.2, 158.9, 139.0, 138.6, 132.3, 130.3, 129.6, 129.57, 127.0, 123.6, 118.1, 114.9, 111.3, 86.1, 64.6, 64.4, 55.5, 14.5. Mass spec.: 416.0 (MH)+.

Example 95 and Example 96

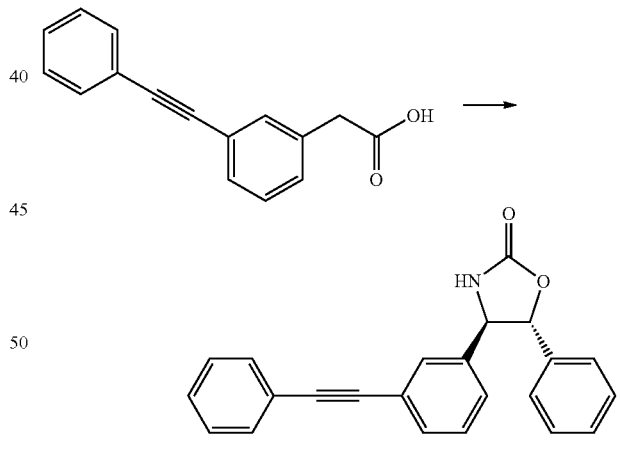

Example 95

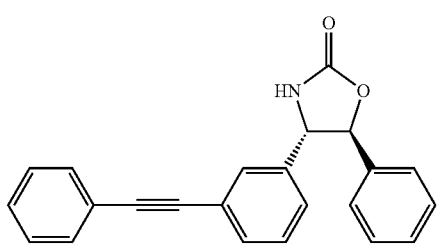

Example 96

(4R,5R)-5-phenyl-4-(3-(phenylethynyl)phenyl)ox-azolidin-2-one and (4S,5S)-5-phenyl-4-(3-(phenyl-ethynyl)phenyl)oxazolidin-2-one To diisopropylamine (0.241 mL, 1.693 mmol) in tetrahydrofuran (10 mL) under nitrogen at −78° C. was added n-BuLi (0.677 mL, 1.693 mmol). After 60 min, the colorless solution was warmed to −20° C. and a solution of 2-(3-(phenylethynyl)phenyl)acetic acid (200 mg, 0.847 mmol; Araldi, G. L.; Liao, Y.; Brugger, N. Hydrazide Deriviatives as Prostaglandin Receptor Modulators. WO 2005/012232 A2, 2005) in tetrahydrofuran (5 mL) was added resulting in a red solution which was allowed to stir for 45 min as the cooling bath temperature rose to 5° C. The reaction was recooled to −30° C., benzaldehyde (0.103 mL, 1.016 mmol) was added dropwise resulting in immediate disappearance of the red color and the cooling bath was removed. After 48 h, the reaction mixture was quenched with 1N HCl (20 mL), extracted with ethyl acetate (3×20 mL), washed with brine, dried over MgSO$_4$, filtered and concentrated providing (2S, 3R)-3-hydroxy-3-phenyl-2-(3-(phenylethynyl)phenyl)propanoic acid as an amber oil which was used in the next step without further purification or characterization.

To (2S,3R)-3-hydroxy-3-phenyl-2-(3-(phenylethynyl)phenyl)propanoic acid (290 mg, 0.847 mmol) in Toluene (10 mL) was added Hunig'sBase (0.192 mL, 1.101 mmol) followed by diphenyl phosphorazidate (0.183 mL, 0.847 mmol). The reaction mixture was heated to 60° C. for 18 h and an add'l portion of diphenyl phosphorazidate (0.183 mL, 0.847 mmol) was added with continued heating. After 1 h, the reaction was cooled and concentrated to 3 mL volume and applied to 12 g silica gel cartridge which was pre-equilibrated with 5% ethyl acetate/hexanes. Elution with 5 to 40% ethyl acetate/hexanes over 300 mL provided 179 mg racemic trans-5-phenyl-4-(3-(phenylethynyl)phenyl)oxazolidin-2-one which was rechromatographed under identical conditions providing 79 mg racemic trans-5-phenyl-4-(3-(phenylethynyl)phenyl)oxazolidin-2-one as a colorless oil. The enantiomers were separated via chiral preparative HPLC (Preparative HPLC Method 2) in two portions solubilizing in 1:1 CH$_2$Cl$_2$/MeOH providing 36 mg (12%) (4R,5R)-5-phenyl-4-(3-(phenylethynyl)phenyl)oxazolidin-2-one (enantiomer 1; Retention time=8.48 min) and 35 mg (12%) (4S,5S)-5-phenyl-4-(3-(phenylethynyl)phenyl)oxazolidin-2-one (enantiomer 2; Retention time=16.36 min) $^1$H NMR (500 MHz, CHLOROFORM-d) δ ppm 7.48-7.58 (4H, m), 7.28-7.45 (9H, m), 7.22-7.28 (1H, m), 5.32 (2H, d, J=7.32 Hz), 4.75 (1H, d, J=7.32 Hz). LC/MS (Analytical HPLC Method 1) 1.92 min, Anal. Calcd. for [M+H]$^+$ C$_{23}$H$_{17}$NO$_2$: 340.13. found 340.05.

Example 96 and Example 97

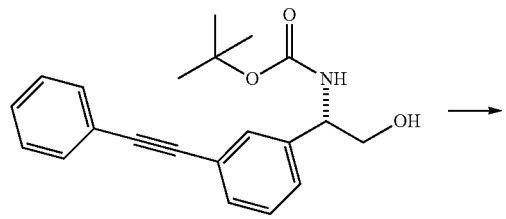

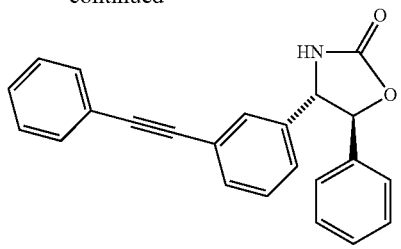

Example 96

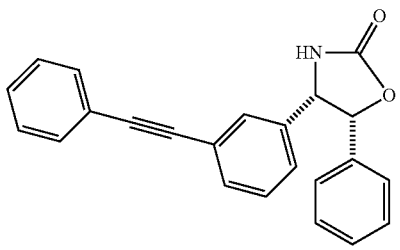

Example 97

(4S,5S)-5-phenyl-4-(3-(phenylethynyl)phenyl)ox-azolidin-2-one and (4S,5R)-5-phenyl-4-(3-(phenyl-ethynyl)phenyl)oxazolidin-2-one To (S)-tert-butyl 2-hydroxy-1-(3-(phenylethynyl)phenyl)ethylcarbamate (100 mg, 0.296 mmol) in dichloromethane (2 mL) was added sodium bicarbonate (124 mg, 1.482 mmol) followed by Dess-Martin Periodinane (151 mg, 0.356 mmol). After 1 h, the reaction was quenched with 1:1 saturated NaHCO$_3$/Na$_2$SO$_3$ and extracted into ethyl acetate (10 mL). The organic layer was dried with MgSO$_4$, filtered and concentrated to 96 mg (S)-tert-butyl 2-oxo-1-(3-(phenylethynyl)phenyl)ethylcarbamate as an amber oil which was concentrated from toluene under high vacuum and used directly in the next step without further purification. R$_f$=0.5 (silica gel, 25% ethyl acetate/hexane, UV and phophomolybdic acid).

To (S)-tert-butyl 2-oxo-1-(3-(phenylethynyl)phenyl)ethylcarbamate (95 mg, 0.283 mmol) in tetrahydrofuran (5 mL) at −78° C. was added phenylmagnesium bromide (0.198 mL, 0.595 mmol) dropwise. After half of the phenylmagnesium bromide was added the stir bar stopped spinning due to a gum which formed around it. The ice bath was removed allowing the reaction to warm until the stir bar began to stir again. The addition of Grignard reagent was continued and after 1 h, a fine precipitate was evident. TLC (25% ethyl acetate/hexane; UV and phosphomolybdic acid) showed a single major spot just below starting material (R$_f$=0.45). After 1.5 h total, the reaction was quenched with 1N HCl (10 mL) and extracted into ethyl acetate (3×10 mL). The combined organics were washed with saturated NaHCO$_3$, brine, dried over MgSO$_4$, filtered and concentrated in vacuo to 126 mg amber oil which was loaded with dichloromethane onto a 12 g silica gel column prepacked with 5% ethyl acetate/hexanes. Elution with 5 to 30% ethyl acetate/hexanes over 250 mL provided 62 mg tert-butyl (1S,2S)-2-hydroxy-2-phenyl-1-(3-(phenylethynyl)phenyl)ethylcarbamate as a colorless oil which was used directly in the next step.

To (S)-tert-butyl 2-hydroxy-2-phenyl-1-(3-(phenylethynyl)phenyl)ethylcarbamate (62 mg, 0.150 mmol) in tetrahydrofuran (3 mL) at −78° C. was added NaH (17.99 mg, 0.450 mmol). After 10 min, the ice bath was removed and the reaction was allowed to stir at ambient temperature for 24 h at which time TLC showed two spots at R$_f$=0.2 and R$_f$=0.15 (25% ethyl acetate/hexanes, UV) with the top one as major. The reaction was quenched with 1N HCl (15 mL), extracted into ethyl acetate (3×20 mL), washed with saturated NaHCO$_3$, brine, dried over MgSO$_4$, filtered, and concentrated to 51 mg colorless solid which was dissolved in dichloromethane and applied to a 12 g silica gel cartridge prepacked with 5% ethyl acetate/hexanes. Elution with 5 to 40% ethyl acetate/hexanes over 300 mL provided 29 mg (57%) (4S,5S)-5-phenyl-4-(3-(phenylethynyl)phenyl)oxazolidin-2-one as a colorless oil (top spot) and 5 mg (11%) (4S,5R)-5-phenyl-4-(3-(phenylethynyl)phenyl)oxazolidin-2-one as a colorless solid. Analytical data for (4S,5R)-5-phenyl-4-(3-(phenylethynyl)phenyl)oxazolidin-2-one: $^1$H NMR (500 MHz, CHLOROFORM-d) δ ppm 7.45-7.57 (2H, m), 7.31-7.41 (3H, m), 7.27 (1H, d, J=7.63 Hz), 7.18 (1H, s), 7.10-7.17 (3H, m), 7.06 (1H, t, J=7.78 Hz), 7.00 (2H, dd, J=7.32, 2.14 Hz), 6.84 (1H, d, J=7.63 Hz), 5.97 (1H, d, J=8.24 Hz), 5.42 (1H, s), 5.18 (1H, d, J=8.24 Hz). LC/MS (Analytical HPLC Method 1) 1.83 min, Anal. Calcd. for [M+H]$^+$ C$_{23}$H$_{17}$NO$_2$: 340.13. found 340.13.

The following analogs were prepared using the same procedure as described for the preparation of (4S,5S)-5-phenyl-4-(3-(phenylethynyl)phenyl)oxazolidin-2-one and (4S,5R)-5-phenyl-4-(3-(phenylethynyl)phenyl)oxazolidin-2-one using the appropriate Grignard reagent:

| Example | Structure | Analytical Data |
| --- | --- | --- |
| 98 | cis-4-(3-(phenylethynyl)phenyl)-5-m-tolyloxazolidin-2-one (+/-) Used tert-butyl 2-hydroxy-1-(3-(phenylethynyl)phenyl)ethylcarbamate and m-tolylmagnesium bromide | $^1$H NMR (500 MHz, CHLOROFORM-d) δ ppm 7.46-7.54 (2 H, m), 7.32-7.39 (3 H, m), 7.27 (1 H, d, J = 7.63 Hz), 7.19 (1 H, s), 7.06 (1 H, t, J = 7.78 Hz), 7.01 (1 H, t, J = 7.63 Hz), 6.92 (1 H, d, J = 7.63 Hz), 6.80-6.87 (2 H, m), 6.77 (1 H, d, J = 7.63 Hz), 5.93 (1 H, d, J = 8.24 Hz), 5.47 (1 H, s), 5.16 (1 H, d, J = 8.24 Hz), 2.18 (3 H, s). LC/MS (Analytical HPLC Method 2) 1.83 min, Anal. Calcd. for [M + H]$^+$ C$_{24}$H$_{19}$NO$_2$: 353.14; found 354.21. Rf = 0.13 (silica gel, 25% EtOAc/Hex, UV) |
| 99 | trans-4-(3-(phenylethynyl)phenyl)-5-m-tolyloxazolidin-2-one (+/-) Used tert-butyl 2-hydroxy-1-(3-(phenylethynyl)phenyl)ethylcarbamate and m-tolylmagnesium Bromide | $^1$H NMR (500 MHz, CHLOROFORM-d) δ ppm 7.47-7.61 (4 H, m), 7.33-7.43 (4 H, m), 7.13-7.32 (4 H, m), 7.07 (1 H, d, J = 7.63 Hz), 5.93 (1 H, s), 5.26 (1 H, d, J = 7.02 Hz), 4.76 (1 H, d, J = 7.32 Hz), 2.37 (3 H, s). LC/MS (Analytical HPLC Method 2) 1.98 min, Anal. Calcd. for [M + H]$^+$ C$_{24}$H$_{19}$NO$_2$: 354.14; found 354.22. Rf = 0.13 (silica gel, 25% EtOAc/Hex, UV) |

-continued

| Example | Structure | Analytical Data |
|---|---|---|
| 100 | 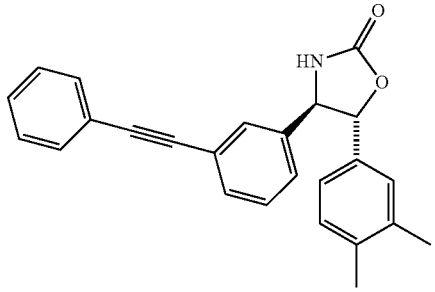 [SMILES: Cc1ccc([C@H]2OC(=O)N[C@@H]2c2cccc(C#Cc3ccccc3)c2)cc1C]<br>(+/−)<br>Trans-5-(3,4-dimethylphenyl)-4-(3-(phenylethynyl)phenyl)oxazolidin-2-one<br>Used (±)-tert-butyl 2-hydroxy-1-(3-(phenylethynyl)phenyl)ethylcarbamate and 3,4-dimethylmagnesium bromide. | $^1$H NMR (500 MHz, CHLOROFORM-d) δ ppm 7.47-7.57 (4 H, m), 7.31-7.43 (5 H, m), 7.09-7.19 (2 H, m), 6.96-7.06 (1 H, m), 5.99 (1 H, s), 5.23 (1 H, d, J = 7.32 Hz), 4.77 (1 H, d, J = 7.02 Hz), 2.23-2.29 (6 H, m). LC/MS (Analytical HPLC Method 2) 2.03 min, Anal. Calcd. for [M + H]$^+$ C$_{25}$H$_{21}$NO$_2$: 368.16; found 368.26. Rf = 0.20 (silica gel, 25% EtOAc/Hex, UV) |
| 101 | 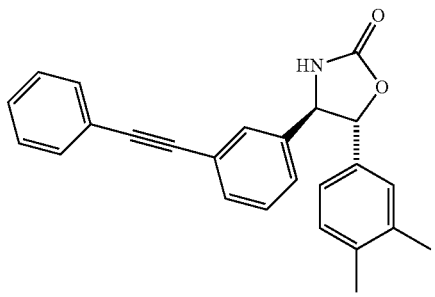<br>(4R,5R)-5-(3,4-dimethylphenyl)-4-(3-(phenylethynyl)phenyl)oxazolidin-2-one<br>Enantiomer 1 from trans-5-(3,4-dimethylphenyl)-4-(3-(phenylethynyl)phenyl)oxazolidin-2-one | separated via Preparative HPLC method 2—retention time 8.1 min |
| 102 | 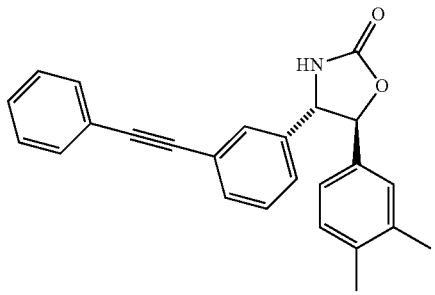 [SMILES: Cc1ccc([C@@H]2OC(=O)N[C@H]2c2cccc(C#Cc3ccccc3)c2)cc1C]<br>(4S,5S)-5-(3,4-dimethylphenyl)-4-(3-(phenylethynyl)phenyl)oxazolidin-2-one<br>Enantiomer 2 from trans-5-(3,4-dimethylphenyl)-4-(3-(phenylethynyl)phenyl)oxazolidin-2-one | separated via Preparative HPLC method 2—retention time 12.2 min |

| Example | Structure | Analytical Data |
|---|---|---|
| 103 | (+/-)<br>trans-4-(3-(phenylethynyl)phenyl)-5-(thiophen-2-yl)oxazolidin-2-one<br>Used (±)-tert-butyl 2-hydroxy-1-(3-(phenylethynyl)phenyl)ethylcarbamate and 2-thienylmagnesium bromide | $^1$H NMR (500 MHz, CHLOROFORM-d) δ ppm 7.48-7.58 (4 H, m), 7.32-7.44 (5 H, m), 7.27 (1 H, d, J = 7.93 Hz), 7.08 (1 H, d, J = 3.36 Hz), 7.03 (1 H, dd, J = 4.88, 3.66 Hz), 5.95 (1 H, s), 5.51 (1 H, d, J = 7.63 Hz), 4.95 (1 H, d, J = 7.63 Hz). LC/MS (Analytical HPLC Method 2) 1.83 min, Anal. Calcd. for [M + H]$^+$ C$_{21}$H$_{15}$NO$_2$: 346.08; found 368.19. Rf = 0.18 (silica gel, 25% EtOAc/Hex, UV) |
| 104 | (4R,5R)-(3-(phenylethynyl)phenyl)-5-(thiophen-2-yl)oxazolidin-2-one<br>Enantiomer 1 from trans-4-(3-(phenylethynyl)phenyl)-5-(thiophen-2-yl)oxazolidin-2-one | separated via Preparative HPLC method 2—retention time 9.3 min |
| 105 | (4S 5S)-(phenylethynyl)phenyl)-5-(thiophen-2-yl)oxazolidin-2-one<br>Enantiomer 2 from trans-4-(3-(phenylethynyl)phenyl)-5-(thiophen-2-yl)oxazolidin-2-one | separated via Preparative HPLC method 2—retention time 15.6 min |
| 106 | (±)-(phenylethynyl)phenyl)-5-p-tolyloxazolidin-2-one<br>Used (±)-tert-butyl 2-hydroxy-1-(3-(phenylethynyl)phenyl)ethylcarbamate and p-tolylmagnesium bromide | $^1$H NMR (500 MHz, CHLOROFORM-d) δ ppm 7.46-7.59 (4 H, m), 7.32-7.43 (4 H, m), 7.13-7.25 (5 H, m), 5.72 (1 H, s), 5.27 (1 H, d, J = 7.32 Hz), 4.75 (1 H, d, J = 7.32 Hz), 2.37 (3 H, s). LC/MS (Analytical HPLC Method 2) 1.97 min, Anal. Calcd. for [M + H]$^+$ C$_{24}$H$_{19}$NO$_2$: 354.14; found 354.22. Rf = 0.18 (silica gel, 25% EtOAc/Hex, UV) |

| Example | Structure | Analytical Data |
|---|---|---|
| 107 | (4R,5R)-(phenylethynyl)phenyl)-5-p-tolyloxazolidin-2-one Enantiomer 1 from (±)-(phenylethynyl)phenyl)-5-p-tolyloxazolidin-2-one | separated via Preparative HPLC method 2—retention time 8.4 min |
| 108 | (4S,5S)-(phenylethynyl)phenyl)-5-p-tolyloxazolidin-2-one Enantiomer 2 from from (±)-(phenylethynyl)phenyl)-5-p-tolyloxazolidin-2-one | separated via Preparative HPLC method 2—retention time 13.3 min |

The following analogs were prepared using the same procedure as described for the preparation of (4R,5R)-5-phenyl-4-(3-(phenylethynyl)phenyl)oxazolidin-2-one and (4S,5S)-5-phenyl-4-(3-(phenylethynyl)phenyl)oxazolidin-2-one, starting from 2-(3-(phenylethynyl)phenyl)acetic acid and the appropriate aldehyde:

| Example | Structure | Analytical Data |
|---|---|---|
| 109 | (4R,5R)-5-(2-fluorophenyl)-4-(3-(phenylethynyl)phenyl)oxazolidin-2-one Used 2-fluorobenzaldehyde and Preparative HPLC method 4, and then Preparative HPLC method 3 for purification | HPLC retention time (Analytical HPLC method 3): 10.0 min |

| Example | Structure | Analytical Data |
|---|---|---|
| 110 | 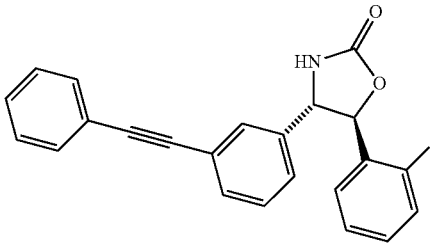<br>(4S,5S)-5-(2-fluorophenyl)-4-(3-(phenylethynyl)phenyl)oxazolidin-2-one<br>Used 2-fluorobenzaldehyde and Preparative HPLC method 3 for purification | $^1$H NMR (500 MHz, CHLOROFORM-d) δ ppm 7.48-7.61 (5 H, m), 7.31-7.46 (6 H, m), 7.26 (1 H, t, J = 7.63 Hz), 7.11-7.18 (1 H, m), 5.76 (1 H, s), 5.59 (1 H, d, J = 5.49 Hz), 4.84 (1 H, d, J = 5.49 Hz). HPLC retention time (Analytical HPLC method 3): 9.9 min. LC/MS (Analytical HPLC Method 1) 1.90 min, Anal. Calcd. for [M + H]$^+$ C$_{23}$H$_{16}$FNO$_2$: 358.12; found 358.07. |
| 111 | 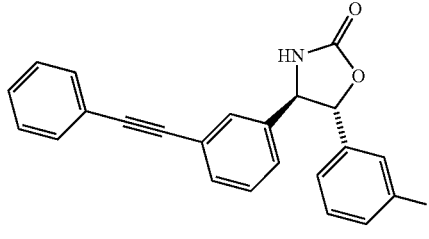<br>(+/-)<br>Trans-5-(3-fluorophenyl)-4-(3-(phenylethynyl)phenyl)oxazolidin-2-one<br>Used 3-fluorobenzaldehyde | $^1$H NMR (500 MHz, CHLOROFORM-d) δ ppm 7.52-7.62 (4 H, m), 7.32-7.46 (5 H, m), 7.23-7.31 (1 H, m), 6.99-7.16 (3 H, m), 6.16 (1 H, s), 5.32 (1 H, d, J = 7.02 Hz), 4.75 (1 H, d, J = 7.32 Hz). LC/MS (Analytical HPLC Method 1) 1.91 min, Anal. Calcd. for [M + H]$^+$ C$_{23}$H$_{16}$FNO$_2$: 358.12; found 358.03. |
| 112 | 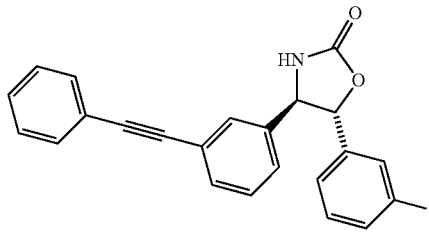<br>(4R,5R)-5-(2-fluorophenyl)-4-(3-(phenylethynyl)phenyl)oxazolidin-2-one<br>Enantiomer 1 from Trans-5-(3-fluorophenyl)-4-(3-(phenylethynyl)phenyl)oxazolidin-2-one 19 using preparative HPLC method 2 | 98.2% ee; HPLC retention time (Analytical HPLC method 3): 10.0 min |

| Example | Structure | Analytical Data |
|---|---|---|
| 113 | (4S,5S)-5-(2-fluorophenyl)-4-(3-(phenylethynyl)phenyl)oxazolidin-2-one<br>Enantiomer 2 from Trans-5-(3-fluorophenyl)-4-(3-(phenylethynyl)phenyl)oxazolidin-2-one using preparative HPLC method 2 | 97.8% ee; HPLC retention time (Analytical HPLC method 3): 10.0 min |
| 114 | (4R,5R)-5-(4-fluorophenyl)-4-(3-(phenylethynyl)phenyl)oxazolidin-2-one<br>Enantiomer 1 from Trans-5-(4-fluorophenyl)-4-(3-(phenylethynyl)phenyl)oxazolidin-2-one using preparative HPLC method 2 then preparative HPLC method 4 | $^1$H NMR (500 MHz, CHLOROFORM-d) δ ppm 7.49-7.60 (4 H, m), 7.21-7.45 (7 H, m), 7.03-7.18 (2 H, m), 6.26 (1 H, s), 5.29 (1 H, d, J = 7.32 Hz), 4.75 (1 H, d, J = 7.63 Hz). LC/MS (Analytical HPLC Method 1) 1.91 min, Anal. Calcd. for [M + H]$^+$ C$_{23}$H$_{16}$FNO$_2$: 358.12; found 358.03. HPLC retention time (Analytical HPLC method 3): 10.0 min |
| 115 | (4S,5S)-5-(4-fluorophenyl)-4-(3-(phenylethynyl)phenyl)oxazolidin-2-one<br>Enantiomer 2 from Trans-5-(4-fluorophenyl)-4-(3-(phenylethynyl)phenyl)oxazolidin-2-one using preparative HPLC method 2 | HPLC retention time (Analytical HPLC method 3): 10.0 min |

Example 116 and Example 117 and Example 118

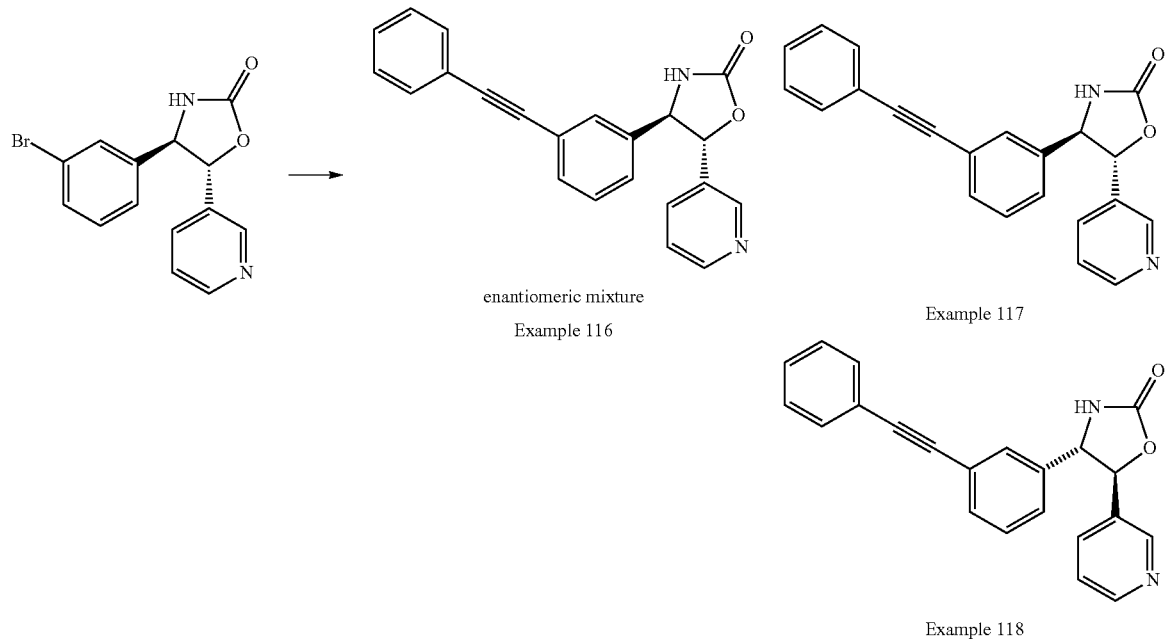

Example 116 (enantiomeric mixture)

Example 117

Example 118

Trans-4-(3-(phenylethynyl)phenyl)-5-(pyridin-3-yl)oxazolidin-2-one and (4R,5R)-4-(3-(phenylethynyl)phenyl)-5-(pyridin-3-yl)oxazolidin-2-one and (4S,5S)-4-(3-(phenylethynyl)phenyl)-5-(pyridin-3-yl)oxazolidin-2-one To trans-4-(3-bromophenyl)-5-(pyridin-3-yl)oxazolidin-2-one (46 mg, 0.144 mmol) slurried in triethylamine (3 mL) was added ethynylbenzene (0.021 mL, 0.187 mmol), copper (I) iodide (2.74 mg, 0.014 mmol), and triphenylphosphine (26.5 mg, 0.101 mmol). The reaction mixture was cooled to −78° C. under nitrogen and subjected to three rounds of pump/nitrogen purge. The mixture was then warmed to ambient temperature and $(Ph_3P)_2PdCl_2$ (10.12 mg, 0.014 mmol) was added. The vessel was fitted with a reflux condensor and placed in an oil bath at 93° C. for 18 h at which time the vessel was removed from the heat and the residue was solubilized in 1:1 dimethylformamide/methanol and purified via preparative HPLC method 4. Pooling and concentration of the fractions containing the peak eluting at 7.37 min provided 14.3 mg trans-4-(3-(phenylethynyl)phenyl)-5-(pyridin-3-yl)oxazolidin-2-one as an indeterminate enantiomeric mixture. $^1$H NMR (500 MHz, MeOD) δ ppm 8.44 (1H, d, J=7.32 Hz), 8.16 (1H, br. s.), 7.57-7.63 (2H, m), 7.47-7.57 (4H, m), 7.44 (1H, d, J=7.63 Hz), 7.36-7.42 (4H, m), 5.68 (1H, d, J=6.41 Hz), 4.98 (1H, d, J=6.71 Hz). LC/MS (Analytical HPLC Method 6) 1.97 min, Anal. Calcd. for [M+H]$^+$ $C_{22}H_{16}N_2O_2$: 341.12. found 341.29. HPLC retention time (Analytical HPLC method 3): 7.30 min. Further purification via preparative SFC method 5 provided 2.2 mg (4%) (4R,5R)-4-(3-(phenylethynyl)phenyl)-5-(pyridin-3-yl)oxazolidin-2-one (5.8 min retention time) as a colorless oil and 2.0 mg (4%) (4S,5S)-4-(3-(phenylethynyl)phenyl)-5-(pyridin-3-yl)oxazolidin-2-one as a colorless oil. HPLC retention time for (4R,5R)-4-(3-(phenylethynyl)phenyl)-5-(pyridin-3-yl)oxazolidin-2-one (Analytical HPLC method 3): 7.12 min. HPLC retention time for (4S,5S)-4-(3-(phenylethynyl)phenyl)-5-(pyridin-3-yl)oxazolidin-2-one (Analytical HPLC method 3): 7.10 min.

The examples in the following table were prepared using the same method for preparation of (+)-(4R,5R)-5-(3-Methoxyphenyl)-4-(3-(phenylethynyl)phenyl)oxazolidin-2-one:

| Example | Structure | Analytical Data |
| --- | --- | --- |
| 119 | (4R,5R)-5-(3-methoxyphenyl)-4-(3-((4-(trifluoromethyl)phenyl)ethynyl)phenyl)oxazolidin-2-one | $^1$H NMR (500 MHz, DMSO-d$_6$) δ ppm 8.42 (1H, s), 7.80 (4 H, s), 7.58-7.65 (2 H, m), 7.51 (1 H, t, J = 7.8 Hz), 7.40 (1 H, d, J = 7.9 Hz), 7.36 (1 H, t, J = 7.8 Hz), 6.88-7.03 (3 H, m), 5.33 (1 H, d, J = 7.3 Hz), 4.89 (1 H, d, J = 7.3 Hz), 3.78 (3 H, s). Anal. Calcd. for [M + H]$^+$ $C_{25}H_{19}F_3NO_3$: 438.13; found 438.16. |

| Example | Structure | Analytical Data |
|---|---|---|
| 120 | 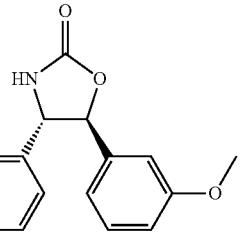<br>(4S,5S)-5-(3-methoxyphenyl)-4-(3-((4-(trifluoromethyl)phenyl)ethynyl)phenyl)oxazolidin-2-one | 1H NMR (500 MHz, DMSO-$d_6$) δ ppm 8.42 (1 H, s), 7.80 (4 H, s), 7.57-7.65 (2 H, m), 7.51 (1 H, t, J = 7.6 Hz), 7.40 (1 H, d, J = 7.9 Hz), 7.36 (1 H, t, J = 7.8 Hz), 6.91-7.03 (3 H, m), 5.33 (1 H, d, J = 7.3 Hz), 4.88 (1 H, d, J = 7.0 Hz), 3.78 (3 H, s). Anal. Calcd. for [M + H]$^+$ $C_{25}H_{19}F_3NO_3$: 438.13; found 438.14. |
| 121 | 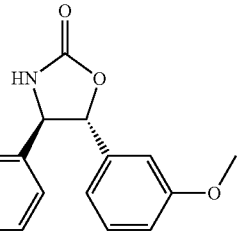<br>(4R,5R)-4-(3-((2-fluorophenyl)ethynyl)phenyl)-5-(3-methoxyphenyl)oxazolidin-2-one | $^1$H NMR (500 MHz, DMSO-$d_6$) δ ppm 8.42 (1 H, s), 7.66 (1 H, td, J = 7.6, 1.7 Hz), 7.53-7.60 (2 H, m), 7.46-7.53 (2 H, m), 7.33-7.42 (3 H, m), 7.28 (1 H, t, J = 7.6 Hz), 6.89-7.03 (3 H, m), 5.33 (1 H, d, J = 7.3 Hz), 4.89 (1 H, d, J = 7.0 Hz), 3.78 (3 H, s). Anal. Calcd. for [M + H]$^+$ $C_{24}H_{19}FNO_3$: 388.14; found 438.18. |
| 122 | 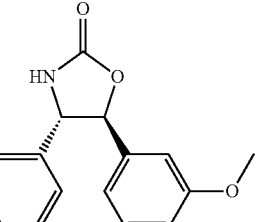<br>(4S,5S)-4-(3-((2-fluorophenyl)ethynyl)phenyl)-5-(3-methoxyphenyl)oxazolidin-2-one | $^1$H NMR (500 MHz, DMSO-$d_6$) δ ppm 8.42 (1 H, s), 7.66 (1 H, td, J = 7.5, 1.8 Hz), 7.54-7.61 (2 H, m), 7.46-7.54 (2 H, m), 7.32-7.42 (3 H, m), 7.25-7.31 (1 H, m), 6.92-7.01 (3 H, m), 5.33 (1 H, d, J = 7.0 Hz), 4.89 (1 H, d, J = 7.3 Hz), 3.78 (3 H, s). Anal. Calcd. for [M + H]$^+$ $C_{24}H_{19}FNO_3$: 388.14; found 388.18. |
| 123 | 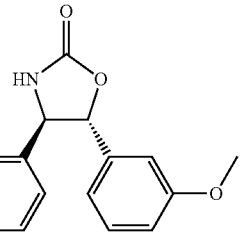<br>(4R,5R)-4-(3-((3,5-difluorophenyl)ethynyl)phenyl)-5-(3-methoxyphenyl)oxazolidin-2-one | $^1$H NMR (500 MHz, DMSO-$d_6$) δ ppm 8.42 (1 H, s), 7.55-7.63 (2 H, m), 7.50 (1 H, t, J = 7.9 Hz), 7.31-7.43 (5 H, m), 6.88-7.03 (3 H, m), 5.31 (1 H, d, J = 7.0 Hz), 4.88 (1 H, d, J = 7.3 Hz), 3.78 (3 H, s) Anal. Calcd. for [M + H]$^+$ $C_{24}H_{18}F_2NO_3$: 406.13; found 406.11. |

| Example | Structure | Analytical Data |
|---|---|---|
| 124 | 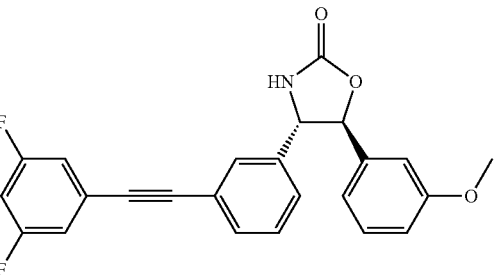<br>(4S,5S)-4-(3-((3,5-difluorophenyl)ethynyl)phenyl)-5-(3-methoxyphenyl)oxazolidin-2-one | $^1$H NMR (500 MHz, DMSO-$d_6$) δ ppm 8.42 (1 H, s), 7.56-7.61 (2 H, m), 7.50 (1 H, t, J = 7.9 Hz), 7.31-7.44 (5 H, m), 6.88-7.02 (3 H, m), 5.31 (1 H, d, J = 7.0 Hz), 4.88 (1 H, d, J = 7.0 Hz), 3.78 (3 H, s). Anal. Calcd. for [M + H]$^+$ $C_{24}H_{18}F_2NO_3$: 406.13; found 406.19. |
| 125 | 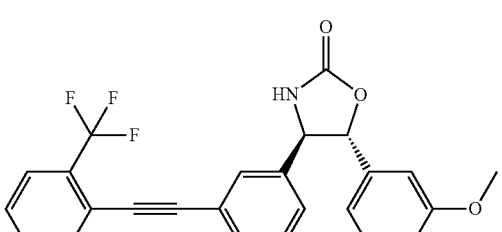<br>(4R,5R)-5-(3-methoxyphenyl)-4-(3-((2-(trifluoromethyl)phenyl)ethynyl)phenyl)oxazolidin-2-one | $^1$H NMR (500 MHz, DMSO-$d_6$) δ ppm 8.43 (1 H, s), 7.84 (2 H, t, J = 6.7 Hz), 7.74 (1 H, t, J = 7.6 Hz), 7.64 (1 H, t, J = 7.8 Hz), 7.47-7.58 (3 H, m), 7.41 (1 H, d, J = 7.9 Hz), 7.36 (1 H, t, J = 7.8 Hz), 6.88-7.05 (3 H, m), 5.32 (1 H, d, J = 7.0 Hz), 4.90 (1 H, d, J = 7.0 Hz), 3.78 (3 H, s). Anal. Calcd. for [M + H]$^+$ $C_{25}H_{19}F_3NO_3$: 438.13; found 438.17. |
| 126 | 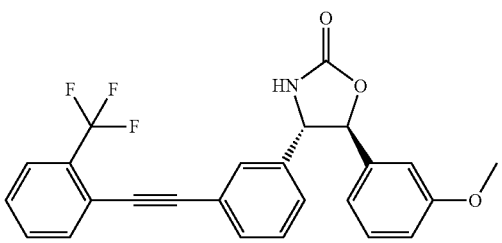 [SMILES: COc1cccc([C@@H]2OC(=O)N[C@H]2c2cccc(C#Cc3ccccc3C(F)(F)F)c2)c1]<br>(4S,5S)-5-(3-methoxyphenyl)-4-(3-((2-(trifluoromethyl)phenyl)ethynyl)phenyl)oxazolidin-2-one | $^1$H NMR (500 MHz, DMSO-$d_6$) δ ppm 8.43 (1 H, s), 7.84 (2 H, t, J = 6.7 Hz), 7.74 (1 H, t, J = 7.5 Hz), 7.64 (1 H, t, J = 7.6 Hz), 7.48-7.59 (3 H, m), 7.32-7.43 (2 H, m), 6.91-7.01 (3 H, m), 5.32 (1 H, d, J = 7.0 Hz), 4.90 (1 H, d, J = 7.0 Hz), 3.78 (3 H, s). Anal. Calcd. for [M + H]$^+$ $C_{25}H_{19}F_3NO_3$: 438.13; found 438.17. |
| 127 | 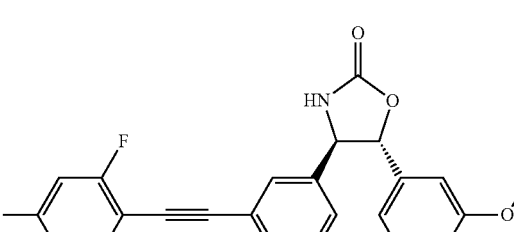<br>(4R,5R)-4-(3-((2,4-difluorophenyl)ethynyl)phenyl)-5-(3-methoxyphenyl)oxazolidin-2-one | $^1$H NMR (500 MHz, DMSO-$d_6$) δ ppm 8.41 (1 H, s), 7.74 (1 H, td, J = 8.5, 6.6 Hz), 7.53-7.60 (2 H, m), 7.43-7.52 (2 H, m), 7.31-7.42 (2 H, m), 7.20 (1 H, td, J = 8.4, 2.4 Hz), 6.90-7.01 (3 H, m), 5.32 (1 H, d, J = 7.0 Hz), 4.89 (1 H, d, J = 7.0 Hz), 3.77 (3 H, s). Anal. Calcd. for [M + H]$^+$ $C_{24}H_{18}F_2NO_3$: 406.13; found 406.19. |

| Example | Structure | Analytical Data |
|---|---|---|
| 128 | 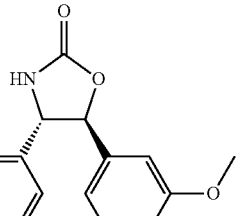<br>(4S,5S)-4-(3-((2,4-difluorophenyl)ethynyl)phenyl)-5-(3-methoxyphenyl)oxazolidin-2-one | $^1$H NMR (500 MHz, DMSO-$d_6$) δ ppm 8.41 (1 H, s), 7.74 (1 H, td, J = 8.5, 6.7 Hz), 7.52-7.60 (2 H, m), 7.42-7.53 (2 H, m), 7.32-7.42 (2 H, m), 7.20 (1 H, td, J = 8.3, 2.6 Hz), 6.90-7.02 (3 H, m), 5.32 (1 H, d, J = 7.0 Hz), 4.89 (1 H, d, J = 7.3 Hz), 3.77 (3 H, s). Anal. Calcd. for [M + H]$^+$ $C_{24}H_{18}F_2NO_3$: 406.13; found 406.19. |
| 129 | 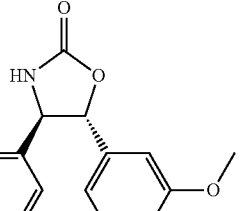<br>(4R,5R)-5-(3-methoxyphenyl)-4-(3-((3-(trifluoromethyl)phenyl)ethynyl)phenyl)oxazolidin-2-one | $^1$H NMR (500 MHz, DMSO-$d_6$) δ ppm 8.42 (1 H, s), 7.95 (1 H, s), 7.89 (1 H, d, J = 7.6 Hz), 7.80 (1 H, d, J = 7.9 Hz), 7.69 (1 H, t, J = 7.8 Hz), 7.59-7.62 (2 H, m), 7.50 (1 H, t, J = 8.1 Hz), 7.32-7.43 (2 H, m), 6.90-7.01 (3 H, m), 5.32 (1 H, d, J = 7.0 Hz), 4.88 (1 H, d, J = 7.0 Hz), 3.78 (3 H, s). Anal. Calcd. for [M + H]$^+$ $C_{25}H_{19}F_3NO_3$: 438.13; found 438.17. |
| 130 | 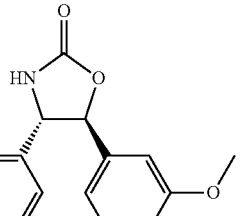<br>(4S,5S)-5-(3-methoxyphenyl)-4-(3-((3-(trifluoromethyl)phenyl)ethynyl)phenyl)oxazolidin-2-one | $^1$H NMR (500 MHz, DMSO-$d_6$) δ ppm 8.42 (1 H, s), 7.95 (1 H, s), 7.89 (1 H, d, J = 7.9 Hz), 7.80 (1 H, d, J = 7.9 Hz), 7.69 (1 H, t, J = 7.9 Hz), 7.57-7.63 (2 H, m), 7.50 (1 H, t, J = 8.1 Hz), 7.33-7.42 (2 H, m), 6.91-7.01 (3 H, m), 5.32 (1 H, d, J = 7.0 Hz), 4.88 (1 H, d, J = 7.3 Hz), 3.78 (3 H, s). Anal. Calcd. for [M + H]$^+$ $C_{25}H_{19}F_3NO_3$: 438.13; found 438.17. |
| 131 | 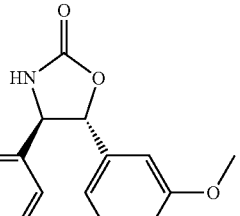<br>(4R,5R)-4-(3-((4-fluorophenyl)ethynyl)phenyl)-5-(3-methoxyphenyl)oxazolidin-2-one | $^1$H NMR (500 MHz, DMSO-$d_6$) δ ppm 8.41 (1 H, s), 7.61-7.68 (2 H, m), 7.52-7.58 (2 H, m), 7.48 (1 H, t, J = 7.6 Hz), 7.36 (2 H, t, J = 7.8 Hz), 7.29 (2 H, t, J = 8.9 Hz), 6.91-7.01 (3 H, m), 5.32 (1 H, d, J = 7.0 Hz), 4.87 (1 H, d, J = 7.3 Hz), 3.78 (3 H, s). Anal. Calcd. for [M + H]$^+$ $C_{24}H_{19}FNO_3$: 388.14; found 388.09. |

| Example | Structure | Analytical Data |
|---|---|---|
| 132 | 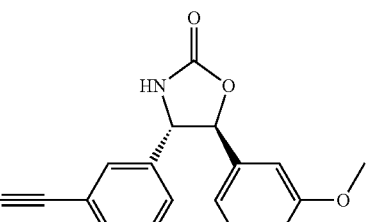<br>(4S,5S)-4-(3-((4-fluorophenyl)ethynyl)phenyl)-5-(3-methoxyphenyl)oxazolidin-2-one | $^1$H NMR (500 MHz, DMSO-$d_6$) δ ppm 8.40 (1 H, s), 7.61-7.68 (2 H, m), 7.52-7.58 (2 H, m), 7.48 (1 H, t, J = 7.6 Hz), 7.36 (2 H, t, J = 7.8 Hz), 7.29 (2 H, t, J = 8.9 Hz), 6.91-7.01 (3 H, m), 5.32 (1 H, d, J = 7.0 Hz), 4.87 (1 H, d, J = 7.0 Hz), 3.78 (3 H, s)<br>Anal. Calcd. for [M + H]$^+$ $C_{24}H_{19}FNO_3$: 388.14; found 388.18. |
| 133 | 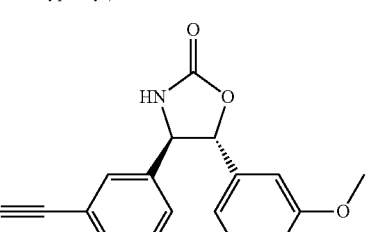<br>(4R,5R)-4-(3-((3-fluorophenyl)ethynyl)phenyl)-5-(3-methoxyphenyl)oxazolidin-2-one | $^1$H NMR (500 MHz, DMSO-$d_6$) δ ppm 8.41 (1 H, s), 7.54-7.60 (2 H, m), 7.41-7.52 (4 H, m), 7.34-7.40 (2 H, m), 7.26-7.33 (1 H, m), 6.91-7.01 (3 H, m), 5.32 (1 H, d, J = 7.0 Hz), 4.88 (1 H, d, J = 7.0 Hz), 3.78 (3 H, s)<br>Anal. Calcd. for [M + H]$^+$ $C_{24}H_{19}FNO_3$: 388.14; found 388.18. |
| 134 | 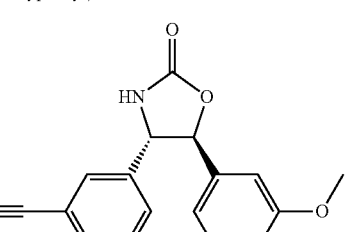<br>(4S,5S)-4-(3-((3-fluorophenyl)ethynyl)phenyl)-5-(3-methoxyphenyl)oxazolidin-2-one | $^1$H NMR (500 MHz, DMSO-$d_6$) δ ppm 8.41 (1 H, s), 7.54-7.60 (2 H, m), 7.33-7.52 (6 H, m), 7.30 (1 H, td, J = 8.6, 1.7 Hz), 6.92-7.01 (3 H, m), 5.32 (1 H, d, J = 7.0 Hz), 4.88 (1 H, d, J = 7.0 Hz), 3.75-3.80 (3 H, m)<br>Anal. Calcd. for [M + H]$^+$ $C_{24}H_{19}FNO_3$: 388.14; found 388.11. |

Example 135 and Example 136

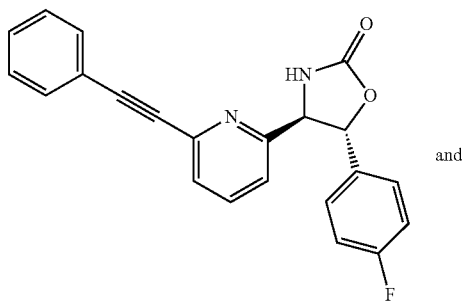

and

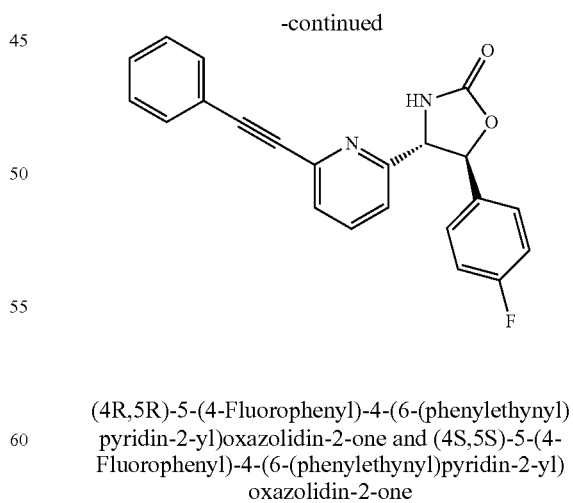

(4R,5R)-5-(4-Fluorophenyl)-4-(6-(phenylethynyl)pyridin-2-yl)oxazolidin-2-one and (4S,5S)-5-(4-Fluorophenyl)-4-(6-(phenylethynyl)pyridin-2-yl)oxazolidin-2-one Prepared according to the same procedure as (+)-(4R,5R)-5-(3-methoxyphenyl)-4-(3-(phenylethynyl)phenyl)oxazolidin-2-one, starting with optically enriched-(4R,5R)-4-(6-bromopyridin-2-yl)-5-(4-fluorophenyl)oxazolidin-2-one and phenylacetylene. $^1$H-NMR (CDCl$_3$, 500 MHz) δ 7.78 (dd, J=7.9, 7.6, 1H), 7.63 (m, 2H), 7.54 (d, J=7.6, 1H), 7.47 (dd, J=8.6, 5.5, 2H), 7.42 (m, 4H), 7.13 (dd, J=8.6, 8.6, 2H), 6.81 (bs, 1H), 5.64 (d, J=5.8, 1H), 4.96 (d, J=5.8, 1H). $^{13}$C-NMR (CDCl$_3$, 126 MHz) δ 163.1 (d, J=248, 158.9 (d, J=36), 143.9, 137.8, 134.1, 132.2, 129.4, 128.6, 127.8, 127.3, 122.0, 119.8, 116.1, 116.0, 90.3, 88.3, 83.3, 65.0. Enantiomers were resolved by Prep HPLC (Chiralcel OD, A=heptane, B=ethanol, 40% B for 30 min) Enantiomer 1=first enantiomer to elute from Prep (Example 135): Mass spec.: 359.3 (MH)$^+$. Enantiomer 2=second enantiomer to elute from Prep (Example 136): Mass spec.: 359.3 (MH)$^+$.

Example 137 and Example 138

Enantiomer 1

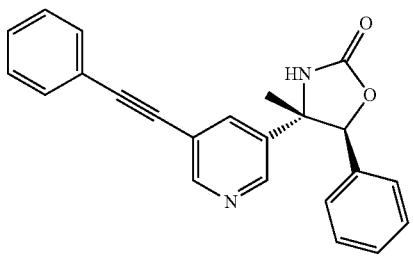

Enantiomer 2

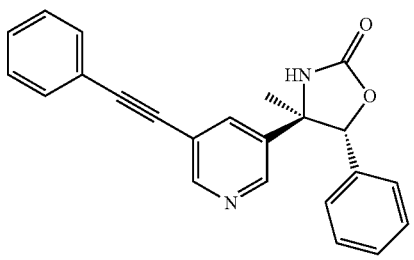

(4S,5S)-4-Methyl-5-phenyl-4-(5-(phenylethynyl)pyridin-3-yl)oxazolidin-2-one and (4R,5R)-4-Methyl-5-phenyl-4-(5-(phenylethynyl)pyridin-3-yl)oxazolidin-2-one A solution of (±)-(4R,5R)-4-(5-bromopyridin-3-yl)-4-methyl-5-phenyloxazolidin-2-one (60.0 mg, 0.180 mmol) and ethynylbenzene (19.78 μl, 0.180 mmol) in triethylamine (1129 μl, 8.10 mmol) was purged with nitrogen for 30 minutes. The reaction was treated with triphenylphosphine (12.75 mg, 0.049 mmol), and purged for another 10 minutes. To this was added dichlorobis(triphenylphosphine)palladium(II) (2.91 mg, 4.14 μmol) and copper(I) iodide (0.686 mg, 3.60 μmol). After purging 10 minutes longer, the reaction was sealed and placed in a 90° C. oil bath. The reaction was stirred at this temperature for 16 hours. It was cooled to room temperature, solvent was removed and the residue was taken in ether and ethyl acetate, washed with water, brine, dried over magnesium, filtered and concentrated. Biotage purification (50% EtOAc/Hex) gave title compounds (70 mg, quantitative yield). $^1$H-NMR (CDCl$_3$, 500 MHz) δ 8.77 (s, 1H), 8.60 (s, 1H), 7.99 (m, 1H), 7.58 (m, 2H), 7.41-7.39 (m, 6H), 7.21 (m, 2H), 6.99 (s, 1H), 5.46 (s, 1H), 1.35 (s, 3H). $^{13}$C-NMR (CDCl$_3$, 126 MHz) δ 171.3, 158.7, 151.8, 146.3, 138.4, 136.1, 133.3, 131.9, 129.3, 129.2, 128.8, 128.6, 126.2, 122.3, 120.8, 93.8, 88.1, 85.5, 63.3, 60.5, 22.8, 21.2, 14.3. Mass spec.: 355.5 (MH)$^+$. Enantiomers were resolved by Prep HPLC (Chiralpak AS 21×250 mm, 27% B isocratic, flow rate: 15 ml/min, UV 220, 50 min run, solvent A: 0.1% diethylamine/heptane, solvent B: ethanol). Enantiomer 1=first enantiomer to elute from Prep (Example 137). Enantiomer 2=second enantiomer to elute from Prep (Example 138).

Example 139

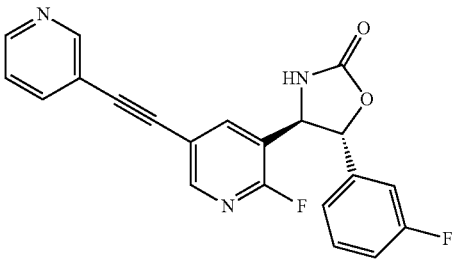 [SMILES: O=C1N[C@H](c2cc(C#Cc3cccnc3)cnc2F)[C@@H](c2cccc(F)c2)O1]

(4R,5R)-4-(2-Fluoro-5-(pyridin-3-ylethynyl)pyridin-3-yl)-5-(3-fluorophenyl)oxazolidin-2-one To a 15 ml sealable vial was added a 60:40 mixture of (4R,5R)-4-(5-bromo-2-fluoropyridin-3-yl)-5-(3-fluorophenyl)oxazolidin-2-one (42 mg, 0.118 mmol) and its regioisomer in triethylamine (2 mL). To this suspension was added 3-ethynylpyridine (14.63 mg, 0.142 mmol), triphenylphosphine (9.31 mg, 0.035 mmol) and copper(I) iodide (0.450 mg, 2.365 μmol). The solution was degassed with nitrogen for 20 min, then bis(triphenylphosphine)palladium(II) chloride (1.660 mg, 2.365 μmol) was quickly added and the vial was sealed, heated to 90° C., and allowed to stir overnight. The next day the suspension had turned homogeneous and the reaction was cooled to room temperature and the solvent was evaporated in vacuo. The crude residue was purified by reverse phase chromatography (Xterra Prep RP18.5 uM 30 mm×100 mm: 0-100% A to B, A=90% H$_2$O/10% MeOH, B=90% MeOH/10% H$_2$O, Modifier 0.1% TFA) to isolate a single peak. This single peak was a 60:40 mixture of regioisomers and was subsequently purified by chiral supercritical fluid chromatography Chiralpak AD-H column, 4.6×250 mm, 5 um particle size mobile phase: 35% MeOH in CO2 (w/0.1% diethylamine) column temp: 35 C flow rate: 2 mL/min., affording (4R,5R)-4-(2-fluoro-5-(pyridin-3-ylethynyl)pyridin-3-yl)-5-(3-fluorophenyl)oxazolidin-2-one (12 mg, 0.031 mmol, 26.6% yield). $^1$H-NMR (CD$_3$OD, 400 MHz) δ 8.73 (s, 1H), 8.54 (d, J=4.0, 1H), 8.42 (s, 1H), 8.19 (d, J=8.0, 1H), 8.01 (d, J=8.0, 1H), 7.49-7.44 (m, 2H), 7.25-7.13 (m, 3H), 5.53 (d, J=4.0, 1H), 5.03 (d, J=4.0, 1H), LC/Mass spec. (Analytical HPLC method 2): RT=1.99 min. Mass=378.10 (MH)$^+$.

Example 140

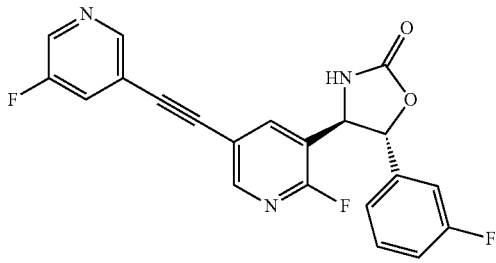 [SMILES: O=C1N[C@H](c2cc(C#Cc3cncc(F)c3)cnc2F)[C@@H](c2cccc(F)c2)O1]

(4R,5R)-4-(2-Fluoro-5-((5-fluoropyridin-3-yl)ethynyl)pyridin-3-yl)-5-(3-fluorophenyl)oxazolidin-2-one To a 15 ml sealable vial was added a mixture of (4R,5R)-4-(5-bromo-2-fluoropyridin-3-yl)-5-(3-fluorophenyl)oxazolidin-2-one (30 mg, 0.084 mmol) and its regioisomer in triethylamine (2 mL). To this suspension was added 3-ethynyl-5-fluoropyridine (12.28 mg, 0.101 mmol), triphenylphosphine (6.65 mg, 0.025 mmol) and copper(I) iodide (0.322 mg, 1.690 μmol). The solution was degassed with nitrogen for 20 min, then bis(triphenylphosphine)palladium(II) chloride (1.186 mg, 1.690 μmol) was quickly added and the vial was sealed, heated to 90° C., and allowed to stir overnight. The next day the suspension had turned homogeneous and the reaction was cooled to room temperature and the solvent was evaporated in vacuo. The crude residue was purified by silica gel chromotagraphy 1% MeOH/99% CH2Cl2 affording a single peak. This single peak was a 60:40 mixture of regioisomers and was subsequently purified by chiral supercritical fluid chromatography Chiralpak AD-H column, 4.6×250 mm, 5 um particle size mobile phase: 35% MeOH in CO2 (w/0.1% diethylamine) column temp: 35 C flow rate: 2 mL/min., affording (4R,5R)-4-(2-fluoro-5-((5-fluoropyridin-3-yl)ethynyl)pyridin-3-yl)-5-(3-fluorophenyl)oxazolidin-2-one (25 mg, 0.062 mmol, 73.4% yield). $^1$H-NMR (CDCl$_3$, 400 MHz) δ 8.63 (s, 1H), 8.51 (d, J=4.0, 1H), 8.45 (s, 1H), 8.14 (dd, J=8.0, 4.0, 1H), 7.69-7.64 (m, 1H), 7.60-7.54 (m, 1H), 7.50-7.43 (m, 1H), 7.21-7.13 (m, 2H), 6.05 (brs, 1H), 5.39 (d, J=4.0, 1H), 5.04 (d, J=4.0, 1H), LC/Mass spec. (Analytical HPLC method 2): RT=2.01 min. Mass=396.20 (MH)$^+$.

Example 141

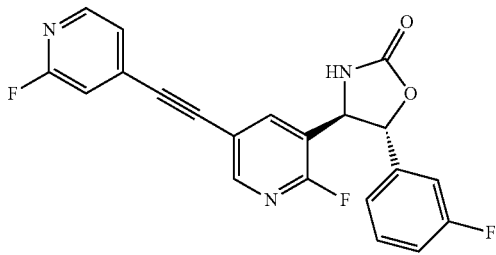 [SMILES: O=C1N[C@H](c2cc(C#Cc3ccnc(F)c3)cnc2F)[C@@H](c2cccc(F)c2)O1]

(4R,5R)-4-(2-Fluoro-5-((2-fluoropyridin-4-yl)ethynyl)pyridin-3-yl)-5-(3-fluorophenyl)oxazolidin-2-one To a 15 ml sealable vial was added (4R,5R)-4-(5-ethynyl-2-fluoropyridin-3-yl)-5-(3-fluorophenyl)oxazolidin-2-one (20 mg, 0.067 mmol) in triethylamine (2 mL). To this suspension was added 4-bromo-2-fluoropyridine (15.24 mg, 0.087 mmol), triphenylphosphine (5.24 mg, 0.020 mmol) and copper(I) iodide (0.254 mg, 1.332 μmol). The solution was degassed with nitrogen for 20 min, then bis(triphenylphosphine)palladium(II) chloride (0.935 mg, 1.332 μmol) was quickly added and the vial was sealed, heated to 90° C., and allowed to stir overnight. The next day the suspension had turned homogeneous and the reaction was cooled to room temperature and the solvent was evaporated in vacuo. The crude residue was purified by silica gel chromotagraphy eluting first with 100% CH2Cl2 then 1% MeOH/99% CH2Cl2 affording (4R,5R)-4-(2-fluoro-5-((2-fluoropyridin-4-yl)ethynyl)pyridin-3-yl)-5-(3-fluorophenyl)oxazolidin-2-one (9.1 mg, 0.021 mmol, 31.4% yield) as a light yellow solid. $^1$H-NMR (CDCl$_3$, 400 MHz) δ 8.63 (s, 1H), 8.51 (d, J=4.0, 1H), 8.45 (s, 1H), 8.14 (dd, J=8.0, 4.0, 1H), 7.69-7.64 (m, 1H), 7.60-7.54 (m, 1H), 7.50-7.43 (m, 1H), 7.21-7.13 (m, 2H), 6.05 (brs, 1H), 5.39 (d, J=4.0, 1H), 5.04 (d, J=4.0, 1H), LC/Mass spec. (Analytical HPLC method 2): RT=2.01 min. Mass=396.20 (MH)$^+$.

Example 142

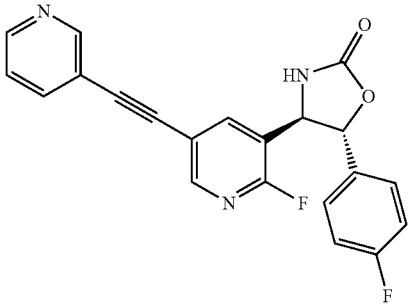

(4R,5R)-4-(2-Fluoro-5-(pyridin-3-ylethynyl)pyridin-3-yl)-5-(4-fluorophenyl)oxazolidin-2-one To a 15 ml sealable vial was added a mixture of (4R,5R)-4-(5-bromo-2-fluoropyridin-3-yl)-5-(4-fluorophenyl)oxazolidin-2-one (270 mg, 0.760 mmol) in triethylamine (15 mL). To this suspension was added 3-ethynylpyridine (94 mg, 0.912 mmol), triphenylphosphine (59.8 mg, 0.228 mmol) and copper(I) iodide (2.90 mg, 0.015 mmol). The solution was degassed with nitrogen for 20 min, then bis(triphenylphosphine)palladium(II) chloride (10.67 mg, 0.015 mmol) was quickly added and the vial was sealed, heated to 90° C., and allowed to stir overnight. The next day the suspension had turned homogeneous and the reaction was cooled to room temperature and the solvent was evaporated in vacuo. The crude residue was purified by silica gel chromatography 2% MeOH/98% CH2Cl2 affording (4R,5R)-4-(2-fluoro-5-(pyridin-3-ylethynyl)pyridin-3-yl)-5-(4-fluorophenyl)oxazolidin-2-one (210 mg, 0.540 mmol, 71.0% yield) $^1$H-NMR (CDCl$_3$, 400 MHz) δ 8.82 (s, 1H), 8.64 (d, J=4.0, 1H), 8.44 (s, 1H), 8.14 (d, J=8.0, 1H), 7.86, (d, J=8.0, 1H), 7.44-7.40 (m, 2H), 7.38-7.36 (m, 1H), 7.19-7.15 (m, 2H), 5.64 (brs, 1H), 5.38 (d, J=4.0, 1H), 5.05 (d, J=4.0, 1H), LC/Mass spec. (Analytical HPLC method 2): RT=1.78 min. Mass=378.16 (MH)+.

Example 143

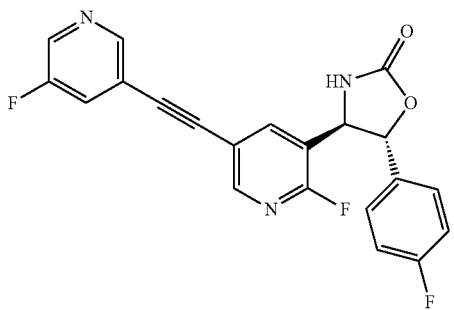 [SMILES: O=C1N[C@H](c2cc(C#Cc3cncc(F)c3)cnc2F)[C@@H](c2ccc(F)cc2)O1]

(4R,5R)-4-(2-Fluoro-5-((5-fluoropyridin-3-yl)ethynyl)pyridin-3-yl)-5-(4-fluorophenyl)oxazolidin-2-one LC/Mass spec. (Analytical HPLC method 2): RT=1.95 min. Mass=395.99 (MH)+.

Example 144

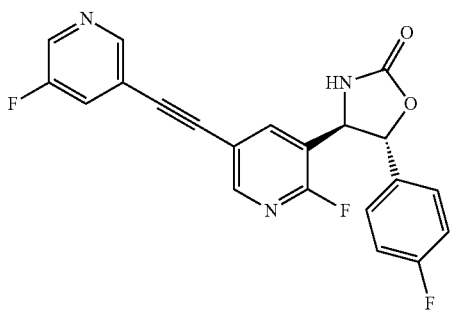 [SMILES: O=C1N[C@H](c2cc(C#Cc3cncc(F)c3)cnc2F)[C@@H](c2ccc(F)cc2)O1]

(4R,5R)-4-(5-Fluoro-2-((5-fluoropyridin-3-yl)ethynyl)pyridin-4-yl)-5-(4-fluorophenyl)oxazolidin-2-one To a 15 ml sealable vial was added a 60:40 mixture of (4R,5R)-4-(2-bromo-5-fluoropyridin-4-yl)-5-(4-fluorophenyl)oxazolidin-2-one (50 mg, 0.141 mmol) and its regioisomer in triethylamine (3 mL). To this suspension was added 3-ethynyl-5-fluoropyridine (22.17 mg, 0.183 mmol), triphenylphosphine (11.08 mg, 0.042 mmol) and copper(I) iodide (0.536 mg, 2.82 mmol). The solution was degassed with nitrogen for 20 min, then bis(triphenylphosphine)palladium (II) chloride (1.976 mg, 2.82 mmol) was quickly added and the vial was sealed, heated to 90° C., and allowed to stir overnight. The next day the suspension had turned homogeneous and the reaction was cooled to room temperature and the solvent was evaporated in vacuo. The crude residue was purified by reverse phase chromatography to isolate a single peak (4R,5R)-5-(5-fluoro-2-((5-fluoropyridin-3-yl)ethynyl)pyridin-4-yl)-4-(4-fluorophenyl)oxazolidin-2-one (18.4 mg, 0.046 mmol, 49.8% yield). This single peak was still a mixture of the regioisomers. This single peak was a 65:35 mixture of regioisomers and was subsequently purified by chiral supercritical fluid chromatography Chiralpak AD-H column, 4.6×250 mm, 5 um particle size mobile phase: 35% MeOH in CO2 (w/0.1% diethylamine) column temp: 35 C flow rate: 2 mL/min., affording 1H-NMR (CDCl3, 400 MHz) δ 8.67 (s, 1H), 8.54 (s, 1H), 8.51 (d, J=4.0, 1H), 7.79 (d, J=4.0, 1H), 7.64-7.60 (m, 1H), 7.42-7.39 (m, 2H), 7.19-7.15 (m, 2H), 6.00 (brs, 1H), 5.36 (d, J=4.0, 1H), 5.12 (d, J=4.0, 1H), LC/Mass spec. (Analytical HPLC method 2): RT=1.95 min. Mass=395.99 (MH)+.

Example 145

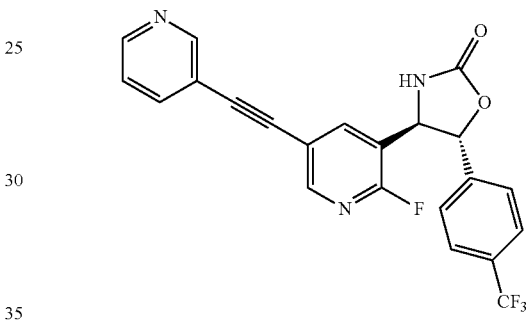

(4R,5R)-4-(2-Fluoro-5-(pyridin-3-ylethynyl)pyridin-3-yl)-5-(4-(trifluoromethyl)phenyl)oxazolidin-2-one To a 15 ml sealable vial was added a 60:40 mixture of (4R,5R)-4-(5-bromo-2-fluoropyridin-3-yl)-5-(4-(trifluoromethyl)phenyl)oxazolidin-2-one (84 mg, 0.207 mmol) and its regioisomer in triethylamine (3 mL). To this suspension was added 3-ethynylpyridine (25.7 mg, 0.249 mmol), triphenylphosphine (16.31 mg, 0.062 mmol) and copper(I) iodide (0.790 mg, 4.15 mmol). The solution was degassed with nitrogen for 20 min, then bis(triphenylphosphine)palladium (II) chloride (2.91 mg, 4.15 mmol) was quickly added and the vial was sealed, heated to 90° C., and allowed to stir overnight. The next day the suspension had turned homogeneous and the reaction was cooled to room temperature and the solvent was evaporated in vacuo. The crude residue was purified by reverse phase chromatography (Xterra Prep RP 18.5 uM 30 mm×100 mm: 0-100% A to B, A=90% H2O/10% MeOH, B=90% MeOH/10% H2O, Modifier 0.1% TFA) to isolate a single peak. This single peak was still a mixture of the regioisomers and was further purified by chiral supercritical fluid chromatography: Chiralpak AD-H column, 4.6×250 mm, 5 um particle size mobile phase: 35% MeOH in CO2 (w/0.1% diethylamine) column temp: 35 C flow rate: 2 mL/min., affording (4R,5R)-4-(2-fluoro-5-(pyridin-3-ylethynyl)pyridin-3-yl)-5-(4-(trifluoromethyl)phenyl)oxazolidin-2-one (12 mg, 27% yield). 1H-NMR (CDCl3, 400 MHz) δ 8.80 (s, 1H), 8.62 (d, J=4.0, 1H), 8.45 (s, 1H), 8.13 (d, J=8.0, 1H), 7.86 (d, J=4.0, 1H) 7.77 (d, J=8.0, 2H), 7.57 (d, J=8.0, 2H) 7.37-7.34 (m, 1H), 5.98 (brs, 1H), 5.52 (d, J=4.0, 1H), 4.87 (d, J=4.0, 1H), LC/Mass spec. (Analytical HPLC method 2): RT=2.05 min. Mass=427.98 (MH)+.

Example 146

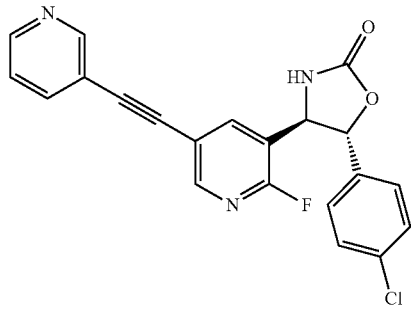 [SMILES: O=C1N[C@H](c2cc(C#Cc3cccnc3)cnc2F)[C@@H](c2ccc(Cl)cc2)O1]

(4R,5R)-5-(4-Chlorophenyl)-4-(2-fluoro-5-(pyridin-3-ylethynyl)pyridin-3-yl)oxazolidin-2-on LC/Mass spec. (Analytical HPLC method 2): RT=1.91 min. Mass=393.92 (MH)+.

Example 147

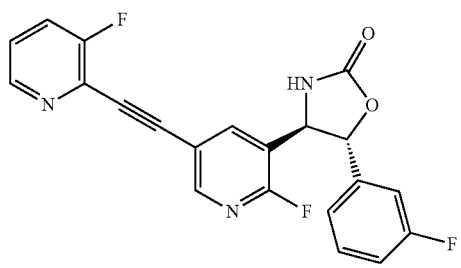 [SMILES: O=C1N[C@H](c2cc(C#Cc3ncccc3F)cnc2F)[C@@H](c2cccc(F)c2)O1]

(4R,5R)-4-(2-Fluoro-5-((3-fluoropyridin-2-yl)ethynyl)pyridin-3-yl)-5-(3-fluorophenyl)oxazolidin-2-one LC/Mass spec. (Analytical HPLC method 2): RT=1.98 min. Mass=396.13 (MH)+.

Example 148

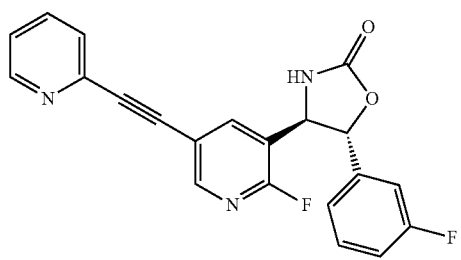 [SMILES: O=C1N[C@H](c2cc(C#Cc3ccccn3)cnc2F)[C@@H](c2cccc(F)c2)O1]

(4R,5R)-4-(2-Fluoro-5-(pyridin-2-ylethynyl)pyridin-3-yl)-5-(3-fluorophenyl)oxazolidin-2-one LC/Mass spec. (Analytical HPLC method 2): RT=1.89 min. Mass=378.23 (MH)+.

Example 149

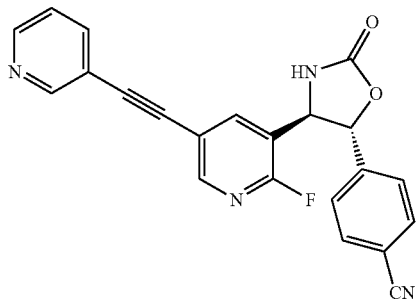 [SMILES: N#Cc1ccc([C@H]2OC(=O)N[C@@H]2c2cc(C#Cc3cccnc3)cnc2F)cc1]

4-((4R,5R)-4-(2-Fluoro-5-(pyridin-2-ylethynyl)pyridin-3-yl)-2-oxooxazolidin-5-yl)benzonitrile LC/Mass spec. (Analytical HPLC method 1): RT=1.71 min. Mass=385.01 (MH)+.

Example 150

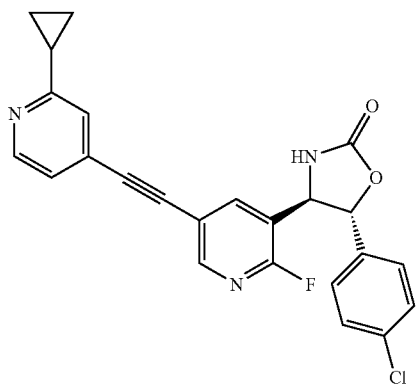 [SMILES: O=C1N[C@H](c2cc(C#Cc3ccnc(C4CC4)c3)cnc2F)[C@@H](c2ccc(Cl)cc2)O1]

(4R,5R)-5-(4-Chlorophenyl)-4-(5-((2-cyclopropylpyridin-4-yl)ethynyl)-2-fluoropyridin-3-yl)oxazolidin-2-one LC/Mass spec. (Analytical HPLC method 1): RT=1.90 min. Mass=433.98 (MH)+.

Example 151

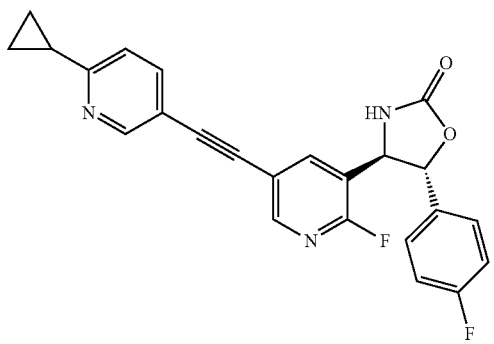 [SMILES: O=C1N[C@H](c2cc(C#Cc3ccc(C4CC4)nc3)cnc2F)[C@@H](c2ccc(F)cc2)O1]

(4R,5R)-4-(5-((6-Cyclopropylpyridin-3-yl)ethynyl)-
2-fluoropyridin-3-yl)-5-(4-fluorophenyl)oxazolidin-
2-one LC/Mass spec. (Analytical HPLC method 2): RT=1.59 min. Mass=418.17 (MH)$^+$.

Example 152

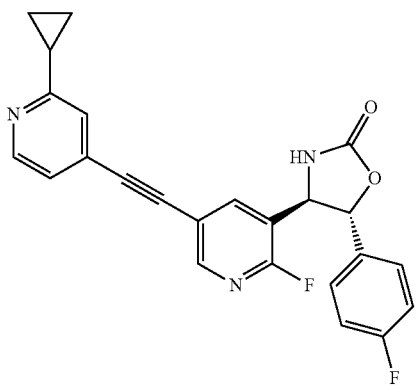 [SMILES: O=C1N[C@H](c2cc(C#Cc3ccnc(C4CC4)c3)cnc2F)[C@@H](c2ccc(F)cc2)O1]

(4R,5R)-4-(5-((2-Cyclopropylpyridin-4-yl)ethynyl)-
2-fluoropyridin-3-yl)-5-(4-fluorophenyl)oxazolidin-
2-one LC/Mass spec. (Analytical HPLC method 2): RT=1.16 min. Mass=418.17 (MH)$^+$.

Example 153

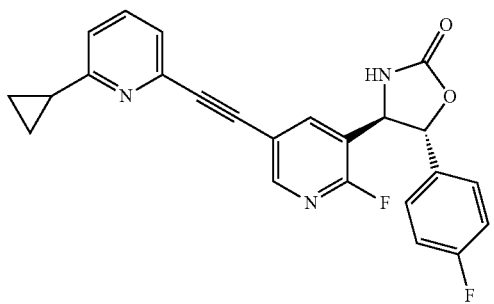 [SMILES: O=C1N[C@H](c2cc(C#Cc3cccc(C4CC4)n3)cnc2F)[C@@H](c2ccc(F)cc2)O1]

(4R,5R)-4-(5-((6-Cyclopropylpyridin-2-yl)ethynyl)-
2-fluoropyridin-3-yl)-5-(4-fluorophenyl)oxazolidin-
2-one LC/Mass spec. (Analytical HPLC method 2): RT=1.50 min. Mass=418.17 (MH)$^+$.

Example 154

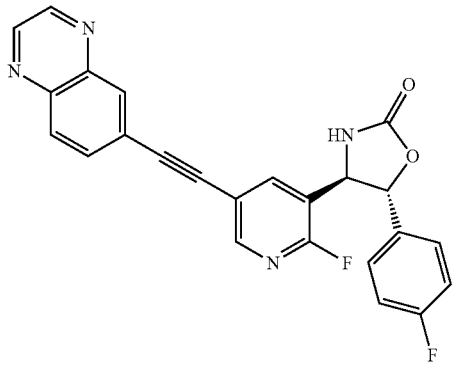 [SMILES: O=C1N[C@H](c2cc(C#Cc3ccc4nccnc4c3)cnc2F)[C@@H](c2ccc(F)cc2)O1]

(4R,5R)-4-(2-fluoro-5-(quinoxalin-6-ylethynyl)pyri-
din-3-yl)-5-(4-fluorophenyl)oxazolidin-2-one LC/Mass spec. (Analytical HPLC method 2): RT=1.66 min. Mass=429.16 (MH)$^+$.

Example 155

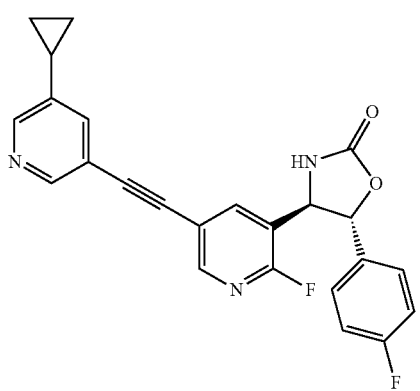 [SMILES: O=C1N[C@H](c2cc(C#Cc3cncc(C4CC4)c3)cnc2F)[C@@H](c2ccc(F)cc2)O1]

(4R,5R)-4-(5-((5-Cyclopropylpyridin-3-yl)ethynyl)-2-fluoropyridin-3-yl)-5-(4-fluorophenyl)oxazolidin-2-one LC/Mass spec. (Analytical HPLC method 3): RT=3.14 min. Mass=418.10 (MH)+.

Example 156

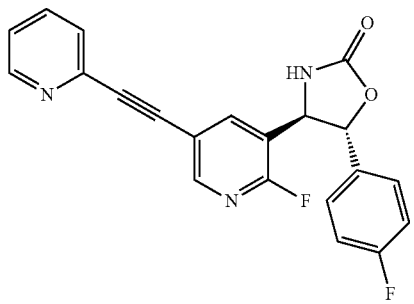 [SMILES: O=C1N[C@H](c2cc(C#Cc3ccccn3)cnc2F)[C@@H](c2ccc(F)cc2)O1]

(4R,5R)-4-(2-Fluoro-5-(pyridin-2-ylethynyl)pyridin-3-yl)-5-(4-fluorophenyl)oxazolidin-2-one LC/Mass spec. (Analytical HPLC method 2): RT=1.31 min. Mass=378.16 (MH)+.

Example 157

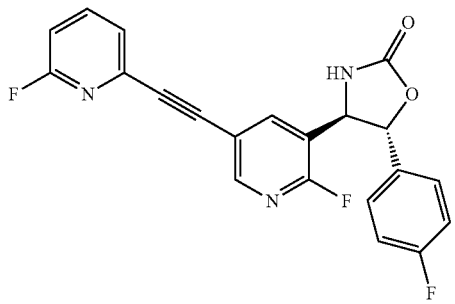 [SMILES: O=C1N[C@H](c2cc(C#Cc3cccc(F)n3)cnc2F)[C@@H](c2ccc(F)cc2)O1]

(4R,5R)-4-(2-Fluoro-5-((6-fluoropyridin-2-yl)ethynyl)pyridin-3-yl)-5-(4-fluorophenyl)oxazolidin-2-one LC/Mass spec. (Analytical HPLC method 2): RT=1.53 min. Mass=352.18 (MH)+.

The following analogs were prepared using the same methods for preparation of (+)-(4R,5R)-5-(3-Methoxyphenyl)-4-(3-(phenylethynyl)phenyl)oxazolidin-2-one.

| Example | Structure | Mass | Retention Time (min) | Analytical HPLC Method |
|---|---|---|---|---|
| 158 | 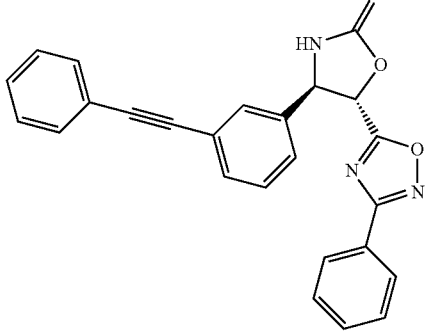 | 406.09 (M − H)− | 2.14 | 8 |
| 159 | 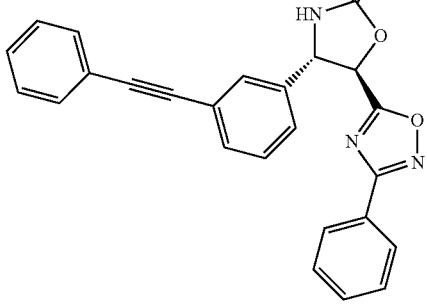 | 406.13 (M − H)− | 2.15 | 8 |

-continued

| Example | Structure | Mass | Retention Time (min) | Analytical HPLC Method |
|---------|-----------|------|----------------------|------------------------|
| 160 | 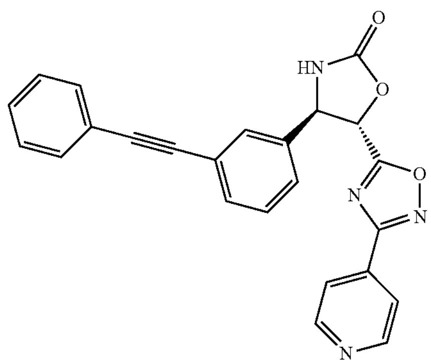 [SMILES: O=C1N[C@H](c2cccc(C#Cc3ccccc3)c2)[C@@H](c2nc(-c3ccncc3)no2)O1] | 409.11 (MH)+ | 1.98 | 8 |
| 161 | 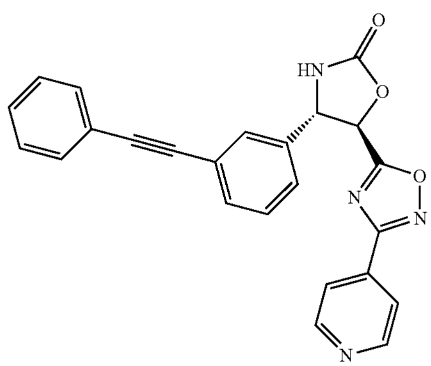 [SMILES: O=C1N[C@@H](c2cccc(C#Cc3ccccc3)c2)[C@H](c2nc(-c3ccncc3)no2)O1] | 409.10 (MH)+ | 1.99 | 8 |
| 162 | 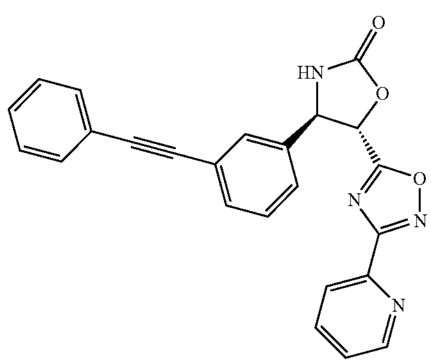 [SMILES: O=C1N[C@H](c2cccc(C#Cc3ccccc3)c2)[C@@H](c2nc(-c3ccccn3)no2)O1] | 408.97 (MH)+ | 1.93 | 8 |
| 163 | 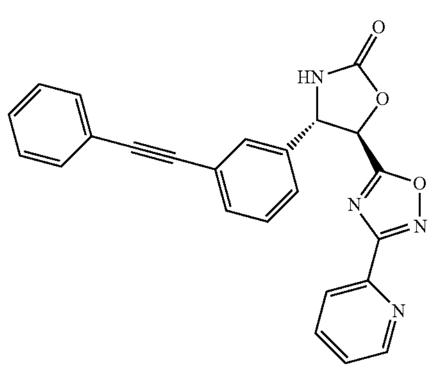 | 408.99 (MH)+ | 1.93 | 8 |

-continued

| Example | Structure | Mass | Retention Time (min) | Analytical HPLC Method |
|---|---|---|---|---|
| 164 | 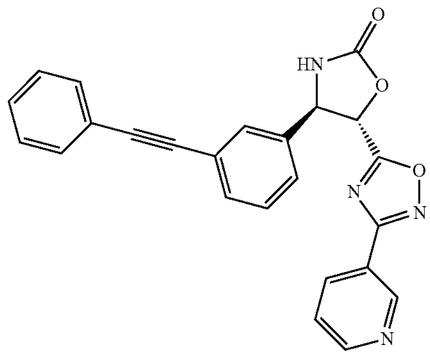 [SMILES: O=C1N[C@H](c2cccc(C#Cc3ccccc3)c2)[C@@H](c2nc(-c3cccnc3)no2)O1] | 409.05 (MH)+ | 1.97 | 8 |
| 165 | 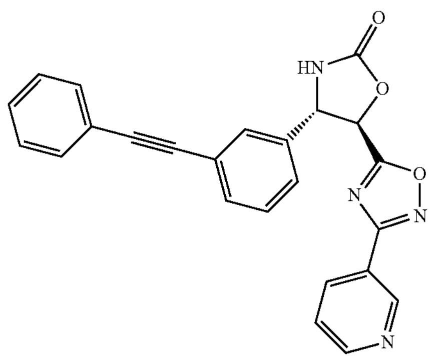 [SMILES: O=C1N[C@@H](c2cccc(C#Cc3ccccc3)c2)[C@H](c2nc(-c3cccnc3)no2)O1] | 409.00 (MH)+ | 1.96 | 8 |
| 166 | 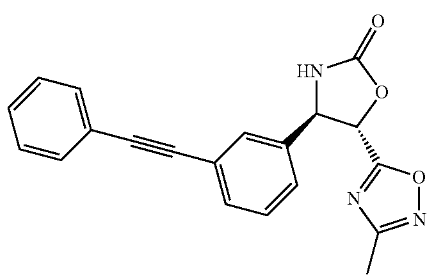 [SMILES: Cc1noc([C@H]2OC(=O)N[C@@H]2c2cccc(C#Cc3ccccc3)c2)n1] | 344.07 (M − H)− | 1.91 | 8 |
| 167 | 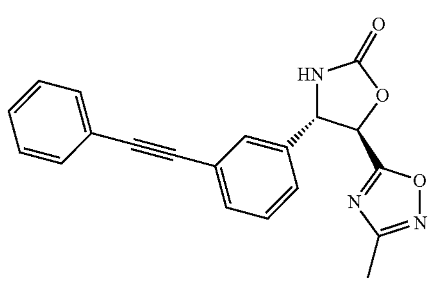 [SMILES: Cc1noc([C@@H]2OC(=O)N[C@H]2c2cccc(C#Cc3ccccc3)c2)n1] | 344.08 (M − H)− | 1.90 | 8 |

Example 168

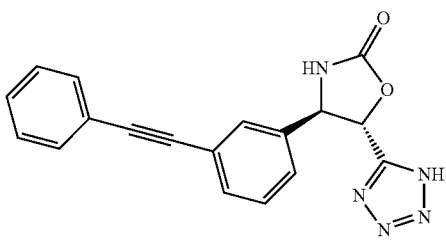 [SMILES: O=C1N[C@H](c2cccc(C#Cc3ccccc3)c2)[C@@H](c2nnn[nH]2)O1]

(4R,5S)-4-(3-(Phenylethynyl)phenyl)-5-(1H-tetrazol-5-yl)oxazolidin-2-one

To a solution of (4R,5S)-2-oxo-4-(3-(phenylethynyl)phenyl)oxazolidine-5-carbonitrile (35 mg, 0.121 mmol) in Toluene (2 mL) was added triethylamine hydrochloride (50.6 mg, 0.364 mmol) and sodium azide (23.68 mg, 0.364 mmol) and the reaction was heated to reflux. After 2 days, the reaction was poured into water (1 ml) and extracted with ethylacetate (10 mL×2). The combined organic layers were dried over magnesium sulfate, filtered, and concentrated to an off white solid that was purified by Preparative HPLC method 4 providing (4R,5S)-4-(3-(phenylethynyl)phenyl)-5-(1H-tetrazol-5-yl)oxazolidin-2-one (30 mg, 0.090 mmol, 73.8% yield) $^1$H NMR (500 MHz, DMSO-d$_6$) δ ppm 5.21-5.55 (m, 2H) 7.10 (br. s., 3H) 7.34 (d, J=7.93 Hz, 1H) 7.39-7.49 (m, 4H) 7.51 (d, J=7.32 Hz, 1H) 7.57 (dd, J=6.41, 3.05 Hz, 2H) 8.27 (s, 1H). Mass spec.: 331.99 (MH)$^+$.

Example 169

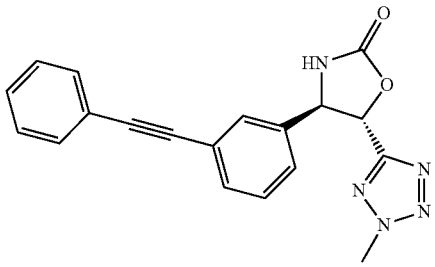 [SMILES: Cn1nnc([C@H]2OC(=O)N[C@@H]2c2cccc(C#Cc3ccccc3)c2)n1]

(4R,5S)-5-(2-Methyl-2H-tetrazol-5-yl)-4-(3-(phenylethynyl)phenyl)oxazolidin-2-one To a solution of (4R,5S)-4-(3-(phenylethynyl)phenyl)-5-(1H-tetrazol-5-yl)oxazolidin-2-one (18.6 mg, 0.056 mmol) in tetrahydrofuran (5 mL) was added potassium carbonate (38.8 mg, 0.281 mmol) and iodomethane (0.035 mL, 0.561 mmol) and the reaction mixture was held at 50° C. for 6 hours. The reaction mixture was concentrated and purified by Preparative HPLC Method 16 providing (4R,5S)-5-(2-methyl-2H-tetrazol-5-yl)-4-(3-(phenylethynyl)phenyl)oxazolidin-2-one (2.4 mg, 6.60 mmol, 11.76% yield). $^1$H NMR (500 MHz, DMSO-d$_6$) δ ppm 4.43 (s, 3H) 5.27 (s, 1H) 5.75 (s, 1H) 7.39-7.46 (m, 4H) 7.49 (t, J=7.63 Hz, 1H) 7.55-7.62 (m, 3H) 8.69 (s, 1H). Mass spec.: 344.11 (M−H)$^−$.

The compounds in the following table were prepared by A: Formation of 'stilbene', asymmetric aminohydroxylation, formation of oxazolidinone, Sonagashira coupling; B: Sonagashira coupling of (4R,5R)-4-(3-ethynylphenyl)-5-(3-methoxyphenyl)oxazolidin-2-one with an appropriate arylhalide; C: Sonagashira coupling of (4R,5R)-4-(5-ethynylpyridin-3-yl)-5-(4-fluorophenyl)oxazolidin-2-one with an appropriate arylhalide; D: Aldol, TBS protection, Curtius rearrangement/trapping with BnOH, formation of oxazolidinone, Sonagashira Coupling; E: Aldol, Curtius rearrangement/internal trapping to give oxazolidinone, Sonagashira Coupling.

| Example | Structure | | Mass Spec. | Retention Time (min) | Analytical HPLC Method | Synthetic Method |
|---|---|---|---|---|---|---|
| 170 | 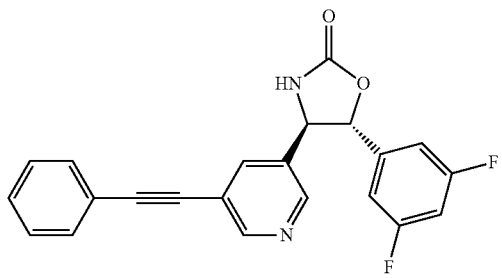 | Chiral | 377.04 (MH)+ | 3.56 | 7 | A |

-continued

| Example | Structure | | Mass Spec. | Retention Time (min) | Analytical HPLC Method | Synthetic Method |
|---|---|---|---|---|---|---|
| 171 | 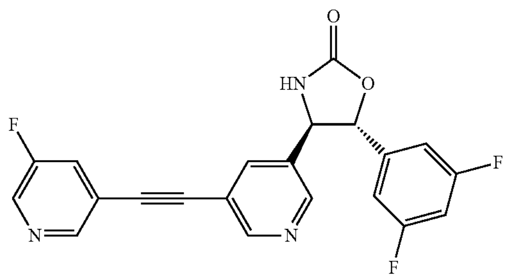 | Chiral | 396.1 (MH)+ | 2.54 | 15 | A |
| 172 | 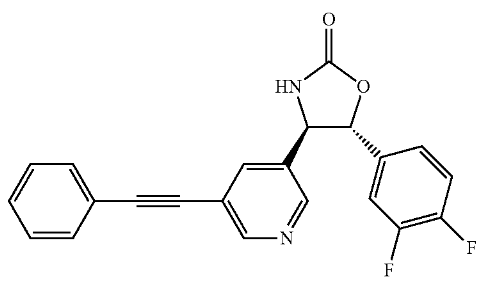 | Chiral | 377.1 (MH)+ | 2.9 | 15 | A |
| 173 | 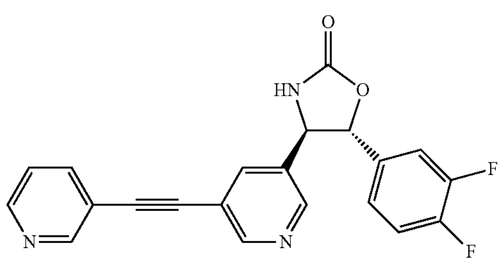 | Chiral | 378.1 (MH)+ | 1.91 | 15 | A |
| 174 | 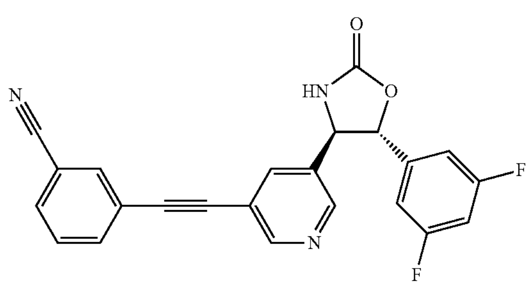 | Chiral | 401.96 (MH)+ | 3.28 | 7 | A |
| 175 | 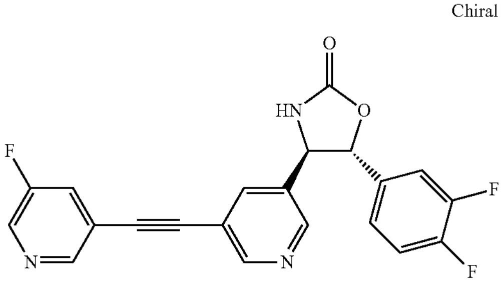 [SMILES: O=C1N[C@H](c2cncc(C#Cc3cncc(F)c3)c2)[C@@H](c2ccc(F)c(F)c2)O1] | Chiral | 395.95 (MH)+ | 3.18 | 7 | A |

-continued

| Example | Structure | | Mass Spec. | Retention Time (min) | Analytical HPLC Method | Synthetic Method |
|---|---|---|---|---|---|---|
| 176 | 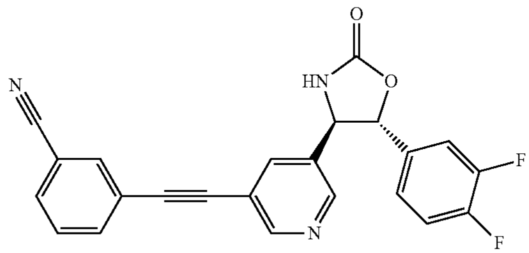 | Chiral | 401.96 (MH)+ | 3.26 | 7 | A |
| 177 | 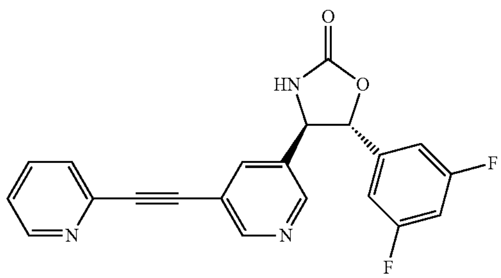 | Chiral | 378.01 (MH)+ | 2.3 | 7 | A |
| 178 | 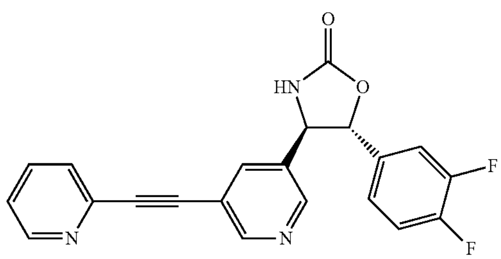 | Chiral | 378.01 (MH)+ | 2.98 | 7 | A |
| 179 | 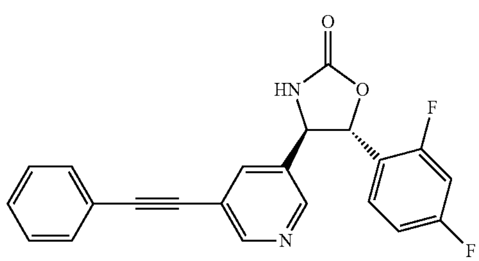 | Chiral | 377.05 (MH)+ | 3.53 | 7 | A |
| 180 | 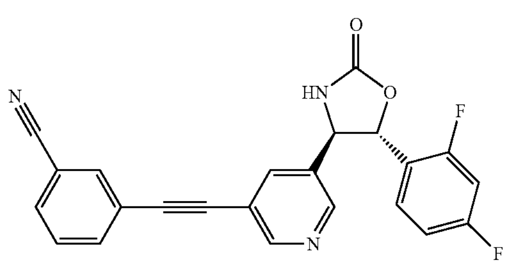 | Chiral | 401.95 (MH)+ | 3.25 | 7 | A |

-continued

| Example | Structure | Mass Spec. | Retention Time (min) | Analytical HPLC Method | Synthetic Method |
|---|---|---|---|---|---|
| 181 | Chiral | 378.01 (MH)+ | 3.02 | 7 | A |
| 182 | Chiral | 395.97 (MH)+ | 3.18 | 7 | A |
| 183 | Chiral | 377.95 (MH)+ | 2.93 | 7 | A |
| 184 | Chiral | 378.04 (MH)+ | 3 | 7 | A |
| 185 | Chiral | 378.04 (MH)+ | 3.48 | 7 | A |

-continued

| Example | Structure | Mass Spec. | Retention Time (min) | Analytical HPLC Method | Synthetic Method |
|---------|-----------|------------|----------------------|------------------------|------------------|
| 186 | Chiral | 378.01 (MH)+ | 2.89 | 7 | A |
| 187 | Chiral | 396 (MH)+ | 3.01 | 7 | A |
| 188 | Chiral | 402 (MH)+ | 3.19 | 7 | A |
| 189 | Chiral | 378.06 (MH)+ | 2.9 | 7 | A |

-continued

| Example | Structure | Mass Spec. | Retention Time (min) | Analytical HPLC Method | Synthetic Method |
|---|---|---|---|---|---|
| 190 | Chiral | 402.2 (MH)+ | 2.78 | 15 | A |
| 191 | Chiral | 378.2 (MH)+ | 2.04 | 15 | A |
| 192 | Chiral | 377.3 (MH)+ | 2.92 | 15 | A |
| 193 | Chiral | 389.0 (MH)+ | 2.36 | 1 | B |

-continued

| Example | Structure | Mass Spec. | Retention Time (min) | Analytical HPLC Method | Synthetic Method |
|---------|-----------|------------|----------------------|------------------------|------------------|
| 194 | Chiral | 395.0 (MH)+ | 2.27 | 1 | B |
| 195 | Chiral | 389.0 (MH)+ | 2.33 | 13 | B |
| 196 | Chiral | 389.0 (MH)+ | 2.33 | 13 | B |
| 197 | Chiral | 410.0 (MH)+ | 2.34 | 13 | B |

-continued

| Example | Structure | Mass Spec. | Retention Time (min) | Analytical HPLC Method | Synthetic Method |
|---|---|---|---|---|---|
| 198 | Chiral | 342.1 (MH)+ | 2.05 | 13 | A |
| 199 | Chiral | 342.1 (MH)+ | 2.05 | 13 | A |
| 200 | Chiral | 372.0 (MH)+ | 2.01 | 13 | B |
| 201 | Chiral | 361.0 (MH)+ | 1.68 | 13 | A |

-continued

| Example | Structure | Mass Spec. | Retention Time (min) | Analytical HPLC Method | Synthetic Method |
|---------|-----------|------------|----------------------|------------------------|------------------|
| 202 | Chiral | 361.0 (MH)+ | 1.68 | 13 | A |
| 203 | Chiral | 373.2 (MH)+ | 2.08 | 14 | A |
| 204 | Chiral | 373.2 (MH)+ | 2.08 | 14 | A |
| 205 | Chiral | 373.1 (MH)+ | 2.08 | 14 | A |

-continued

| Example | Structure | Mass Spec. | Retention Time (min) | Analytical HPLC Method | Synthetic Method |
|---|---|---|---|---|---|
| 206 | Chiral | 373.1 (MH)+ | 2.08 | 14 | A |
| 207 | Chiral | 392.1 (MH)+ | 1.93 | 14 | A |
| 208 | Chiral | 392.1 (MH)+ | 1.93 | 14 | A |
| 209 | Chiral | 378.2 (MH)+ | 1.84 | 14 | C |

-continued

| Example | Structure | Mass Spec. | Retention Time (min) | Analytical HPLC Method | Synthetic Method |
|---|---|---|---|---|---|
| 210 | Chiral | 360.1 (MH)+ | 1.69 | 14 | C |
| 211 | Chiral | 385.1 (MH)+ | 1.81 | 14 | C |
| 212 | Chiral | 361.2 (MH)+ | 1.7 | 14 | C |
| 213 | Chiral | 360.2 (MH)+ | 1.42 | 14 | C |

-continued

| Example | Structure | Mass Spec. | Retention Time (min) | Analytical HPLC Method | Synthetic Method |
|---|---|---|---|---|---|
| 214 | Chiral | 378.2 (MH)+ | 1.9 | 14 | C |
| 215 | Chiral | 384.2 (MH)+ | 1.9 | 14 | C |
| 216 | Chiral | 378.1 (MH)+ | 1.84 | 14 | C |
| 217 | Chiral | 359.3 (MH)+ | 2.09 | 14 | A |

-continued

| Example | Structure | Mass Spec. | Retention Time (min) | Analytical HPLC Method | Synthetic Method |
|---|---|---|---|---|---|
| 218 | Chiral | 359.3 (MH)+ | 2.1 | 14 | A |
| 219 | Chiral | 373.3 (MH)+ | 2.07 | 14 | D |
| 220 | Chiral | 373.3 (MH)+ | 2.08 | 14 | D |
| 221 | Chiral | 373.3 (MH)+ | 2.23 | 14 | A |

-continued

| Example | Structure | Mass Spec. | Retention Time (min) | Analytical HPLC Method | Synthetic Method |
|---|---|---|---|---|---|
| 222 | Chiral | 373.3 (MH)+ | 2.23 | 14 | A |
| 223 | Chiral | 373.5 (MH)+ | 2.13 | 14 | A |
| 224 | Chiral | 373.5 (MH)+ | 2.13 | 14 | A |
| 225 | Chiral | 355.5 (MH)+ | 2.07 | 14 | D |
| 226 | Chiral | 355.5 (MH)+ | 2.07 | 14 | D |

-continued

| Example | Structure | Mass Spec. | Retention Time (min) | Analytical HPLC Method | Synthetic Method |
|---------|-----------|------------|----------------------|------------------------|------------------|
| 227 | Chiral | 355.1 (MH)+ | 2.22 | 14 | A |
| 228 | Chiral | 355.1 (MH)+ | 2.17 | 14 | A |
| 229 | Chiral | 374.1 (MH)+ | 2 | 14 | D |
| 230 | Chiral | 374.1 (MH)+ | 1.9 | 14 | D |
| 231 | Chiral | 340.9 (MH)+ | 2.44 | 6 | A |

-continued

| Example | Structure | Mass Spec. | Retention Time (min) | Analytical HPLC Method | Synthetic Method |
|---|---|---|---|---|---|
| 232 | Chiral | 340.9 (MH)⁺ | 2.44 | 6 | A |
| 233 | Chiral | 342.0 (MH)⁺ | 0.8 | 6 | A |
| 234 | Chiral | 341.0 (MH)⁺ | 1.89 | 6 | A |
| 235 | Chiral | 342.0 (MH)⁺ | 0.81 | 6 | A |
| 236 | Chiral | 342.0 (MH)⁺ | 0.81 | 6 | A |

-continued

| Example | Structure | Mass Spec. | Retention Time (min) | Analytical HPLC Method | Synthetic Method |
|---------|-----------|------------|----------------------|------------------------|------------------|
| 237 | Chiral | 360.0 (MH)+ | 1.2 | 6 | A |
| 238 | Chiral | 342.2 (MH)+ | 2.39 | 6 | E |
| 239 | Chiral | 342.2 (MH)+ | 2.39 | 6 | E |
| 240 | Chiral | 343.2 (MH)+ | 1.36 | 6 | E |
| 241 | Chiral | 343.2 (MH)+ | 1.35 | 6 | E |

-continued

| Example | Structure | | Mass Spec. | Retention Time (min) | Analytical HPLC Method | Synthetic Method |
|---|---|---|---|---|---|---|
| 242 | 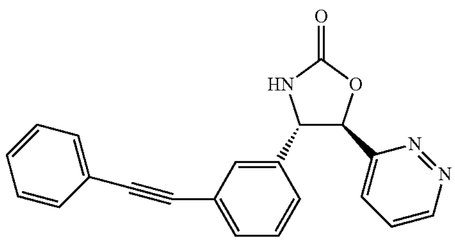 | Chiral | 340.1 (M − H)⁻ | 3.23 | 12 | E |
| 243 | 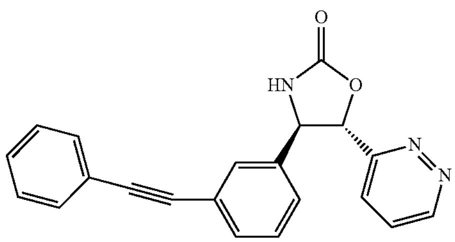 | Chiral | 340.1 (M − H)⁻ | 3.21 | 12 | E |
| 244 | 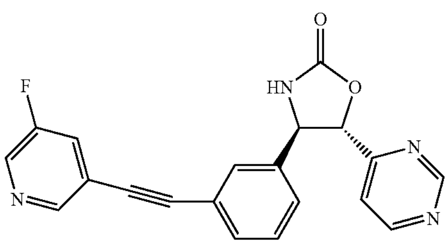 | Chiral | 359.1 (M − H)⁻ | 2.87 | 12 | E |
| 245 | 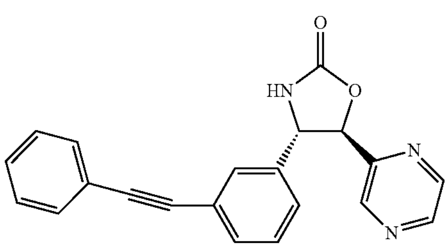 | Chiral | 340.1 (M − H)⁻ | 3.37 | 12 | E |
| 246 | 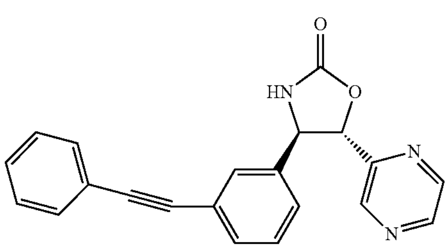 | Chiral | 340.1 (M − H)⁻ | 3.38 | 12 | E |

-continued

| Example | Structure | Mass Spec. | Retention Time (min) | Analytical HPLC Method | Synthetic Method |
|---|---|---|---|---|---|
| 247 | Chiral | 340.1 (M − H)⁻ | 3 | 12 | E |
| 248 | Chiral | 341.1 (M − H)⁻ | 2.7 | 12 | E |
| 249 | Chiral | 341.1 (M − H)⁻ | 2.72 | 12 | E |
| 250 | Chiral | 341.1 (M − H)⁻ | 2.36 | 12 | E |
| 251 | Chiral | 341.1 (MH)⁻ | 2.33 | 12 | E |

-continued

| Example | Structure | Mass Spec. | Retention Time (min) | Analytical HPLC Method | Synthetic Method |
|---|---|---|---|---|---|
| 252 | Chiral | 360.1 (MH)+ | 1.74 | 10 | A |
| 253 | Chiral | 361.1 (MH)+ | 1.54 | 10 | A |
| 254 | Chiral | 342.0 (MH)+ | 3.01 | 11 | A |
| 255 | Chiral | 367.0 (MH)+ | 2.47 | 12 | A |

-continued
| Example | Structure | Mass Spec. | Retention Time (min) | Analytical HPLC Method | Synthetic Method |
|---|---|---|---|---|---|
| 256 | Chiral 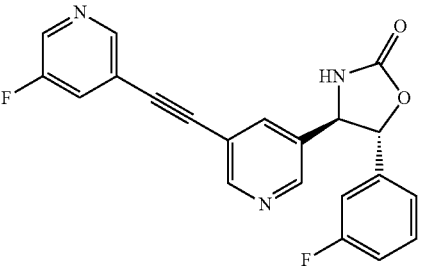 | 378.1 (MH)+ | 2.08 | 2 | A |
| 257 | Chiral 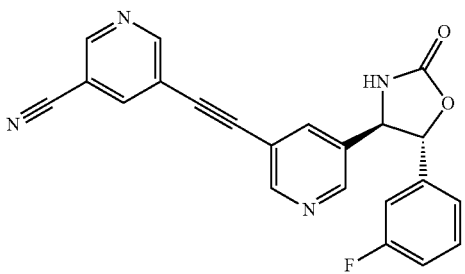 | 385.2 (MH)+ | 2.26 | 2 | A |
| 258 | Chiral 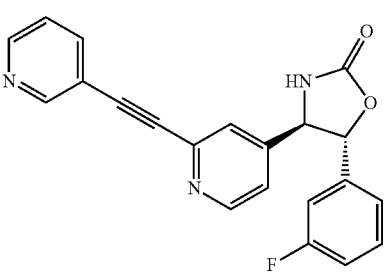 | 360.1 (MH)+ | 1.72 | 1 | A |
| 259 | Chiral 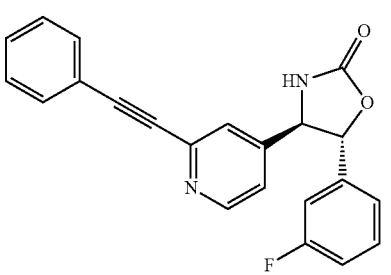 | 359.1 (MH)+ | 2.05 | 1 | A |

-continued

| Example | Structure | | Mass Spec. | Retention Time (min) | Analytical HPLC Method | Synthetic Method |
|---|---|---|---|---|---|---|
| 260 | 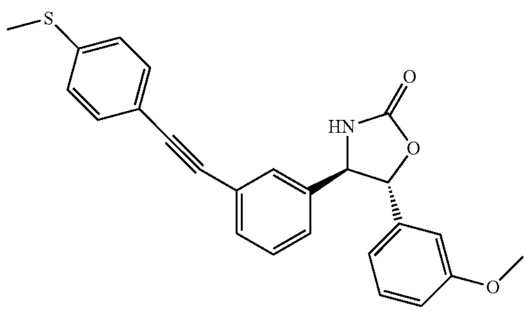 | Chiral | 416.16 (MH)+ | 6.4 | 9 | B |
| 261 | 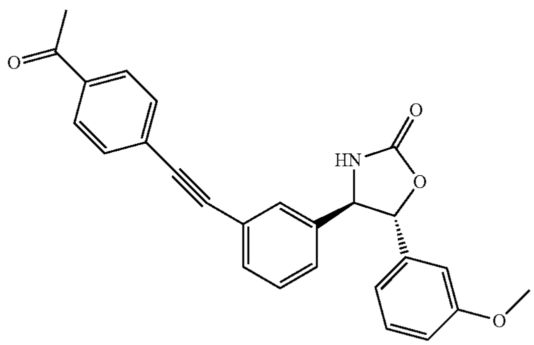 | Chiral | 412.26 (MH)+ | 5.3 | 9 | B |
| 262 | 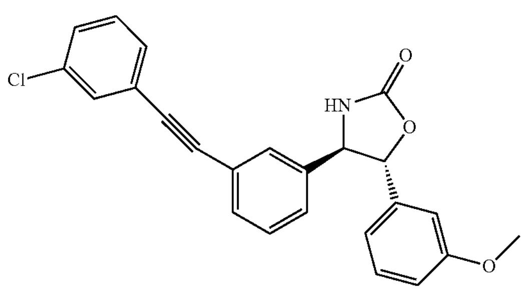 | Chiral | 404.20 (MH)+ | 6.7 | 9 | B |
| 263 | 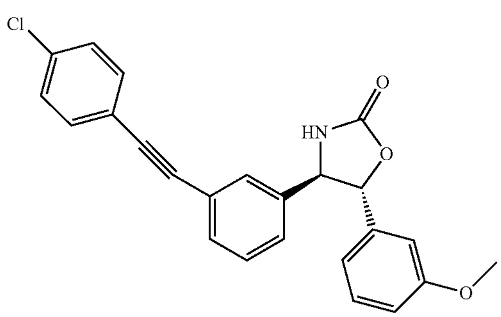 | Chiral | 404.22 (MH)+ | 6.7 | 9 | B |

-continued

| Example | Structure | Mass Spec. | Retention Time (min) | Analytical HPLC Method | Synthetic Method |
|---|---|---|---|---|---|
| 264 | Chiral | 395.27 (MH)+ | 5.4 | 9 | B |
| 265 | Chiral | 385.25 (MH)+ | 5.2 | 9 | B |
| 266 | Chiral | 428.25 (MH)+ | 5.8 | 9 | B |
| 267 | Chiral | 428.23 (MH)+ | 5.9 | 9 | B |

| Example | Structure | Mass Spec. | Retention Time (min) | Analytical HPLC Method | Synthetic Method |
|---|---|---|---|---|---|
| 268 | Chiral | 454.17 (MH)+ | 6.8 | 9 | B |
| 269 | Chiral | 454.17 (MH)+ | 6.8 | 9 | B |

Example 185

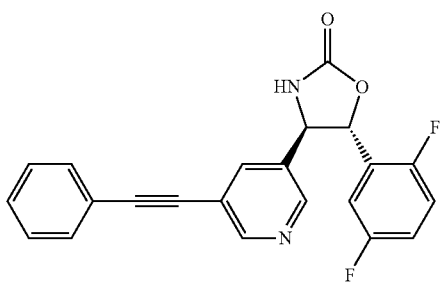 [SMILES: O=C1N[C@H](c2cncc(C#Cc3ccccc3)c2)[C@@H](c2cc(F)ccc2F)O1]

(4R,5R)-5-(2,5-difluorophenyl)-4-(5-(phenylethynyl)-3-pyridinyl)-1,3-oxazolidin-2-one To a stirred solution of optically enriched (4R,5R)-4-(5-bromopyridin-3-yl)-5-(2,5-difluorophenyl)oxazolidin-2-one (1.25 g, 3.25 mmol) in triethylamine (70 mL) was added ethynylbenzene (0.592 mL, 5.28 mmol), copper(I) iodide (67 mg, 0.352 mmol), and triphenylphosphine (653 mg, 2.464 mmol). Nitrogen was bubbled through the mixture for 10 minutes before adding dichlorobis(triphenylphosphine)-palladium(II) (202 mg, 0.282 mmol) with continued nitrogen gas bubbling. After an additional 10 minutes the reaction mixture was heated to reflux for 16 hours, cooled to ambient temperature, diluted with EtOAc, washed with water (3×), brine, dried over magnesium sulfate, and concentrated in vacuo. Column chromatography (25%-->40% EtOAc/Hex) provided optically enriched (4R,5R)-5-(2,5-difluorophenyl)-4-(5-(phenylethynyl)pyridin-3-yl)oxazolidin-2-one which was separated by chiral SFC chromatography (Chiralcel OJ-H preparative column, 30×250 mm, 5 μm, Mobile Phase: 40% MeOH (0.1% DEA) in $CO_2$ @ 150 Bar, Temp: 35° C., Flow rate: 70.0 mL/min. for 16 min, UV monitored @ 280 nM. $t_R$=9.23 min) to provide (1.38 g, 2.99 mmol, 85% yield) of pure single enantiomer (4R,5R)-5-(2,5-difluorophenyl)-4-(5-(phenylethynyl)pyridin-3-yl)oxazolidin-2-one. $^1$H NMR (500 MHz, DMSO-$d_6$) δ ppm 8.77 (d, J=2.21 Hz, 1H) 8.57 (s, 1H) 8.56 (d, J=2.20 Hz, 1H) 8.07 (t, J=2.05 Hz, 1H) 7.58-7.66 (m, 2H) 7.44-7.52 (m, 3H) 7.39-7.45 (m, 1H) 7.28-7.39 (m, 2H) 5.67 (d, J=6.62 Hz, 1H) 5.04 (d, J=6.62 Hz, 1H). $^{13}$C NMR (126 MHz, DMSO-$d_6$) δ ppm 157.28; 157.24 (d, J=240.70 Hz) 155.92 (d, J=245.20 Hz) 151.63; 147.70; 136.78; 135.02; 131.57; 129.43; 128.89; 126.63 (dd, J=14.99, 7.72 Hz) 121.51; 119.47; 117.83 (dd, J=23.60, 9.10 Hz) 117.50 (dd, J=24.50, 8.20 Hz); 114.60 (dd, J=26.34, 4.54 Hz); 92.86; 85.76; 78.12; 59.43; LCMS (ESI) m/z calcd for $C_{22}H_{15}F_2N_2O_2$: 377.11. found 377.20 [M+H]+; HRMS (ESI) m/z calcd for $C_{22}H_{15}F_2N_2O_2$: 377.1096. found 377.1096 [M+H]+.

The following analogs were prepared by using the same methods for preparation of (4R,5R)-5-(2,5-difluorophenyl)-4-(5-(phenylethynyl)pyridin-3-yl)oxazolidin-2-one.

| Example # | Structure | Analytical Data |
|---|---|---|
| Example 270 | 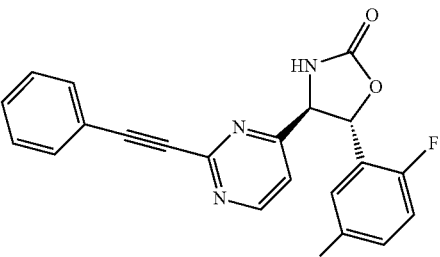<br>racemate | $^1$H NMR (500 MHz, DMSO-$d_6$) δ 8.94 (d, J = 5.2 Hz, 1H), 8.69 (br. s., 1H), 7.71-7.66 (m, 2H), 7.62 (d, J = 5.2 Hz, 1H), 7.57-7.47 (m, 3H), 7.43-7.33 (m, 3H), 5.73 (d, J = 5.5 Hz, 1H), 5.03 (d, J = 5.5 Hz, 1H). MS Anal. Calcd. for [M + H]$^+$ $C_{21}H_{14}F_2N_3O_2$: 378.1; found 378.2. |
| Example 271 | 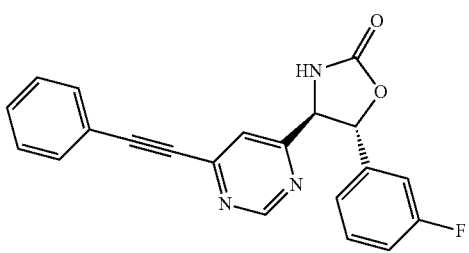 [SMILES: O=C1N[C@H](c2cc(C#Cc3ccccc3)ncn2)[C@@H](c2cccc(F)c2)O1]<br>racemate | $^1$H NMR (500 MHz, DMSO-$d_6$) δ 9.27 (d, J = 1.2 Hz, 1H), 8.57 (s, 1H), 7.88 (d, J = 0.9 Hz, 1H), 7.73-7.67 (m, 2H), 7.59-7.48 (m, 4H), 7.35-7.30 (m, 2H), 7.27 (td, J = 8.4, 2.1 Hz, 1H), 5.64 (d, J = 5.2 Hz, 1H), 4.93 (d, J = 5.2 Hz, 1H). MS Anal. Calcd. for [M + H]$^+$ $C_{21}H_{15}FN_3O_2$: 360.1; found 360.2. |
| Example 272 | 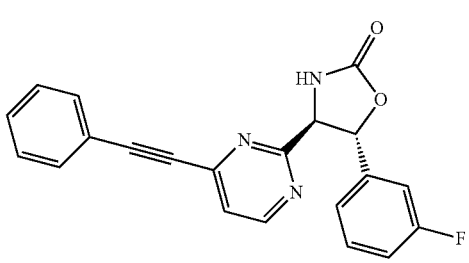 [SMILES: O=C1N[C@H](c2nccc(C#Cc3ccccc3)n2)[C@@H](c2cccc(F)c2)O1]<br>racemate | $^1$H NMR (500 MHz, DMSO-$d_6$) δ 9.04-8.90 (m, 1H), 8.66-8.53 (m, 1H), 7.77 (d, J = 5.2 Hz, 1H), 7.72-7.69 (m, 2H), 7.56-7.48 (m, 4H), 7.33-7.23 (m, 3H), 5.71 (d, J = 4.6 Hz, 1H), 4.89 (d, J = 4.6 Hz, 1H). MS Anal. Calcd. for [M + H]$^+$ $C_{21}H_5FN_3O_2$: 360.1; found 360.2. |
| Example 273 | 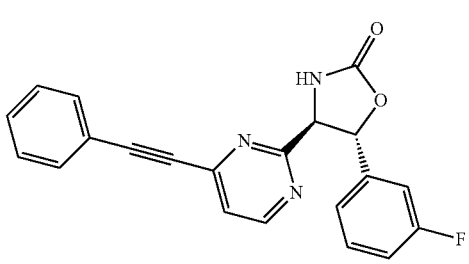 [SMILES: O=C1N[C@H](c2nccc(C#Cc3ccccc3)n2)[C@@H](c2cccc(F)c2)O1] | $^1$H NMR (500 MHz, DMSO-$d_6$) δ 8.98 (d, J = 5.2 Hz, 1H), 8.59 (s, 1H), 7.77 (d, J = 5.2 Hz, 1H), 7.73-7.69 (m, 2H), 7.59-7.46 (m, 4H), 7.34-7.23 (m, 3H), 5.71 (d, J = 4.6 Hz, 1H), 4.89 (d, J = 4.6 Hz, 1H). MS Anal. Calcd. for [M + H]$^+$ $C_{21}H_5FN_3O_2$: 360.1; found 360.3. |
| Example 274 | 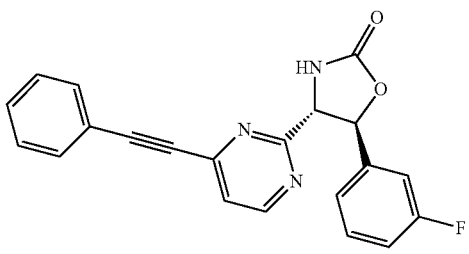 [SMILES: O=C1N[C@@H](c2nccc(C#Cc3ccccc3)n2)[C@H](c2cccc(F)c2)O1] | $^1$H NMR (500 MHz, DMSO-$d_6$) δ 8.98 (d, J = 5.2 Hz, 1H), 8.59 (s, 1H), 7.77 (d, J = 4.9 Hz, 1H), 7.73-7.68 (m, 2H), 7.60-7.48 (m, 4H), 7.34-7.23 (m, 3H), 5.71 (d, J = 4.6 Hz, 1H), 4.89 (d, J = 4.6 Hz, 1H). MS Anal. Calcd. for [M + H]$^+$ $C_{21}H_{15}FN_3O_2$: 360.1; found 360.3. |

| Example # | Structure | Analytical Data |
|---|---|---|
| Example 275 | 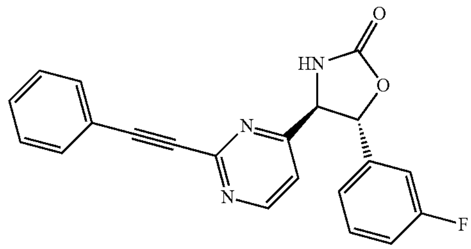 [SMILES: O=C1N[C@H](c2ccnc(C#Cc3ccccc3)n2)[C@@H](c2cccc(F)c2)O1] | $^1$H NMR (500 MHz, DMSO-$d_6$) δ 8.94 (d, J = 5.2 Hz, 1H), 8.63 (br. s., 1H), 7.72-7.66 (m, 2H), 7.62 (d, J = 5.2 Hz, 1H), 7.57-7.46 (m, 4H), 7.35-7.24 (m, 3H), 5.63 (d, J = 5.2 Hz, 1H), 4.94 (d, J = 5.2 Hz, 1H). MS Anal. Calcd. for [M + H]$^+$ $C_{21}H_{15}FN_3O_2$: 360.1; found 360.2. |
| Example 276 | 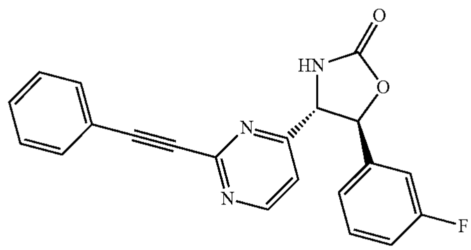 [SMILES: O=C1N[C@@H](c2ccnc(C#Cc3ccccc3)n2)[C@H](c2cccc(F)c2)O1] | $^1$H NMR (500 MHz, DMSO-$d_6$) δ 8.94 (d, J = 5.2 Hz, 1H), 8.64 (br. s., 1H), 7.72-7.66 (m, 2H), 7.62 (d, J = 5.2 Hz, 1H), 7.57-7.48 (m, 4H), 7.35-7.25 (m, 3H), 5.63 (d, J = 4.9 Hz, 1H), 4.94 (d, J = 4.9 Hz, 1H). MS Anal. Calcd. for [M + H]$^+$ $C_{21}H_{15}FN_3O_2$: 360.1; found 360.2. |
| Example 277 | 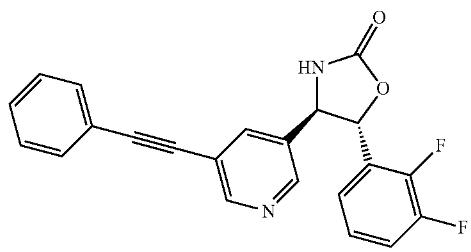 [SMILES: O=C1N[C@H](c2cncc(C#Cc3ccccc3)c2)[C@@H](c2cccc(F)c2F)O1] | $^1$H NMR (500 MHz, DMSO-$d_6$) δ 8.78 (d, J = 2.1 Hz, 1H), 8.64-8.52 (m, 2H), 8.07 (t, J = 2.0 Hz, 1H), 7.65-7.60 (m, 2H), 7.58-7.50 (m, 1H), 7.50-7.45 (m, 3H), 7.37-7.30 (m, 2H), 5.73 (d, J = 6.7 Hz, 1H), 5.07 (d, J = 6.4 Hz, 1H). MS Anal. Calcd. for [M + H]$^+$ $C_{22}H_{15}F_2N_2O_2$: 377.1; found 377.3. |
| Example 278 | 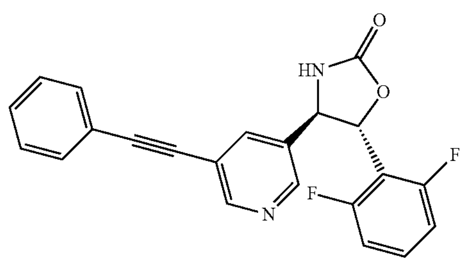 [SMILES: O=C1N[C@H](c2cncc(C#Cc3ccccc3)c2)[C@@H](c2c(F)cccc2F)O1] | $^1$H NMR (500 MHz, DMSO-$d_6$) δ 8.77 (d, J = 2.1 Hz, 1H), 8.63-8.50 (m, 2H), 8.11 (t, J = 2.0 Hz, 1H), 7.67-7.53 (m, 3H), 7.51-7.42 (m, 3H), 7.23 (t, J = 8.5 Hz, 2H), 5.69 (d, J = 7.6 Hz, 1H), 5.16 (d, J = 7.6 Hz, 1H). MS Anal. Calcd. for [M + H]$^+$ $C_{22}H_{15}F_2N_2O_2$: 377.1; found 377.2. |
| Example 279 | 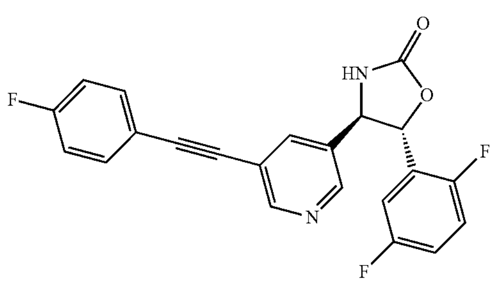 [SMILES: O=C1N[C@H](c2cncc(C#Cc3ccc(F)cc3)c2)[C@@H](c2cc(F)ccc2F)O1] | $^1$H NMR (500 MHz, DMSO-$d_6$) δ 8.77 (d, J = 1.8 Hz, 1H), 8.56 (s, 2H), 8.06 (t, J = 2.0 Hz, 1H), 7.74-7.65 (m, 2H), 7.47-7.27 (m, 5H), 5.66 (d, J = 6.7 Hz, 1H), 5.04 (d, J = 7.0 Hz, 1H). MS Anal. Calcd. for [M + H]$^+$ $C_{22}H_{14}F_3N_2O_2$: 395.1; found 395.2. |
| Example 280 | 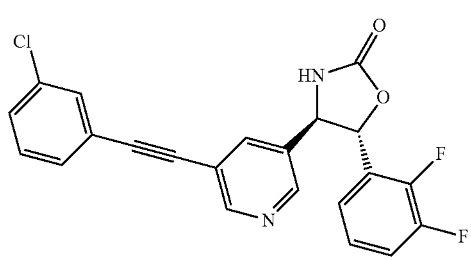 | $^1$H NMR (500 MHz, DMSO-$d_6$) δ 8.79 (d, J = 1.8 Hz, 1H), 8.60 (d, J = 1.8 Hz, 2H), 8.09 (t, J = 2.0 Hz, 1H), 7.73 (t, J = 1.7 Hz, 1H), 7.63-7.44 (m, 4H), 7.38-7.28 (m, 2H), 5.72 (d, J = 6.4 Hz, 1H), 5.07 (d, J = 6.4 Hz, 1H). MS Anal. Calcd. for [M + H]$^+$ $C_{22}H_{14}ClF_2N_2O_2$: 411.1; found 411.2. |

| Example # | Structure | Analytical Data |
|---|---|---|
| Example 281 | 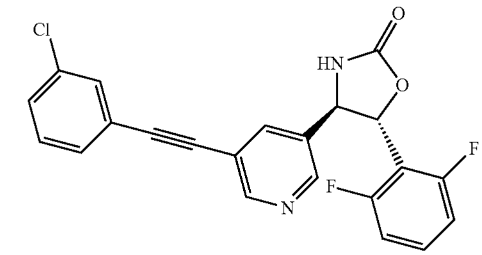 [SMILES: O=C1N[C@H](c2cncc(C#Cc3cccc(Cl)c3)c2)[C@@H](c2c(F)cccc2F)O1] | ¹H NMR (500 MHz, DMSO-d₆) δ 8.78 (d, J = 1.8 Hz, 1H), 8.59 (d, J = 2.1 Hz, 2H), 8.14 (t, J = 2.0 Hz, 1H), 7.71 (t, J = 1.7 Hz, 1H), 7.64-7.53 (m, 3H), 7.52-7.46 (m, 1H), 7.23 (t, J = 8.5 Hz, 2H), 5.68 (d, J = 7.3 Hz, 1H), 5.16 (d, J = 7.3 Hz, 1H). MS Anal. Calcd. for [M + H]⁺ $C_{22}H_{14}ClF_2N_2O_2$: 411.1; found 411.2. |
| Example 282 | 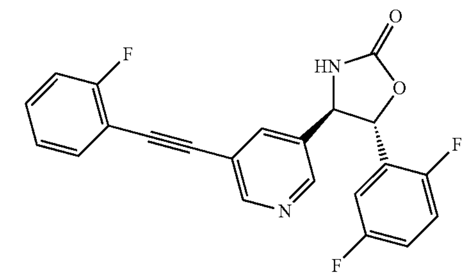 [SMILES: O=C1N[C@H](c2cncc(C#Cc3ccccc3F)c2)[C@@H](c2cc(F)ccc2F)O1] | ¹H NMR (500 MHz, DMSO-d₆) δ 8.79 (d, J = 1.8 Hz, 1H), 8.65-8.52 (m, 2H), 8.09 (t, J = 2.0 Hz, 1H), 7.71 (td, J = 7.5, 1.8 Hz, 1H), 7.58-7.51 (m, 1H), 7.46-7.26 (m, 5H), 5.68 (d, J = 6.7 Hz, 1H), 5.05 (d, J = 7.0 Hz, 1H). MS Anal. Calcd. for [M + H]+ $C_{22}H_{14}F_3N_2O_2$: 395.1; found 395.1. |
| Example 283 | 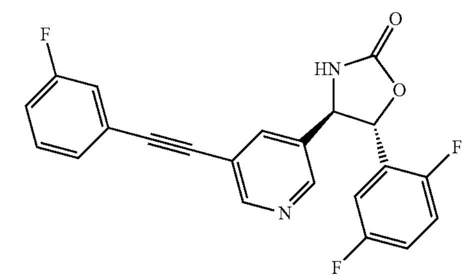 [SMILES: O=C1N[C@H](c2cncc(C#Cc3cccc(F)c3)c2)[C@@H](c2cc(F)ccc2F)O1] | ¹H NMR (500 MHz, DMSO-d₆) δ 8.79 (d, J = 1.8 Hz, 1H), 8.65-8.53 (m, 2H), 8.09 (t, J = 2.0 Hz, 1H), 7.56-7.46 (m, 3H), 7.45-7.31 (m, 4H), 5.66 (d, J = 6.7 Hz, 1H), 5.04 (d, J = 6.7 Hz, 1H). MS Anal. Calcd. for [M + H]⁺ $C_{22}H_{14}F_3N_2O_2$: 395.1; found 395.1. |
| Example 284 | 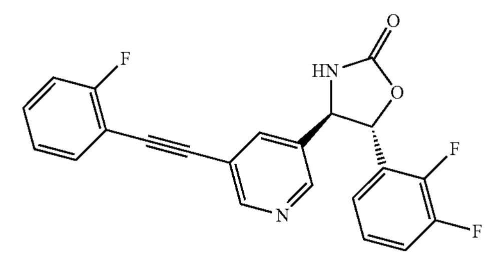 [SMILES: O=C1N[C@H](c2cncc(C#Cc3ccccc3F)c2)[C@@H](c2cccc(F)c2F)O1] | ¹H NMR (500 MHz, DMSO-d₆) δ 8.79 (d, J = 1.8 Hz, 1H), 8.64-8.56 (m, 2H), 8.08 (t, J = 2.0 Hz, 1H), 7.71 (td, J = 7.5, 1.5 Hz, 1H), 7.58-7.49 (m, 2H), 7.43-7.28 (m, 4H), 5.74 (d, J = 6.7 Hz, 1H), 5.09 (d, J = 6.4 Hz, 1H). MS Anal. Calcd. for [M + H]⁺ $C_{22}H_{14}F_3N_2O_2$: 395.1; found 395.1. |
| Example 285 | 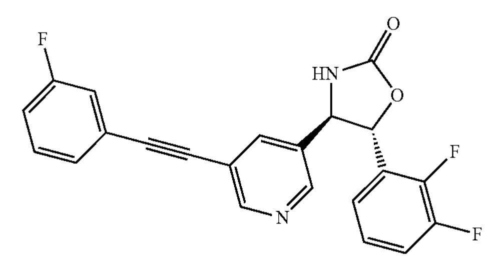 [SMILES: O=C1N[C@H](c2cncc(C#Cc3cccc(F)c3)c2)[C@@H](c2cccc(F)c2F)O1] | ¹H NMR (500 MHz, DMSO-d₆) δ 8.79 (d, J = 2.1 Hz, 1H), 8.60 (d, J = 2.1 Hz, 2H), 8.09 (t, J = 2.0 Hz, 1H), 7.65-7.44 (m, 4H), 7.40-7.30 (m, 3H), 5.72 (d, J = 6.4 Hz, 1H), 5.08 (d, J = 6.4 Hz, 1H). MS Anal. Calcd. for [M + H]⁺ $C_{22}H_{14}F_3N_2O_2$: 395.1; found 395.1. |
| Example 286 | 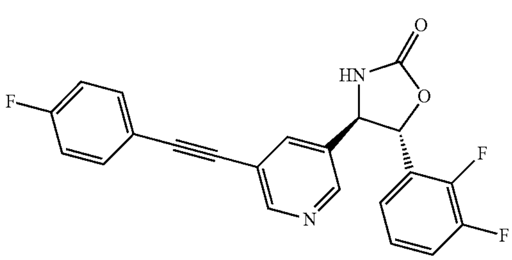 [SMILES: O=C1N[C@H](c2cncc(C#Cc3ccc(F)cc3)c2)[C@@H](c2cccc(F)c2F)O1] | ¹H NMR (500 MHz, DMSO-d₆) δ 8.77 (d, J = 1.8 Hz, 1H), 8.66-8.54 (m, 2H), 8.06 (t, J = 2.0 Hz, 1H), 7.76-7.64 (m, 2H), 7.59-7.47 (m, 1H), 7.40-7.24 (m, 4H), 5.72 (d, J = 6.4 Hz, 1H), 5.07 (d, J = 6.4 Hz, 1H). MS Anal. Calcd. for [M + H]⁺ $C_{22}H_{14}F_3N_2O_2$: 395.1; found 395.2. |

| Example # | Structure | Analytical Data |
|---|---|---|
| Example 287 | 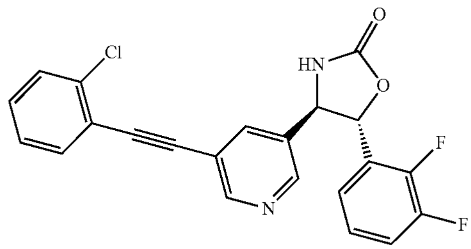 | $^1$H NMR (500 MHz, DMSO-$d_6$) δ 8.80 (d, J = 1.8 Hz, 1H), 8.65-8.53 (m, 2H), 8.08 (t, J = 2.1 Hz, 1H), 7.75 (dd, J = 7.6, 1.8 Hz, 1H), 7.64 (dd, J = 7.9, 0.9 Hz, 1H), 7.57-7.47 (m, 2H), 7.47-7.42 (m, 1H), 7.36-7.30 (m, 2H), 5.74 (d, J = 6.7 Hz, 1H), 5.09 (d, J = 6.4 Hz, 1H). MS Anal. Calcd. for [M + H]$^+$ $C_{22}H_{14}ClF_2N_2O_2$: 411.1; found 411.2. |
| Example 288 | 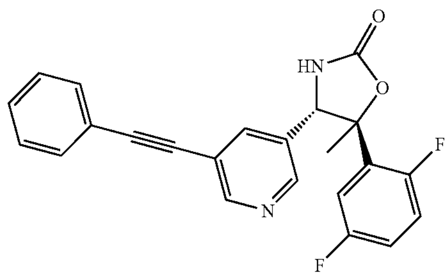 [SMILES: C[C@@]1(c2cc(F)ccc2F)OC(=O)N[C@H]1c1cncc(C#Cc2ccccc2)c1] | $^1$H NMR (500 MHz, DMSO-$d_6$) δ 8.81 (d, J = 2.1 Hz, 1H), 8.62-8.45 (m, 2H), 7.88 (t, J = 2.0 Hz, 1H), 7.71-7.60 (m, 2H), 7.53-7.43 (m, 4H), 7.41-7.32 (m, 1H), 7.27 (ddd, J = 9.2, 6.0, 3.1 Hz, 1H), 5.16 (d, J = 1.2 Hz, 1H), 1.26 (s, 3H). MS Anal. Calcd. for [M + H]$^+$ $C_{22}H_{16}F_2N_2O_2$: 391.1; found 391.2. |
| Example 289 | 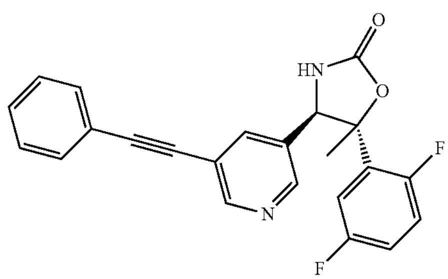 [SMILES: C[C@]1(c2cc(F)ccc2F)OC(=O)N[C@@H]1c1cncc(C#Cc2ccccc2)c1] | $^1$H NMR (500 MHz, DMSO-$d_6$) δ 8.81 (d, J = 2.1 Hz, 1H), 8.66-8.45 (m, 2H), 7.88 (t, J = 2.0 Hz, 1H), 7.71-7.59 (m, 2H), 7.54-7.42 (m, 4H), 7.40-7.32 (m, 1H), 7.27 (ddd, J = 9.2, 6.0, 3.1 Hz, 1H), 5.16 (d, J = 1.2 Hz, 1H), 1.26 (s, 3H). MS Anal. Calcd. for [M + H]$^+$ $C_{22}H_{16}F_2N_2O_2$: 391.1; found 391.2. |
| Example 290 | 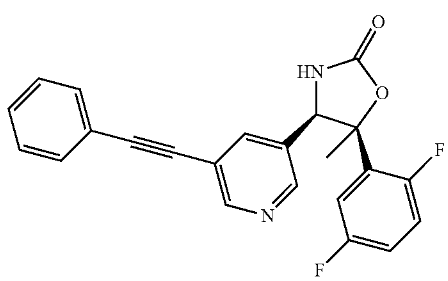 [SMILES: C[C@@]1(c2cc(F)ccc2F)OC(=O)N[C@@H]1c1cncc(C#Cc2ccccc2)c1] | $^1$H NMR (500 MHz, DMSO-$d_6$) δ 8.65 (s, 1H), 8.52 (d, J = 1.8 Hz, 1H), 8.30 (s, 1H), 7.65-7.54 (m, 3H), 7.50-7.41 (m, 3H), 7.20 (ddd, J = 9.2, 5.9, 3.2 Hz, 1H), 7.12-7.06 (m, 1H), 7.01 (td, J = 9.8, 4.6 Hz, 1H), 5.17 (d, J = 1.5 Hz, 1H), 1.90 (s, 3H). MS Anal. Calcd. for [M + H]$^+$ $C_{22}H_{16}F_2N_2O_2$: 391.1; found 391.2. |
| Example 291 | 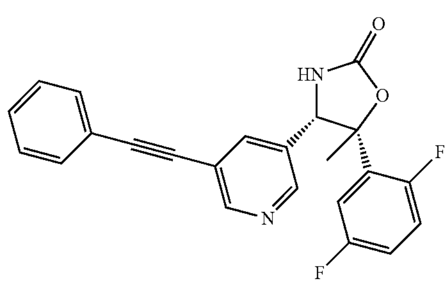 [SMILES: C[C@]1(c2cc(F)ccc2F)OC(=O)N[C@H]1c1cncc(C#Cc2ccccc2)c1] | $^1$H NMR (500MHz, DMSO-$d_6$) δ 8.65 (s, 1H), 8.52 (d, J = 1.8 Hz, 1H), 8.30 (s, 1H), 7.65-7.53 (m, 3H), 7.51-7.37 (m, 3H), 7.20 (ddd, J = 9.2, 5.8, 3.4 Hz, 1H), 7.12-7.06 (m, 1H), 7.01 (td, J = 9.8, 4.6 Hz, 1H), 5.17 (d, J = 1.8 Hz, 1H), 1.90 (s, 3H). MS Anal. Calcd. for [M + H]$^+$ $C_{22}H_{16}F_2N_2O_2$: 391.1; found 391.2. |

| Example # | Structure | Analytical Data |
|---|---|---|
| Example 292 | 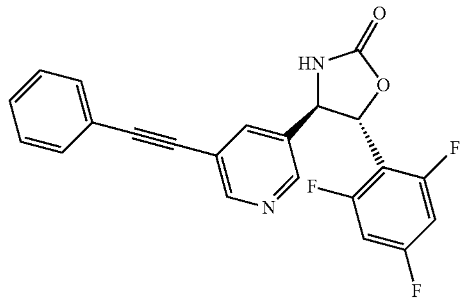 [SMILES: O=C1N[C@H](c2cncc(C#Cc3ccccc3)c2)[C@@H](c2c(F)cc(F)cc2F)O1] | $^1$H NMR (500 MHz, DMSO-$d_6$) δ 8.76 (d, J = 2.1 Hz, 1H), 8.63-8.47 (m, 2H), 8.11 (t, J = 2.0 Hz, 1H), 7.61 (dd, J = 6.6, 2.9 Hz, 2H), 7.52-7.43 (m, 3H), 7.36 (t, J = 9.2 Hz, 2H), 5.64 (d, J = 7.6 Hz, 1H), 5.14 (d, J = 7.6 Hz, 1H). MS Anal. Calcd. for [M + H]$^+$ $C_{22}H_{14}F_3N_2O_2$: 395.1; found 395.3. |
| Example 293 | 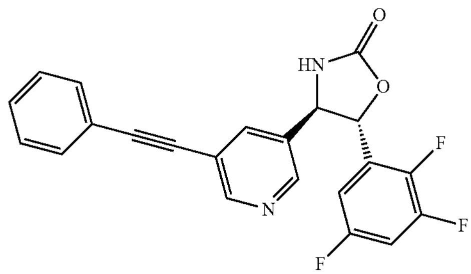 [SMILES: O=C1N[C@H](c2cncc(C#Cc3ccccc3)c2)[C@@H](c2cc(F)cc(F)c2F)O1] | $^1$H NMR (500 MHz, DMSO-$d_6$) δ 8.78 (d, J = 2.1 Hz, 1H), 8.67-8.54 (m, 2H), 8.08 (t, J = 2.0 Hz, 1H), 7.74-7.58 (m, 3H), 7.53-7.39 (m, 3H), 7.35-7.24 (m, 1H), 5.73 (d, J = 6.7 Hz, 1H), 5.08 (d, J = 6.7 Hz, 1H). MS Anal. Calcd. for [M + H]$^+$ $C_{22}H_{14}F_3N_2O_2$: 395.1; found 395.2. |
| Example 294 | 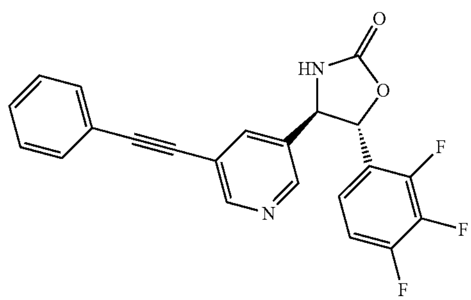 [SMILES: O=C1N[C@H](c2cncc(C#Cc3ccccc3)c2)[C@@H](c2ccc(F)c(F)c2F)O1] | $^1$H NMR (500 MHz, DMSO-$d_6$) δ 8.78 (d, J = 1.8 Hz, 1H), 8.65-8.50 (m, 2H), 8.06 (s, 1H), 7.62 (dd, J = 6.6, 2.9 Hz, 2H), 7.53-7.32 (m, 5H), 5.69 (d, J = 6.7 Hz, 1H), 5.08 (d, J = 6.4 Hz, 1H). MS Anal. Calcd. for [M + H]$^+$ $C_{22}H_{14}F_3N_2O_2$: 395.1; found 395.2. |
| Example 295 | 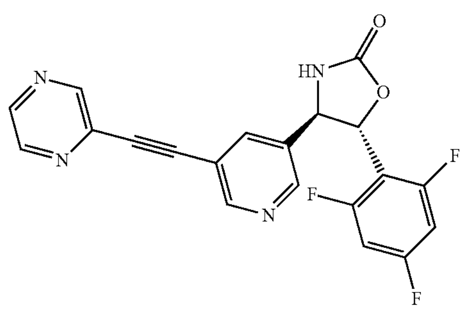 [SMILES: O=C1N[C@H](c2cncc(C#Cc3cnccn3)c2)[C@@H](c2c(F)cc(F)cc2F)O1] | $^1$H NMR (500 MHz, DMF) δ 9.38 (d, J = 0.9 Hz, 1H), 9.29 (d, J = 1.5 Hz, 1H), 9.20-9.05 (m, 3H), 8.65 (s, 1H), 7.79 (t, J = 9.2 Hz, 2H), 6.08 (d, J = 7.3 Hz, 1H), 5.60 (d, J = 7.6 Hz, 1H). MS Anal. Calcd. for [M + H]$^+$ $C_{20}H_{12}F_3N_4O_2$: 397.1; found 392.2. |
| Example 296 | 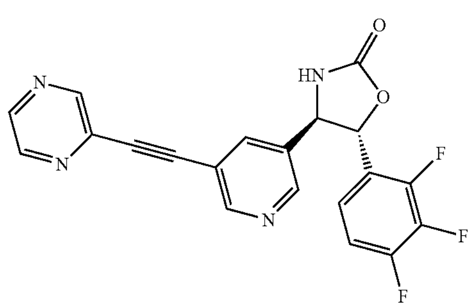 [SMILES: O=C1N[C@H](c2cncc(C#Cc3cnccn3)c2)[C@@H](c2ccc(F)c(F)c2F)O1] | $^1$H NMR (500 MHz, DMF) δ 9.39 (d, J = 1.5 Hz, 1H), 9.30 (d, J = 1.8 Hz, 1H), 9.20-9.05 (m, 3H), 8.60 (t, J = 1.8 Hz, 1H), 7.95-7.78 (m, 2H), 6.12 (d, J = 6.7 Hz, 1H), 5.53 (d, J = 6.7 Hz, 1H). MS Anal. Calcd. for [M + H]$^+$ $C_{20}H_{12}F_3N_4O_2$: 397.1; found 397.2. |

Example 297 and Example 298

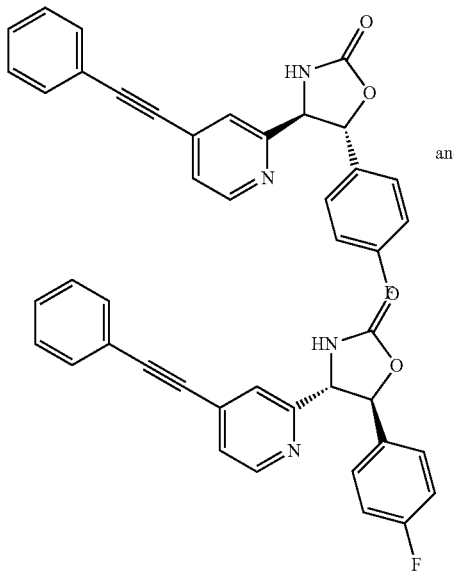

(4R,5R)-5-(4-Fluorophenyl)-4-(4-(phenylethynyl)pyridin-2-yl)oxazolidin-2-one and (4S,5S)-5-(4-fluorophenyl)-4-(4-(phenylethynyl)pyridin-2-yl)oxazolidin-2-one Prepared according to the same procedure as (4R,5R)-5-phenyl-4-(4-(phenylethynyl)pyridin-2-yl)oxazolidin-2-one and (4S,5S)-5-phenyl-4-(4-(phenylethynyl)pyridin-2-yl)oxazolidin-2-one, starting with (E)-4-bromo-2-(4-fluorostyryl)pyridine. $^1$H NMR (CDCl$_3$) δ: 8.64 (d, J=5.2 Hz, 1H), 7.58 (dd, J=7.8, 1.7 Hz, 2H), 7.53 (s, 1H), 7.35-7.49 (m, 6H), 7.13 (t, J=8.5 Hz, 2H), 6.66 (br. s., 1H), 5.59 (d, J=5.8 Hz, 1H), 4.92 (d, J=5.8 Hz, 1H). $^{13}$C NMR (CDCl$_3$) δ: 163.1, 159.0, 158.4, 150.3, 134.1, 133.2, 132.1, 129.6, 128.7, 127.8, 125.5, 122.6, 121.8, 116.1, 95.2, 86.4, 83.3, 65.0. Enantiomers were resolved by chiral Prep HPLC (Chiralpak AD, 40% EtOH/Heptane/0.1% DEA). Enantiomer 1=first enantiomer to elute from Prep (Example 297): Mass spec.: 359.3 (MH)$^+$. Enantiomer 2=second enantiomer to elute from Prep (Example 298): Mass spec.: 359.4 (MH)$^+$.

Example 299

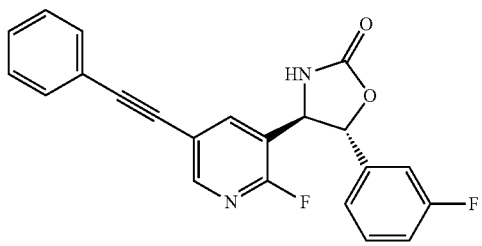 [SMILES: O=C1N[C@H](c2cc(C#Cc3ccccc3)cnc2F)[C@@H](c2cccc(F)c2)O1]

(4R,5R)-4-(2-Fluoro-5-(phenylethynyl)pyridin-3-yl)-5-(3-fluorophenyl)oxazolidin-2-one Prepared according to the same procedure as (+)-(4R,5R)-5-(3-methoxyphenyl)-4-(3-(phenylethynyl)phenyl)oxazolidin-2-one, starting with (4R,5R)-4-(5-bromo-2-fluoropyridin-3-yl)-5-(3-fluorophenyl)oxazolidin-2-one and phenylacetylene. $^1$H NMR (CDCl$_3$) δ: 8.39 (d, J=0.9 Hz, 1H), 8.11 (dd, J=9.0, 2.0 Hz, 1H), 7.56 (dd, J=7.8, 1.7 Hz, 2H), 7.35-7.46 (m, 4H), 7.07-7.22 (m, 3H), 6.77 (s, 1H), 5.37 (d, J=5.2 Hz, 1H), 5.04 (d, J=5.2 Hz, 1H). $^{19}$F NMR (CDCl$_3$) δ: −70.65 (d, J=13.0 Hz, 1F), −111.45 (br. s., 1F). $^{13}$C NMR (CDCl$_3$) δ: 163.2, 158.8, 159.6, 150.5, 140.8, 139.8, 131.8, 131.0, 129.3, 128.7, 122.0, 121.2, 121.2, 119.8, 116.6, 112.7, 93.8, 84.0, 83.6, 58.0. Mass spec.: 377.2 (MH)$^+$.

Example 300

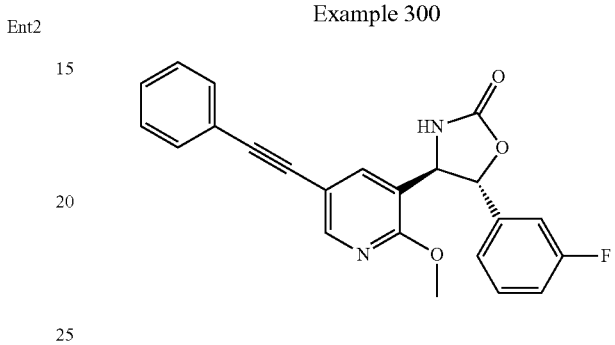

(4R,5R)-5-(3-Fluorophenyl)-4-(2-methoxy-5-(phenylethynyl)pyridin-3-yl)oxazolidin-2-one To a solution of (4R,5R)-4-(2-fluoro-5-(phenylethynyl)pyridin-3-yl)-5-(3-fluorophenyl)oxazolidin-2-one (10 mg, 0.027 mmol) in methanol (0.25 mL) at 0° C. was added a solution of potassium hydroxide (14.9 mg, 0.266 mmol) in methanol (0.25 mL, 6.18 mmol). After 1 h at 0° C., the reaction was allowed to stir at room temperature for 24 h. The reaction was quenched by addition of solid ammonium chloride (30 mg) and concentrated. The resulting residue was dissolved in dichloromethane, diluted with ethyl acetate, washed with brine, dried over magnesium sulfate, and concentrated. The product was purified by Prep HPLC (TFA/MeOH, sunfire column) and concentrated to give 7.7 mg (73%). $^1$H NMR (CDCl$_3$) δ: 8.38 (d, J=2.1 Hz, 1H), 7.84-7.88 (m, 1H), 7.53-7.58 (m, 2H), 7.43 (td, J=7.9, 5.8 Hz, 1H), 7.36-7.40 (m, 3H), 7.24 (dd, J=7.6, 0.6 Hz, 1H), 7.19 (dt, J=9.4, 2.0 Hz, 1H), 7.09-7.15 (m, 1H), 5.90 (s, 1H), 5.37 (d, J=4.3 Hz, 1H), 4.98 (d, J=4.3 Hz, 1H), 4.00 (s, 3H). $^{13}$C NMR (CDCl$_3$) δ: 163.1, 160.1, 158.8, 150.1, 141.1, 137.8, 131.7, 130.7, 128.7, 128.6, 122.7, 121.4, 121.1, 121.1, 116.0, 114.1, 112.8, 91.8, 85.4, 83.1, 58.6, 54.1. Mass spec.: 389.2 (MH)$^+$.

Example 301

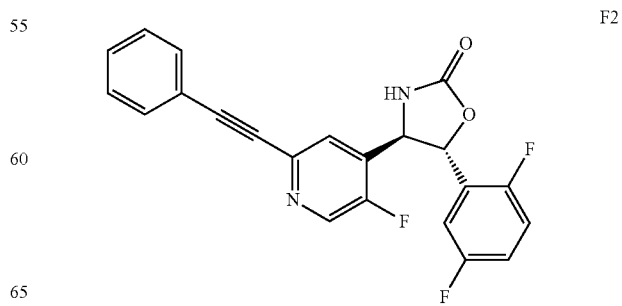

(4R,5R)-5-(2,5-Difluorophenyl)-4-(5-fluoro-2-(phenylethynyl)pyridin-4-yl)oxazolidin-2-one In a 1 mL scint vial, a suspension of optically-enriched (4R,5R)-4-(2-bromo-5-fluoropyridin-4-yl)-5-(2,5-difluorophenyl)oxazolidin-2-one (20 mg, 0.054 mmol), and ethynylbenzene (0.014 mL, 0.129 mmol) in triethyl amine (1.5 mL) was purged with nitrogen for 30 min. Triphenylphosphine (3.7 mg, 0.014 mmol) was added and the suspension stirred for 5 min. To this was added copper (I) iodide (0.408 mg, 2.144 µmol), and bis(triphenylphosphine)palladium(II) chloride (1.8 mg, 2.6 µmol). The vial was purged with nitrogen for an additional 5 min, capped, and immersed in a 90° C. bath for 5 h. The reaction was cooled to room temperature and concentrated. The resulting residue was dissolved in dichloromethane and poured into water. The mixture was diluted with ethyl acetate, washed with water, brine, dried over magnesium sulfate, and concentrated. The material was purified first by reversed phase HPLC (TFA/MeOH/sunfire column) to give an optically enriched mixture of regioisomers. The material was further purified by chiral prep HPLC (Chiralpak AD, A=heptane/0.1% DEA, B=ethanol, 40%→60% over 35 min) to give the title compound (3.4 mg). $^1$H NMR (CDCl$_3$) δ: 8.52 (d, J=0.9 Hz, 1H), 7.75 (d, J=5.8 Hz, 1H), 7.63 (dd, J=7.3, 2.1 Hz, 2H), 7.38-7.44 (m, 3H), 7.23-7.27 (m, 1H), 7.11-7.17 (m, 2H), 5.79 (br. s., 1H), 5.64 (d, J=5.5 Hz, 1H), 5.08 (d, J=5.5 Hz, 1H). $^1$H NMR (CDCl$_3$) δ: 8.51 (d, J=0.9 Hz, 1H), 7.73 (d, J=5.5 Hz, 1H), 7.63 (dd, J=7.6, 1.8 Hz, 2H), 7.39-7.46 (m, 3H), 7.23-7.27 (m, 1H), 7.10-7.16 (m, 2H), 5.95 (br. s., 1H), 5.61 (d, J=5.5 Hz, 1H), 5.13 (d, J=5.8 Hz, 1H). Mass spec.: 395.2 (MH)$^+$.

Example 302

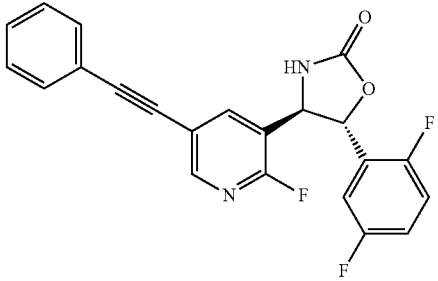 [SMILES: O=C1N[C@H](c2cc(C#Cc3ccccc3)cnc2F)[C@@H](c2cc(F)ccc2F)O1]

((4R,5R)-5-(2,5-Difluorophenyl)-4-(2-fluoro-5-(phenylethynyl)pyridin-3-yl)oxazolidin-2-one Prepared according to the same procedure as (+)-(4R,5R)-5-(3-methoxyphenyl)-4-(3-(phenylethynyl)phenyl)oxazolidin-2-one, starting with (4R,5R)-4-(5-bromo-2-fluoropyridin-3-yl)-5-(2,5-difluorophenyl)oxazolidin-2-one and phenylacetylene. $^1$H NMR (CDCl$_3$) δ: 8.37 (d, J=1.2 Hz, 1H), 8.11 (dd, J=8.9, 2.1 Hz, 1H), 7.56 (dd, J=7.6, 1.8 Hz, 2H), 7.35-7.42 (m, 3H), 7.21-7.26 (m, 1H), 7.07-7.14 (m, 2H), 6.99 (s, 1H), 5.57 (d, J=5.8 Hz, 1H), 5.07 (d, J=5.8 Hz, 1H). $^{19}$F NMR (CDCl$_3$) δ: −71.32 (br. s., 1F), −117.12 (br. s., 1F), −123.54 (d, J=8.7 Hz, 1F). Mass spec.: 395.1 (MH)$^+$.

Example 303

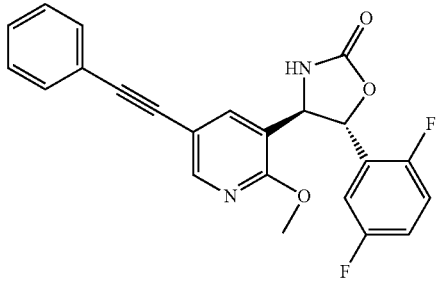 [SMILES: COc1ncc(C#Cc2ccccc2)cc1[C@H]1NC(=O)O[C@@H]1c1cc(F)ccc1F]

(4R,5R)-5-(2,5-Difluorophenyl)-4-(2-methoxy-5-(phenylethynyl)pyridin-3-yl)oxazolidin-2-one Prepared according to the same procedure as (4R,5R)-5-(3-fluorophenyl)-4-(2-methoxy-5-(phenylethynyl)pyridin-3-yl)oxazolidin-2-one, starting with ((4R,5R)-5-(2,5-difluorophenyl)-4-(2-fluoro-5-(phenylethynyl)pyridin-3-yl)oxazolidin-2-one. $^1$H NMR (CDCl$_3$) δ: 8.33 (d, J=2.1 Hz, 1H), 7.83 (d, J=1.8 Hz, 1H), 7.50-7.54 (m, 2H), 7.33-7.38 (m, 3H), 7.20-7.25 (m, 1H), 7.03-7.10 (m, 2H), 6.06 (s, 1H), 5.54 (d, J=5.2 Hz, 1H), 4.98 (d, J=5.2 Hz, 1H), 3.88 (s, 3H). $^{19}$F NMR (CDCl$_3$) δ: −119.97-115.26 (m, 1F), −123.84 (br. s., 1F). Mass spec.: 407.1 (MH)$^+$.

Example 304

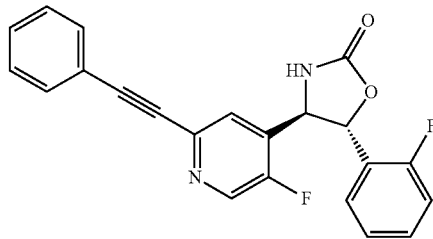

(4R,5R)-4-(5-Fluoro-2-(phenylethynyl)pyridin-4-yl)-5-(2-fluorophenyl)oxazolidin-2-one A suspension of optically-enriched (4R,5R)-4-(2-bromo-5-fluoropyridin-4-yl)-5-(2-fluorophenyl)oxazolidin-2-one (38 mg, 0.107 mmol) in triethylamine (1.1 mL, 8.03 mmol) was degassed by bubbling with nitrogen for 30 min. To this was added ethynylbenzene (15 µl, 0.134 mmol) and triphenylphosphine (3.7 mg, 0.014 mmol). After bubbling 5 min longer, the reaction was treated with copper(I) iodide (0.408 mg, 2.14 µmol) and bis(triphenylphosphine)palladium(II) chloride (1.8 mg, 2.6 µmol), bubbled briefly with nitrogen, sealed, and heated at 90° C. for 5 h. The reaction was concentrated, dissolved in a minimum of dichloromethane, diluted with ethyl acetate, washed with brine, dried over magnesium sulfate, and concentrated. Column chromatography (25%→50% EtOAc/Hex) gave a mixture of the two regioisomers. This material was further purified by chiral prep HPLC (Chiralcel OD, 40% EtOH/heptane/0.1% DEA) to give 9.6 mg (23%). $^1$H NMR (CDCl$_3$) δ: 8.49 (d, J=1.2 Hz, 1H), 7.76 (d, J=5.8 Hz, 1H), 7.58-7.67 (m, 2H), 7.51 (td, J=7.5, 1.5 Hz, 1H), 7.35-7.48 (m, 4H), 7.23-7.28 (m, 1H), 7.16 (ddd, J=9.8, 8.9, 0.8 Hz, 1H), 6.28 (br. s., 1H), 5.62 (d, J=5.8 Hz, 1H), 5.17 (d, J=5.8 Hz, 1H). $^{13}$C NMR (CDCl$_3$) δ: 160.1, 158.4, 156.2, 140.8, 139.2, 135.3, 132.2, 131.4, 129.5, 128.6, 127.5, 125.2, 124.9, 124.5, 121.8, 116.2, 90.2, 87.3, 79.3, 56.6. $^{19}$F NMR (CDCl$_3$) δ: −117.69 (d, J=8.7 Hz, 1F), −132.34 (d, J=8.7 Hz, 1F). Mass spec.: 377.2 (MH)$^+$.

Example 305 and Example 306

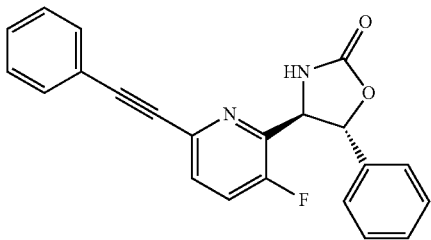

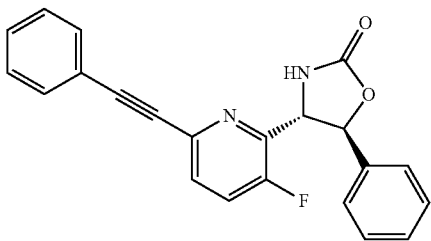

(4R,5R)-4-(3-Fluoro-6-(phenylethynyl)pyridin-2-yl)-5-phenyloxazolidin-2-one and (4S,5S)-4-(3-fluoro-6-(phenylethynyl)pyridin-2-yl)-5-phenyloxazolidin-2-one A suspension of optically-enriched (4R,5R)-4-(6-bromo-3-fluoropyridin-2-yl)-5-phenyloxazolidin-2-one (96 mg, 0.285 mmol) in triethylamine (3.0 mL, 21.4 mmol) was degassed by bubbling with nitrogen for 30 min. To this was added ethynylbenzene (39 μl, 0.36 mmol) and triphenylphosphine (9.7 mg, 0.037 mmol). After bubbling 5 min longer, the reaction was treated with copper(I) iodide (1.1 mg, 5.7 μmol) and bis(triphenylphosphine)palladium(II) chloride (4.8 mg, 6.8 μmol), bubbled briefly with nitrogen, sealed, and heated at 90° C. for 5 h. The reaction was concentrated, dissolved in a minimum of dichloromethane, diluted with ethyl acetate, washed with brine, dried over magnesium sulfate, and concentrated. Column chromatography (25%→50% EtOAc/Hex) gave the racemate. $^1$H NMR (CDCl$_3$) δ: 7.58-7.69 (m, 3H), 7.34-7.51 (m, 9H), 5.92 (br. s., 1H), 5.62-5.69 (m, 2H). $^{13}$C NMR (CDCl$_3$) δ: 158.2, 157.6, 143.5, 143.4, 139.6, 139.0, 132.2, 129.8, 129.4, 129.0, 128.6, 126.5, 124.5, 121.9, 89.8, 87.5, 80.5, 59.2. $^{19}$F NMR (CDCl$_3$) δ: −124.54 (br. s., 1F). Enantiomers were resolved by Prep HPLC (Chiralcel OD, 13% EtOH/Heptane/0.1% DEA). Enantiomer 1=first enantiomer to elute from Prep (Example 305): Mass spec.: 359.2 (MH)$^+$. Enantiomer 2=second enantiomer to elute from Prep (Example 306): Mass spec.: 359.2 (MH)$^+$.

Example 307 and Example 308

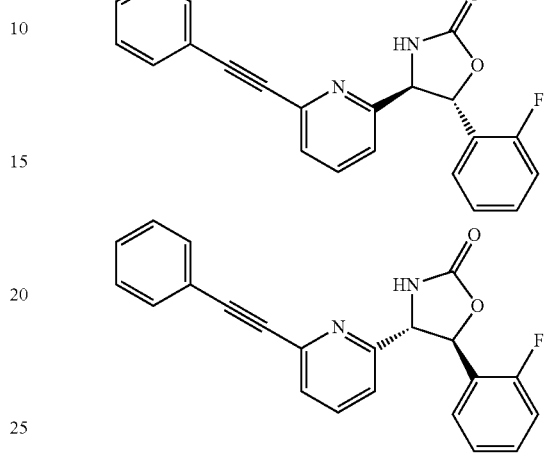

(4R,5R)-5-(2-Fluorophenyl)-4-(6-(phenylethynyl)pyridin-2-yl)oxazolidin-2-one and (4S,5S)-5-(2-fluorophenyl)-4-(6-(phenylethynyl)pyridin-2-yl)oxazolidin-2-one Prepared according to the same procedure as (+)-(4R,5R)-5-(3-methoxyphenyl)-4-(3-(phenylethynyl)phenyl)oxazolidin-2-one, starting with optically-enriched (4R,5R)-4-(6-bromopyridin-2-yl)-5-(2-fluorophenyl)oxazolidin-2-one and phenylacetylene. $^1$H NMR (CDCl$_3$) δ: 7.77 (t, J=7.8 Hz, 1H), 7.61 (dd, J=7.3, 1.8 Hz, 2H), 7.47-7.57 (m, 2H), 7.33-7.46 (m, 5H), 7.20-7.28 (m, 1H), 7.06-7.17 (m, 1H), 6.75 (s, 1H), 5.84 (d, J=5.2 Hz, 1H), 5.00 (d, J=5.2 Hz, 1H). $^{13}$C NMR (CDCl$_3$) δ: 160.2, 159.1, 158.8, 143.7, 137.7, 132.2, 130.9, 129.3, 128.5, 127.8, 127.3, 125.6, 124.8, 122.1, 120.1, 116.0, 90.1, 88.4, 79.0, 64.1. $^{19}$F NMR (CDCl$_3$) δ: −117.43 (br. s., 1F). Enantiomers were resolved by Prep HPLC (Chiralcel OD, 37% EtOH/Heptane/0.1% DEA). Enantiomer 1=first enantiomer to elute from Prep (Example 307): Mass spec.: 359.3 (MH)$^+$. Enantiomer 2=second enantiomer to elute from Prep (Example 308): Mass spec.: 360.2 (MH)$^+$.

Example 309 and Example 310

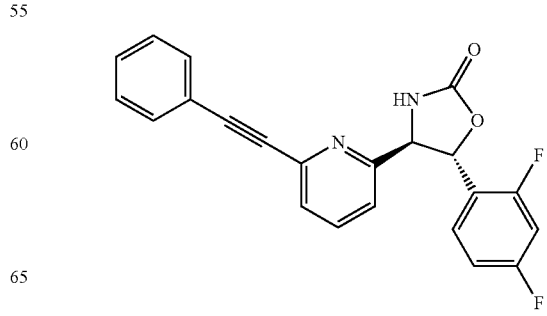

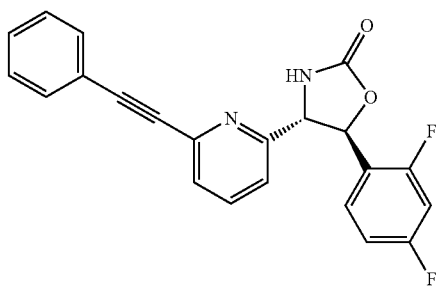

(4R,5R)-5-(2,4-Difluorophenyl)-4-(6-(phenylethynyl)pyridin-2-yl)oxazolidin-2-one and (4S,5S)-5-(2,4-difluorophenyl)-4-(6-(phenylethynyl)pyridin-2-yl)oxazolidin-2-one Prepared according to the same procedure as (4R,5R)-5-(2-fluorophenyl)-4-(6-(phenylethynyl)pyridin-2-yl)oxazolidin-2-one and (4S,5S)-5-(2-fluorophenyl)-4-(6-(phenylethynyl)pyridin-2-yl)oxazolidin-2-one, starting with diethyl (6-bromopyridin-2-yl)methylphosphonate and 2,4-difluorobenzaldehyde. $^1$H NMR (CDCl$_3$) δ: 7.79 (t, J=7.8 Hz, 1H), 7.61 (dd, J=7.3, 1.8 Hz, 2H), 7.48-7.57 (m, 2H), 7.37-7.44 (m, 4H), 6.98 (td, J=8.2, 1.8 Hz, 1H), 6.89 (ddd, J=10.5, 8.5, 2.3 Hz, 1H), 6.52 (br. s., 1H), 5.79 (d, J=5.5 Hz, 1H), 4.99 (d, J=5.5 Hz, 1H). $^{13}$C NMR (CDCl$_3$) δ: 163.5, 160.4, 158.7, 158.5, 143.8, 137.7, 132.2, 129.4, 129.0, 128.5, 127.4, 122.0, 121.6, 119.9, 112.1, 104.6, 90.2, 88.3, 78.7, 64.0. $^{19}$F NMR (CDCl$_3$) δ: −108.67 (d, J=8.7 Hz, 1F), −113.26 (br. s., 1F). Enantiomers were resolved by Prep HPLC (Chiralcel OD, 38% EtOH/Heptane/0.1% DEA). Enantiomer 1=first enantiomer to elute from Prep (Example 309): Mass spec.: 377.2 (MH)$^+$. Enantiomer 2=second enantiomer to elute from Prep (Example 310): Mass spec.: 377.2 (MH)$^+$.

Example 311 and Example 312

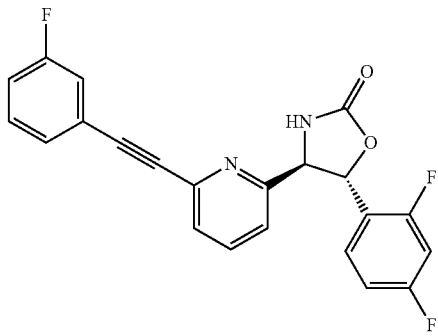

(4R,5R)-5-(2,4-Difluorophenyl)-4-(6-((3-fluorophenyl)ethynyl)pyridin-2-yl)oxazolidin-2-one and (4S,5S)-5-(2,4-difluorophenyl)-4-(6-((3-fluorophenyl)ethynyl)pyridin-2-yl)oxazolidin-2-one Prepared according to the same procedure as (4R,5R)-5-(2-fluorophenyl)-4-(6-(phenylethynyl)pyridin-2-yl)oxazolidin-2-one and (4S,5S)-5-(2-fluorophenyl)-4-(6-(phenylethynyl)pyridin-2-yl)oxazolidin-2-one, starting with diethyl (6-bromopyridin-2-yl)methylphosphonate, 2,4-difluorobenzaldehyde, and 3-fluorophenylacetylene. $^1$H NMR (CDCl$_3$) δ: 7.82 (t, J=7.8 Hz, 1H), 7.50-7.59 (m, 2H), 7.30-7.46 (m, 4H), 7.09-7.16 (m, 1H), 6.97-7.03 (m, 1H), 6.90 (ddd, J=10.6, 8.6, 2.4 Hz, 1H), 6.16 (s, 1H), 5.79 (d, J=5.5 Hz, 1H), 4.98 (d, J=5.5 Hz, 1H). $^{19}$F NMR (CDCl$_3$) δ: −108.57 (t, J=8.7 Hz, 1F), −112.91 (q, J=8.7 Hz, 1F), −113.52-113.23 (m, 1F). Enantiomers were resolved by Prep HPLC (Chiralcel OJ, 30% EtOH/Heptane/0.1% DEA). Enantiomer 1=first enantiomer to elute from Prep (Example 311): Mass spec.: 395.2 (MH)$^+$. Enantiomer 2=second enantiomer to elute from Prep (Example 312): Mass spec.: 395.3 (MH)$^+$.

Example 313 and Example 314

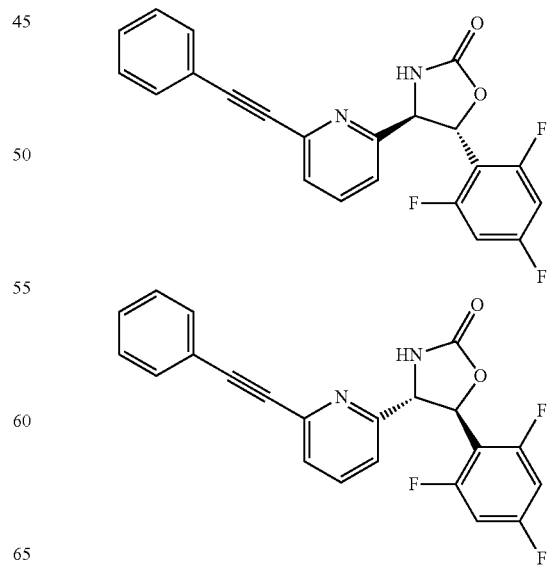

(4R,5R)-4-(6-(Phenylethynyl)pyridin-2-yl)-5-(2,4,6-trifluorophenyl)oxazolidin-2-one and (4S,5S)-4-(6-(phenylethynyl)pyridin-2-yl)-5-(2,4,6-trifluorophenyl)oxazolidin-2-one Prepared according to the same procedure as (4R,5R)-5-(2-fluorophenyl)-4-(6-(phenylethynyl)pyridin-2-yl)oxazolidin-2-one and (4S,5S)-5-(2-fluorophenyl)-4-(6-(phenylethynyl)pyridin-2-yl)oxazolidin-2-one, starting with diethyl (6-bromopyridin-2-yl)methylphosphonate and 2,4,6-trifluorobenzaldehyde. $^1$H NMR (CDCl$_3$) δ: 7.81 (t, J=7.8 Hz, 1H), 7.57-7.65 (m, 2H), 7.54 (d, J=7.9 Hz, 1H), 7.34-7.48 (m, 4H), 6.77 (t, J=8.4 Hz, 2H), 6.69 (br. s., 1H), 5.84 (d, J=6.7 Hz, 1H), 5.21 (d, J=6.7 Hz, 1H). $^{19}$F NMR (CDCl$_3$) δ: −104.95 (br. s., 1F), −113.52-109.06 (m, 2F). Enantiomers were resolved by Prep HPLC (Chiralcel OJ, 42% EtOH/Heptane/0.1% DEA). Enantiomer 1=first enantiomer to elute from Prep (Example 313): Mass spec.: 395.2 (MH)$^+$. Enantiomer 2=second enantiomer to elute from Prep (Example 314): Mass spec.: 396.2 (MH)$^+$.

Example 315 and Example 316

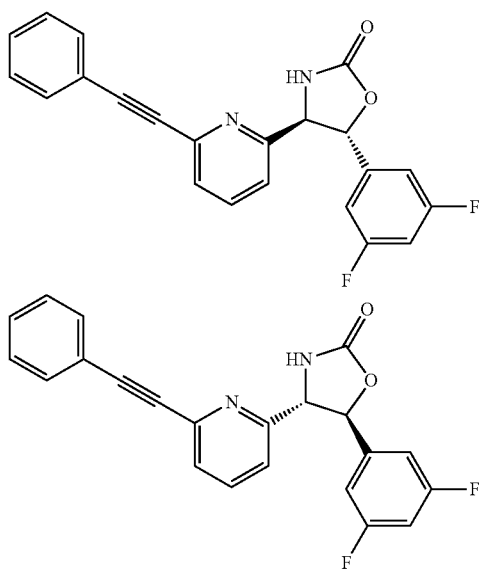

(4R,5R)-5-(3,5-Difluorophenyl)-4-(6-(phenylethynyl)pyridin-2-yl)oxazolidin-2-one and (4S,5S)-5-(3,5-difluorophenyl)-4-(6-(phenylethynyl)pyridin-2-yl)oxazolidin-2-one Prepared according to the same procedure as (4R,5R)-5-(2-fluorophenyl)-4-(6-(phenylethynyl)pyridin-2-yl)oxazolidin-2-one and (4S,5S)-5-(2-fluorophenyl)-4-(6-(phenylethynyl)pyridin-2-yl)oxazolidin-2-one, starting with diethyl (6-bromopyridin-2-yl)methylphosphonate and 3,5-difluorobenzaldehyde. $^1$H NMR (CDCl$_3$) δ: 7.81 (t, J=7.9 Hz, 1H), 7.60-7.68 (m, 2H), 7.56 (d, J=7.9 Hz, 1H), 7.36-7.47 (m, 4H), 7.05-7.13 (m, 2H), 7.03 (s, 1H), 6.84 (tt, J=8.7, 2.3 Hz, 1H), 5.68 (d, J=5.5 Hz, 1H), 4.94 (d, J=5.5 Hz, 1H). $^{13}$C NMR (CDCl$_3$) δ: 163.4, 158.8, 158.4, 144.0, 142.4, 137.9, 132.2, 129.4, 128.6, 127.3, 121.9, 119.7, 108.8, 108.8, 104.4, 90.4, 88.2, 82.2, 64.6. $^{19}$F NMR (CDCl$_3$) δ: −108.32 (d, J=8.7 Hz, 1F). Enantiomers were resolved by Prep HPLC (Chiralpak AD, 40% EtOH/Heptane/0.1% DEA). Enantiomer 1=first enantiomer to elute from Prep (Example 315): Mass spec.: 377.2 (MH)$^+$. Enantiomer 2=second enantiomer to elute from Prep (Example 316): Mass spec.: 377.2 (MH)$^+$.

Example 317 and Example 318 and Example 319 and Example 320

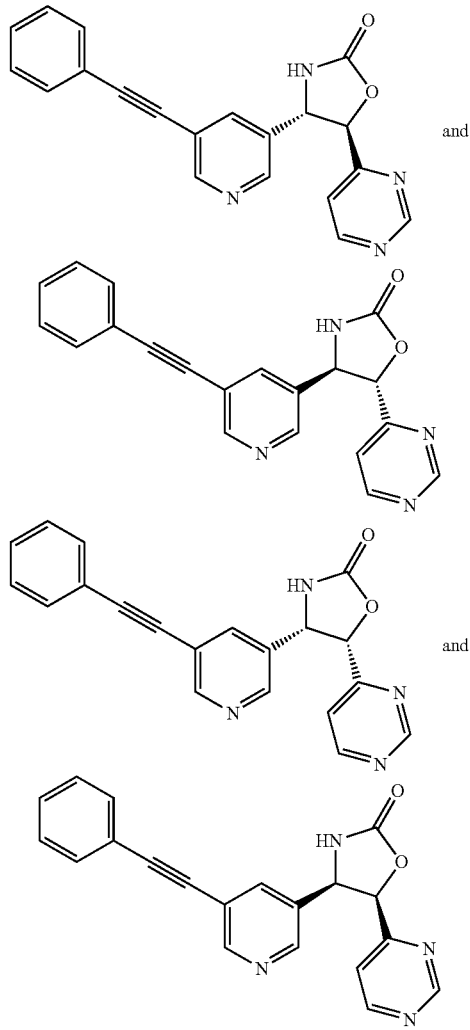

(4S,5R)-4-(5-(Phenylethynyl)pyridin-3-yl)-5-(pyrimidin-4-yl)oxazolidin-2-one and (4R,5S)-4-(5-(phenylethynyl)pyridin-3-yl)-5-(pyrimidin-4-yl)oxazolidin-2-one and (4S,5S)-4-(5-(phenylethynyl)pyridin-3-yl)-5-(pyrimidin-4-yl)oxazolidin-2-one and (4R,5R)-4-(5-(phenylethynyl)pyridin-3-yl)-5-(pyrimidin-4-yl)oxazolidin-2-one A flask was charged with N-(diphenylmethylene)-1-(5-(phenylethynyl)pyridin-3-yl)methanamine (0.21 g/mL in toluene, 1.5 mL, 0.85 mmol) and concentrated. The residue was dissolved in tetrahydrofuran (5.5 mL), and cooled to −78° C. To this was added t-BuLi (1.7M in pentane, 0.60 mL, 1.02 mmol) dropwise. After 20 min, the resulting solution was treated with pyrimidine-4-carbaldehyde (91 mg, 0.85 mmol). After stirring at −78° C. for 10 min, the reaction was allowed to gradually warm to room temperature in the bath. The reaction was diluted with ether, quenched by addition of water, and warmed to room temperature with stirring. The layers were separated. The organics were washed with brine and concentrated to give a gummy solid. The crude product was dissolved in methanol (6 mL) and treated with methoxyamine hydrochloride (212 mg, 2.54 mmol). The reaction was stirred at room temperature overnight. The reaction was concentrated, dissolved in methanol, and loaded on a medium cation exchange cartridge (6 g cartridge). The cartridge was flushed with several volumes of methanol which were discarded. The product was eluted with 2M ammonia in methanol and concentrated to afford 277 mg as an orange gum. The crude amino alcohol was dissolved in tetrahydrofuran (5 mL), cooled to 0° C., and treated with carbonyldiimidazole (149 mg, 0.919 mmol). The ice bath was removed and stirring continued overnight. The material was purified by prep HPLC (Sunfire Column, TFA/MeOH) to isolate the two major fractions (F1=first to elute, F2=second to elute). F1(trans): $^1$H NMR (CDCl$_3$) d: 9.29 (d, J=1.4 Hz, 1H), 8.87 (d, J=5.2 Hz, 1H), 8.78 (d, J=1.7 Hz, 1H), 8.70 (d, J=1.8 Hz, 1H), 8.03 (t, J=1.9 Hz, 1H), 7.63 (dd, J=5.0, 0.5 Hz, 1H), 7.54-7.61 (m, 2H), 7.37-7.43 (m, 3H), 6.50 (br. s., 1H), 5.41 (d, J=5.2 Hz, 1H), 5.23 (d, J=5.2 Hz, 1H). $^{13}$C NMR (CDCl$_3$) d: 165.3, 158.9, 158.4, 157.7, 152.6, 146.9, 136.3, 134.7, 131.8, 129.2, 128.6, 122.1, 121.2, 117.6, 94.0, 85.2, 82.8, 58.9. Enantiomers of F1 were resolved by Prep HPLC (Chiralpak AD, 78% EtOH/Heptane/0.1% DEA). Enantiomer 1=first enantiomer to elute from Prep (Example 317): Mass spec.: 343.3 (MH)$^+$. Enantiomer 2=second enantiomer to elute from Prep (Example 318): Mass spec.: 343.3 (MH)$^+$. F2(cis): $^1$H NMR (CDCl$_3$) d: 9.28 (d, J=1.2 Hz, 1H), 8.86 (d, J=5.2 Hz, 1H), 8.77 (d, J=0.9 Hz, 1H), 8.69 (s, 1H), 8.02 (t, J=1.8 Hz, 1H), 7.62 (d, J=5.0 Hz, 1H), 7.53-7.59 (m, 2H), 7.35-7.43 (m, 3H), 6.79 (br. s., 1H), 5.40 (d, J=5.2 Hz, 1H), 5.22 (d, J=5.2 Hz, 1H). $^{13}$C NMR (CDCl$_3$) d: 165.4, 158.9, 158.4, 157.8, 152.5, 146.8, 136.3, 134.8, 131.8, 129.2, 128.6, 122.1, 121.2, 117.6, 93.9, 85.2, 82.8, 58.9. Enantiomers of F2 were resolved by Prep HPLC (Chiralpak AD, 78% EtOH/Heptane/0.1% DEA). Enantiomer 1=first enantiomer to elute from Prep (Example 319): Mass spec.: 343.3 (MH)$^+$. Enantiomer 2=second enantiomer to elute from Prep (Example 320): Mass spec.: 343.3 (MH)$^+$.

Example 321 and Example 322 and Example 323 and Example 324

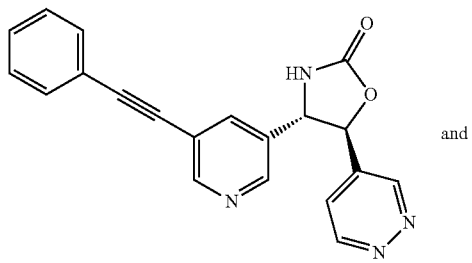

and

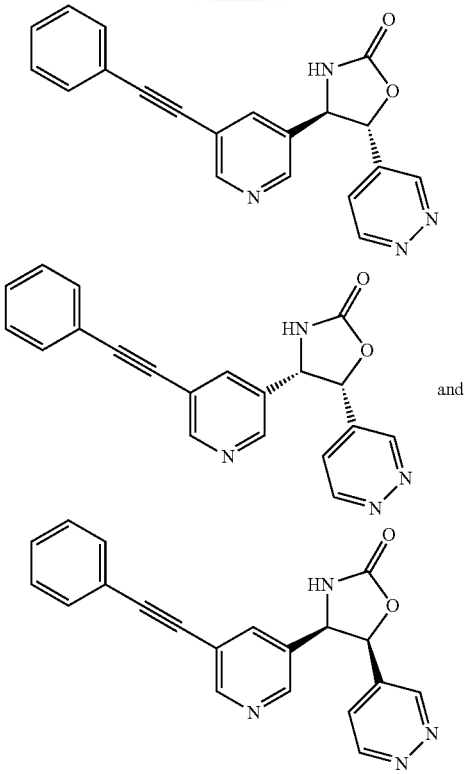

(4S,5S)-4-(5-(Phenylethynyl)pyridin-3-yl)-5-(pyridazin-4-yl)oxazolidin-2-one and (4R,5R)-4-(5-(phenylethynyl)pyridin-3-yl)-5-(pyridazin-4-yl)oxazolidin-2-one and (4S,5R)-4-(5-(phenylethynyl)pyridin-3-yl)-5-(pyridazin-4-yl)oxazolidin-2-one and (4R,5S)-4-(5-(phenylethynyl)pyridin-3-yl)-5-(pyridazin-4-yl)oxazolidin-2-one Prepared according to the same procedure as (4R,5R)-4-(5-phenylethynyl)pyridin-3-yl)-5-(pyrimidin-4-yl)oxazolidin-2-one and (4R,5S)-4-(5-(phenylethynyl)pyridin-3-yl)-5-(pyrimidin-4-yl)oxazolidin-2-one and (4S,5R)-4-(5-(phenylethynyl)pyridin-3-yl)-5-(pyrimidin-4-yl)oxazolidin-2-one and (4S,5S)-4-(5-(phenylethynyl)pyridin-3-yl)-5-(pyrimidin-4-yl)oxazolidin-2-one using pyridazine-4-carbaldehyde. F1 (trans): $^1$H NMR (CDCl$_3$) d: 9.33 (dd, J=5.3, 1.1 Hz, 1H), 9.18 (d, J=1.1 Hz, 1H), 8.86 (d, J=1.8 Hz, 1H), 8.53 (d, J=2.1 Hz, 1H), 7.94 (t, J=2.0 Hz, 1H), 7.56-7.61 (m, 2H), 7.52 (dt, J=5.3, 1.2 Hz, 1H), 7.39-7.45 (m, 3H), 5.89 (br. s., 1H), 5.43 (d, J=7.0 Hz, 1H), 4.80 (d, J=7.0 Hz, 1H). $^{13}$C NMR (CDCl$_3$) d: 156.7, 153.6, 151.6, 148.3, 146.7, 136.3, 136.3, 132.5, 131.8, 129.4, 128.6, 122.6, 121.8, 121.8, 94.7, 84.7, 81.4, 61.5. Enantiomers of F1 were resolved by Prep HPLC (Chiralpak AD, 78% EtOH/Heptane/0.1% DEA). Enantiomer 1=first enantiomer to elute from Prep (Example 321): Mass spec.: 343.3 (MH)$^+$. Enantiomer 2=second enantiomer to elute from Prep (Example 322): Mass spec.: 343.3 (MH)$^+$. F2: $^1$H NMR (CDCl$_3$) d: 9.30 (dd, J=5.3, 1.1 Hz, 1H), 9.17 (d, J=0.9 Hz, 1H), 8.84 (d, J=1.8 Hz, 1H), 8.52 (d, J=2.0 Hz, 1H), 7.93 (t, J=2.0 Hz, 1H), 7.54-7.62 (m, 2H), 7.48-7.54 (m, 1H), 7.36-7.45 (m, 3H), 6.47 (br. s., 1H), 5.42 (d, J=7.0 Hz, 1H), 4.82 (d, J=7.0 Hz, 1H). $^{13}$C NMR (CDCl$_3$) d: 157.1, 153.4, 151.5, 148.4, 146.7, 136.4, 136.4, 132.7, 131.8, 129.4, 128.6, 122.7, 121.8, 121.7, 94.7, 84.7, 81.4, 61.5. Enantiomers of F2 were resolved by Prep HPLC (Chiralpak AD, 70% EtOH/Heptane/0.1% DEA). Enantiomer 1=first enantiomer to elute from Prep (Example 323): Mass spec.: 343.3 (MH)⁺. Enantiomer 2=second enantiomer to elute from Prep (Example 324): Mass spec.: 343.3 (MH)⁺.

Example 325 and Example 326 and Example 327 and Example 328

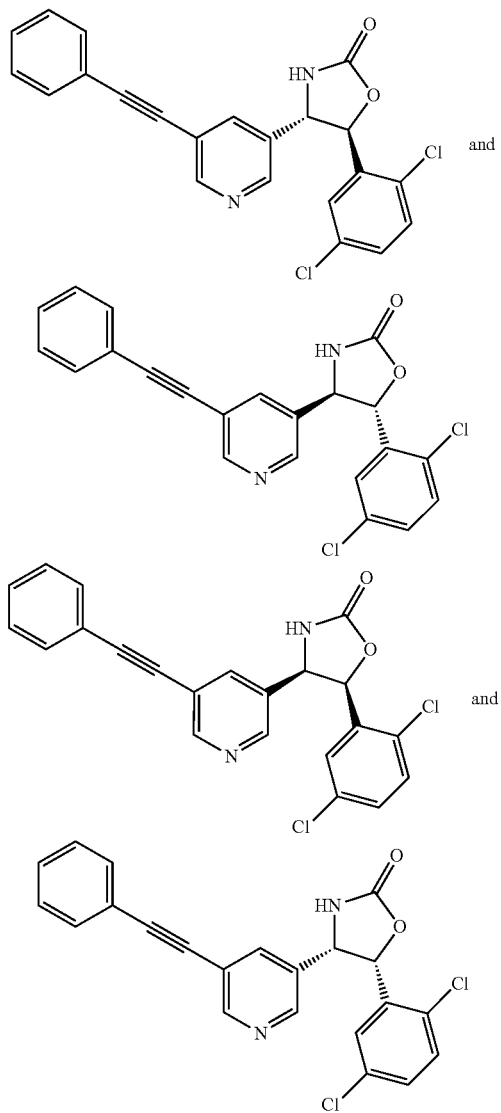

(4S,5S)-5-(2,5-Dichlorophenyl)-4-(5-(phenylethynyl)pyridin-3-yl)oxazolidin-2-one and (4R,5R)-5-(2,5-dichlorophenyl)-4-(5-(phenylethynyl)pyridin-3-yl)oxazolidin-2-one, (4R,5S)-5-(2,5-dichlorophenyl)-4-(5-(phenylethynyl)pyridin-3-yl)oxazolidin-2-one and (4S,5R)-5-(2,5-dichlorophenyl)-4-(5-(phenylethynyl)pyridin-3-yl)oxazolidin-2-one Prepared according to the same procedure as (4R,5R)-4-(5-(phenylethynyl)pyridin-3-yl)-5-(pyrimidin-4-yl)oxazolidin-2-one and (4R,5S)-4-(5-(phenylethynyl)pyridin-3-yl)-5-(pyrimidin-4-yl)oxazolidin-2-one and (4S,5R)-4-(5-(phenylethynyl)pyridin-3-yl)-5-(pyrimidin-4-yl)oxazolidin-2-one and (4S,5S)-4-(5-(phenylethynyl)pyridin-3-yl)-5-(pyrimidin-4-yl)oxazolidin-2-one using 2,5-dichlorobenzaldehyde. The material was purified by Biotage (35-45% EtOAc/Hex) to isolate the two major fractions (F1=first to elute, F2=second to elute). F1(trans): ¹H NMR (CDCl₃, 400 MHz) δ: 8.72 (d, J=1.8 Hz, 1H), 8.49 (d, J=2.0 Hz, 1H), 7.94 (t, J=2.0 Hz, 1H), 7.52-7.56 (m, 3H), 7.45 (s, 1H), 7.37 (d, J=1.8 Hz, 1H), 7.36 (d, J=2.0 Hz, 1H), 7.31 (dd, J=3.0, 1.3 Hz, 2H), 5.66 (d, J=4.5 Hz, 1H), 5.01-5.20 (m, 1H), 4.72 (d, J=4.5 Hz, 1H). ¹³C-NMR (CDCl₃, 101 MHz) δ: 158.2, 157.5, 152.2, 146.5, 136.8, 135.9, 134.4, 133.5, 131.4, 130.8, 130.0, 129.9, 129.3, 128.8, 128.1, 126.6, 121.7, 120.8, 93.5, 84.8, 80.8, 60.8. Mass spec.: 409.1 (MH)⁺. Enantiomers were resolved by Prep HPLC (Chiralpak AD 21×250 mm, 10 um, 50% B isocratic, flow rate: 15 mL/min, UV 220, 25 min run, solvent A: 0.1% diethylamine/heptane, solvent B: ethanol). Enantiomer 1=first enantiomer to elute from Prep (Example 325). Enantiomer 2=second enantiomer to elute from Prep (Example 326). F2(cis): ¹H NMR (CDCl₃, 400 MHz) δ: 8.53 (d, J=1.8 Hz, 1H), 8.26 (d, J=2.0 Hz, 1H), 7.56 (td, J=4.6, 2.9 Hz, 3H), 7.37-7.43 (m, 4H), 7.11-7.14 (m, 2H), 6.26 (d, J=8.0 Hz, 1H), 6.09 (br. s., 1H), 5.44 (d, J=8.3 Hz, 1H). ¹³C-NMR (CDCl₃, 101 MHz) δ: 157.5, 152.0, 146.6, 136.2, 133.7, 133.3, 131.4, 131.0, 130.1, 129.7, 128.7, 128.5, 128.1, 126.9, 121.7, 119.9, 101.4, 93.4, 84.5, 78.3, 56.5. Mass spec.: 409.1 (MH)⁺. Enantiomers were resolved by Prep HPLC (Chiralcel OD 2 1×250 mm, 10 um, 25% B isocratic, flow rate: 15 mL/min, UV 220, 50 min run, solvent A: 0.1% diethylamine/heptane, solvent B: ethanol). Enantiomer 1=first enantiomer to elute from Prep (Example 327). Enantiomer 2=second enantiomer to elute from Prep (Example 328).

Example 329 and Example 330 and Example 331 and Example 332

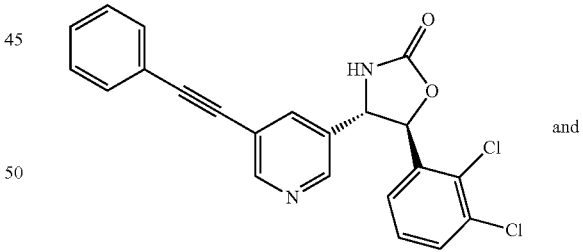

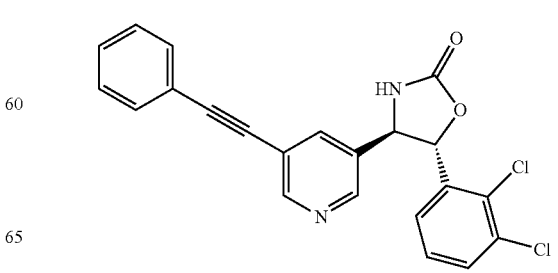

-continued

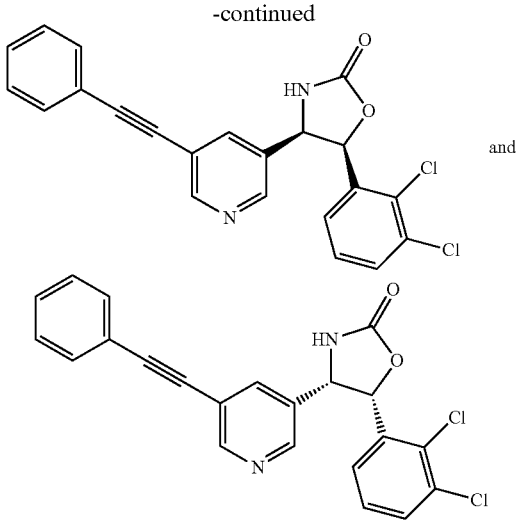

(4S,5S)-5-(2,3-Dichlorophenyl)-4-(5-(phenylethynyl)pyridin-3-yl)oxazolidin-2-one and (4R,5R)-5-(2,3-dichlorophenyl)-4-(5-(phenylethynyl)pyridin-3-yl)oxazolidin-2-one, (4R,5S)-5-(2,3-Dichlorophenyl)-4-(5-(phenylethynyl)pyridin-3-yl)oxazolidin-2-one and (4S,5R)-5-(2,3-dichlorophenyl)-4-(5-(phenylethynyl)pyridin-3-yl)oxazolidin-2-one Prepared according to the same procedure as (4R,5R)-4-(5-(phenylethynyl)pyridin-3-yl)-5-(pyrimidin-4-yl)oxazolidin-2-one and (4R,5S)-4-(5-(phenylethynyl)pyridin-3-yl)-5-(pyrimidin-4-yl)oxazolidin-2-one and (4S,5R)-4-(5-(phenylethynyl)pyridin-3-yl)-5-(pyrimidin-4-yl)oxazolidin-2-one and (4S,5S)-4-(5-(phenylethynyl)pyridin-3-yl)-5-(pyrimidin-4-yl)oxazolidin-2-one using 2,3-dichlorobenzaldehyde. The material was purified by Biotage (35-40% EtOAc/Hex) to isolate the two major fractions (F1=first to elute, F2=second to elute). F1(trans): $^1$H NMR (CDCl$_3$, 400 MHz) δ: 8.74 (d, J=1.8 Hz, 1H), 8.53 (d, J=2.0 Hz, 1H), 7.95 (t, J=2.0 Hz, 1H), 7.54-7.58 (m, 2H), 7.51 (dd, J=8.0, 1.5 Hz, 1H), 7.43-7.47 (m, 1H), 7.37-7.40 (m, 3H), 7.30-7.36 (m, 1H), 7.06 (s, 1H), 5.73 (d, J=4.0 Hz, 1H), 4.71 (d, J=4.0 Hz, 1H). $^{13}$C-NMR (CDCl$_3$, 101 MHz) δ: 170.9, 158.3, 152.2, 146.5, 137.6, 136.0, 134.6, 133.6, 131.4, 130.6, 129.3, 128.8, 128.2, 127.8, 124.4, 121.7, 120.8, 93.6, 84.8, 81.4, 60.6, 60.1. Mass spec.: 409.1 (MH)$^+$. Enantiomers were resolved by Prep HPLC (Chiralpak AS 2 1×250 mm, 10 um, 50% B isocratic, flow rate: 15 mL/min, UV 220, 25 min run, solvent A: 0.1% diethylamine/heptane, solvent B: ethanol). Enantiomer 1=first enantiomer to elute from Prep (Example 329). Enantiomer 2=second enantiomer to elute from Prep (Example 330). F2(cis): $^1$H NMR (CDCl$_3$, 400 MHz) δ: 8.50 (s, 1H), 8.23 (s, 1H), 7.53-7.57 (m, 3H), 7.39-7.41 (m, 3H), 7.29-7.31 (m, 1H), 7.27 (dd, J=7.9, 0.9 Hz, 1H), 7.08-7.13 (m, 1H), 6.28-6.35 (m, 2H), 5.46 (d, J=8.0 Hz, 1H). $^{13}$C-NMR (CDCl$_3$, 101 MHz) δ: 157.8, 151.8, 146.4, 136.2, 134.2, 132.9, 131.5, 131.4, 130.2, 128.8, 128.6, 128.2, 127.8, 127.4, 125.0, 124.4, 121.7, 119.9, 93.3, 89.8, 84.6, 79.0. Mass spec.: 409.1 (MH)$^+$. Enantiomers were resolved by Prep HPLC (Chiralcel OD 21×250 mm, 10 um, 15% B isocratic, flow rate: 60 mL/min, UV 220, 50 min run, solvent A: 0.1% diethylamine/heptane, solvent B: ethanol). Enantiomer 1=first enantiomer to elute from Prep (Example 331). Enantiomer 2=second enantiomer to elute from Prep (Example 332).

Example 333 and Example 334 and Example 335 and Example 336

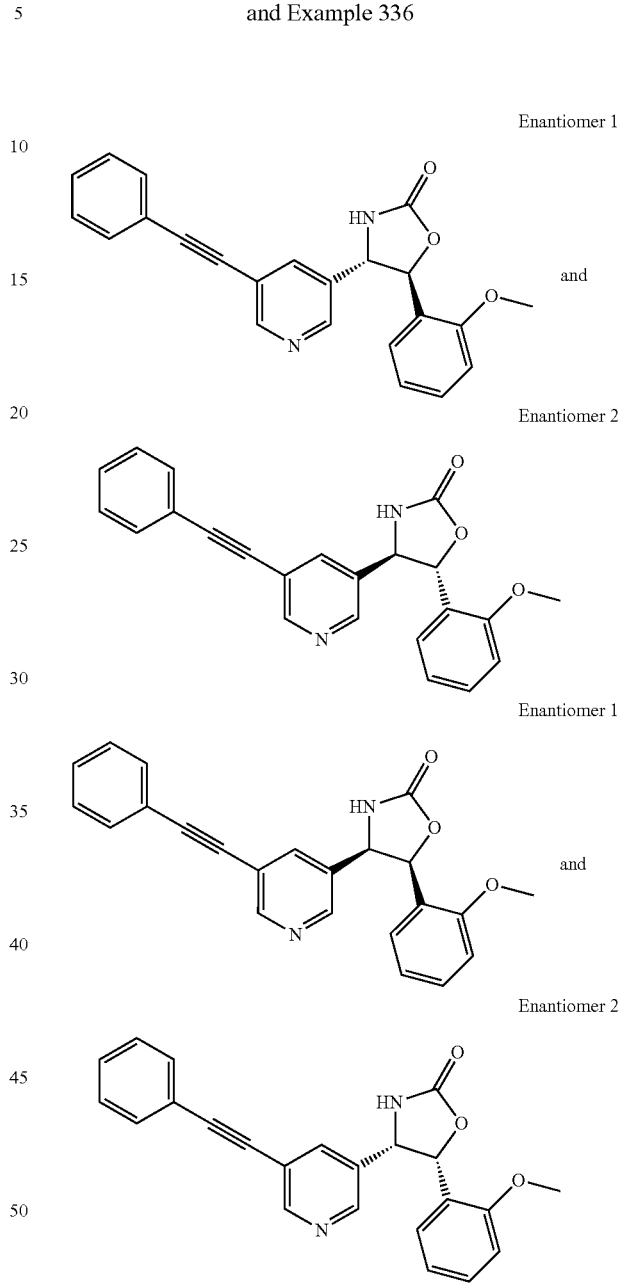

(4S,5S)-5-(2-Methoxyphenyl)-4-(5-(phenylethynyl)pyridin-3-yl)oxazolidin-2-one and (4R,5R)-5-(2-methoxyphenyl)-4-(5-(phenylethynyl)pyridin-3-yl)oxazolidin-2-one, (4R,5S)-5-(2-Methoxyphenyl)-4-(5-(phenylethynyl)pyridin-3-yl)oxazolidin-2-one and (4S,5R)-5-(2-methoxyphenyl)-4-(5-(phenylethynyl)pyridin-3-yl)oxazolidin-2-one Prepared according to the same procedure as (4R,5R)-4-(5-(phenylethynyl)pyridin-3-yl)-5-(pyrimidin-4-yl)oxazolidin-2-one and (4R,5S)-4-(5-(phenylethynyl)pyridin-3-yl)-5-(pyrimidin-4-yl)oxazolidin-2-one and (4S,5R)-4-(5-

(phenylethynyl)pyridin-3-yl)-5-(pyrimidin-4-yl)oxazolidin-2-one and (4S,5S)-4-(5-(phenylethynyl)pyridin-3-yl)-5-(pyrimidin-4-yl)oxazolidin-2-one using 2-methoxybenzaldehyde. The material was purified by Biotage (60-80% EtOAc/Hex) to isolate the two major fractions (F1=first to elute, F2=second to elute). F1(trans): $^1$H NMR (CDCl$_3$, 400 MHz) δ: 8.74 (d, J=1.5 Hz, 1H), 8.49 (d, J=2.0 Hz, 1H), 7.94 (t, J=2.0 Hz, 1H), 7.55-7.59 (m, 2H), 7.43 (dd, J=7.5, 1.3 Hz, 1H), 7.35-7.40 (m, 4H), 7.00-7.07 (m, 1H), 6.91-6.96 (m, 2H), 5.57 (d, J=5.0 Hz, 1H), 4.78 (d, J=5.0 Hz, 1H), 3.76 (s, 3H). $^{13}$C-NMR (CDCl$_3$, 101 MHz) δ: 159.0, 155.6, 151.7, 146.6, 135.8, 135.5, 131.4, 129.7, 128.7, 128.1, 125.7, 125.6, 121.9, 120.6, 120.5, 110.3, 93.2, 85.1, 81.3, 60.5, 54.8. Mass spec.: 371.2 (MH)$^+$. Enantiomers were resolved by Prep HPLC (Chiralpak AS 21×250 mm, 10 um, 30% B isocratic, flow rate: 15 mL/min, UV 220, 45 min run, solvent A: 0.1% diethylamine/heptane, solvent B: ethanol). Enantiomer 1=first enantiomer to elute from Prep (Example 333). Enantiomer 2=second enantiomer to elute from Prep (Example 334). F2(cis): $^1$H NMR (CDCl$_3$, 400 MHz) δ: 8.40 (d, J=2.0 Hz, 1H), 8.12 (d, J=2.0 Hz, 1H), 7.49-7.53 (m, 2H), 7.46 (t, J=2.0 Hz, 1H), 7.35-7.38 (m, 3H), 7.27 (dd, J=7.7, 0.6 Hz, 1H), 7.08-7.14 (m, 1H), 6.93 (s, 1H), 6.79-6.87 (m, 1H), 6.58 (d, J=7.8 Hz, 1H), 6.20 (d, J=8.3 Hz, 1H), 5.33 (d, J=8.5 Hz, 1H), 3.70 (s, 3H). $^{13}$C-NMR (CDCl$_3$, 101 MHz) δ: 159.1, 154.1, 151.1, 146.9, 136.5, 132.1, 131.3, 129.3, 128.6, 128.1, 125.3, 122.7, 121.9, 120.3, 119.2, 109.2, 92.6, 85.0, 77.7, 60.1, 57.4, 54.6. Mass spec.: 371.2 (MH)$^+$. Enantiomers were resolved by Prep HPLC (Chiralpak AS 21×250 mm, 10 um, 25% B isocratic, flow rate: 15 mL/min, UV 220, 40 min run, solvent A: 0.1% diethylamine/heptane, solvent B: ethanol). Enantiomer 1=first enantiomer to elute from Prep (Example 335). Enantiomer 2=second enantiomer to elute from Prep (Example 336).

Example 337 and Example 338 and Example 339

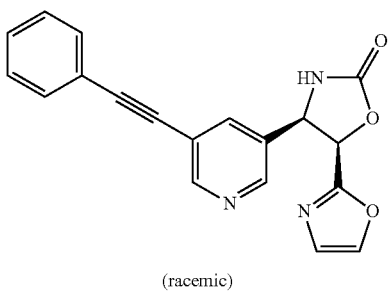

(racemic)

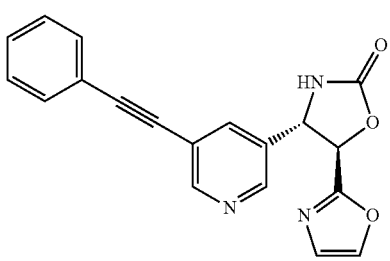

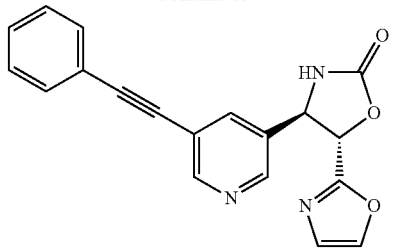

(±)-(4R,5R)-5-(Oxazol-2-yl)-4-(5-(phenylethynyl)pyridin-3-yl)oxazolidin-2-one and (4S,5R)-5-(oxazol-2-yl)-4-(5-(phenylethynyl)pyridin-3-yl)oxazolidin-2-one and (4R,5S)-5-(oxazol-2-yl)-4-(5-(phenylethynyl)pyridin-3-yl)oxazolidin-2-one Prepared according to the same procedure as (4R,5R)-4-(5-(phenylethynyl)pyridin-3-yl)-5-(pyrimidin-4-yl)oxazolidin-2-one and (4R,5S)-4-(5-(phenylethynyl)pyridin-3-yl)-5-(pyrimidin-4-yl)oxazolidin-2-one and (4S,5R)-4-(5-(phenylethynyl)pyridin-3-yl)-5-(pyrimidin-4-yl)oxazolidin-2-one and (4S,5S)-4-(5-(phenylethynyl)pyridin-3-yl)-5-(pyrimidin-4-yl)oxazolidin-2-one using oxazole-2-carbaldehyde. The reaction mixture was purified by silica gel chromatography (25%→55% EtOAc/DCM) to give two fractions, F1 (faster eluting, trans) and F2 (slower eluting, cis). F2(Example 337, racemic): $^1$H NMR (400 MHz, CD$_3$OD) δ: 8.53 (d, J=2.0 Hz, 1H), 8.35 (d, J=2.3 Hz, 1H), 7.88-7.70 (m, 2H), 7.60-7.48 (m, 2H), 7.46-7.29 (m, 3H), 7.00 (d, J=0.8 Hz, 1H), 6.19 (d, J=9.0 Hz, 1H), 5.61 (d, J=9.0 Hz, 1H); $^{13}$C NMR (101 MHz, CD$_3$OD) δ: 159.6, 152.3, 147.6, 141.8, 138.2, 133.5, 132.7, 130.3, 129.7, 128.1, 121.8, 94.4, 85.5, 76.0, 58.2; LC/Mass spec. (Analytical HPLC method 15): RT=2.10 min. Mass=332.2 (MH)$^+$. Enantiomers of F1 were resolved by Prep HPLC (Chiralpak AD, EtOH/Heptane/0.1% DEA). Enantiomer 1=first enantiomer to elute from Prep (Example 338, F1 Ent1). Enantiomer 2=second enantiomer to elute from Prep (Example 339, F1 Ent2). F1 Ent1: $^1$H NMR (400 MHz, CDCl$_3$) δ: 8.77 (s, 1H), 8.58 (s, 1H), 7.96 (t, J=1.9 Hz, 1H), 7.80 (d, J=0.8 Hz, 1H), 7.60-7.53 (m, 2H), 7.44-7.36 (m, 3H), 7.25 (d, J=0.5 Hz, 1H), 6.54 (s, 1H), 5.60 (d, J=6.8 Hz, 1H), 5.39 (d, J=6.8 Hz, 1H); $^{13}$C NMR (101 MHz, CDCl$_3$) δ: 157.7, 156.9, 152.1, 146.0, 140.8, 136.2, 133.1, 131.4, 128.9, 128.2, 127.6, 121.6, 93.9, 84.5, 57.0, 40.5, 13.8. Mass Spec.: 332.2 (MH)$^+$. F1 Ent2: $^1$H NMR (400 MHz, CDCl$_3$) δ: 8.77 (s, 1H), 8.59 (br. s., 1H), 7.97 (s, 1H), 7.80 (d, J=0.8 Hz, 1H), 7.65-7.48 (m, 2H), 7.47-7.31 (m, 3H), 7.25 (d, J=0.8 Hz, 1H), 6.45 (s, 1H), 5.60 (d, J=7.0 Hz, 1H), 5.40 (d, J=7.0 Hz, 1H); $^{13}$C NMR (101 MHz, CDCl$_3$) δ: 157.7, 156.8, 152.0, 145.9, 140.8, 136.2, 133.2, 131.4, 128.9, 128.2, 127.6, 121.6, 94.0, 84.5, 56.9, 22.3, 13.8. Mass Spec.: 332.2 (MH)$^+$.

Example 340 and Example 341 and Example 342

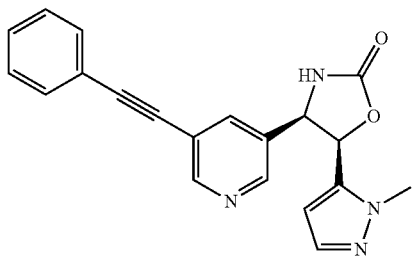

(racemic)

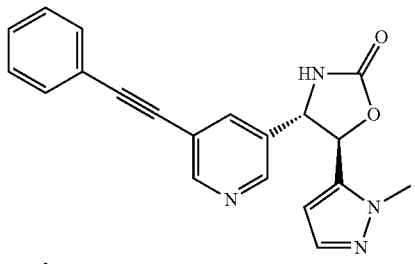

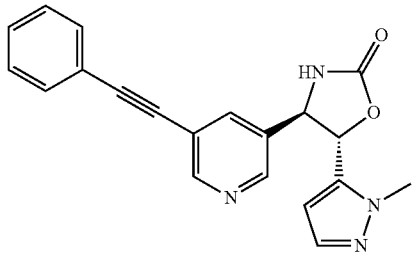

(±)-(4R,5R)-5-(Oxazol-2-yl)-4-(5-(phenylethynyl)
pyridin-3-yl)oxazolidin-2-one and (4S,5R)-5-(1-
methyl-1H-pyrazol-5-yl)-4-(5-(phenylethynyl)pyri-
din-3-yl)oxazolidin-2-one and (4R,5S)-5-(1-methyl-
1H-pyrazol-5-yl)-4-(5-(phenylethynyl)pyridin-3-yl)
oxazolidin-2-one Prepared according to the same procedure as (4R,5R)-4-(5-(phenylethynyl)pyridin-3-yl)-5-(pyrimidin-4-yl)oxazolidin-2-one and (4R,5S)-4-(5-(phenylethynyl)pyridin-3-yl)-5-(pyrimidin-4-yl)oxazolidin-2-one and (4S,5R)-4-(5-(phenylethynyl)pyridin-3-yl)-5-(pyrimidin-4-yl)oxazolidin-2-one and (4S,5S)-4-(5-(phenylethynyl)pyridin-3-yl)-5-(pyrimidin-4-yl)oxazolidin-2-one using 1-methyl-1H-pyrazole-5-carbaldehyde. The reaction mixture was purified by silica gel chromatography (0%→50% EtOAc/DCM) to give two fractions, F1 (faster eluting, trans) and F2 (slower eluting, cis). F2(Example 340, racemic): $^1$H NMR (400 MHz, CD$_3$OD) δ 8.55 (d, J=1.8 Hz, 1H), 8.31 (d, J=2.0 Hz, 1H), 7.69 (t, J=1.9 Hz, 1H), 7.61-7.49 (m, 2H), 7.47-7.35 (m, 3H), 7.29 (d, J=1.8 Hz, 1H), 6.31 (d, J=8.3 Hz, 1H), 6.15 (dd, J=2.0, 0.5 Hz, 1H), 5.53 (d, J=8.3 Hz, 1H), 3.60 (s, 3H). Mass Spec.: 345.3 (MH)$^+$. Enantiomers of F1 were resolved by Prep HPLC (Chiralpak AD, EtOH/Heptane/0.1% DEA). Enantiomer 1=first enantiomer to elute from Prep (Example 341, F1 Ent1). Enantiomer 2=second enantiomer to elute from Prep (Example 342, F1 Ent2). F1 Ent1: $^1$H NMR (400 MHz, CDCl$_3$) δ 8.78 (d, J=1.5 Hz, 1H), 8.57 (s, 1H), 7.93 (s, 1H), 7.60-7.54 (m, 2H), 7.53 (d, J=1.8 Hz, 1H), 7.44-7.36 (m, 3H), 6.53 (s, 1H), 6.50 (d, J=2.0 Hz, 1H), 5.41 (d, J=7.8 Hz, 1H), 5.20 (d, J=7.8 Hz, 1H), 3.87 (s, 3H); $^{13}$C NMR (101 MHz, CDCl$_3$) δ 157.1, 152.2, 145.8, 138.3, 136.1, 135.8, 133.0, 131.4, 129.0, 128.2, 121.5, 121.1, 105.6, 94.2, 84.4, 58.8, 36.9, 29.3. Mass Spec.: 345.3 (MH)$^+$. F1 Ent2: $^1$H NMR (400 MHz, CDCl$_3$) δ 8.78 (s, 1H), 8.57 (br. s., 1H), 7.93 (s, 1H), 7.59-7.54 (m, 2H), 7.53 (d, J=2.0 Hz, 1H), 7.45-7.36 (m, 3H), 6.50 (d, J=1.8 Hz, 1H), 6.44 (s, 1H), 5.41 (d, J=7.8 Hz, 1H), 5.19 (d, J=7.8 Hz, 1H), 3.88 (s, 3H); $^{13}$C NMR (101 MHz, CDCl$_3$) δ 157.0, 152.3, 145.9, 138.3, 136.0, 135.9, 131.4, 129.0, 128.2, 121.5, 105.5, 94.1, 84.4, 58.8, 36.9, 29.3. Mass Spec.: 345.3 (MH)$^+$.

Example 343 and Example 344

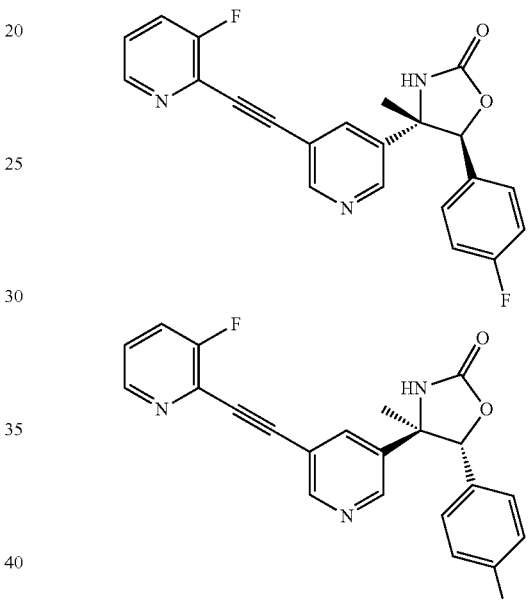

(4S,5S)-5-(4-Fluorophenyl)-4-(5-((3-fluoropyridin-2-yl)ethynyl)pyridin-3-yl)-4-methyloxazolidin-2-one
and (4S,5S)-5-(4-fluorophenyl)-4-(5-((3-fluoropyridin-2-yl)ethynyl)pyridin-3-yl)-4-methyloxazolidin-2-one Prepared according to the same procedure as (4S,5S)-4-methyl-5-phenyl-4-(5-(phenylethynyl)pyridin-3-yl)oxazolidin-2-one and (4R,5R)-4-methyl-5-phenyl-4-(5-(phenylethynyl)pyridin-3-yl)oxazolidin-2-one, starting with 4-fluorobenzaldehyde, 2-bromo-3-fluoropyridine. $^1$H-NMR (CDCl$_3$, 500 MHz) δ: 8.85 (s, 1H), 8.70 (s, 1H), 8.50 (m, 1H), 8.03 (m, 1H), 7.55-7.52 (m, 1H), 7.40-7.37 (m, 1H), 7.22-7.20 (m, 2H), 7.14-7.11 (m, 2H), 6.69 (s, 1H), 5.45 (s, 1H), 1.37 (s, 3H). $^{13}$C-NMR (CDCl$_3$, 126 MHz) δ: 163.3 (d, J=249), 160.4 (d, J=263), 158.2, 152.3, 147.3, 146.2, 138.1, 136.6, 131.7, 128.8, 128.1, 125.2, 123.7, 123.5, 119.5, 116.1, 90.9, 87.4, 86.7, 60.5, 22.7. Mass spec.: 392.1 (MH)$^+$. Enantiomers were resolved by Prep HPLC (Chiralpak AS 21×250 mm, 10 um, 40% B isocratic, flow rate: 15 mL/min, UV 220, 60 min run, solvent A: 0.1% diethylamine/heptane, solvent B:

ethanol). Enantiomer 1=first enantiomer to elute from Prep (Example 343). Enantiomer 2=second enantiomer to elute from Prep (Example 344).

Example 345 and Example 346

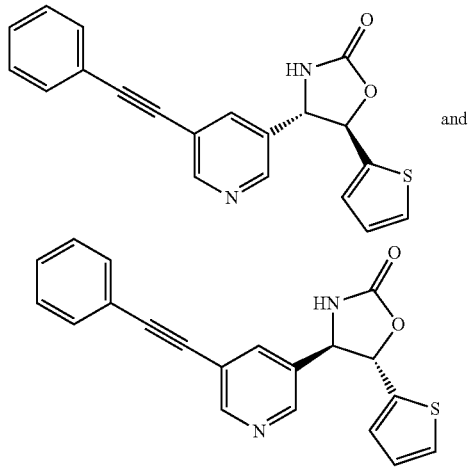

(4S,5R)-4-(5-(Phenylethynyl)pyridin-3-yl)-5-(thiophen-2-yl)oxazolidin-2-one and (4R,5S)-4-(5-(phenylethynyl)pyridin-3-yl)-5-(thiophen-2-yl)oxazolidin-2-one Prepared according to the same procedure as (4S,5S)-5-(4-fluorophenyl)-4-(5-(phenylethynyl)pyridin-3-yl)oxazolidin-2-one and (4R,5R)-5-(4-Fluorophenyl)-4-(5-(phenylethynyl)pyridin-3-yl)oxazolidin-2-one, starting with 2-(5-bromopyridin-3-yl)acetic acid and thiophene-2-carbaldehyde. $^1$H-NMR (CDCl$_3$, 500 MHz) δ: 8.74 (d, J=1.8, 1H), 8.43 (d, J=2.1, 1H), 7.88 (m, 1H), 7.57-7.55 (m, 2H), 7.44 (m, 1H), 7.39-7.38 (m, 2H), 7.14 (bs, 1H), 7.10 (m, 1H), 7.05-7.03 (m, 1H), 5.50 (d, J=7.9, 1H), 5.04 (d, J=7.9, 1H). $^{13}$C-NMR (CDCl$_3$, 126 MHz) δ: 158.4, 152.8, 146.8, 138.3, 136.3, 133.4, 132.2, 131.9, 129.3, 128.7, 127.8, 127.5, 122.2, 121.2, 94.0, 85.3, 81.7, 62.7, 60.6. Mass spec.: 347.0 (MH)$^+$. Enantiomers were resolved by Prep HPLC (Chiralpak AD 21×250 mm, 10 um, 40% B isocratic, flow rate: 15 mL/min, UV 220, min run, solvent A: 0.1% diethylamine/heptane, solvent B: ethanol). Enantiomer 1=first enantiomer to elute from Prep (Example 345). Enantiomer 2=second enantiomer to elute from Prep (Example 346).

Example 347 and Example 348

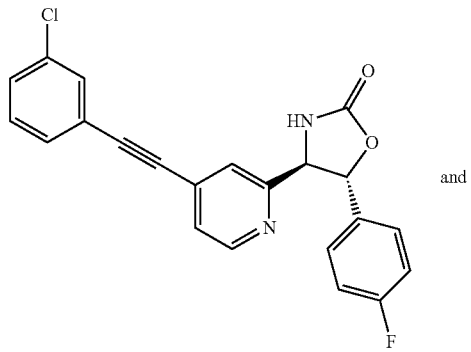

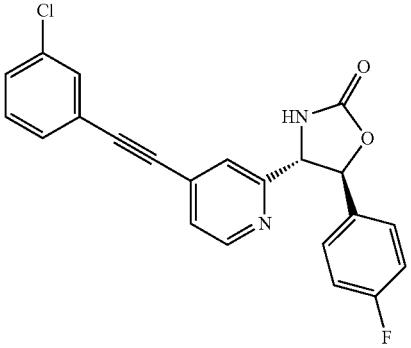

(4R,5R)-4-(4-((3-Chlorophenyl)ethynyl)pyridin-2-yl)-5-(4-fluorophenyl)oxazolidin-2-one and (4S,5S)-4-(5-((3-chlorophenyl)ethynyl)pyridin-2-yl)-5-(4-fluorophenyl)oxazolidin-2-one Prepared according to the same procedure as (4R,5R)-5-phenyl-4-(4-(phenylethynyl)pyridin-2-yl)oxazolidin-2-one and (4S,5S)-5-phenyl-4-(4-(phenylethynyl)pyridin-2-yl)oxazolidin-2-one, starting with (4R,5R)-4-(4-bromopyridin-2-yl)-5-(4-fluorophenyl)oxazolidin-2-one, (4S,5S)-4-(4-bromopyridin-2-yl)-5-(4-fluorophenyl)oxazolidin-2-one and 1-chloro-3-ethnylbenzene. $^1$H-NMR (CDCl$_3$, 500 MHz) δ: 8.67 (d, J=5.2, 1H), 7.57 (m, 1H), 7.53 (s, 1H), 7.48-7.45 (m, 3H), 7.43-7.41 (m, 2H), 7.37-7.34 (m, 1H), 7.16-7.13 (m, 2H), 6.08 (s, 1H), 5.60 (d, J=5.8, 1H), 4.93 (d, J=5.8, 1H). $^{13}$C-NMR (CDCl$_3$, 126 MHz) δ: 163.1 (d, J=243), 130.0, 129.9, 158.6, 158.5, 150.4, 134.6, 134.0, 132.7, 131.9, 130.2, 130.0, 129.9, 127.8, 127.7, 125.5, 123.5, 122.5, 116.2, 116.0, 93.5, 87.2, 83.3, 64.9. Mass spec.: 393.0 (MH)$^+$. Enantiomers were resolved by Prep HPLC (Chiralpak AD 21×250 mm, 10 um, 20% B isocratic, flow rate: 15 mL/min, UV 220, 30 min run, solvent A: 0.1% diethylamine/heptane, solvent B: ethanol). Enantiomer 1=first enantiomer to elute from Prep (Example 347). Enantiomer 2=second enantiomer to elute from Prep (Example 348).

Example 349 and Example 350

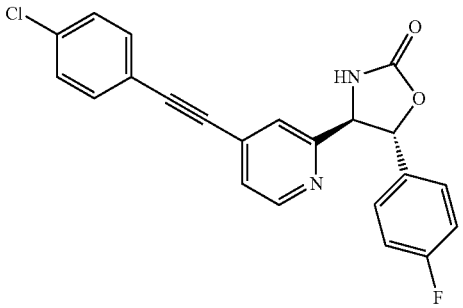

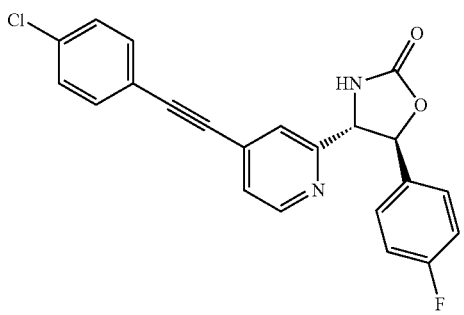

(4R,5R)-4-(4-((4-Chlorophenyl)ethynyl)pyridin-2-yl)-5-(4-fluorophenyl)oxazolidin-2-one and (4S,5S)-4-(5-((4-chlorophenyl)ethynyl)pyridin-2-yl)-5-(4-fluorophenyl)oxazolidin-2-one Prepared according to the same procedure as (4R,5R)-5-phenyl-4-(4-(phenylethynyl)pyridin-2-yl)oxazolidin-2-one and (4S,5S)-5-phenyl-4-(4-(phenylethynyl)pyridin-2-yl)oxazolidin-2-one, starting with (4R,5R)-4-(4-bromopyridin-2-yl)-5-(4-fluorophenyl)oxazolidin-2-one, (4S,5S)-4-(4-bromopyridin-2-yl)-5-(4-fluorophenyl)oxazolidin-2-one and 1-chloro-4-ethnylbenzene. $^1$H-NMR (CDCl$_3$, 500 MHz) δ: 8.66 (d, J=4.3, 1H), 7.52-7.50 (m, 3H), 7.47-7.45 (m, 2H), 7.41-7.38 (m, 3H), 7.16-7.13 (m, 2H), 6.21 (s, 1H), 5.60 (d, J=5.8, 1H), 4.92 (d, J=5.8, 1H). $^{13}$C-NMR (CDCl$_3$, 126 MHz) δ: 163.1 (d, J=248.6), 158.7, 158.5, 150.4, 135.9, 134.1, 133.3, 132.9, 129.1, 127.8, 127.7, 125.5, 122.5, 120.3, 116.2, 116.0, 94.0, 87.2, 83.3, 64.9, 50.5, 42.4. Mass spec.: 392.9 (MH)$^+$. Enantiomers were resolved by Prep HPLC (Chiralpak AD 21×250 mm, 10 um, 17% B isocratic, flow rate: 15 mL/min, UV 220, 35 min run, solvent A: 0.1% diethylamine/heptane, solvent B: ethanol). Enantiomer 1=first enantiomer to elute from Prep (Example 349). Enantiomer 2=second enantiomer to elute from Prep (Example 350).

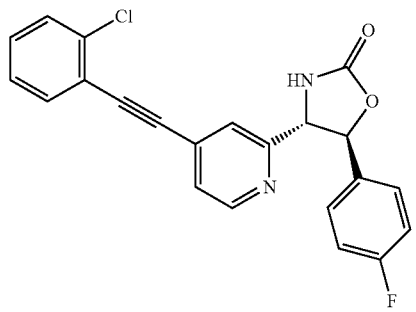

(4R,5R)-4-(4-((2-Chlorophenyl)ethynyl)pyridin-2-yl)-5-(4-fluorophenyl)oxazolidin-2-one and (4S,5S)-4-(5-((2-chlorophenyl)ethynyl)pyridin-2-yl)-5-(4-fluorophenyl)oxazolidin-2-one Prepared according to the same procedure as (4R,5R)-5-phenyl-4-(4-(phenylethynyl)pyridin-2-yl)oxazolidin-2-one and (4S,5S)-5-phenyl-4-(4-(phenylethynyl)pyridin-2-yl)oxazolidin-2-one, starting with (4R,5R)-4-(4-bromopyridin-2-yl)-5-(4-fluorophenyl)oxazolidin-2-one, (4S,5S)-4-(4-bromopyridin-2-yl)-5-(4-fluorophenyl)oxazolidin-2-one and 1-chloro-2-ethynylbenzene. $^1$H-NMR (CDCl$_3$, 500 MHz) δ: 8.68 (d, J=5.5, 1H), 7.62-7.60 (m, 1H), 7.55 (bs, 1H), 7.50-7.45 (m, 4H), 7.39-7.36 (m, 1H), 7.33-7.30 (m, 1H), 7.16-7.13 9 m, 2H), 6.07 (s, 1H), 5.62 (d, J=5.8, 1H), 4.93 (d, J=5.8, 1H). $^{13}$C-NMR (CDCl$_3$, 126 MHz) δ: 163.1 (d, J=248.6), 158.6, 158.4, 150.4, 136.5, 134.0, 133.7, 132.8, 130.7, 129.7, 127.8, 127.7, 126.8, 125.6, 122.6, 121.9, 116.2, 116.0, 91.7, 83.3, 64.9, 42.2. Mass spec.: 392.9 (MH)$^+$. Enantiomers were resolved by Prep HPLC (Chiralpak AD 21×250 mm, 10 um, 45% B isocratic, flow rate: 15 mL/min, UV 220, 35 min run, solvent A: 0.1% diethylamine/heptane, solvent B: ethanol). Enantiomer 1=first enantiomer to elute from Prep (Example 351). Enantiomer 2=second enantiomer to elute from Prep (Example 352).

Example 351 and Example 352

Enantiomer 1

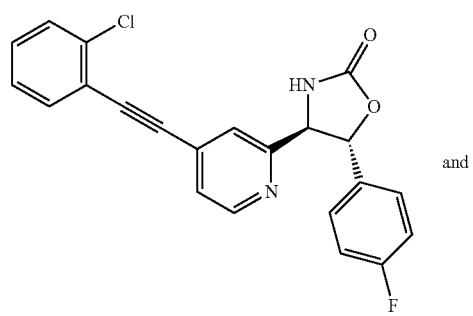

and

Example 353 and Example 354

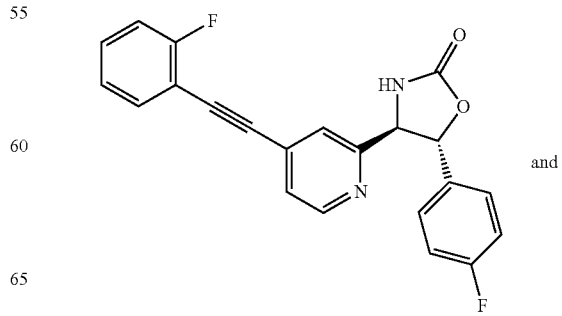

and

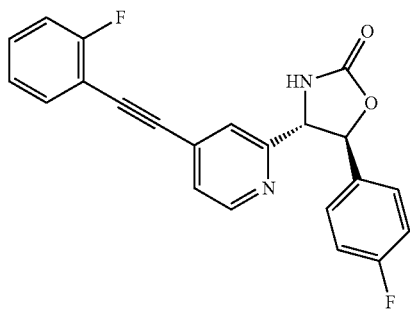

(4R,5R)-5-(4-Fluorophenyl)-4-(4-((2-fluorophenyl)ethynyl)pyridin-2-yl)oxazolidin-2-one and (4S,5S)-5-(4-fluorophenyl)-4-(4-((2-fluorophenyl)ethynyl)pyridin-2-yl)oxazolidin-2-one Prepared according to the same procedure as (4R,5R)-5-phenyl-4-(4-(phenylethynyl)pyridin-2-yl)oxazolidin-2-one and (4S,5S)-5-phenyl-4-(4-(phenylethynyl)pyridin-2-yl)oxazolidin-2-one, starting with (4R,5R)-4-(4-bromopyridin-2-yl)-5-(4-fluorophenyl)oxazolidin-2-one, (4S,5S)-4-(4-bromopyridin-2-yl)-5-(4-fluorophenyl)oxazolidin-2-one and 1-ethynyl-2-fluorobenzene. $^1$H NMR (CDCl$_3$, 500 MHz) δ: 8.62-8.71 (m, 1H), 7.51-7.61 (m, 2H), 7.38-7.50 (m, 4H), 7.09-7.23 (m, 4H), 6.27 (s, 1H), 5.61 (d, J=5.8 Hz, 1H), 4.92 (d, J=5.8 Hz, 1H). $^{13}$C-NMR (CDCl$_3$, 126 MHz) δ: 163.1 (d, J=247.6), 163.0 (d, J=253.4), 158.7, 158.4, 150.4, 134.0, 133.8, 132.8, 131.5, 127.8, 127.7, 125.6, 124.4, 122.6, 116.2, 116.0, 115.8, 110.7, 91.1, 88.5, 83.3, 64.9. Mass spec.: 377.0 (MH)$^+$. Enantiomers were resolved by Prep HPLC (Chiralpak AD 21×250 mm, 10 um, 12% B isocratic, flow rate: 15 mL/min, UV 220, 45 min run, solvent A: 0.1% diethylamine/heptane, solvent B: ethanol). Enantiomer 1=first enantiomer to elute from Prep (Example 353). Enantiomer 2=second enantiomer to elute from Prep (Example 354).

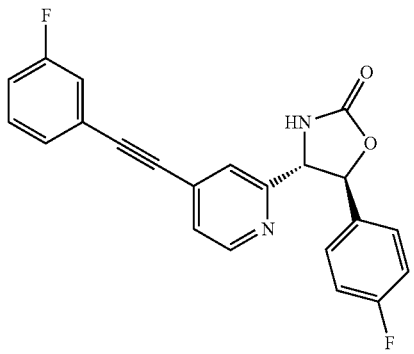

(4R,5R)-5-(4-Fluorophenyl)-4-(4-((3-fluorophenyl)ethynyl)pyridin-2-yl)oxazolidin-2-one and (4S,5S)-5-(4-fluorophenyl)-4-(4-((3-fluorophenyl)ethynyl)pyridin-2-yl)oxazolidin-2-one Prepared according to the same procedure as (4R,5R)-5-phenyl-4-(4-(phenylethynyl)pyridin-2-yl)oxazolidin-2-one and (4S,5S)-5-phenyl-4-(4-(phenylethynyl)pyridin-2-yl)oxazolidin-2-one, starting with (4R,5R)-4-(4-bromopyridin-2-yl)-5-(4-fluorophenyl)oxazolidin-2-one, (4S,5S)-4-(4-bromopyridin-2-yl)-5-(4-fluorophenyl)oxazolidin-2-one and 1-ethynyl-3-fluorobenzene. $^1$H NMR (CDCl$_3$, 500 MHz) δ: 8.67 (d, J=4.9 Hz, 1H), 7.53 (s, 1H), 7.44-7.49 (m, 2H), 7.40-7.43 (m, 1H), 7.36-7.40 (m, 2H), 7.26-7.28 (m, 1H), 7.12-7.17 (m, 3H), 6.21 (s, 1H), 5.60 (d, J=5.8 Hz, 1H), 4.93 (d, J=5.8 Hz, 1H). $^{13}$C-NMR (CDCl$_3$, 126 MHz) δ: 163.1 (d, J=247.6), 162.5 (d, J=247.6), 158.7, 158.5, 150.4, 134.0, 132.7, 130.4, 130.3, 128.0, 127.8, 125.5, 123.7, 122.6, 119.0, 118.8, 117.1, 116.2, 93.7, 87.0, 83.3, 64.9. Mass spec.: 377.0 (MH)$^+$. Enantiomers were resolved by Prep HPLC (Chiralpak AD 21×250 mm, 10 um, 10% B isocratic, flow rate: 15 mL/min, UV 220, 55 min run, solvent A: 0.1% diethylamine/heptane, solvent B: ethanol). Enantiomer 1=first enantiomer to elute from Prep (Example 355). Enantiomer 2=second enantiomer to elute from Prep (Example 356).

Example 355 and Example 356

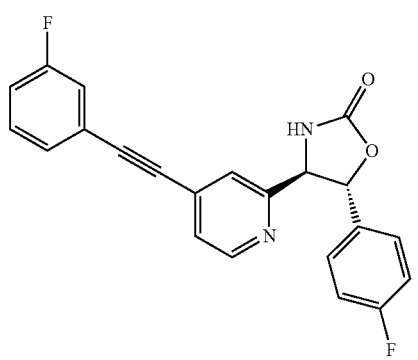

and

Example 357 and Example 358

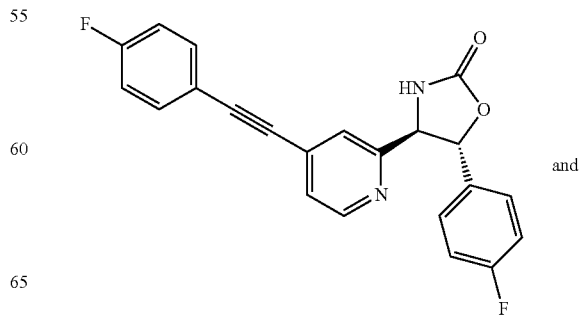

and

273
-continued

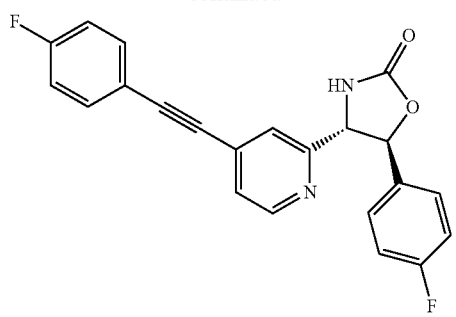

(4R,5R)-5-(4-Fluorophenyl)-4-(4-((4-fluorophenyl)
ethynyl)pyridin-2-yl)oxazolidin-2-one and (4S,5S)-
5-(4-fluorophenyl)-4-(4-((4-fluorophenyl)ethynyl)
pyridin-2-yl)oxazolidin-2-one Prepared according to the same procedure as (4R,5R)-5-phenyl-4-(4-(phenylethynyl)pyridin-2-yl)oxazolidin-2-one and (4S,5S)-5-phenyl-4-(4-(phenylethynyl)pyridin-2-yl)oxazolidin-2-one, starting with (4R,5R)-4-(4-bromopyridin-2-yl)-5-(4-fluorophenyl)oxazolidin-2-one, (4S,5S)-4-(4-bromopyridin-2-yl)-5-(4-fluorophenyl)oxazolidin-2-one and 1-ethynyl-4-fluorobenzene. $^1$H NMR (CDCl$_3$, 500 MHz) δ: 8.65 (d, J=4.9 Hz, 1H), 7.55-7.60 (m, 2H), 7.52 (s, 1H), 7.44-7.49 (m, 2H), 7.40 (dd, J=5.0, 1.4 Hz, 1H), 7.08-7.17 (m, 4H), 6.27 (s, 1H), 5.59 (d, J=5.8 Hz, 1H), 4.92 (d, J=5.8 Hz, 1H). $^{13}$C-NMR (CDCl$_3$, 126 MHz) δ: 163.3 (d, J=252.4), 163.1 (d, J=248.6), 158.7, 158.5, 150.3, 134.2, 134.1, 134.0, 133.0, 127.8, 127.7, 125.4, 122.5, 118.0, 117.9, 116.2, 116.0, 94.2, 86.1, 83.3, 65.0. Mass spec.: 377.0 (MH)$^+$. Enantiomers were resolved by Prep HPLC (Chiralpak AD 21×250 mm, 10 um, 12% B isocratic, flow rate: 15 mL/min, UV 220, 55 min run, solvent A: 0.1% diethylamine/heptane, solvent B: ethanol). Enantiomer 1=first enantiomer to elute from Prep (Example 357). Enantiomer 2=second enantiomer to elute from Prep (Example 358).

Example 359 and Example 360

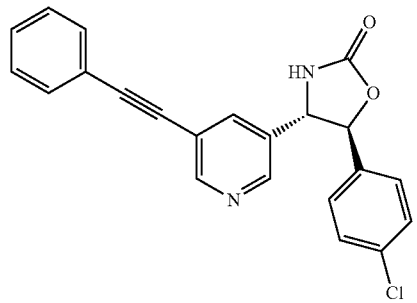

and

274
-continued

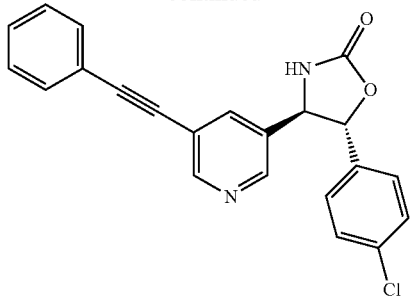

(4S,5S)-5-(4-Chlorophenyl)-4-(5-(phenylethynyl)
pyridin-3-yl)oxazolidin-2-one and (4R,5R)-5-(4-
chlorophenyl)-4-(5-(phenylethynyl)pyridin-3-yl)
oxazolidin-2-one Prepared according to the same procedure as (4R,5R)-5-(3-fluorophenyl)-4-(5-(phenylethynyl)pyridin-3-yl)oxazolidin-2-one, starting with diethyl-4-chlorobenzylphosphonate. $^1$H NMR (CDCl$_3$, 500 MHz) δ: 8.80 (s, 1H), 8.42 (s, 1H), 7.89 (t, J=2.1 Hz, 1H), 7.55-7.63 (m, 2H), 7.38-7.46 (m, 5H), 7.27 (d, J=8.5 Hz, 2H), 6.18 (s, 1H), 5.30 (d, J=7.3 Hz, 1H), 4.80 (d, J=7.6 Hz, 1H). $^{13}$C-NMR (CDCl$_3$, 126 MHz) δ: 158.3, 153.1, 146.9, 136.3, 135.7, 134.9, 133.4, 131.9, 129.6, 129.3, 128.7, 127.4, 122.1, 121.5, 94.3, 85.1, 62.6. Mass spec.: 374.8 (MH)$^+$. Enantiomers were resolved by Prep HPLC (Chiralpak AD 2 1×250 mm, 10 um, 25% B isocratic, flow rate: 15 mL/min, UV 220, 75 min run, solvent A: 0.1% diethylamine/heptane, solvent B: ethanol). Enantiomer 1=first enantiomer to elute from Prep (Example 359). Enantiomer 2=second enantiomer to elute from Prep (Example 360).

Example 361 and Example 362

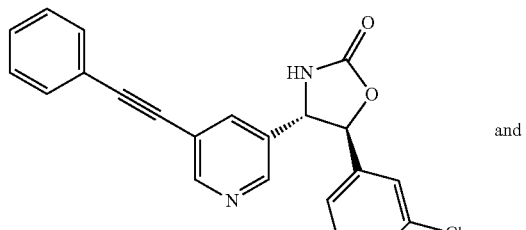

and

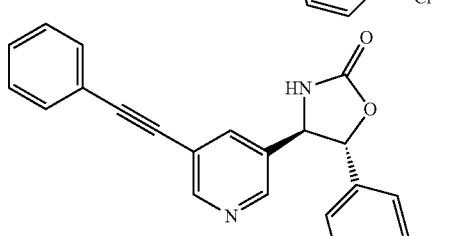

(4S,5S)-5-(3-Chlorophenyl)-4-(5-(phenylethynyl)
pyridin-3-yl)oxazolidin-2-one and (4R,5R)-5-(3-
chlorophenyl)-4-(5-(phenylethynyl)pyridin-3-yl)
oxazolidin-2-one Prepared according to the same procedure as (4R,5R)-5-(3-fluorophenyl)-4-(5-(phenylethynyl)pyridin-3-yl)oxazolidin-2-one, starting with 1-(bromomethyl)-3-chlorobenzene. ¹H NMR (CDCl₃, 500 MHz) δ: 8.81 (br. s., 1H), 8.43 (br. s., 1H), 7.91 (t, J=2.0 Hz, 1H), 7.54-7.64 (m, 2H), 7.36-7.47 (m, 6H), 7.13-7.21 (m, 1H), 6.39 (s, 1H), 5.30 (d, J=7.3 Hz, 1H), 4.83 (d, J=7.3 Hz, 1H). ¹³C-NMR (CDCl₃, 126 MHz) δ: 158.3, 153.1, 146.9, 138.6, 136.3, 135.4, 133.5, 131.9, 130.6, 129.9, 129.3, 128.7, 126.1, 124.1, 122.1, 121.5, 94.2, 85.1, 84.9, 62.4, 53.6. Mass spec.: 374.8 (MH)⁺. Enantiomers were resolved by Prep HPLC (Chiralpak AD 21×250 mm, 10 um, 25% B isocratic, flow rate: 15 mL/min, UV 220, 60 min run, solvent A: 0.1% diethylamine/heptane, solvent B: ethanol). Enantiomer 1=first enantiomer to elute from Prep (Example 361). Enantiomer 2=second enantiomer to elute from Prep (Example 362).

Example 363 and Example 364

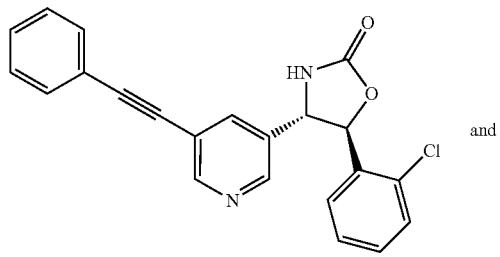

and

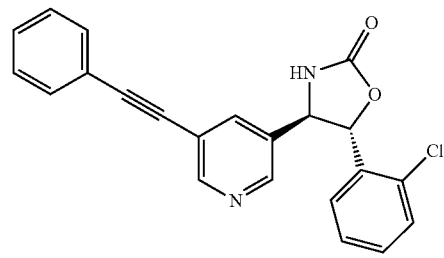

(4S,5S)-5-(2-Chlorophenyl)-4-(5-(phenylethynyl)pyridin-3-yl)oxazolidin-2-one and (4R,5R)-5-(2-chlorophenyl)-4-(5-(phenylethynyl)pyridin-3-yl)oxazolidin-2-one Prepared according to the same procedure as (4R,5R)-5-(3-fluorophenyl)-4-(5-(phenylethynyl)pyridin-3-yl)oxazolidin-2-one, starting with 1-(bromomethyl)-2-chlorobenzene. ¹H NMR (CDCl₃, 500 MHz) δ: 8.79 (d, J=1.5 Hz, 1H), 8.55 (d, J=2.1 Hz, 1H), 7.98 (t, J=2.1 Hz, 1H), 7.56-7.62 (m, 3H), 7.36-7.48 (m, 6H), 6.08 (br. s., 1H), 5.77 (d, J=4.6 Hz, 1H), 4.78 (d, J=4.6 Hz, 1H). ¹³C-NMR (CDCl₃, 126 MHz) δ: 158.5, 152.9, 147.1, 136.3, 135.4, 134.8, 131.9, 131.7, 130.5, 130.3, 129.2, 128.6, 127.7, 127.0, 122.2, 121.3, 94.0, 85.3, 82.1, 61.2. Mass spec.: 374.8 (MH)⁺. Enantiomers were resolved by Prep HPLC (Chiralpak AD 21×250 mm, 10 um, 25% B isocratic, flow rate: 15 mL/min, UV 220, 55 min run, solvent A: 0.1% diethylamine/heptane, solvent B: ethanol).

Enantiomer 1=first enantiomer to elute from Prep (Example 363). Enantiomer 2=second enantiomer to elute from Prep (Example 364).

Example 365

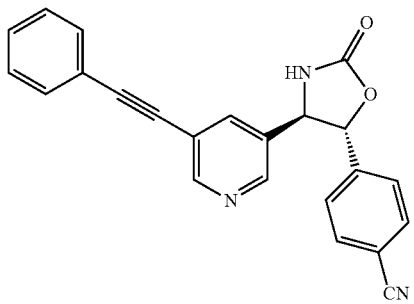 [SMILES: N#Cc1ccc([C@H]2OC(=O)N[C@@H]2c2cncc(C#Cc3ccccc3)c2)cc1]

4-((4R,5R)-2-Oxo-4-(5-(phenylethynyl)pyridin-3-yl)oxazolidin-5-yl)benzonitrile

Prepared according to the same procedure as (4R,5R)-5-(3-fluorophenyl)-4-(5-(phenylethynyl)pyridin-3-yl)oxazolidin-2-one, starting with 4-(bromomethyl)benzonitrile. ¹H NMR (CDCl₃, 500 MHz) δ: 8.80 (d, J=1.8 Hz, 1H), 8.44 (d, J=2.1 Hz, 1H), 7.90 (t, J=2.0 Hz, 1H), 7.75 (d, J=8.5 Hz, 2H), 7.53-7.63 (m, 2H), 7.35-7.48 (m, 5H), 5.39 (d, J=7.3 Hz, 1H), 4.77 (d, J=7.3 Hz, 1H). ¹³C-NMR (CDCl₃, 126 MHz) δ: 158.1, 153.2, 146.8, 141.7, 136.4, 133.3, 133.2, 131.9, 129.4, 128.7, 126.4, 122.0, 121.6, 118.1, 113.6, 94.5, 85.0, 84.5, 62.4, 43.8, 15.0. Mass spec.: 365.9 (MH)⁺. The sample was further purified by SFC Prep HPLC (Chiralpak AS-H, 20% MeOH in CO2).

Example 366 and Example 367

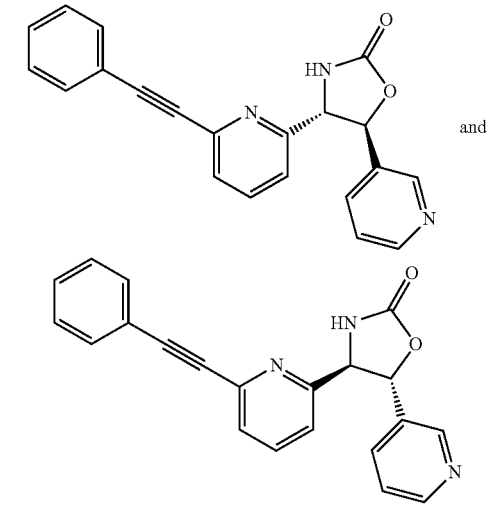

(4S,5S)-4-(6-(Phenylethynyl)pyridin-2-yl)-5-(pyridin-3-yl)oxazolidin-2-one and (4R,5R)-4-(6-(phenylethynyl)pyridin-2-yl)-5-(pyridin-3-yl)oxazolidin-2-one Prepared according to the same procedure as (4R,5R)-5-(3-fluorophenyl)-4-(5-(phenylethynyl)pyridin-3-yl)oxazolidin-2-one, starting with diethyl (6-bromopyridin-2-yl)methylphosphonate and nicotinaldehyde. ¹H NMR (CDCl₃, 500 MHz) δ: 8.78 (d, J=2.1 Hz, 1H), 8.67 (dd, J=4.9, 1.5 Hz, 1H), 7.92 (dt, J=7.9, 1.7 Hz, 1H), 7.78-7.84 (m, 1H), 7.62-7.67 (m, 2H), 7.58 (d, J=7.6 Hz, 1H), 7.51 (d, J=7.9 Hz, 1H), 7.38-7.45 (m, 4H), 5.84 (br. s., 1H), 5.47 (d, J=5.2 Hz, 1H), 5.35 (d, J=5.5 Hz, 1H). ¹³C-NMR (CDCl₃, 126 MHz) δ: 157.9, 157.1, 150.5, 148.6, 143.7, 137.6, 134.2, 132.2, 129.4, 128.6, 127.5, 124.2, 122.0, 120.0, 90.2, 88.3, 84.5, 77.7, 59.4. Mass spec.: 342.2 (MH)⁺. Enantiomers were resolved by Prep HPLC (Chiralpak AD 21×250 mm, 10 um, 55% B isocratic, flow rate: 15 mL/min, UV 220, 30 min run, solvent A: 0.1% diethylamine/heptane, solvent B: ethanol). Enantiomer 1=first enantiomer to elute from Prep (Example 366). Enantiomer 2=second enantiomer to elute from Prep (Example 367).

Example 368 and Example 369

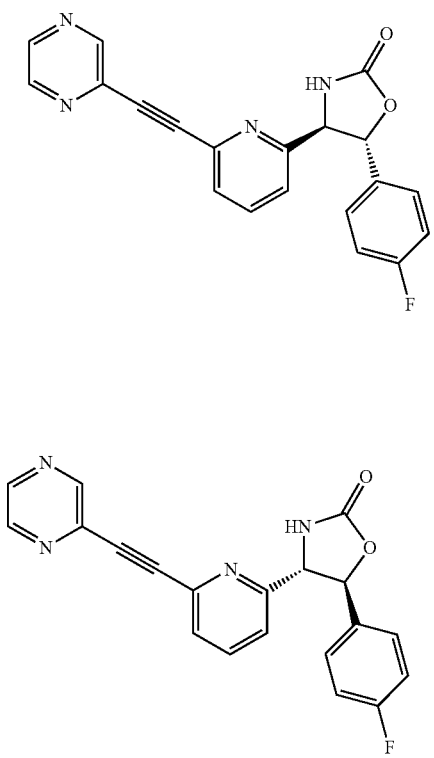

(4R,5R)-5-(4-Fluorophenyl)-4-(6-(pyrazine-2-ylethynyl)pyridin-2-yl)oxazolidin-2-one and (4S,5S)-5-(4-fluorophenyl)-4-(6-(pyrazine-2-ylethynyl)pyridin-2-yl)oxazolidin-2-one Prepared according to the same procedure as (+)-(4R,5R)-5-(3-Methoxyphenyl)-4-(3-(phenylethynyl)phenyl)oxazolidin-2-one, starting with (4R,5R)-4-(6-bromopyridin-2-yl)-5-(3-fluorophenyl)oxazolidin-2-one, (4S,5S)-4-(6-bromopyridin-2-yl)-5-(3-fluorophenyl)oxazolidin-2-one and 2-bromopyrazine. ¹H NMR (CDCl₃, 500 MHz) δ: 8.89 (d, J=1.5 Hz, 1H), 8.64-8.70 (m, 1H), 8.60 (d, J=2.7 Hz, 1H), 7.87 (t, J=7.8 Hz, 1H), 7.68 (d, J=7.6 Hz, 1H), 7.44-7.52 (m, 3H), 7.15 (t, J=8.5 Hz, 2H), 5.96 (br. s., 1H), 5.62 (d, J=5.8 Hz, 1H), 4.96 (d, J=5.5 Hz, 1H). ¹³C-NMR (CDCl₃, 126 MHz) δ: 163.2 (d, J=248.6), 159.1, 158.4, 148.3, 144.8, 143.9, 142.5, 139.4, 138.0, 133.9, 128.0, 127.8, 120.8, 116.2, 116.1, 91.0, 85.8, 83.3, 77.7, 64.9, 58.6. Mass spec.: 361.1 (MH)⁺. Enantiomers were resolved by Prep HPLC (Chiralpak AD 2 1×250 mm, 10 um, 50% B isocratic, flow rate: 15 mL/min, UV 254, 30 min run, solvent A: 0.1% diethylamine/heptane, solvent B: ethanol). Enantiomer 1=first enantiomer to elute from Prep (Example 368). Enantiomer 2=second enantiomer to elute from Prep (Example 369).

Example 370 and Example 371

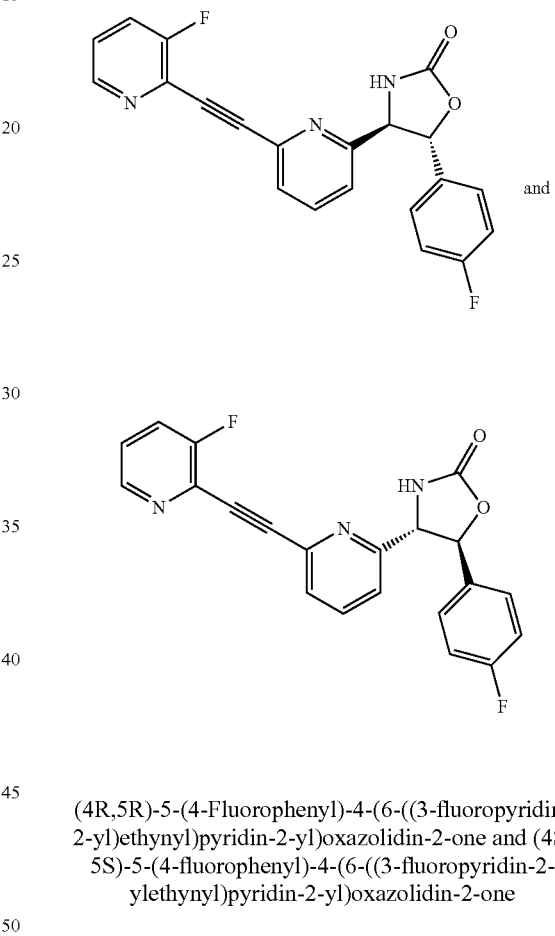

(4R,5R)-5-(4-Fluorophenyl)-4-(6-((3-fluoropyridin-2-yl)ethynyl)pyridin-2-yl)oxazolidin-2-one and (4S,5S)-5-(4-fluorophenyl)-4-(6-((3-fluoropyridin-2-ylethynyl)pyridin-2-yl)oxazolidin-2-one Prepared according to the same procedure as (+)-(4R,5R)-5-(3-Methoxyphenyl)-4-(3-(phenylethynyl)phenyl)oxazolidin-2-one, starting with (4R,5R)-4-(6-bromopyridin-2-yl)-5-(3-fluorophenyl)oxazolidin-2-one, (4S,5S)-4-(6-bromopyridin-2-yl)-5-(3-fluorophenyl)oxazolidin-2-one and 2-bromo-3-fluoropyridine. ¹H NMR (CDCl₃, 500 MHz) δ: 8.52 (dt, J=4.7, 1.3 Hz, 1H), 7.83 (t, J=7.8 Hz, 1H), 7.60-7.68 (m, 1H), 7.36-7.57 (m, 5H), 7.08-7.18 (m, 2H), 6.54 (br. s., 1H), 5.63 (d, J=5.5 Hz, 1H), 4.97 (d, J=5.5 Hz, 1H). ¹³C-NMR (CDCl₃, 126 MHz) δ: 164.1 (d, J=247.6), 160.6 (d, J=264), 159.2, 158.7, 146.2, 142.6, 137.9, 134.1, 131.6, 127.8, 127.7, 125.2, 123.6, 123.5, 120.5, 116.1, 116.0, 93.2, 83.2, 82.6, 64.8, 58.6. Mass spec.: 378.1 (MH)⁺. Enantiomers were resolved by Prep HPLC (Chiralpak AD 21×250 mm, 10 um, 40% B isocratic, flow rate: 15 mL/min, UV 220, 40 min run, solvent A: 0.1% diethylamine/heptane, solvent B: ethanol). Enantiomer 1=first enantiomer to elute from Prep (Example 370). Enantiomer 2=second enantiomer to elute from Prep (Example 371).

Example 372 and Example 373

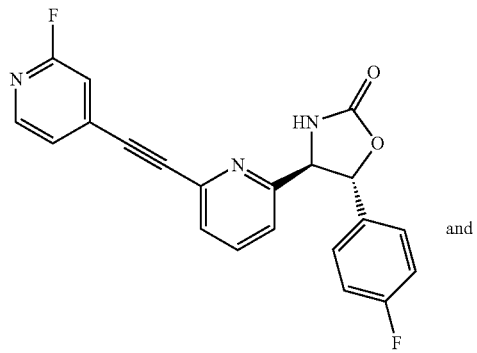

and

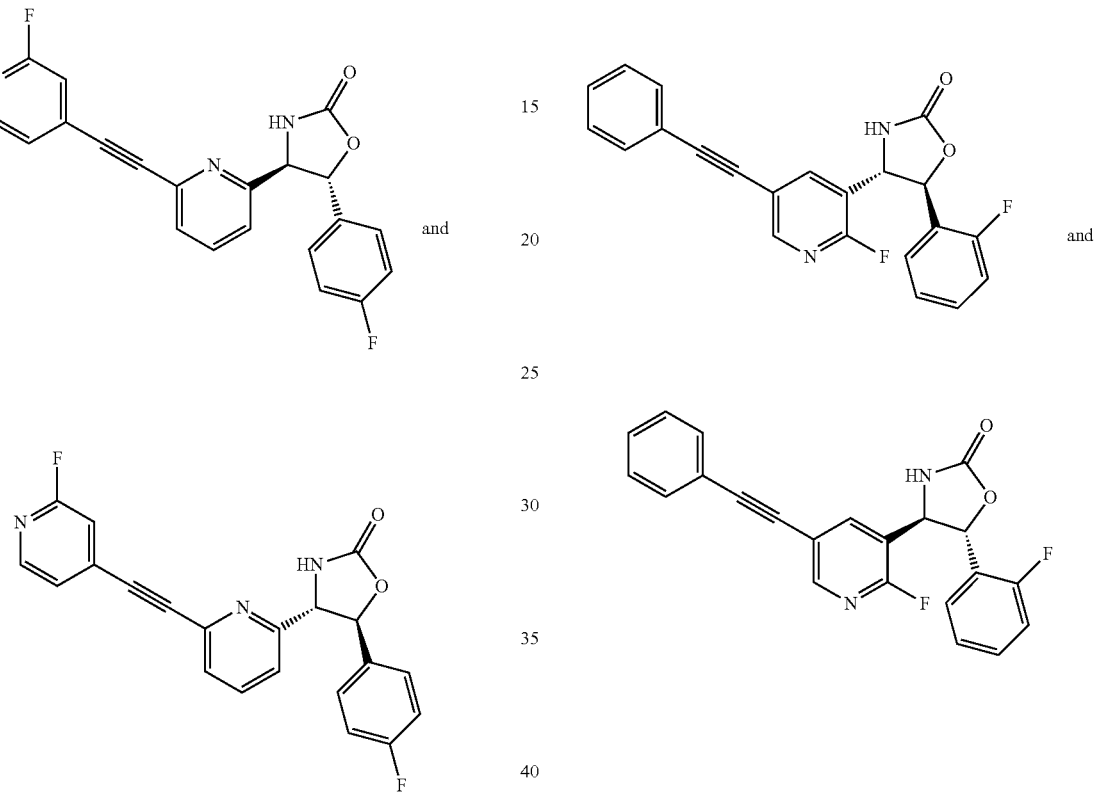

(4R,5R)-5-(4-Fluorophenyl)-4-(6-((2-fluoropyridin-4-yl)ethynyl)pyridin-2-yl)oxazolidin-2-one and (4S,5S)-5-(4-fluorophenyl)-4-(6-((2-fluoropyridin-4-yl)ethynyl)pyridin-2-yl)oxazolidin-2-one Prepared according to the same procedure as (+)-(4R,5R)-5-(3-Methoxyphenyl)-4-(3-(phenylethynyl)phenyl)oxazolidin-2-one, starting with (4R,5R)-4-(6-bromopyridin-2-yl)-5-(3-fluorophenyl)oxazolidin-2-one, (4S,5S)-4-(6-bromopyridin-2-yl)-5-(3-fluorophenyl)oxazolidin-2-one and 4-bromo-2-fluoropyridine. $^1$H NMR (CDCl$_3$, 500 MHz) δ: 8.29 (d, J=5.2 Hz, 1H), 7.87 (t, J=7.8 Hz, 1H), 7.61 (d, J=7.6 Hz, 1H), 7.43-7.51 (m, 3H), 7.38 (d, J=5.2 Hz, 1H), 7.09-7.21 (m, 3H), 6.24 (s, 1H), 5.61 (d, J=5.5 Hz, 1H), 4.96 (d, J=5.8 Hz, 1H). $^{13}$C-NMR (CDCl$_3$, 126 MHz) δ: 163.7 (d, J=239), 163.2 (d, J=248.6), 148.2, 148.1, 142.5, 138.1, 135.1, 133.9, 127.8, 123.8, 120.9, 116.3, 116.1, 112.3, 112.0, 93.0, 85.7, 83.3, 64.9, 58.6, 53.6. Mass spec.: 378.1 (MH)$^+$. Enantiomers were resolved by Prep HPLC (Chiralcel OD 21×250 mm, 10 um, 15% B isocratic, flow rate: 15 mL/min, UV 220, 50 min run, solvent A: 0.1% diethylamine/heptane, solvent B: ethanol). Enantiomer 1=first enantiomer to elute from Prep (Example 372). Enantiomer 2=second enantiomer to elute from Prep (Example 373).

Example 374 and Example 375

(4S,5S)-4-(2-Fluoro-5-(phenylethynyl)pyridin-3-yl)-5-(2-fluorophenyl)oxazolidin-2-one and (4R,5R)-4-(2-fluoro-5-(phenylethynyl)pyridin-3-yl)-5-(2-fluorophenyl)oxazolidin-2-one Prepared according to the same procedure as (4S,5S)-4-(6-(phenylethynyl)pyridin-2-yl)-5-(pyridin-3-yl)oxazolidin-2-one and (4R,5R)-4-(6-(phenylethynyl)pyridin-2-yl)-5-(pyridin-3-yl)oxazolidin-2-one, starting with diethyl (5-bromo-2-fluoropyridin-3-yl)methylphosphonate and 2-fluorobenzaldehyde. $^1$H NMR (CDCl$_3$, 500 MHz) δ: 8.35 (d, J=1.5 Hz, 1H), 8.12 (dd, J=8.9, 2.1 Hz, 1H), 7.45-7.61 (m, 3H), 7.34-7.44 (m, 4H), 7.19-7.27 (m, 1H), 7.08-7.16 (m, 1H), 5.59 (d, J=5.8 Hz, 1H), 5.09 (d, J=5.8 Hz, 1H). $^{13}$C-NMR (CDCl$_3$, 126 MHz) δ: 160.1 (d, J=247.6), 159.8 (d, J=243.8), 159.1, 150.4, 150.3, 141.1, 131.8, 131.3, 129.2, 128.6, 127.6, 124.9, 124.7, 122.1, 121.5, 121.3, 119.5, 116.2, 116.0, 93.5, 84.2, 79.6, 57.5. Mass spec.: 377.1 (MH)$^+$. Enantiomers were resolved by Prep HPLC (Chiralpak AD 2 1×250 mm, 10 um, 45% B isocratic, flow rate: 15 mL/min, UV 220, 40 min run, solvent A: 0.1% diethylamine/heptane, solvent B:

ethanol). Enantiomer 1=first enantiomer to elute from Prep (Example 374). Enantiomer 2=second enantiomer to elute from Prep (Example 375).

Example 376 and Example 377 and Example 378 and Example 379

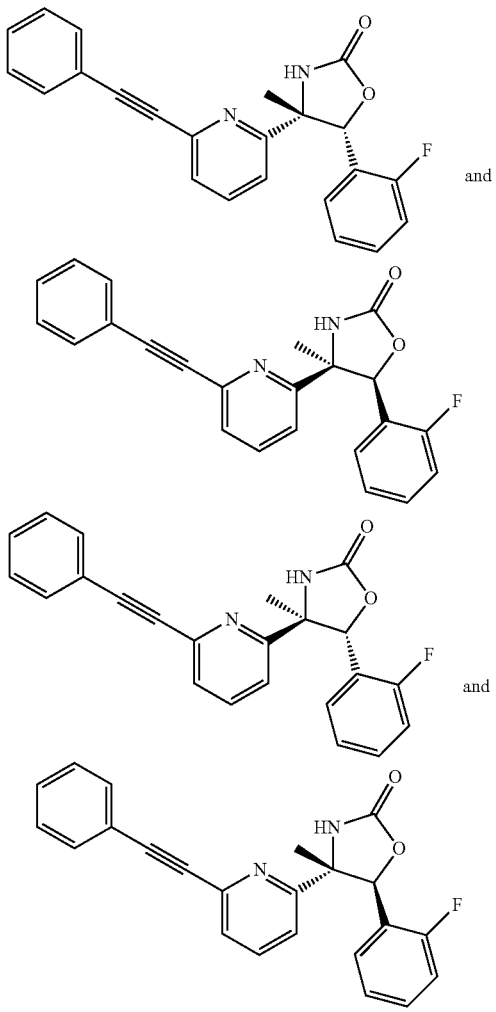

and and (4S,5R)-5-(2-Fluorophenyl)-4-methyl-4-(6-(phenyl-ethynyl)pyridin-2-yl)oxazolidin-2-one and (4R,5S)-5-(2-fluorophenyl)-4-methyl-4-(6-(phenylethynyl)pyridin-2-yl)oxazolidin-2-one, (4R,5R)-5-(2-Fluorophenyl)-4-methyl-4-(6-(phenylethynyl)pyridin-2-yl)oxazolidin-2-one and (4S,5S)-5-(2-fluorophenyl)-4-methyl-4-(6-(phenylethynyl)pyridin-2-yl)oxazolidin-2-one Prepared according to the same procedure as (+)-(4R,5R)-5-(3-methoxyphenyl)-4-(3-(phenylethynyl)phenyl)oxazolidin-2-one, starting with a mixture of 4-(6-bromopyridin-2-yl)-5-(2-fluorophenyl)-4-methyloxazolidin-2-one and 4-(6-chloropyridin-2-yl)-5-(2-fluorophenyl)-4-methyloxazolidin-2-one. The material was purified by prep HPLC (Phenomenex Luna Column, TFA/MeOH) to isolate the two major fractions (F1=first to elute, F2=second to elute). F1(cis): $^1$H NMR (CDCl$_3$, 500 MHz) δ: 7.57-7.64 (m, 2H), 7.36-7.44 (m, 4H), 7.23 (d, J=7.3 Hz, 1H), 7.10-7.17 (m, 1H), 6.90-7.02 (m, 3H), 6.84-6.89 (m, 1H), 6.43 (s, 1H), 5.96 (s, 1H), 2.04 (s, 3H). $^{13}$C-NMR (CDCl$_3$, 126 MHz) δ: 159.8 (d, J=247.6), 159.4, 159.1, 142.5, 136.3, 132.2, 130.3, 129.2, 128.5, 127.7, 126.0, 124.0, 122.6, 122.2, 119.6, 115.1, 114.9, 89.6, 88.4, 82.5, 66.4, 60.6, 27.1. Mass spec.: 373.2 (MH)$^+$. Enantiomers were resolved by Prep HPLC (Chiralcel OD 21×250 mm, 10 um, 13% B isocratic, flow rate: 15 mL/min, UV 220, 60 min run, solvent A: 0.1% diethylamine/heptane, solvent B: ethanol). Enantiomer 1=first enantiomer to elute from Prep (Example 376). Enantiomer 2=second enantiomer to elute from Prep (Example 377). F2(trans): $^1$H NMR (CDCl$_3$, 500 MHz) δ: 7.80 (t, J=7.8 Hz, 1H), 7.63-7.69 (m, 2H), 7.50-7.60 (m, 3H), 7.38-7.45 (m, 4H), 7.29-7.32 (m, 1H), 7.11-7.18 (m, 1H), 6.17-6.26 (m, 2H), 1.34 (s, 3H). $^{13}$C-NMR (CDCl$_3$, 126 MHz) δ: 161.0 (d, J=246.7), 159.1, 158.5, 143.0, 137.5, 132.2, 130.7, 129.3, 128.5, 128.1, 126.6, 124.7, 123.3, 122.2, 118.5, 115.7, 115.4, 89.7, 88.9, 81.2, 65.2, 53.5, 14.2. Mass spec.: 373.2 (MH)$^+$. Enantiomers were resolved by Prep HPLC (Chiralcel OJ 21×250 mm, 10 um, 15% B isocratic, flow rate: 15 mL/min, UV 220, 50 min run, solvent A: 0.1% diethylamine/heptane, solvent B: ethanol). Enantiomer 1=first enantiomer to elute from Prep (Example 378). Enantiomer 2=second enantiomer to elute from Prep (Example 379).

Example 380

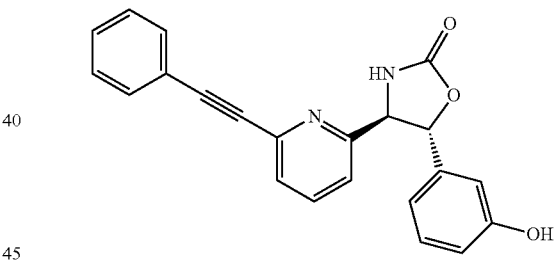

(4R,5R)-5-(3-Hydroxyphenyl)-4-(3-phenylethynyl) phenyl)oxazolidin-2-one (4R,5R)-5-(3-Methoxyphenyl)-4-(3-(phenylethynyl)phenyl)oxazolidin-2-one in dichloromethane (3 mL) was cooled to −78° C. under nitrogen, boron tribromide (0.406 mL, 0.406 mmol) was added slowly. The reaction mixture was stirred at −78° C. for one hour and then allowed to warm to room temperature overnight. The reaction was quenched by addition of a 2% sodium carbonate solution and extracted with dichloromethane. The combined organic layers were washed with brine, dried over magnesium sulfate, filtered, and concentrated. Biotage purification eluting with 40% ethyl acetate in hexane gave 37 mg (71.5% yield). $^1$H NMR (CDCl$_3$, 500 MHz) δ: 7.58 (s, 1H), 7.48-7.54 (m, 3H), 7.44 (s, 1H), 7.31-7.39 (m, 4H), 7.18 (dt, J=7.7, 3.9 Hz, 2H), 7.00 (s, 1H), 6.88 (dd, J=8.0, 1.7 Hz, 1H), 6.64 (d, J=7.6 Hz, 1H), 6.41 (s, 1H), 5.20 (d, J=7.3 Hz, 1H), 4.73 (d, J=7.3 Hz, 1H). $^{13}$C-NMR (CDCl$_3$, 126 MHz) δ: 171.5, 159.6, 157.1, 138.7, 138.5, 132.1, 131.7, 130.2, 129.4, 129.3, 128.6, 128.4, 126.3, 124.3, 122.8, 118.0, 116.7, 112.3, 90.4, 88.7, 86.1, 64.5, 60.6. Mass spec.: 356.2 (MH)+.

Example 381

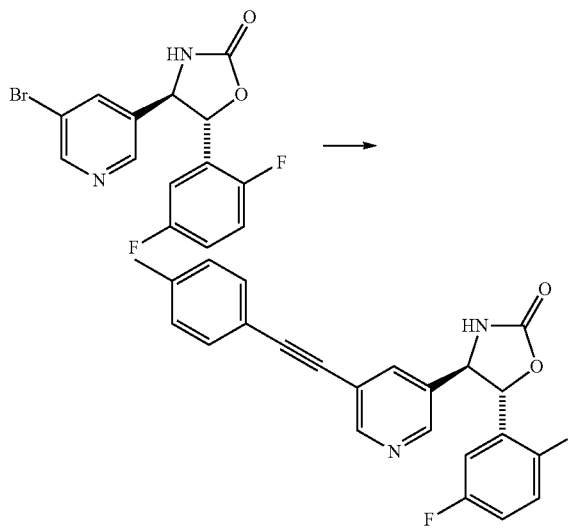

(4R,5R)-5-(2,5-Difluorophenyl)-4-(5-(p-tolylethynyl)pyridin-3-yl)oxazolidin-2-one To a mixture of (4R,5R)-4-(5-bromopyridin-3-yl)-5-(2,5-difluorophenyl)oxazolidin-2-one (33 mg, 0.093 mmol) in triethylamine (Volume: 1 mL) was bubbled nitrogen for 20 min followed by the addition of 1-ethynyl-4-methylbenzene (13 mg; 0.112 mmol) bis(triphenylphosphine)palladium (II) chloride (4.89 mg, 6.97 μmol), triphenylphosphine (4.39 mg, 0.017 mmol), and copper (I) iodide (5.31 mg, 0.028 mmol). After 5 min bubbling nitrogen, the vessel was capped and placed in a 70° C. bath. After 18 h, the reaction was allowed to cool to ambient temperature, concentrated and dissolved in 0.25 mL dimethylformamide/0.5 mL methanol and purified via preparative liquid chromatography (Sunfire C18 OBD 30×100 mm 5 μm, A=95% H₂O/5% Acetonitrile, B=95% Acetonitrile/5% H₂O, Modifier 10 mM Ammonium Acetate, 0.00 min=20% B, 8.0 min=100% B, 13.0 min=100% B, Flow rate=40 mL/min) providing (4R,5R)-5-(2,5-difluorophenyl)-4-(5-(p-tolylethynyl)pyridin-3-yl)oxazolidin-2-one (25 mg; 67%) as a colorless oil. $^1$H NMR (500 MHz, CDCl$_3$) δ ppm 8.81 (1H, br. s.), 8.54 (1H, br. s.), 7.90 (1H, br. s.), 7.34-7.55 (3H, m), 7.20-7.32 (1H, m), 7.17 (1H, d, J=7.93 Hz), 6.93-7.13 (2H, m), 6.46 (1H, br. s.), 5.53 (1H, d, J=5.19 Hz), 4.82 (1H, d, J=4.88 Hz), 2.38 (3H, s). Mass Spectral Anal. Calcd. for [M+H]+ C$_{23}$H$_{16}$F$_2$N$_2$O$_2$: 391.12. found 391.08. Chiral HPLC retention time (Chiralpak AS-H analytical column, 4.6×250 mm, 5 μm, Mobile Phase: A=100% Heptane with 0.1% Diethylamine, B=100% Ethanol, Flow rate: 1.0 mL/min, 30% A Isocratic): 3.57 min.

The following examples were prepared using a modification of the procedure describing the preparation of (4R,5R)-5-(2,5-difluorophenyl)-4-(5-(p-tolylethynyl)pyridin-3-yl)oxazolidin-2-one employing the appropriately substituted commercially available aryl acetylene:

| Number | Structure | Analytical Data |
|---|---|---|
| Example 382 | (4R,5R)-5-(2,5-difluorophenyl)-4-(5-((4-methoxyphenyl)ethynyl)pyridin-3-yl)oxazolidin-2-one | $^1$H NMR (500 MHz, CDCl$_3$) δ ppm 8.80 (1 H, br. s.), 8.53 (1 H, br. s.), 7.89 (1 H, br. s.), 7.49 (2 H, d, J = 8.85 Hz), 7.15-7.34 (1 H, m), 7.00-7.15 (2 H, m), 6.89 (2 H, d, J = 8.55 Hz), 6.25 (1 H, br. s.), 5.54 (1 H, d, J = 4.88 Hz), 4.82 (1 H, d, J = 4.27 Hz), 3.84 (3 H, s). Mass Spectral Anal. Calcd. for [M + H]+ C$_{23}$H$_{16}$F$_2$N$_2$O$_3$: 407.11; found 407.00. Chiral HPLC retention time (Chiralpak AS-H analytical column, 4.6 × 250 mm, 5 1μm, Mobile Phase: A = 100% Heptane with 0.1% Diethylamine, B = 100% Ethanol, Flow rate. 1 0 mL/min, 30% A Isocratic): 5.09 min. |

| Number | Structure | Analytical Data |
|---|---|---|
| Example 383 | 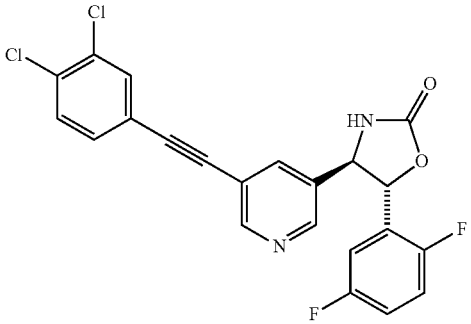 [SMILES: O=C1N[C@H](c2cncc(C#Cc3ccc(Cl)c(Cl)c3)c2)[C@@H](c2cc(F)ccc2F)O1]<br>(4R,5R)-4-(5-((3,4-dichlorophenyl)ethynyl)pyridin-3-yl)-5-(2,5-difluorophenyl)oxazolidin-2-one | $^1$H NMR (500 MHz, CDCl$_3$) δ ppm 8.78 (1 H, s), 8.52 (1 H, s), 7.91 (1 H, s), 7.66 (1 H, d, J = 1.83 Hz), 7.41-7.53 (2 H, m), 7.35-7.43 (1 H, m), 7.32 (1 H, t, J = 7.32 Hz), 7.03-7.16 (1 H, m), 5.66 (1 H, br. s.), 5.55 (1 H, d, J = 5.49 Hz), 4.81 (1 H, d, J = 5.19 Hz), Mass Spectral Anal. Calcd. for [M + H]$^+$ C$_{22}$H$_{12}$Cl$_2$F$_2$N$_2$O$_2$: 445.02; found 445.10. |
| Example 384 | 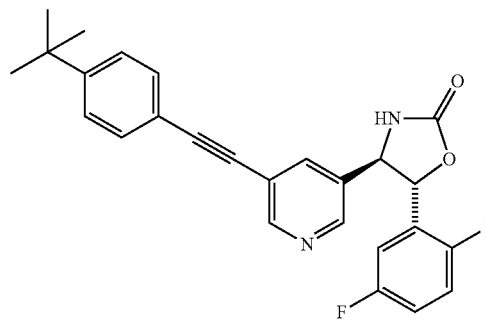<br>(4R,5R)-4-(5-((4-tert-butylphenyl)ethynyl)pyridin-3-yl)-5-(2,5-difluorophenyl)oxazolidin-2-one | $^1$H NMR (500 MHz, CDCl$_3$) δ ppm 8.84 (1 H, br. s.), 8.55 (1 H, br. s.), 7.91 (1 H, br. s.), 7.45-7.54 (2 H, m), 7.41 (2 H, d, J = 8.55 Hz), 7.20-7.28 (1 H, m), 7.03-7.15 (2 H, m), 5.58-5.70 (1 H, m), 5.56 (1 H, d, J = 5.49 Hz), 4.82 (1 H, d, J = 5.19 Hz), 1.33 (9 H, s), Mass Spectral Anal. Calcd. for [M + H]$^+$ C$_{26}$H$_{22}$F$_2$N$_2$O$_2$: 433.16; found 433.2. Chiral HPLC retention time (Chiralpak AS-H analytical column, 4.6 × 100 mm, 51.μm, Mobile Phase: A = 100% Heptane with 0.1% Diethylamine, B = 100% Ethanol, Flow rate. 1 0 mL/min, 50% A Isocratic): 2.20 min |
| Example 385 | 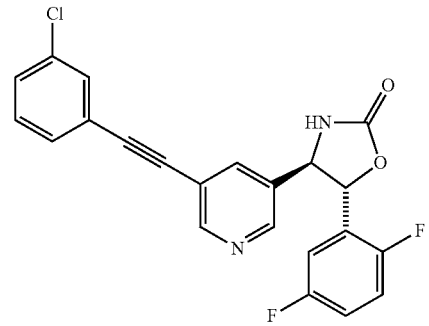 [SMILES: O=C1N[C@H](c2cncc(C#Cc3cccc(Cl)c3)c2)[C@@H](c2cc(F)ccc2F)O1]<br>(4R,5R)-4-(5-((3-chlorophenyl)ethynyl)pyridin-3-yl)-5-(2,5-difluorophenyl)oxazolidin-2-one | $^1$H NMR (500 MHz, CDCl$_3$) δ ppm 8.79 (1 H, br. s.), 8.52 (1 H, br. s.), 7.91 (1 H, s), 7.56 (1 H, t, J = 1.53 Hz), 7.42-7.48 (1 H, m), 7.35-7.41 (1 H, m), 7.29-7.35 (1 H, m), 7.20-7.29 (1 H, m), 7.06-7.15 (2 H, m), 5.56 (1 H, d, J = 5.49 Hz), 5.36 (1 H, s), 4.82 (1 H, d, J = 5.49 Hz), Mass Spectral Anal. Calcd. for [M + H]$^+$ C$_{22}$H$_{13}$ClF$_2$N$_2$O$_2$: 411.06; found 411.20. Chiral HPLC retention time (Chiralpak AS-H analytical column, 4.6 × 100 mm, 51μm, Mobile Phase: A = 100% Heptane with 0.1% Diethylamine, B = 100% Ethanol, Flow rate. 1 0 mL/min, 40% A Isocratic): 3.05 min |

-continued

| Number | Structure | Analytical Data |
|---|---|---|
| Example 386 | 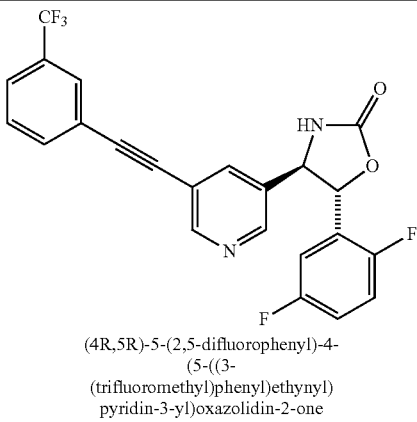<br>(4R,5R)-5-(2,5-difluorophenyl)-4-(5-((3-(trifluoromethyl)phenyl)ethynyl)pyridin-3-yl)oxazolidin-2-one | $^1$H NMR (500 MHz, CDCl$_3$) δ ppm 8.81(1 H, d, J = 1.83 Hz), 8.53 (1 H, d, J = 1.83 Hz), 7.94 (1 H, t, J = 2.14 Hz), 7.84 (1 H, s), 7.74 (1 H, d, J = 7.63 Hz), 7.65 (1 H, d, J = 7.63 Hz), 7.46-7.59 (1 H, m), 7.16-7.34 (1 H, m), 7.03-7.18 (2 H, m), 5.56 (1 H, d, J = 5.49 Hz), 5.37 (1 H, s), 4.82 (1 H, d, J = 5.49 Hz), Mass Spectral Anal. Calcd. for [M + H]$^+$ C$_{23}$H$_{13}$F$_5$N$_2$O$_2$: 445.09; found 445.20 .Chiral HPLC retention time (Chiralpak AS-H analytical column, 4.6 × 100 mm, 5 µm, Mobile Phase: A = 100% Heptane with 0.1% Diethylamine, B = 100% Ethanol, Flow rate. 1.0 mL/min, 40% A Isocratic): 2.40 min |
| Example 387 | 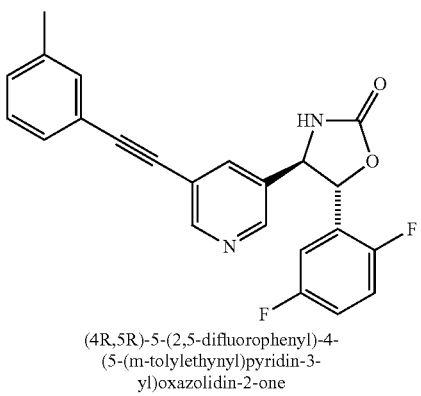<br>(4R,5R)-5-(2,5-difluorophenyl)-4-(5-(m-tolylethynyl)pyridin-3-yl)oxazolidin-2-one | $^1$H NMR (500 MHz, CDCl$_3$) δ ppm 8.77 (1 H, br. s.), 8.51 (1 H, br. s.), 7.93 (1 H, s), 7.30-7.45 (2 H, m), 7.15-7.30 (3 H, m), 6.98-7.15 (2 H, m), 6.61 (1 H, s), 5.54 (1 H, d, J = 5.49 Hz), 4.84 (1 H, d, J = 5.49 Hz), 2.36 (3 H, s), Mass Spectral Anal. Calcd. for [M + H]$^+$ C$_{23}$H$_{16}$F$_2$N$_2$O$_2$: 391.12; found 391.20 |
| Example 388 | 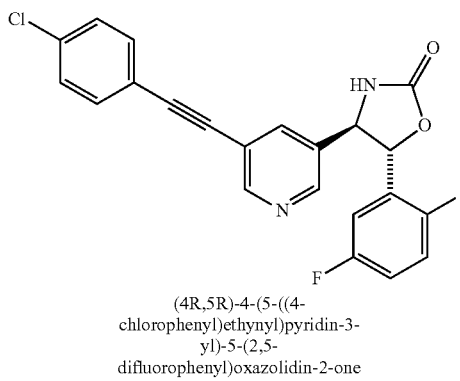<br>(4R,5R)-4-(5-((4-chlorophenyl)ethynyl)pyridin-3-yl)-5-(2,5-difluorophenyl)oxazolidin-2-one | $^1$H NMR (500 MHz, CDCl$_3$) δ ppm 8.85 (1 H, br. s.), 8.31-8.70 (1 H, br. s.), 7.92 (1 H, br. s.), 7.48 (2 H, d, J = 8.24 Hz), 7.36 (2 H, d, J = 8.55 Hz), 7.18-7.30 (1 H, m), 6.97-7.16 (2 H, m), 6.27 (1 H, br. s.), 5.55 (1 H, d, J = 4.88 Hz), 4.84 (1 H, d, J = 4.27 Hz). Mass Spectral Anal. Calcd. for [M + H]$^+$ C$_{22}$H$_{13}$ClF$_2$N$_2$O$_2$: 411.1; found 411.0 |

Example 389

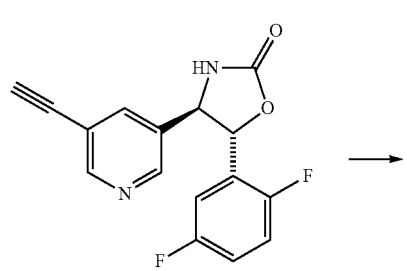

→

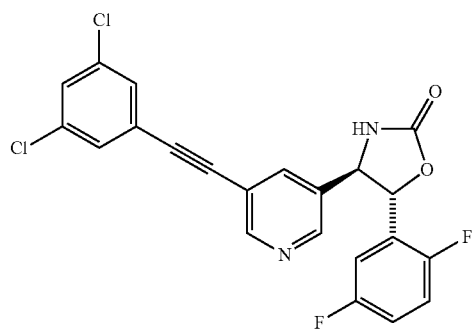

(4R,5R)-4-(5-((3,5-Dichlorophenyl)ethynyl)pyridin-3-yl)-5-(2,5-difluorophenyl)oxazolidin-2-one To a slurry of (4R,5R)-5-(2,5-difluorophenyl)-4-(5-ethynylpyridin-3-yl)oxazolidin-2-one (50 mg, 0.167 mmol) in Triethylamine (Volume: 2 mL) was bubbled nitrogen for 20 min at which time 1-bromo-3,5-dichlorobenzene (49 mg, 0.22 mmol) was added with continued nitrogen bubbling for 5 min before adding bis(triphenylphosphine) palladium (II) chloride (8.8 mg, 0.012 mmol), triphenylphosphine (7.9 mg, 0.030 mmol), and copper (I) iodide (9.5 mg, 0.050 mmol) together in 1 portion. After 5 min additional nitrogen bubbling, the vessel was capped and placed in a 70° C. bath. After 18 h, the reaction was cooled, concentrated and diluted with methanol and purified via preparative liquid chromatography (Sunfire C18 OBD 30×100 mm 5 μm, A=95% H$_2$O/5% Acetonitrile, B=95% Acetonitrile/5% H$_2$O, Modifier 10 mM Ammonium Acetate, 0.00 min=20% B, 8.0 min=100% B, 13.0 min=100% B, Flow rate=40 mL/min) providing (4R,5R)-4-(5-((3,5-dichlorophenyl)ethynyl)pyridin-3-yl)-5-(2,5-difluorophenyl)oxazolidin-2-one (24 mg; 32%) as a colorless oil. $^1$H NMR (500 MHz, CDCl$_3$) δ ppm 8.78 (1H, d, J=1.83 Hz), 8.54 (1H, d, J=1.83 Hz), 7.79-7.97 (1H, m), 7.45 (2H, d, J=1.83 Hz), 7.39 (1H, t, J=1.83 Hz), 7.18-7.32 (2H, m), 7.00-7.18 (1H, m), 5.55 (1H, d, J=5.49 Hz), 5.40 (1H, s), 4.82 (1H, d, J=5.49 Hz), Mass Spectral Anal. Calcd. for [M+H]$^+$ C$_{22}$H$_{12}$Cl$_2$F$_2$N$_2$O$_2$: 445.02. found 445.10.

The following examples were prepared using a modification of the procedure describing the preparation of (4R,5R)-4-(5-((3,5-dichlorophenyl)ethynyl)pyridin-3-yl)-5-(2,5-difluorophenyl)oxazolidin-2-one employing the appropriately substituted commercially available aryl halide:

Example 390

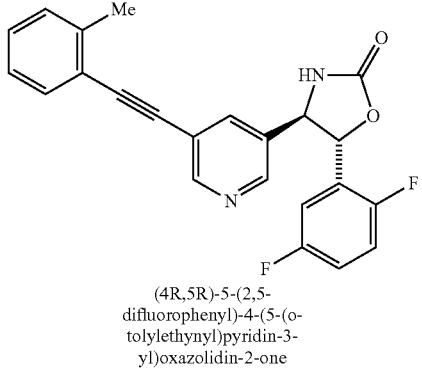

(4R,5R)-5-(2,5-difluorophenyl)-4-(5-(o-tolylethynyl)pyridin-3-yl)oxazolidin-2-one LC/MS (Phenomenex Luna C18 30 × 2 mm 31 μm, A = 90% H$_2$O/10% Acetonitrile, B = 90% Acetonitrile/10% H$_2$O, Modifier 0.1% TFA, 0.00 min = 0% B, 2.0 min = 100% B, 3.0 min = 100% B, Flow rate = 1 mL/min) 1.68 min, Anal. Calcd. for [M + H]$^+$ C$_{23}$H$_{16}$F$_2$N$_2$O$_2$: 391.12; found 391.20

Example 391

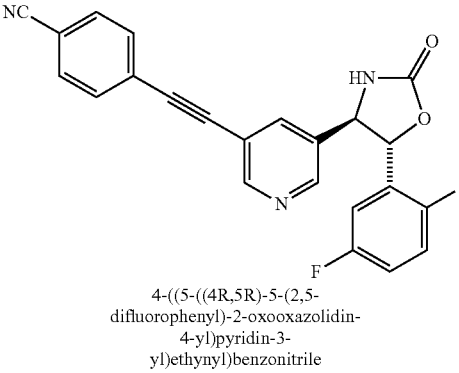

4-((5-((4R,5R)-5-(2,5-difluorophenyl)-2-oxooxazolidin-4-yl)pyridin-3-yl)ethynyl)benzonitrile LC/MS (Phenomenex Luna C18 30 × 2 mm 3 μm, A = 90% H$_2$O/10% Acetonitrile, B = 90% Acetonitrile/10% H$_2$O, Modifier 0.1% TFA, 0.00 min = 0% B, 2.0 min = 100% B, 3.0 min = 100%B, Flow rate = 1 mL/min) 1.56 min, Anal. Calcd. for [M + H]$^+$ C$_{23}$H$_{13}$F$_2$N$_3$O$_2$: 402.1; found 402.2

Example 392

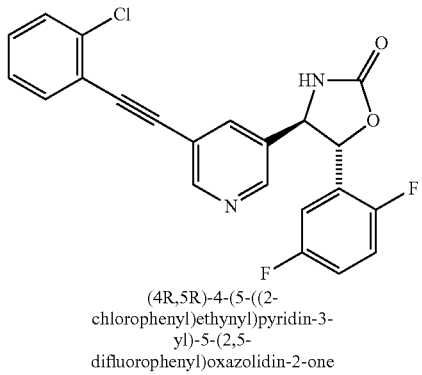

(4R,5R)-4-(5-((2-chlorophenyl)ethynyl)pyridin-3-yl)-5-(2,5-difluorophenyl)oxazolidin-2-one $^1$H NMR (500 MHz, CDCl$_3$) δ ppm 8.85 (2 H, br. s.), 8.23 (1 H, br. s.), 7.60 (1 H, d, J = 7.32 Hz), 7.47 (1 H, d, J = 7.93 Hz), 7.36 (1 H, t, J = 7.63 Hz), 7.19-7.33 (2 H, m), 6.99-7.19 (2 H, m), 6.74 (1 H, br. s.), 5.60 (1 H, d, J = 1.22 Hz), 5.00 (1 H, br. s. Mass Spectral Anal. Calcd. for [M + H]$^+$ C$_{22}$H$_{13}$ClF$_2$N$_2$O$_2$: 411.1; found 411.2

| | | |
|---|---|---|
| Example 393 | 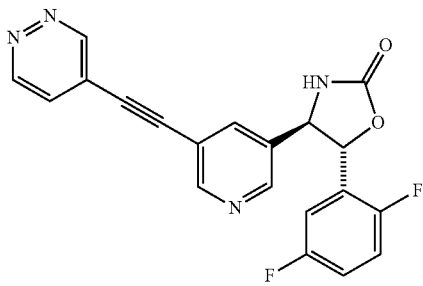 [SMILES: O=C1N[C@H](c2cncc(C#Cc3ccnnc3)c2)[C@@H](c2cc(F)ccc2F)O1]<br>(4R,5R)-5-(2,5-difluorophenyl)-4-(5-(pyridazin-4-ylethynyl)pyridin-3-yl)oxazolidin-2-one | $^1$H NMR (500 MHz, CDCl$_3$) δ ppm 9.28 (1 H, s), 9.25 (1 H, d, J = 5.19 Hz), 8.85 (1 H, d, J = 1.83 Hz), 8.61 (1 H, d, J = 2.14 Hz), 7.99 (1 H, t, J = 1.98 Hz), 7.58 (1 H, dd, J = 5.34, 2.29 Hz), 7.21-7.30 (1 H, m), 7.04-7.16 (2 H, m), 5.83 (1 H, s), 5.56 (1 H, d, J = 5.49 Hz), 4.85 (1 H, d, J = 5.19 Hz). Mass Spectral Anal. Calcd. for [M + H]$^+$ C$_{20}$H$_{12}$F$_2$N$_4$O$_2$: 379.1; found 379.2 |
| Example 394 | 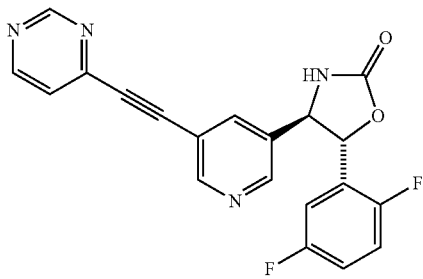 [SMILES: O=C1N[C@H](c2cncc(C#Cc3ccncn3)c2)[C@@H](c2cc(F)ccc2F)O1]<br>(4R,5R)-5-(2,5-difluorophenyl)-4-(5-(pyrimidin-4-ylethynyl)pyridin-3-yl)oxazolidin-2-one | LC/MS (Phenomenex Luna C18 30 × 2 mm 3 μm, A = 90% H$_2$O/10% Acetonitrile, B = 90% Acetonitrile/10% H$_2$O, Modifier 0.1% TFA, 0.00 min = 0% B, 2.0 min = 100% B, 3.0 min = 100% B, Flow rate = 1 mL/min) 1.40 min, Anal. Calcd. for [M + H]$^+$ C$_{20}$H$_{12}$F$_2$N$_4$O$_2$: 379.1; found 379.2 |
| Example 395 | 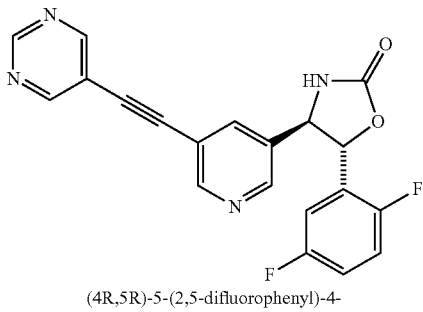<br>(4R,5R)-5-(2,5-difluorophenyl)-4-(5-(pyrimidin-5-ylethynyl)pyridin-3-yl)oxazolidin-2-one | $^1$H NMR (500 MHz, CDCl$_3$) δ ppm 9.19 (1 H, s), 8.90 (2 H, s), 8.82 (1 H, d, J = 2.14 Hz), 8.57 (1 H, d, J = 2.14 Hz), 7.96 (1 H, t, J = 2.14 Hz), 7.18-7.33 (1 H, m), 7.03-7.16 (2 H, m), 6.15 (1 H, s), 5.55 (1 H, d, J = 5.49 Hz), 4.85 (1 H, d, J = 5.49 Hz), Mass Spectral Anal. Calcd. for [M + H]$^+$ C$_{20}$H$_{12}$F$_2$N$_4$O$_2$: 379.1; found 379.2 |
| Example 396 | 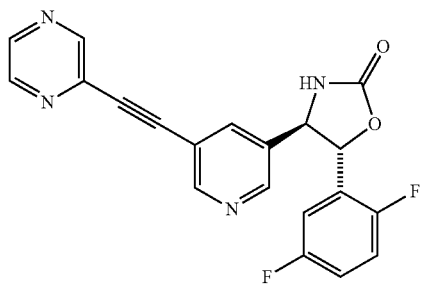 [SMILES: O=C1N[C@H](c2cncc(C#Cc3cnccn3)c2)[C@@H](c2cc(F)ccc2F)O1]<br>(4R,5R)-5-(2,5-difluorophenyl)-4-(5-(pyrazin-2-ylethynyl)pyridin-3-yl)oxazolidin-2-one | $^1$H NMR (500 MHz, CDCl$_3$) δ ppm 8.87 (1 H, d, J = 1.83 Hz), 8.81 (1 H, d, J = 1.22 Hz), 8.60-8.65 (1 H, m), 8.59 (1 H, d, J = 2.14 Hz), 8.56 (1 H, d, J = 2.44 Hz), 8.00 (1 H, t, J = 1.98 Hz), 7.19-7.30 (1 H, m), 7.02-7.17 (2 H, m), 5.99 (1 H, s), 5.55 (1 H, d, J = 5.80 Hz), 4.84 (1 H, d, J = 5.80 Hz), Mass Spectral Anal. Calcd. for [M + H]$^+$ C$_{20}$H$_{12}$F$_2$N$_4$O$_2$: 379.1; found 379.2 |

Example 397

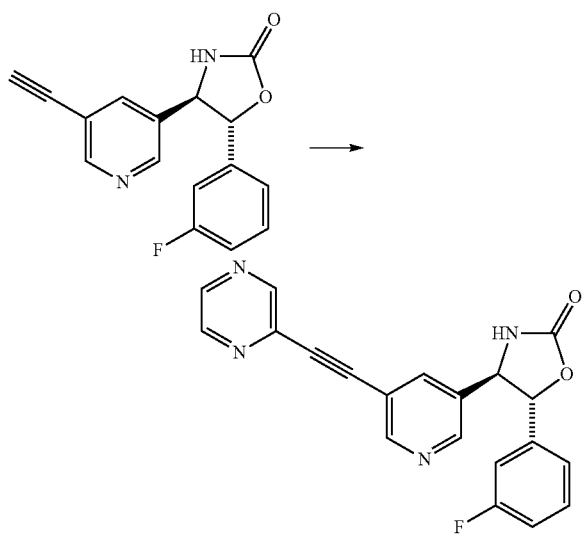

(4R,5R)-5-(3-Fluorophenyl)-4-(5-(pyrazin-2-ylethynyl)pyridin-3-yl)oxazolidin-2-one (4R,5R)-4-(5-ethynylpyridin-3-yl)-5-(3-fluorophenyl)oxazolidin-2-one (50 mg, 0.177 mmol; prepared in analogous fashion to the preparation of (4R,5R)-5-(2,5-difluorophenyl)-4-(5-ethynylpyridin-3-yl)oxazolidin-2-one starting from 3-fluorobenzaldehyde in place of 2,5-difluorobenzaldehyde), 2-bromopyrazine (31.0 mg, 0.195 mmol), bis(triphenylphosphine) palladium (II) chloride (6.22 mg, 8.86 mmol), triphenylphosphine (9.29 mg, 0.035 mmol), and copper (I) iodide (1.687 mg, 8.86 mmol) were combined in a microwave vial. Dimethylformamide (0.250 mL) and diisopropylethylamine (0.75 mL) were added resulting in a biphasic mixture. Nitrogen was bubbled through the vessel for 10 min, the vessel was capped and the reaction was run at 120° C. for 25 min on a Biotage microwave reactor. The diisopropylethylamine removed in vacuo, the remaining solution was diluted with methanol and the solution was purified via preparative liquid chromatography (Sunfire C18 19×100 mm 5 nm, A=95% $H_2O$/5% Acetonitrile, B=95% Acetonitrile/5% $H_2O$, Modifier 10 mM Ammonium Acetate, 0.00 min=20% B, 8.0 min=100% B, 13.0 min=100% B, Flow rate=25 mL/min) providing (4R,5R)-5-(3-fluorophenyl)-4-(5-(pyrazin-2-ylethynyl)pyridin-3-yl)oxazolidin-2-one (31 mg; 48%) as an amber foam. $^1$H NMR (500 MHz, $CDCl_3$) δ ppm 8.89 (1H, br. s.), 8.81 (1H, s), 8.63 (1H, d, J=1.53 Hz), 8.57 (1H, d, J=2.44 Hz), 8.52 (1H, br. s.), 7.97 (1H, s), 7.41 (1H, td, J=7.93, 5.49 Hz), 6.94-7.19 (3H, m), 5.61 (1H, br. s.), 5.30 (1H, d, J=7.32 Hz), 4.81 (1H, d, J=7.32 Hz), Mass Spectral Anal. Calcd. for [M+H]$^+$ $C_{20}H_{13}FN_4O_2$: 361.1. found 361.2.

The following examples were prepared using a modification of the procedure describing the preparation of (4R,5R)-5-(3-fluorophenyl)-4-(5-(pyrazin-2-ylethynyl)pyridin-3-yl)oxazolidin-2-one. employing the appropriately substituted commercially available aryl halide:

| Example 398 | 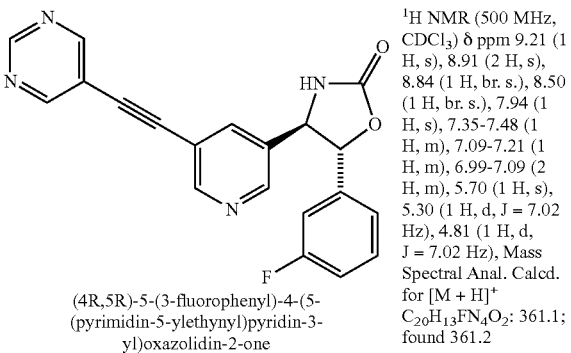<br>(4R,5R)-5-(3-fluorophenyl)-4-(5-(pyrimidin-5-ylethynyl)pyridin-3-yl)oxazolidin-2-one | $^1$H NMR (500 MHz, $CDCl_3$) δ ppm 9.21 (1 H, s), 8.91 (2 H, s), 8.84 (1 H, br. s.), 8.50 (1 H, br. s.), 7.94 (1 H, s), 7.35-7.48 (1 H, m), 7.09-7.21 (1 H, m), 6.99-7.09 (2 H, m), 5.70 (1 H, s), 5.30 (1 H, d, J = 7.02 Hz), 4.81 (1 H, d, J = 7.02 Hz), Mass Spectral Anal. Calcd. for [M + H]$^+$ $C_{20}H_{13}FN_4O_2$: 361.1; found 361.2 |
|---|---|---|
| Example 399 | 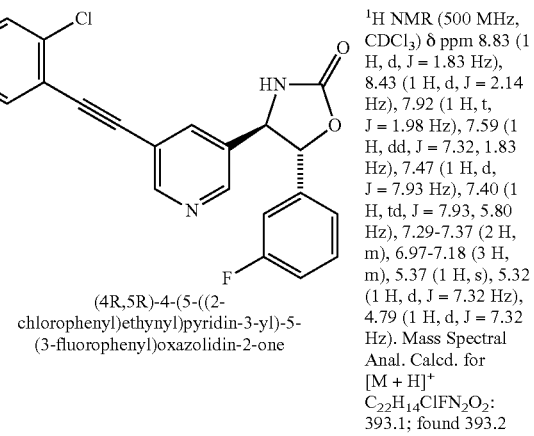<br>(4R,5R)-4-(5-((2-chlorophenyl)ethynyl)pyridin-3-yl)-5-(3-fluorophenyl)oxazolidin-2-one | $^1$H NMR (500 MHz, $CDCl_3$) δ ppm 8.83 (1 H, d, J = 1.83 Hz), 8.43 (1 H, d, J = 2.14 Hz), 7.92 (1 H, t, J = 1.98 Hz), 7.59 (1 H, dd, J = 7.32, 1.83 Hz), 7.47 (1 H, d, J = 7.93 Hz), 7.40 (1 H, td, J = 7.93, 5.80 Hz), 7.29-7.37 (2 H, m), 6.97-7.18 (3 H, m), 5.37 (1 H, s), 5.32 (1 H, d, J = 7.32 Hz), 4.79 (1 H, d, J = 7.32 Hz). Mass Spectral Anal. Calcd. for [M + H]$^+$ $C_{22}H_{14}ClFN_2O_2$: 393.1; found 393.2 |

| | | |
|---|---|---|
| Example 400 | 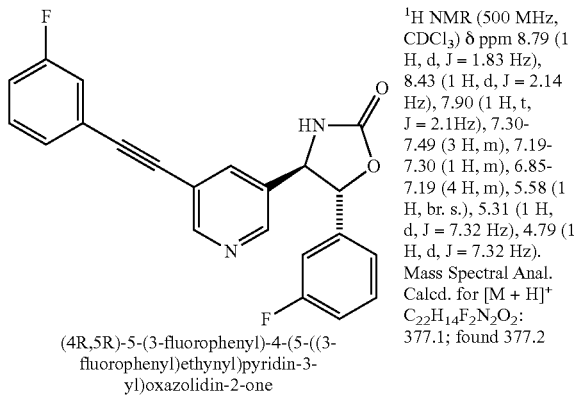<br>(4R,5R)-5-(3-fluorophenyl)-4-(5-((3-fluorophenyl)ethynyl)pyridin-3-yl)oxazolidin-2-one | $^1$H NMR (500 MHz, CDCl$_3$) δ ppm 8.79 (1 H, d, J = 1.83 Hz), 8.43 (1 H, d, J = 2.14 Hz), 7.90 (1 H, t, J = 2.1Hz), 7.30-7.49 (3 H, m), 7.19-7.30 (1 H, m), 6.85-7.19 (4 H, m), 5.58 (1 H, br. s.), 5.31 (1 H, d, J = 7.32 Hz), 4.79 (1 H, d, J = 7.32 Hz). Mass Spectral Anal. Calcd. for [M + H]$^+$ C$_{22}$H$_{14}$F$_2$N$_2$O$_2$: 377.1; found 377.2 |
| Example 401 | 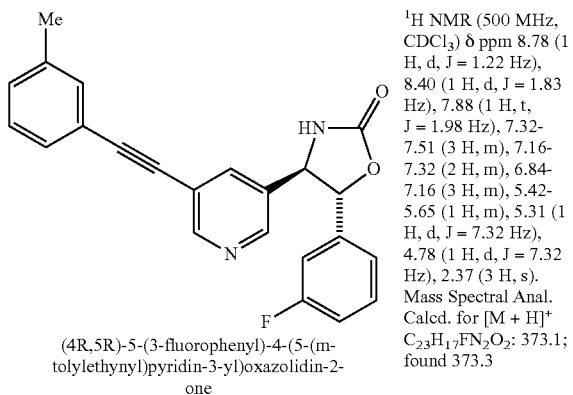<br>(4R,5R)-5-(3-fluorophenyl)-4-(5-(m-tolylethynyl)pyridin-3-yl)oxazolidin-2-one | $^1$H NMR (500 MHz, CDCl$_3$) δ ppm 8.78 (1 H, d, J = 1.22 Hz), 8.40 (1 H, d, J = 1.83 Hz), 7.88 (1 H, t, J = 1.98 Hz), 7.32-7.51 (3 H, m), 7.16-7.32 (2 H, m), 6.84-7.16 (3 H, m), 5.42-5.65 (1 H, m), 5.31 (1 H, d, J = 7.32 Hz), 4.78 (1 H, d, J = 7.32 Hz), 2.37 (3 H, s). Mass Spectral Anal. Calcd. for [M + H]$^+$ C$_{23}$H$_{17}$FN$_2$O$_2$: 373.1; found 373.3 |
| Example 402 | 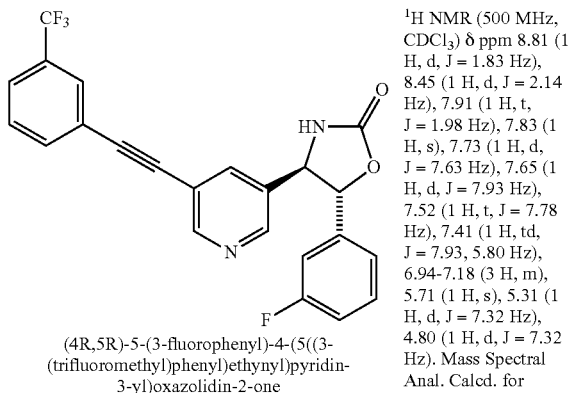<br>(4R,5R)-5-(3-fluorophenyl)-4-(5((3-(trifluoromethyl)phenyl)ethynyl)pyridin-3-yl)oxazolidin-2-one | $^1$H NMR (500 MHz, CDCl$_3$) δ ppm 8.81 (1 H, d, J = 1.83 Hz), 8.45 (1 H, d, J = 2.14 Hz), 7.91 (1 H, t, J = 1.98 Hz), 7.83 (1 H, s), 7.73 (1 H, d, J = 7.63 Hz), 7.65 (1 H, d, J = 7.93 Hz), 7.52 (1 H, t, J = 7.78 Hz), 7.41 (1 H, td, J = 7.93, 5.80 Hz), 6.94-7.18 (3 H, m), 5.71 (1 H, s), 5.31 (1 H, d, J = 7.32 Hz), 4.80 (1 H, d, J = 7.32 Hz). Mass Spectral Anal. Calcd. for [M + H]$^+$ C$_{23}$H$_{14}$F$_4$N$_2$O$_2$: 427.1; found 427.2 |
| Example 403 | 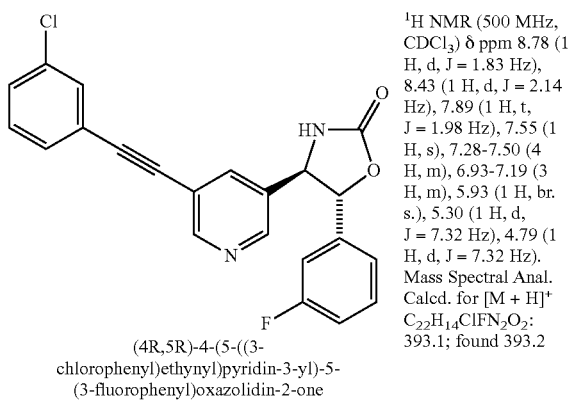<br>(4R,5R)-4-(5-((3-chlorophenyl)ethynyl)pyridin-3-yl)-5-(3-fluorophenyl)oxazolidin-2-one | $^1$H NMR (500 MHz, CDCl$_3$) δ ppm 8.78 (1 H, d, J = 1.83 Hz), 8.43 (1 H, d, J = 2.14 Hz), 7.89 (1 H, t, J = 1.98 Hz), 7.55 (1 H, s), 7.28-7.50 (4 H, m), 6.93-7.19 (3 H, m), 5.93 (1 H, br. s.), 5.30 (1 H, d, J = 7.32 Hz), 4.79 (1 H, d, J = 7.32 Hz). Mass Spectral Anal. Calcd. for [M + H]$^+$ C$_{22}$H$_{14}$ClFN$_2$O$_2$: 393.1; found 393.2 |

Example 404

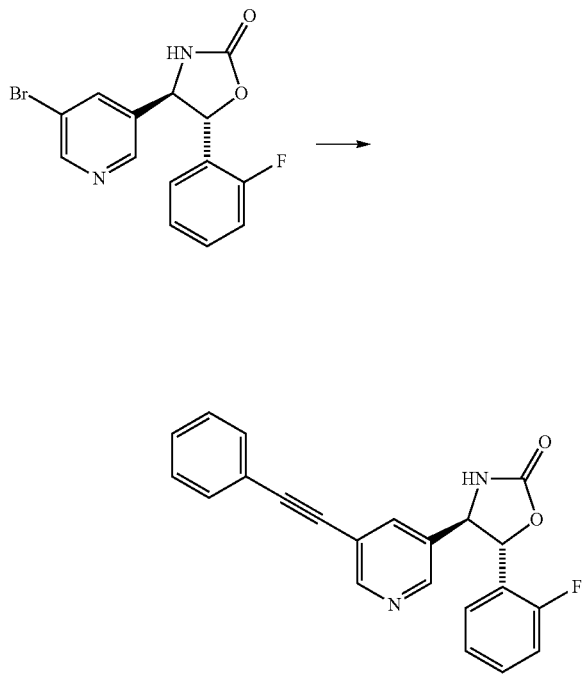

(4R,5R)-5-(2-Fluorophenyl)-4-(5-(phenylethynyl)pyridin-3-yl)oxazolidin-2-one

To a slurry of (4R,5R)-4-(5-bromopyridin-3-yl)-5-(2-fluorophenyl)oxazolidin-2-one (100 mg, 0.297 mmol; prepared in analogous fashion to the preparation of (4R,5R)-5-(2,5-difluorophenyl)-4-(5-ethynylpyridin-3-yl)oxazolidin-2-one starting from 2-fluorobenzaldehyde in place of 2,5-difluorobenzaldehyde) in triethylamine (Volume: 5 mL) was bubbled nitrogen for 20 min. Ethynylbenzene (0.049 mL, 0.445 mmol) was added and nitrogen bubbling was continued for 5 min before adding bis(triphenylphosphine) palladium (II) chloride (15.61 mg, 0.022 mmol), triphenylphosphine (14.00 mg, 0.053 mmol), and copper (I) iodide (4.24 mg, 0.022 mmol) in 1 portion. After 5 min of additional nitrogen bubbling, the vessel was placed in a 70° C. bath under nitrogen for 18 h at which time it was cooled and concentrated. The residue was dissolved in methanol and purified via preparative liquid chromatography (Sunfire C18 OBD 30×100 mm 5 μm, A=95% H$_2$O/5% Acetonitrile, B=95% Acetonitrile/5% H$_2$O, Modifier 10 mM Ammonium Acetate, 0.00 min=20% B, 8.0 min=100% B, 13.0 min=100% B, Flow rate=40 mL/min) and then by chiral HPLC (Chiralpak AD 21×250 10 μm, A=Heptane with 0.1% diethylamine, B=Ethanol, Isocratic 50% A, Flow Rate=15 mL/min providing (4R,5R)-5-(2-fluorophenyl)-4-(5-(phenylethynyl)pyridin-3-yl)oxazolidin-2-one (61 mg; 57%). $^1$H NMR (500 MHz, CDCl$_3$) δ ppm 8.78 (1H, d, J=1.83 Hz), 8.48 (1H, d, J=1.83 Hz), 7.92 (1H, t, J=1.98 Hz), 7.56 (2H, dd, J=6.71, 2.75 Hz), 7.46-7.53 (1H, m), 7.34-7.46 (4H, m), 7.20-7.31 (1H, m), 7.06-7.20 (1H, m), 5.58 (1H, d, J=5.80 Hz), 5.44 (1H, br. s.), 4.86 (1H, d, J=5.80 Hz). Mass Spectral Anal. Calcd. for [M+H]$^+$ C$_{22}$H$_{15}$FN$_2$O$_2$: 359.1. found 359.1.

Example 405

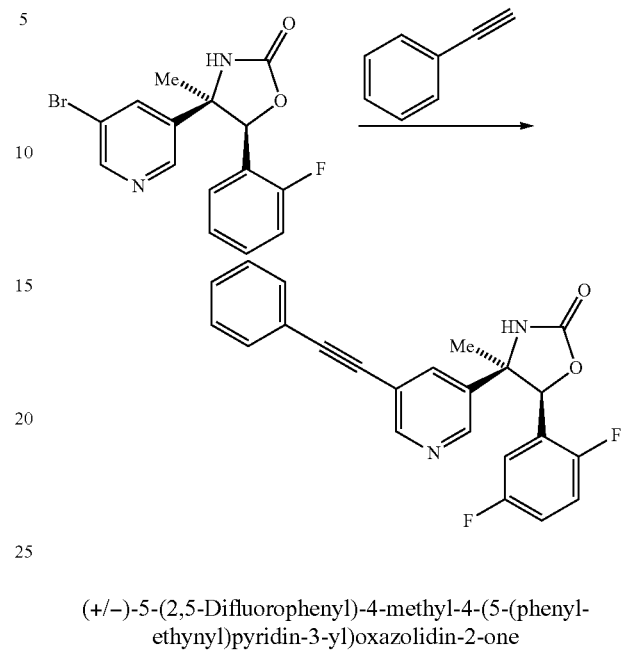

(+/−)-5-(2,5-Difluorophenyl)-4-methyl-4-(5-(phenylethynyl)pyridin-3-yl)oxazolidin-2-one To a slurry of 4-(5-bromopyridin-3-yl)-5-(2-fluorophenyl)-4-methyloxazolidin-2-one (9 mg, 0.026 mmol) in triethylamine (0.5 mL) was bubbled nitrogen for 20 min. Ethynylbenzene (4.22 μl, 0.038 mmol) was added with continued nitrogen bubbling for an additional 5 min before adding bis(triphenylphosphine) palladium (II) chloride (1.349 mg, 1.922 μmol), triphenylphosphine (1.210 mg, 4.61 μmol), and copper (I) iodide (1.464 mg, 7.69 μmol) together in 1 portion. After 5 min bubbling nitrogen, the vessel was placed in a 70° C. bath. After 18 h the reaction was concentrated, dissolved in 50% dimethylformamide/methanol and purified via preparative liquid chromatography (Sunfire C18 19×100 mm 5 μm, A=95% H$_2$O/5% Acetonitrile, B=95% Acetonitrile/5% H$_2$O, Modifier 10 mM Ammonium Acetate, 0.00 min=10% B, 10.0 min=100% B, 15.0 min=100% B, Flow rate=25 mL/min) providing racemic 5-(2,5-difluorophenyl)-4-methyl-4-(5-(phenylethynyl)pyridin-3-yl)oxazolidin-2-one (2.2 mg; 22%) as a colorless oil. $^1$H NMR (500 MHz, CDCl$_3$) δ ppm 8.51 (1H, br. s.), 8.26 (1H, br. s.), 7.61 (1H, s), 7.48-7.57 (2H, m), 7.32-7.43 (3H, m), 6.71-6.92 (3H, m), 5.84 (1H, s), 5.65 (1H, s), 2.05 (3H, s). Mass Spectral Anal. Calcd. for [M+H]$^+$ C$_{23}$H$_{16}$F$_2$N$_2$O$_2$: 391.1. found 391.2.

Example 406 and Example 407

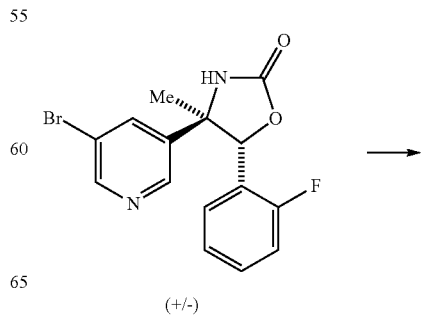

(+/−)

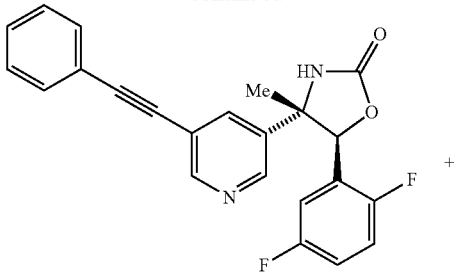

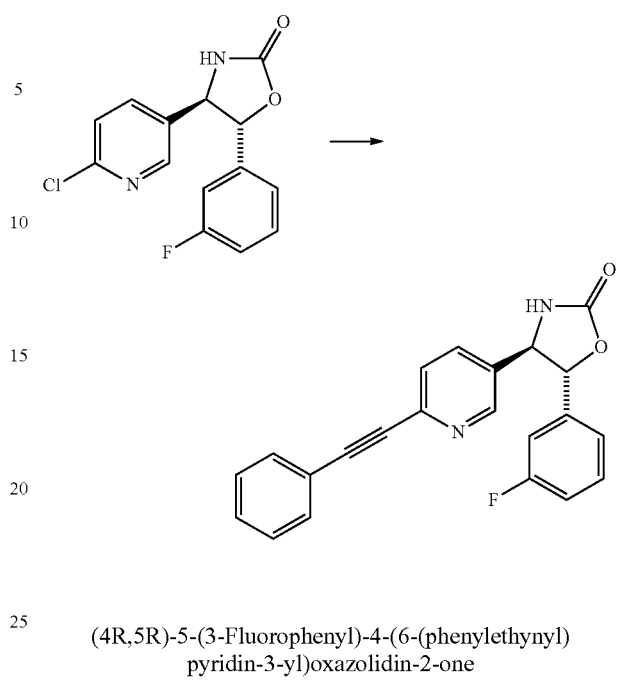

Example 408

(4R,5R)-5-(3-Fluorophenyl)-4-(6-(phenylethynyl)pyridin-3-yl)oxazolidin-2-one (4S,5S)-5-(2,5-Difluorophenyl)-4-methyl-4-(5-(phenylethynyl)pyridin-3-yl)oxazolidin-2-one and (4R,5R)-5-(2,5-difluorophenyl)-4-methyl-4-(5-(phenylethynyl)pyridin-3-yl)oxazolidin-2-one To a slurry of racemic 4-(5-bromopyridin-3-yl)-5-(2-fluorophenyl)-4-methyloxazolidin-2-one (22 mg, 0.063 mmol) in triethylamine (0.5 mL) was bubbled nitrogen for 20 min. Ethynylbenzene (10.3 μl, 0.094 mmol) was added with continued nitrogen bubbling for an additional 5 min before adding bis(triphenylphosphine) palladium (II) chloride (3.30 mg, 4.70 μmol), triphenylphosphine (2.96 mg, 0.011 mmol), and copper (I) iodide (3.58 mg, 0.019 mmol) together in 1 portion. After 5 min bubbling nitrogen, the vessel was placed in a 70° C. bath. After 18 h the reaction was concentrated, dissolved in 50% dimethylformamide/methanol and purified via preparative liquid chromatography (Sunfire C18 19×100 mm 5 μm, A=95% H$_2$O/5% Acetonitrile, B=95% Acetonitrile/5% H$_2$O, Modifier 10 mM Ammonium Acetate, 0.00 min=10% B, 10.0 min=100% B, 15.0 min=100% B, Flow rate=25 mL/min) providing racemic trans-5-(2,5-difluorophenyl)-4-methyl-4-(5-(phenylethynyl)pyridin-3-yl)oxazolidin-2-one. $^1$H NMR (500 MHz, CDCl$_3$) δ ppm 8.82 (2H, br. s.), 7.99 (1H, s), 7.48-7.63 (2H, m), 7.32-7.46 (3H, m), 7.19-7.32 (1H, m), 7.00-7.14 (2H, m), 6.64 (1H, br. s.), 5.77 (1H, s), 1.42 (3H, s). Mass Spectral Anal. Calcd. for [M+H]$^+$ C$_{23}$H$_{16}$F$_2$N$_2$O$_2$: 391.1. found 391.2. The two enantiomers were separated via chiral preparative liquid chromatography (Chiralpak AS 21×250 10 μm, A=0.1% Diethylamine/Heptane, B=Ethanol, Isocratic 20% B for 40 min, Flow Rate=15 mL/min) providing 7.5 mg (30%) peak 1 ((4S,5S)-5-(2,5-difluorophenyl)-4-methyl-4-(5-(phenylethynyl)pyridin-3-yl)oxazolidin-2-one; Example 406) and 7.7 mg (31%) peak 2 ((4R,5R)-5-(2,5-difluorophenyl)-4-methyl-4-(5-(phenylethynyl)pyridin-3-yl)oxazolidin-2-one; Example 407).

(4R,5R)-4-(6-chloropyridin-3-yl)-5-(3-fluorophenyl)oxazolidin-2-one (52 mg; 0.18 mmol), ethynylbenzene (20.0 mg, 0.19 mmol), bis(triphenylphosphine) palladium (II) chloride (6.2 mg, 8.88 μmol), triphenylphosphine (9.3 mg, 0.036 mmol), and copper (I) iodide (1.6 mg, 8.88 μmol) were combined in a microwave vial. dimethylformamide (0.5 mL) and diisopropylethylamine (1.5 mL) were added resulting in a biphasic mixture. Nitrogen was bubbled through the vessel for 10 min, the vessel was capped and the reaction was run at 120° C. for 25 min on a Biotage microwave reactor. The diisopropylethylamine removed in vacuo, the remaining solution was diluted with methanol and the solution was purified via preparative liquid chromatography (Sunfire C18 OBD 30×100 mm 5 μm, A=95% H$_2$O/5% Acetonitrile, B=95% Acetonitrile/5% H$_2$O, Modifier 10 mM Ammonium Acetate, 0.00 min=20% B, 10.0 min=100% B, 15.0 min=100% B, Flow rate=40 mL/min) providing 31 mg (48%) (4R,5R)-5-(3-fluorophenyl)-4-(6-(phenylethynyl)pyridin-3-yl)oxazolidin-2-one. $^1$H NMR (500 MHz, CDCl$_3$) δ ppm 8.49 (1H, d, J=2.14 Hz), 7.75 (1H, dd, J=8.24, 2.44 Hz), 7.56-7.66 (3H, m), 7.32-7.46 (4H, m), 7.11 (1H, td, J=8.39, 2.44 Hz), 6.98-7.09 (2H, m), 5.34 (1H, s), 5.28 (1H, d, J=7.63 Hz), 4.79 (1H, d, J=7.32 Hz). Mass Spectral Anal. Calcd. for [M+H]$^+$ C$_{22}$H$_{15}$FN$_2$O$_2$: 359.1. found 359.3.

Example 409 and Example 410

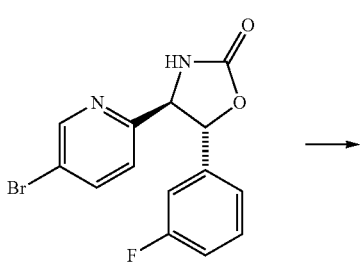

-continued

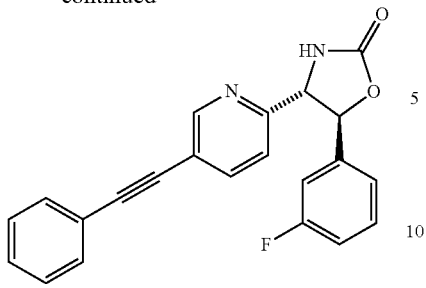

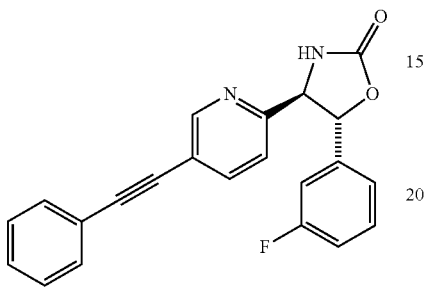

(4S,5S)-5-(3-Fluorophenyl)-4-(5-(phenylethynyl)pyridin-2-yl)oxazolidin-2-one and (4R,5R)-5-(3-fluorophenyl)-4-(5-(phenylethynyl)pyridin-2-yl)oxazolidin-2-one Prepared from (4R,5R)-4-(5-bromopyridin-2-yl)-5-(3-fluorophenyl)oxazolidin-2-one using the same procedure as that used to prepare (4R,5R)-5-(3-fluorophenyl)-4-(6-(phenylethynyl)pyridin-3-yl)oxazolidin-2-one from 5-bromo-2-(bromomethyl)pyridine. The two enantiomers were purified via chiral preparative liquid chromatography (Chiralpak AS 21×250 10 µm, A=0.1% Diethylamine/Heptane, B=Ethanol, Isocratic 45% B for 15 min, Flow Rate=15 mL/min) providing 8.5 mg (15%) (4S,5S)-5-(3-fluorophenyl)-4-(5-(phenylethynyl)pyridin-2-yl)oxazolidin-2-one and 6.2 mg (11%) (4R,5R)-5-(3-fluorophenyl)-4-(5-(phenylethynyl)pyridin-2-yl)oxazolidin-2-one. $^1$H NMR (500 MHz, CDCl$_3$) δ ppm 8.79 (1H, d, J=1.53 Hz), 7.90 (1H, dd, J=8.09, 1.98 Hz), 7.51-7.62 (2H, m), 7.32-7.45 (5H, m), 7.14-7.24 (2H, m), 7.08 (1H, td, J=8.32, 1.98 Hz), 5.77 (1H, s), 5.57 (1H, d, J=5.80 Hz), 4.90 (1H, d, J=5.19 Hz). Chiral LC for (4S,5S)-5-(3-fluorophenyl)-4-(5-(phenylethynyl)pyridin-2-yl)oxazolidin-2-one; example 409 (Chiralpak OJ-H analytical column, 4.6×100 mm, 5 µm, Mobile Phase: A=100% Heptane with 0.1% Diethylamine, B=100% Ethanol, Flow rate: 2.0 mL/min, 40% A Isocratic) 4.57 min. Chiral LC for (4R,5R)-5-(3-fluorophenyl)-4-(5-(phenylethynyl)pyridin-2-yl)oxazolidin-2-one; example 410 (Chiralpak OJ-H analytical column, 4.6×100 mm, 5 µm, Mobile Phase: A=100% Heptane with 0.1% Diethylamine, B=100% Ethanol, Flow rate: 2.0 mL/min, 40% A Isocratic) 9.94 min.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

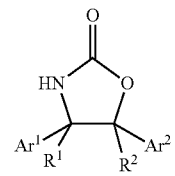

(I)

where;
$R^1$ is hydrogen or alkyl;
$R^2$ is hydrogen or alkyl;
$R^3$ is

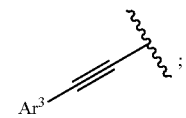

Ar$^1$ is phenyl, pyridinyl, pyrazinyl, pyrimidinyl, or pyridazinyl, and is substituted with 1 R$^3$ substituent and with 0-3 substituents selected from halo, alkyl, haloalkyl, alkoxy, and haloalkoxy;
Ar$^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from halo, cyano, alkyl, haloalkyl, hydroxy, alkoxy, haloalkoxy, and phenyl; and
Ar$^3$ is phenyl, pyridinyl, pyrazinyl, pyrimidinyl, pyridazinyl, imidazolyl, oxazolyl, thiazolyl, quinolinyl, isoquinolinyl, quinoxalinyl, or pyrrolopyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino;
or a pharmaceutically acceptable salt thereof.

2. A compound of claim 1 where R$^1$ is hydrogen or alkyl; R$^2$ is hydrogen or alkyl; R$^3$ is

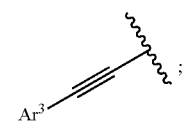

Ar$^1$ is phenyl, pyridinyl, or pyrimidinyl and is substituted with 1 R$^3$ substituent and with 0-1 halo or alkoxy substituents; Ar$^2$ is phenyl, pyridinyl, pyrazinyl, pyrimidinyl, pyridazinyl, thienyl, pyrazolyl, oxazolyl, oxadiazolyl, or tetrazolyl, and is substituted with 0-3 substituents selected from halo, cyano, alkyl, haloalkyl, hydroxy, alkoxy, and phenyl; and Ar$^3$ is phenyl, pyridinyl, pyrazinyl, pyrimidinyl, pyridazinyl, imidazolyl, thiazolyl, isoquinolinyl, quinolinyl, quinoxalinyl, or pyrrolopyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

3. A compound of claim 2 where $R^1$ is hydrogen or alkyl; $R^2$ is hydrogen or alkyl; $R^3$ is

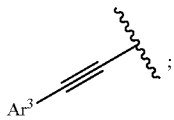

$Ar^1$ is phenyl, pyridinyl, halopyridinyl, alkoxypyridinyl, or pyrimidinyl; $Ar^2$ is phenyl, cyanophenyl, halophenyl, dihalophenyl, (haloalkyl)phenyl, alkylphenyl, dealkylphenyl, hydroxyphenyl, alkoxyphenyl, pyridinyl, pyrazinyl, pyrimidinyl, pyridazinyl, thienyl, (alkyl)pyrazolyl, oxazolyl, (alkyl)oxadiazolyl, (phenyl)oxadiazolyl, or tetrazolyl; and $Ar^3$ is phenyl, cyanophenyl, halophenyl, dihalophenyl, alkylphenyl, (haloalkyl)phenyl, alkoxyphenyl, (haloalkoxy)phenyl, (alkylthio)phenyl, (amino)phenyl, alkylaminophenyl, dialkylaminophenyl, alkoxycarbonylphenyl, alkylcarbonylphenyl, pyridinyl, cyanopyridinyl, halopyridinyl, alkylpyridinyl, cycloalkylpyridinyl, alkoxypyridinyl, pyrazinyl, pyrimidinyl, alkoxypyrimidinyl, aminopyrimidinyl, alkylaminopyrimidinyl, dialkylaminopyrimidinyl, pyridazinyl, isoquinolinyl, quinoxalinyl, imidazolyl, thiazolyl, or alkylthiazolyl or a pharmaceutically acceptable salt thereof.

4. A compound of claim 3 where $R^1$ is hydrogen or methyl; $R^2$ is hydrogen or methyl; $R^3$ is

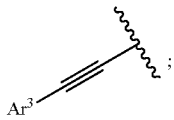

$Ar^1$ is phenyl, pyridinyl, fluoropyridinyl, methoxypyridinyl, or pyrimidinyl and is substituted with 1 $R^3$ substituent; $Ar^2$ is phenyl, cyanophenyl, chlorophenyl, dichlorophenyl, fluorophenyl, difluorophenyl, trifluoromethylphenyl, methylphenyl, dimethylphenyl, hydroxyphenyl, methoxyphenyl, pyridinyl, pyrazinyl, pyrimidinyl, pyridazinyl, thienyl, (methyl)pyrazolyl, oxazolyl, (methyl)oxadiazolyl, (phenyl)oxadiazolyl, or tetrazolyl; and $Ar^3$ is phenyl, cyanophenyl, chlorophenyl, dichlorophenyl, fluorophenyl, difluorophenyl, methylphenyl, t-butylphenyl, trifluoromethylphenyl, methoxyphenyl, trifluoromethoxyphenyl, methylthiophenyl, (amino)phenyl, dimethylaminophenyl, methoxycarbonylphenyl, methylcarbonylphenyl, pyridinyl, cyanopyridinyl, chloropyridinyl, fluoropyridinyl, methylpyridinyl, cyclopropylpyridinyl, methoxypyridinyl, pyrazinyl, pyrimidinyl, ethoxypyrimidinyl, methylaminopyrimidinyl, pyridazinyl, isoquinolinyl, quinoxalinyl, imidazolyl, thiazolyl, or methylthiazolyl; or a pharmaceutically acceptable salt thereof.

5. A compound of claim 4 where $R^1$ is hydrogen; $R^2$ is hydrogen; $Ar^1$ is phenyl, pyridinyl, halopyridinyl, alkoxypyridinyl, or pyrimidinyl substituted in the meta position with $R^3$.

6. A compound of claim 5 where; $Ar^2$ is phenyl, pyridinyl, pyrazinyl, pyrimidinyl, pyridazinyl, pyrrolyl, (uranyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from halo, cyano, alkyl, haloalkyl, hydroxy, alkoxy, haloalkoxy, and phenyl; $Ar^3$ is phenyl or pyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

7. A compound of claim 6 where $Ar^2$ is phenyl, pyridinyl, pyrazinyl, pyrimidinyl, pyridazinyl, thienyl, pyrazolyl, oxazolyl, oxadiazolyl, or tetrazolyl, and is substituted with 0-3 substituents selected from halo, cyano, alkyl, haloalkyl, hydroxy, alkoxy, and phenyl; $Ar^3$ is phenyl or pyridinyl, and is substituted with 0-3 substituents selected from halo, cyano, alkyl, haloalkyl, cycloalkyl, hydroxy, alkoxy, haloalkoxy, alkylcarbonyl, alkoxycarbonyl, alkylthio, amino, alkylamino, and dialkylamino; or a pharmaceutically acceptable salt thereof.

8. A compound of claim 7 where; $A^2$ is phenyl, cyanophenyl, halophenyl, dihalophenyl, (haloalkyl)phenyl, alkylphenyl, dialkylphenyl, hydroxyphenyl, alkoxyphenyl, pyridinyl, pyrazinyl, pyrimidinyl, pyridazinyl, thienyl, (alkyl)pyrazolyl, oxazolyl, (alkyl)oxadiazolyl, (phenyl)oxadiazolyl, or tetrazolyl; $Ar^3$ is phenyl, cyanophenyl, halophenyl, dihalophenyl, dihalophenyl, alkylphenyl, (haloalkyl)phenyl, alkoxyphenyl, (haloalkoxy)phenyl, (alkylthio)phenyl, (amino)phenyl, alkylaminophenyl, dialkylaminophenyl, alkoxycarbonylphenyl, alkylcarbonylphenyl, pyridinyl, cyanopyridinyl, halopyridinyl, alkylpyridinyl, cycloalkylpyridinyl, alkoxypyridinyl; or a pharmaceutically acceptable salt thereof.

9. A compound of claim 8 where $Ar^2$ is phenyl, cyanophenyl, chlorophenyl, dichlorophenyl, fluorophenyl, difluorophenyl, trifluoromethylphenyl, methylphenyl, dimethylphenyl, hydroxyphenyl, methoxyphenyl, pyridinyl, pyrazinyl, pyrimidinyl, pyridazinyl, thienyl, (methyl)pyrazolyl, oxazolyl, (methyl)oxadiazolyl, (phenyl)oxadiazolyl, or tetrazolyl; $Ar^3$ is phenyl, cyanophenyl, chlorophenyl, dichlorophenyl, fluorophenyl, difluorophenyl, methylphenyl, t-butylphenyl, trifluoromethylphenyl, methoxyphenyl, trifluoromethoxyphenyl, methylthiophenyl, (amino)phenyl, dimethylaminophenyl, methoxycarbonylphenyl, methylcarbonylphenyl, pyridinyl, cyanopyridinyl, chloropyridinyl, fluoropyridinyl, methylpyridinyl, cyclopropylpyridinyl, methoxypyridinyl, thiazolyl, or methylthiazolyl; or a pharmaceutically acceptable salt thereof.

10. A compound of claim 1 with the indicated stereochemistry

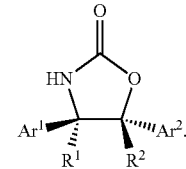

11. A compound of claim 1 selected from the group consisting of
(4R,5R)-5-phenyl-4-(6-(phenylethynyl)-2-pyridinyl)-1,3-oxazolidin-2-one;
(4R,5R)-5-phenyl-4-(2-(phenylethynyl)-4-pyridinyl)-1,3-oxazolidin-2-one;
(4R,5R)-5-(3-fluorophenyl)-4-(5-(phenylethynyl)-3-pyridinyl)-1,3-oxazolidin-2-one;
(4R,5R)-5-phenyl-4-(2-(3-pyridinylethynyl)-4-pyridinyl)-1,3-oxazolidin-2-one;
(4R,5R)-5-(3-methoxyphenyl)-4-(5-(phenylethynyl)-3-pyridinyl)-1,3-oxazolidin-2-one;
(4R,5R)-5-(3-fluorophenyl)-4-(5-(3-pyridinylethynyl)-3-pyridinyl)-1,3-oxazolidin-2-one;

(4R,5R)-5-(3-methoxyphenyl)-4-(2-(phenylethynyl)-4-pyridinyl)-1,3-oxazolidin-2-one;
(4R,5R)-5-phenyl-4-(5-(phenylethynyl)-3-pyridinyl)-1,3-oxazolidin-2-one;
(4R,5R)-5-(4-fluorophenyl)-4-(5-(phenylethynyl)-3-pyridinyl)-1,3-oxazolidin-2-one;
(4R,5R)-5-(4-fluorophenyl)-4-(5-(3-pyridinylethynyl)-3-pyridinyl)-1,3-oxazolidin-2-one;
(4R,5R)-5-(4-fluorophenyl)-4-(5-((5-fluoro-3-pyridinyl)ethynyl)-3-pyridinyl)-1,3-oxazolidin-2-one;
(4R,5R)-5-(3-methoxyphenyl)-4-(3-(2-pyridinylethynyl)phenyl)-1,3-oxazolidin-2-one;
(4R,5R)-5-(3-methoxyphenyl)-4-(3-(4-pyridinylethynyl)phenyl)-1,3-oxazolidin-2-one;
(4R,5R)-5-(3-methoxy phenyl)-4-(3-((6-methoxy-2-pyridinyl)ethynyl)phenyl)-1,3-oxazolidin-2-one;
(4R,5R)-5-(3-methoxyphenyl)-4-(3-(1,3-thiazol-4-yl-ethynyl)phenyl)-1,3-oxazolidin-2-one;
(4R,5R)-4-(3-((6-fluoro-3-pyridinyl)ethynyl)phenyl)-5-(3-methoxyphenyl)-1,3-oxazolidin-2-one;
(4R,5R)-4-(3-((2-fluoro-4-pyridinyl)ethynyl)phenyl)-5-(3-methoxyphenyl)-1,3-oxazolidin-2-one;
5-((3-((4R,5R)-5-(3-methoxyphenyl)-2-oxo-1,3-oxazolidin-4-yl)phenyl)ethynyl)nicotinonitrile;
(4R,5R)-4-(3-((5-fluoro-3-pyridinyl)ethynyl)phenyl)-5-(3-methoxyphenyl)-1,3-oxazolidin-2-one;
(4R,5R)-5-phenyl-4-(3-(phenylethynyl)phenyl)-1,3-oxazolidin-2-one;
(4R,5R)-5-(3,4-dimethylphenyl)-4-(3-(phenylethynyl)phenyl)-1,3-oxazolidin-2-one;
(4R,5S)-4-(3-(phenylethynyl)phenyl)-5-(2-thienyl)-1,3-oxazolidin-2-one;
(4R,5R)-5-(4-methylphenyl)-4-(3-(phenylethynyl)phenyl)-1,3-oxazolidin-2-one;
(4R,5R)-5-(2-fluorophenyl)-4-(3-(phenylethynyl)phenyl)-1,3-oxazolidin-2-one;
(4R,5R)-5-(3-fluorophenyl)-4-(3-(phenylethynyl)phenyl)-1,3-oxazolidin-2-one;
(4R,5R)-5-(4-fluorophenyl)-4-(3-(phenylethynyl)phenyl)-1,3-oxazolidin-2-one;
(4R,5R)-4-(3-(phenylethynyl)phenyl)-5-(3-pyridinyl)-1,3-oxazolidin-2-one;
(4R,5R)-4-(3-((2-fluorophenyl)ethynyl)phenyl)-5-(3-methoxyphenyl)-1,3-oxazolidin-2-one;
(4R,5R)-4-(3-((3-fluorophenyl)ethynyl)phenyl)-5-(3-methoxyphenyl)-1,3-oxazolidin-2-one;
(4R,5R)-5-(4-fluorophenyl)-4-(6-(phenylethynyl)-2-pyridinyl)-1,3-oxazolidin-2-one;
(4R,5R)-4-methyl-5-phenyl-4-(5-(phenylethynyl)-3-pyridinyl)-1,3-oxazolidin-2-one;
(4R,5R)-5-(3-fluorophenyl)-4-(2-fluoro-5-(3-pyridinylethynyl)-3-pyridinyl)-1,3-oxazolidin-2-one;
(4R,5R)-4-(2-fluoro-5-((5-fluoro-3-pyridinyl)ethynyl)-3-pyridinyl)-5-(3-fluorophenyl)-1,3-oxazolidin-2-one;
(4R,5R)-4-(2-fluoro-5-((2-fluoro-4-pyridinyl)ethynyl)-3-pyridinyl)-5-(3-fluorophenyl)-1,3-oxazolidin-2-one;
(4R,5R)-5-(4-fluorophenyl)-4-(2-fluoro-5-(3-pyridinylethynyl)-3-pyridinyl)-1,3-oxazolidin-2-one;
(4R,5R)-4-(2-fluoro-5-((5-fluoro-3-pyridinyl)ethynyl)-3-pyridinyl)-5-(4-fluorophenyl)-1,3 oxazolidin-2-one;
(4R,5R)-4-(5-fluoro-2-((5-fluoro-3-pyridinyl)ethynyl)-4-pyridinyl)-5-(4-fluorophenyl)-1,3-oxazolidin-2-one;
(4R,5R)-5-(4-chlorophenyl)-4-(2-fluoro-5-(3-pyridinyl)ethynyl)-3-pyridinyl)-1,3-oxazolidin-2-one;
(4R,5R)-4-(2-fluoro-5-((6-fluoro-2-pyridinyl)ethynyl)-3-pyridinyl)-5-(4-fluorophenyl)-1,3-oxazolidin-2-one;

(4R,5R)-5-(3,5-difluorophenyl)-4-(5-(phenylethynyl)-3-pyridinyl)-1,3-oxazolidin-2-one;
(4R,5R)-5-(3,4-difluorophenyl)-4-(5-(phenylethynyl)-3-pyridinyl)-1,3-oxazolidin-2-one;
(4R,5R)-5-(3,4-difluorophenyl)-4-(5-(3-pyridinylethynyl)-3-pyridinyl)-1,3-oxazolidin-2-one;
(4R,5R)-5-(3,4-difluorophenyl)-4-(5-((5-fluoro-3-pyridinyl)ethynyl)-3-pyridinyl)-1,3-oxazolidin-2-one;
3-((5-((4R,5R)-5-(3,4-difluorophenyl)-2-oxo-1,3-oxazolidin-4-yl)-3-pyridinyl)ethynyl)benzonitrile;
(4R,5R)-5-(2,4-difluorophenyl)-4-(5-(phenylethynyl)-3-pyridinyl)-1,3-oxazolidin-2-one;
(4R,5R)-5-(2,4-difluorophenyl)-4-(5-((5-fluoro-3-pyridinyl)ethynyl)-3-pyridinyl)-1,3-oxazolidin-2-one;
(4R,5R)-5-(2,4-difluorophenyl)-4-(5-pyridinylethynyl)-3-pyridinyl)-1-oxazolidin-2-one;
(4R,5R)-5-(2,5-difluorophenyl)-4-(5-(phenylethynyl)-3-pyridinyl)-1,3-oxazolidin-2-one;
(4R,5R)-5-(2,5-difluorophenyl)-4-(5-((5-fluoro-3-pyridinyl)ethynyl)-3-pyridinyl)-1,3-oxazolidin-2-one;
(4R,5R)-4-(3-((4-fluoro-2-pyridinyl)ethynyl)phenyl)-5-(3-methoxyphenyl)-1,3-oxazolidin-2-one;
(4R,5R)-4-(3-((3-fluoro-2-pyridinyl)ethynyl)phenyl)-5-(3-methoxyphenyl)-1,3-oxazolidin-2-one;
(4R,5R)-4-(5-(phenylethynyl)-3-pyridinyl)-5-(3-pyridinyl)-1,3-oxazolidin-2-one;
(4R,5R)-5-(4-fluorophenyl)-5-methyl-4-(5-(phenylethynyl)-3-pyridinyl)-1,3-oxazolidin-2-one;
(4R,5S)-5-(4-fluorophenyl)-5-methyl-4-(5-(phenylethynyl)-3-pyridinyl)-1,3-oxazolidin-2-one;
(4R,5R)-5-(4-fluorophenyl)-4-(5-((5-fluoro-3-pyridinyl)ethynyl)-3-pyridinyl)-5-methyl-1,3-oxazolidin-2-one;
(4R,5R)-5-(4-fluorophenyl)-4-(5-((3-fluoro-2-pyridinyl)ethynyl)-3-pyridinyl)-1,3-oxazolidin-2-one;
(4R,5R)-5-(4-fluorophenyl)-4-(5-(2-pyrazinylethynyl)-3-pyridinyl)-1,3-oxazolidin-2-one;
(4R,5R)-5-(4-fluorophenyl)-4-(5-(4-pyridinylethynyl)-3-pyridinyl)-1,3-oxazolidin-2-one;
(4R,5R)-5-(4-fluorophenyl)-4-(5-((2-fluoro-4-pyridinyl)ethynyl)-3-pyridinyl)-1,3-oxazolidin-2-one;
3-((5-((4R,5R)-5-(4-fluorophenyl)-2-oxo-1,3-oxazolidin-4-yl)-3-pyridinyl)ethynyl)benzonitrile;
(4R,5R)-5-(4-fluorophenyl)-4-(5-((6-fluoro-2-pyridinyl)ethynyl)-3-pyridinyl)-1,3-oxazolidin-2-one;
(4R,5R)-5-(3-fluorophenyl)-4-(6-(phenylethynyl)-2-pyridinyl)-1,3-oxazolidin-2-one;
(4R,5R)-5-(4-fluorophenyl)-4-methyl-4-(5-(phenylethynyl)-3-pyridinyl)-1,3-oxazolidin-2-one;
(4R,5R)-5-(3-fluorophenyl)-5-methyl-4-(5-(phenylethynyl)-3-pyridinyl)-1,3-oxazolidin-2-one;
(4R,5S)-4-methyl-5-phenyl-4-(5-(phenylethynyl)-3-pyridinyl)-1,3-oxazolidin-2-one;
(4R,5R)-5-methyl-5-phenyl-4-(5-(phenylethynyl)-3-pyridinyl)-1,3-oxazolidin-2-one;
(4R,5R)-4-(5-((3-fluoro-2-pyridinyl)ethynyl)-3-pyridinyl)-4-methyl-5-phenyl-1,3-oxazolidin-2-one;
(4R,5S)-4-(3-(phenylethynyl)phenyl)-5-(2-pyridinyl)-1,3-oxazolidin-2-one;
(4R,5R)-5-(4-pyridinyl)-4-(3-(2-pyridinylethynyl)phenyl)-1,3-oxazolidin-2-one;
(4R,5R)-4-(3-(phenylethynyl)phenyl)-5-(4-pyridinyl)-1,3-oxazolidin-2-one;
(4R,5S)-4-(3-(phenylethynyl)phenyl)-5-(4-pyrimidinyl)-1,3-oxazolidin-2-one;
(4R,5R)-5-(3-fluorophenyl)-4-(5-((5-fluoro-3-pyridinyl)ethynyl)-3-pyridinyl)-1,3-oxazolidin-2-one;

(4R,5R)-5-(3-fluorophenyl)-4-(2-(3-pyridinylethynyl)-4-pyridinyl)-1,3-oxazolidin-2-one;
(4R,5R)-5-(3-fluorophenyl)-4-(2-(phenylethynyl)-4-pyridinyl)-1,3-oxazolidin-2-one;
(4R,5R)-5-(3-fluorophenyl)-4-(2-(phenylethynyl)-4-pyrimidinyl)-1,3-oxazolidin-2-one;
(4R,5R)-5-(2,3-difluorophenyl)-4-(5-(phenylethynyl)-3-pyridinyl)-1,3-oxazolidin-2-one;
(4R,5R)-5-(2,5-difluorophenyl)-4-(5-((4-fluorophenyl)ethynyl)-3-pyridinyl)-1,3-oxazolidin-2-one;
(4R,5R)-5-(2,5-difluorophenyl)-4-(5-((2-fluorophenyl)ethynyl)-3-pyridinyl)-1,3-oxazolidin-2-one;
(4R,5R)-5-(2,3-difluorophenyl)-4-(5((2-fluorophenyl)ethynyl)-3-pyridinyl)-1,3-oxazolidin-2-one;
(4R,5R)-5-(2,3-difluorophenyl)-4-(5-((4-fluorophenyl)ethynyl)-3-pyridinyl)-1,3-oxazolidin-2-one;
(4R,5R)-4-(5-(phenylethynyl)-3-pyridinyl)-5-(2,4,6-trifluorophenyl)-1,3-oxazolidin-2-one;
(4R,5R)-4-(5-(phenylethynyl)-3-pyridinyl)-5-(2,3,4-trifluorophenyl)-1,3-oxazolidin-2-one;
(4R,5R)-5-(4-fluorophenyl)-4-(4-(phenylethynyl)-2-pyridinyl)-1,3-oxazolidin-2-one;
(4R,5R)-5-(3-fluorophenyl)-4-(2-fluoro-5-(phenylethynyl)-3-pyridinyl)-1,3-oxazolidin-2-one;
(4R,5R)-5-(3-fluorophenyl)-4-(2-methoxy-5-(phenylethynyl)-3-pyridinyl)-1,3-oxazolidin-2-one;
(4R,5R)-5-(2,5-difluorophenyl)-4-(5-fluoro-2-(phenylethynyl)-4-pyridinyl)-1,3-oxazolidin-2-one;
(4R,5R)-5-(2,5-difluorophenyl)-4-(2-fluoro-5-(phenylethynyl)-3-pyridinyl)-1,3-oxazolidin-2-one;
(4R,5R)-5-(2-fluorophenyl)-4-(5-fluoro-2-(phenylethynyl)-4-pyridinyl)-1,3-oxazolidin-2-one;
(4R,5R)-5-(2,4-difluorophenyl)-4-(6-(phenylethynyl)-2-pyridinyl-1,3-oxazolidin-2-one;
(4R,5R)-5-(2,4-difluorophenyl)-4-(6-((3-fluorophenyl)ethynyl)-2-pyridinyl)-1,3-oxazolidin-2-one;
(4R,5R)-4-(5-(phenylethynyl)-3-pyridinyl)-5-(4-pyrimidinyl)-1,3-oxazolidin-2-one;
(4R,5R)-5-(2,3-dichlorophenyl)-4-(5-(phenylethynyl)-3-pyridinyl)-1,3-oxazolidin-2-one;
(4S,5R)-5-(1-methyl-1H-pyrazol-5-yl)-4-(5-(phenylethynyl)-3-pyridinyl)-1,3-oxazolidin-2-one;
(4R,5R)-5-(4-fluorophenyl)-4-(5-((3-fluoro-2-pyridinyl)ethynyl)-3-pyridinyl)-4-methyl-1,3-oxazolidin-2-one;
(4R,5S)-4-(5-(phenylethynyl)-3-pyridinyl)-5-(2-thienyl-1,3-oxazolidin-2-one;
(4R,5R)-5-(4-fluorophenyl)-4-(4-((2-fluorophenyl)ethynyl)-2-pyridinyl)-1,3-oxazolidin-2-one;
(4R,5R)-5-(4-fluorophenyl)-4-(4-((3-fluorophenyl)ethynyl)-2-pyridinyl)-1,3-oxazolidin-2-one;
(4R,5R)-5-(4-fluorophenyl)-4-(4-((4-fluorophenyl)ethynyl)-2-pyridinyl)-1,3-oxazolidin-2-one;
(4R,5R)-5-(4-chlorophenyl)-4-(5-(phenylethynyl)-3-pyridinyl)-1,3-oxazolidin-2-one;
(4R,5R)-5-(3-chlorophenyl-4-(5-(phenylethynyl)-3-pyridinyl)-1,3-oxazolidin-2-one;
(4R,5S)-5-(2-chlorophenyl)-4-(5-(phenylethynyl)-3-pyridinyl)-1,3-oxazolidin-2-one;
4-((4R,5R)-2-oxo-4-(5-(phenylethynyl)-3-pyridinyl)-1,3-oxazolidin-5-yl)benzonitrile;
(4R,5R)-5-(4-fluorophenyl)-4-(6-((3-fluoro-2-pyridinyl)ethynyl)-2-pyridinyl)-1,3-oxazolidin-2-one;
(4R,5R)-5-(4-fluorophenyl)-4-(6-((2-fluoro-4-pyridinyl)ethynyl)-2-pyridinyl)-1,3-oxazolidin-2-one;
(4R,5R)-4-(2-fluoro-5-(phenylethynyl)pyridin-3-yl)-5-(2-fluorophenyl)-1,3-oxazolidin-2-one;
(4R,5R)-5-(2,5-difluorophenyl)-4-(5-(2-pyrazinylethynyl)-3-pyridinyl)-1,3-oxazolidin-2-one;
(4R,5R)-4-(5-((2-chlorophenyl)ethynyl)-3-pyridinyl)-5-(3-fluorophenyl)-1,3-oxazolidin-2-one;
(4R,5R)-5-(3-fluorophenyl)-4-(5-((3-fluorophenyl)ethynyl)-3-pyridinyl)-1,3-oxazolidin-2-one;
(4R,5R)-5-(3-fluorophenyl)-4-(5-((3-methylphenyl)ethynyl)-3-pyridinyl)-1,3-oxazolidin-2-one;
(4R,5R)-4-(5-((3-chlorophenyl)ethynyl)-3-pyridinyl)-5-(3-fluorophenyl)-1,3-oxazolidin-2-one;
(4R,5R)-5-(2-fluorophenyl)-4-(5-(phenylethynyl)-3-pyridinyl)-1,3-oxazolidin-2-one; and
5R)-5-(2,5-difluorophenyl)-4-methyl-4-(5-(phenylethynyl)-3-pyridinyl)-1,3-oxazolidin-2-one;

or a pharmaceutically acceptable salt thereof.

12. The compound of claim 1 which is (4R,5R)-5-(2,5-difluorophenyl)-4-(5-(phenylethynyl)-3-pyridinyl)-1,3-oxazolidin-2-one

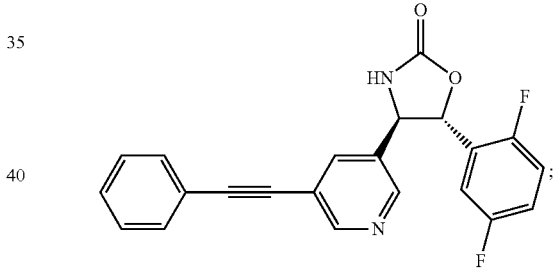

or a pharmaceutically salt thereof.

13. A composition comprising a compound of claim 1, or a pharmaceutically acceptable salt thereof, and a pharmaceutically acceptable carrier.

14. A method for the treatment of schizophrenia which comprises administering to a patient a therapeutically affective amount of a compound of claim 1.

* * * * *

UNITED STATES PATENT AND TRADEMARK OFFICE
CERTIFICATE OF CORRECTION

PATENT NO. : 8,691,821 B2  
APPLICATION NO. : 13/287487  
DATED : April 8, 2014  
INVENTOR(S) : Andrew P. Degnan et al.

Page 1 of 1

It is certified that error appears in the above-identified patent and that said Letters Patent is hereby corrected as shown below:

In the Claims:

Claim 6:

Column 303, line 60, change "(uranyl," to -- furanyl, --.

Claim 8:

Column 304, line 14, change "$A^2$" to -- $Ar^2$ --.

Claim 9:

Column 304, line 20, before "alkylphenyl,", delete "dihalophenyl,".

Claim 11:

Column 308, line 26, change "5R)-5-(2,5-difluorophenyl)-" to -- (4R,5R)-5-(2,5-difluorophenyl)- --.

Signed and Sealed this  
Seventh Day of April, 2015

Michelle K. Lee  
*Director of the United States Patent and Trademark Office*